United States Patent
Moshkevich et al.

(10) Patent No.: US 12,234,509 B2
(45) Date of Patent: *Feb. 25, 2025

(54) METHODS FOR DETECTION OF DONOR-DERIVED CELL-FREE DNA

(71) Applicant: Natera, Inc., San Carlos, CA (US)

(72) Inventors: Solomon Moshkevich, Menlo Park, CA (US); Bernhard Zimmermann, Manteca, CA (US); Tudor Pompiliu Constantin, Berkley, CA (US); Huseyin Eser Kirkizlar, Los Angeles, CA (US); Allison Ryan, Belmont, CA (US); Styrmir Sigurjonsson, San Jose, CA (US); Felipe Acosta Archila, Foster City, CA (US); Ryan Swenerton, Millbrae, CA (US)

(73) Assignee: Natera, Inc., San Carlos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/165,592

(22) Filed: Feb. 2, 2021

(65) Prior Publication Data

US 2021/0198733 A1 Jul. 1, 2021

Related U.S. Application Data

(63) Continuation of application No. 17/252,068, filed as application No. PCT/US2019/040603 on Jul. 3, 2019.

(60) Provisional application No. 62/834,315, filed on Apr. 15, 2019, provisional application No. 62/781,882, filed on Dec. 19, 2018, provisional application No.
(Continued)

(51) Int. Cl.
*C12Q 1/68* (2018.01)
*C12Q 1/6851* (2018.01)
*C12Q 1/6869* (2018.01)
*C12Q 1/6876* (2018.01)

(52) U.S. Cl.
CPC ........ *C12Q 1/6869* (2013.01); *C12Q 1/6851* (2013.01); *C12Q 1/6876* (2013.01)

(58) Field of Classification Search
CPC ..................................................... C12Q 1/68
USPC ......................................................... 435/6
See application file for complete search history.

(56) References Cited

U.S. PATENT DOCUMENTS

| | | |
|---|---|---|
| 3,957,654 A | 5/1976 | Ayres |
| 4,040,785 A | 8/1977 | Kim et al. |
| 4,683,195 A | 7/1987 | Mullis et al. |

(Continued)

FOREIGN PATENT DOCUMENTS

| | | |
|---|---|---|
| BR | 112017023232 A2 | 8/2018 |
| CA | 2875281 A1 | 12/2013 |

(Continued)

OTHER PUBLICATIONS

US 8,501,409 B2, 08/2013, Simen et al. (withdrawn)
(Continued)

*Primary Examiner* — Aaron A Priest

(57) ABSTRACT

The present disclosure provides methods for determining the status of an allograft within a transplant recipient from genotypic data measured from a mixed sample of DNA comprising DNA from both the transplant recipient and from the donor. The mixed sample of DNA may be preferentially enriched at a plurality of polymorphic loci in a way that minimizes the allelic bias, for example using massively multiplexed targeted PCR.

19 Claims, 65 Drawing Sheets

Related U.S. Application Data

62/715,178, filed on Aug. 6, 2018, provisional application No. 62/693,833, filed on Jul. 3, 2018.

(56) References Cited

U.S. PATENT DOCUMENTS

| | | |
|---|---|---|
| 4,942,124 A | 7/1990 | Church et al. |
| 5,180,812 A | 1/1993 | Dower et al. |
| 5,314,809 A | 5/1994 | Erlich et al. |
| 5,319,071 A | 6/1994 | Dower et al. |
| 5,464,937 A | 11/1995 | Sims et al. |
| 5,486,477 A | 1/1996 | Carver |
| 5,488,032 A | 1/1996 | Dower et al. |
| 5,492,888 A | 2/1996 | Dower et al. |
| 5,569,582 A | 10/1996 | Tavernarakis et al. |
| 5,595,890 A | 1/1997 | Newton et al. |
| 5,635,366 A | 6/1997 | Cooke et al. |
| 5,645,988 A | 7/1997 | Vande Woude et al. |
| 5,648,220 A | 7/1997 | Bianchi et al. |
| 5,714,320 A | 2/1998 | Kool |
| 5,716,776 A | 2/1998 | Bogart |
| 5,736,033 A | 4/1998 | Coleman et al. |
| 5,753,467 A | 5/1998 | Jensen et al. |
| 5,824,467 A | 10/1998 | Mascarenhas |
| 5,854,033 A | 12/1998 | Lizardi |
| 5,860,917 A | 1/1999 | Comanor et al. |
| 5,891,734 A | 4/1999 | Gill et al. |
| 5,952,170 A | 9/1999 | Stroun et al. |
| 5,962,223 A | 10/1999 | Whiteley et al. |
| 5,972,602 A | 11/1999 | Hyland et al. |
| 5,976,790 A | 11/1999 | Pinkel et al. |
| 5,994,148 A | 11/1999 | Stewart et al. |
| 6,001,611 A | 12/1999 | Will |
| 6,025,128 A | 2/2000 | Veltri et al. |
| 6,066,454 A | 5/2000 | Lipshutz et al. |
| 6,100,029 A | 8/2000 | Lapidus et al. |
| 6,108,635 A | 8/2000 | Herren et al. |
| 6,124,120 A | 9/2000 | Lizardi |
| 6,143,496 A | 11/2000 | Brown et al. |
| 6,156,504 A | 12/2000 | Gocke et al. |
| 6,180,349 B1 | 1/2001 | Ginzinger |
| 6,235,472 B1 | 2/2001 | Landegren et al. |
| 6,214,558 B1 | 4/2001 | Shuber et al. |
| 6,221,603 B1 | 4/2001 | Mahtani |
| 6,258,540 B1 | 7/2001 | Lo et al. |
| 6,300,077 B1 | 10/2001 | Shuber et al. |
| 6,329,179 B1 | 12/2001 | Kopreski |
| 6,335,167 B1 | 1/2002 | Pinkel et al. |
| 6,440,706 B1 | 8/2002 | Vogelstein et al. |
| 6,479,235 B1 | 11/2002 | Schumm et al. |
| 6,489,135 B1 | 12/2002 | Parrott et al. |
| 6,605,451 B1 | 8/2003 | Marmaro et al. |
| 6,617,137 B2 | 9/2003 | Dean et al. |
| 6,720,140 B1 | 4/2004 | Hartley et al. |
| 6,794,140 B1 | 9/2004 | Goldsborough |
| 6,807,491 B2 | 10/2004 | Pavlovic et al. |
| 6,858,412 B2 | 2/2005 | Willis et al. |
| 6,927,028 B2 | 8/2005 | Lo et al. |
| 6,852,487 B1 | 10/2005 | Barany et al. |
| 6,958,211 B2 | 10/2005 | Vingerhoets et al. |
| 6,964,847 B1 | 11/2005 | Englert |
| 7,035,739 B2 | 4/2006 | Schadt et al. |
| 7,058,517 B1 | 6/2006 | Denton et al. |
| 7,058,616 B1 | 6/2006 | Larder et al. |
| 7,101,663 B2 | 9/2006 | Godfrey et al. |
| 7,153,656 B2 | 12/2006 | Nolan et al. |
| 7,218,764 B2 | 5/2007 | Vaisberg et al. |
| 7,297,485 B2 | 11/2007 | Bornarth et al. |
| 7,332,277 B2 | 2/2008 | Dhallan |
| 7,410,764 B2 | 8/2008 | Gocke et al. |
| 7,414,118 B1 | 8/2008 | Mullah et al. |
| 7,442,506 B2 | 12/2008 | Dhallan |
| 7,459,273 B2 | 12/2008 | Jones et al. |
| 7,537,897 B2 | 5/2009 | Brenner et al. |
| 7,645,576 B2 | 1/2010 | Lo et al. |
| 7,655,399 B2 | 2/2010 | Cantor et al. |
| 7,700,325 B2 | 4/2010 | Cantor et al. |
| 7,718,367 B2 | 5/2010 | Lo et al. |
| 7,718,370 B2 | 6/2010 | Dhallan |
| 7,741,463 B2 | 6/2010 | Gormley et al. |
| 7,785,798 B2 | 8/2010 | Cantor et al. |
| 7,727,720 B2 | 9/2010 | Dhallan |
| 7,790,393 B2 | 9/2010 | Lyamichev et al. |
| 7,790,418 B2 | 9/2010 | Mayer |
| 7,805,282 B2 | 11/2010 | Casey |
| 7,838,647 B2 | 11/2010 | Hahn et al. |
| 7,981,609 B2 | 7/2011 | Rubin et al. |
| 7,888,017 B2 | 8/2011 | Quake |
| 8,008,018 B2 | 9/2011 | Quake et al. |
| 8,024,128 B2 | 9/2011 | Rabinowitz |
| 8,133,719 B2 | 3/2012 | Drmanac et al. |
| 8,137,912 B2 | 5/2012 | Kapur et al. |
| 8,173,370 B2 | 5/2012 | Oeth et al. |
| 8,168,389 B2 | 6/2012 | Shoemaker et al. |
| 8,236,503 B2 | 8/2012 | Faham et al. |
| 8,195,415 B2 | 10/2012 | Fan et al. |
| 8,296,076 B2 | 11/2012 | Fan et al. |
| 8,304,187 B2 | 11/2012 | Fernando |
| 8,318,430 B2 | 11/2012 | Chuu et al. |
| 8,318,434 B2 | 11/2012 | Cuppens et al. |
| 8,323,897 B2 | 12/2012 | Andersen et al. |
| 8,372,584 B2 | 2/2013 | Shoemaker et al. |
| 8,389,557 B2 | 3/2013 | Singh et al. |
| 8,389,578 B2 | 3/2013 | Went et al. |
| 8,450,063 B2 | 5/2013 | Dube et al. |
| 8,467,976 B2 | 8/2013 | Lo et al. |
| 8,515,679 B2 | 8/2013 | Rabinowitz et al. |
| 8,532,930 B2 | 9/2013 | Rabinowitz et al. |
| 8,609,338 B2 | 12/2013 | Mitchell et al. |
| 8,679,741 B2 | 3/2014 | Hoyal-Wrightson et al. |
| 8,682,592 B2 | 3/2014 | Rabinowitz et al. |
| 8,703,652 B2 | 4/2014 | Quake et al. |
| 8,706,422 B2 | 4/2014 | Lo et al. |
| 8,748,103 B2 | 6/2014 | Faham et al. |
| 8,822,153 B2 | 9/2014 | Hayes et al. |
| 8,825,412 B2 | 9/2014 | Rabinowitz et al. |
| 9,005,894 B2 | 4/2015 | Ladner et al. |
| 9,051,602 B2 | 6/2015 | Oliphant et al. |
| 9,085,798 B2 | 7/2015 | Chee |
| 9,206,475 B2 | 12/2015 | gerdes et al. |
| 9,228,234 B2 | 1/2016 | Rabinowitz et al. |
| 9,290,815 B2 | 3/2016 | Di Pasquale et al. |
| 9,323,888 B2 | 4/2016 | Rava et al. |
| 9,364,829 B2 | 6/2016 | Heid et al. |
| 9,404,150 B2 | 8/2016 | Lee et al. |
| 9,424,392 B2 | 8/2016 | Rabinowitz et al. |
| 9,453,257 B2 | 9/2016 | Hoyal-Wrightson et al. |
| 9,476,095 B2 | 10/2016 | Vogelstein et al. |
| 9,487,829 B2 | 11/2016 | Vogelstein et al. |
| 9,493,828 B2 | 11/2016 | Rava et al. |
| 9,506,119 B2 | 11/2016 | Faham et al. |
| 9,598,731 B2 | 3/2017 | Talasaz |
| 9,677,118 B2 | 6/2017 | Zimmermann et al. |
| 9,784,742 B2 | 10/2017 | Benz et al. |
| 9,926,593 B2 | 3/2018 | Ehrich et al. |
| 9,957,558 B2 * | 5/2018 | Leamon ............... C12Q 1/6855 |
| 10,017,810 B2 | 7/2018 | Iafrate et al. |
| 10,041,127 B2 | 8/2018 | Talasaz |
| 10,061,890 B2 | 8/2018 | Rabinowitz et al. |
| 10,081,839 B2 | 9/2018 | Rabinowitz et al. |
| 10,083,273 B2 | 9/2018 | Rabinowitz et al. |
| 10,174,369 B2 | 1/2019 | Rabinowitz et al. |
| 10,179,937 B2 | 1/2019 | Babiarz et al. |
| 10,227,652 B2 | 3/2019 | Rabinowitz et al. |
| 10,229,244 B2 | 3/2019 | Ghosh |
| 10,240,202 B2 | 3/2019 | Rabinowitz et al. |
| 10,260,096 B2 | 4/2019 | Rabinowitz et al. |
| 10,262,755 B2 | 4/2019 | Babiarz et al. |
| 10,266,893 B2 | 4/2019 | Rabinowitz et al. |
| 10,308,981 B2 | 6/2019 | Sparks et al. |
| 10,316,362 B2 | 6/2019 | Babiarz et al. |
| 10,351,906 B2 | 7/2019 | Zimmermann et al. |
| 10,385,396 B2 | 8/2019 | Mitchell et al. |
| 10,392,664 B2 | 8/2019 | Rabinowitz et al. |
| 10,450,597 B2 | 10/2019 | Iafrate et al. |

(56) References Cited

U.S. PATENT DOCUMENTS

| | | |
|---|---|---|
| 10,472,680 B2 | 11/2019 | Mitchell et al. |
| 10,522,242 B2 | 12/2019 | Rabinowitz et al. |
| 10,526,658 B2 | 1/2020 | Babiarz et al. |
| 10,538,814 B2 | 1/2020 | Babiarz et al. |
| 10,557,172 B2 | 2/2020 | Babiarz et al. |
| 10,597,708 B2 | 3/2020 | Zimmermann et al. |
| 10,597,709 B2 | 3/2020 | Zimmermann et al. |
| 10,597,723 B2 | 3/2020 | Babiarz et al. |
| 10,640,819 B2 | 5/2020 | Rosenfeld et al. |
| 10,655,180 B2 | 5/2020 | Babiarz et al. |
| 10,683,552 B2 | 6/2020 | McCarroll et al. |
| 10,711,309 B2 | 7/2020 | Rabinowitz et al. |
| 10,731,220 B2 | 8/2020 | Babiarz et al. |
| 10,774,380 B2 | 9/2020 | Ryan et al. |
| 10,793,912 B2 | 10/2020 | Babiarz et al. |
| 10,894,976 B2 | 1/2021 | Stray et al. |
| 11,111,543 B2 | 9/2021 | Rabinowitz et al. |
| 11,111,544 B2 | 9/2021 | Rabinowitz et al. |
| 11,111,545 B2 | 9/2021 | Babiarz et al. |
| 11,130,995 B2 | 9/2021 | Quake et al. |
| 11,319,596 B2 | 5/2022 | Babiarz et al. |
| 11,371,100 B2 | 6/2022 | Babiarz et al. |
| 11,519,035 B2 | 12/2022 | Rabinowitz et al. |
| 2001/0051341 A1 | 12/2001 | Lo et al. |
| 2001/0053519 A1 | 12/2001 | Fodor et al. |
| 2002/0006622 A1 | 1/2002 | Bradley et al. |
| 2002/0107640 A1 | 8/2002 | Ideker et al. |
| 2002/0119478 A1 | 8/2002 | Umansky et al. |
| 2002/0182622 A1 | 12/2002 | Nakamura et al. |
| 2002/0197630 A1 | 12/2002 | Knapp et al. |
| 2003/0009295 A1 | 1/2003 | Markowitz et al. |
| 2003/0040620 A1 | 2/2003 | Langmore et al. |
| 2003/0044388 A1 | 3/2003 | Lo et al. |
| 2003/0065535 A1 | 4/2003 | Karlov et al. |
| 2003/0077586 A1 | 4/2003 | Pavlovic et al. |
| 2003/0087276 A1 | 5/2003 | Kopreski et al. |
| 2003/0101000 A1 | 5/2003 | Bader et al. |
| 2003/0108900 A1 | 6/2003 | Oliphant et al. |
| 2003/0119004 A1 | 6/2003 | Wenz et al. |
| 2003/0138780 A1 | 7/2003 | Gill et al. |
| 2003/0148301 A1 | 8/2003 | Aono et al. |
| 2003/0191005 A1 | 10/2003 | Coelho et al. |
| 2003/0211489 A1 | 11/2003 | Shen et al. |
| 2003/0228613 A1 | 12/2003 | Bornarth et al. |
| 2003/0232348 A1 | 12/2003 | Jones et al. |
| 2003/0232353 A1 | 12/2003 | Kennedy et al. |
| 2003/0235848 A1 | 12/2003 | Neville et al. |
| 2004/0009518 A1 | 1/2004 | Lo et al. |
| 2004/0033596 A1 | 2/2004 | Threadgill et al. |
| 2004/0067493 A1 | 4/2004 | Matsuzaki et al. |
| 2004/0096874 A1 | 5/2004 | Neville et al. |
| 2004/0115629 A1 | 6/2004 | Panzer et al. |
| 2004/0117346 A1 | 6/2004 | Stoffel et al. |
| 2004/0126760 A1 | 7/2004 | Broude |
| 2004/0136967 A1 | 7/2004 | Weiss et al. |
| 2004/0137470 A1 | 7/2004 | Dhallan et al. |
| 2004/0146866 A1 | 7/2004 | Fu |
| 2004/0157243 A1 | 8/2004 | Huang et al. |
| 2004/0185495 A1 | 9/2004 | Schueler et al. |
| 2004/0197797 A1 | 10/2004 | Inoko et al. |
| 2004/0209299 A1* | 10/2004 | Pinter ............... C12N 15/1093 536/25.4 |
| 2004/0229231 A1 | 11/2004 | Frudakis et al. |
| 2004/0236518 A1 | 11/2004 | Pavlovic et al. |
| 2004/0259100 A1 | 12/2004 | Gunderson et al. |
| 2005/0009069 A1 | 1/2005 | Liu et al. |
| 2005/0043894 A1 | 2/2005 | Fernandez |
| 2005/0049793 A1 | 3/2005 | Paterlini-brechot |
| 2005/0053950 A1 | 3/2005 | Ubani et al. |
| 2005/0064476 A1 | 3/2005 | Huang et al. |
| 2005/0079521 A1 | 4/2005 | Beaulieu et al. |
| 2005/0079535 A1 | 4/2005 | Kirchgesser et al. |
| 2005/0123914 A1 | 6/2005 | Katz et al. |
| 2005/0130173 A1 | 6/2005 | Leamon et al. |
| 2005/0142577 A1 | 6/2005 | Jones et al. |
| 2005/0144664 A1 | 6/2005 | Smith et al. |
| 2005/0164241 A1 | 7/2005 | Hahn et al. |
| 2005/0164252 A1 | 7/2005 | Yeung |
| 2005/0216207 A1 | 9/2005 | Kermani |
| 2005/0221341 A1 | 10/2005 | Shimkets et al. |
| 2005/0227263 A1 | 10/2005 | Green et al. |
| 2005/0250111 A1 | 11/2005 | Xie et al. |
| 2005/0255508 A1 | 11/2005 | Casey et al. |
| 2005/0272073 A1 | 12/2005 | Vaisberg et al. |
| 2005/0282185 A1 | 12/2005 | Lo et al. |
| 2006/0014179 A1 | 1/2006 | Roberts |
| 2006/0019278 A1 | 1/2006 | Lo et al. |
| 2006/0040300 A1 | 2/2006 | Dapprich et al. |
| 2006/0046258 A1 | 3/2006 | Lapidus et al. |
| 2006/0051799 A1 | 3/2006 | Iwaki et al. |
| 2006/0052945 A1 | 3/2006 | Rabinowitz et al. |
| 2006/0057618 A1 | 3/2006 | Piper et al. |
| 2006/0068369 A1 | 3/2006 | Coelho et al. |
| 2006/0068394 A1 | 3/2006 | Langmore et al. |
| 2006/0088574 A1 | 4/2006 | Manning et al. |
| 2006/0088871 A1 | 4/2006 | Finkelstein et al. |
| 2006/0088912 A1 | 4/2006 | Yan et al. |
| 2006/0094010 A1 | 5/2006 | Giles et al. |
| 2006/0099614 A1 | 5/2006 | Gill et al. |
| 2006/0121452 A1 | 6/2006 | Dhallan |
| 2006/0134662 A1 | 6/2006 | Pratt et al. |
| 2006/0141499 A1 | 6/2006 | Sher et al. |
| 2006/0229823 A1 | 8/2006 | Liu |
| 2006/0210997 A1 | 9/2006 | Myerson et al. |
| 2006/0216153 A1 | 9/2006 | Wobben et al. |
| 2006/0216738 A1 | 9/2006 | Wada et al. |
| 2006/0228721 A1 | 10/2006 | Leamon et al. |
| 2006/0234264 A1 | 10/2006 | Hardenbol |
| 2006/0248031 A1 | 11/2006 | Kates et al. |
| 2006/0281105 A1 | 12/2006 | Li et al. |
| 2006/0292599 A1 | 12/2006 | Ritz et al. |
| 2007/0020640 A1 | 1/2007 | McCloskey et al. |
| 2007/0027636 A1 | 2/2007 | Rabinowitz |
| 2007/0031857 A1 | 2/2007 | Makarov et al. |
| 2007/0037166 A1 | 2/2007 | Wohlgemuth et al. |
| 2007/0042384 A1 | 2/2007 | Li et al. |
| 2007/0059700 A1 | 3/2007 | Tao et al. |
| 2007/0059707 A1 | 3/2007 | Cantor et al. |
| 2007/0122805 A1 | 5/2007 | Cantor et al. |
| 2007/0128624 A1 | 6/2007 | Gormley et al. |
| 2007/0134658 A1 | 6/2007 | Bohmer |
| 2007/0178478 A1 | 8/2007 | Dhallan |
| 2007/0178501 A1 | 8/2007 | Rabinowitz et al. |
| 2007/0184467 A1 | 8/2007 | Rabinowitz et al. |
| 2007/0202525 A1 | 8/2007 | Quake et al. |
| 2007/0202536 A1 | 8/2007 | Yamanishi et al. |
| 2007/0207466 A1 | 9/2007 | Cantor et al. |
| 2007/0212689 A1 | 9/2007 | Bianchi et al. |
| 2007/0231823 A1 | 10/2007 | McKernan et al. |
| 2007/0243549 A1 | 10/2007 | Bischoff |
| 2007/0259351 A1 | 11/2007 | Chinitz |
| 2008/0020390 A1 | 1/2008 | Mitchell et al. |
| 2008/0026390 A1 | 1/2008 | Stoughton et al. |
| 2008/0038733 A1 | 2/2008 | Bischoff et al. |
| 2008/0050739 A1 | 2/2008 | Stoughton et al. |
| 2008/0070792 A1 | 3/2008 | Stoughton |
| 2008/0071076 A1 | 3/2008 | Hahn et al. |
| 2008/0085836 A1 | 4/2008 | Kearns et al. |
| 2008/0090239 A1 | 4/2008 | Shoemaker et al. |
| 2008/0096766 A1 | 4/2008 | Lee |
| 2008/0102455 A1 | 5/2008 | Poetter |
| 2008/0138809 A1 | 6/2008 | Kapur et al. |
| 2008/0161420 A1 | 7/2008 | Shuber et al. |
| 2008/0164204 A1 | 7/2008 | Hatamian et al. |
| 2008/0182244 A1 | 7/2008 | Tafas et al. |
| 2008/0193927 A1 | 8/2008 | Mann et al. |
| 2008/0220422 A1 | 9/2008 | Shoemaker et al. |
| 2008/0234142 A1 | 9/2008 | Lietz |
| 2008/0243398 A1 | 10/2008 | Rabinowitz et al. |
| 2008/0280292 A1 | 11/2008 | Wangh et al. |
| 2008/0286783 A1 | 11/2008 | Hosono et al. |
| 2008/0299562 A1 | 12/2008 | Oeth et al. |
| 2008/0305473 A1 | 12/2008 | Chowdary et al. |
| 2009/0023190 A1 | 1/2009 | Lao et al. |

(56) References Cited

U.S. PATENT DOCUMENTS

| | | |
|---|---|---|
| 2009/0029377 A1 | 1/2009 | Lo et al. |
| 2009/0053719 A1 | 2/2009 | Lo et al. |
| 2009/0087847 A1 | 4/2009 | Lo et al. |
| 2009/0098534 A1 | 4/2009 | Weier et al. |
| 2009/0099041 A1 | 4/2009 | Church et al. |
| 2009/0143570 A1 | 6/2009 | Jiang et al. |
| 2009/0176234 A1 | 7/2009 | Drmanac et al. |
| 2009/0176662 A1 | 7/2009 | Rigatti et al. |
| 2009/0221620 A1 | 9/2009 | Luke et al. |
| 2009/0228299 A1 | 9/2009 | Kangarloo et al. |
| 2009/0233802 A1 | 9/2009 | Bignell et al. |
| 2009/0253183 A1 | 10/2009 | Han |
| 2009/0263800 A1 | 10/2009 | Wohlgemuth et al. |
| 2009/0280479 A1 | 11/2009 | Hoon et al. |
| 2009/0317817 A1 | 12/2009 | Oeth et al. |
| 2010/0012598 A1 | 1/2010 | Dicesare et al. |
| 2010/0035232 A1 | 2/2010 | Ecker et al. |
| 2010/0041048 A1 | 2/2010 | Diehl et al. |
| 2010/0086914 A1 | 4/2010 | bentley et al. |
| 2010/0105049 A1 | 4/2010 | Ehrich et al. |
| 2010/0112575 A1 | 5/2010 | Fan et al. |
| 2010/0112586 A1 | 5/2010 | Stoughton et al. |
| 2010/0112590 A1 | 5/2010 | Lo et al. |
| 2010/0120038 A1 | 5/2010 | Mir et al. |
| 2010/0124751 A1 | 5/2010 | Quake et al. |
| 2010/0129792 A1 | 5/2010 | Makrigiorgos et al. |
| 2010/0129874 A1 | 5/2010 | Mitra et al. |
| 2010/0138165 A1 | 6/2010 | Fan et al. |
| 2010/0155343 A1 | 6/2010 | Battles et al. |
| 2010/0171954 A1 | 7/2010 | Quake et al. |
| 2010/0173394 A1 | 7/2010 | Colston et al. |
| 2010/0184043 A1 | 7/2010 | Mitchell et al. |
| 2010/0184069 A1 | 7/2010 | Fernando et al. |
| 2010/0184152 A1 | 7/2010 | Sandler |
| 2010/0196892 A1 | 8/2010 | Quake et al. |
| 2010/0203538 A1 | 8/2010 | Dube et al. |
| 2010/0216145 A1 | 8/2010 | Duvdevani |
| 2010/0216151 A1 | 8/2010 | Lapdus et al. |
| 2010/0216153 A1 | 8/2010 | Lapidus et al. |
| 2010/0248231 A1 | 9/2010 | Wei et al. |
| 2010/0255492 A1 | 10/2010 | Quake et al. |
| 2010/0256013 A1 | 10/2010 | Quake et al. |
| 2010/0273159 A1 | 10/2010 | Melo |
| 2010/0273219 A1 | 10/2010 | May et al. |
| 2010/0273678 A1 | 10/2010 | Alexandre et al. |
| 2010/0285478 A1 | 11/2010 | Chen et al. |
| 2010/0285537 A1 | 11/2010 | Zimmermann |
| 2010/0291572 A1 | 11/2010 | Stoughton et al. |
| 2010/0291635 A1 | 11/2010 | Peleg |
| 2010/0323352 A1 | 12/2010 | Lo et al. |
| 2010/0326218 A1 | 12/2010 | Boeckh et al. |
| 2011/0015096 A1 | 1/2011 | Chiu |
| 2011/0033862 A1 | 2/2011 | Rabinowitz et al. |
| 2011/0039724 A1 | 2/2011 | Lo et al. |
| 2011/0045462 A1 | 2/2011 | Fu et al. |
| 2011/0064824 A1 | 3/2011 | Lascoste et al. |
| 2011/0071031 A1 | 3/2011 | Khripin et al. |
| 2011/0086769 A1 | 4/2011 | Oliphant et al. |
| 2011/0092763 A1 | 4/2011 | Rabinowitz et al. |
| 2011/0105353 A1 | 5/2011 | Lo et al. |
| 2011/0110931 A1 | 5/2011 | Matsui |
| 2011/0111410 A1 | 5/2011 | Ryan et al. |
| 2011/0130558 A1 | 6/2011 | Ritt et al. |
| 2011/0151442 A1 | 6/2011 | Fan et al. |
| 2011/0159499 A1 | 6/2011 | Hindson et al. |
| 2011/0160078 A1 | 6/2011 | Fodor et al. |
| 2011/0178719 A1 | 7/2011 | Rabinowitz et al. |
| 2011/0189677 A1 | 8/2011 | Adli et al. |
| 2011/0201507 A1 | 8/2011 | Rava et al. |
| 2011/0212446 A1 | 9/2011 | Wang et al. |
| 2011/0212846 A1 | 9/2011 | Spier |
| 2011/0224087 A1 | 9/2011 | Quake et al. |
| 2011/0246083 A1 | 10/2011 | Fan et al. |
| 2011/0251149 A1 | 10/2011 | Perrine et al. |
| 2011/0288780 A1 | 11/2011 | Rabinowitz et al. |
| 2011/0294699 A1 | 12/2011 | Lee et al. |
| 2011/0300608 A1 | 12/2011 | Ryan et al. |
| 2011/0301854 A1 | 12/2011 | Curry et al. |
| 2011/0312503 A1 | 12/2011 | Chuu et al. |
| 2011/0318734 A1 | 12/2011 | Lo et al. |
| 2012/0003635 A1 | 1/2012 | Lo et al. |
| 2012/0003637 A1 | 1/2012 | Lo et al. |
| 2012/0010085 A1 | 1/2012 | Rava et al. |
| 2012/0021442 A1 | 1/2012 | Buhimschi et al. |
| 2012/0028814 A1 | 2/2012 | Toloue et al. |
| 2012/0034603 A1 | 2/2012 | Oliphant et al. |
| 2012/0034685 A1 | 2/2012 | Sparks et al. |
| 2012/0108460 A1 | 5/2012 | Quake et al. |
| 2012/0115140 A1 | 5/2012 | Rivkees et al. |
| 2012/0122701 A1 | 5/2012 | Ryan et al. |
| 2012/0122702 A1 | 5/2012 | Leproust et al. |
| 2012/0135872 A1 | 5/2012 | Chuu et al. |
| 2012/0165203 A1 | 6/2012 | Quake et al. |
| 2012/0185176 A1 | 7/2012 | Rabinowitz et al. |
| 2012/0190020 A1 | 7/2012 | Oliphant et al. |
| 2012/0190021 A1 | 7/2012 | Oliphant et al. |
| 2012/0190557 A1 | 7/2012 | Oliphant et al. |
| 2012/0191358 A1 | 7/2012 | Oliphant et al. |
| 2012/0196754 A1 | 8/2012 | Quake et al. |
| 2012/0208706 A1 | 8/2012 | Downing et al. |
| 2012/0214678 A1 | 8/2012 | Rava et al. |
| 2012/0251411 A1 | 10/2012 | Jeon |
| 2012/0264121 A1 | 10/2012 | Rava et al. |
| 2012/0264618 A1 | 10/2012 | Nygren |
| 2012/0270212 A1 | 10/2012 | Rabinowitz et al. |
| 2012/0270739 A1 | 10/2012 | Rava et al. |
| 2012/0295810 A1 | 11/2012 | Quake et al. |
| 2012/0295819 A1 | 11/2012 | Leamon et al. |
| 2013/0017549 A1 | 1/2013 | Hong |
| 2013/0022973 A1 | 1/2013 | Hansen et al. |
| 2013/0024127 A1 | 1/2013 | Stuelpnagel |
| 2013/0034546 A1 | 2/2013 | Rava et al. |
| 2013/0040375 A1 | 2/2013 | Sparks et al. |
| 2013/0059733 A1 | 3/2013 | Lo et al. |
| 2013/0060483 A1 | 3/2013 | Struble et al. |
| 2013/0069869 A1 | 3/2013 | Akao et al. |
| 2013/0071844 A1 | 3/2013 | Makino et al. |
| 2013/0073214 A1 | 3/2013 | Hyland et al. |
| 2013/0085681 A1 | 4/2013 | Deciu et al. |
| 2013/0090250 A1 | 4/2013 | Sparks et al. |
| 2013/0116130 A1 | 5/2013 | Fu et al. |
| 2013/0123120 A1 | 5/2013 | Zimmermann et al. |
| 2013/0130923 A1 | 5/2013 | Ehrich et al. |
| 2013/0143219 A1 | 6/2013 | Mitchell et al. |
| 2013/0150253 A1 | 6/2013 | Deciu et al. |
| 2013/0157870 A1 | 6/2013 | Pushkarev et al. |
| 2013/0172211 A1 | 7/2013 | Oliphant et al. |
| 2013/0178373 A1 | 7/2013 | Rabinowitz et al. |
| 2013/0190653 A1 | 7/2013 | Alvarez Ramos |
| 2013/0196862 A1 | 8/2013 | Rabinowitz et al. |
| 2013/0210644 A1 | 8/2013 | Stoughton et al. |
| 2013/0225422 A1 | 8/2013 | Rabinowitz et al. |
| 2013/0231252 A1 | 9/2013 | Mitchell et al. |
| 2013/0237431 A1 | 9/2013 | Lo et al. |
| 2013/0252824 A1 | 9/2013 | Rabinowitz |
| 2013/0253369 A1 | 9/2013 | Rabinowitz et al. |
| 2013/0261004 A1 | 10/2013 | Ryan et al. |
| 2013/0274116 A1 | 10/2013 | Rabinowitz et al. |
| 2013/0274135 A1 | 10/2013 | Zhang et al. |
| 2013/0288252 A1 | 10/2013 | Sparks et al. |
| 2013/0303461 A1 | 11/2013 | Iafrate et al. |
| 2013/0310260 A1 | 11/2013 | Kim et al. |
| 2013/0323727 A1 | 12/2013 | Huang et al. |
| 2013/0323731 A1 | 12/2013 | Lo et al. |
| 2013/0325360 A1 | 12/2013 | Deciu et al. |
| 2013/0344066 A1 | 12/2013 | Faham et al. |
| 2014/0032128 A1 | 1/2014 | Rabinowitz et al. |
| 2014/0038830 A1 | 2/2014 | Srinivasan et al. |
| 2014/0045181 A1 | 2/2014 | Lo et al. |
| 2014/0051585 A1 | 2/2014 | Prosen et al. |
| 2014/0065621 A1 | 3/2014 | Mhatre et al. |
| 2014/0066317 A1 | 3/2014 | Talasaz |
| 2014/0087385 A1 | 3/2014 | Rabinowitz et al. |
| 2014/0094373 A1 | 4/2014 | Zimmermann et al. |

(56) References Cited

U.S. PATENT DOCUMENTS

| | | |
|---|---|---|
| 2014/0100121 A1 | 4/2014 | Lo et al. |
| 2014/0100126 A1 | 4/2014 | Rabinowitz |
| 2014/0100134 A1 | 4/2014 | Rabinowitz et al. |
| 2014/0106975 A1 | 4/2014 | Stoughton et al. |
| 2014/0113795 A1 | 4/2014 | Emerson et al. |
| 2014/0141981 A1 | 5/2014 | Zimmermann et al. |
| 2014/0154682 A1 | 6/2014 | Rabinowitz et al. |
| 2014/0155274 A1 | 6/2014 | Xie et al. |
| 2014/0162269 A1 | 6/2014 | Rabinowitz |
| 2014/0186827 A1 | 7/2014 | Pieprzyk et al. |
| 2014/0193816 A1 | 7/2014 | Rabinowitz et al. |
| 2014/0206552 A1 | 7/2014 | Rabinowitz et al. |
| 2014/0227691 A1 | 8/2014 | May et al. |
| 2014/0227705 A1 | 8/2014 | Vogelstein et al. |
| 2014/0242588 A1 | 8/2014 | Van Den Boom et al. |
| 2014/0256558 A1 | 9/2014 | Varley et al. |
| 2014/0256569 A1 | 9/2014 | Rabinowitz et al. |
| 2014/0272956 A1 | 9/2014 | Huang et al. |
| 2014/0274740 A1 | 9/2014 | Srinivasan et al. |
| 2014/0287934 A1 | 9/2014 | Szelinger et al. |
| 2014/0296081 A1 | 10/2014 | Diehn et al. |
| 2014/0329245 A1 | 11/2014 | Spier et al. |
| 2014/0336060 A1 | 11/2014 | Rabinowitz |
| 2015/0051087 A1 | 2/2015 | Rabinowitz et al. |
| 2015/0056617 A1 | 2/2015 | Whitt et al. |
| 2015/0064695 A1 | 3/2015 | Katz et al. |
| 2015/0086477 A1 | 3/2015 | Mitchell et al. |
| 2015/0087535 A1 | 3/2015 | Patel |
| 2015/0099673 A1 | 4/2015 | Fodor |
| 2015/0147815 A1 | 5/2015 | Babiarz et al. |
| 2015/0157606 A1 | 6/2015 | Maneval et al. |
| 2015/0167069 A1 | 6/2015 | Schutz et al. |
| 2015/0167077 A1 | 6/2015 | Fehr et al. |
| 2015/0197786 A1 | 7/2015 | Osborne et al. |
| 2015/0211050 A1 | 7/2015 | Iafrate et al. |
| 2015/0218631 A1 | 8/2015 | Chuu et al. |
| 2015/0232938 A1 | 8/2015 | Mhatre |
| 2015/0246103 A1 | 9/2015 | Hazout |
| 2015/0265995 A1 | 9/2015 | Head et al. |
| 2015/0299812 A1 | 10/2015 | Talasaz |
| 2015/0315657 A1 | 11/2015 | Rhodes et al. |
| 2015/0322507 A1 | 11/2015 | Zimmermann et al. |
| 2015/0329891 A1 | 11/2015 | Tan et al. |
| 2016/0024581 A1 | 1/2016 | Sarwal et al. |
| 2016/0032396 A1 | 2/2016 | Diehn et al. |
| 2016/0046986 A1 | 2/2016 | Eltoukhy et al. |
| 2016/0053320 A1 | 2/2016 | Schuh et al. |
| 2016/0115541 A1 | 4/2016 | Schutz et al. |
| 2016/0138106 A1 | 5/2016 | Schulze |
| 2016/0138112 A1 | 5/2016 | Janne et al. |
| 2016/0145682 A1 | 5/2016 | Woodward et al. |
| 2016/0186239 A1 | 6/2016 | Sinha |
| 2016/0186253 A1 | 6/2016 | Talasaz et al. |
| 2016/0201124 A1 | 7/2016 | Donahue et al. |
| 2016/0239602 A1 | 8/2016 | Shendure et al. |
| 2016/0244838 A1 | 8/2016 | Babiarz et al. |
| 2016/0257993 A1 | 9/2016 | Fu et al. |
| 2016/0289740 A1 | 10/2016 | Fu et al. |
| 2016/0289753 A1 | 10/2016 | Osborne et al. |
| 2016/0312276 A1 | 10/2016 | Fu et al. |
| 2016/0319345 A1 | 11/2016 | Gnerre et al. |
| 2016/0369333 A1* | 12/2016 | Babiarz ............... C12Q 1/6883 |
| 2017/0011166 A1 | 1/2017 | Rabinowitz et al. |
| 2017/0107576 A1 | 4/2017 | Babiarz et al. |
| 2017/0114411 A1* | 4/2017 | Mitchell ............... C12Q 1/6886 |
| 2017/0121716 A1 | 5/2017 | Rodi et al. |
| 2017/0137882 A1 | 5/2017 | Goossens et al. |
| 2017/0145475 A1 | 5/2017 | Hunsley et al. |
| 2017/0152561 A1 | 6/2017 | Hamamah et al. |
| 2017/0218458 A1 | 8/2017 | Fan et al. |
| 2017/0275689 A1 | 9/2017 | Maguire et al. |
| 2017/0283788 A1 | 10/2017 | Khoja et al. |
| 2017/0298427 A1 | 10/2017 | Buis et al. |
| 2017/0314014 A1 | 11/2017 | Green et al. |
| 2017/0342477 A1 | 11/2017 | Jensen et al. |
| 2017/0362649 A1 | 12/2017 | Lieberman-Aiden et al. |
| 2018/0023128 A1 | 1/2018 | Yanai et al. |
| 2018/0025109 A1 | 2/2018 | Rabinowitz et al. |
| 2018/0105807 A1 | 4/2018 | Lo et al. |
| 2018/0127744 A1 | 5/2018 | Hu et al. |
| 2018/0142296 A1 | 5/2018 | Mitchell et al. |
| 2018/0148777 A1 | 5/2018 | Kirkizlar et al. |
| 2018/0155775 A1 | 6/2018 | Zimmermann et al. |
| 2018/0155776 A1 | 6/2018 | Zimmermann et al. |
| 2018/0155779 A1 | 6/2018 | Zimmermann et al. |
| 2018/0155785 A1 | 6/2018 | Rabinowitz et al. |
| 2018/0155786 A1 | 6/2018 | Rabinowitz et al. |
| 2018/0155792 A1 | 6/2018 | Rabinowitz et al. |
| 2018/0171409 A1 | 6/2018 | Rabinowitz et al. |
| 2018/0171420 A1 | 6/2018 | Babiarz et al. |
| 2018/0173845 A1 | 6/2018 | Sigurjonsso et al. |
| 2018/0173846 A1 | 6/2018 | Sigurjonsso et al. |
| 2018/0187241 A1 | 7/2018 | Selvaraj et al. |
| 2018/0201995 A1 | 7/2018 | Rabinowitz et al. |
| 2018/0237841 A1 | 8/2018 | Stray et al. |
| 2018/0251553 A1 | 9/2018 | McGranahan et al. |
| 2018/0265917 A1 | 9/2018 | Barany et al. |
| 2018/0288982 A1 | 10/2018 | Sinha |
| 2018/0298439 A1 | 10/2018 | Ryan et al. |
| 2018/0300448 A1 | 10/2018 | Rabinowitz et al. |
| 2018/0303870 A1 | 10/2018 | Golobish et al. |
| 2018/0320171 A1 | 11/2018 | Withey |
| 2018/0320239 A1 | 11/2018 | Babiarz et al. |
| 2018/0371531 A1 | 12/2018 | Quake et al. |
| 2019/0010543 A1 | 1/2019 | Babiarz et al. |
| 2019/0106737 A1 | 4/2019 | Underhill |
| 2019/0106751 A1 | 4/2019 | Zimmermann et al. |
| 2019/0112661 A1 | 4/2019 | Khan et al. |
| 2019/0153521 A1 | 5/2019 | Mitchell et al. |
| 2019/0153525 A1 | 5/2019 | Mitchell et al. |
| 2019/0185913 A1 | 6/2019 | Zimmermann et al. |
| 2019/0185936 A1 | 6/2019 | Babiarz et al. |
| 2019/0194743 A1 | 6/2019 | Ryan et al. |
| 2019/0194758 A1 | 6/2019 | Babiarz et al. |
| 2019/0194759 A1 | 6/2019 | Babiarz et al. |
| 2019/0203290 A1 | 7/2019 | Rabinowitz et al. |
| 2019/0203294 A1 | 7/2019 | Babiarz et al. |
| 2019/0211376 A1 | 7/2019 | Quake et al. |
| 2019/0211385 A1 | 7/2019 | Sarwal et al. |
| 2019/0211391 A1 | 7/2019 | Rabinowitz et al. |
| 2019/0211392 A1 | 7/2019 | Rabinowitz et al. |
| 2019/0211393 A1 | 7/2019 | Rabinowitz et al. |
| 2019/0211399 A1 | 7/2019 | Rabinowitz et al. |
| 2019/0211402 A1 | 7/2019 | Babiarz et al. |
| 2019/0211406 A1 | 7/2019 | Babiarz et al. |
| 2019/0218625 A1* | 7/2019 | Lo ........................ C12Q 1/705 |
| 2019/0249241 A1 | 8/2019 | Rabinowitz et al. |
| 2019/0256894 A1 | 8/2019 | Zimmermann et al. |
| 2019/0256906 A1 | 8/2019 | Rabinowitz et al. |
| 2019/0256907 A1 | 8/2019 | Ryan et al. |
| 2019/0256908 A1 | 8/2019 | Rabinowitz et al. |
| 2019/0256909 A1 | 8/2019 | Rabinowitz et al. |
| 2019/0256912 A1 | 8/2019 | Rabinowitz et al. |
| 2019/0256916 A1 | 8/2019 | Babiarz et al. |
| 2019/0256917 A1 | 8/2019 | Babiarz et al. |
| 2019/0256919 A1 | 8/2019 | Babiarz et al. |
| 2019/0256924 A1 | 8/2019 | Vogelstein et al. |
| 2019/0256931 A1 | 8/2019 | Babiarz et al. |
| 2019/0264277 A1 | 8/2019 | Rabinowitz et al. |
| 2019/0264280 A1 | 8/2019 | Rabinowitz et al. |
| 2019/0264288 A1 | 8/2019 | Rabinowitz et al. |
| 2019/0271043 A1 | 9/2019 | Babiarz et al. |
| 2019/0276888 A1 | 9/2019 | Rabinowitz et al. |
| 2019/0284623 A1 | 9/2019 | Rabinowitz et al. |
| 2019/0300950 A1 | 10/2019 | Rabinowitz et al. |
| 2019/0309358 A1 | 10/2019 | Rabinowitz et al. |
| 2019/0309359 A1 | 10/2019 | Zimmermann et al. |
| 2019/0309365 A1 | 10/2019 | Babiarz et al. |
| 2019/0316177 A1 | 10/2019 | Zimmermann et al. |
| 2019/0316184 A1 | 10/2019 | Zimmermann et al. |
| 2019/0316200 A1 | 10/2019 | Rabinowitz et al. |
| 2019/0323076 A1 | 10/2019 | Rabinowitz et al. |
| 2019/0360033 A1 | 11/2019 | Stamm et al. |
| 2019/0360036 A1 | 11/2019 | Rabinowitz et al. |

(56) References Cited

U.S. PATENT DOCUMENTS

| | | |
|---|---|---|
| 2019/0367972 A1 | 12/2019 | Mitchell et al. |
| 2020/0024653 A1 | 1/2020 | Bethke |
| 2020/0032323 A1 | 1/2020 | Talasaz et al. |
| 2020/0032340 A1 | 1/2020 | Mitchell |
| 2020/0109449 A1 | 4/2020 | Stamm et al. |
| 2020/0121718 A1 | 4/2020 | Novik et al. |
| 2020/0123612 A1 | 4/2020 | Babiarz et al. |
| 2020/0126634 A1 | 4/2020 | Sigurjonsso et al. |
| 2020/0140950 A1 | 5/2020 | Babiarz et al. |
| 2020/0141925 A1 | 5/2020 | Liaw et al. |
| 2020/0149111 A1 | 5/2020 | Babiarz et al. |
| 2020/0157629 A1 | 5/2020 | Babiarz et al. |
| 2020/0165678 A1 | 5/2020 | Mitchell et al. |
| 2020/0172977 A1 | 6/2020 | Rabinowitz et al. |
| 2020/0181681 A1 | 6/2020 | Mitchell et al. |
| 2020/0181697 A1 | 6/2020 | Rabinowitz et al. |
| 2020/0190570 A1 | 6/2020 | Ryan et al. |
| 2020/0190573 A1 | 6/2020 | Rabinowitz et al. |
| 2020/0190591 A1 | 6/2020 | Rabinowitz et al. |
| 2020/0208196 A1 | 7/2020 | Zimmermann et al. |
| 2020/0208221 A1 | 7/2020 | Babiarz et al. |
| 2020/0224273 A1 | 7/2020 | Rabinowitz et al. |
| 2020/0232036 A1 | 7/2020 | Rabinowitz et al. |
| 2020/0232037 A1 | 7/2020 | Babiarz et al. |
| 2020/0248264 A1 | 8/2020 | Rabinowitz et al. |
| 2020/0248266 A1 | 8/2020 | Swanton et al. |
| 2020/0316498 A1 | 10/2020 | Mitchell |
| 2020/0318191 A1 | 10/2020 | Babiarz et al. |
| 2020/0347454 A1 | 11/2020 | Babiarz et al. |
| 2020/0350034 A1 | 11/2020 | Rabinowitz et al. |
| 2020/0362415 A1 | 11/2020 | Rabinowitz et al. |
| 2020/0370129 A1 | 11/2020 | Quinn et al. |
| 2020/0385809 A1 | 12/2020 | Ramani et al. |
| 2020/0407788 A1 | 12/2020 | Ryan et al. |
| 2020/0407798 A1 | 12/2020 | Babiarz et al. |
| 2021/0009990 A1 | 1/2021 | Stray et al. |
| 2021/0025005 A1 | 1/2021 | Babiarz et al. |
| 2021/0032692 A1 | 2/2021 | Mitchell et al. |
| 2021/0054459 A1 | 2/2021 | Rabinowitz et al. |
| 2021/0071246 A1 | 3/2021 | Zimmermann et al. |
| 2021/0139969 A1 | 5/2021 | Mitchell et al. |
| 2021/0139983 A1 | 5/2021 | Mitchell et al. |
| 2021/0139988 A1 | 5/2021 | Mitchell et al. |
| 2021/0155988 A1 | 5/2021 | Rabinowitz et al. |
| 2021/0189498 A1 | 6/2021 | Babiarz et al. |
| 2021/0198742 A1 | 7/2021 | Rabinowitz et al. |
| 2021/0198743 A1 | 7/2021 | Rabinowitz et al. |
| 2021/0222230 A1 | 7/2021 | Zimmermann et al. |
| 2021/0222240 A1 | 7/2021 | Moshkevich et al. |
| 2021/0257048 A1 | 8/2021 | Zimmermann et al. |
| 2021/0269879 A1 | 9/2021 | Mitchell et al. |
| 2021/0301320 A1 | 9/2021 | Mitchell et al. |
| 2021/0324463 A1 | 10/2021 | Rabinowitz et al. |
| 2021/0327538 A1 | 10/2021 | Egilsson et al. |
| 2021/0327542 A1 | 10/2021 | Ryan et al. |
| 2021/0348229 A1 | 11/2021 | Maguire et al. |
| 2021/0355536 A1 | 11/2021 | Rabinowitz et al. |
| 2022/0025455 A1 | 1/2022 | Zimmermann et al. |
| 2022/0025456 A1 | 1/2022 | Rabinowitz et al. |
| 2022/0033908 A1 | 2/2022 | Rabinowitz et al. |
| 2022/0033909 A1 | 2/2022 | Babiarz et al. |
| 2022/0042103 A1 | 2/2022 | Rabinowitz et al. |
| 2022/0056509 A1 | 2/2022 | Zimmermann |
| 2022/0056534 A1 | 2/2022 | Rivers |
| 2022/0073978 A1 | 3/2022 | Rabinowitz et al. |
| 2022/0073979 A1 | 3/2022 | Rabinowitz et al. |
| 2022/0098667 A1 | 3/2022 | Rabinowitz et al. |
| 2022/0139495 A1 | 5/2022 | Rabinowitz et al. |
| 2022/0145391 A1 | 5/2022 | Mitchell et al. |
| 2022/0154249 A1 | 5/2022 | Zimmermann et al. |
| 2022/0154290 A1 | 5/2022 | Babiarz et al. |
| 2022/0195526 A1 | 6/2022 | Rabinowitz et al. |
| 2022/0213561 A1 | 7/2022 | Babiarz et al. |
| 2022/0251654 A1 | 8/2022 | Hafez et al. |
| 2022/0267849 A1 | 8/2022 | Mitchell et al. |
| 2022/0282335 A1 | 9/2022 | Babiarz et al. |
| 2022/0307086 A1 | 9/2022 | Babiarz et al. |
| 2022/0340963 A1 | 10/2022 | North et al. |
| 2022/0356522 A1 | 11/2022 | Mitchell et al. |
| 2022/0356526 A1 | 11/2022 | Babiarz et al. |
| 2022/0356530 A1 | 11/2022 | Sharma |
| 2022/0403461 A1 | 12/2022 | Kirkizlar et al. |
| 2022/0411875 A1 | 12/2022 | Rabinowitz et al. |
| 2023/0053752 A1 | 2/2023 | Rabinowitz et al. |
| 2023/0054494 A1 | 2/2023 | Rabinowitz et al. |
| 2023/0060579 A1 | 3/2023 | Bethke et al. |
| 2023/0193387 A1 | 6/2023 | Rabinowitz |
| 2023/0203573 A1 | 6/2023 | Swenerton et al. |
| 2023/0212693 A1 | 7/2023 | Rabinowitz et al. |
| 2023/0242998 A1 | 8/2023 | Babiarz et al. |
| 2023/0360723 A1 | 11/2023 | Rabinowitz et al. |
| 2023/0368865 A1 | 11/2023 | Rabinowitz et al. |
| 2023/0383348 A1 | 11/2023 | Rabinowitz et al. |
| 2023/0420071 A1 | 12/2023 | Rabinowitz et al. |
| 2024/0002938 A1 | 1/2024 | Rabinowitz et al. |
| 2024/0038328 A1 | 2/2024 | Rabinowitz et al. |
| 2024/0060124 A1 | 2/2024 | Ryan et al. |
| 2024/0062846 A1 | 2/2024 | Rabinowitz |
| 2024/0068031 A1 | 2/2024 | Rabinowitz |
| 2024/0132957 A1 | 4/2024 | Mitchell et al. |
| 2024/0132960 A1 | 4/2024 | Demko et al. |
| 2024/0158855 A1 | 5/2024 | Babiarz et al. |
| 2024/0185957 A1 | 6/2024 | Rabinowitz et al. |

FOREIGN PATENT DOCUMENTS

| | | |
|---|---|---|
| CN | 1650032 A | 8/2005 |
| CN | 1674028 A | 9/2005 |
| CN | 101675169 A | 3/2010 |
| CN | 102892901 A | 1/2013 |
| CN | 104736722 A | 6/2015 |
| CN | 105229175 A | 1/2016 |
| CN | 107365769 A | 11/2017 |
| CN | 107849604 A | 3/2018 |
| CN | 109661476 A | 4/2019 |
| CN | 116287197 A | 6/2023 |
| EA | 201792389 A1 | 5/2018 |
| EP | 0270017 A2 | 6/1988 |
| EP | 1325963 A1 | 7/2003 |
| EP | 1524321 A1 | 4/2005 |
| EP | 1325963 B1 | 9/2006 |
| EP | 1524321 B1 | 7/2009 |
| EP | 2163622 A1 | 3/2010 |
| EP | 2128169 A1 | 12/2010 |
| EP | 2551356 A1 | 1/2013 |
| EP | 2653562 A1 | 10/2013 |
| EP | 2902500 A1 | 8/2015 |
| EP | 3026124 A1 | 6/2016 |
| EP | 2315849 B1 | 11/2017 |
| EP | 3285193 A1 | 2/2018 |
| EP | 2877594 B1 | 12/2019 |
| EP | 3187597 B1 | 6/2020 |
| EP | 3134541 B1 | 8/2020 |
| EP | 3760730 A1 | 1/2021 |
| EP | 3760731 A1 | 1/2021 |
| EP | 3760732 A1 | 1/2021 |
| EP | 3443119 B1 | 2/2022 |
| GB | 2488358 | 8/2012 |
| JP | 2965699 | 8/1999 |
| JP | 2002-530121 | 9/2002 |
| JP | 2002-300894 A | 10/2002 |
| JP | 2003/521252 | 7/2003 |
| JP | 2004502466 A | 1/2004 |
| JP | 2004121087 A | 4/2004 |
| JP | 2004533243 A | 11/2004 |
| JP | 2005514956 A | 5/2005 |
| JP | 2005160470 A | 6/2005 |
| JP | 2006-254912 A | 9/2006 |
| JP | 2008-263974 A | 11/2008 |
| JP | 2008/271980 A | 11/2008 |
| JP | 2010-509922 A | 4/2010 |
| JP | 2011/508662 A | 3/2011 |
| JP | 2011/516069 A | 5/2011 |
| JP | 2012-085556 A | 5/2012 |

(56) References Cited

FOREIGN PATENT DOCUMENTS

| | | | |
|---|---|---|---|
| JP | 2013509883 A | 3/2013 |
| JP | 2014118334 A1 | 8/2014 |
| JP | 2015-535681 | 12/2015 |
| JP | 2016502849 A | 2/2016 |
| RU | 2290078 C1 | 12/2006 |
| WO | 95/01796 | 1/1995 |
| WO | 9623067 A1 | 8/1996 |
| WO | 1996036736 A2 | 11/1996 |
| WO | 98/39474 | 9/1998 |
| WO | 98/44151 | 10/1998 |
| WO | 9937773 A1 | 7/1999 |
| WO | 00/18957 | 4/2000 |
| WO | 2001007640 A2 | 2/2001 |
| WO | 0134844 A1 | 5/2001 |
| WO | 01/57269 A2 | 8/2001 |
| WO | 2001/079851 A1 | 10/2001 |
| WO | 200190419 A2 | 11/2001 |
| WO | 2002004672 A2 | 1/2002 |
| WO | 02/44411 A1 | 6/2002 |
| WO | 2002055985 A2 | 7/2002 |
| WO | 02/070751 A1 | 9/2002 |
| WO | 2002076377 | 10/2002 |
| WO | 02/090505 A2 | 11/2002 |
| WO | 03/000919 A2 | 1/2003 |
| WO | 03/018757 A3 | 3/2003 |
| WO | 03/020974 A3 | 3/2003 |
| WO | 2003031646 A1 | 4/2003 |
| WO | 2003/050532 A1 | 6/2003 |
| WO | 2003062441 A1 | 7/2003 |
| WO | 2003/102595 A1 | 12/2003 |
| WO | 2003/106623 A2 | 12/2003 |
| WO | 2004/051218 A2 | 6/2004 |
| WO | 2004069849 A2 | 8/2004 |
| WO | 2004070005 A2 | 8/2004 |
| WO | 2004070007 A2 | 8/2004 |
| WO | 2004078999 A1 | 9/2004 |
| WO | 2004081183 | 9/2004 |
| WO | 2004087863 A2 | 10/2004 |
| WO | 2005003375 A2 | 1/2005 |
| WO | 2005021793 A1 | 3/2005 |
| WO | 2005023091 A2 | 3/2005 |
| WO | 2005030999 A1 | 4/2005 |
| WO | 2005035725 A2 | 4/2005 |
| WO | 2005/039389 A3 | 5/2005 |
| WO | 2005100401 A2 | 10/2005 |
| WO | 2005123779 A2 | 12/2005 |
| WO | 2007145612 A1 | 6/2006 |
| WO | 2006110855 A2 | 10/2006 |
| WO | 2006/128192 A2 | 11/2006 |
| WO | 2007/011903 A3 | 1/2007 |
| WO | 2007/052006 A1 | 5/2007 |
| WO | 2007057647 A1 | 5/2007 |
| WO | 2007062164 A3 | 5/2007 |
| WO | 2007/073171 A2 | 6/2007 |
| WO | 2007/070280 A2 | 6/2007 |
| WO | 2007/070482 A2 | 6/2007 |
| WO | 2007075836 A2 | 7/2007 |
| WO | 2007/092473 A2 | 8/2007 |
| WO | 2007086935 A2 | 8/2007 |
| WO | 2007/117256 A1 | 10/2007 |
| WO | 2007117039 A1 | 10/2007 |
| WO | 2007/132167 A2 | 11/2007 |
| WO | 2007/147073 A2 | 12/2007 |
| WO | 2007/147076 A2 | 12/2007 |
| WO | 2007140417 A2 | 12/2007 |
| WO | 2007147074 A2 | 12/2007 |
| WO | 2007147079 A2 | 12/2007 |
| WO | 2008024473 A2 | 2/2008 |
| WO | 2008048931 A1 | 4/2008 |
| WO | 2008/061213 A2 | 5/2008 |
| WO | 2008051928 A2 | 5/2008 |
| WO | 2008056937 A1 | 5/2008 |
| WO | 2008059578 A1 | 5/2008 |
| WO | 2008079374 A2 | 7/2008 |
| WO | 2008081451 A2 | 7/2008 |
| WO | 2008084405 A2 | 7/2008 |
| WO | 2008115427 A2 | 9/2008 |
| WO | 2008115497 A2 | 9/2008 |
| WO | 2008118988 A1 | 10/2008 |
| WO | 2008135837 A2 | 11/2008 |
| WO | 2008157264 A2 | 12/2008 |
| WO | 2009009769 A2 | 1/2009 |
| WO | 2009013492 A1 | 1/2009 |
| WO | 2009013496 A1 | 1/2009 |
| WO | 2009019215 A1 | 2/2009 |
| WO | 2009019455 A2 | 2/2009 |
| WO | 2009/032779 A2 | 3/2009 |
| WO | 2009/036525 A2 | 3/2009 |
| WO | 2009030100 A1 | 3/2009 |
| WO | 2009032781 A2 | 3/2009 |
| WO | 2009033178 A1 | 3/2009 |
| WO | 2009049889 A1 | 4/2009 |
| WO | 2009017784 A2 | 5/2009 |
| WO | 2009064897 A2 | 5/2009 |
| WO | 2009091934 A2 | 7/2009 |
| WO | 2009092035 A2 | 7/2009 |
| WO | 2009/105531 A1 | 8/2009 |
| WO | 2009099602 A1 | 8/2009 |
| WO | 2009100029 A1 | 8/2009 |
| WO | 2009117122 A2 | 9/2009 |
| WO | 2009120808 A2 | 10/2009 |
| WO | 2009145828 A2 | 12/2009 |
| WO | 2009146335 A1 | 12/2009 |
| WO | 2010014920 A1 | 2/2010 |
| WO | 2010017214 A1 | 2/2010 |
| WO | 2010/033639 A2 | 3/2010 |
| WO | 2010/033652 A1 | 3/2010 |
| WO | 2010033578 A2 | 3/2010 |
| WO | 2010042831 A2 | 4/2010 |
| WO | 2010/045617 A2 | 4/2010 |
| WO | 2010075459 | 7/2010 |
| WO | 2010/088288 A2 | 8/2010 |
| WO | 2010115016 A2 | 10/2010 |
| WO | 2010115154 A1 | 10/2010 |
| WO | 2010118016 A2 | 10/2010 |
| WO | 2010/127186 A1 | 11/2010 |
| WO | 2011015944 A2 | 2/2011 |
| WO | 2011/023078 A1 | 3/2011 |
| WO | 2011/032078 A1 | 3/2011 |
| WO | 2011041485 A1 | 4/2011 |
| WO | 2011/051283 A1 | 5/2011 |
| WO | 2011057061 A1 | 5/2011 |
| WO | 2011057094 | 5/2011 |
| WO | 2011/090556 A1 | 7/2011 |
| WO | 2011087760 | 7/2011 |
| WO | 2011094646 A1 | 8/2011 |
| WO | 2011102998 A2 | 8/2011 |
| WO | 2011/118603 | 9/2011 |
| WO | 2011109440 A1 | 9/2011 |
| WO | 2011118603 A1 | 9/2011 |
| WO | 2011/142836 A2 | 11/2011 |
| WO | 2011140433 A2 | 11/2011 |
| WO | 2011146632 A1 | 11/2011 |
| WO | 2012/019200 A2 | 2/2012 |
| WO | 2012/028746 A1 | 3/2012 |
| WO | 2012042374 A2 | 4/2012 |
| WO | 2012/058488 A1 | 5/2012 |
| WO | 2012-083189 A2 | 6/2012 |
| WO | 201283250 | 6/2012 |
| WO | 2012088456 A2 | 6/2012 |
| WO | 20120071621 | 6/2012 |
| WO | 2012092426 | 7/2012 |
| WO | 2012108920 A1 | 8/2012 |
| WO | 2012122374 A2 | 9/2012 |
| WO | 2012/142531 A2 | 10/2012 |
| WO | 2007/149791 A2 | 12/2012 |
| WO | 2013030577 | 3/2013 |
| WO | 2013/045432 A1 | 4/2013 |
| WO | 2013/049892 A1 | 4/2013 |
| WO | 2013052557 A2 | 4/2013 |
| WO | 2013/078470 A2 | 5/2013 |
| WO | 2013/086464 A1 | 6/2013 |
| WO | 2013/123220 A1 | 8/2013 |
| WO | 2013/138510 A1 | 9/2013 |

(56) References Cited

FOREIGN PATENT DOCUMENTS

| | | |
|---|---|---|
| WO | 2013/138510 A9 | 9/2013 |
| WO | 20130130848 | 9/2013 |
| WO | 2013159035 A2 | 10/2013 |
| WO | 2013/169339 A1 | 11/2013 |
| WO | 2013/177220 A1 | 11/2013 |
| WO | 2013/181651 A1 | 12/2013 |
| WO | 2013190441 A2 | 12/2013 |
| WO | 2014/004726 A1 | 1/2014 |
| WO | 2014/014497 A1 | 1/2014 |
| WO | 20140018080 | 1/2014 |
| WO | 2014026277 A1 | 2/2014 |
| WO | 2014/035986 A1 | 3/2014 |
| WO | 2014039556 A1 | 3/2014 |
| WO | 2014099919 A2 | 6/2014 |
| WO | 2014/122288 A1 | 8/2014 |
| WO | 2014/1424290 A1 | 8/2014 |
| WO | 2014/145078 A1 | 9/2014 |
| WO | 2014/145232 A2 | 9/2014 |
| WO | 2014/149134 A2 | 9/2014 |
| WO | 2014/150300 A2 | 9/2014 |
| WO | 2014/151117 A1 | 9/2014 |
| WO | 2014143989 A1 | 9/2014 |
| WO | 2014194113 A2 | 12/2014 |
| WO | 2015/006668 A1 | 1/2015 |
| WO | 2015035177 A1 | 3/2015 |
| WO | 2015134552 A1 | 3/2015 |
| WO | 2015/048535 A1 | 4/2015 |
| WO | 2015/070086 A1 | 5/2015 |
| WO | 2015069933 A1 | 5/2015 |
| WO | 2015/100427 A1 | 7/2015 |
| WO | 2015138997 A1 | 9/2015 |
| WO | 2015/148494 A1 | 10/2015 |
| WO | 2015/164432 A1 | 10/2015 |
| WO | 2015169947 A1 | 11/2015 |
| WO | 2015178978 A2 | 11/2015 |
| WO | 2016/001411 A1 | 1/2016 |
| WO | 2016001411 A1 | 1/2016 |
| WO | 2016009224 A1 | 1/2016 |
| WO | 2016028316 A1 | 2/2016 |
| WO | 2016/065295 A1 | 4/2016 |
| WO | 2016063122 A1 | 4/2016 |
| WO | 2016/077313 A1 | 5/2016 |
| WO | 2016123698 A1 | 8/2016 |
| WO | 2016/138080 A1 | 9/2016 |
| WO | 2016/183106 A1 | 11/2016 |
| WO | 2016176662 A1 | 11/2016 |
| WO | 2016/193490 A1 | 12/2016 |
| WO | 2016192956 A1 | 12/2016 |
| WO | 2017011329 A1 | 1/2017 |
| WO | 2017-045654 A1 | 3/2017 |
| WO | 2017/058784 A1 | 4/2017 |
| WO | 2017091865 A1 | 6/2017 |
| WO | 2017/176852 A1 | 10/2017 |
| WO | 2017/181146 A1 | 10/2017 |
| WO | 2017/181202 A2 | 10/2017 |
| WO | 2017190106 A1 | 11/2017 |
| WO | 2017205540 A1 | 11/2017 |
| WO | 2018/009723 A1 | 1/2018 |
| WO | 2018/083467 A1 | 5/2018 |
| WO | 2018085597 A1 | 5/2018 |
| WO | 2018085603 A1 | 5/2018 |
| WO | 2018/106798 A1 | 6/2018 |
| WO | 2018119422 A1 | 6/2018 |
| WO | 2018/136562 A2 | 7/2018 |
| WO | 2018/156418 A1 | 8/2018 |
| WO | 2018237078 A1 | 12/2018 |
| WO | 2018237081 A1 | 12/2018 |
| WO | 2019006561 A1 | 1/2019 |
| WO | 2019008408 A1 | 1/2019 |
| WO | 2019/046817 A1 | 3/2019 |
| WO | 2019053243 A1 | 3/2019 |
| WO | 2019109053 A1 | 6/2019 |
| WO | 2019118926 A1 | 6/2019 |
| WO | 2019/140298 A1 | 7/2019 |
| WO | 2019/161244 A1 | 8/2019 |
| WO | 2019/200228 A1 | 10/2019 |
| WO | 2019/241349 A1 | 12/2019 |
| WO | 2020/010255 A1 | 1/2020 |
| WO | 2020/018522 A1 | 1/2020 |
| WO | 2020/041449 A1 | 2/2020 |
| WO | 2020/076957 A1 | 4/2020 |
| WO | 2020/106987 A1 | 5/2020 |
| WO | 2020104670 A1 | 5/2020 |
| WO | 2020/131699 A2 | 6/2020 |
| WO | 2020131955 A1 | 6/2020 |
| WO | 2020/214547 A1 | 10/2020 |
| WO | 2020206290 A1 | 10/2020 |
| WO | 2020/247263 A1 | 12/2020 |
| WO | 2021/055968 A1 | 3/2021 |
| WO | 2007100911 A2 | 9/2021 |
| WO | 2021/243045 A1 | 12/2021 |
| WO | 2022/015676 A1 | 1/2022 |
| WO | 2022182878 | 9/2022 |
| WO | 2022197864 | 9/2022 |
| WO | 2023014597 A1 | 2/2023 |
| WO | 2023034090 A1 | 3/2023 |
| WO | 2023133131 A1 | 7/2023 |
| WO | 2023/244735 A2 | 12/2023 |
| WO | 2024/076485 A1 | 4/2024 |
| WO | WO2024076469 A1 | 4/2024 |
| WO | WO2024076484 A1 | 4/2024 |

OTHER PUBLICATIONS

Ryan et al., Validation of an Enhanced Version of a Single-Nucleotide Polymorphism-Based Noninvasive Prenatal Test for Detection of Fetal Aneuploidies, Fetal diagnosis and therapy, 40(3):219-223 (2016).*

Zimmerman et al, Noninvasive prenatal aneuploidy testing of chromosomes 13, 18, 21, X, and Y, using targeted sequencing of polymorphic loci, Prenat Diagn. Dec. 2012;32(13):1233-41. doi: 10.1002/pd.3993. Epub Oct. 30, 2012.*

Shen et al (MPprimer: a program for reliable multiplex PCR primer design, BMC Bioinformatics vol. 11, Article No. 143 (2010), Mar. 18, 2010).*

Rachlin et al (Computational tradeoffs in multiplex PCR assay design for SNP genotyping, BMC Genomics, 2005; 6: 102. Published online Jul. 25, 2005. doi: 10.1186/1471-2164-6-102).*

Stiller et al (Direct multiplex sequencing (DMPS)—a novel method for targeted high-throughput sequencing of ancient and highly degraded NA, Genome Res. Oct. 2009; 19(10): 1843-1848, Oct. 2009).*

AmpliSeq™ (see e.g. How Ion AmpliSeq Targeted Sequencing Technology Works, available at https://www.thermofisher.com/us/en/home/life-science/sequencing/next-generation-sequencing/ion-torrent-next-generation-sequencing-workflow/ion-torrent-next-generation-sequencing-select-targets/ampliseq-target-selection/how-ampl.*

Xie et al (Designing highly multiplex PCR primer sets with Simulated Annealing Design using Dimer Likelihood Estimation (SADDLE), Nat Commun. Apr. 11, 2022;13(1):1881. doi. 10.1038/s41467-022-29500-4).*

Mamanova et al, Target-enrichment strategies for next-generation sequencing, Nat Methods. Feb. 2010;7(2):111-8. doi. 10.1038/nmeth.1419.*

"European Application No. 014198110, European Search Report dated Apr. 28, 2015, 3 pages.".

PRNewswire (Research Suggests Daily Consumption of Orange Juice Can Reduce Blood Pressure and May Provide Beneficial Effects to Blood Vessel Function: New Study Identified Health Benefits in Orange Juice, Dec. 8, 2010), 3 pages.

"Abstracts for CNAPS III Circulating Nucleic Acids in Plasma and Serum and Serum Proteomics", Clinical Chemistry, vol. 49, No. 11, 2003, 33 pages.

"Abstracts for CNAPS IV Circulating Nucleic Acids in Plasma/Serum", Fourth International Conference on Circulating Nucleic Acids in Plasma/Serum (CNAPS-IV), 2005, 40 pages.

"How Many Carbs in a Potato?, [Online]", New Health Guide, Nov. 1, 2014, 3 pages.

(56) References Cited

OTHER PUBLICATIONS

"Random variable", The Penguin Dictionary of Mathematics, 2008, 1 page.
Abaan, O. D. et al., "The Exomes of the NCI-60 Panel: A Genomic Resource for Cancer Biology and Systems Pharmacology", Cancer Res., vol. 73, No. 14, Jul. 15, 2013, 4372-4382.
Abbosh, C. et al., "Phylogenetic ctDNA analysis depicts early-stage lung cancer evolution", Nature, vol. 545, May 25, 2017, 446-451.
Abidi, S. et al., "Leveraging XML-based electronic medical records to extract experiential clinical knowledge: An automated approach to generate cases for medical case-based reasoning systems", International Journal of Medical Informatics, 68(1-3), 2002, 187-203.
Academic Press, , "Fixed Medium", 1996, 1 pg.
Agarwal, Ashwin, et al., "Commercial Landscape of Noninvasive Prenatal Testing in the United States", Prenatal Diagnosis,33, 2013, 521-531.
Agbor-Enoh, S. et al., "Donor-derived cell-free DNA predicts allograft failure and mortality after lung transplantation", EBioMedicine, vol. 40, 2019, 541-553.
Alaeddini, R. et al., "Forensic implications of genetic analyses from degraded DNA—A review", Forensic Science International: Genetics, vol. 4, 2010, 148-157.
Alberts, B. et al., "Chapter 20: Germ Cells and Fertilization", Molecular Biology of the Cell, Fourth Edition, 2002, 1127-1156.
Alberts, B. et al., "Chapter 4: DNA and Chromosomes", Molecular Biology of the Cell, Fourth Edition, 2002, 191-234.
Alkan, Can et al., "Personalized Copy No. and Segmental Duplication Maps Using Next-Generation Sequencing", Nature Genetics, 41, 10, 2009, 1061-1068.
Allaire, F R. , "Mate selection by selection index theory", Theoretical Applied Genetics, 57(6), 1980, 267-272.
Allan, J. et al., "Micrococcal Nuclease Does Not Substantially Bias Nucleosome Mapping", Journal of Molecular Biology, vol. 417, Jan. 30, 2012, 152-164.
Allawi, Hatim T. et al., "Thermodynamics of internal C•T Mismatches in DNA", Nucleic Acids Research, 26 (11), 1998, 2694-2701.
Ambardar, S. et al., "High Throughput Sequencing: An Overview of Sequencing Chemistry", Indian J. Microbiol., vol. 56, No. 4, 2016, 394-404.
Amicucci, P. et al., "Prenatal Diagnosis of Myotonic Dystrophy Using Fetal DNA Obtained from Maternal Plasma", Clinical Chemistry, vol. 46, No. 2, 2000, 301-302.
Andras, S. C. et al., "Strategies for Signal Amplification in Nucleic Acid Detection", Molecular Biotechnology, vol. 19, 2001, 29-44.
Anker, P. et al., "Circulating DNA in Plasma or Serum", Medicina, vol. 60, 2000, 699-702.
Anker, P. et al., "Detection of circulating tumour DNA in the blood (plasma/serum) of cancer patients", Cancer and Metastasis Reviews, vol. 18, 1999, 65-73.
Anker, P. et al., "The Second International Symposium on Circulating Nucleic Acids in Plasma and Serum (CNAPS-2) held in conjunction with the 6th Annual Scientific Symposium of the Hong Kong Cancer Institute", Clinical Chemistry, vol. 47, No. 2, 2001, 361-370.
Antonarakis, S. E. et al., "Chromosome 21 and Down Syndrome: From Genomics to Pathophysiology", Nature Reviews Genetics, vol. 5, Oct. 2004, 725-738.
Aoki, Yasuhiro , "Statistical and Probabilistic Bases of Forensic DNA Testing", The Journal of the Iwate Medical Association, 2002, vol. 54, p. 81-94.
Ashoor, G. et al., "Fetal fraction in maternal plasma cell-free DNA at 11-13 weeks' gestation: relation to maternal and fetal characteristics", Ultrasound in Obstetrics and Gynecology, vol. 41, 2013, 26-32.
Ashoor, Ghalia et al., "Chromosome-Selective Sequencing of Maternal Plasma Cell-Free DNA for First-Trimester Detection of Trisomy 21 and Trisomy 18", American Journal of Obstetrics & Gynecology, 206, 2012, 322.e1-322.e5.
Ashoor, Ghalia et al., "Fetal Fraction in Maternal Plasma Cell-Free DNA at 11-13 Weeks' Gestation: Effect of Maternal and Fetal Factors", Fetal Diagnosis Therapy, 2012, 1-7.
Auld, D. S. , "Use of Chelating Agents to Inhibit Enzymes", Methods in Enzymology, vol. 158, 1988, 110-114.
Avgidou, K. et al., "Prospective first-trimester screening for trisomy 21 in 30,564 pregnancies", American Journal of Obstetrics and Gynecology, vol. 192, 2005, 1761-1767.
Bada, Michael A. et al., "Computational Modeling of Structural Experimental Data", Methods in Enzymology,317, 2000, 470-491.
Bai, H. et al., "Detection and Clinical Significance of Intratumoral EGFR Mutational Heterogeneity in Chinese Patients with Advanced Non-Small Cell Lung Cancer", PLOS One, vol. 8, No. 2, Feb. 2013, 7 pages.
Bale, J. R. et al., "Reducing Birth Defects: Meeting the Challenge in the Developing World", Institute of Medicine of the National Academies, 2003, 270 pgs.
Ballif, B. C. et al., "Detection of Low-Level Mosaicism by Array CGH in Routine Diagnostic Specimens", American Journal of Medical Genetics Part A, vol. 140A, 2006, 2757-2767.
Banfi, G. et al., "The role of ethylenediamine tetraacetic acid (EDTA) as in vitro anticoagulant for diagnostic purposes", Clin. Chem., vol. 45, No. 5, 2007, 565-576.
Barra, G. B. et al., "EDTA-mediated inhibition of DNases protects circulating cell-free DNA from ex vivo degradation in blood samples", Clinical Biochemistry, vol. 48, 2015, 976-981.
Barski, A. et al.,"High-Resolution Profiling of Histone Methylations in the Human Genome", Cell, vol. 129, May 18, 2007, 823-837.
Bashashati, A. et al., "Distinct evolutionary trajectories of primary high-grade serous ovarian cancers revealed through spatial mutational profiling", Journal of Pathology, vol. 231, 2013, 21-34.
Bauer, M. et al., "A prospective analysis of cell-free fetal DNA concentration in maternal plasma as an indicator for adverse pregnancy outcome", Prenatal Diagnosis, vol. 26, 2006, 831-836.
Baxter, L. L. et al., "Discovery and genetic localization of Down syndrome cerebellar phenotypes using the Ts65Dn mouse", Human Molecular Genetics, vol. 9, No. 2, Jan. 2000, 195-202.
Beaumont, Mark A et al., "The Bayesian Revolution in Genetics", Nature Reviews Genetics, 5, 2004, 251-261.
Beck, J. et al., "Digital Droplet PCR for Rapid Quantification of Donor DNA in the Circulation of Transplant Recipients as a Potential Universal Biomarker of Graft Injury", Clinical Chemistry, vol. 59, No. 12, 2013, 1732-1741.
Beck, J. et al., "Profile of the Circulating DNA in Apparently Healthy Individuals", Clinical Chemistry, vol. 55, No. 4, 2009, 730-738.
Beer, Alan E. et al., "The Biological Basis of Passage of Fetal Cellular Material into the Maternal Circulation", Annals New York Academy of Sciences, 731, 1994, 21-35.
Beerenwinkel, et al., "Methods for Optimizing Antiviral Combination Therapies", Bioinformatics, 19(1), 2003, i16-i25.
Beerenwinkel, N. et al., "Geno2pheno: estimating phenotypic drug resistance from HIV-1 genotypes", Nucleic Acids Research, 31(13), 2003, 3850-3855.
Benn, P. et al., "Non-lnvasive Prenatal Testing for Aneuploidy: Current Status and Future Prospects", Ultrasound Obstet Gynecol, 42, 2013, 15-33.
Benn, P et al., "Non-Invasive prenatal Diagnosis for Down Syndrome: the Paradigm Will Shift, but Slowly", Ultrasound Obstet. Gynecol., 39, 2012, 127-130.
Bennett, S. T. et al., "Toward the $1000 human genome", Pharmacogenomics, vol. 6, No. 4, 2005, 373-382.
Bentley, David R et al., "Accurate Whole Human Genome Sequencing Using Reversible Terminator Chemistry", Nature, 456, 6, 2008, 53-59.
Bergen, A. W. et al., "Effects of DNA mass on multiple displacement whole genome amplification and genotyping performance", BMC Biotechnology, vol. 5, No. 24, Sep. 16, 2005, 11 pgs.
Bermudez, M. et al., "Single-cell sequencing and mini-sequencing for preimplantation genetic diagnosis", Prenatal Diagnosis, 23, 2003, 669-677.

(56) References Cited

OTHER PUBLICATIONS

Beroud, C. et al., "Prenatal diagnosis of spinal muscular atrophy by genetic analysis of circulating fetal cells", The Lancet, vol. 361, Mar. 22, 2003, 1013-1014.
Bevinetto, Gina, Bevinetto (5 Foods All Pregnant Women Need, American Baby, available at http://www.parents.com/pregnancy/mybody/nutrition/5greatpregnancyfoods/, Apr. 15, 2008), 8 pgs.
Bianchi, D W. et al., "Fetal gender and aneuploidy detection using fetal cells maternal blood: analysis of NIFTY I data", Prenat Diagn 2002; 22, 2002, 609-615.
Bianchi, D W. et al., "Insights Into Fetal and Neonatal Development Through Analysis of Cell-Free RNA in Body Fluids", Early Human Development, vol. 86, No. 11, Nov. 2010, 747-752.
Bianchi, D. W., "Circulating Fetal DNA: Its Origin and Diagnostic Potential—A Review", Placenta, vol. 25, Supplemental A, May 2004, S93-S101.
Bianchi, D. W. et al., "Genome-Wide Fetal Aneuploidy Detection by Maternal Plasma DNA Sequencing", Obstetrics & Gynecology, vol. 119, No. 5, May 2012, 890-901.
Bianchi, D. W., "Review: Fetal Cells in the Maternal Circulation: Feasibility for Prenatal Diagnosis", British Journal of Haematology, vol. 105, 1999, 574-583.
Binladen, J. et al., "The Use of Coded PCR Primers Enables High-Throughput Sequencing of Multiple Homolog Amplification Products by 454 Parallel Sequencing", PLOS One, Issue 2, Feb. 2007, 9 pages.
Birch, Lyndsey et al., "Accurate and Robust Quantification of Circulating Fetal and Total DNA in Maternal Plasma from 5 to 41 Weeks of Gestation", Clinical Chemistry, 51(2), 2005, 312-320.
Birkenkamp-Demtroder, K. et al., "Abstract 3653: Sequencing of plasma cfDNA from patients with locally advanced bladder cancer for surveillance and therapeutic efficacy monitoring", Cancer Research, vol. 78, No. 13 Supplement, Jul. 2019, 1 page.
Bischoff, F. Z. et al., "Cell-free fetal DNA in maternal blood: kinetics, source and structure", Human Reproduction Update, vol. 11, No. 1, 2005, 59-67.
Bischoff, F. Z. et al., "Intact fetal cells in maternal plasma: are they really there?", Lancet, vol. 361, 2003, 139-140.
Bisignano, et al., "PGD and Aneuploidy Screening for 24 Chromosomes: Advantages and Disadvantages of Competing Platforms", Reproductive BioMedicine Online, 23, 2011, 677-685.
Blomquist, T M. et al., "Targeted RNA-Sequencing with Competitive Multiplex-PCR Amplicon Libraries", Plos One, vol. 8, Issue 11, Nov. 2013, 14 pages.
Blow, N., "The personal side of genomics", Nature, vol. 449, Oct. 4, 2007, 627-630.
Board, R.E. et al., "Detection of BRAF mutations in the tumour and serum of patients enrolled in the AZD6244 (ARRY-142886) advanced melanoma phase II study", British Journal of Cancer, vol. 101, 2009, 1724-1730.
Bodenreider, O., "The Unified Medical Language System (UMLS): Integrating Biomedical Terminology", Nucleic Acids Research, 32, (Database issue), 2004, D267-D270.
Boudsocq, F. et al., "Sulfolobus solfataricus P2 DNA polymerase IV (Dpo4): an archael DinB-like DNA polymerase with lesion-bypass properties akin to eukaryotic poln", Nucleic Acids Research, vol. 29, No. 22, 2001, 4607-4616.
Bouma, B. N. et al., "Human Blood Coagulation Factor", The Journal of Biological Chemistry, vol. 252, No. 18, 1977, 6432-6437.
Breithaupt, Holger, "The Future of Medicine", EMBO Reports, 21(61), 2001, 465-467.
Brinza, D. et al., "2SNP: scalable phasing based on 2-SNP haplotypes", Bioinformatics, vol. 22, No. 3, 2006, 371-373.
Broude, N E. et al., "High-Level Multiplex DNA Amplification", Antisense & Nucleic Acid Drug Development, vol. 11, 2001, 327-332.
Broude, N. E. et al., "High Multiplexity PCR Based on PCR Suppression", DNA Amplification Current Technologies and Applications, 2004, 61-76.
Broude, N. E. et al., "Multiplex Allele-specific Target Amplification based on PCR Suppression", PNAS, vol. 98, No. 1, Jan. 2, 2001, 206-211.
Brownie, Jannine et al., "The Elimination of Primer-Dimer Accumulation in PCR", Nucleic Acids Research, 25(16), 1997, 3235-3241.
Browning, S. R. et al., "Rapid and Accurate Haplotype Phasing and Missing-Data Inference for Whole-Genome Association Studies By Use of Localized Haplotype Clustering", The American Journal of Human Genetics, vol. 81, Nov. 2007, 1084-1097.
Bryant, A. P., "Terminology of Sugars", Ind. Eng. Chem., vol. 26, No. 2, 1933, 231.
Burkey, B. F. et al., "Hepatic apolipoprotein J is secreted as a lipoprotein", Journal of Lipid Research, vol. 33, 1992, 1517-1526.
Burkova, E. E. et al., "Extremely Stable Soluble High Molecular Mass Multi-Protein Complex with DNase Activity in Human Placental Tissue", PLOS One, vol. 9, No. 11: e011234, Nov. 26, 2014, 26 pages.
Burnham, P. et al., "Myriad Applications of Circulating Cell-Free DNA in Precision Organ Transplant Monitoring", Annals of the American Thoracic Society, vol. 14, Supplement 3, Sep. 2017, S237-S241.
Butler, J. et al., "The Development of Reduced Size STR Amplicons as Tools for Analysis of Degraded DNA*", Journal of Forensic Sciences, vol. 48, No. 5, 2003, 1054-1064.
Butt, A. N. et al., "Overview of Circulating Nucleic Acids in Plasma/Serum: Update on Potential Prognostic and Diagnostic Value in Diseases Excluding Fetal Medicine and Oncology", Ann. N.Y. Acad. Sci., vol. 1137, 2008, 236-242.
Cairns, Paul et al., "Homozygous Deletions of 9p21 in Primary Human Bladder Tumors Detected by Comparative Multiplex Polymerase Chain Reaction", Cancer Research, 54, 1994, 1422-1424.
Caliendo, Angela, "Multiplex PCR and Emerging Technologies for the Detection of Respiratory Pathogens", Clinical Infectious Diseases, 52(4), 2011, S326-S330.
Calin, G. A. et al., "A MicroRNA Signature Associated with Prognosis and Progression in Chronic Lymphocytic Leukemia", N Engl J Med, vol. 353, 2005, 1793-1801.
Campbell, P. J. et al., "Subclonal phylogenetic structures in cancer revealed by ultra-deep sequencing", PNAS, vol. 105, No. 35, Sep. 2, 2008, 13081-13086.
Canick, J. A. et al., "The impact of maternal plasma DNA fetal fraction on next generation sequencing tests for common fetal aneuploidies", Prenatal Diagnosis, vol. 33, 2013, 667-674.
Cansar, , "Hs-578-T—Copy Number Variation—Cell Line Synopsis", ICR Cancer Research UK, Retrieved on Mar. 26, 2018 from https://cansar.icr.ac.uk/cansar/cell-lines/Hs-578-T/copy_number_variation/chromosome_8/, Mar. 26, 2018, 50 pgs.
Cao, Y. et al., "Clinical Evaluation of Branched DNA Signal Amplification for Quantifying HIV Type 1 in Human Plasma", AIDS Research and Human Retroviruses, vol. 11, No. 3, 1995, 353-361.
Carnevale, Alessandra et al., "Attitudes of Mexican Geneticists Towards Prenatal Diagnosis and Selective Abortion", American Journal of Medical Genetics, 75, 1998, 426-431.
Carvalho, B. et al., "Exploration, normalization, and genotype calls of high-density oligonucleotide SNP array data", Biostatistics, vol. 8, No. 2, 2007, 485-499.
Casbon, J. A. et al., "A method for counting PCR template molecules with application to next-generation sequencing", Nucleic Acids Research, vol. 39, No. 12, Apr. 13, 2011, 1-8.
Chakraborty, R. et al., "Paternity Exclusion by DNA Markers: Effects of Paternal Mutations", Journal of Forensic Sciences, vol. 41, No. 4, Jul. 1996, 671-677.
Chan, K.C. et al., "Size Distributions of Maternal and Fetal DNA in Maternal Plasma", Clinical Chemistry, vol. 50, No. 1, 2004, 88-92.
Chang, H.W. et al., "Assessment of Plasma DNA Levels, Allelic Imbalance, and CA 125 as Diagnostic Tests for Cancer", Journal of the National Cancer Institute, vol. 94, No. 22, Nov. 20, 2002, 1697-1703.
Chen, E. et al., "Noninvasive Prenatal Diagnosis of Fetal Trisomy 18 and Trisomy 13 by Maternal Plasma DNA Sequencing", PLoS ONE, 6 (7), e21791, 2011, 7 pgs.

(56) References Cited

OTHER PUBLICATIONS

Chen, C. P. et al., "Fetal DNA in maternal plasma: the prenatal detection of a paternally inherited fetal aneuploidy", Prenatal Diagnosis, vol. 20, 2000, 353-357.
Chen, X. Q. et al., "Microsatellite alterations in plasma DNA of small cell lung cancer patients", Nature Medicine, vol. 2, No. 9, Sep. 1996, 1033-1035.
Chetty, Shilpa et al., "Uptake of Noninvasive Prenatal Testing (NIPT) in Women Following Positive Aneuploidy Screening", Prenatal Diagnosis,33, 2013, 542-546.
Cheung, S. W. et al., "Rapid Publication: Microarray-Based CGH Detects Chromosomal Mosaicism Not Revealed by Conventional Cytogenetics", American Journal of Medical Genetics Part A, vol. 143A, 2007, 1679-1686.
Cheung, V. G. et al., "Whole genome amplification using a degenerate oligonucleotide primer allows hundreds of genotypes to be performed on less than one nanogram of genomic DNA", Proceedings of the National Academy of Sciences, USA, vol. 93, Dec. 1996, 14676-14679.
Chim, S. S. et al., "Detection and Characterization of Placental MicroRNAs in Maternal Plasma", Clinical Chemistry, vol. 54, No. 3, 2008, 482-490.
Chinnapapagari, S. K. et al., "Treatment of Maternal Blood Samples with Formaldehyde Does Not Alter the Proportion of Circulatory Fetal Nucleic Acids (DNA and mRNA) in Maternal Plasma", Clinical Chemistry, vol. 51, No. 3, 2005, 653-655.
Chitty, L. S. et al., "Noninvasive Prenatal Screening for Genetic Diseases Using Massively Parallel Sequencing of Maternal Plasma DNA", Cold Spring Harbor Perspectives in Medicine, vol. 5, No. 9, 2015, 20 pages.
Chiu, R. et al., "Non-Invasive Prenatal Assessment of Trisomy 21 by Multiplexed Maternal Plasma DNA Sequencing: Large Scale Validity Study", BMJ, 342, c7401, 2011, 9 pgs.
Chiu, R.W.K. et al., "Hypermethylation of RASSF1A in Human and Rhesus Placentas", The American Journal of Pathology, vol. 170, No. 3, Mar. 2007, 941-950.
Chiu, Rossa W. et al., "Effects of Blood-Processing Protocols on Fetal and Total DNA Quantification in Maternal Plasma", Clinical Chemistry, 47(9), 2001, 1607-1613.
Chiu, Rossa W.K. et al., "Maternal Plasma DNA Analysis with Massively Parallel Sequencing by Litigation for Noninvasive Prenatal Diagnosis of Trisomy 21", Clinical Chemistry, 56, 3, 2010, 459-463.
Chiu, Rossa W.K. et al., "Non-Invasive Prenatal Diagnosis by Single Molecule Counting Technologies", Trends in Genetics, 25 (7), 2009, 324-331.
Chiu, Rossa W.K. et al., "Noninvasive Prenatal Diagnosis of Fetal Chromosomal Aneuploidy by Massively Parallel Genomic Sequencing of DNA in Maternal Plasma (with Supporting Information)", PNAS, vol. 105, No. 51, 2008, 20458-20463.
Choi, M. et al., "Genetic diagnosis by whole exome capture and massively parallel DNA sequencing", PNAS, vol. 106, No. 45, Nov. 10, 2009, 19096-19101.
Choi, Y. et al., "Comparison of phasing strategies for whole human genomes", PLOS Genetics, Apr. 5, 2018, 26 pages.
Chu, T. et al., "Statistical Considerations for Digital Approaches to Non-Invasive Fetal Genotyping", Bioinformatics (Advance Access publication), 26 (22), 2010, 2863-2866.
Chu, Tianjiao et al., "Statistical Model for Whole Genome Sequencing and its Application to Minimally Invasive Diagnosis of Fetal Genetic Disease", Bioinformatics, 25(10), 2009, 1244-1250.
Chu, Tianjiao. et al., "A Novel Approach Toward the Challenge of Accurately Quantifying Fetal DNA in Maternal Plasma", Prenatal Diagnosis,30, 2010, 1226-1229.
Chung, G. T. et al., "Lack of Dramatic Enrichment of Fetal DNA in Maternal Plasma by Formaldehyde Treatment", Clinical Chemistry, vol. 51, No. 3, 2005, 655-658.
Ciriello, G. et al., "Emerging landscape of oncogenic signatures across human cancers", Nature Genetics, vol. 45, No. 10, Oct. 2013, 1127-1135.
Clausen, F. B. et al., "Improvement in fetal DNA extraction from maternal plasma. Evaluation of the NucliSens Magnetic Extraction system and the QIAamp DSP Virus Kit in comparison with the QIAamp DNA Blood Mini Kit", Prenatal Diagnosis, vol. 27, 2007, 6-10.
Cole, Neal W. et al., "Hyperglycemia-Induced Membrane Lipid Peroxidation and Elevated Homocysteine Levels Are Poorly Attenuated by Exogenous Folate in Embryonic Chick Brains", Comparative Biochemistry and Physiology, Part B, 150, 2008, 338-343.
Colella, S. et al., "QuantiSNP: an Objectives Bayes Hidden-Markov Model to Detect and Accurately Map Copy Number Variation Using SNP Genotyping Data", Nucleic Acids Research, 35 (6), 2007, 2013-2025.
Conlin, L. K. et al., "Mechanisms of mosaicism, chimerism and uniparental disomy identified by single nucleotide polymorphism array analysis", Human Molecular Genetics, vol. 19, No. 7, Jan. 6, 2010, 1263-1275.
Coombes, R. C., "Abstract P4-01-02: Early detection of residual breast cancer through a robust, scalable and personalized analysis of circulating tumour DNA (ctDNA) antedates overt metastatic recurrence", Cancer Research, vol. 79, No. 4 Supplement, Feb. 15, 2019.
Cossu, Gianfranco et al., "Rh D/d Genotyping by Quantitative Polymerase Chain Reaction and Capillary Zone Electrophoresis", Electrophoresis, 17, 1996, 1911-1915.
Coyle, J. F. et al., "Standards for detailed clinical models as the basis for medical data exchange and decision support", International Journal of Medical Informatics, 69(2-3), 2003, 157-174.
Craig, D. W. et al., "Identification of genetic variants using barcoded multiplexed sequencing", Nature Methods, vol. 5, Oct. 2008, 887-893.
Cronn, R. et al., "Multiplex sequencing of plant chloroplast genomes using Solexa sequencing-by-synthesis technology", Nucleic Acids Research, vol. 36, No. 19, Aug. 27, 2008, 11 pgs.
Cross, Jillian et al., "Resolution of trisomic mosaicism in prenatal diagnosis: estimated performance of a 50K SNP microarray", Prenat Diagn 2007; 27, 2007, 1197-1204.
D'Aquila, Richard et al., "Maximizing sensitivity and specificity of PCR by pre-amplification heating", Nucleic Acids Research, 19(13), 1991, p. 3749.
Daruwala, Raoul-Sam et al., "A Versatile Statistical Analysis Algorithm to Detect Genome Copy Number Variation", PNAS, 101(46), 2004, 16292-16297.
Dawson, S.J. et al., "Analysis of Circulating Tumor DNA to Monitor Metastatic Breast Cancer", The New England Journal of Medicine, vol. 368, No. 13, Mar. 28, 2013, 1199-1209.
De Bruin, E. et al., "Spatial and temporal diversity in genomic instability processes defines lung cancer evolution", Science, vol. 346, No. 6206, Oct. 10, 2014, 251-256.
De Jong, M. M. et al., "Genes other than BRCA 1 and BRCA2 involved in breast cancer susceptibility", J. Med. Genet., vol. 39, 2009, 225-242.
De Vries, et al., "Diagnostic genome profiling in mental retardation", Am J Hum Genet, 77, published online Aug. 30, 2005, 2005, 606-616.
Deangelis, M. et al., "Solid-phase Reversible Immobilization for the Isolation of PCR Products", Nucleic Acids Research, 23 (22), 1995, 4742-4743.
Delaneau, O. et al., "Shape-IT: new rapid and accurate algorithm for haplotype inference", BMC Bioinformatics, vol. 9, No. 540, Dec. 16, 2008, 14 pages.
Deng, S. et al., "TNER: A Novel Background Error Suppression Method for Mutation Detection in Circulating Tumor DNA", bioRxiv, http://dx.doi.org/10.1101/214379, Nov. 5, 2017, 12 pgs.
Deutsch, S. et al., "Detection of aneuploidies by paralogous sequence quantification", J Med Genet, vol. 41, 2004, 908-915.
Devaney, S. et al., "Noninvasive Fetal Sex Determination Using Cell-Free Fetal DNA: A Systematic Review and Meta-analysis", JAMA, 306 (6), 2011, 627-636.
Dhallan, et al., "Methods to Increase the Percentage of Free Fetal DNA Recovered from the Maternal Circulation", JAMA, 291(9), 2004, 1114-1119.

(56) References Cited

OTHER PUBLICATIONS

Dhallan, Ravinder et al., "A non-invasive test for prenatal diagnosis based on fetal DNA present in maternal blood: a preliminary study", The Lancet, 369, 2007, 474-481.
Di, X. et al., "Dynamic model based algorithms for screening and genotyping", Bioinformatics, vol. 21, No. 9, 2005, 1958-1963.
Dias-Santagata, D. et al., "BRAF V600E Mutations Are Common in Pleomorphic Xanthoastrocytoma: Diagnostic and Therapeutic Implications", PLoS One, vol. 6, No. 3, Mar. 2011, 9 pages.
Dickover, R. E. et al., "Optimization of Specimen-Handling Procedures for Accurate Quantitation of Levels of Human Immunodeficiency Virus RNA in Plasma by Reverse Transcriptase PCR", Journal of Clinical Microbiology, vol. 36, No. 4, 1998, 1070-1073.
Dieffenbach, C W. et al., "General concepts for PCR primer design", Genome Research. PCR methods and Applications vol. 3, 1993, S30-S37.
Diehl, F. et al., "Circulating mutant DNA to assess tumor dynamics", Nature Medicine, vol. 14, No. 9, Jul. 31, 2008, 985-990.
Diehl, F. et al., "Detection and quantification of mutations in the plasma of patients with colorectal tumors", PNAS, vol. 102, No. 45, Nov. 8, 2005, 16368-16373.
Dietmaier, W. et al., "Multiple Mutation Analyses in Single Tumor Cells with Improved Whole Genome Amplification", American Journal of Pathology, vol. 154, No. 1, Jan. 1999, 83-95.
Ding, C et al., "Direct molecular haplotyping of long-range genomic DNA with M1-PCR", PNAS 100(13), 2003, 7449-7453.
Ding, C. et al., "MS analysis of single-nucleotide differences in circulating nucleic acids: Application to noninvasive prenatal diagnosis", PNAS, vol. 101, No. 29, Jul. 20, 2004, 10762-10767.
Dodge, Y. , "Bayes' Theorem", The Concise Encyclopedia of Statistics, 2008, 30-31.
Dohm, J. et al., "Substantial Biases in Ultra-Short Read Data Sets From High-Throughput DNA Sequencing", Nucleic Acids Research, 36 (16), e105, 2008, 10 pgs.
Dolganov, Gregory et al., "A Novel Method of Gene Transcript Profiling in Airway Biopsy Homogenates Reveals Increased Expression of a Na—K+—Cl-Cotransporter (NKCC1) in Asthmatic Subjects", Genome Res.,11, 2001, 1473-1483.
Donaghue, C. et al., "Detection of mosaicism for primary trisomies in prenatal samples by QF-PCR and karyotype analysis", Prenatal Diagnosis, vol. 25, 2005, 65-72.
Donohoe, Gerard G et al., "Rapid Single-Tube Screening of the C282Y Hemochromatosis Mutation by Real-Time Multiplex Allele-specific PCR without Fluorescent Probes", Clinical Chemistry, 46, 10, 2000, 1540-1547.
Donoso, P. et al., "Current Value of Preimplantation Genetic Aneuploidy Screening in IVF", Human Reproduction Update, 13(1), 2007, 15-25.
Dowd, P. et al., "On the mechanism of the anticlotting action of vitamin R quinone", Proc. Natl. Acad. Sci. USA, vol. 92, 1995, 8171-8175.
Downward, J. , "Targeting RAS Signalling Pathways in Cancer Therapy", Nature Reviews, vol. 3, Jan. 2003, 11-22.
Dressman, D. et al., "Transforming single DNA molecules into fluorescent magnetic particles for detection and enumeration of genetic variations", PNAS, vol. 100, No. 15, Jul. 22, 2003, 8817-8822.
Echeverri, et al., "Caffeine's Vascular Mechanisms of Action", International Journal of Vascular Medicine vol. 2010(2010), 10 pages, Aug. 25, 2010.
Edwards, M. C. et al., "Multiplex PCR: Advantages, Development, and Applications", Genome Research, vol. 3, 1994, S65-S75.
Ehrich, Mathias et al., "Noninvasive Detection of Fetal Trisomy 21 by Sequencing of DNA in Maternal Blood: A Study in a Clinical Setting", American Journal of Obstetrics & Gynecology, 204, 2011, 205.e1-205.e11.
Eichler, H , "Mild Course of Fetal Rh D Haemolytic Disease due to Maternal Alloimmunisation to Paternal HLA Class I and II Antigens", Vox Sang, 68, 1995, 243-247.
Ellison, Aaron M. , "Bayesian Inference in Ecology", Ecology Letters, vol. 7, 2004, 509-520.
Ellonen, P. et al., "Development of SNP Microarray for Supplementary Paternity Testing", International Congress Series,1261, 2004, 12-14.
Eltoukhy, H. et al., "Modeling and Base-Calling for DNA Sequencing-by-Synthesis", IEEE, 2006, II-1032-II-1035.
EP06838311.6, , "European Communication and Extended European Search Report", dated Dec. 30, 2008, 8 pgs.
EP08742125.1, , "European Communication pursuant to Article 94(3) EPC and Examination Report", dated Feb. 12, 2010, 5 pgs.
Erlich, R. L. et al., "Next-generation sequencing for HLA typing of class loci", BMC Genomics, vol. 12, No. 42, 2011, 13 pages.
Eronen, L. et al., "HaploRec: efficient and accurate large-scale reconstruction of haplotypes", BMC Bioinformatics, vol. 7, No. 542, Dec. 22, 2006, 18 pages.
Everitt, B. S. , "Medical Statistics From A to Z", 2003, 3 pages.
Fackenthal, J. D. et al., "Aberrant RNA splicing and its functional consequences in cancer cells", Disease Models & Mechanisms, vol. 1, 2008, 37-42.
Faham, M. et al., "Deep-sequencing approach for minimal residual disease detection in acute lymphoblastic leukemia", Blood Journal, vol. 120, No. 26, Dec. 20, 2012, 5173-5180.
Falcon, O. , "Screening for trisomy 21 by fetal tricuspid regurgitation, nuchal translucency and maternal serum free b-hCG and PAPP-A at 11+0 to 13+6 weeks", Ultrasound Obstet Gynecol, vol. 27, 2006, 151-155.
Fan, et al., "Whole-genome molecular haplotyping of single cells", Nature Biotechnology, vol. 29, No. 1, Jan. 1, 2011, 51-57.
Fan, C H. et al., "Detection of Aneuploidy with Digital Polymerase Chain Reaction", Analytical Chemistry, vol. 79, No. 19, Oct. 1, 2007, 7576-7579.
Fan, Christina H. et al., "Non-Invasive Prenatal Measurement of the Fetal Genome", Nature, doi:10.1038/nature11251, 2012, 26 pgs.
Fan, Christina H et al., "Noninvasive Diagnosis of Fetal Aneuploidy by Shotgun Sequencing DNA from Maternal Blood", PNAS, 105, 42, 2008, 16266-16271.
Fan, H. C. et al., "Microfluidic digital PCR enables rapid prenatal diagnosis of fetal aneuploidy", American Journal of Obstetrics & Gynecology, vol. 200, May 2009, 543.e1-543.e7.
Fan, H. Christina et al., "Sensitivity of Noninvasive Prenatal Detection of Fetal Aneuploidy from Maternal Plasma Using Shotgun Sequencing Is Limited Only by Counting Statistics", PLoS ONE, vol. 5, Issue 5 (e10439), May 3, 2010, 1-6.
Fan, J.-B. et al., "Highly Parallel SNP Genotyping", Cold Spring Harbor Symposia on Quantitative Biology, vol. LXVIII, Feb. 2003, 69-78.
Fan, Jian-Bing et al., "Highly Parallel Genomic Assay", Nature Reviews, 7, 2006, 632-644.
Fat Secret, , "5 Foods to Never Eat", https://www.fatsecret.com/calories-nutrition/food/white-bread/carboyhydrate (printed from internet Nov. 1, 2014)., 2 pages.
Fazio, Gennaro, et al., "Identification of RAPD Markers Linked to Fusarium Crown and Root Rot Resistance (Frl) in Tomato", Euphytica 105, 1999, 205-210.
Fiorentino, F. et al., "Development and Clinical Application of a Strategy for Preimplantation Genetic Diagnosis of Single Gene Disorders Combined with HLA Matching", Molecular Human Reproduction (Advance Access publication), 10 (6), 2004, 445-460.
Fiorentino, F et al., "Strategies and Clinical Outcome of 250 Cycles of Preimplantation Genetic Diagnosis for Single Gene Disorders", Human Reproduction, 21, 3, 2006, 670-684.
Fiorentino, Francesco et al., "Short Tandem Repeats Haplotyping of the HLA Region in Preimplantation HLA Matching", European Journal of Human Genetics, 13, 2005, 953-958.
Ford, E. et al., "A method for generating highly multiplexed ChIP-seq libraries", BMC Research Notes, vol. 7, No. 312, May 22, 2014, 1-5.
Forejt, et al., "Segmental trisomy of mouse chromosome 17: introducing an alternative model of Down's syndrome", Genomics, 4(6), 2003, 647-652.
Forshew, et al., "Noninvasive Identification and Monitoring of Cancer Mutations by Targeted Deep Sequencing of Plasma DNA",

(56) References Cited

OTHER PUBLICATIONS

Noninvasive identification and monitoring of cancer mutations by targeted deep sequencing of plasma DNA. Sci. Transl. Med. 4, 136 30 (2012)., 1-12.
Forshew, T. et al., "Supplementary Materials for Noninvasive Identification and Monitoring of Cancer Mutations by Targeted Deep Sequencing of Plasma DNA", Sci. Transl. Med, vol. 4, May 30, 2012, 20 pgs.
Fortina, P. et al., "Detection of the most common mutations causing beta-thalassemia in Mediterraneans using a multiplex amplification refractory mutation system (MARMS)", Genome Res., vol. 2, 1992, 163-166.
Fortina, P. et al., "DOP-PCR Amplification of Whole Genomic DNA and Microchip-Based Capillary Electrophoresis", Methods in Molecular Biology: Capillary Electrophoresis of Nucleic Acids, vol. II Practical Applications of Capillary Electrophoresis, 2001, 211-219.
Fouquet, C. et al., "Rapid and Sensitive p53 Alteration Analysis in Biopsies from Lung Cancer Patients Using a Functional Assay and A Universal Oligonudeotide Array: A Prospective Study", Clinical Cancer Research, vol. 10, May 15, 2004, 3479-3489.
Fredriksson, et al., "Multiplex amplification of all coding sequences within 10 cancer genes by Gene-Collector", Nucleic Acids Research, 2007, vol. 35, No. 7 e47, 1-6.
Freeman, Jennifer L. et al., "Copy Number Variation: New Insights in Genome Diversity", Genome Research, 16, 2006, 949-961.
Frohman, M A. et al., "On Beyond Classic RACE (Rapid Amplification of cDNA Ends)", Genome Research, vol. 4, 1994, S40-S58.
Frost, Mackenzie S et al., "Differential Effects of Chronic Pulsatile Versus Chronic Constant Maternal Hyperglycemia on Fetal Pancreatic B-Cells", Journal of Pregnancy, 2012,, Article ID 812094, 2012, 8.
Fu, G. K. et al., "Counting individual DNA molecules by the stochastic attachment of diverse labels", PNAS, vol. 108, No. 22, May 31, 2011, 9026-9031.
Fu, G. K. et al., "Digital Encoding of Cellular mRNAs Enabling Precise and Absolute Gene Expression Measurement by Single-Molecule Counting", Analytical Chemistry, vol. 86, Mar. 3, 2014, 2867-2870.
Ganshirt-Ahlert, D. et al., "Ratio of Fetal to Maternal DNA is Less Than 1 in 5000 at different Gestational Ages in Maternal Blood", Clinical Genetics,38, 1990, 38-43.
Ganshirt-Ahlert, D. et al., "Fetal DNA in Uterine Vein Blood", Obstetrics & Gynecology, 80 (4), 1992, 601-603.
Ganshirt-Ahlert, Dorothee et al., "Three Cases of 45,X/46,XYnf Mosaicism", Human Genetics, 76, 1987, 153-156.
Gao, F. et al., "Characterizing Immunoglobulin Repertoire from Whole Blood by a Personal Genome Sequencer", PLOS One, vol. 8, No. 9, Sep. 13, 2013, 8 pgs.
Garcia-Murillas, I. et al., "Mutation tracking in circulating tumor DNA predicts relapse in early breast cancer", Science Translational Medicine, vol. 7, No. 302, Aug. 26, 2015, 34 pgs.
Gardina, P. et al., "Ploidy Status and Copy Number Aberrations in Primary Glioblastomas Defined by Integrated Analysis of Allelic Ratios, Signal Ratios and Loss of Heterozygosity Using 500K SNP Mapping Arrays", BMC Genomics, 9 (489), (doi:10.1186/1471-2164-9-489), 2008, 16 pgs.
Gautier, E. et al., "Fetal RhD genotyping by maternal serum analysis: A two-year experience", American Journal of Obstetrics and Gynecology, vol. 192, 2005, 666-669.
Geiss, G. K. et al., "Direct multiplexed measurement of gene expression with color-coded probe pairs", Nature Biotechnology, vol. 26, No. 3, Feb. 17, 2008, 317-325.
Ghanta, Sujana et al., "Non-Invasive Prenatal Detection of Trisomy 21 Using Tandem Single Nucleotide Polymorphisms", PLoS ONE, 5 (10), 2010, 10 pgs.
Gholami, M. et al., "A tailed PCR procedure for cost-effective, two-order multiplex sequencing of candidate genes in polyploid plants", Plant Biotechnology Journal, vol. 10, 2012, 635-645.
Gielis, E. M. et al., "Plasma donor-derived cell-free DNA kinetics after kidney transplantation using a single tube multiplex PCR assay", PLOS One, vol. 13, No. 12, e0208207, Dec. 6, 2018, 16 pgs.
Gjertson, David W. et al., "Assessing Probability of Paternity and the Product Rule in DNA Systems", Genetica, 96, 1995, 89-98.
Gnirke, A. et al., "Solution hybrid selection with ultra-long oligonucleotides for massively parallel targeted sequencing", Nature Biotechnology, vol. 27, No. 2, Feb. 2009, 182-189.
Greenwalt, T. et al., "The Quantification of Fetomaternal Hemorrhage by an Enzyme-Linked Antibody Test with Glutaraldehyde Fixation", Vox Sang, 63, 1992, 268-271.
Griffiths, A. J. et al., "An Introduction to Genetic Analysis", Sixth Edition, 1996, 5 pages.
Grskovic, M. et al., "Validation of a Clinical-Grade Assay to Measure Donor-Derived Cell-Free DNA in Solid Organ Transplant Recipients", The Journal of Molecular Diagnostics, vol. 18, No. 6 + Supplemental Appendix S1, Nov. 2016, 890-902.
Grunenwald, H. , "Optimization of Polymerase Chain Reactions", Methods in Biology, vol. 226, 2003, 89-99.
Gu, H. et al., "Diagnostic role of microRNA expression profile in the serum of pregnant women with fetuses with neural tube defects", Journal of Neurochemistry, vol. 122, 2012, 641-649.
Guerra, J. , "Terminal Contributions for Duplex Oligonucleotide Thermodynamic Properties in the Context of Nearest Neighbor Models", Biopolymers, 95(3), (2010), 2011, 194-201.
Guetta, Esther et al., "Analysis of Fetal Blood Cells in the Maternal Circulation: Challenges, Ongoing Efforts, and Potential Solutions", Stem Cells and Development, 13, 2004, 93-99.
Guichoux, et al., "Current Trends in Microsatellite Genotyping", Molecular Ecology Resources, 11, 2011, 591-911.
Gunderson, K. L. et al., "A genome-wide scalable SNP genotyping assay using microarray technology", Nature Genetics, vol. 37, No. 5, May 2005, 549-554.
Gundry, C. N. et al., "Base-pair neutral homozygotes can be discriminated by calibrated high-resolution melting of small amplicons", Nucleic Acids Research, vol. 36, No. 10, Apr. 29, 2008, 3401-3408.
Guo, H et al., "A Specific and Versatile Genome Walking Technique", Gene, vol. 381, 2006, 18-23.
Hahn, S. et al., "Current applications of single-cell PCR", CMLS Cellular and Molecular. Life Sciences, vol. 57, 2000, 96-105.
Hall, M. , "Panorama Non-Invasive Prenatal Screening for Microdeletion Syndromes", Apr. 1, 2014 (Apr. 1, 2014), XP055157224, Retrieved from the Internet: URL:http://www.panoramatest.com/sites/default/files/files/PanoramaMicrodeletionsWhite Paper-2.pdf [retrieved on Aug. 12, 2014].
Han, S-W et al., "Predictive and Prognostic Impact of Epidermal Growth Factor Receptor Mutation in Non-Small-Cell Lung Cancer Patients Treated With Gefitinib", Journal of Clinical Oncology, vol. 23, No. 11, Apr. 10, 2005, 2493-2501.
Handyside, et al., "Isothermal whole genome amplification from single and small numbers of cells: a new era for preimplantation genetic diagnosis of inherited disease", Molecular Human Reproduction vol. IO, No. 10 pp. 767-772, 2004.
Hara, Eiji et al., "Subtractive eDNA cloning using oligo(dT)3o-latex and PCR: isolation of eDNA clones specific to undifferentiated human embryonal carcinoma cells", Nucleic Acids Research, 19(25), 1991, 7097-7104.
Hardenbol, P. , "Multiplexed Genotyping With Sequence-Tagged Molecular Inversion Probes", Nature Biotechnology, 21 (6), 2003, 673-678.
Hardenbol, Paul et al., "Highly multiplexed molecular inversion probe genotyping: Over 10,000 targeted SNPs genotyped in a singled tube assay", Genome Research, 15, 2005, 269-275.
Harismendy, O. et al., "Method for Improving Sequence Coverage Uniformity of Targeted Genomic Intervals Amplified by LR-PCR Using Illumina GA Sequencing-By-Synthesis Technology", Bio Techniques, 46(3), 2009, 229-231.
Harper, J. C. et al., "Recent Advances and Future Developments in PGD", Prenatal Diagnosis, 19, 1999, 1193-1199.
Harton, G.L. et al., "Preimplantation Genetic Testing for Marfan Syndrome", Molecular Human Reproduction, 2 (9), 1996, 713-715.

(56) References Cited

OTHER PUBLICATIONS

Hartwell, L. H. et al., "Chapter 11: The Direct Detection of Genotype Distinguishes Individual Genomes", Genetics: From Genes to Genomes, Second Edition, 2004, 371-414.
Hartwell, L. H. et al., "Chapter 13: Chromosomal Rearrangements and Changes in Chromosome Number Reshape Eukaryotic Genomes", Genetics: From Genes to Genomes, Second Edition, 2004, 441-486.
Hattori, M. et al., "The DNA sequence of human chromosome 21", Nature, vol. 405, May 18, 2000, 311-319.
Hawkins, T. et al., "Whole genome amplification—applications and advances", Current Opinion in Biotechnology, 13, 2002, 65-67.
Hayden, et al., "Multiplex-Ready PCR: A new method for multiplexed SSR and SNP genotyping", BMC Genomics 2008, 9(80), 1-12.
He, QZ et al., "A method for improving the accuracy of non-invasive prenatal screening by cell-free foetal DNA size selection", British Journal of Biomedical science, vol. 75, No. 3, Jul. 2018, 133-138.
Hellani, A. et al., "Clinical Application of Multiple Displacement Amplification in Preimplantation Genetic Diagnosis", Reproductive BioMedicine Online, 10 (3), 2005, 376-380.
Hellani, Ali et al., "Multiple displacement amplification on single cell and possible PGD applications", Molecular Human Reproduction, 10(11), 2004, 847-852.
Hodgkinson, C. L. et al., "Tumorigenicity and genetic profiling of circulating tumor cells in small-cell lung cancer", Nature Medicine, vol. 20, No. 8, Aug. 2014, 897-905.
Hojsgaard, S. et al., "Bifrost— Block recursive models induced from relevant knowledge, observations, and statistical techniques", Computational Statistics & Data Analysis, 19(2), 1995, 155-175.
Hollas, B. et al., "A stochastic approach to count RN A molecules using DNA sequencing methods", Lecture Notes in Computer Science, vol. 2812, 2003, 55-62.
Holleley, et al., "Multiplex Manager 1.0: a Cross-Platform Computer Program that Plans and Optimizes Multiplex PCR", BioTechniques46:511-517 (Jun. 2009), 511-517.
Hollox, E. et al., "Extensive Normal Copy Number Variation of a β-Defensin Antimicrobial-Gene Cluster", Am. J. Hum. Genet., 73, 2003, 591-600.
Homer, et al., "Resolving Individuals Contributing Trace Amounts of DNA to Highly Complex Mixtures Using High-Density SNP Genotyping Microarrays", PLOS Genetics, 4(8), 2008, 9 pgs.
Hoogendoorn, Bastiaan et al., "Genotyping Single Nucleotide Polymorphisms by Primer Extension and High Performance Liquid Chromatography", Hum Genet, 104, 1999, 89-93.
Hornak, M. et al., "Aneuploidy Detection in Pigs Using Comparative Genomic Hybridization: From the Oocytes to Blastocysts", PLoS ONE, vol. 7, No. 1, Jan. 2012, 6 pages.
Hosono, S. et al., "Unbiased Whole-Genome Amplification Directly From Clinical Samples", Genome Research, vol. 13, 2003, 954-964.
Hospital, F. et al., "A General Algorithm to Compute Multilocus Genotype Frequencies Under Various Mating Systems" vol. 12, No. 6, Jan. 1, 1996 (Jan. 1, 1996), pp. 455-462.
Hou, X. et al., "Analysis of the Repertoire Features of TCR Beta Chain CDR3 in Human by High-Throughput Sequencing", Cellular Physiology and Biochemistry, vol. 39, Jul. 21, 2019, 651-667.
Howie, et al., "Fast and accurate genotype imputation in genome-wide association studies through pre-phasing", Nature Genetics, vol. 44, No. 8, Jul. 22, 2012, 955-959.
Howie, B. N. et al., "A Flexible and Accurate Genotype Imputation Method for the Next Generation of Genome-Wide Association Studies", PLoS Genetics, vol. 5, No. 6, Jun. 2009, 15 pages.
Hu, Dong Gui et al., "Aneuploidy Detection in Single Cells Using DNA Array-Based Comparative Genomic Hybridization", Molecular Human Reproduction, 10(4), 2004, 283-289.
Hu, Y. et al., "Detection of Extrahepatic Hepatitis C Virus Replication by a Novel, Highly Sensitive, Single-Tube Nested Polymerase Chain Reaction", Am. J. Clin Pathol., vol. 119, 2003, 95-100.
Huang, D. J. et al., "Use of an Automated Method Improves the Yield and Quality of Cell-Free Fetal DNA Extracted from Maternal Plasma", Clinical Chemistry, vol. 51, No. 12, 2005, 2419-2420.
Huang, J. et al., "Whole genome DNA copy number changes identified by high density oligonucleotide arrays", Human Genomics, vol. 1, No. 4, May 2004, 287-299.
Hug, H. et al., "Measurement of the number of molecules of a single mRNA species in a complex mRNA preparation", J. Theor. Biol., vol. 221, 2003, 615-624.
Hultin, E. et al., "Competitive enzymatic reaction to control allele-specific extensions", Nucleic Acids Research, vol. 33, No. 5, Mar. 14, 2005, 1-10.
Hung, E.C.W. et al., "Detection of circulating fetal nucleic acids: a review of methods and applications", J. Clin. Pathol., vol. 62, 2009, 308-313.
Hyndman, D L. et al., "PCR Primer Design", Methods in Molecular Biology, vol. 226, Second Edition, 2003, 81-88.
Ido, Yasuo et al., "Hyperglycemia-Induced Apoptosis in Human Umbilical Vein Endothelial Cells: Inhibition by the AMP-Activated Protein Kinase Activation", Diabetes, 51, 2002, 159-167.
Illumina, , "Automated GoldenGate™ Genotyping on the BeadStation 500", Pub. No. 970-2004-002, 2004, 2 pages.
Illumina, , "GoldenGate Assay Workflow: Illumina's GoldenGate assay protocol provides high-quality, high-multiplex genotyping results with a streamlined workflow", Pub. No. 370-2004-006, 2004, 2 pages.
Illumina, , "HiSeq 2500 Sequencing System", System Specification Sheet: Sequencing, available via URL https://www.illumina.com/documents/products/datasheets/datasheet_hiseq2500.pdf, 2015, 4 pgs.
Illumina, , "History of Sequencing by Synthesis", https://www.illumina.com/science/technology/next-generation-sequencing/illumina-sequencing-history.html, 2020, 3 pages.
Illumina, , "Illumina Extends BeadArray Technology to Address Wider Range of SNP Genotyping Projects; New Microarray Offerings Enable Genotyping at 384 and 786 Multiplex", Businesswire, May 4, 2004, 2 pages.
Illumina, , "Illumina® Beadstation 500: A Scalable System That Grows With Your Research Requirements", Pub. No. 970-2005-003, Jul. 1, 2005, 4 pages.
Illumina, , "Illumina Announces Benchtop SNP Genotyping System", Press Release, Nov. 5, 2003, 3 pages.
Illumina, , "Illumina Begins Shipment of BeadStation 500G Benchtop Genotyping System", Press Release, Apr. 15, 2004, 3 pages.
Illumina, , "MiSeq System Information Sheet", 2018, 3 pgs.
Illumina, , "Patent Owner Illumina'S Preliminary Response to Petition", Oct. 17, 2018, 75 pgs.
Illumina, , "Petition for Inter Partes Review of U.S. Pat. No. 8,682,592", Jun. 13, 2019, 91 pages.
Illumina, , "Plaintiff/Counterclaim Defendant Illumina, Inc.'S Amended Patent L.R. 3-3 Preliminary Invalidity Contentions for U.S. Pat. No. 8,682,592", Oct. 30, 2018, 22 pages.
Illumina, , "Plaintiff/Counterclaim-Defendant Illumina, Inc.'S Patent L.R. 3-3 Contentions for U.S. Patent Preliminary Invalidity Contentions for U.S. Pat. No. 8,682,592", Oct. 9, 2018, 81 pages.
Illumina, , "Preparing Samples for Sequencing Genomic DNA", Part # 11251892 Rev. A, 2007, 18 pages.
Illumina, , "Preparing Samples for Sequencing Genomic DNA", Part # 1003806 Rev. A, 2007, 20 pages.
Illumina, , "Products & Services", Product Literature, Mar. 21, 2007, 3 pages.
Illumina, , "Technology: Solexa Sequencing Technology", May 21, 2007, 1 page.
Illumina, , "TruSeq™ RNA and DNA Library Preparation Kits v2", Data Sheet: Illumina® Sequencing, 2014, 4.
Illumina Catalog, , "Paired-End Sample Preparation Guide, Illumina Catalog# PE-930-1 001, Part# 1005063 Rev. E", 2011, 1-40.
Illumina, Inc., , "Declaration of David Peters, Ph.D. in Support of Petition for Inter Partes Review of U.S. Pat. No. 8,682,592", Jun. 13, 2019, 136 pages.
*Illumina, Inc. V. Natera, Inc.*, , "Order Re: Claim Construction", Jan. 30, 2019, 16 pgs.

(56) References Cited

OTHER PUBLICATIONS

Imielinski, M. et al., "Mapping the Hallmarks of Lung Adenocarcinoma with Massively Parallel Sequencing", Cell, vol. 150, Sep. 14, 2012, 1107-1120.
Innan, H. et al., "The Pattern of Polymorphism on Human Chromosome 21", Genome Research, vol. 13, 2003, 1158-1168.
International Human, Genome Sequencing Consortium, "Finishing the Euchromatic Sequence of the Human Genome", Nature, vol. 431, Oct. 21, 2004, 931-945.
Ishii, et al., "Optimization of Annealing Temperature To Reduce Bias Caused by a Primer Mismatch in Multitemplate PCR", Applied and Environmental Microbiology, Aug. 2001, p. 3753-3755.
Iskow, R. C. et al., "Natural Mutagenesis of Human Genomes by Endogenous Retrotransposons", Cell, vol. 141, Jun. 25, 2010, 1253-1261.
Ivanov, M. et al., "Non-random fragmentation patterns in circulating cell-free DNA reflect epigenetic regulation", BMC Genomics, vol. 16 (Suppl 13):S1, Jun. 2015, 12 pgs.
Jabara, C. B. et al., "Accurate sampling and deep sequencing of the HIV-1 protease gene using a Primer ID", PNAS, vol. 108, No. 50, Dec. 13, 2011, 20166-20171.
Jahr, S. et al., "DNA Fragments in the Blood Plasma of Cancer Patients: Quantitations and Evidence for Their Origin from Apoptotic and Necrotic Cells", Cancer Research, vol. 61, Feb. 15, 2001, 1659-1665.
Jamal-Hanjani, M. et al., "Detection of ubiquitous and heterogeneous mutations in cell-free DNA from patients with early-stage non-small-cell lung cancer", Annals of Oncology, vol. 27, No. 5, Jan. 28, 2016, 862-867.
Jamal-Hanjani, M. et al., "Tracking Genomic Cancer Evolution for Precision Medicine: The Lung TRACERx Study", PLOS Biology, vol. 12, No. 7, Jul. 2014, 1-7.
Jamal-Hanjani, M. et al., "Tracking the Evolution of Non-Small-Cell Lung Cancer", The New England Journal of Medicine, vol. 376, No. 22, Jun. 1, 2017, 2109-2121.
Jarvie, T., "Next generation sequencing technologies", Drug Discovery Today: Technologies, vol. 2, No. 3, 2005, 255-260.
Jenkins, S. et al., "High-throughput SNP genotyping", Comparative and Functional Genomics, vol. 3, Dec. 5, 2001, 57-66.
Jennings, C. et al., "Investigation of Effects of Acid Citrate Dextrose and EDTA on Ability to Quantitatively Culture Human Immunodeficiency Virus", Journal of Clinical Microbiology, vol. 38, No. 9, 2000, 3522.
Jett, K. et al., "Clinical and genetic aspects of neurofibromatosis 1", Genetics In Medicine, vol. 12, No. 1, Jan. 2010, 11 pages.
Jewesburty, E.C.O., "Reactions after Transfusion of Stored Blood", The British Medical Journal, vol. 1, No. 4191, 1941, 664-665.
Jiang, P. et al., "The Long and Short of Circulating Cell-Free DNA and the Ins and Outs of Molecular Diagnostics", Trends in Genetics, vol. 32, No. 6, Jun. 2016, 360-371.
Johnson, D. S. et al., "Genome-Wide Mapping of in Vivo Protein-DNA Interactions", Science, vol. 316, Jun. 8, 2007, 1497-1502.
Johnson, D.S. et al., "Comprehensive Analysis of Karyotypic Mosaicism Between Trophectoderm and Inner Cell Mass", Molecular Human Reproduction, 16(12), 2010, 944-949.
Johnson, J. B. et al., "Differential mechanisms of complement mediated neutralization of the closely related paramyxoviruses simian virus 5 and mumps virus", Virology, vol. 376, No. 1, 2008, 112-123.
Johnson, K. L. et al., "Interlaboratory Comparison of Fetal Male DNA Detection from Common Maternal Plasma Samples by Real-Time PC", Clinical Chemistry, vol. 50, No. 3, 2004, 516-521.
Johnson D.S, et al., "Preclinical Validation of a Microarray Method for Full Molecular Karyotyping of Blastomeres in a 24-h Protocol", Human Reproduction, 25 (4), 2010, 1066-1075.
Juppner, H. et al., "Functional Properties of the PTH/PTHrP Receptor", Bone, vol. 17, No. 2 Supplement, Aug. 1995, 39S-42S.
Kamat, A. A. et al., "Quantification of total plasma cell-free DNA in ovarian cancer using real-time PCR", Ann N Y Acad Sci., vol. 1075, Sep. 2006, 230-234.
Kamel, A. M. et al., "A simple strategy for breakpoint fragment determination in chronic myeloid leukemia", Cancer Genetics and Cytogenetics, vol. 122, 2000, 110-115.
Kane, M. et al., "Application of Less Primer Method to Commercial Kits", Forensic Science International: Genetics Supplement Series, vol. 1, Issue 1, 2008, 41-43.
Kanou, et al., "Cell-free DNA in human ex vivo lung perfusate as a potential biomarker to predict the risk of primary graft dysfunction in lung transplantation", The Journal of Heart and Lung Transplantation, vol. 36, No. 45, 2017, S187.
Kaplinski, Lauris et al., "MultiPLX: Automatic Grouping and Evaluation of PCR Primers", Bioinformatics, 21(8), 2005, 1701-1702.
Kazakov, V.I. et al., "Extracellular DNA in the Blood of Pregnant Women", Tsitologia, vol. 37, No. 3, 1995, 1-8.
Keith, L. et al., "Clinical Experience With the Prevention of Rh-Isoimmunization: A Historical Comparative Analysis", American Journal of Reproductive Immunology, vol. 5, 1984, 84-89.
Keller, M. C. et al., "Non-Pathological Paternal Isodisomy of Chromosome 2 Detected From a Genome-Wide SNP Scan", American Journal of Medical Genetics, Part A, 2009, 1823-1826.
Kiernan, J. A., "Formaldehyde, formalin, paraformaldehyde and glutaraldehyde: What they are and what they do.", Microscopy Today, vol. 1, 2000, 8-12.
Kijak, G. et al., "Discrepant Results in the Interpretation of HIV-1 Drug-Resistance Genotypic Data Among Widely Used Algorithms", HIV Medicine, 4, 2003, 72-78.
Kim, H. et al., "Whole-genome and multisector exome sequencing of primary and post-treatment glioblastoma reveals patterns of tumor evolution", Genome Research, vol. 25, No. 3, Feb. 3, 2015, 316-327.
Kimmel, G. et al., "GERBIL: Genotype resolution and block identification using likelihood", PNAS, vol. 102, No. 1, Jan. 4, 2005, 158-162.
Kinde, I. et al., "Detection and quantification of rare mutations with massively parallel sequencing", PNAS, vol. 108, No. 23, Jun. 7, 2011, 9530-9535.
Kinnings, S. L. et al., "Factors affecting levels of circulating cell-free fetal DNA in maternal plasma and their implications for noninvasive prenatal testing", Prenatal Diagnosis, vol. 35, 2015, 816-822.
Kirkizlar, E. et al., "Detection of Clonal and Subclonal Copy-Number Variants in Cell-Free DNA from Patients with Breast Cancer Using a Massively Multiplexed PCR Methodology", Translational Oncology, vol. 8, No. 5, Oct. 2015, pp. 407-416.
Kirkness, E. F. et al., "Sequencing of isolated sperm cells for direct haplotyping of a human genome", Genome Research, vol. 23, 2013, 826-832.
Kivioja, T. et al., "Counting absolute number of molecules using unique molecular identifiers", Nature Proceedings, Apr. 14, 2011, 18 pgs.
Kivioja, T. et al., "Counting absolute numbers of molecules using unique molecular identifiers", Nature Methods, Advance Online Publication, Nov. 20, 2011, 1-5.
Kivioja, T. et al., "Counting absolute numbers of molecules using unique molecular identifiers", Nature Methods, vol. 9, No. 1, Jan. 2012, 72-76.
Kohler, C. et al., "Levels of plasma circulating cell free nuclear and mitochondrial DNA as potential biomarkers for breast tumors", Molecular Cancer, vol. 8, No. 105, Nov. 17, 2009, 9 pages.
Konfortov, B A. et al., "A High-Resolution HAPPY Map of Dictyostelium discoideum Chromosome 6", Genome Research, vol. 10, No. 11, Nov. 2000, 1737-1742.
Konfortov, Bernard A. et al., "An Efficient Method for Multi-Locus Molecular Haplotyping", Nucleic Acids Research, 35(1), e6, 2007, 8 pgs.
Kopreski, MS et al., "Detection of mutant K-ras DNA in plasma or serum of patients with colorectal cancer", British Journal of Cancer, vol. 76, No. 10, 1997, 1293-1299.
Krjutskov, K. et al., "Development of a single tube 640-plex genotyping method for detection of nucleic acid variations on microarrays", Nucleic Acids Research, vol. 36, No. 12, May 23, 2008, 7 pages.

(56) References Cited

OTHER PUBLICATIONS

Kukita, Y. et al., "High-fidelity target sequencing of individual molecules identified using barcode sequences: de nova detection and absolute quantitation of mutations in plasma cell-free DNA from cancer patients", DNA Research, vol. 22, No. 4, Jun. 29, 2015, 269-277.

Kuliev, Anver et al., "Thirteen Years' Experience on Preimplantation Diagnosis: Report of the Fifth International Symposium on Preimplantation Genetics", Reproductive BioMedicine Online, 8, 2, 2004, 229-235.

Kumar, P. et al., "Ethylenegycol-Bis-(B-Aminoethylether)Tetraacetate as a Blood Anticoagulant: Preservation of Antigen-Presenting Cell Function and Antigen-Specific Proliferative Response of Peripheral Blood Mononuclear Cells from Stored Blood", Clinical and Diagnostic Laboratory Immunology, vol. 7, No. 4, 2000, 578-583.

Kunishima, S. et al., "First description of somatic mosaicism in MYH9 disorders", British Journal of Haematology, vol. 128, 2005, 360-365.

Kwok, P. Y. , "High-throughput genotyping assay approaches", Pharmacogenomics, vol. 1, No. 1, 2000, 1-5.

Lambert-Messerlian, G. et al., "Adjustment of Serum Markers in First Trimester Screening", Journal of Medical Screening, 16 (2), 2009, 102-103.

Landegren, U. et al., "Padlock and proximity probes for in situ and array-based analyses: tools for the post-genomic era", Comparative and Functional Genomics, vol. 4, 2003, 525-530.

Lander, E. S. et al., "Initial sequencing and analysis of the human genome", Nature, vol. 409, Feb. 15, 2001, 860-921.

Lapaire, O. et al., "Array-CGH analysis of cell-free fetal DNA in 10 mL of amniotic fluid supernatant", Prenatal Diagnosis, vol. 27, May 17, 2007, 616-621.

Lapierre, J.M. et al., "Analysis of uncultured amniocytes by comparative genomic hybridization: a prospective prenatal study", Prenatal Diagnosis, vol. 20, 2000, 123-131.

Lasken, R. S. et al., "Whole genome amplification: abundant supplies of DNA from precious samples or clinical specimens", Trends in Biotechnology, vol. 21, No. 12, Dec. 2003, 531-535.

Lathi, Ruth B. et al., "Informatics Enhanced SNP Microarray Analysis of 30 Miscarriage Samples Compared to Routine Cytogenetics", PLoS ONE, 7(3), 2012, 5 pgs.

Lavrentieva, I et al., "High Polymorphism Level of Genomic Sequences Flanking Insertion Sites of Human Endogenous Retroviral Long Terminal Repeats", FEBS Letters, vol. 443, No. 3, Jan. 29, 1999, 341-347.

Leary, R. J. et al., "Development of Personalized Tumor Biomarkers Using Massively Parallel Sequencing", Science Translational Medicine, vol. 2, No. 20, Feb. 24, 2010, 1-8.

Leary, Rebecca J et al., "Detection of Chromosomal Alterations in the Circulation of Cancer Patients with Whole-Genome Sequencing", Science Translational Medicine, 4, 162, 2012, 12.

Lecomte, T. et al., "Detection of Free-Circulating Tumor-Associated DNA in Plasma of Colorectal Cancer Patients and Its Association With Prognosis", Int. J. Cancer, vol. 100, 2002, 542-548.

Lee, J et al., "Anchored Multiplex PCR Enables Sensitive and Specific Detection of Variants in Circulating Tumor DNA by Next-Generation Sequencing", DOI:https://doi.org/10.1016/j.cancergen.2017.04.049, Cancer Genetics 214-215, 2017, 47.

Lee, T. et al., "Down syndrome and cell-free fetal DNA in archived maternal serum", AmJ Obstet Gynecol, vol. 187, No. 5, 1217-1221, Nov. 2002.

Lee, T.H. et al., "Quantitation of genomic DNA in plasma and serum samples: higher concentrations of genomic DNA found in serum than in plasma", Transfusion, vol. 41, Feb. 2001, 276-282.

Levsky, J. M. et al., "Fluorescence in situ hybridization: past, present and future", Journal of Cell Science, vol. 116, No. 14, 2003, 2833-2838.

Li, B. , "Highly Multiplexed Amplicon Preparation for Targeted Re-Sequencing of Sample Limited Specimens Using the Ion AmpliSeq Technology and Semiconductor Sequencing", Proceedings of the Annual Meeting of the American Society of Human Genetics [retrieved on Oct. 30, 2012]. Retrieved from the Internet: <URL: http://www.ashg.org/2012meeting/abstracts/fulltext/f120121811.htm>, 2012, 1 pg.

Li, R. et al., "SNP detection for massively parallel whole-genome resequencing", Genome Research, vol. 19, 2009, 1124-1132.

Li, Y. et al., "Detection of Paternally Inherited Fetal Point Mutations for b-Thalassemia Using Size-Fractionated Cell-Free DNA in Maternal Plasma", JAMA, vol. 293, No. 7, Apr. 13, 2005, 843-849.

Li, Y. et al., "Non-Invasive Prenatal Diagnosis Using Cell-Free Fetal DNA in Maternal Plasma from PGD Pregnancies", Reproductive BioMedicine Online, 19 (5), 2009, 714-720.

Li, Ying et al., "Size Separation of Circulatory DNA in Maternal Plasma Permits Ready Detection of Fetal DNA Polymorphisms", Clinical Chemistry, 50, 6, 2004, 1002-1011.

Liao, Gary J.W. et al., "Targeted Massively Parallel Sequencing of Maternal Plasma DNA Permits Efficient and Unbiased Detection of Fetal Alleles", Clinical Chemistry, 57 (1), 2011, 92-101.

Liao, J. et al., "An Alternative Linker-Mediated Polymerase Chain Reaction Method Using a Dideoxynucleotide to Reduce Amplification Background", Analytical Biochemistry 253, 137-139 (1997).

Lichtenstein, A. V. et al., "Circulating Nucleic Acids and Apoptosis", Annals New York Academy of Sciences, vol. 945, 1993, 239-249.

Liew, Michael et al., "Genotyping of Single-Nucleotide Polymorphisms", Clinical Chemistry, 50(7), 2004, 1156-1164.

Life Technologies, , "Ion AmpliSeq Comprehensive Cancer Panel", 2012, 2 pgs.

Life Technologies, , "Ion AmpliSeq™ Designer provides full flexibility to sequence genes of your choice", 2012, 4 pages.

Lindberg, J. et al., "Exome Sequencing of Prostate Cancer Supports the Hypothesis of Independent Tumour Origins", European Urology, vol. 63, 2013, 347-353.

Lindroos, Katarina et al., "Genotyping SNPs by Minisequencing Primer Extension Using Oligonucleotide Microarrays", Methods in Molecular Biology, 212, Single Nucleotide Polymorphisms: Methods and Protocols, P-K Kwok (ed.), Humana Press, Inc., Totowa, NJ, 2003, 149-165.

Lo, et al., "Digital PCR for the Molecular Detection of Fetal Chromosomal Aneuploidy", PNAS, vol. 104, No. 32, Aug. 7, 2007, 13116-13121.

Lo, et al., "Fetal Nucleic Acids in Maternal Blood: the Promises", Clin. Chem. Lab. Med., 50(6), 2012, 995-998.

Lo, et al., "Free Fetal DNA in Maternal Circulation", JAMA, 292(23), (Letters to the Editor), 2004, 2835-2836.

Lo, , "Non-Invasive Prenatal Diagnosis by Massively parallel Sequencing of Maternal Plasma DNA", Open Biol 2: 120086, 2012, 1-5.

Lo, et al., "Prenatal Sex Determination by DNA Amplification from Maternal Peripheral Blood", The Lancet,2, 8676, 1989, 1363-1365.

Lo, et al., "Rapid Clearance of Fetal DNA from Maternal Plasma", Am. J. Hum. Genet., 64, 1999, 218-224.

Lo, et al., "Strategies for the Detection of Autosomal Fetal DNA Sequence from Maternal Peripheral Blood", Annals New York Academy of Sciences,731, 1994, 204-213.

Lo, et al., "Two-way cell traffic between mother and fetus: biologic and clinical implications", Blood, 88(11), Dec. 1, 1996, 4390-4395.

Lo, Y. , "Noninvasive prenatal detection of fetal chromosomal aneuploidies by maternal plasma nucleic acid analysis: a review of the current state of the art", BJOG An International Journal of Obstetrics and Gynaecology, vol. 116, 2009, 152-157.

Lo, Y.M. Dennis , "Fetal Nucleic Acids in Maternal Plasma: Toward the Development of Noninvasive Prenatal Diagnosis of Fetal Chromosomal Aneuploidies", Ann. N.Y. Acad. Sci., 1137, 2008, 140-143.

Lo, Y.M. Dennis et al., "Maternal Plasma DNA Sequencing Reveals the Genome-Wide Genetic and Mutational Profile of the Fetus", Science Translational Medicine,, 2 (61), 2010, 13.

Lo, Y.M. Dennis et al., "Plasma placental RNA allelic ratio permits noninvasive prenatal chromosomal aneuploidy detection", Nature Medicine, 13 (2), 2007, 218-223.

Lo, Y.M. Dennis et al., "Presence of Fetal DNA in Maternal Plasma and Serum", The Lancet, 350, 1997, 485-487.

(56) References Cited

OTHER PUBLICATIONS

Lo, Y.M. Dennis et al., "Quantitative Analysis of Fetal DNA in Maternal Plasma and Serum: Implications for Noninvasive Prenatal Diagnosis", Am. J. Hum. Genet., 62, 1998, 768-775.

Lo, Y.M.D. , "Fetal DNA in Maternal Plasma: Biology and Diagnostic Applications", Clinical Chemistry, vol. 46, No. 12, 2000, 1903-1906.

Lo, Y.M.D. et al., "Prenatal diagnosis: progress through plasma nucleic acids", Nature Reviews, vol. 8, 2007, 71-77.

Lo, Y-M D. , "Non-invasive prenatal diagnosis using fetal cells in maternal blood", J. Clin. Pathol., vol. 47, 1994, 1060-1065.

Lo, Y-M.D et al., "Detection of Single-Copy Fetal DNA Sequence from Maternal Blood", The Lancet, 335, 1990, 1463-1464.

Lo, Y-M.D et al., "Prenatal Determination of Fetal Rhesus D Status by DNA Amplification of Peripheral Blood of Rhesus-Negative Mothers", Annals New York Academy of Sciences, 731, 1994, 229-236.

Lo, Y-M.D. et al., "Detection of Fetal RhD Sequence from Peripheral Blood of Sensitized RhD-Negative Pregnant Women", British Journal of Haematology, 87, 1994, 658-660.

Lo, Y-M.D. et al., "Prenatal Determination of Fetal RhD Status by Analysis of Peripheral Blood of Rhesus Negative Mothers", The Lancet, 341, 1993, 1147-1148.

Lovmar, L. et al., "Quantitative evaluation by minisequencing and microarrays reveals accurate multiplexed SNP genotyping of whole genome amplified DN", Nucleic Acids Research, vol. 31, No. 21, 2003,, 9 pgs.

Lu, I. et al., "Establishment of a system based on universal multiplex-PCR for screening genetically modified crops", Anal. Bioanal. Chem, vol. 396, Oct. 24, 2009, 2055-2064.

Lu, S. et al., "Probing Meiotic Recombination and Aneuploidy of Single Sperm Cells by Whole-Genome Sequencing", Science, vol. 338, Dec. 21, 2012, 1627-1630.

Lui, Y. Y. et al., "Predominant Hematopoietic Origin of Cell-Free DNA in Plasma and Serum after Sex-Mismatched Bone Marrow Transplantation", Clinical Chemistry, vol. 48, vol. 3, 2002, 421-427.

Lun, Fiona M. et al., "Noninvasive Prenatal Diagnosis of Monogenic Diseases by Digital Size Selection and Relative Mutation Dosage on DNA in Maternal Plasma", PNAS, 105(50), 2008, 19920-19925.

Ma, Xiaotu et al., "Rise and fall of subclones from diagnosis to relapse in pediatric B-acute lymphoblastic leukaemia", Nature Communications, vol. 6, Mar. 19, 2015, 1-12.

Mackiewicz, D. et al., "Distribution of Recombination Hotspots in the Human Genome—A Comparison of Computer Simulations with Real Data", PLOS One, vol. 8, No. 6, Jun. 2013, 11 pages.

Magbanua, M. J. et al., "Abstract PD2-01: Personalized serial circulating tumor DNA (ctDNA) analysis in high-risk early stage breast cancer patients to monitor and predict response to neoadjuvant therapy and outcome in the I-Spy 2 Trial", Cancer Research, vol. 79, No. 4 Supplement, Feb. 15, 2019.

Mamon, H. et al., "Letters to the Editor: Preferential Amplification of Apoptotic DNA from Plasma: Potential for Enhancing Detection of Minor DNA Alterations in Circulating DNA", Clinical Chemistry, vol. 54, No. 9, 2008, 1582-1584.

Maniatis, T. et al., "In: Molecular Cloning: A Laboratory Manual", Cold Spring Harbor Laboratory, New York, Thirteenth Printing, 1986, 458-459.

Mansfield, Elaine S , "Diagnosis of Down Syndrome and Other Aneuploidies Using Quantitative Polymerase Chain Reaction and Small Tandem Repeat Polymorphisms", Human Molecular Genetics, 2, 1, 1993, 43-50.

Mardis, E. R. , "The impact of next-generation sequencing technology on genetics", Trends in Genetics, vol. 24, No. 3, Feb. 11, 2008, 133-141.

Margulies, M. et al., "Genome sequencing in microfabricated high-density picolitre reactors", Nature, vol. 437, Sep. 15, 2005, 376-380.

Margulies, M. et al., "Genome sequencing in microfabricated high-density picolitre reactors plus Supplemental Methods", Nature, vol. 437, Sep. 15, 2005, 40 pgs.

Markoulatos, P. et al., "Multiplex Polymerase Chain Reaction: A Practical Approach", Journal of Clinical Laboratory Analysis, vol. 16, 2002, 47-51.

Masuzaki, H. et al., "Detection of cell free placental DNA in maternal plasma: direct evidence from three cases of confined placental mosaicism", J Med Genet, vol. 41, 2004, 289-292.

Matsuzaki, H. et al., "Genotyping over 100,000 SNPs on a pair of oligonucleotide arrays", Nature Methods, vol. 1, No. 2, Nov. 2004, 109-111.

May, Robert M. , "How Many Species Are There on Earth?", Science, 241, Sep. 16, 1988, 1441-1449.

McBride, D. et al., "Use of Cancer-Specific Genomic Rearrangements to Quantify Disease Burden in Plasma from Patients with Solid Tumors", Genes, Chromosomes & Cancer, vol. 49, Aug. 19, 2010, 1062-1069.

McCloskey, M. L. et al., "Encoding PCR Products with Batch-stamps and Barcodes", Biochem Genet., vol. 45, Oct. 23, 2007, 761-767.

McCray, Alexa T. et al., "Aggregating UMLS Semantic Types for Reducing Conceptual Complexity", Medinfo 2001: Proceedings of the 10th World Congress on Medical Informatics (Studies in Health Technology and Informatics, 84, V. Patel et al. (eds.), IOS Press Amsterdam, 2001, 216-220.

McDonald, B. R. et al., "Abstract P4-01-21: Multiplexed targeted digital sequencing of circulating tumor DNA to detect minimal residual disease in early and locally advanced breast cancer", Cancer Research, vol. 79, No. 4 Supplement, Feb. 15, 2019.

McDonald, J. P. et al., "Novel thermostable Y-family polymerases: applications for the PCR amplification of damaged or ancient DNAs", Nucleic Acids Research, vol. 34, No. 4, 2006, 1102-1111.

Mennuti, M. et al., "Is It Time to Sound an Alarm About False-Positive Cell-Free DNA Testing for Fetal Aneuploidy?", American Journal of Obstetrics, 2013, 5 pgs.

Merriam-Webster, , "Medical Definition of Stimulant", http://www.merriam-webster.com/medical/stimulant, Mar. 14, 2016, 7 pages.

Merriam-Webster, , "Universal Definition", Merriam-Webster.com, 3 pages.

Mersy, et al., "Noninvasive Detection of Fetal Trisomy 21: Systematic Review and Report of Quality and Outcomes of Diagnostic Accuracy Studies Performed Between 1997 and 2012", Human Reproduction Update, 19(4), 2013, 318-329.

Mertes, F. et al., "Targeted enrichment of genomic DNA regions for next-generation sequencing", Briefings in Functional Genomics, vol. 10, No. 6, Nov. 26, 2011, 374-386.

Metzker, M. L. et al., "Polymerase Chain Reaction", Encyclopedia of Medical Devices and Instrumentation, vol. 5, Second Edition, 2006, 380-387.

Metzker, M. L. et al., "Quantitation of Mixed-Base Populations of HIV-1 Variants by Automated DNA Sequencing with Bodipy* Dye-Labeled Primers", BioTechniques, vol. 25, Sep. 1998, 446-462.

Meyer, M et al., "Illumina Sequencing Library Preparation for Highly Multiplexed Target Capture and Sequencing", Cold Spring Harbor Protocols, vol. 2010, Issue 6, Jun. 2010, 1-10.

Meyerson, M. et al., "Advances in understanding cancer genomes through second-generation sequencing", Nature Reviews: Genetics, vol. 11, Oct. 2010, 685-696.

Mikkelsen, T. S. et al., "Genome-wide maps of chromatin state in pluripotent and lineage-committed cells", Nature, vol. 448, No. 2, Aug. 2007, 553-562.

Miller, Robert , "Hyperglycemia-Induced Changes in Hepatic Membrane Fatty Acid Composition Correlate with Increased Caspase-3 Activities and Reduced Chick Embryo Viability", Comparative Biochemistry and Physiology, Part B, 141, 2005, 323-330.

Miller, Robert R. , "Homocysteine-Induced Changes in Brain Membrane Composition Correlate with Increased Brain Caspase-3 Activities and Reduced Chick Embryo Viability", Comparative Biochemistry and Physiology Part B, 136, 2003, 521-532.

Miner, B. E. et al., "Molecular barcodes detect redundancy and contamination in hairpin-bisulfite PCR", Nucleic Acids Research, vol. 32, No. 17, Sep. 30, 2004, 1-4.

Minkoff, E. et al., "Stem Cells, Cell Division, and Cancer", Biology Today Third Edition, Chapter 12, 2004, 10 pages.

(56) References Cited

OTHER PUBLICATIONS

Morand, et al., "Hesperidin contributes to the vascular protective effects of orange juice: a randomized crossover study in healthy volunteers", Am J Clin Nutr. Jan. 2011;93(1):73-80. Epub Nov. 10, 2010.
Morris, J. K. et al., "Trends in Down's syndrome live births and antenatal diagnoses in England and Wales from 1989 to 2008: analysis of data from the National Down Syndrome Cytogenetic Register", BMJ Online, vol. 339, Oct. 2009, 5 pages.
Munne, S. et al., "Chromosome Abnormalities in Human Embryos", Textbook of Assisted Reproductive Techniques, 2004, pp. 355-377.
Munne, S. et al., "Chromosome abnormalities in human embryos", European Society of Human Reproduction and Embryology: Human Reproduction Update, vol. 4, No. 6, 1998, 842-855.
Munne, S. et al., "Improved implantation after preimplantation genetic diagnosis of aneuploidy", Reproductive BioMedicine Online, vol. 7., No. 1., May 15, 2003, 91-97.
Murali, R. et al., "Crystal structure of Taq DNA polymerase in complex with an inhibitory Fab: The Fab is directed against an intermediate in the helix-coil dynamics of the enzyme", Proc. Natl. Acad. Sci. USA, vol. 95, Oct. 1998, 12562-12567.
Murtaza, M. et al., "Non-Invasive Analysis of Acquired Resistance to Cancer Therapy by Sequencing of Plasma DNA", Nature (doi:10.1038/nature12065), 2013, 6 pgs.
Muse, Spencer V., "Examining rates and patterns of nucleotide substitution in plants", Plant Molecular Biology 42: 25-43, 2000.
Myers, Chad L. et al., "Accurate Detection of Aneuploidies in Array CGH and Gene Expression Microarray Data", Bioinformatics, 20(18), 2004, 3533-3543.
Nagalla, S. R. et al., "Proteomic Analysis of Maternal Serum in Down Syndrome: Identification of Novel Protein Biomarkers", Journal of Proteome Research, vol. 6, Mar. 21, 2007, 1245-1257.
Namlos, H. M. et al., "Noninvasive Detection of ctDNA Reveals Intratumor Heterogeneity and Is Associated with Tumor Burden in Gastrointestinal Stromal Tumor", Molecular Cancer Therapeutics, vol. 17, No. 11, 2018, 2473-2480.
Nannya, Yasuhito et al., "A Robust Algorithm for Copy Number Detection Using High-density Oligonucleotide Single Nucleotide Polymorphism Genotyping Arrays", Cancer Res., 65, 14, 2005, 6071-6079.
Narayan, A. et al., "Ultrasensitive measurement of hotspot mutations in tumor DNA in blood using error-suppressed multiplexed deep sequencing", Cancer Research, vol. 72, No. 14, Jul. 15, 2012, 3492-3498.
Natera, Inc., , "Declaration of Sandra L. Haberny", May 16, 2019, 3 pages.
Natera, Inc., , "Defendant Natera, Inc.'s Invalidity Contentions Under Patent L.R. 3-3; Document Production Accompanying Invalidity Contentions Under Patent L.R. 3-4", Aug. 20, 2018, 17 pages.
Natera, Inc., , "Exhibit 8 EHRICH Invalidity Chart", Aug. 20, 2018, 16 pages.
Natera, Inc., , "Exhibits A-H to Haberny Declaration", May 16, 2019, 192 pages.
Natera, Inc., , "Motion to Dismiss", May 16, 2019, 2 pages.
Natera, Inc., , "Natera Inc.'s First Amended Answer, Affirmative Defenses and Counterclaims", Aug. 16, 2018, 28 pages.
Natera, Inc., , "Natera, Inc.'s Supplemental Objections and Response to Plaintiff Illumina, Inc.'s Interrogatory No. 8", Mar. 20, 2019, 29 pages.
Natera, Inc., , "Opening Brief in Support of Motion to Dismiss", May 16, 2019, 26 pages.
Natera, Inc., , "Petitioner Reply Per Board Order of Nov. 2, 2018 (Paper No. 10)", Nov. 9, 2018, 8 pgs.
National Institutes of Health, , "Genetics Home Reference: Your Guide to Understanding Genetic Conditions", Feb. 28, 2014, 2 pgs.
Nawroz, H et al., "Microsatellite Alterations in Serum DNA of Head and Neck Cancer Patients", Nature Medicine, vol. 2, No. 9, Sep. 1996, 1035-1037.
NCBI, , "Blast of AAAAAAAAATTTAAAAAAAATTT", 2015, 9 pages.
NCBI, , "db SNP rs2056688", 2015, 3 pages.
NCBI, , "dbSNP record for rs1294331", Retrieved from the Internet: <URL: www.ncbi.nlm.nih.gov/snp/?term=rs 1294331 >, 2019, 2 pgs.
NCBI, , "dbSNP record for rs1872575", Retrieved from the Internet: <URL: www.ncbi.nlm.nih.gov/snp/?term=rs1872575, 2019, 2 pgs.
NCBI, , "dbSNP record for rs2362450", Retrieved from the Internet: <URL: www.ncbi.nlm.nih.gov/snp/?term=rs2362450>, 2019, 1 pg.
NCBI, , "dbSNP record for rs2384571", Retrieved from the Internet: <URL: www.ncbi.nlm.nih.gov/snp/?term=rs2384571>, 2019, 2 pgs.
NCBI, , "dbSNP record for rs2498982", Retrieved from the Internet: <URL: www.ncbi.nlm.nih.gov/snp/?term=rs2498982>, 2019, 3 pgs.
NCBI, , "dbSNP record for rs3731877", Retrieved from the Internet: <URL: www.ncbi.nlm.nih.gov/snp/?term=rs3731877>, 2019, 2 pgs.
New England Biolabs, , "Nucleic Acids, Linkers and Primers: Random Primers", 1998/99Catalog, 1998, 121 and 284.
Newman, A. M. et al., "Integrated digital error suppression for improved detection of circulating tumor DNA", Nature Biotechnology, vol. 34, No. 5, May 2016, 547-555.
Ng, S. B. et al., "Individualised multiplexed circulating tumour DNA assays for monitoring of tumour presence in patients after colorectal cancer surgery", Scientific Reports, vol. 7, No. 40737, Jan. 19, 2017, 11 pages.
Nguyen-Dumont, T. , "A high-plex PCR approach for massively parallel sequencing", BioTechniques, vol. 55, No. 2, Aug. 2013, 69-74.
Nicolaides, K. et al., "Noninvasive Prenatal Testing for Fetal Trisomies in a Routinely Screened First-Trimester Population", American Journal of Obstetrics (article in press), 207, 2012, 1.e1-1.e6.
Nicolaides, K.H et al., "Validation of Targeted Sequencing of Single-Nucleotide Polymorphisms for Non-Invasive Prenatal Detection of Aneuploidy of Chromosomes 13, 18, 21, X, and Y", Prenatal Diagnosis, 33, 2013, 575-579.
Nicolaides, Kypros H. et al., "Prenatal Detection of Fetal Triploidy from Cell-Free DNA Testing in Maternal Blood", Fetal Diagnosis and Therapy, 2013, 1-6.
Nilsson, M. et al., "Padlock Probes: Circularizing Oligonucleotides for Localized DNA Detection", Science, vol. 265, Sep. 10, 1994, 2085-2088.
Nishigaki, K. et al., "Random PCR-Based Genome Sequencing: A Non-Divide-and-Conquer Strategy", DNA Research, vol. 7, 2000, 19-26.
Nygren, et al., "Quantification of Fetal DNA by Use of Methylation-Based DNA Discrimination", Clinical Chemistry 56:10 1627-1635 (2010).
Ogino, S. et al., "Bayesian Analysis and Risk Assessment in Genetic Counseling and Testing", Journal of Molecular Diagnostics, 6 (1), 2004, 9 pgs.
Ohara, O et al., "One-sided Polymerase Chain Reaction: The Amplification of cDNA", Proceedings of the National Academy of Sciences, vol. 86, 1989, 5673-5677.
Ohsawa, M. et al., "Prenatal Diagnosis of Two Pedigrees of Fukuyama Type Congenital Muscular Dystrophy by Polymorphism Analysis", The Health and Welfare Ministry, 1994, 5 pgs.
Oliphant, A. et al., "Bead.Array™ Technology: Enabling an Accurate, Cost-Effective Approach to High-Throughput Genotyping", Bio Techniques, vol. 32, Jun. 2002, S56-S6.
Olivarius, S et al., "High-throughput Verification of Transcriptional starting Sites by Deep-RACE", Bio Techniques, vol. 46, No. 2, Feb. 2009, 130-132.
Olive, M. et al., "Characterization of the DiFi Rectal Carcinoma Cell Line Derived from a Familial Adenomatous Polyposis Patient", In Vitro Cellular & Developmental Biology, vol. 29A, No. 3, Part 1, Mar. 1993, 239-248.
Olney, R. S. et al., "Chorionic Villus Sampling and Amniocentesis: Recommendations for Prenatal Counseling", MMWR: Recommendations and Reports, 44(RR-9), Jul. 21, 1995, 1-12.
O'Malley, R. et al., "An adapter ligation-mediated PCR method for high-throughput mapping of T-DNA inserts in the *Arabidopsis* genome", Nat. Protoc., 2, 2007, 2910-2917.

(56) References Cited

OTHER PUBLICATIONS

Orozco A.F., et al., "Placental Release of Distinct DNA-Associated Micro-Particles into Maternal Circulation: Reflective of Gestation Time and Preeclampsia", Placenta,30, 2009, 891-897.

Ozawa, Makiko et al., "Two Families with Fukuyama Congenital Muscular Dystrophy that Underwent In Utero Diagnosis Based on Polymorphism Analysis", Clinical Muscular Dystrophy: Research in Immunology and Genetic Counseling—FY 1994 Research Report, (including text in Japanese), 1994, 8.

Paez, Guillermo J. et al., "Genome coverage and sequence fidelity of ϕ29 polymerase-based multiple strand displacement whole genome amplification", Nucleic Acids Research, 32(9), 2004, 1-11.

Page, S. L. et al., "Chromosome Choreography: The Meiotic Ballet", Science, 301, 2003, 785-789.

Palomaki, G. E. et al., "DNA sequencing of maternal plasma to detect Down syndrome: An international clinical validation study", Genetics In Medicine, vol. 13, No. 1, Nov. 2011, 913-920.

Palomaki, Glenn et al., "DNA Sequencing of Maternal Plasma Reliably Identifies Trisomy 18 and Trisomy 13 as Well as Down Syndrome: an International Collaborative Study", Genetics in Medicine, 2012, 10.

Palomaki, Glenn E. et al., "DNA Sequencing of Maternal Plasma to Detect Down Syndrome: An International Clinical Validation Study", Genetics in Medicine (pre-print version), 13, 2011, 8 pgs.

Papadopoulou, E. et al., "Cell-Free DNA and RNA in Plasma as a New Molecular Marker for Prostate Cancer", Oncology Research, vol. 14, 2004, 439-445.

Papageorgiou, Elisavet A. et al., "Fetal-Specific DNA Methylation Ratio Permits Noninvasive Prenatal Diagnosis of Trisomy 21", Nature Medicine (advance online publication), 17, 2011, 5 pgs.

Parameswaran, P. et al., "A pyrosequencing-tailored nucleotide barcode design unveils opportunities for large-scale sample multiplexing", Nucleic Acids Research, vol. 35, No. 19, Oct. 11, 2007, 9 pages.

Parker, A. V. et al., "The Effect of Sodium Citrate on the Stimulation of Polymorphonuclear Leukocytes", Investigative Ophthalmology & Visual Science, vol. 26, 1985, 1257-1261.

Pask, R. et al., "Investigating the utility of combining 29 whole genome amplification and highly multiplexed single nucleotide polymorphism BeadArray TM genotyping", BMC Biotechnology, vol. 4, No. 15, Jul. 27, 2004, 8 pages.

Pastinen, T. et al., "Minisequencing: A Specific Tool for DNA Analysis and Diagnostics on Oligonucleotide Arrays", Genome Research, vol. 7, 1997, 606-614.

Pathak, A. et al., "Circulating Cell-Free DNA in Plasma/Serum of Lung Cancer Patients as a Potential Screening and Prognostic Tool", Clinical Chemistry, 52, 2006, 1833-1842.

Patil, N. et al., "Blocks of Limited Haplotype Diversity Revealed by High-Resolution Scanning of Human Chromosome 21", Science, vol. 294, Nov. 23, 2001, 1719-1723.

Paunio, T. et al., "Preimplantation diagnosis by whole-genome amplification, PCR amplification, and solid-phase minisequencing of blastomere DNA", Clinical Chemistry, vol. 42, No. 9, 1996, 1382-1390.

PCT/US2006/045281, , "International Preliminary Report on Patentability", dated May 27, 2008, 1 pg.

PCT/US2006/045281, , "International Search Report and Written Opinion", dated Sep. 28, 2007, 7 pgs.

PCT/US2008/003547, , "International Search Report", dated Apr. 15, 2009, 5 pgs.

PCT/US2009/034506, , "International Search Report", dated Jul. 8, 2009, 2 pgs.

PCT/US2009/045335, , "International Search Report", dated Jul. 27, 2009, 1 pg.

PCT/US2009/052730, , "International Search Report", dated Sep. 28, 2009, 1 pg.

PCT/US2010/050824, , "International Search Report", dated Nov. 15, 2010, 2 pgs.

PCT/US2011/037018, , "International Search Report", dated Sep. 27, 2011, 2 pgs.

PCT/US2011/061506, , "International Search Report", dated Mar. 16, 2012, 1 pgs.

PCT/US2011/066938, , "International Search Report", dated Jun. 20, 2012, 1 pg.

PCT/US2012066339, , "International Search Report", dated Mar. 5, 2013, 1 pg.

PCT/US2013/028378, , "International Search Report and Written Opinion", dated May 28, 2013, 11 pgs.

PCT/US2013/57924, , "International Search Report and Written Opinion", dated Feb. 18, 2014, 8 pgs.

PCT/US2014/051926, , "International Search Report and Written Opinion", dated Dec. 9, 2014, 3 pgs.

Pearson, K. , "On the criterion that a given system of deviations from the probable in the case of a correlated system of variables is such that it can be reasonably supposed to have arisen from random sampling", Philosophical Magazine Series 5, vol. 50, Issue 302, 1900, 157-175.

Pelizzari, C. A. et al., "Quantitative analysis of DNA array autoradiographs", Nucleic Acids Research, vol. 28, No. 22, 2000, 4577-4581.

Pena, Sergio D.J et al., "Paternity Testing in the DNA Era", Trends In Genetics, 10, 6, 1994, 204-209.

Perakis, S. et al., "Advances in Circulating Tumor DNA Analysis", Advances in Clinical Chemistry, vol. 80, 2017, 73-153.

Pergament, E. et al., "Single-Nucleotide Polymorphism-Based Noninvasive Prenatal Screening in a High-Risk and Low-Risk Cohort", Obstetrics & Gynecology, vol. 124, No. 2, Part 1, Aug. 2014, 210-218 + Appendices.

Perkel, Jeffrey M. , "Overcoming the Challenges of Multiplex PCR", Biocompare Editorial Article, 2012, 1-5.

Perry, George H. et al., "The Fine-Scale and Complex Architecture of Human Copy-Number Variation", The American Journal of Human Genetics,82, 2008, 685-695.

Pertl, B. et al., "Detection of Male and Female Fetal DNA in Maternal Plasma by Multiplex Fluorescent Polymerase Chain Reaction Amplification of Short Tandem Repeats", Hum. Genet., 106, 2000, 45-49.

Peters, D. , "List of Materials Considered By David Peters, Ph.D.", Jun. 13, 2019, 2 pages.

Peters, David P. et al., "Noninvasive Prenatal Diagnosis of a Fetal Microdeletion Syndrome", New England Journal of Medicine, 365(19), 2011, 1847-1848.

Pfaffl, Michael W. , "Relative Expression Software Tool (REST ©) for Group-Wise Comparison and Statistical Analysis of Relative Expression Results in real-Time PCR", Nucleic Acids Research, 30(9), 2002, 10 pgs.

Philip, J. et al., "Late First-Trimester Invasive Prenatal Diagnosis: Results of an International Randomized Trial", American College of Obstetricians and Gynecologists, vol. 103, No. 6, Jun. 2004, 1164-1173.

Phillips, C. et al., "Resolving Relationship Tests that Show Ambiguous STR Results Using Autosomal SNPs as Supplementary Markers", Forensic Science International: Genetics 2, 2008, 198-204.

Pirker, C. et al., "Whole Genome Amplification for CGH Analysis: Linker-Adapter PCR as the Method of Choice for Difficult and Limited Samples", Cytometry Part A, vol. 61A, 2004, 26-34.

Podder, Mohua et al., "Robust SN P genotyping by multiplex PCR and arrayed primer", BMC Medical Genomics,1(5), 2008, 1-15.

Poirier, K. et al., "Maternal mosaicism for mutations in the ARX gene in a family with X linked mental retardation", Human Genetics, vol. 118, Aug. 3, 2005, 45-48.

Pont-Kingdon, G. et al., "Rapid Detection of Aneuploidy (Trisomy 21) by Allele Quantification Combined with Melting Curves Analysis of Single-Nucleotide Polymorphism Loci", Clinical Chemistry, vol. 49, No. 7, 2003, 1087-1094.

Poon, L. L. et al., "Differential DNA Methylation between Fetus and Mother as a Strategy for Detecting Fetal DNA in Maternal Plasma", Clinical Chemistry, vol. 48, No. 1, 2002, 35-41.

Popova, T. et al., "Genome Alteration Print (GAP): a tool to visualize and mine complex cancer genomic profiles obtained by SNP arrays", Genome Biology, vol. 10, R128, Nov. 11, 2009, 1-14.

(56) References Cited

OTHER PUBLICATIONS

Porreca, Gregory J et al., "Multiplex Amplification of Large Sets of Human Exons", Nature Methods, 4, (advance online publication), 2007, 6.
Price, T.S. et al., ""SW-ARRAY: a dynamic programming solution for the identification of copy-number changes in genomic DNA using array comparative genome hybridization data",", Nucleic Acids Research, vol. 33, No. 11, Jun. 16, 2005, 3455-3464.
Primdahl, H. et al., "Allelic Imbalances in Human Bladder Cancer: Genome-Wide Detection With High-Density Single-Nucleotide Polymorphism Arrays", Journal of the National Cancer Institute, vol. 94, No. 3, Feb. 6, 2002, 216-223.
Profitt, J et al., "Isolation And Characterisation of Recombination Events Involving Immunoglobulin Heavy Chain Switch Regions in Multiple Myeloma Using Long Distance Vectorette PCR (Ldv-pcr)", Leukemia, vol. 13, No. 7, Jul. 1999, 1100-1107.
Qin, Z. S. et al., "Partition-Ligation-Expectation-Maximization Algorithm for Haplotype Inference with Single-Nucleotide Polymorphisms", Am. J. Hum Genet., vol. 71, 2002, 1242-1247.
Quan, P. C. et al., "Studies on the mechanism of NK cell lysis", The Journal of Immunology, vol. 128, 1982, 1786-1791.
Quinlan, M. P., "Amniocentesis: Indications and Risks", American Medical Association Journal of Ethics: Virtual Mentor, vol. 10, No. 5, May 2008, 304-306.
Quinn, G. P. et al., "Experimental Design and Data Analysis for Biologists", Graphical Exploration of Data, 2002, 64-67.
Rabinowitz, et al., "Accurate Prediction of HIV-1 Drug Response from the Reverse Transcriptase and Protease Amino Acid Sequences Using Sparse Models Created by Convex Optimization", Bioinformatics, 22, 5, 2006, 541-549.
Rabinowitz, M., "A System and Method for Integrating, Validating and Applying Genetic and Clinical Data to Enhance Medical Decisions", Nov. 29, 2005, 155 pgs.
Rabinowitz, Matthew et al., "Origins and rates of aneuploidy inhuman blastomeres", Fertility and Sterility, vol. 97, No. 2, Feb. 2012, 395-401.
Rabinowitz, Matthew. et al., "Non-Invasive Prenatal Aneuploidy Testing of Chromosomes 13, 18, 21, X, and Y Using Targeted Sequencing of Polymorphic Loci", The American Society of Human Genetics, meeting poster, 2012, 1 pg.
Rachlin, J. et al., "Computational tradeoffs in multiplex PCR assay design for SNP genotyping", BMC Genomics, vol. 6, No. 102, Jul. 25, 2005, 11 pages.
Ragoussis, J., "Genotyping Technologies for Genetic Research", Annual Review of Genomics and Human Genetics, vol. 10 (1), Sep. 1, 2009, 117-133.
Rahmann, Sven et al., "Mean and variance of the Gibbs free energy of oligonucleotides in the nearest neighbor model under varying conditions", Bioinformatics, 20(17), 2004, 2928-2933.
Raindance Technologies, , "Multiplexing with RainDrop Digital PCR", Application Note, 2013, 2 pgs.
Rava, Richard P. et al., "Circulating Fetal Cell-Free DNA Fraction Differ in Autosomal Aneuploidies and Monosomy X", Clinical Chemistry, 60(1), (papers in press), 2013, 8 pgs.
Rechitsky, Svetlana et al., "Preimplantation Genetic Diagnosis with HLA Matching", Reproductive Bio Medicine Online, 9, 2, 2004, 210-221.
Reeves, R. H. et al., "Too much of a good thing: mechanisms of gene action in Down syndrome", Trends in Genetics, vol. 17, No. 2, Feb. 2, 2001, 83-88.
Reinert, T. et al., "Analysis of circulating tumour DNA to monitor disease burden following colorectal cancer surgery", Gut, vol. 65, 2016, 625-634.
Renwick, P. et al., "Proof of Principle and First Cases Using Preimplantation Genetic Haplotyping—A Paradigm Shift for Embryo Diagnosis", Reproductive BioMedicine Online, 13 (1), 2006, 110-119.
Rhoads, A. et al., "PacBio Sequencing and Its Applications", Genomics Proteomics Bioinformatics, vol. 13, Nov. 2, 2015, 278-289.

Ricciotti, Hope , "Eating by Trimester", Online]. Retrieved from Internet:<http://www.youandyourfamily.com/article.php?story=Eating+by+Trimester>, 2014, 3.
Riley, D. E., "DNA Testing: An Introduction For Non-Scientists An Illustrated Explanation", Scientific Testimony: An Online Journal, http://www.scientific.org/tutorials/articles/riley/riley.html, Apr. 6, 2005, 22 pages.
Riva, F., "Patient-Specific Circulating Tumor DNA Detection during Neoadjuvant Chemotherapy in Triple-Negative Breast Cancer", Clinical Chemistry, vol. 63, No. 3, 2017, 691-699.
Robertson, G. et al., "Genome-wide profiles of STAT1 DNA association using chromatin immunoprecipitation and massively parallel sequencing", Nature Methods, vol. 4, No. 8, Aug. 2007, 651-657.
Rogaeva, E. et al., "The Solved and Unsolved Mysteries of the Genetics of Early-Onset Alzheimer's Disease", NeuroMolecular Medicine, vol. 2, 2002, 1-10.
Roman, B. L. et al., "Non-Radioisotopic AFLP Method Using PCR Primers Fluorescently Labeled with CyA 5", BioTechniques, vol. 26, Feb. 1999, 236-238.
Roper, Stephen M. et al., "Forensic Aspects of DNA-Based Human Identity Testing", Journal of Forensic Nursing, 4, 2008, 150-156.
Rosado, J. A. et al., "Tyrosine kinases activate store-mediated Ca2+ entry in human platelets through the reorganization of the actin cytoskeleton", Biochem. J., vol. 351, 2000, 429-437.
Rosen, D. R. et al., "Mutations in Cu/Zn superoxide dismutase gene are associated with familial amyotrophic lateral sclerosis", Nature, vol. 362, Mar. 4, 1993, 59-62.
Roux, K., "Optimization and Troubleshooting in PCR", PCR Methods Appl. 4, 1995, 185-194.
Rozen, Steve et al., "Primer3 on the WWW for General Users and for Biologis Programmers", Methods in Molecular Biology, 132: Bioinformatics Methods and Protocols, 1999, 365-386.
Ruano, G. et al., "Haplotype of multiple polymorphisms resolved by enzymatic amplification of single DNA molecules", Proc. Nati. Acad. Sci. USA, vol. 87, Aug. 1990, 6296-6300.
Russell, L. M., "X Chromosome Loss and Ageing", Cytogenetic and Genome Res., 116, 2007, 181-185.
Ryan, A. et al., "Informatics-Based, Highly Accurate, Noninvasive Prenatal Paternity Testing", Genetics in Medicine (advance online publication), 2012, 5 pgs.
Ryan, B. M. et al., "A prospective study of circulating mutant KRAS2 in the serum of patients with colorectal neoplasia: strong prognostic indicator in postoperative follow up", Gut, vol. 52, 2003, 101-108.
Rychlik, et al., "Optimization of the annealing temperature for DNA amplification in vitro", Nucleic Acids Research, 18(21), 1990, 6409-6412.
Sahota, A., "Evaluation of Seven PCR-Based Assays for the Analysis of Microchimerism", Clinical Biochemistry, vol. 31, No. 8., 1998, 641-645.
Sahukhal, G. S. et al., "msaABCR operon positively regulates biofilm development by repressing proteases and autolysis in *Staphlococcus aureus*", FEMS Microbiology Letters, vol. 362, No. 4, 2015, 1-10.
Saito, H. et al., "Prenatal DNA diagnosis of a single-gene disorder from maternal plasma", The Lancet, vol. 356, Sep. 30, 2000, 1170.
Saker, A. et al., "Genetic characterisation of circulating fetal cells allows non-invasive prenatal diagnosis of cystic fibrosis", Prenatal Diagnosis, vol. 26, Jul. 11, 2006, 906-916.
Samango-Sprouse, C. et al., "SNP-Based Non-Invasive Prenatal Testing Detects Sex Chromosome Aneuploidies with High Accuracy", Prenatal Diagnosis, 33, 2013, 1-7.
Samura, O. et al., "Diagnosis of Trisomy 21 in Fetal Nucleated Erythrocytes from Maternal Blood by Use of Short Tandem Repeat Sequences", Clinical Chemistry, vol. 47, No. 9, 2001, 1622-1626.
Sanchez, C. et al., "New insights into structural features and optimal detection of circulating tumor DNA determined by single-strand DNA analysis", Nature Partner Journals, vol. 3, No. 31, Nov. 23, 2018, 12 pgs.
Sander, Chris , "Genetic Medicine and the Future of Health Care", Science, 287(5460), 2000, 1977-1978.
Santalucia, J. et al., "The Thermodynamics of DNA Structural Motifs", Annu. Rev. Biophys. Biomol. Struct., 33, 2004, 415-440.

(56) References Cited

OTHER PUBLICATIONS

Santalucia, John J.R et al., "Improved Nearest-Neighbor Parameters for Predicting DNA Duplex Stability", Biochemistry, 35, 1996, 3555-3562.
Santalucia, Jr., J. , "Physical Principles and Visual-OMP Software for Optimal PCR Design", Methods in Molecular Biology, vol. 402, 2007, 3-33.
Sasabe, Yutaka , "Genetic Diagnosis of Gametes and Embryos Resulting from ART", Japanese Journal of Fertility and Sterility, vol. 46, No. 1, 2001, 43-46.
Scarpa, A. et al., "Molecular Typing of Lung Adenocarcinoma on Cytological Samples Using a Multigene Next Generation Sequencing Panel", PLOS One, vol. 8, No. 11, Nov. 13, 2013, 6 pgs.
Scheet, P. et al., "A Fast and Flexible Statistical Model for Large-Scale Population Genotype Data: Applications to Inferring Missing Genotypes and Haplotypic Phase", The American Journal of Human Genetics, vol. 78, Apr. 2006, 629-644.
Schmitt, M. W. et al., "Detection of ultra-rare mutations by nextgeneration sequencing", PNAS, vol. 109, No. 36, Sep. 4, 2012, 14508-14513.
Schoske, R et al., "Multiplex PCR Design Strategy used for the Simultaneous Amplification of 10 Y Chromosome Short Tandem Repeat (STR) Loci", Analytical and Bioanalytical Chemistry, vol. 375, 2003, 333-343.
Schoumans, J et al., "Detection of chromosomal imbalances in children with idiopathic mental retardation by array based comparative genomic hybridisation (array-CGH)", JMed Genet, 42, 2005, 699-705.
Schubert, , "Picking out prenatal DNA", Nature Medicine, vol. 10, No. 785, Aug. 2004, 1 page.
Schwarzenbach, H. et al., "Cell-free nucleic acids as biomarkers in cancer patients", Nature Reviews: Cancer, vol. 11, Jun. 2011, 426-437.
Schwarzenbach, H. et al., "Evaluation of cell-free tumour DNA and RNA in patients with breast cancer and benign breast disease", Molecular BioSystems, vol. 7, 2011, 2848-2854.
Sebat, Jonathan et al., "Strong Association of De Novo Copy Number Mutations with Autism", Science, 316, 2007, 445-449.
Sehnert, A. et al., "Optimal Detection of Fetal Chromosomal Abnormalities by Massively Parallel DNA Sequencing of Cell-Free Fetal DNA from Maternal Blood", Clinical Chemistry (papers in press), 57 (7), 2011, 8 pgs.
Seppo, A. et al., "Detection of circulating fetal cells utilizing automated microscopy: potential for noninvasive prenatal diagnosis of chromosomal aneuploidies", Prenatal Diagnosis, vol. 28, Jul. 22, 2008, 815-821.
Sermon, Karen et al., "Preimplantation genetic diagnosis", The Lancet, Lancet Limited. 363(9421), 2000, 1633-1641.
Servin, B et al., "MOM: A Program to Compute Fully Informative Genotype Frequencies in Complex Breeding Schemes", Journal of Heredity, vol. 93, No. 3, Jan. 1, 2002 (Jan. 1, 2002), pp. 227-228.
Sham, P. et al., "DNA Pooling: A Tool for Large-Scale Association Studies", Nature Reviews Genetics, vol. 3, Nov. 2002, 862-871.
Shapero, M. H. et al., "MARA: A Novel Approach for Highly Multiplexed Locus-specific SNP Genotyping Using High-density DNA Oligonucleotide Arrays", Nucleic Acids Research, vol. 32, No. 22, 2004, 1-9.
Shaw-Smith, et al., "Microarray Based Comparative Genomic Hybridisation (array-CGH) Detects Submicroscopic Chromosomal Deletions and Duplications in Patients with Learning Disability/Mental Retardation and Dysmorphic Features", J. Med. Genet., 41, 2004, 241-248.
Shen, et al., "High-quality DNA sequence capture of 524 disease candidate genes", High-quality DNA sequence capture of 524 disease candidate genes, Proceedings of the National Academy of Sciences, vol. 108, No. 16, Apr. 5, 2011 (Apr. 5, 2011), pp. 6549-6554.
Shen, R. et al., "High-throughput SNP genotyping on universal bead arrays", Mutation Research, vol. 573, Feb. 11, 2005, 70-82.

Shen, Zhiyong , "MPprimer: a program for reliable multiplex PCR primer design", BMC Bioinformatics 2010, 11:143, 1-7.
Shendure, J. et al., "Accurate Multiplex Polony Sequencing of an Evolved Bacterial Genome", Science, Nov. 30, 2007, 18-24.
Shendure, J. et al., "Next-generation DNA sequencing", Nature Biotechnology, vol. 26, No. 10, Oct. 2008, 1135-1145.
Sherlock, J et al., "Assessment of Diagnostic Quantitative Fluorescent Multiplex Polymerase Chain Reaction Assays Performed on Single Cells", Annals of Human Genetics,62, 1, 1998, 9-23.
Shi, H. et al., "Melanoma whole-exome sequencing identifies V600E B-RAF amplification-mediated acquired B-RAF inhibitor resistance", Nature Communications, vol. 3, No. 724, Mar. 6, 2012, 8 pages.
Shinozaki, M. et al., "Utility of Circulating B-RAF DNA Mutation in Serum for Monitoring Melanoma Patients Receiving Biochemotherapy", Clin Cancer Res, vol. 13, No. 7, Apr. 1, 2007, 2068-2074.
Shiroguchi, K. et al., "Digital RNA sequencing minimizes sequence-dependent bias and amplification noise with optimized single-molecule barcodes", PNAS, vol. 109, No. 4, Jan. 24, 2012, 1347-1352.
Shokralla, S. et al., "Next-generation DNA barcoding: using next-generation sequencing to enhance and accelerate DNA barcode capture from single specimens", Molecular Ecology Resources, vol. 14, 2014, 892-901.
Short, N. J. et al., "Targeted next-generation sequencing of circulating cell-free DNA vs bone marrow in patients with acute myeloid leukemia", Blood Advances, vol. 4, No. 8, Apr. 23, 2020, 1670-1677.
Siebert, P. D. et al., "An improved PCR method for walking in uncloned genomic DNA", Nucleic Acids Research, vol. 23, No. 6, 1995, 1087-1088.
Sigdel, T. et al., "Plasma Donor-Derived Cell-Free DNA Quantification by massively multiplex PCR Distinguishes Kidney Transplant Acute Rejection", Transplantation, vol. 102, No. 7S, Jul. 2018, S178-S179.
Sigdel, T. K. et al., "Optimizing Detection of Kidney Transplant Injury by Assessment of Donor-Derived Cell-Free DNA via Massively Multiplex PCR", Journal of Clinical Medicine, vol. 8, No. 19, Dec. 23, 2018, 17 pages.
Simpson, J. et al., "Fetal Cells in Maternal Blood: Overview and Historical Perspective", Annals New York Academy of Sciences, 731, 1994, 1-8.
Sint, Daniela et al., "Advances in Multiplex PCR: Balancing Primer Efficiencies and Improving Detection Success", Methods in Ecology and Evolution, 3, 2012, 898-905.
Sivertsson, A. et al., "Pyrosequencing as an Alternative to Single-Strand Conformation Polymorphism Analysis for Detection of N-ras Mutations in Human Melanoma Metastases", Clinical Chemistry, vol. 48, No. 12, 2002, 2164-2170.
Slater, Howard et al., "High-Resolution Identification of Chromosomal Abnormalities Using Oligonucleotide Arrays Containing 116,204 SNPs", Am. J. Hum. Genet., 77, 5, 2005, 709-726.
Snijders, Antoine et al., "Assembly of Microarrays for Genome-Wide Measurement of DNA Copy Number", Nature Genetic, 29, 2001, 263-264.
Snyder, T. M. et al., "Universal noninvasive detection of solid organ transplant rejection", PNAS, vol. 108, No. 15, Apr. 12, 2011, 6229-6234.
Societies Related to Genetic Med, , "Guideline related to genetic examination", Japanese Society for Genetic Counseling, Japanese Society for Gene Diagnosis and Therapy, Japan Society of Obstetrics and Gynecology, 2003, 2-15.
Solomon, M. J. et al., "Formaldehyde-mediated DNA-protein crosslinking: A probe for in vivo chromatin structures", Proc. Natl. Acad. Sci. USA, vol. 82, 1985, 6470-6474.
sourceforge.net, , "Primer3", 2009, 1 pg.
Sparks, A. et al., "Non-Invasive Prenatal Detection and Selective Analysis of Cell-Free DNA Obtained from Maternal Blood: Evaluation for Trisomy 21 and Trisomy 18", American Journal of Obstetrics & Gynecology 206, 2012, 319.e1-319.e9.

(56) References Cited

OTHER PUBLICATIONS

Sparks, Andrew B. et al., "Selective Analysis of Cell-Free DNA in Maternal Blood for Evaluation of Fetal Trisomy", Prenatal Diagnosis, 32, 2012, 1-7.
Spencer, K. et al., "Maternal serum levels of dimeric inhibin A in pregnancies affected by trisomy 21 in the first trimester", Prenatal Diagnosis, vol. 21, 2001, 441-444.
Spencer, K. et al., "Maternal serum levels of total activin-A in first-trimester trisomy 21 pregnancies", Prenatal Diagnosis, vol. 21, 2001, 270-273.
Spertini, D. et al., "Screening of Transgenic Plants by Amplification of Unknown Genomic DNA Flanking T-DNA", BioTechniques, vol. 27, Aug. 1999, 308-314.
Spiro, Alexander et al., "A Bead-Based Method for Multiplexed Identification and Quantitation of DNA Sequences Using Flow Cytometry", Applied and Environmental Microbiology, 66, 10, 2000, 4258-4265.
Spits, C et al., "Optimization and Evaluation of Single-Cell Whole Genome Multiple Displacement Amplification", Human Mutation, 27(5), 496-503, 2006.
Srinivasan, et al., "Noninvasive Detection of Fetal Subchromosome Abnormalities via Deep Sequencing of Maternal Plasma", The American Journal of Human Genetics 92, 167-176, Feb. 7, 2013.
Stephens, M. et al., "Accounting for Decay of Linkage Disequilibrium in Haplotype Inference and Missing-Data Imputation", Am. J. Hum. Genet., vol. 76, 2005, 449-462.
Stephens, Mathews. et al., "A Comparison of Bayesian Methods for Haplotype Reconstruction from Population Genotype Data", Am. J. Hum. Genet.,73, 2003, 1162-1169.
Stevens, Robert et al., "Ontology-Based Knowledge Representation for Bioinformatics", Briefings in Bioinformatics, 1, 4, 2000, 398-414.
Stewart, C. M. et al., "Circulating cell-free DNA for non-invasive cancer management", Cancer Genetics, vol. 228-229, 2018, 169-179.
Steyerberg, E.W et al., "Application of Shrinkage Techniques in Logistic Regression Analysis: A Case Study", Statistica Neerlandica, 55(1), 2001, 76-88.
Strom, C. et al., "Three births after preimplantation genetic diagnosis for cystic fibrosis with sequential first and second polar body analysis", American Journal of Obstetrics and Gynecology, 178 (6), 1998, 1298-1306.
Strom, Charles M. et al., "Neonatal Outcome of Preimplantation Genetic Diagnosis by Polar Body Removal: The First 109 Infants", Pediatrics, 106( 4), 2000, 650-653.
Stroun, Maurice et al., "Prehistory of the Notion of Circulating Nucleic Acids in Plasma/Serum (CNAPS): Birth of a Hypothesis", Ann. N.Y. Acad. Sci., 1075, 2006, 10-20.
Su, S.Y. et al., ""Inferring combined CNV/SNP haplotypes from genotype data"", Bioinformatics, vol. 26, No. 11,1, Jun. 1, 2010, 1437-1445.
Su, Z. et al., "A Platform for Rapid Detection of Multiple Oncogenic Mutations With Relevance to Targeted Therapy in Non-Small-Cell Lung Cancer", The Journal of Molecular Diagnostics,, vol. 13, No. 1, Jan. 2011, 74-84.
Sun, Guihua et al., "SNPs in human miRNA genes affect biogenesis and function", RNA, 15(9), 2009, 1640-1651.
Sweet-Kind Singer, J. A. et al., "Log-penalized linear regression", IEEE International Symposium on Information Theory, 2003. Proceedings, 2003, 286.
Swinkels, D. W. et al., "Effects of Blood-Processing Protocols on Cell-free DNA Quantification in Plasma", Clinical Chemistry, vol. 49, No. 3, 2003, 525-526.
Syvanen, A.C. , "Toward genome-wide SNP genotyping", Nature Genetics Supplement, vol. 37, Jun. 2005, S5-S10.
Taback, B. et al., "Quantification of Circulating DNA in the Plasma and Serum of Cancer Patients", Ann. N.Y. Acad. Sci, vol. 1022, 2004, 17-24.
Takano, T. et al., "Epidermal Growth Factor Receptor Gene Mutations and Increased Copy Numbers Predict Gefitinib Sensitivity in Patients With Recurrent Non-Small-Cell Lung Cancer", Journal of Clinical Oncology, vol. 23, No. 28, Oct. 1, 2005, 6829-6837.
Takara Biomedicals, , "Competitive PCR Guide", Lit. # L0126, Aug. 1999, 9 pages.
Taliun, D. et al., "Efficient haplotype block recognition of very long and dense genetic sequences", BMC Bioinformatics, vol. 15 (10), 2014, 1-18.
Tamura, et al., "Sibling Incest and formulation of paternity probability: case report", Legal Medicine, 2000, vol. 2, p. 189-196.
Tang, et al., , Multiplex fluorescent PCR for noninvasive prenatal detection of fetal-derived paternally inherited diseases using circulatory fetal DNA in maternal plasma, Eur J Obstet Gynecol Reprod Biol, 2009, v.144, No. 1, p. 35-39.
Tang, N. et al., "Detection of Fetal-Derived Paternally Inherited X-Chromosome Polymorphisms in Maternal Plasma", Clinical Chemistry, 45 (11), 1999, 2033-2035.
Tebbutt, S. J. et al., "Microarray genotyping resource to determine population stratification in genetic association studies of complex disease", BioTechniques, vol. 37, Dec. 2004, 977-985.
Ten Bosch, J. , "Keeping Up With the Next Generation Massively Parallel Sequencing in Clinical Diagnostics", Journal of Molecular Diagnostics, vol. 10, No. 6, 2008, 484-492.
Tewhey, R. et al., "Microdroplet-based PCR enrichment for large-scale targeted sequencing", Nature Biotechnology, vol. 27, No. 11, Nov. 2009, 1025-1031.
Tewhey, R. et al., "The importance of phase information for human genomics", Nature Reviews Genetics, vol. 12, No. 3, Mar. 1, 2011, 215-223.
Thavarajah, R. et al., "Chemical and physical basics of routine formaldehyde fixation", Journal of Oral and Maxillofacial Pathology, vol. 16, No. 3, 2012, 400-405.
The Bump Message Boards, , The Bump (Panorama Test, attached), Jul. 1, 2013, 8 pages.
The International Hapmap Consort, , "The International HapMap Project", Nature, vol. 426, Dec. 18, 2003, 789-796.
Thermofisher Scientific, , "Ion AmpliSeq Cancer Hotspot Panel v2", Retrieved from the Internet: https://tools.thermofisher.com/content/sfs/brochures/Ion-AmpliSeq-Cancer-Hotspot-Panel-Flyer.pdf, 2015, 2 pages.
Thomas, M.R et al., "The Time of Appearance and Disappearance of Fetal DNA from the Maternal Circulation", Prenatal Diagnosis, 15, 1995, 641-646.
Tiersch, T. R. et al., "Reference Standards for Flow Cytometry and Application in Comparative Studies of Nuclear DNA Content", Cytometry, vol. 10, Mar. 21, 1989, 706-710.
Tong, Yu et al., "Noninvasive Prenatal Detection of Fetal Trisomy 18 by Epigenetic Allelic Ratio Analysis in Maternal Plasma: Theoretical and Empirical Considerations", Clinical Chemistry, 52(12), 2006, 2194-2202.
Tong, Yu K. et al., "Noninvasive Prenatal Detection of Trisomy 21 by Epigenetic-Genetic Chromosome-Dosage Approach", Clinical Chemistry, 56(1), 2010, 90-98.
Tounta, G et al., "Non-invasive prenatal diagnosis using cell-free fetal nucleic acids in maternal plasma: Progress overview beyond predictive and personalized diagnosis", EPMA Journal, vol. 2, Issue 2, 2011, 163-171.
Tounta, G. et al., "A Multiplex PCR for Non-invasive Fetal RHD Genotyping Using Cell-free Fetal DNA", in vivo, vol. 25, 2011, 411-418.
Treff, N. R. et al., "Single Cell Whole Genome Amplification Technique Significantly Impacts the Accuracy and Precision of Microarray Based 23 Chromosome Aneuploidy Screening", Poster Presentations Preimplantation Genetic Diagnosis, vol. 88, Supplement 1, Sep. 1, 2007, S231.
Troutt, et al., "Ligation-anchored PCR: A Simple Amplification Technique with Single-sided Specificity", Proceedings of the National Academy of Sciences, vol. 89, Oct. 1992, 9823-9825.
Troyanskaya, Olga G. et al., "A Bayesian Framework for Combining Heterogeneous Data Sources for Gene Function Prediction (in *Saccharomyces cerevisiae*)", PNAS, 100(14), 2003, 8348-8353.
Tsangaris, G. T. et al., "Proteomic analysis of amniotic fluid in pregnancies with Down syndrome", Proteomics, vol. 6, 2006, 4410-4419.

(56) References Cited

OTHER PUBLICATIONS

Tsui, N. B. et al., "Systematic micro-array based identification of placental mRNA in maternal plasma: towards non-invasive prenatal gene expression profiling", J. Med. Genet, vol. 41, 2004, 461-467.

Tsui, Nancy B.Y et al., "Non-Invasive Prenatal Detection of Fetal Trisomy 18 by RNA-SNP Allelic Ratio Analysis Using Maternal Plasma SERPINB2 mRNA: A Feasibility Study", Prenatal Diagnosis, 29, 2009, 1031-1037.

Tu, J. et al., "Pair-barcode high-throughput sequencing for large-scale multiplexed sample analysis", BMC Genomics, vol. 13, No. 43, Jan. 25, 2012, 1-9.

Tufan, N L. et al., "Analysis of Cell-Free Fetal DNA from Maternal Plasma and Serum Using a Conventional Multiplex PCR: Factors Influencing Success", The Turkish Journal of Medical Sciences, vol. 35, 2005, 85-92.

Turner, E. et al., "Massively Parallel Exon Capture and Library-Free Resequencing Across 16 Genomes", Nature Methods, 6 (5), 2009, 315-316.

Tynan, J. A. et al., "Restriction Enzyme-Mediated Enhanced Detection of Circulating Cell-Free Fetal DNA in Maternal Plasma", The Journal of Molecular Diagnostics, vol. 13, No. 4, Jul. 2011, 382-389.

Tzimagiorgis, G. et al., "Recovering circulating extracellular or cell-free RNA from bodily fluids", Cancer Epidemiology, vol. 35, 2011, 580-589.

Urbaniak, S. J. et al., "RhD haemolytic disease of the fetus and the newborn", Blood Reviews, vol. 14, 2000, 44-61.

Vallone, P. M. et al., "A multiplex allele-specific primer extension assay for forensically informative SNPs distributed throughout the mitochondrial genome", Int J Legal Medicine, vol. 118, Feb. 4, 2004, 147-157.

Vallone, Peter , "AutoDimer: a Screening Tool for Primer-Dimer and Hairpin Structures", Bio Techniques, 37, 2004, 226-231.

Van Den Oever, J. M. et al., "Single Molecule Sequencing of Free DNA from Maternal Plasma for Noninvasive Trisomy 21 Detection", Clinical Chemistry, vol. 58, No. 4, 2012, 699-706.

Van Uitert, I. et al., "The influence of different membrane components on the electrical stability of bilayer lipid membranes", Biochimica et Biophysica Acta, vol. 1798, 2010, 21-31.

Varley, Katherine Elena et al., "Nested Patch PCR Enables Highly Multiplexed Mutation Discovery in Candidate Genes", Genome Res., 18(11), 2008, 1844-1850.

Verlinsky, Y. et al., "Over a Decade of Experience with Preimplantation Genetic Diagnosis", Fertility and Sterility, 82 (2), 2004, 302-303.

Vogelstein, B. et al., "Digital PCR", Proc. Natl. Acad. Sci. USA, vol. 96, Aug. 1999, 9236-9241.

Von Eggeling, F. et al., "Applications of Random PCR", Cellular and Molecular Biology, vol. 41, No. 5, 1995, 653-670.

Wagner, Jasenka et al., "Non-Invasive Prenatal Paternity Testing from Maternal Blood", Int. J. Legal Med., 123, 2009, 75-79.

Wang, D. G. et al., "Large-Scale Identification, Mapping, and Genotyping of Single-Nucleotide Polymorphisms in the Human Genome", Science, vol. 280, May 15, 1998, 1077-1082.

Wang, Eric et al., "Gestational Age and Maternal Weight Effects on Fetal Cell-Free DNA in Maternal Plasma", Prenatal Diagnosis, 33, 2013, 662-666.

Wang, Hui-Yun et al., "A genotyping system capable of simultaneously analyzing >1000 single nucleotide polymorphisms in a haploid genome", Genome Res., 15, 2005, 276-283.

Wang, J. et al., "Genome-wide Single-Cell Analysis of Recombination Activity and De Novo Mutation Rates in Human Sperm", Cell, vol. 150, Jul. 20, 2012, 402-412.

Wang, S. et al., "Potential Clinical Significance of a Plasma-Based KRAS Mutation Analysis in Patients with Advanced Non-Small Cell Lung Cancer", Clin Cancer Res, vol. 16, No. 4, Feb. 15, 2010, 1324-1330.

Wang, T.L. et al., "Digital karyotyping", PNAS, vol. 99, No. 25, Dec. 10, 2002, 16156-16161.

Wang, W.-P. et al., "Multiplex single nucleotide polymorphism genotyping by adapter ligation-mediated allele-specific amplification", Analytical Biochemistry, vol. 355, May 5, 2006, 240-248.

Wang, Yuker et al., "Allele quantification using molecular inversion probes (MIP)", Nucleic Acids Research, vol. 33, No. 21, Nov. 28, 2005, 14 pgs.

Wapner, R. et al., "Chromosomal Microarray Versus Karyotyping for Prenatal Diagnosis", The New England Journal of Medicine, 367 (23), 2012, 2175-2184.

Wapner, R. et al., "First-Trimester Screening for Trisomies 21 and 18", The New England Journal of Medicine, vol. 349, No. 15, Oct. 9, 2003, 1405-1413.

Wapner, R. J. et al., "Expanding the scope of noninvasive prenatal testing: detection of fetal microdeletion syndromes", American Journal of Obstetrics & Gynecology, vol. 212, Dec. 17, 2014, 1.e1-1.e9.

Watkins, N. et al., "Thermodynamic contributions of single internal rA •dA, rC • dC, rG • dG and rU • dT mismatches in RNA/DNA duplexes", Nucleic Acids Research, 9 (5),, 2010, 1894-1902.

Wei, C. et al., "Detection and Quantification by Homogeneous PCR of Cell-free Fetal DNA in Maternal Plasma", Clinical Chemistry, vol. 47, No. 2, 2001, 336-338.

Weiss, C. A. , "Chapter 8: Confidence Intervals for One Population Mean", Introductory Statistics, Sixth Edition, 2002, 340-381.

Wells, D , "Microarray for Analysis and Diagnosis of Human Embryos", 12th International Congress on Prenatal Diagnosis and Therapy, Budapest, Hungary, 2004, 9-17.

Wells, Dagan , "Advances in Preimplantation Genetic Diagnosis", European Journal of Obstetrics and Gynecology and Reproductive Biology, 115S, 2004, S97-S101.

Wells, Dagan , "Detailed Chromosomal and Molecular Genetic Analysis of Single Cells by Whole Genome Amplification and Comparative Genomic Hybridisation", Nucleic Acids Research, 27, 4, 1999, 1214-1218.

Wen, Daxing et al., "Universal Multiples PCR: A Novel Method of Simultaneous Amplification of Multiple DNA Fragments", Plant Methods, 8(32), Null, 2012, 1-9.

What to Expect Message Boards, , What To Expect (Weird Harmony results), May 1, 2015, 7 pages.

Widlak, P. et al., "Cleavage Preferences of the Apoptotic Endonuclease DFF 40 (Caspase~activated DNase or Nuclease) on Naked DNA and Chromatin Substrates", The Journal of Biological Chemistry, vol. 275, No. 11, Mar. 17, 2000, 8228-8232.

Wikipedia, , "Buffy coat", Retrieved from "https://en.wikipedia.orgJw/index.php?title=Buffy_coat&oldid=900992886", Jun. 9, 2019, 2 pgs.

Wikipedia, , "Maximum a posteriori estimation", https://en.wikipedia.org/w/index.php?title=Maximum_ajoosteriori_estimation&oldid=26878808, [retrieved on Aug. 1, 2017], Oct. 30, 2005, 2 pages.

Wikipedia, , "Stimulant", 17 pages.

Wilton, et al., "Birth of a Healthy Infant After Preimplantation Confirmation of Euploidy by Comparative Genomic Hybridization", N. Engl. J. Med., 345(21), 2001, 1537-1541.

Wilton, L. , "Preimplantation Genetic Diagnosis and Chromosome Analysis of Blastomeres Using Comparative Genomic Hybridization", Human Reproduction Update, 11 (1), 2005, 33-41.

Winsor, E. J. et al., "Maternal Cell Contamination in Uncultured Amniotic Fluid", Prenatal Diagnosis, vol. 16, 1996, 49-54.

Wittwer, C. T. et al., "Real-Time Multiplex PCR Assays", Methods, vol. 25, 2001, 430-448.

Wong, K. K. et al., "Allelic imbalance analysis by high-density single nucleotide polymorphic allele (SNP) array with whole genome amplified DNA", Nucleic Acids Research, vol. 32, No. 9, May 17, 2004, 8 pages.

Wright, C. et al., "The use of cell-free fetal nucleic acids in maternal blood for non-invasive prenatal diagnosis", Human Reproduction Update, vol. 15, No. 1, 2009, 139-151.

Wright, C. F. et al., "Cell-free fetal DNA and RNA in maternal blood: implications for safer antenatal testing", BMJ, vol. 39, Jul. 18, 2009, 161-165.

Wu, T.L. et al., "Cell-free DNA: measurement in various carcinomas and establishment of normal reference range", Clinica Chimica Acta, vol. 321, 2002, 77-87.

(56) References Cited

OTHER PUBLICATIONS

Wu, Y. Y. et al., "Rapid and/or high-throughput genotyping for human red blood cell, platelet and leukocyte antigens, and forensic applications", Clinica Chimica Acta, vol. 363, 2006, 165-176.
Xia, Tianbing et al., "Thermodynamic Parameters for an Expanded Nearest-Neighbor Model for Formation of RNA Duplexes with Watson-Crick Base Pairs", Biochemistry, 37, 1998, 14719-14735.
Xu, N. et al., "A Mutation in the Fibroblast Growth Factor Receptor 1 Gene Causes Fully Penetrant Normosmic Isolated Hypogonadotropic Hypogonadism", The Journal of Clinical Endocrinology & Metabolism, vol. 92, No. 3, 2007, 1155-1158.
Xu, S. et al., "Circulating tumor DNA identified by targeted sequencing in advanced-stage non-small cell lung cancer patients", Cancer Letters, vol. 370, 2016, 324-331.
Yamada, T. et al., "Detection of K-ras Gene Mutations in Plasma DNA of Patients with Pancreatic Adenocarcinoma: Correlation with Clinicopathological Features", Clinical Cancer Research, vol. 4, Jun. 1998, 1527-1532.
Yamada, T. et al., "PrimerStation: a highly specific multiplex genomic PCR primer design server for the human genome", Nucleic Acids Research, vol. 34, 2006, W665-W669.
Yaron, Y. , "The implications of non-invasive prenatal testing failures: a review of an under-discussed phenomenon", Prenatal Diagnosis, vol. 36, 2016, 391-396.
Yeh, Iwei et al., "Knowledge Acquisition, Consistency Checking and Concurrency Control for Gene Ontology (GO)", Bioinformatics, 19, 2, 2003, 241-248.
You, Frank M. et al., "BatchPrimer3: A high throughput web application for PCR and sequencing primer design", BMC Bioinformatics, Biomed Central, London, GB, vol. 9, No. 1, May 29, 2008 (May 29, 2008), p. 253.
Yuan, X. et al., "Probability Theory-based SNP Association Study Method for Identifying Susceptibility Loci and Genetic Disease Models in Human Case-Control Data", IEEE Trans Nanobioscience, vol. 9, No. 4, Dec. 2010, 232-241.
Yung, T. K. et al., "Single-Molecule Detection of Epidermal Growth Factor Receptor Mutations in Plasma by Microfluidics Digital PCR in Non-Small Cell Lung Cancer Patients", Clinical Cancer Research, vol. 15, Mar. 10, 2009, 2076-2084.
Zachariah, R. et al., "Circulating cell-free DNA as a potential biomarker for minimal and mild endometriosis", Reproductive BioMedicine Online, vol. 18, No. 3, Jan. 27, 2009, 4007-411.
Zhang, J. et al., "Presence of Donor-and Recipient-derived DNA in Cell-free Urine Samples of Renal Transplantation Recipients: Urinary DNA Chimerism", Clinical Chemistry, vol. 45, No. 10, 1999, 1741-1746.
Zhang, L. et al., "Whole genome amplification from a single cell: Implications for genetic analysis", Proc. Nat'l. Acad. Sci. USA, vol. 89, Jul. 1992, 5847-5851.
Zhang, Rui et al., "Quantifying RNA allelic ratios by microfluidic multiplex PCR and sequencing", Nature Methods, 11(1), 2014, 51-56.
Zhao, Xiaojun et al., "An Integrated View of Copy Number and Allelic Alterations in the Cancer Genome Using Single Nucleotide Polymorphism Arrays", Cancer Research,64, 2004, 3060-3071.
Zheng, S. et al., "Whole Genome Amplification Increases the Efficiency and Validity of Buccal Cell Genotyping in Pediatric Populations1", Cancer Epidemiology, Biomarkers & Prevention, vol. 10, Jun. 2001, 697-700.
Zheng, Z et al., "Anchored Multiplex PCR for Targeted Next-generation Sequencing", Nature Medicine, vol. 20, No. 12, Dec. 2014, 1479-1486.
Zhong, X Y. et al., "Detection of Fetal Rhesus D And Sex Using Fetal DNA from Maternal Plasma by Multiplex Polymerase Chain Reaction", British Journal of Obstetrics and Gynaecology, vol. 107, Jun. 2000, 766-769.
Zhong, X. et al., "Risk free simultaneous prenatal identification of fetal Rhesus D status and sex by multiplex real-time PCR using cell free fetal DNA in maternal plasma", Swiss Medical Weekly, vol. 131, Mar. 2001, 70-74.
Zhou, W. et al., "Counting Alleles Reveals a Connection Between Chromosome 18q Loss and Vascular Invasion", Nature Biotechnology, 19, 2001, 78-81.
Zhou, W. et al., "Counting alleles to predict recurrence of early-stage colorectal cancers", The Lancet, vol. 359, Jan. 19, 2002, 219-225.
Zimmermann, et al., "Noninvasive Prenatal Aneuploidy Testing of Chromosomes 13, 18, 21 X, and Y, Using targeted Sequencing of Polymorphic Loci", Prenatal Diagnosis, 32, 2012, 1-9.
Zimmermann, B. , "Declaration Under 37 CFR 1.32", filed in U.S. Appl. No. 14/171,587, filed Feb. 3, 2014, 4 pgs.
Zimmermann, B. et al., "Digital PCR: a powerful new tool for noninvasive prenatal diagnosis?", Prenatal Diagnosis, vol. 28, Nov. 10, 2008, 1087-1093.
Zimmermann, B. , "Noninvasive prenatal aneuploidy testing of chromosomes 13, 18, 21, X, and Y, using targeted sequencing of polymorphic loci, Supplemental Information", Prenatal Diagnosis, vol. 32, 2012, 7 pages.
Zimmermann, B. et al., "Novel Real-Time Quantitative PCR Test for Trisomy 21", Clinical Chemistry, vol. 48, No. 2, 2002, 362-363.
Zimmermann, B. et al., "Optimized Real-Time Quantitative PCR Measurement of Male Fetal DNA in Maternal Plasma", Clinical Chemistry, vol. 51, No. 9, 2005, 1598-1604.
Zimmermann, B. et al., "Real-Time Quantitative Polymerase Chain Reaction Measurement of Male Fetal DNA in Maternal Plasma", Methods in Molecular Medicine, vol. 132, 2007, 43-49.
Zimmermann, B. et al., "Use of Real-Time Polymerase Chain Reaction for the Detection of Fetal Aneuploidies", Methods in Molecular Biology, vol. 336, Feb. 2006, 83-100.
Zlotogora, J. , "Penetrance and expressivity in the molecular age", Genetics in Medicine, vol. 5, No. 5, 2003, 347-352.
Abd-Elsalam, Kamel A. , "Bioinformatic Tools And Guideline for PCR Primer Design", African Journal of Biotechnology, vol. 2, 2003, pp. 91-95.
Adalsteinsson, V. A. et al., "Scalable whole-exome sequencing of cell-free DNA reveals high concordance with metastatic tumors", Nature Communications, vol. 18, No. 1324, 2017, 13 pages.
Adinolfi, M. et al., "Rapid Detection of Aneuploidies by Microsatellite and the Quantitative Fluorescent Polymerase Chain Reaction", Prenatal Diagnosis, vol. 17, No. 13, 1997, 1299-1311.
Alizadeh, Mehdi et al., "Quantitative Assessment of Hematopoietic Chimerism after Bone Marrow Transplantation by Real-time Quantitative Polymerase Chain Reaction", Blood, vol. 99, No. 12, Jun. 15, 2002, 4618-4625.
Ansorge, Wilhelm J. , "Next-generation DNA Sequencing Techniques", New Biotechnology, vol. 25, No. 4, Feb. 2, 2009, 195-203.
Arandjelovic, M. et al., "Two-Step Multiplex Polymerase Chain Reaction improves the Speed and Accuracy of Genotyping Using DNA from Noninvasive and Museum Samples", Molecular Ecology Resources, vol. 9, 2009, pp. 28-36.
Avent, Neil D. et al., "Cell-free Fetal DNA in The Maternal Serum And Plasma: Current And Evolving Applications", Current Opinion in Obstretrics and Gynecology, vol. 21, No. 2, Apr. 1, 2009, 175-179.
Ayala, et al., "Long-Term Follow-Up of Donor Chimerism Tolerance After Human Liver Transplantation", Liver Transplantation, vol. 15, No. 6,, May 28, 2009, 581-591.
Balavoine, Guillaume , "Identification of Members of Several Homeobox Genes in a Planarian Using a Ligation-Mediated Polymerase Chain Reaction Technique", Nucleic Acids Research, vol. 24, 1996, pp. 1547-1553.
Balduini, et al., "Utility of Biochemical Markers in The Follow-up Heart Transplant Recipients", Transplantation Proceedings, vol. 35, No. 8, Dec. 1, 2003, 3075-3078.
Barbazuk, et al., "SNP Discovery via 454 Transcriptome Sequencing", The Plant Journal, vol. 51, Jul. 27, 2007, 910-918.
Bartlett, John M. et al., "PCR Protocols", PCR Protocols, vol. 226, 2003, 519 pages.
Baxter-Lowe, et al., "Tracking Microchimeric DNA In Plasma To Diagnose And Manage Organ Transplant Rejection", Clinical Chemistry, vol. 52, No. 4, Apr. 1, 2006, 559-561.
Beck, et al., "Next Generation Sequencing of Serum Circulating Nucleic Acids from Patients with Invasive Ductal Breast Cancer

(56) References Cited

OTHER PUBLICATIONS

Reveals Differences to Healthy and Nonmalignant Controls", Molecular Cancer Research, vol. 8, No. 3, Mar. 1, 2010, 335-342.
Belostotsky, Dmitry A. et al., "Plant Systems Biology", Methods in Molecular Biology, vol. 553, Aug. 25, 2009, 3-408.
Bender, et al., "A Multiplex SNP Typing Approach For The DNA Pyrosequencing Technology", International Congress Series, vol. 1288, Apr. 20, 2006, 73-75.
Benjamini, Y. et al., "Controlling the False Discovery Rate: A Practical and Powerful Approach to Multiple Testing", Journal of the Royal Statistical Society, Series B (Methodological), vol. 57, No. 1, 1995, 289-300.
Bentley, et al., "High-resolution, High-throughput HLA Genotyping by Next-generation Sequencing", Tissue Antigens, vol. 74, No. 5, Nov. 1, 2009, 393-403.
Bordoni, et al., "Evaluation Of Human Gene Variant Detection In Amplicon Pools By The GS-FLX Parallel Pyrosequencer", BMC Genomics, vol. 9, Oct. 8, 2008, 1-8.
Brastianos, P. K. et al., "Genomic Characterization of Brain Metastases Reveals Branched Evolution and Potential Therapeutic Targets", Cancer Discovery, vol. 5, Sep. 26, 2015, 1164-1177.
Brockman, et al., "Quality Scores And SNP Detection In Sequencing-by-synthesis Systems", Genome Research, vol. 18, No. 5, May 1, 2008, 763-770.
Bustamante-Aragones, Ana et al., "New Strategy for The Prenatal Detection/Exclusion of Paternal Cystic Fibrosis Mutations in Maternal Plasma", Journal of Cystic Fibrosis, vol. 7, Issue 6, Nov. 1, 2008, 505-510.
Butler, et al., "Cardiovascular Magnetic Resonance In The Diagnosis Of Acute Heart Transplant Rejection: A Review", Journal of Cardiovascular Magnetic Resonance, vol. 11, No. 1, Mar. 12, 2009, 1-11.
Castleberry, C. D. et al., "Quantification of Circulating Cell-Free DNA in Pediatric Heart Transplant Recipients", Journal of Heart and Lung Transplantation, vol. 30, No. 4, Apr. 1, 2011, S139.
Chan, Allen K. et al., "Cell-free Nucleic Acids In Plasma, Serum And Urine: A New Tool In Molecular Diagnosis", Annals of Clinical Biochemistry, vol. 40, Issue 2, Mar. 1, 2003, 122-130.
Chavali, Sreenivas et al., "Oligonucleotide Properties Determination And Primer Designing: A Critical Examination of Predictions", Bioinformatics, vol. 21, 2005, pp. 3918-3925.
Chen, Bing-Yuan et al., "PCR Cloning Protocols", PCR Cloning Protocols, vol. 192, 2002, 434 pages.
Church, et al., "Multiplex DNA Sequencing", Science, vol. 240, No. 4849, Apr. 8, 1988, 185-188.
Couraud, S. et al., "Noninvasive Diagnosis of Actionable Mutations by Deep Sequencing of Circulating Free DNA in lung Cancer from Never-Smokers: A Proof-of-Concept Study from BioCAST / IFCT-1002", Clinical Cancer Research, vol. 20, No. 17, Jul. 10, 2014, 4613-4624.
Couraud, S. et al., "Supplementary Data for Noninvasive Diagnosis of Actionable Mutations by Deep Sequencing of Circulating Free DNA in lung Cancer from Never-Smokers: A Proof-of-Concept Study from BioCAST / IFCT-1002", 2014, 13 pages.
Crespo-Leiro, et al., "Gene Expression Profiling for Monitoring Graft Rejection in Heart Transplant Recipients", Transplantation Proceedings, vol. 41, No. 6, Jul. 1, 2009, 2240-2243.
Cunningham, K. S. et al., "An approach to endomyocardial biopsy interpretation", Journal of Clinical Pathology, vol. 59, No. 2, Mar. 2006, 121-129.
Dahl, et al., "Multigene Amplification and Massively Parallel Sequencing for Cancer Mutation Discovery", Proceedings of the National Academy of Sciences, vol. 104, No. 22, May 29, 2007, 9387-9392.
Dambrin, et al., "A New Rejection Criteria In The Heterotopically Placed Rat Heart By Non-invasive Measurement Of Dp/Dtmax", The Journal of Heart and Lung Transplantation, vol. 18, No. 6, Jun. 18, 1999, 524-531.
Deb, Mahua et al., "Development of a Multiplexed PCR Detection Method for Barley and Cereal Yellow Dwarf Viruses, Wheat Spindle Streak Virus, Wheat Streak Mosaic Virus and Soil-Borne Wheat Mosaic Virus", Journal of Virological Methods, vol. 148, 2008, pp. 17-24.
Delgado, P. O. et al., "Characterization of cell-free circulating DNA in plasma in patients with prostate cancer", Tumor Biol., vol. 34, 983-986, 2013.
Doostzadeh, et al., "High Throughput Automated Allele Frequency Estimation by Pyrosequencing", PLoS ONE, vol. 3, No. 7, Jul. 16, 2008, 1-4.
Dorit, D. L. , "cDNA Amplification Using One-sided (Anchored) Per", Current Protocols in Molecular Biology, vol. 17, 1992, p. 15.6.1-15.6.10.
Dorit, Robert L. et al., "One-sided Anchored Polymerase Chain Reaction for Amplification and Sequencing of Complementary DNA", Methods in Enzymology, vol. 218., 1993, pp. 36-47.
Efron, B. et al., "Bootstrap Methods for Standard Errors, Confidence Intervals, and Other Measures of Statistical Accuracy", Statistical Science, vol. 1, No. 1, 1986, 54-77.
Elnifro, Elfath M. , "Multiplex PCR: Optimization and Application in Diagnostic Virology", Clinical Microbiology Reviews, vol. 13, 2000, pp. 559-570.
Erijman, Ariel et al., "Transfer-PCR (TPCR): A Highway For DNA Cloning and Protein Engineering", Journal of Structural Biology, vol. 175, 2011, pp. 171-177.
European Commission, , "The 7th International Conference on Circulating Nucleic Acids in Plasma and Serum (CNAPS VII) in Madrid—Spain", The International Conference on Circulating Nucleic Acids in Plasma and Serum, Oct. 24, 2011, 2 pgs.
Fan, H. C. et al., "In Principle Method for Noninvasive Determination of the Fetal Genome", Nat. Prec., 2010, 16 pgs.
Fitzgerald, , "Intravascular Ultrasound Imaging Of Coronary Arteries: Is Three Layers The Norm?", Circulation, vol. 86, No. 1, Jul. 1, 1992, 154-158.
Fournie, et al., "Plasma DNA As A Marker Of Cancerous Cell Death. Investigations In Patients Suffering From Lung Cancer And In Nude Mice Bearing Human Tumours", Cancer Letters, vol. 91, No. 2, May 8, 1995, 221-227.
Fredriksson, M et al., "Assessing Hematopoietic Chimerism After Allogeneic Stem Cell Transplantation by Multiplexed SNP Genotyping Using Microarrays and Quantitive Analysis of SNP Alleles", Leukemia, vol. 18, Issue 2, Dec. 4, 2003, 255-266.
Fu, Yao-Wen et al., "Presence Of Donor-and-recipientderived Dna Microchimerism In The Cell-free Blood Samples Of Renal Transplantation Recipients Associates With The Acceptance Of Transplanted Kidneys", Asian Journal of Andrology, vol. 8, No. 4, Jul. 1, 2006, 477-482.
Gadi, V. K. et al., "Soluble Donor DNA Concentrations in Recipient Serum Correlate with Pancreas-Kidney Rejection", Clinical Chemistry, vol. 52, No. 3, 2006, 379-382.
Gao, et al., "Relation Of Donor Age And Preexisting Coronary Artery Disease On Angiography And Intracoronary Ultrasound To Later Development Of Accelerated Allograft Coronary Artery Disease", The American Journal of Cardiology, vol. 29, No. 3, Mar. 1, 1997, 623-629.
Gao, Ming et al., "Characterization of dull1, a Maize Gene Coding for a Novel Starch Synthase", The Plant Cell, vol. 10, 1998, pp. 399-412.
Garcia Moreira, V. et al., "Cell-Free DNA as a Noninvasive Acute Rejection Marker in Renal Transplantation", Clinical Chemistry, vol. 55, No. 11, 2009, 1958-1966.
Geifman-Holtzman, et al., "Prenatal Diagnosis: Update On Invasive Versus Noninvasive Fetal Diagnostic Testing From Maternal Blood", Expert Review of Molecular Diagnostics, vol. 8, No. 6, Nov. 1, 2008, 727-751.
Gielis, E. M. et al., "Cell-Free DNA: An Upcoming Biomarker in Transplantation", American Journal of Transplantation, vol. 15, 2015, 2541-2551.
Gineikiene, Egle et al., "Single Nucleotide Polymorphism-based System Improves The Applicability Of Quantitative PCR For Chimerism Monitoring", Journal of Molecular Diagnostics, vol. 11, No. 1, Jan. 1, 2009, 66-74.
Gingeras, et al., "Fifty Years of Molecular (DNA/RNA) Diagnostics", Clinical Chemistry, vol. 51, No. 3, Jan. 13, 2005, 661-671.

(56) References Cited

OTHER PUBLICATIONS

Girnita, Diana M. et al., "Disparate Distribution of 16 Candidate Single Nucleotide Polymorphisms Among Racial and Ethnic Groups of Pediatric Heart Transplant Patients", Transplantation, vol. 82, No. 12, Dec. 27, 2006, 1774-1780.
Go, A. T. et al., "Non-invasive aneuploidy detection using free fetal DNA and RNA in maternal plasma: recent progress and future possibilities", Human Reproduction Update, vol. 17, No. 3, 2011, 372-382.
Goncalves-Primo, A. et al., "Investigation of Apoptosis-Related Gene Expression Levels in Preimplantation Biopsies as Predictors of Delayed Kidney Graft Function", Transplantation, vol. 97, No. 12, Jun. 27, 2014.
Gordon, et al., "Disease-Specific Motifs Can Be Identified In Circulating Nucleic Acids From Live Elk And Cattle Infected With Transmissible Spongiform Encephalopathies", Nucleic Acids Research, vol. 37. No. 2, Feb. 1, 2009, 550-556.
Gorringe, et al., "Large-scale Genomic Analysis of Ovarian Carcinomas", Molecular oncology, vol. 3, No. 2, Apr. 1, 2009, 157-164.
Gouya, et al., "Coronary Artery Stenosis In High-risk Patients: 64-section Ct And Coronary Angiography—Prospective Study And Analysis of Discordance", Radiology, vol. 252, No. 2, Aug. 1, 2009, 377-385.
Gregory, et al., "Comparison of Sixty-Four-Slice Multidetector Computed Tomographic Coronary Angiography To Coronary Angiography With Intravascular Ultrasound For The Detection Of Transplant Vasculopathy", The American Journal of Cardiology, vol. 98, No. 7, Aug. 4, 2006, 877-884.
Gwee, Pai-Chung et al., "Simultaneous Genotyping of Seven Single-nucleotide Polymorphisms in the Mdr1 Gene by Single-tube Multiplex Minisequencing", Pai-Chung Gwee. et al., "Simultaneous Genotyping of Seven Single-nucleotide Polymorphisms in the Mdr1 Gene by Single-tube Multiplex Minisequencing", Clinical chemistry, Apr. 2003, vol. 49, Issue. 3, pp. 672-676., Apr. 1, 2003, 672-676.
Hahn, et al., "Non-invasive Prenatal Diagnostics Using Next Generation Sequencing: Technical, Legal And Social Challenges", Expert Opinion on Medical Diagnostics, vol. 6, No. 6, Nov. 1, 2012, 517-528.
Hahn, S. et al., "Quantification of Circulating DNA: In the Preparation Lies the Rub", Clinical Chemistry, vol. 47, No. 9, 2001, 1577-1578.
Halford, William P. , "The Essential Prerequisites for Quantitative RT-PCR", Nature Biotechnology, vol. 17, 1999, 1 page.
Handley, D. et al., "Noninvasive prenatal chromosomal aneuploidy detection using plasma cell-free nucleic acid", Expert Rev Obstet. Gynecol, vol. 5, No. 5, 2010, 581-590.
Hao, T. B. et al., "Circulating cell-free DNA in serum as a biomarker for diagnosis and prognostic prediction of colorectal cancer", British Journal of Cancer, vol. 111, Aug. 26, 2014, 1482-1489.
Heaton, Paul R. et al., "Heminested PCR Assay for Detection of Six Genotypes of Rabies and Rabies-related Viruses", Journal of Clinical Microbiology, vol. 35, 1997, pp. 2762-2766.
Heidary, M. et al., "The dynamic range of circulating tumor DNA in metastatic breast cancer", Breast Cancer Research, vol. 16, No. 421, 2014, 10 pages.
Henegariu, O. et al., "Multiplex PCR: Critical Parameters and Step-by-Step Protocol", Biotechniques, vol. 23, 1997, pp. 504-511.
Hidestrand, M. et al., "Highly Sensitive Noninvasive Cardiac Transplant Rejection Monitoring Using Targeted Quantification of Donor-Specific Cell-Free Deoxyribonucleic Acid", Journal of the American College of Cardiology, vol. 63, No. 12, 1224-1226, 2014.
Hoberman, Rose et al., "A Probabilistic Approach for SNP Discovery in High-throughput Human Resequencing Data", Genome Research, vol. 19, Jul. 15, 2009, 1542-1552.
Hochberg, et al., "A Novel Rapid Single Nucleotide Polymorphism (SNP)-Based Method For Assessment Of Hematopoietic Chimerism After Allogeneic Stem Cell Transplantation", Blood, vol. 101, No. 1, Jan. 1, 2003, 363-369.
Hodges, et al., "Genome-wide In Situ Exon Capture For Selective Resequencing", Nature Genetics, vol. 3 9, No. 12, Nov. 4, 2007, 1522-1527.
Hoffmann, Steven et al., "Donor Genomics Influence Graft Events: The Effect Of Donor Polymorphisms On Acute Rejection And Chronic Allograft Nephropathy", Kidney International, vol. 66, No. 4, Oct. 1, 2004, 1686-1693.
Holt, et al., "Detecting SNPS And Estimating Allele Frequencies In Clonal Bacterial Populations By Sequencing Pooled DNA", Bioinformatics, vol. 25, No. 16, Aug. 15, 2009, 2074-2075.
Horai, et al., "Novel Implantable Device To Detect Cardiac Allograft Rejection", Circulation, vol. 120, No. Suppl 1, Sep. 15, 2009, 185-190.
Hosmillo, Myra D. et al., "Development of Universal SYBR Green Real-time RT-PCR for The Rapid Detection and Quantitation of Bovine and Porcine Toroviruses", Journal of Virological Methods, vol. 168, 2010, pp. 212-217.
Hu, Hao et al., "Mutation Screening in 86 Known X-linked Mental Retardation Genes by Droplet-based Multiplex Pcr and Massive Parallel Sequencing", Hao Hu. et al., "Mutation Screening in 86 Known X-linked Mental Retardation Genes by Droplet-based Multiplex Pcr and Massive Parallel Sequencing", Hugo J, Dec. 2009, vol. 3, pp. 41-49., Dec. 1, 2009, 41-49.
Huang, D. J. et al., "Reliable detection of Trisomy 21 using MALDI-TOF mass spectrometry", Genetics in Medicine, vol. 8, Nov. 2006, 728-734.
Hubacek, et al., "Detection of Donor DNA After Heart Transplantation: How Far Could It Be Affected by Blood Transfusion and Donor Chimerism?", Transplantation Proceedings, vol. 39, Jun. 1, 2007, 1593-1595.
Illumina, , "Genomic Sequencing", Data Sheet: Sequencing, 2010, 38939-38944.
Ingman, et al., "SNP Frequency Estimation Using Massively Parallel Sequencing of Pooled DNA", European Journal of Human Genetics, vol. 17, No. 3, Oct. 15, 2008, 383-386.
Interewicz, B. et al., "DNA Released from Ischemic and Rejecting Organs as an Indicator of Graft Cellular Damage", Annals of Transplantation, vol. 9, No. 2, May 1, 2004, 42-45.
Jen, J. et al., "An Overview on the Isolation and Analysis of Circulating Tumor DNA in Plasma and Serum", Annals New York Academy of Sciences, 2000, 8-12.
Jung, K. et al., "Cell-free DNA in the blood as a solid tu1nor biomarker—A critical appraisal of the literature", Clinica Chimica Acta, vol. 411, 2010, 1611-1624.
Kalendar, Ruslan et al., "Java Web Tools for PCR, in Silico PCR, and Oligonucleotide Assembly and Analysis", Genomics, vol. 98, 2011, pp. 137-144.
Kane, M. , "Application of Less Primer Method To Multiplex PCR", International Congress Series, vol. 1288, 2006, pp. 694-696.
Kapadia, Samir R. et al., "Impact of Intravascular Ultrasound in Understanding Transplant Coronary Artery Disease", Current Opinion In Cardiology, vol. 14, No. 2, Mar. 1, 1999, 1-19.
Karger, et al., "DNA Sequencing By Capillary Electrophoresis", Electrophoresis, vol. 30, Supplement 1, Jun. 1, 2009, 1-11.
Karoui, Noureddine E. et al., "Getting More from Digital SNP Data", Statistics in Medicine, vol. 25, Issue 18, Jan. 5, 2006, 3124-3133.
Kass, et al., "Diagnosis Of Graft Coronary Artery Disease", Current Opinion in Cardiology, vol. 22, No. 2, Mar. 1, 2007, 139-145.
Kathiresan, Sekar et al., "Genome-wide Association of Early-onset Myocardial Infarction With Common Single Nucleotide Polymorphisms, Common Copy Number Variants, and Rare Copy Number Variants", Nature Genetics, vol. 41, No. 3, Mar. 1, 2009, 1-23.
Kennedy, S. R. et al., "Detecting ultralow-frequency mutations by Duplex Sequencing", Nature Protocols, vol. 9, No. 11, 2014, 2586-2606.
Kibbe, Warren A. , "Oligocalc: An Online Oligonucleotide Properties Calculator", Nucleic Acids Research, vol. 35, 2007, pp. W43-W46.
Kircher, Martin et al., "Improved Base Calling for the Illumina Genome Analyzer Using Machine Learning Strategies", Genome Biology, vol. 10, Issue 8, Article No. R83, Aug. 14, 2009, 83.2-83.9.

(56) References Cited

OTHER PUBLICATIONS

Kobashigawa, et al., "Multicenter Intravascular Ultrasound Validation Study Among Heart Transplant Recipients", Journal of the American College of Cardiology, vol. 45, No. 9, May 3, 2005, 1532-1537.
Koboldt, et al., "VarScan: Variant Detection In Massively Parallel Sequencing Of Individual And Pooled Samples", Bioinformatics, vol. 25, No. 17, Jun. 19, 2009, 2283-2285.
Koelman, et al., "Donor-derived Soluble HLA Plasma Levels Can Not Be Used To Monitor Graft Rejection In Heart Transplant Recipients", Transplant Immunology, vol. 8, No. 1, Mar. 1, 2000, 57-64.
Koide, K. et al., "Fragmentation of cell-free fetal DNA in plasma and urine of pregnant women", Prenatal Diagnosis, vol. 25, 2005, 604-607.
Koldehoff, Michael et al., "Quantitative analysis of chimerism after allogeneic stem cell transplantation by real-time polymerase chain reaction with single nucleotide polymorphisms, standard tandem repeats, and Y-chromosome-specific sequences", American Journal of Hematology, vol. 81, No. 10, Jul. 12, 2006, 735-746.
Koressaar, Triinu et al., "Enhancements and Modifications of Primer Design Program Primer3", Bioinformatics, vol. 23, 2007, pp. 1289-1291.
Korn, et al., "Integrated Genotype Calling And Association Analysis Of SNPS, Common Copy Number Polymorphisms And Rare CNVS", Nature Genetics, vol. 40, No. 10, Oct. 1, 2008, 1253-1260.
Kuhn, H. et al., "Rolling-circle amplification under topological constraints", Nucleic Acids Research, vol. 30, No. 2, 2002, 574-580.
Lambert, et al., "Quantification of Maternal Microchimerism by HLA-Specific Real-time Polymerase Chain Reaction", Arthritis and Rheumatism, vol. 50, No. 3, Mar. 1, 2004, 906-914.
Langmore, J. , "Quality Control and Pre-Qualifications of NGS Libraries Made from Clinical Samples", ABRF 2013 Satellite Workshop, Mar. 2, 2013, 35 pages.
Lardeux, Frederic et al., "Optimization of a Semi-nested Multiplex PCR to Identify Plasmodium Parasites in Wild-Caught Anopheles in Bolivia, and Its Application to Field Epidemiological Studies", Transactions of the Royal Society of Tropical Medicine and Hygiene, vol. 102, 2008, pp. 485-492.
Larsen, J. B. et al., "Single-step Nested Multiplex PCR to Differentiate Between Various Bivalve Larvae", Marine Biology, vol. 146, 2005, pp. 1119-1129.
Lavebrat, et al., "Single Nucleotide Polymorphism (SNP) Allele Frequency Estimation in DNA Pools Using Pyrosequencing", Nature Protocols, vol. 1, No. 6, Jan. 11, 2007, 2573-2582.
Lavebratt, Catharina et al., "Pyrosequencing-based SNP Allele Frequency Estimation In DNA Pools", Human Mutation, vol. 23, Issue 1, Dec. 19, 2003, 92-97.
Leamon, John H. et al., "A massively parallel PicoTiterPlate based platform for discrete picoliter-scale polymerase chain reactions", Electrophoresis, vol. 24, No. 21, Nov. 1, 2003, 3769-3777.
Levsky, Jeffrey M. et al., "Efficacy of Coronary Ct Angiography: Where We Are, Where We Are Going and Where We Want to Be", Journal Of Cardiovascular Computed Tomography, vol. 3, Supplement 2, Nov. 2, 2009, s99-s108.
Li, et al., "Detection of SNPs in the Plasma of Pregnant Women and in the Urine of Kidney Transplant Recipients by Mass Spectrometry", Annals of the New York Academy of Sciences, vol. 1075, Sep. 5, 2006, 144-147.
Li, et al., "Mapping Short DNA Sequencing Reads And Calling Variants Using Mapping Quality Scores", Genome Research, vol. 18, No. 11,, Aug. 19, 2008, 1851-1858.
Li, et al., "Multiplex Padlock Targeted Sequencing Reveals Human Hypermutable CpG Variations", Genome Research, vol. 19, No. 9, Jun. 12, 2009, 1606-1615.
Li, et al., "SOAP2: An Improved Ultrafast Tool For Short Read Alignment", Bioinformatics, vol. 25, No. 15, Aug. 1, 2009, 1966-1967.

Li, Ying et al., "Detection of Donor-specific DNA Polymorphisms in the Urine of Renal Transplant Recipients", Clinical Chemistry, vol. 49, No. 4, Apr. 1, 2003, 655-658.
Li, Ying et al., "Ready detection of donor-specific single-nucleotide polymorphisms in the urine of renal transplant recipients by matrix-assisted laser desorption/ionization time-of-flight mass spectrometry", Ying Li. et al., "Ready detection of donor-specific single-nucleotide polymorphisms in the urine of renal transplant recipients by matrix-assisted laser desorption/ionization time-of-flight mass spectrometry",Clin Chem,Oct. 2005,vol. 51,Issue.10,pp. 1903-1904, Oct. 1, 2005, 1903-1904.
Liljedahl, Ulrika et al., "Detecting Imbalanced Expression Of SNP Alleles by Minisequencing On Microarrays", BMC Biotechnology, vol. 4, Article No. 24, Oct. 22, 2004, 1-10.
Lo, et al., "Next-generation Sequencing Of Plasma/Serum DNA: An Emerging Research And Molecular Diagnostic Tool", Clinical Chemistry, vol. 55, No. 4, Apr. 1, 2009, 607-608.
Lo, et al., "Presence Of Donor-specific Dna In Plasma Of Kidney And Liver-transplant Recipients", Lancet, vol. 351, No. 9112, May 2, 1998, 1329-1330.
Lo, Y M. et al., "Circulating Nucleic Acids in Plasma and Serum: An Overview", Annals of the New York Academy of Sciences, vol. 945, Sep. 1, 2001, 1-7.
Loh, Elwyn , "Anchored PCR: Amplification with Single-sided Specificity", Methods, vol. 2, 1991, pp. 11-19.
Lui, Yanni Y. et al., "Circulating DNA in Plasma and Serum: Biology, Preanalytical Issues And Diagnostic Applications", Clinical Chemistry and Laboratory Medicine, vol. 40, No. 10, Oct. 29, 2002, 962-968.
Lui, Yanni Y. et al., "Origin of Plasma Cell-Free DNA after Solid Organ Transplantation", Clinical Chemistry, vol. 49, No. 3, Mar. 1, 2003, 495-496.
Lun, Fiona M. et al., "Microfluidics Digital PCR Reveals A Higher Than Expected Fraction Of Fetal DNA In Maternal Plasma", Clinical Chemistry, vol. 54, No. 10, Aug. 14, 2008, 1664-1672.
Marguiles, M. et al., "Genome Sequencing in Open Microfabricated High Density Picoliter Reactors", Nature, vol. 437, No. 7057, Sep. 15, 2005, 376-380.
Marianes, Alexis E. et al., "Targets of Somatic Hypermutation within Immunoglobulin Light Chain Genes in Zebrafish", Immunology, vol. 132, 2010, pp. 240-255.
Maron, Jill L. et al., "Cell-free Fetal DNA Plasma Extraction and Real-time Polymerase Chain Reaction Quantification", Methods In Molecular Medicine, vol. 132, Aug. 1, 2007, 51-63.
Marshutina, N. V. et al., "Comparative Clinical and Diagnostic Significance of Some Serological Tumor Associated Markers for Different Histological Types of Lung Cancer", Russian Oncological Journal, vol. 3, 2010, 13-16.
Martinez- Lopez, J. et al., "Real-time PCR Quantification of Haematopoietic Chimerism after Transplantation: A Comparison Between TaqMan And Hybridization Probes Technologies", International Journal of Laboratory Hematology, vol. 32, Issue 1, Part 1, May 12, 2009, e17-e25.
Martins, et al., "Quantification Of Donor-derived DNA In Serum: A New Approach Of Acute Rejection Diagnosis In A Rat Kidney Transplantation Model", Transplantation Proceedings, vol. 37, No. 1,, Jan. 1, 2005, 87-88.
Matsubara, T. et al., "Pantropic Retroviral Vectors Integrate and Express In Cells of the Malaria Mosquito, Anopheles Gambiae", PNAS, vol. 93, 1996, pp. 6181-6185.
Messmer, Trudy O. et al., "Application of a Nested, Multiplex PCR to Psittacosis Outbreaks", Journal of Clinical Microbiology, vol. 35, No. 8, 1997, pp. 2043-2046.
Meuzelaar, Linda S. et al., "Megaplex PCR: A Strategy for Multiplex Amplification", Nature Methods, vol. 4, 2007, pp. 835-837.
Milani, et al., "Genotyping Single Nucleotide Polymorphisms By Multiplex Minisequencing Using Tag-arrays", DNA Microarrays for Biomedical Research, vol. 529, Jan. 16, 2009, 215-229.
Miramontes, Pedro et al., "DNA Dimer Correlations Reflect in Vivo Conditions and Discriminate Among Nearest-neighbor Base Pair Free Energy Parameter Measures", Physica A, vol. 321, 2003, pp. 577-586.

(56) References Cited

OTHER PUBLICATIONS

Mitra, S. et al., "Chapter 4 Classification Techniques", Introduction to Machine Learning and Bioinformatics, First Edition, 2008, 101-127.
Moreau, Valerie et al., "Zip Nucleic Acids: New High Affinity Oligonucleotides as Potent Primers for PCR and Reverse Transcription", Nucleic Acids Research, vol. 37, No. 19, e130, 2009, 14 pages.
Moreira, et al., "Increase In And Clearance Of Cell-free Plasma DNA In Hemodialysis Quantified By Real-time PCR", Clinical Chemistry and Laboratory Medicine, vol. 44, No. 12, Dec. 13, 2006, 1410-1415.
Nakamura, N. et al., "Ex Vivo Liver Perfusion with Arterial Blood from A Pig with Ischemic Liver Failure", Artificial Organs, vol. 23, No. 2, 1999, 153-160.
Neve, B. et al., "Rapid SNP Allele Frequency Determination in Genomic DNA Pools by Pyrosequencing", BioTechniques, vol. 32, No. 5, May 1, 2002, 1138-1142.
Ng, et al., "Multiplex Sequencing Of Paired-end Ditags (MS-PET): A Strategy For The Ultra-high-throughput Analysis Of Transcriptomes And Genomes", Nucleic Acids Research, vol. 34, No. 12, Jul. 13, 2006, 1-10.
Nishiwaki, Morie et al., "Genotyping of Human Papillomaviruses by A Novel One-step Typing Method With Multiplex PCR and Clinical Applications", Journal of Clinical Microbiology, vol. 46, 2008, pp. 1161-1168.
Norton, S. E. et al., "A stabilizing reagent prevents cell-free DNA contamination by cellular DNA in plasma during blood sample storage and shipping as determined by digital PCR", Clin Biochem., vol. 46, No. 15, Oct. 2013, 1561-1565.
Nui, A. et al., "The Functional Integrity of a Normothermic Perfusion System Using Artificial Blood in Pig Liver", Journal of Surgical Research, Vo. 131, 2006, 189-198.
O'Connell, G. C. et al., "High Interspecimen Variability in Nucleic Acid Extraction Efficiency Necessitates the Use of Spike-In Control for Accurate qPCR-based Measurement of Plasma Cell-Free DNA Levels", Lab Medicine, vol. 48, 2017, 332-338.
Oeth, et al., "iPLEX™ Assay: Increased Plexing Efficiency and Flexibility for MassARRAY System Through Single Base Primer Extension with Mass-Modified Terminators", Sequenom Application Note Doc. No. 8876-006, Apr. 28, 2005, 1-12.
Ohira, T. et al., "Tumor volume determines the feasibility of cell-free DNA sequencing for mutation detection in non-small cell lung cancer", Cancer Science, vol. 107, 2016, 1660-1666.
Okou, et al., "Microarray-based Genomic Selection For High-throughput Resequencing", Nature Methods, vol. 4, No. 11, Oct. 14, 2007, 907-909.
Okou, David T. et al., "Combining Microarray-based Genomic Selection (MGS) with The Illumina Genome Analyzer Platform To Sequence Diploid Target Regions", Annals of Human Genetics, vol. 73, No. 5, Aug. 6, 2009, 502-513.
Olerup, O. et al., "HLA-DR typing by PCR amplification with sequence-specific primers (PCR-SSP) in 2 hours: an alternative to serological DR typing in clinical practice including donor-recipient matching in cadaveric transplantation", Tissue Antigens, vol. 39, No. 5, May 1992, 225-235.
Oliver, Dwight H. et al., "Use of Single Nucleotide Polymorphisms (SNP) and Real-time Polymerase Chain Reaction for Bone Marrow Engraftment Analysis", The Journal of Molecular Diagnostics, vol. 2, No. 4, Nov. 1, 2000, 202-208.
Olivier, et al., "The Invader Assay for SNP Genotyping", Mutation Research, vol. 573, No. 1-2, Jun. 3, 2005, 103-110.
Orsouw, et al., "Complexity Reduction Of Polymorphic Sequences (Crops): A Novel Approach For Large-scale Polymorphism Discovery In Complex Genomes", PLoS ONE, vol. 11:e1172, Nov. 14, 2017, 1-10.
Owczarzy, Richard et al., "Melting Temperatures of Nucleic Acids: Discrepancies in Analysis", Biophysical Chemistry, vol. 117, 2005, pp. 207-215.

Paik, P. K. et al., "Next-Generation Sequencing of Stage IV Squamous Cell Lung Cancers Reveals an Association of P13K Aberrations and Evidence of Clonal Heterogeneity in Patients with Brain Metastases", Cancer Discovery, vol. 5, Apr. 30, 2015, 610-621.
Pakstis, et al., "Candidate SNPs For A Universal Individual Identification Panel", Human Genetics, vol. 121, No. 3-4,, Feb. 27, 2007, 305-317.
Pakstis, et al., "SNPS for Individual Identification", Forensic Science International, vol. 1, May 22, 2008, 479-481.
Palka-Santini, Maria et al., "Large Scale Multiplex PCR Improves Pathogen Detection by DNA Microarrays", BMC Microbiology, vol. 9, No. 1, 2009, 14 pages.
Panjkovich, Alejandro et al., "Comparison of Different Melting Temperature Calculation Methods for Short DNA Sequences", Bioinformatics, vol. 21, 2005, pp. 711-722.
Pfaffl, Michael W. , "Quantification Strategies in Real-time PCR", A-Z of quantitative PCR, 2004, pp. 87-112.
Pinard, et al., "Assessment of Whole Genome Amplification-induced Bias Through High-throughput, Massively Parallel Whole Genome Sequencing", BMC Genomics, vol. 7:216, Aug. 23, 2006, 1-21.
Pourmand, et al., "Multiplex Pyrosequencing", Nucleic Acid Research, vol. 30, No. 7, Apr. 1, 2002, 1-5.
Prabhu, et al., "Overlapping Pools for High-throughput Targeted Resequencing", Genome Research, vol. 19, May 15, 2009, 1254-1261.
Puszyk, William M. et al., "Noninvasive Prenatal Diagnosis Of Aneuploidy Using Cell-free Nucleic Acids In Maternal Blood: Promises And Unanswered Questions", Prenatal Diagnosis, vol. 28, No. 1, Nov. 16, 2007, 1-6.
Qiagen, , "QIAamp DNA Mini Kit and QIAamp DNA Blood Mini Kit Handbook", QIAamp DNA Mini Kit and QIAamp DNA Blood Mini Kit Handbook, Feb. 2003 ("Qiagen (2003)"), 2003, 68 pages.
RainDance Technologies, et al., "RainDance Technologies Introduces the RDT 1000", RainDance Technologies, Nov. 12, 2008.
Ravipati, Goutham et al., "Comparison of Sensitivity, Specificity, Positive Predictive Value, and Negative Predictive Value of Stress Testing Versus 64-Multislice Coronary Computed Tomography Angiography in Predicting Obstructive Coronary Artery Disease Diagnosed by Coronary Angiogr", The American Journal of Cardiology, Coronary Artery Disease. vol. 101, Issue 6, Mar. 15, 2008, 774-775.
Roche Diagnostics, et al., "Versatile Nucleic Acid Purification", MagnaPure Manual, Feb. 3, 2012.
Ross, P. et al., "Quantitative Approach to Single-Nucleotide Polymorphism Analysis Using MALDI-TOF Mass Spectrometry", BioTechniques, vol. 29, Sep. 2000, 620-629.
Rothberg, et al., "The Development and Impact of 454 Sequencing", Nature Biotechnology, vol. 26, No. 10, Oct. 9, 2008, 1117-1124.
Rubio, J. M. et al., "Semi-nested, Multiplex Polymerase Chain Reaction for Detection of Human Malaria Parasites and Evidence of Plasmodium Vivax Infection in Equatorial Guinea", The American Journal of Tropical Medicine And Hygiene, vol. 60, 1999, pp. 183-187.
Ruschendorf, et al., "Alohomora: A Tool For Linkage Analysis Using 10K SNP Array Data", Bioinformatics Applications Notes, vol. 21, No. 9, Jan. 12, 2005, 2123-2125.
Sanger, et al., "Nucleotide Sequence of Bacteriophage Lambda DNA", Journal of Molecular Biology, vol. 162, No. 4, Dec. 25, 1982, 729-773.
Schaaf, C. P. et al., "Copy Number and SNP Arrays In Clinical Diagnostics", Annu. Rev. Genomics Hum. Genet., vol. 12, 2011, 25-51.
Schwarzenbach, H. et al., "Detection and Characterization of Circulating Microsatellite-DNA in Blood of Patients with Breast Cancer", Ann. N.Y. Acad. Sci., vol. 1022, 2004, 25-32.
Sharples, et al., "Diagnostic Accuracy Of Coronary Angiography And Risk Factors For Post-heart-transplant Cardiac Allograft Vasculopathy", Transplantation, vol. 76, No. 4, Aug. 27, 2003, 679-682.
Shyamala, Venkatakrishna et al., "Genome Walking by Single-Specific-Primer Polymerase Chain Reaction: SSP-PCR", Gene, vol. 84, 1989, pp. 1-8.

(56) References Cited

OTHER PUBLICATIONS

Singh, Vinayak K. et al., "PCR Primer Design", Molecular Biology Today, vol. 2, 2001, pp. 27-32.
Smith, et al., "Rapid Whole-genome Mutational Profiling using Next-generation Sequencing Technologies", Genome Research, vol. 18, Sep. 4, 2008, 1638-1642.
Smith, James F. et al., "Cell-free Fetal DNA in Maternal Plasma", Neo Reviews, vol. 9, No. 8, Aug. 1, 2008, e332-e337.
Solexa, , "Application Note: DNA Sequencing", 2006, 1-2.
Sorenson, G. D. et al., "Soluble Normal and Mutated DNA Sequences from Single-Copy Genes in Human Blood", Cancer Epdemiology, Biomarkers & Prevention, vol. 3, Jan./Feb. 1994, 67-71.
Spes, et al., "Diagnostic And Prognostic Value Of Serial Dobutamine Stress Echocardiography For Noninvasive Assessment Of Cardiac Allograft Vasculopathy: A Comparison With Coronary Angiography And Intravascular Ultrasound", Circulation, vol. 100, No. 5, Aug. 3, 1999, 509-515.
Spindler, K.L. G. et al., "Cell-free DNA in healthy individuals, noncancerous disease and strong prognostic value in colorectal cancer", International Journal of Cancer, vol. 135, 2014, 2984-2991.
Spindler, K.-L. G. et al., "Cell-Free DNA in Metastatic Colorectal Cancer: A Systematic Review and Meta-Analysis", The Oncologist, vol. 22, 2017, 1049-1055.
Stewart, S. et al., "Revision of the 1990 Working Formulation for the Standardization of Nomenclature in the Diagnosis of Heart Rejection", The Journal of Heart and Lung Transplantation, vol. 24, No. 11, Nov. 2005, 1710-1720.
Stiller, et al., "Direct Multiplex Sequencing (DMPS)—A Novel Method For Targeted High-thoroughput Sequencing Of Ancient And Highly Degraded DNA", Genome Research, vol. 19, No. 10, Jul. 27, 2009, 1843-1848.
Stolerman, Elliot S. et al., "Haplotype structure of the ENPP1 Gene and Nominal Association of the K121Q missense single nucleotide polymorphism with glycemic traits in the Framingham Heart Study", Diabetes, vol. 57, Issue 7, Jul. 1, 2008, 1971-1977.
Stone, J. P. et al., "Ex Vivo Normothermic Perfusion Induces Donor-Derived Leukocyte Mobilization and Removal Prior to Renal Transplantation", Kidney Int Rep., vol. 1, No. 4, Aug. 6, 2016, 230-239.
Swarup, V. et al., "Circulating (cell-free) nucleic acids—A promising, non-invasive tool for early detection of several human diseases", FEBS Letters, vol. 581, 2007, 795-799.
Takala, et al., "A High-throughput Method for Quantifying Alleles and Haplotypes of The Malaria Vaccine Candidate Plasmodium Falciparum Merozoite Surface Protein-1 19 kDa", Malaria Journal, vol. 5:31, Apr. 20, 2006, 1-10.
Takashima, Y. et al., "Expansion-contraction of photoresponsive artificial muscle regulated by host-guest interactions", Nature Communications, vol. 3, No. 1270, Dec. 11, 2012, 8 pages.
Thompson, J. C. et al., "Detection of Therapeutically Targetable Driver and Resistance Mutations in Lung Cancer Patients by Next-Generation Sequencing of Cell-Free Circulating Tumor DNA", Clin Cancer Res, vol. 22, No. 23, Dec. 1, 2016, 5772-5782.
Thornton, Brenda et al., "Real-time Pcr (qPCR) Primer Design Using Free Online Software", Biochemistry and Molecular Biology Education, vol. 39, 2011, pp. 145-154.
Tong, et al., "Diagnostic Developments Involving Cell-free (Circulating) Nucleic Acids", Clinica Chimica Acta, vol. 363, No. (1-2), Aug. 26, 2005, 187-196.
Toshikazu, et al., "Estimation Of Haplotype Frequencies, Linkage-disequilibrium Measures, And Combination of Haplotype Copies in Each Pool By Use Of Pooled DNA Data", American Journal of Human Genetics, vol. 72, Jan. 17, 2003, 384-398.
Troeger, C. et al., "Approximately Half of The Erythroblasts in Maternal Blood are of Fetal Origin", Molecular Human Reproduction, vol. 5, No. 12, Dec. 1, 1999, 1162-1165.
Tsang, Jason C. et al., "Circulating Nucleic Acids in Plasma/Serum", Pathology, vol. 39, No. 2, Apr. 1, 2007, 197-207.
Tuzcu, et al., "Intravascular Ultrasound Evidence Of Angiographically Silent Progression In Coronary Atherosclerosis Predicts Long-term Morbidity And Mortality After Cardiac Transplantation", The American Journal of Cardiology, vol. 45, No. 9, May 3, 2005, 1538-1542.
Umetani, N. et al., "Increased Integrity of Free Circulating DNA in Sera of Patients with Colorectal or Periampullary Cancer: Direct Quantitative PCR for ALU Repeats", Clinical Chemistry, vol. 52, No. 6, 2006, 1062-1069.
Urbanova, M. et al., "Circulating Nucleic Acids as a New Diagnostic Tool", Cellular & Molecular Biology Letters, vol. 15, 2010, 242-259.
Vallone, Peter M. et al., "Demonstration of Rapid Multiplex PCR Amplification Involving 16 Genetic Loci", Forensic Science International: Genetics, vol. 3, 2008, pp. 42-45.
Vanneste, Marion et al., "Functional Genomic Screening Independently Identifies CUL3 as a Mediator of Vemurafenib Resistance via Src-RAC1 Signaling Axis", Frontiers in Oncology, vol. 10, 2020, 16 pages.
Verlaan, et al., "Allele-specific Chromatin Remodeling in The ZPBP22/GSDMB/ORMDL3 Locus Associated with the Risk of Asthma And Autoimmune Disease", The American Journal of Human Genetics, vol. 85, No. 3, Sep. 11, 2009, 377-393.
Verlaan, et al., "Targeted Screening of Cis-Regulatory Variation in Human Haplotypes", Genome Research, vol. 19, No. 1, Jan. 1, 2009, 118-127.
Vlaminck, I. D. et al., "Circulating Cell-Free DNA Enables Noninvasive Diagnosis of Heart Transplant Rejection", Sci Transl Med., vol. 6, No. 241, Jun. 18, 2018, 26 pages.
Voelkerding, et al., "Next-generation Sequencing: From Basic Research To Diagnostics", Clinical Chemistry, vol. 55, No. 4, Apr. 1, 2009, 641-658.
Von Ahsen, Nicolas et al., "Oligonucleotide Melting Temperatures under PCR Conditions: Nearest-Neighbor Corrections for Mg2+, Deoxynucleotide Triphosphate, and Dimethyl Sulfoxide Concentrations with Comparison to Alternative Empirical Formulas", Clinical Chemistry, vol. 47, 2001, pp. 1956-1961.
Wartell, Roger M. et al., "Thermal Denaturation of DNA Molecules: A Comparison of Theory with Experiment", Physics Reports, vol. 126, 1985, pp. 67-107.
Wasson, Jon et al., "Assessing Allele Frequencies of Single Nucleotide Polymorphisms in DNA Pools by Pyrosequencing Technology", BioTechniques, vol. 32, No. 5, May 1, 2002, 1144-1152.
Watt, Heather L. , "Sex Diagnosis of Preimplantation Porcine Embryos through PCR Amplification of The Sry Gene", Sex Diagnosis of Preimplantation Porcine Embryos Through PCR Amplification of the SRY Gene (1998) ("Watt (1998)"), 1998, 151 pages.
Wei, Ting et al., "Novel Approaches to Mitigate Primer Interaction and Eliminate Inhibitors in Multiplex PCR, Demonstrated Using an Assay for Detection of three Strawberry Viruses", Journal of Virological Methods, vol. 151, 2008, pp. 132-139.
Wellnhofer, et al., "Angiographic Assessment Of Cardiac Allograft Vasculopathy: Results Of A Consensus Conference Of The Task Force For Thoracic Organ Transplantation of the German Cardiac Society", Transplant International, vol. 23, No. 11, Aug. 19, 2010, 1094-1104.
Wiedmann, Ralph T. et al., "SNP Discovery in Swine by Reduced Representation and High Throughput Pyrosequencing", BMC Genetics, vol. 9, Article No. 81, Dec. 4, 2008, 1-7.
Wilkening, Stefan et al., "Determination of Allele Frequency In Pooled DNA: Comparison of Three PCR-based Methods", Bio Techniques, vol. 39, No. 6, May 30, 2005, 853-857.
Wilkinson, Sarah T. et al., "Decreased MHC Class II Expression in Diffuse Large B-Cell Lymphoma does not Correlate with CPG Methylation of Ciita Promoters III and IV", Leuk Lymphoma, vol. 50, 2009, pp. 1875-1878.
Witherspoon, David J. et al., "Mobile Element Scanning (Me-scan) by Targeted High-throughput Sequencing", BMC Genomics, vol. 410, 2010, 15 pages.
Wong, K. H. et al., "Multiplex Illumina Sequencing Using DNA Barcoding", Current Protocols in Molecular Biology, vol. 101, Jan. 2013, 7.11.1-7.11.11.
Wright, Caroline et al., "Cell-free Fetal Nucleic Acids for Noninvasive Prenatal Diagnosis", PHG Foundation, Jan. 1, 2009, 1-64.

(56) References Cited

OTHER PUBLICATIONS

Xia, et al., "Simultaneous Quantitative Assessment Of Circulating Cell-free Mitochondrial And Nuclear DNA By Multiplex Real-time PCR", Genetics and Molecular Biology, vol. 32, No. 1, Mar. 1, 2009, 20-24.
Xian, et al., "Advances On Circulating Fetal DNA In Maternal Plasma", Chinese Medical Journal, vol. 120, No. 14, Jul. 2, 2007, 1256-1259.
Xie, et al., "CNV-SEQ, A New Method to Detect Copy Number Variation Using Highthroughput Sequencing", BMC Bioinformatics, vol. 10:80, Mar. 6, 2009, 1-9.
Xu, W. et al., "A Novel Universal Primer-Multiplex-PCR Method with Sequencing Gel Electrophoresis Analysis", PLOS One, vol. 7, No. 1, Jan. 17, 2012, 10 pgs.
Xue, et al., "Optimizing The Yield And Utility Of Circulating Cell-free DNA From Plasma And Serum", Clinica Chimica Acta, vol. 404, No. 2, Jun. 27, 2009, 100-104.
Yang, Lin et al., "64-MDCT Coronary Angiography of Patients With Atrial Fibrillation: Influence of Heart Rate On Image Quality and Efficacy In Evalution of Coronary Artery Disease", AJR, vol. 193, No. 3, Sep. 1, 2009, 795-801.
Yijen, et al., "Noninvasive Evaluation Of Cardiac Allograft Rejection By Cellular And Functional Cardiac Magnetic Resonance", JACC Cardiovacular Imaging, vol. 2, No. 6, Jun. 1, 2009, 731-741.
Yilmaz, A. et al., "Comparative Evaluation of Left and Right Ventricular Endomyocardial Biopsy", Circulation, vol. 122, No. 9, Aug. 31, 2010, 900-909.
Yuanxin, Yan et al., "T-linker-specific Ligation PCR (T-linker Pcr): An Advanced PCR Technique for Chromosome Walking or for Isolation of Tagged DNA Ends", Nucleic Acids Research, vol. 31, No. 12, e68, 2003, 7 pages.
Zhang, et al., "Diagnosis of Acute Rejection by Analysis of Urinary DNA of Donor Origin in Renal Transplant Recipients", Transplantation Proceedings, vol. 33, No. 1-2, Feb. 2001, 380-381.
Zhang, et al., "Use Of PCR And PCR-SSP For Detection Of Urinary Donor-Origin Dna In Renal Transplant Recipients With Acute Rejection", Chinese Medical Journal, vol. 116, No. 2, Feb. 2003, 191-194.
Zhang, Kun et al., "Digital RNA Alleotyping Reveals Tissue-specific and Allele-specific Gene Expression in Human", Nature Methods, vol. 6, No. 8, Jul. 20, 2009, 613-618.
Zhao, et al., "Urinary Thromboxane B2 In Cardiac Transplant Patients As A Screening Method Of Rejection", Prostaglandins, vol. 54, No. 6, Dec. 1, 1997, 881-889.
Zhong, Xiao Y. et al., "Cell-free DNA In Urine: A Marker for Kidney Graft Rejection, but Not for Prenatal Diagnosis ?", Annals of the New York Academy of Sciences, vol. 945, Sep. 1, 2001, 250-257.
Zhou, et al., "Pyrosequencing, A High-throughput Method For Detecting Single Nucleotide Polymorphisms In The Dihydrofolate Reductase And Dihydropteroate Synthetase Genes Of Plasmodiym Falciparum", Journal of Clinical Microbiology, vol. 44, No. 11, Nov. 1, 2006, 3900-3910.
Zimmer, et al., "Transplant Coronary Artery Disease", JACC Cardiovascular Interventions, vol. 3, No. 4, Apr. 1, 2010, 367-377.
Bau, Stephan, et al., "Targeted next-generation sequencing by specific capture of multiple genomic loci using low-volume microfluidic DNA arrays", Anal Bioanal Chem, 2009, 171-175.
Lanman, et al., "Analytical and Clinical Validation of a Digital Sequencing Panel for Quantitative, Highly Accurate Evaluation of Cell-Free Circulating Tumor DNA", PLOS One, 2015, 1-27.
Lee, et al., "ERBB2 kinase domain mutation in the lung squamous cell carcinoma", Cancer Letters, 2006, 89-94.
Park, et al., "First-Line Erlotinib Therapy Until and Beyond Response Evaluation Criteria in Solid Tumors Progression in Asian Patients With Epidermal Growth Factor Receptor Mutation-Positive Non-Small-Cell Lung Cancer", JAMA Oncol., 2015, 305-312.
Tseng, Jeng-Sen, et al., "Dynamic Plasma EGFR Mutation Status as a Predictor of EGFR-TKI Efficacy in Patients with fGFR-Mutant Lung Adenocarcinoma", Thorac Oncol., 2015, 603-610.
Diaz, et al., "Liquid Biopsies: Genotyping Circulating Tumor DNA", Journal of Clinical Oncology, vol. 32, No. 6, 2014, 579-586.
Namlos, H.M. et al., "Use of liquid biopsies to monitor disease progression in a sarcoma patient: a case report", BMC Cancer, vol. 17, No. 1, 2017, 2-3.
Tie, et al., "Circulating tumor DNA as an early marker of therapeutic response in patients with metastatic colorectal cancer", Annals of Oncology, vol. 26, No. 8, 2015, 1715-1722.
Ahmadian, A. et al., "Analysis of the p53 Tumor Suppressor Gene by Pyrosequencing", BioTechniques, vol. 28, Jan. 2000, 140-147.
Cawkwell, L. et al., "Rapid detection of allele loss in colorectal tumours using microsatellites and fluorescent DNA technology", Br. J. Cancer, vol. 67, 1993, 1262-1267.
Chen, et al., "Non-invasive prenatal diagnosis using fetal DNA in maternal plasma: a preliminary study for identification of paternally-inherited alleles using single nucleotide polymorphisms", BMJ Open, 5(7), 2015, 1-8.
Chun, et al., "Dual priming oligonucleotide system for the multiplex detection of respiratory viruses and SNP genotyping of CYP2C19 gene", Nucleic Acids Research, vol. 35, No. 6, 2007, 1-6.
Croft, Jr., Daniel et al., "Performance of Whole-Genome Amplified DNA Isolated from Serum and Plasma on High-Density Single Nucleotide Polymorphism Arrays", Journal of Molecular Diagnostics, 10(3), 2008, 249-257.
Findlay, I. et al., "Allelic drop-out and preferential amplification in single cells and human blastomeres: implications for preimplantation diagnosis of sex and cystic fibrosis", Molecular Human Reproduction, vol. 1, 1995, 1609-1618.
Gusella, J. et al., "Precise localization of human B-globin gene complex on chromosome 11*", Proc. Natl. Acad. Sci USA, vol. 76, No. 10, Oct. 1979, 5239-5243.
Hainer & Fazzio, "High-Resolution Chromatin Profiling Using Cut&Run", Current Protocols in Molecular Biology, 2019, 1-22.
Hiendleder, et al., "Functional genomics: tools for improving farm animal health and welfare", Rev. Sci. Tech. Off. Int. Epiz., 24 (1), 2005, 354-377.
Illumina, "Illumina Adapter Sequences", Published by Illumina, 2018, 1-45.
Jordens, et al., "Amplification with molecular beacon primers and reverse line blotting for the detection and typing of human papillomaviruses", Journal of Virological Methods, vol. 89, 2000, 29-37.
Kaboev, et al., "PCR hot start using primers with the structure of molecular beacons (hairpin-like structure)", Nucleic Acids Research, vol. 28, 2000, 1-2.
Kittler, R. et al., "A Whole Genome Amplification Method to Generate Long Fragments from Low Quantities of Genomic DNA", Analytical Biochemistry, vol. 300, 2002, 237-244.
Landegren, U. et al., "Reading Bits of Genetic Information: Methods for Single-Nucleotide Polymorphism Analysis", Genome Research, vol. 8, No. 8, 769-776, 1997.
Lo, Y.M. D. et al., "Prenatal Diagnosis of Fetal RhD Status by Molecular Analysis of Maternal Plasma", The New England Journal of Medicine, vol. 339, No. 24, 1998, 1734-1738.
Nelson, C. M. et al., "Whole genome transcription profiling of Anaplasma phagocytohilum in human and tick host cells by tiling array analysis", BMC Genomics, vol. 9, No. 364, Jul. 31, 2008, 16 pgs.
Nilsson, et al., "Analyzing genes using closing and replicating circles", Trends in Biotechnology, 24, 2006, 83-88.
Ohya, K. et al., "Detection of the CTG Repeat Expansion in Congenital Myotonic Dystrophy", Jpn J. Human Genet, vol. 42, 1997, 169-180.
Rechitsky, S. et al., "Allele Dropout in Polar Bodies and Blastomeres", Journal of Assisted Reproduction and Genetics, vol. 15, No. 5, 1998, 253-257.
Toth, T. et al., "Prenatal Detection of Trisomy 13 From Amniotic Fluid by Quantitative Fluorescent Polymerase Chain Reaction", Prenatal Diagnosis, vol. 18, 1998, 669-674.
Volckmar, et al., "A field guide for cancer diagnostics using cell-free DNA: From principles to practice and clinical applications", Genes Chromosomes Cancer, 2018, 123-139.
Wagner, F. F. et al., "RHD gene deletion occurred in the Rhesus box", Blood, vol. 95, No. 12, 2000, 3662-3668.

(56) References Cited

OTHER PUBLICATIONS

Wang, et al., "Molecular inversion probes: a novel microarray technology and its application in cancer research", Cancer Genetics, 205, 2012, 341-355.

Lajoie, B. R. et al., "The Hitchhiker's Guide to Hi-C Analysis: Practical guidelines", Methods: Author manuscript, vol. 72, Jan. 2015, 65-75.

Benesova, et al., "Mutation-based detectioin and monitoring of cell-free tumor DNA in peripheral blood of cancer patients", Analytical Biochemistry, vol. 433, 2013, 227-234.

Benn, Peter et al., "Current Controversies in Prenatal Diagnosis 2: NIPT results suggesting maternal cancer should always be disclosed", Prenatal Diagnosis, vol. 39, No. 5, 2018, 339-343.

Bianchi, Diana W. et al., "Noninvasive Prenatal Testing and Incidental Detection of Occult Maternal Malignancies", JAMA The Journal of the American Medical Association, vol. 314, No. 2, 2015, 162.

Birkenkamp-Demtroder, et al., "Longitudinal assessment of multiplex patient-specific ctDNA biomarkers in bladder cancer for diagnosis, surveillance and recurrence", Annals of Oncology, Oxford University Press NLD, vol. 29, No. Supplement 8, 2018, viii26.

Bunnapradist, S. et al., "Using both the fraction and Quantity of Donor-Derived Cell-free DNA to Detect Kidney Allograft Rejection", JASN, vol. 32, 2021, 2439-2441.

Burnham, P. et al., "Single-stranded DNA library preparation uncovers the origin and diversity of ultrashort cell-free DNA in plasma", Scientific Reports, vol. 6, No. 27859, Jun. 14, 2016, 9 pages.

Chen, Ke et al., "Multiplex PCR with the Blunt Harpin Primers for Next Generation Sequencing", Biotechnology and Bioprocess Engineering, vol. 22, 2017, 347-351.

Costa, J.-M. et al., "Fetal RHD genotyping in maternal serum during the first trimester of pregnancy", British Journal of Haematology, vol. 119, 2002, 255-260.

Daniels, G. et al., "Fetal blood group genotyping from DNA from maternal plasma: an important advance in the management and prevention of haemolytic disease of the fetus and newborn", Vox Sanguinis, vol. 87, 2004, 223-232.

Deusen, et al., "Comprehensive Detection of Driver Mutations in Acute Myeloid Leukemia Including Internal Tandem Duplications with Anchored Multiplex PCR and Next-Generation Sequencing", Blood, vol. 128, No. 22, 2016, 5251.

Dharajiya, Nilesh et al., "Detection of Maternal Neoplasia in Noninvasive Prenatal Testing", Clinical Chemistry, vol. 64, No. 2, 2018, 329-335.

Diehl, et al., "Detection and quantification of mutations in the plasma of patients with colorectal tumors", Proceedings of the National Academy of Sciences, vol. 102, 2005, 16368-16373.

Ehlayel, A. et al., "Emerging monitoring in kidney transplantation", Pediatric Nephrology, vol. 36, 2021, 3077-3087.

Glaab, W. E. et al., "A novel assay for allelic discrimination that combines the fluoregenic 5' nuclease polymerase chain reaction (TaqMan) and mismatch amplification mutation assay", Mutation Research, vol. 430, 1999, 12 pgs.

Grenda, R., "Torque teno (TTV) viral load as a biomarker of immunosuppresive strength after kidney transplantation in children", Pediatric Nephrology, vol. 36, May 27, 2020, 3 pages.

Illumina, "HumanOmni1-Quad BeadChip", Illumina DNA Analysis, Pub. No. 370-21009-007, 2009, 1 page.

Illumina, "HumanOmni2.5-8 BeadChips: Next-Generation GWAS Content for Genotyping and CNV Analysis", Data Sheet: DNA Analysis, Pub. No. 370-2011-008, 2011, 1 page.

Ji, Xing et al., "Copy number variation profile in noninvasive prenatal testing (NIPT) can identify co-existing maternal malignancies: Case reports and a literature review", Taiwanese Journal of Obstetrics and Gynecology, vol. 57, No. 6, 2018, 871-877.

Keshavjee, S. H. et al., "The role of dextran 40 and potassium in extended hypothermic lung preservation for transplantation", The Journal of Thoracic and Cardiovascular Surgery, vol. 103, No. 2, 1992.

Kim, et al., "Personalized therapy on the horizon for squamous cell carcinoma of the lung", Lung Cancer, vol. 80, 2013, 249-255.

Ku, et al., "Exome versus transcriptome sequencing in identifying coding region variants", Expert Review of Molecular Diagnostics, vol. 12, 2012, 241-251.

Kulifaj, D. et al., "Development of a standardized real time PCR for Torque teno viruses (TTV) viral load detection and quantification: A new tool for immune monitoring", Journal of Clinical Virology, vol. 105, 2018, 118-127.

Lenaerts, Liesbeth et al., "Noninvasive Prenatal Testing and Detection of Occult Maternal Malignancies", Clinical Chemistry, vol. 65, No. 12, 2019, 1484-1486.

Lin, et al., "A new diagnostic system for ultra-sensitive and specific detection and quantificiation of Candidatus Liberibacter asiaticus, the bacterium associated with citrus Huanglongbing", J Microbial Methods, 2010, 17-25.

Llop, et al., "Development of a highly sensitive nested-PCR procedure using a single closed tube for detection of Erwinia amylovora in asymptomatic plant material", Appl Environ Microbial., 2000, 2071-8.

Marusyk, et al., "Causes and consequences", Biochimica et Biophysica Acta, vol. 1805, 2010, 105-117.

Paruzynski, A. et al., "Genome-wide high-throughput integrome analyses by nrLAM-PCR and next-generation sequencing", Nature Protocols, vol. 5, No. 8, Jul. 8, 2010, 1379-1395.

Raemdonck, Dirk Van et al., "Ex-vivo lung perfusion", Transplant International, vol. 28, Issue 6, Special Issue: Focus Issue: Machine Perfusion, 2014, 643-656.

Schutz, E. et al., "Graft-derived cell-free DNA, a noninvasive early rejection and graft damage marker in liver transplantation: A prospective, observational, multicenter cohort study", PLOS Medicine, vol. 14, No. 4, Apr. 25, 2017, 19 pgs.

Selzner, Markus et al., "Normothermic Ex Vivo Liver Perfusion Using Steen Solution as Perfusate for Human Liver Transplantation: First North American Results", Liver Transplantation, vol. 22, Issue 11, 2016.

Sethi, Himanshu et al., "Analytical validation of the Signatera (TM) RUO assay, a highly ssensitive patient-specific multiplex PCR NGS-based noninvasive cancer recurrence detection and therapy monitoring assay", Cancer Research, vol. 78, No. 13, 2018, 4542.

Sigdel, Tara et al., "Optimizing Detection of Kidney Transplant Injury by Assessment of Donor-Derived Cell-Free DNA via Massively Multiplex PCR", Journal of Clinical Medicine, vol. 8, No. 1, 2018, 19.

Sigdel, Tara et al., "Plasma Donor-Derived Cell-Free DNA Quantification by massively multiplex PCR Distinguishes Kidney ransplant Acute Rejection", Transplantation, vol. 102, No. 7s, 2018, s178-s179.

Thermofisher Scientific, "How Ion AmpliSeq Targeted Sequencing Technology Works", https://www.thermofisher.com/us/en/home/life-science/ sequencing/next-generation-sequencing/ion-torrent-next-generation-sequencing-workflow/ion-torrent-next-generation-sequencing-select-targets/ampliseq-target-selection/how-ampliseq-technology-work.

Tungwiwat, et al., "Non-invasive fetal sex determination using a conventional nested PCR analysis of fetal DNA in maternal plasma", Clinica Chimica Acta, vol. 334, No. 1-2, 2003, 173-177.

Ventura-Aguiar, P. et al., "Donor-derived Cell-free DNA Shows High Sensitivity for the Diagnosis of Pancreas Graft Rejection in Simultaneous Pancreas-Kidney Transplantation", Transplantation, vol. 00, No. 00, 2022, 8 pages.

Wangkumhang, P. et al., "WASP: a Web-based Allele-Specific PCR assay designing tool for detecting SNPs and mutations", BMC Genomics, vol. 8, No. 275, Aug. 14, 2007, 9 pgs.

Whitlam, J. B. et al., "Diagnostic application of kidney allograft-derived absolute cell-free DNA levels during transport dysfunction", Am J Transplant, vol. 19, 2019, 1037-1049.

Wood, et al., "Molecular histology of lung cancer: From targets to treatments", Cancer Treatment Reviews, vol. 41, 2015, 361-375.

Xie, et al., "Designing highly multiplex PCR primer sets with Simulated Annealing Design using Dimer Likelihood Estimation (SADDLE)", Nat Commun., 2022, 1881.

(56) References Cited

OTHER PUBLICATIONS

Ye, et al., "Primer-BLAST: a tool to design target-specific primers for polymerase chain reaction", BMC Bioinformatics, 13:134, 2012, 11 pages.
Zheng, et al., "Whole-exome sequencing to identify novel somatic mutations in squamous cell lung cancers", International Journal of Oncology, vol. 43, 2015, 755-764.
Norton, et al., Perinatal and genetic outcomes associated with no call cfDNA results in 18,496 pregnancies, American Journal of Obstetrics & Gynecology , S3, 2021.
Livergood, Adverse perinatal outcomes and cell free DNA no calls: Beyond low fetal fractiction, American Journal of Obstetrics & Gynecology, S169, 2018.
Chung, et al., Cell-free DNA fetal fraction and pregnancy outcome, American Journal of Obstetrics & Gynecology, S157, 2019.
Scheffer, et al., Association between low fetal fraction in cell-free DNA testing and adverse pregnancy outcome: A systematic review, Prenatal Diagnosis, 1287-1295, 2021.
Wang, et al., DNA Degradation Test Predicts Success in Whole-Genome Amplification from Diverse Clinical Samples, Journal of Molecular Diagnostics, 441-451, 2007.
Margulies, et al., Genome Sequencing in Open Microfabricated High Density Picoliter Reactors, Nature, 376-380, 2005.
Gordon, Paul, et al., An Algorithm Measuring Donor Cell-Free DNA in Plasma of Cellular and Solid Organ Transplant Recipients That Does Not Require Donor or Recipient Genotyping, Frontiers in Cardiovascular Medicine, vol. 3, 2016.
Adamek, Martina, et al., A fast and simple method for detecting and quantifying donor-derived cell-free DNA in sera of solid organ transplant recipients as a biomarker for graft function, Clinical Chemistry and Laboratory Medicine: Journal of the Forum of the European Societies of Clinical Chemistry, pp. 1147-1155.
Asbor-Enoh, et al., Applying rigor and reproductibility standards to assay donor-derived cell-free DNA as a non-invasive method for detection of acute rejection and graft injury after heart transplantation, J Heart Lung Transplant, 17 pages.
Ahmed, et al., Cell Free DNA and Procalcitonin as Early Markers of Complications in ICU Patients with Multiple Trauma and Major Surgery, CLin Lab, 2395-2404.
Alachkar, Serum and urinary biomarkers in acute kidney transplant rejection, Nephrol Ther., 13-19.
Almeida, et al., Evaluation of 16 SNPs allele-specific to quantify post hSCT chimerism by SYBR green-based qRT-PCR, J Clin Pathol., 238-242.
Andargie, et al., Cell-free DNA maps COVID-19 tissue injury and risk of death and can cause tissue injury, JCI Insight, 20 pages.
Arshad, et al., Elevated Cell-Free Mitochondrial DNA in Filtered Plasma Is Associated With HIV Infection and Inflammation. J Acquir Immune Defic Syndr., 111-118.
Avriel, et al., Admission Cell-Free DNA Levels Predict 28-Day Mortality in Patients with Severe Sepsis in Intensive Care, PLoS One., 7 pages.
Ayyadevara, et al., Discrimination of primer 3'-nucleotide mismatch by taq DNA polymerasa during polymerase chain reaction, Anal Biochem. Aug. 15, 2000, 11-18.
Bai, et al., Detection and quantification of heteroplasmic mutant mitochondrial DNA by real-time amplification refractory mutation system quantitative PCR analysis: a single-step approach, Clin Chem., 996-1001.
Bergallo, et al., A novel TaqMAMA assay for allelic discrimination of TLR9 rs352140 polymorphism, J Virol Methods, 25-30.
Bergallo, et al., Evaluation of IFN-y polymorphism+874 T/A in patients with recurrent tonsillitis by PCR real time mismatch amplification mutation assay (MAMA real time PCR), Cytokine., 278-282.
Bezieau, et al., High incidence of N and K-Ras activating mutations in multiple myeloma and primary plasma cell leukemia at diagnosis, Hum Mutat., 212-224.

Board, et al., Detection of PIK3CA mutations in circulating free DNA in patients with breast cancer, Breast Cancer Res Treat, 461-467.
Board, et al., Multiplexed assays for detection of mutations in PIK3CA, Clin Chem., 757-760.
Braun, et al., Limitation of Circulating cfDNA Under the Use of a Cytokine Elimination Adsorber (CytoSorb) in Cardiac Surgery, The Thoracic and Cardiovascular Surgeon, 1 page.
Bronkhorst, et al., The emerging role of cell-free DNA as a molecular marker for cancer management, Biomol Detect Quantif, 23 pages.
Burgstaller, et al., Mitochondrial DNA heteroplasmy in ovine fetuses and sheep cloned by somatic cell nuclear transfer, BMC Dev Biol., 10 pages.
Cabel, et al., Circulating tumor DNA changes for early monitoring of anti-PDI immunotherapy: a proof-of-concept study, Ann Oncol., 1996-2001.
Castells, et al., K-ras mutations in DNA extracted from the plasma of patients with pancreatic carcinoma: diagnostic utility and prognostic significance, J Clin Oncol., 578-584.
Cagliani, et al., Deoxyribonuclease Reduces Tissue Injury and Improves Survival After Hemorrhagic Shock, J Surg Res., 104-113.
Castleberry, et al., Quantification of Circulating Cell-Free DNA in Pediatric Heart Transplant Recipients, Journal of Heart and Lung Transplantation, S139.
Chen, et al., Non-invasive prenatal diagnosis using fetal DNA in maternal plasma: a preliminary study for identification of paternally-inherited alleles using single nucleotide polymorphisms, BMJ Open, 8 pages.
Chan, et al., Bioinformatics analysis of circulating cell-free DNA sequencing data, Clin Biochem., 962-975.
Cheng, et al., Cell-Free DNA in Blood Reveals Significant Cell, Tissue and Organ Specific injury and Predicts COVID-19 Severity, medRxiv., 16 pages.
Chiu, et al., Effects of blood-processing protocols on fetal and total DNA quantification in maternal plasma, Clin Chem., 1607-1613.
Chiu, et al., Noninvasive prenatal exclusion of congenital adrenal hyperplasia by maternal plasma analysis: a feasible studyt, Clin Chem., 778-780.
Chu, et al., A novel approach toward the challenge of accurately quantifying fetal DNA in maternal plasma, Prenat Diagn., 1226-1229.
Clementi, et al., The Role of Cell-Free Plasma DNA in Critically III Patients with Sepsis, Blood Purif., 34-40.
Daly, Circulating donor-derived cell-free DNA: a true biomarker for cardiac allograft rejection?, Ann Transl Med., 6 pages.
Dandel, et al., Non-invasive cardiac allograft rejection surveillance: reliability and clinical value for prevention of heart failure, Heart Fail Rev., 319-336.
Dastsooz, et al., Multiplex ARMS PCR to Detect 8 Common Mutations of ATP7B Gene in Patients With Wilson Disease, Hepat Mon., 7 pages.
De Vlaminck, et al., Circulating cell-free DNA enables noninvasive diagnosis of heart transplant rejection, Sci Transl Med., 20 pages.
De Vlaminck, et al., Circulating cell-free DNA enables noninvasive diagnosis of heart transplant rejection, Sci Transl Med., 6 pages.
De Vlaminck, et al., Noninvasive motoring of infection and rejection after lung transplantation, Proc Natl Acad Sci U S A, 13336-13341.
Delgado, et al., Characterization of cell-free circulating DNA in plasma in patients with prostate cancer, Tumour Biol., 983-986.
Dey, et al., A plasma telomeric cell-free DNA level in unaffected women with BRCA1 or/and BRCA2 mutations: a pilot study. Oncotarget, Oncotarget, 4214-4222.
Ding, et al., New Progress in Plasma Cell-free DNA in Clinical Applications, Progress in Modern Biomedicine, 3593-3596.
Dwivedi, et al., Prognostic utility and characterization of cell-free DNA in patients with severe sepsis. Crit Care, 11 pages.
Fleischhacker, et al., Circulating nucleic acids (CNAs) and cancer—a survey, Biochim Biophys Acta, 181-232.
García Moreira, et al., Cell-free DNA as a noninvasive acute rejection marker in renal transplantation, Clin Chem., 1958-1966.

(56) References Cited

OTHER PUBLICATIONS

Garnacho-Montero, et al., Prognostic and diagnostic value of eosinopenia, C-relative protein, procalcitonin, and circulating cell-free DNA in critically ill patients admitted with suspicion of sepsis, Crit Care, 9 pages.
Strausberg, et al., Homo sapiens placenta-specific 4, mRNA (cDNA clone MGC:120720 IMAGE:7939530), complete cds, GenBank Submission; Accession No. Bc093685, version BC093685.1., 2 Pages.
Gripp, et al., Homo sapiens KRAS proto-oncogene, GTPase (KRAS), RefSeqGene (LRG_344) on chromosome 12, GenBank Submission; Accession No. NG_007524, version NG_007524.2, 16 Pages.
Huang, et al., Homo sapiens TSC complex subunit 1 (TSC1), RefSeqGene (LRG_486) on chromosome 9, GenBank Submission; Accession No. NG_012386, version NG_012386.1, 20 Pages.
Ghanta, et al., Non-invasive prenatal detection of trisomy 21using tandem single nucleotide polymorphisms, PLoS One, 10 pages.
Gielis, et al., Cell-Free DNA: An Upcoming Biomarker in Transplantation, Am J Transplant, 2541-2551.
Gielis, et al., Plasma donor-derived cell-free DNA kinetics after kidney transplantation using a single tube multiplex PCR assay, PLoS One, 16 pages.
Glaab, et al., A novel assay for allelic discrimination that combines the fluorogenic 5' nuclease polymerase chain reaction (TaqMan) and mismatch amplification mutation assay, Mutat Res., 1-12.
Gordon, et al., An Algorithm Measuring Donor Cell-Free DNA in Plasma of Cellular and Solid Organ Transplant Recipients That Does Not Require Donor or Recipient Genotyping, Front Cardiovasc Med., 10 pages.
Gormally, et al., Amount of DNA in plasma and cancer risk: a prospective study, Int J Cancer, 746-749.
Gotoh, et al., Prediction of MYCN amplification in neuroblastoma using serum DNA and real-time quantitative polymerase chain reaction, J Clin Oncol., 5205-5210.
Grskovic, et al., Validation of a Clinical-Grade Assay to Measure Donor-Derived Cell-Free DNA in Solid Organ Transplant Recipients, J Mol Diagn., 890-902.
Guedj, et al., A refined molecular taxonomy of breast cancer, Oncogene, 34 pages.
Hasi, et al., Acetaldehyde dehydrogenase 2 SNP rs671 and susceptibility to essential hypertension in Mongolians: a case control study, Genet Mol Res., 537-543.
Hidestrand, et al., Highlt sensitive noninvasive cardiac transplant rejection monitoring using targeted quantification of donor-specific cell-free deoxyribonucleic acid, J Am Coll Cardiol., 1224-1226.
Hidestrand, et al., Highlt Sensitive Transplant Rejection Surveillance Using Targeted Detection of Donor Specific Cell Free DNA, J Heart Lung Transplant, S91-S92.
Hidestrand, et al., Influencce of temperature during transportation on cellfree DNA analysis, Fetal Diagn Ther., 122-128.
Hidestrand, et al., Quantification of Circulating Donor Specific Cell Free DNA Is an Exquisitely Sensitive Non-Invasive Indicator of Injury to the Donor Heart, J Heart Lung Transplant, S101-S102.
Hoerning, et al., Quantitative real-time ARMS-qPCR for mitochondrial DNA enables accurate detection of microchimerism in real transplant recipients, Pediatr Transplant, 809-818.
Hou, et al., Application of tetra primer ARMS-PCR approach for detection of Fusarium graminearum genotypes with resistance to carbendazim, Australian Plant Pathology, 73-78.
Hudecova, Digital PCR analysis of circulating nucleic acids, Clin Biochem., 948-956.
Huang, et al., Circulating cell-free DNA levels correlate with postresuscitation survival rates in out-of-hospital cardiac arrest patients, Resuscitation, 213-218.
Hugon, et al., Influence of intention to adhere, beliefs and satisfaction about medicines on adherence in solid organ transplant recipients, Transplantation, 222-228.
Jordan, et al., Donor-derived Cell-free DNA Identifies Antibody-mediated Rejection in Donor Specific Antibody Positive Kidney Transplant Recipients, Transplant Direct, 5 pages.
Jung, et al., Cell-free DNA in the blood as a solid tumor biomarker—a critical appraisal of the literature, Clin Chim Acta., 1611-1624.
Karapetis, et al., K-ras mutations and benefit from cetuximab in advanced colorectal cancer, N Engl J Med., 1757-1765.
Khush, et al., Circulating cell-free DNA as a non-invasive marker of pediatric heart transplant rejection and immuno suppressive treatment, J Heart Lung Transplantation, S75.
Kindel, et al., Early Changes in Donor Fraction Cell-free DNA in Newly Transplanted Heart Transplant PAtients, ISHLT DF cfDNA declanation poster, 1 Page.
Kuo, et al., Preimplantation and prenatal genetic diagnosis of aromatic L-amino acid decarboxylase deficiency with an amplification refractory mutation system-quantitative polymerase chain reaction, Taiwan J Obstet Gynecol, 468-473.
Kustanovich, et al., Life and death of circulating cell-free DNA, Cancer Biol Ther., 1057-1067.
Lajin, et al., A quadruplex tetra-primer ARMS-PCR method for the simultaneous detection of TP53 Arg72Pro, IVS3 16bp Del/Ins and IVS6+62A>G, and NQO1 C609T polymorphisms, Gene., 268-273.
Lang, et al., Optimized allele-specific real-time PCR assays for the detection of common mutations in KRAS and BRAF, J Mol Diagn., 23-28.
Laurent-Puig, et al., Clinical relevance of KRAS-mutated subclones detected with picodroplet digital PCR in advanced colorectal cancer treated with anti-EGFR therapy, Clin Cancer Res., 1087-1097.
Lecomte, et al., Detection of free-circulating tumor-associated DNA in plasma of colorectal cancer patients and its association with prognosis, Int J Cancer, 542-548.
Lee, et al., Allele-Specific Quantitative PCR for Accurate, Rapid, and Cost-Effective Genotyping, Hum Gene Ther., 425-435.
Lefebure, et al., Prognostic value of circulating mutant DNA in unresectable metastatic colorectal cancer, Ann Surg., 275-280.
Levy, et al., Analysis of Cell-Free DNA to Assess Risk of Tumoremia Following Endoscopic Ultrasound Fine-Needle Aspiration of Pancreatic Adenocarcinomas, Clin Gastroenterol Hepatol., 1632-1640.
Li, et al., Multiplex co-amplification of 24 retinoblastoma gene exons after pre-amplification by long-distance PCR, Nucleic Acids Res., 538-539.
Lievre, et al., KRAS mutations as an independent prognostic factor in patients with advanced colorectal cancer treated with cetuximab, J Clin Oncol., 374-379.
Liu, et al., ABO chimerism determined by real-time polymerase chain reaction analysis after ABO-incompatible haematopoietic stem cell transplantation, Blood Tranfus, 43-52.
Liu, et al., Comparison of next-generation sequencing systems, J Biomed Biotechnol., 1-11.
Lo, et al., Plasma placental RNA allelic ratio permits noninvasive prenatal chromosomal aneuploidy detection, Nat Med., 218-223.
Lo, et al., Transsplantation monitoring by plasma DNA sequencing, Clin Chem., 941-942.
Luo, et al., Detection of usual and atypical aldehyde dehydrogenase alleles by mismatch amplification mutation assay, Clin Chem Lab Med., 1195-1197.
Mak, et al., Rapid diagnosis of Wilson disease by a 28-mutation panel: real-time amplification refractory mutation system in diagnosing acute Wilsonian liver failure, Clin Chim Acta., 39-42.
Manage, et al., Genotyping single nucleotide polymorphisms in human genomic DNA with an automated and self-contained PCR cassette, J Mol Diagn., 550-557.
Martinez-Herrero, et al., Cancer protection elicited by a single nucleotide polymorphism close to the adrenomedullin gene, J Clin Endocrinol Metab.,. E807-E810.
Mehra, et al., Gene expression profiles and B-type natriuretic peptide elevation in heart transplantation: more than a hemodynamic marker, Circulation, i21-I26.
Mehra, et al., International Society for Heart and Lung Transplantation working formultaion of a standardized nomenclature for cardiac allograft vasculopathy-2010, J Heart Lung Transplant, 717-727.
Misale, et al., Emergence of KRAS mutations and acquired resistance to anti-EGFR therapy in colorectal cancer, Nature, 532-536.

(56) References Cited

OTHER PUBLICATIONS

Mouliere, et al., Circulating Cell-Free DNA from Colorectal Cancer Patients May Reveal High KRAS or BRAF Mutation Load, Transl Oncol., 319-328.
Myers, et al., ACB-PCR quantification of somatic oncomutation, Methods Mol Biol., 345-363.
Newton, et al., Analysis of any point mutation in DNA. The amplification refractory mutation system (ARMS), Nucleic Acids Res., 2503-2516.
No Author Listed, Quantitative Detection of Circulating Donor-Specific DNA in Organ Transplant Recipients (DTRT-Multi-Center Study) (DTRT), ClinicalTrials.gov, Identifier: NCT02109575., 9 pages.
Oeth, et al., Qualitative and quantitative genotyping using single base primer extension coupled with matrix-assisted laser desorption/ionization time-of-flight mass spectrometry (MassARRAY®)., Methods Mol. Biol., 307-343.
Orou, et al., Allele-specific competitive blocker PCR: a one-step method with applicability to pool screening, Hum Mutat., 163-169.
Parsons, et al., allel-specific competitive blocker-PCR detection of rare base substitution, Methods Mol Biol., 235-245.
Peng, et al., Comparison of K-ras mutations in lung, colorectal and gastric cancer, Oncol Lett., 561-565.
Price, et al., Cost-effective interrogation of single nucleotide polymorphisms using the mismatch amplification mutation assay and capillary electrophoresis, Electrophoresis, 3881-3888.
Purhonen, et al., Human plasma cell-free DNA as a predictor of infectious complications of neutropenic fever in hematological patients, Infect Dis (Lond)., 255-259.
Qin, et al., Qunatitative assessment of hematopoietic chimerism by quantitative real-time polymerase chain reaction of sequence polymorphism systems after hemapoietic stem cell transplantation, Chin Med J (Engl), 2301-2308.
Quail, et al., A tale of three next generation sequencing platforms: comparison of Ion torrent, pacific biosciences and illumina MiSeq sequencers, BMC Genomics, 13 pages.
Ragalie, et al., Description of Longitudinal Measurement of Donor Fraction of Cell-Free DNA and Correlation to Clinical Outcomes, ISHLT poster, 1 page.
Ragalie, et al., Noninvasive Assay for Donor Fraction of Cell-Free DNA in Pediatric Heart Transplant Recipients, J Am Coll Cardiol., 2982-2983.
Roedder, et al., Biomarkers in solid organ transplantation: establishing personalized transplantation medicine, Genome Med., 12 pages.
Sanmamed, et al., Quantitative cell-free circulating BRAFV600E mutation analysis by use of droplet digital PCR in the follow-up of patients with melanoma being treated with BRAF inhibitors, Clin Chem., 297-304.
Sapio, et al., Detection of BRAF mutation in thyroid papillary carcinomas by mutant allele-specific PCR amplification (MASA), Eur J Endocrinol., 341-348.
Saukkonen, et al., Cell-free plasma DNA as a predictor of outcome in severe sepsis and septic shock., Clin Chem., 1000-1007.
Schnittger, et al., Development and validation of a real-time quantification assay to detect and monitor BRAFV600E mutations in hairy cell leukemia, Blood., 3151-3154.
Schutz, et al., Graft-derived cell-free DNA, a noninvasive early rejection and graft damage marker in liver trasnportation: A prospective, observational, multicenter cohort study, PLoS Med., 19 pages.
Schwarzenbach, et al., Cell-free nucleic acids as biomarkers in cancer patients, Nat Rev Cancer, 426-437.
Sefrioui, et al., Clinical value of chip-based digital-PCR platform for the detection of circulating DNA in metastatic colorectal cancer, Dig Liver Dis., 884-890.
Sheffield, et al., Attachment of a 40-base-pair G + C-rich sequence (GC-clamp) to genomic DNA fragments by the polymerase chain reaction results in improved detection of single-base changes, Proc Natl Acad Sci U S A, 232-236.

Shi, et al., Development of a single multiplex amplification reractory mutation system PCR for the detection of rifampin-resistant Mycobacterium tuberculosis, Gene., 95-99.
Shimabukuo-Vornhagen, et al., Cytokine release syndrome, J Immunother Cancer, 14 pages.
Sigdel, et al., A rapid noninvasive assay for the detection of renal transplant injury, Transplantation, 97-101.
Singh, et al., Aspergillus infections in transplant recipients, Clin Microbiol Rev., 44-69.
Snyder, et al., Universal noninvasive detection of solid organ transplant rejection, Proc Natl Acad Sci U S A, 6229-6234.
Sparks, et al., Noninvasive prenatal detection and selective analysis of cell-free DNA obtained from maternal blood: evaluation for trisomy 21 and trisomy 18, Am J Obstet Gynecol., 319.e1-319.e9.
Sparks, et al., Selective analysis of cell-free DNA in maternal blood evaluation of fetal trisomy, Prenat Diagn., 3-9.
Spindler, et al., Cell-free DNA in healthy individuals, noncancerous disease and strong prognostic value in colorectal cancer, Int J Cancer, 2984-2991.
Spindler, et al., KRAS-mutated plasma DNA as predictor of outcome from irinotecan monotherapy in metastatic colorectal cancer, Br J Cancer, 3067-3072.
Spindler, et al., Quantitative cell-free DNA, KRAS, and BRAF mutations in plasma from patients with metastatic colorectal cancer during treatment with cetuximab and irinotecan, Clin Cancer Res., 1177-1185.
Stein, Next-Generation Sequencing Update, Genetic Engineering & Biotechnology News, 10 pages.
Steinborn, et al., Coexistence of Bos taurus and B. indicus mitochondrial DNAs in nuclear transfer-derived somatic cattle clones, Genetics, 823-829.
Stemmer, et al., Use of magnetic beads for plasma cell-free DNA extraction: toward automation of plasma DNA analysis for molecular diagnostics, Clin Chem., 1953-1955.
Strohmeier, et al., Multiplex genotyping of KRAS point mutations in tumor cell DNA by allele-specific real-time PCR on a centrifugal microfluidic disk segment, Microchimica Acta., 1681-1688.
Suzuki, et al., Characterization of circulating DNA in healthy human plasma, Clin Chim Acta., 55-58.
Swinkels, et al., Effects of blood-processing protocols on cell-free DNA quantification in plasma, Clin Chem., 525-526.
Tabernero, et al., Analysis of circulating DNA and protein biomarkers to predict the clinical activity of regorafenib and assess prognosis in patients with metastatic colorectal cancer: a retrospective, exploratory analysis of the Correct trial, Lancet Oncol., 937-948.
Taira, et al., Novel high-speed droplet-allele specific-polymerase chain reaction: application in the rapid genotyping of single nucleotide polymorphisms, Clin Chim Acta., 39-46.
Taira, et al., Quantitative monitoring of single nucleotide mutations by allele-specific quantitative PCR can be used for the assessment of minimal residual disease in patients with hematological malignancies throughout their clinical course, Clin Chim Acta., 53-58.
Takai, et al., Clinical utility of circulating tumor DNA for molecular assessment in pancreatic cancer, Sci Rep., 10 pages.
Taly, et al., Multiplex picodroplet digital PCR to detect KRAS mutations in circulating DNA from the plasma of colorectal cancer patients, Clin Chem., 1722-1731.
Tamkovich, et al., Circulating nucleic acids in blood of healthy male and female donors, Clin Chem., 1317-1319.
Thierry, et al., Clinical validation of the detection of KRAS and BRAF mutations from circulating tumor DNA, Nat Med., 430-435.
Thierry, et al., A Targeted Q-PCR-Based Method for Point Mutation Testing by Analyzing Circulating DNA for Cancer Management Care, Methods Mol Biol., 1-16.
Tomita-Mitchell, et al., Human gene copy number spectra analysis in congenital heart malformations, Physiol Genomics, 518-541.
Tong, et al., Diagnostic developments involving cell-free (circulating) nucleic acids, Clin Chim Acta., 187-196.
Van Orsouw, et al., Rapid design of denaturing gradient-based two-dimensional electrophoretic gene mutational scanning test, Nucleic Acids Res., 2398-2406.

(56) References Cited

OTHER PUBLICATIONS

Vannucchi, et al., A quantitative assay for JAK2(V617F) mutation in myeloproliferative disorders by ARMS-PCR and capillary electrophoresis, Leukemia, 1055-1060.

Veseloskva, The use of cell-free nucleic acids in maternal plasma for non-invasive prenatal diagnosis of monogenic diseases, placental insufficiency-related complications and Down syndrom, These from Charles University in Prague, 104 pages.

Wangkumhang, et al., WASP: a Web-based Allele-Specific PCR assay designing tool for detecting SNPs and mutations, BMC Genomics, 9 Pages.

Wilkins, et al., IMP PCR primers detect single nucleotide polymorphisms for Anopheles gambiae species identification, Mopti and Savanna r DNA typles, and resistance to dieldrin in Anopheles arabiensis, Malar J., 7 pages.

Yamada, et al., Detection of K-ras gene mutations in plasma DNA of patients with pancreatic adenocarcinoma: correlation with clinicopathological features, Clin Cancer Res., 1527-1532.

Yi, et al., PCR/LDR/capillary electrophoresis for detection of single-nucleotide differences between fetal and maternal DNA in maternal plasma, Prenat Diagn., 217-222.

Zhang, et al., A novel multiplex tetra-primer ARMS-PCR for the simultaneous genotyping of six single nucleotide polymorphisms associated with female cancers, PLoS One, 8 pages.

Wapner, et al., Expanding the scope of noninvasive prenatal testing: detection of fetal microdeletion syndromes, Am J Obstet Gynecol., 332.e1-332.e9.

Zangwill, et al., Effect of endomyocardial biopsy on levels of donor-specific cell-free DNA, J Heart Lung Transplant, 1118-1120.

Richmond, et al., Donor fraction cell-free DNA and rejection in adult and pediatric heart transplantation, J Heart Lung Transplant, 454-463.

Peyster, et al., Advanced Morphologic Analysis for Diagnosing Allograft Rejection: The Case of Cardian Transplant Rejection, Transplantation, 1230-1239.

Mengel, et al., The molecular phenotype of heart ransplant biopsies: relationship to histopathological and clinical variables, Am J Transplant, 2105-2115.

Khush, et al., Noninvasive detection of graft injury after heart transplant using donor/\derived cell/\free DNA: A prospective multicenter study, Am J Transplant, 2889-2899.

Bienkowski, et al., Liquid biopsy for minimally invasive heart transplant monitoring: a pilot study, J Clin Pathol., 507-510.

Agbor-Enoh, et al., Cell-Free DNA to Detect Heart Allograft Acute Rejection, Circulation, 1184-1197.

Deshpande, et al., Relationship Between Donor Fraction Cell-Free DNA and Treatment for Rejection in Heart Transplantation, Pediatric Transplantation, 11 pages.

Kirkizlar, et al., Detection of Clonal and Subclonal Copy-Number Variants in Cell-Free DNA from Patients with Breast Cancer Using a Massively Multiplexed PCR Methodology, Transl Oncol., 407-416.

Liang, et al., Cationic nanoparticle as an inhibitor of cell-free DNA-induced inflammation, Nat Commun., 14 pages.

North, et al., Cell-free DNA donor fraction analysis in pediatric and adult heart transplant patients by multiplexed allele-specific quantitative PCR: Validation of a rapid and highly sensitive clinical test for stratification of rejection probability, PLoS One, 48 pages.

Tanem, et al., Abstract 16873: Association of Preoperative Cell-Free DNA Levels and Outcome Following Pediatric Cardiopulmonary Bypass, Circulation, 1-6.

Scott, et al., Total Cell-Free DNA Predicts Death and Infection Following Pediatric and Adult Heart Transplantation, Ann Thorac Surg., 1282-1289.

Scott, et al., Elevated nuclear and mitochondrial cell-free deoxyribonucleic acid measurements are associated with death after infant cardiac surgery, J Thorac Cardiovasc Surg., 367-375.

Jing, et al., Cell-free DNA: characteristics, detection and its applications in myocardial infarction, Curr Pharm Des., 5135-5145.

No Author Listed, The Journal of Heart and Lung Transplantation, Apr. 2012, vol. 31, Issue 4, Supplement, pp. A1-A4, S1-S310. https://www.google.de/searchq=The+Journal+of+Heart+and+Lung+Transplantation+Volume+31,+Issue+4,+Supplement&sourceid=ie7&rls=com.microsoft:en-US:IE-Address&ie=&oe=#spf=1604593918239, A1-A4.

Woude, et al., Methods of identifying drugs with selective effects against cancer cells, Oct. 7, 1997, Nucleic acid sequence search reports AC: 151794, 2 Pages.

PCT/US2017/059808, International Search Report and Written Opinion for Application, , 12 pages, mailed Jan. 25, 2018.

PCT/US2017/059808, International Preliminary Report on PAtentability, 8 pages, mailed May 16, 2019.

18820195.8, Extended European Search Report, 9 pages, mailed Jan. 27, 2021.

PCT/US2018/038598, International Search Report and Written Opinion, 8 pages, mailed Sep. 7, 2018.

PCT/US2018/038598, International Preliminary Report on Patentability, 6 pages, mailed Jan. 2, 2020.

18821381.3, Extended European Search Report, 9 pages, mailed Feb. 15, 2021.

PCT/US2018/038609, International Search Report and Written Opinion, 9 pages, mailed Sep. 10, 2018.

PCT/US2018/038609, International Preliminary Report on Patentability, 7 pages, mailed Jan. 2, 2020.

Khater & Khauli, Pseudorejection and true rejection after kidney transplantation: classification and clinical significance, Urol Int., 373-80, 2012.

Kiyomi, Morita, et al., Clearance of Somatic Mutations at Remission and the Risk of Relapse in Acute Myeloid Leukemia, J Clin Oncol, 1788-1797, 2018.

Bewersdorf, Jan Philipp, et al., From clonal hematopoiesis to myeloid leukemia and what happens in between: Will improved understanding lead to new therapeutic and preventive opportunites?, Blood Review, 6, 2019.

Jaiswal, Siddhartha, et al., Clonal hematopoiesis in human aging and disease, Science, 4, 2019.

Coombs, Catherine, et al., Therapy-Related Clonal Hematopoiesis in Patients with Non-hematologic Cancers Is Common and Associated with Adverse Clinical Outcomes, Cell Stem Cell, 374, 2017.

Giulio, Genovese, et al., Hematopoiesis and Blood-Cancer Risk Inferred from Blood DNA Sequence, The New England Journal of Medicine, 2477-2487, 2014.

Steensma, D. P., et al., Clonal hematopoiesus of indeterminate potential and its distinction from myelodysplastic syndromes, BLOOD, 9-16, 2015.

Koeppe, et al., HIV-1-Specific CD4+ T-Cell Responses Are Not Associated With Significant Viral Epitope Variation in Persons With Persistent Plasma Viremia, J Acquir Immune Defic Syndr, 41:140-148, 2006.

Kane, et al., Application of less primer method to PCR, DNA Polymorphism, vol. 13, pp. 34-37, 2004.

Chang, et al., Identification of individual DNA molecule of Mycobacterium tuberculosis by nested PCR-RLFP and capillary electrophoresis, National Library of Medicine, 182-8, 2008.

Metzker, Michael, Declaration of Michael L. Metzker, Ph.D. from IPR2018-01317, 2004.

Vandekerkhove, G, et al., Circulating Tumor DNA Reveals Clinically Actionable Somatic Genome of Metastatic Bladder Cancer, Clinical Cancer Research, 6487-6497, 2017.

No Author Listed, *Natera Inc.* vs. *ArcherDx Verdict Form*, Case 1:20-cv-00125-GBW, 1-12, 2023.

Blomquist, et al., Targeted RNA-Sequencing with Competitive Multiplex-PCR Amplicon Libraries, PLOS ONE, vol. 8, Issue 11, 2013.

No Author Listed, Jury Rules in Favor of Natera, Finding All Asserted Patents Valid and Infrindged by ArcherDX/Invite; Awards $19.35 Million in Past Damages for Royalties and Lost Profits, Natera Press Release, 4 pgs, 2023.

Lizardi, et al., Mutation detection and single-molecule counting using isothermal rolling-circle amplification, Nature Genetics, 225-232, 1998.

(56) References Cited

OTHER PUBLICATIONS

Fire, et al., Rolling replication of short DNA circles, PNAS, 4641-4645, 1995.
Abbosh, et al., Phylogenetic ctDNA analysis depicts early-stage lung cancer evolution, Nature, 446-453, 2017.
Reinert, et al.,, Analysis of Plasma Cell-Free DNA by Ultradeep Sequencing in Patients With Stages I to UI Colorectal Cancer, JAMA Oncology, 1-74, 2019.
Mamanova, L., et al., Target-enrichment strategies for next-generation sequencing, Nat Methods, 111-118, 2010.
Peng, Q, et al., Reducing amplification artifacts in high multiplex amplicon sequencing by using molecular barcodes, BMC Genomics, 12 pages, 2015.
Krishnakumar, S., et al., A comprehensive assay for targeted multiplex amplification of human DNA sequences, PNAS, 9296-9301, Jul. 8, 2008.
Valenza, F., et al., The Consumption of Glucose During Ex Vivo Lung Perfusion Correlates with Lung Edema, Transplantation Proceedings, 993-996, 2011.
Stone, J. P., et al., Altered Immunogenicity of Donor Lungs via Removal of Passenger Leukocytes Using Ex Vivo Lung Perfusion, American Journal of Transplantation, 33-43, 2016.
Mueller, P. R., et al., In Vivo Footprinting of a Muscle Specific Enhancer by Ligation Mediated PCR, Science, 780-786, Nov. 10, 1989.
Maheswaran, S., et al., Detection of Mutations in EGFR in Circulating Lung-Cancer Cells, N Engl J Med, 366-377, Jul. 24, 2008.
Yamauchi Medical Clinic, Chromosome abnormality, http://www.yamauchi-iin.com/kaisetu/1241.html, 3 pages, Dec. 10, 2015.
Mamun, et al., The *Escherichia coli* UVM response is accompanied by an SOS-independent error-prone DNA replication activity demonstrable in vitro, Molecular Microbiology, 368-380, 2000.
Jung, Klaus, et al., Increased cell-free DNA in plasma of patients with metastatic spread in prostate cancer, Cancer Letters, 173-180, 2004.
Kirsch-Gerweck, et al., HaploBlocks: Efficient Detection of Positive Selection in LArge Population Genomic Datasets, Mol. Biol. Evol., 2023.
Ge, et al., Haplotype block: a new type of forensic DNA markers, Int J Legal Med, 353-361, 2010.
Chen, Kevin, et al., Commercial ctDNA Assays for Minimal Residual Disease Detection of Solid Tumors, Molecular Diagnosis & Therapy, vol. 25, Issue 6, 757-774, Nov. 1, 2021.
Avanzine, Stefano, et al., A mathematical model of ctDNA shedding predicts tumor detection size, Science Advances, vol. 6, Issue eabc4308, 9 pages, Dec. 11, 2020.
Goessl, C. et al., "DNA Alterations in Body Fluids as Molecular Tumor Markers for Urological Malignancies", European Urology, vol. 41, 2002, 668-676.
Kaper, Fiona et al., "Abstract 1164: Parallel preparation of targeted resequencing libraries from 480 genomic regions using multiplex PCR on the Access Array system", American Association for Cancer Research, 2010, 1-2.
Kaper, Fiona et al., "Parallel Preparation of Targeted Resequencing Libraries from 480 Genomic Regions Using Multiplex PCR on the Access Array System", Fluidigm Poster, 2011, 1.
Wong, I. H. et al., "Qunatitative Analysis of Tumor-derived Methylated p161NK4a Sequences in Plasma, Serum, and Blood Cells of Hepatocellular Carcinoma Patients", Clinical Cancer Research, vol. 9, Mar. 2003, 1047-1052.
Vargas, D. Y. et al., "Multiplex Real-Time PCR Assays that Measure the Abundance of Extremely Rare Mutations Associated with Cancer", PLOS One, vol. 11, No. 5, May 31, 2016, 26 pgs.
Agbor-Enoh, Sean et al., "Circulating cell free DNA as a bimarker of tissue injury: Assessment in a cardiac xenotransplantation model", Journal of Heart and Long Transplantation, vol. 37, No. 8, 2018, 967-975.
Ali, N. M. et al., "Fetal and Donor-Derived Cell-Free Dna May Assist in Differentiating Pregnancy Related Changes from Allograft Rejection in Kidney Transplant Recipients", American Journal of Transplantation, vol. 23, No. 6, Poster Abstract., 2023.
Antoniou, A. et al., "Data augmentation generative adversarial networks.", arXiv preprint arXiv:1711.04340, (Year: 2017), Nov. 12, 2017, 14 pages.
Li, Ying et al., "Biochemical and Clinical Diagnostic Aspects of Circulating Nucleic Acids", Dissertation, 2005, 103 Pages.
Liao, W et al., "Noninvasice detection of tumor-associated mutations from circulating cell-free DNA in hepatocellular carcinoma patients by targeted deep sequencing.", Oncotarget, 7(26), (Year: 2016), Jun. 28, 2016, 40481-40490.
Malapelle, U. et al., "Next generation sequencing techniques in liquid biopsy: focus on non-small cell lung cancer patients.", Transl Lung Cancer Res., 5(5), (Year: 2016), Oct. 2016, 505-510.
Min, S. et al., "Deep learning in bioinformatics.", Brieg Bioinform., 18(5), (Year: 2017), Sep. 1, 2017, 851-869.
Moscow, J. A. et al., "Engraftment of MDR1 and NeoR Gene-Transduced Hematopoietic Cells After Breast Cancer Chemotherapy", Blood, vol. 94, No. 1, 1999, 52-61.
Neocleous, A. C. et al., "First Trimester Noninvasive Prenatal Diagnosis: A Computational Intelligence Approach", in IEEE Journal of Biomedical and Health Informatics, vol. 20, No. 5, (Year: 2016), Sep. 2016, pp. 1427-1438.
Oustimov, A., "Artificial neural networks in the cancer genomics frontier.", Translational cancer research., 3(3), (Year: 2014), Jun. 2014, 11 pages.
Stephens, Z. D. et al., "Simulating Next-Generation Sequencing Datasets from Empirical Mutation and Sequencing Models.", PLoS One., 11(11):e0167047. (Year: 2016), Nov. 28, 2016, 18 pages.
Tang, Jessica et al., "Donor-derived cell free DNA (dd-cfDNA) in pregnant kidney transplant recipients", American Journal of Obstetrics & Gynecology, vol. 228, No. 1, 2023.

\* cited by examiner

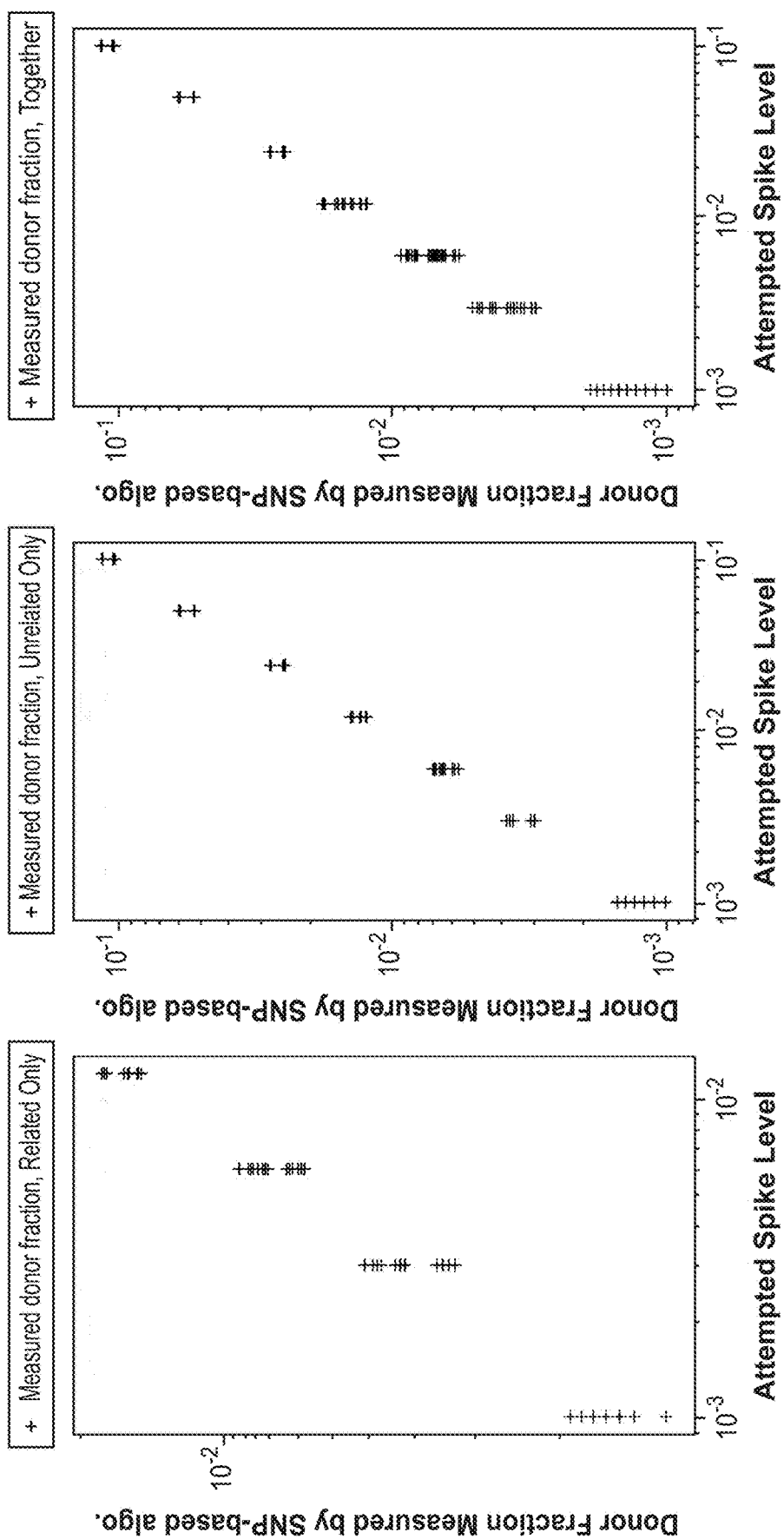

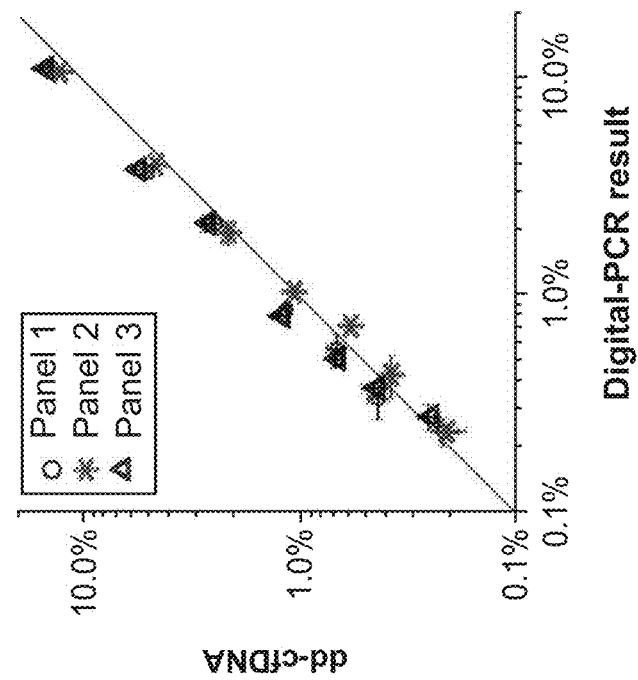
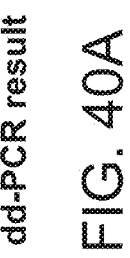
FIG. 40A
FIG. 40B

METHODS FOR DETECTION OF DONOR-DERIVED CELL-FREE DNA

CROSS REFERENCE TO RELATED APPLICATIONS

This application is a continuation of U.S. Utility application Ser. No. 17/252,068, filed Dec. 14, 2020. U.S. Utility application Ser. No. 17/252,068 is a National Stage Entry of PCT Application No. PCT/US2019/040603, filed Jul. 3, 2019. PCT Application No. PCT/US2019/040603 claims priority to U.S. Provisional Application No. 62/693,833 filed Jul. 3, 2018; U.S. Provisional Application No. 62/715,178 filed Aug. 6, 2018; U.S. Provisional Application No. 62/781,882 filed Dec. 19, 2018; and U.S. Provisional Application No. 62/834,315 filed Apr. 15, 2019. Each of these applications cited above is hereby incorporated by reference in its entirety.

FIELD

The present disclosure relates generally to methods for detecting donor-derived DNA within a transplant recipient.

BACKGROUND

There is currently about 190,000 living kidney recipients in the United State and about 20,000 kidney transplant surgeries occur annually. Rapid detection of kidney allograft injury and/or rejection remains a challenge. Previous attempts to use serum creatinine to determine kidney transplant status have lacked specificity, and biopsy transplants are invasive and costly and possibly lead to late diagnosis of transplant injury and/or rejection.

Because the immune system recognizes an allograft as foreign to a body and activates various immune mechanisms to reject the allograft, it is often necessary to medically suppress the normal immune system response to reject a transplant. Therefore, there is a need for a non-invasive test for transplantation rejection that is more sensitive and more specific than conventional tests.

SUMMARY

In one aspect, the present invention relates to a method of quantifying the amount of donor-derived cell-free DNA (dd-cfDNA) in a blood sample of a transplant recipient, comprising: extracting DNA from the blood sample of the transplant recipient, wherein the DNA comprises donor-derived cell-free DNA and recipient-derived cell-free DNA; performing targeted amplification at 500-50,000 target loci in a single reaction volume using 500-50,000 primer pairs, wherein the target loci comprise polymorphic loci and non-polymorphic loci, and wherein each primer pair is designed to amplify a target sequence of no more than 100 bp; and quantifying the amount of donor-derived cell-free DNA in the amplification products.

In another aspect, the present invention relates to a method of quantifying the amount of donor-derived cell-free DNA (dd-cfDNA) in a blood sample of a transplant recipient, comprising: extracting DNA from the blood sample of the transplant recipient, wherein the DNA comprises donor-derived cell-free DNA and recipient-derived cell-free DNA, and wherein the extracting step comprises size selection to enrich for donor-derived cell-free DNA and reduce the amount of recipient-derived cell-free DNA disposed from bursting white-blood cells; performing targeted amplification at 500-50,000 target loci in a single reaction volume using 500-50,000 primer pairs, wherein the target loci comprise polymorphic loci and non-polymorphic loci; and quantifying the amount of donor-derived cell-free DNA in the amplification products.

In another aspect, the present invention relates to a method of detecting donor-derived cell-free DNA (dd-cfDNA) in a blood sample of a transplant recipient, comprising: extracting DNA from the blood sample of the transplant recipient, wherein the DNA comprises donor-derived cell-free DNA and recipient-derived cell-free DNA; performing targeted amplification at 500-50,000 target loci in a single reaction volume using 500-50,000 primer pairs, wherein the target loci comprise polymorphic loci and non-polymorphic loci; sequencing the amplification products by high-throughput sequencing; and quantifying the amount of donor-derived cell-free DNA.

In some embodiments, the method further comprises performing universal amplification of the extracted DNA. In some embodiments, the universal amplification preferentially amplifies donor-derived cell-free DNA over recipient-derived cell-free DNA that are disposed from bursting white-blood cells.

In some embodiments, the transplant recipient is a mammal. In some embodiments, the transplant recipient is a human.

In some embodiments, the transplant recipient has received a transplant selected from organ transplant, tissue transplant, cell transplant, and fluid transplant. In some embodiments, the transplant recipient has received a transplant selected from kidney transplant, liver transplant, pancreas transplant, intestinal transplant, heart transplant, lung transplant, heart/lung transplant, stomach transplant, testis transplant, penis transplant, ovary transplant, uterus transplant, thymus transplant, face transplant, hand transplant, leg transplant, bone transplant, bone marrow transplant, cornea transplant, skin transplant, pancreas islet cell transplant, heart valve transplant, blood vessel transplant, and blood transfusion. In some embodiments, the transplant recipient has received a kidney transplant.

In some embodiments, the quantifying step comprises determining the percentage of donor-derived cell-free DNA out of the total of donor-derived cell-free DNA and recipient-derived cell-free DNA in the blood sample. In some embodiments, the quantifying step comprises determining the number of copies of donor-derived cell-free DNA per volume unit of the blood sample.

In some embodiments, the method further comprises detecting the occurrence or likely occurrence of active rejection of transplantation using the quantified amount of donor-derived cell-free DNA. In some embodiments, the method is performed without prior knowledge of donor genotypes.

In some embodiments, each primer pair is designed to amplify a target sequence of about 50-100 bp. In some embodiments, each primer pair is designed to amplify a target sequence of no more than 75 bp. In some embodiments, each primer pair is designed to amplify a target sequence of about 60-75 bp. In some embodiments, each primer pair is designed to amplify a target sequence of about 65 bp.

In some embodiments, the targeted amplification comprises amplifying at least 1,000 polymorphic loci in a single reaction volume. In some embodiments, the targeted amplification comprises amplifying at least 2,000 polymorphic loci in a single reaction volume. In some embodiments, the targeted amplification comprises amplifying at least 5,000 polymorphic loci in a single reaction volume. In some embodiments, the targeted amplification comprises amplifying at least 10,000 polymorphic loci in a single reaction volume.

In some embodiments, method further comprises measuring an amount of one or more alleles at the target loci that are polymorphic loci. In some embodiments, the polymorphic loci and the non-polymorphic loci are amplified in a single reaction.

In some embodiments, the quantifying step comprises detecting the amplified target loci using a microarray. In some embodiments, the quantifying step does not comprise using a microarray.

In some embodiments, the targeted amplification comprises simultaneously amplifying 500-50,000 target loci in a single reaction volume using (i) at least 500-50,000 different primer pairs, or (ii) at least 500-50,000 target-specific primers and a universal or tag-specific primer 500-50,000 primer pairs.

In a further aspect, the present invention relates to a method of determining the likelihood of transplant rejection within a transplant recipient, the method comprising: extracting DNA from the blood sample of the transplant recipient, wherein the DNA comprises donor-derived cell-free DNA and recipient-derived cell-free DNA; performing universal amplification of the extracted DNA; performing targeted amplification at 500-50,000 target loci in a single reaction volume using 500-50,000 primer pairs, wherein the target loci comprise polymorphic loci and non-polymorphic loci; sequencing the amplification products by high-throughput sequencing; and quantifying the amount of donor-derived cell-free DNA in the blood sample, wherein a greater amount of dd-cfDNA indicates a greater likelihood of transplant rejection.

In a further aspect, the present invention relates to a method of diagnosing a transplant within a transplant recipient as undergoing acute rejection, the method comprising: extracting DNA from the blood sample of the transplant recipient, wherein the DNA comprises donor-derived cell-free DNA and recipient-derived cell-free DNA; performing universal amplification of the extracted DNA; performing targeted amplification at 500-50,000 target loci in a single reaction volume using 500-50,000 primer pairs, wherein the target loci comprise polymorphic loci and non-polymorphic loci; sequencing the amplification products by high-throughput sequencing; and quantifying the amount of donor-derived cell-free DNA in the blood sample, wherein an amount of dd-cfDNA of greater than 1% indicates that the transplant is undergoing acute rejection.

In some embodiments, the transplant rejection is antibody mediated transplant rejection. In some embodiments, the transplant rejection is T cell mediated transplant rejection.

In some embodiments, an amount of dd-cfDNA of less than 1% indicates that the transplant is either undergoing borderline rejection, undergoing other injury, or stable.

In a further aspect, the present invention relates to a method of monitoring immunosuppressive therapy in a subject, the method comprising: extracting DNA from the blood sample of the transplant recipient, wherein the DNA comprises donor-derived cell-free DNA and recipient-derived cell-free DNA; performing universal amplification of the extracted DNA; performing targeted amplification at 500-50,000 target loci in a single reaction volume using 500-50,000 primer pairs, wherein the target loci comprise polymorphic loci and non-polymorphic loci; sequencing the amplification products by high-throughput sequencing; and quantifying the amount of donor-derived cell-free DNA in the blood sample, wherein a change in levels of dd-cfDNA over a time interval is indicative of transplant status.

In some embodiments, the method further comprising adjusting immunosuppressive therapy based on the levels of dd-cfDNA over the time interval.

In some embodiments, an increase in the levels of dd-cfDNA is indicative of transplant rejection and a need for adjusting immunosuppressive therapy. In some embodiments, no change or a decrease in the levels of dd-cfDNA indicates transplant tolerance or stability, and a need for adjusting immunosuppressive therapy.

In some embodiments, an amount of dd-cfDNA of greater than 1% indicates that the transplant is undergoing acute rejection. In some embodiments, the transplant rejection is antibody mediated transplant rejection. In some embodiments, the transplant rejection is T cell mediated transplant rejection.

In some embodiments, an amount of dd-cfDNA of less than 1% indicates that the transplant is either undergoing borderline rejection, undergoing other injury, or stable.

In some embodiments, the method does not comprise genotyping the transplant donor and/or the transplant recipient.

In some embodiments, the method further comprises measuring an amount of one or more alleles at the target loci that are polymorphic loci.

In some embodiments, the target loci comprise at least 1,000 polymorphic loci, or at least 2,000 polymorphic loci, or at least 5,000 polymorphic loci, or at least 10,000 polymorphic loci.

In some embodiments, the target loci that are amplified in amplicons of about 50-100 bp in length, or about 50-90 bp in length, or about 60-80 bp in length, or about 60-75 bp in length, or about 65 bp in length.

In some embodiments, the transplant recipient is a human. In some embodiments, the transplant recipient has received a transplant selected from a kidney transplant, liver transplant, pancreas transplant, islet cell transplant, intestinal transplant, heart transplant, lung transplant, bone marrow transplant, heart valve transplant, or a skin transplant. In some embodiments, the transplant recipient has received a kidney transplant.

In some embodiments, the extracting step comprises size selection to enrich for donor-derived cell-free DNA and reduce the amount of recipient-derived cell-free DNA disposed from bursting white-blood cells.

In some embodiments, the universal amplification step preferentially amplifies donor-derived cell-free DNA over recipient-derived cell-free DNA that are disposed from bursting white-blood cells.

In some embodiments, the method comprises longitudinally collecting a plurality of blood samples from the transplant recipient after transplantation, and repeating steps (a) to (e) for each blood sample collected. In some embodiments, the method comprises collecting and analyzing blood samples from the transplant recipient for a time period of about three months, or about six months, or about twelve months, or about eighteen months, or about twenty-four months, etc. In some embodiments, the method comprises collecting blood samples from the transplant recipient at an interval of about one week, or about two weeks, or about three weeks, or about one month, or about two months, or about three months, etc.

In some embodiments, the method has a sensitivity of at least 80%, or at least 85%, or at least 90%, or at least 95%, or at least 98% in identifying acute rejection (AR) over non-AR with a cutoff threshold of 1% dd-cfDNA and a confidence interval of 95%.

In some embodiments, the method has a specificity of at least 60%, or at least 65%, or at least 70%, or at least 75%, or at least 80%, or at least 85%, or at least 90% in identifying AR over non-AR with a cutoff threshold of 1% dd-cfDNA and a confidence interval of 95%.

In some embodiments, the method has an area under the curve (AUC) of at least 0.8, or 0.85, or at least 0.9, or at least 0.95 in identifying AR over non-AR with a cutoff threshold of 1% dd-cfDNA and a confidence interval of 95%.

In some embodiments, the method has a sensitivity of at least 80%, or at least 85%, or at least 90%, or at least 95%, or at least 98% in identifying AR over normal, stable allografts (STA) with a cutoff threshold of 1% dd-cfDNA and a confidence interval of 95%.

In some embodiments, the method has a specificity of at least 80%, or at least 85%, or at least 90%, or at least 95%, or at least 98% in identifying AR over STA with a cutoff threshold of 1% dd-cfDNA and a confidence interval of 95%.

In some embodiments, the method has an AUC of at least 0.8, or 0.85, or at least 0.9, or at least 0.95, or at least 0.98, or at least 0.99 in identifying AR over STA with a cutoff threshold of 1% dd-cfDNA and a confidence interval of 95%.

In some embodiments, the method has a sensitivity as determined by a limit of blank (LoB) of 0.5% or less, and a limit of detection (LoD) of 0.5% or less. In some embodiments, LoB is 0.23% or less and LoD is 0.29% or less. In some embodiments, the sensitivity is further determined by a limit of quantitation (LoQ). In some embodiments, LoQ is 10 times greater than the LoD; LoQ may be 5 times greater than the LoD; LoQ may be 1.5 times greater than the LoD; LoQ may be 1.2 times greater than the LoD; LoQ may be 1.1 times greater than the LoD; or LoQ may be equal to or greater than the LoD. In some embodiments, LoB is equal to or less than 0.04%, LoD is equal to or less than 0.05%, and/or LoQ is equal to the LoD.

In some embodiments, the method has an accuracy as determined by evaluating a linearity value obtained from linear regression analysis of measured donor fractions as a function of the corresponding attempted spike levels, wherein the linearity value is a R2 value, wherein the R2 value is from about 0.98 to about 1.0. In some embodiments, the R2 value is 0.999. In some embodiments, the method has an accuracy as determined by using linear regression on measured donor fractions as a function of the corresponding attempted spike levels to calculate a slope value and an intercept value, wherein the slope value is from about 0.9 to about 1.2 and the intercept value is from about −0.0001 to about 0.01. In some embodiments, the slope value is approximately 1, and the intercept value is approximately 0.

In some embodiments, the method has a precision as determined by calculating a coefficient of variation (CV), wherein the CV is less than about 10.0%. CV is less than about 6%. In some embodiments, the CV is less than about 4%. In some embodiments, the CV is less than about 2%. In some embodiments, the CV is less than about 1%.

In some embodiments, the AR is antibody-mediated rejection (ABMR). In some embodiments, the AR is T-cell-mediated rejection (TCMR).

Further disclosed herein are methods for detection of transplant donor-derived cell-free DNA (dd-cfDNA) in a sample from a transplant recipient. In some embodiments, in the methods disclosed herein, the transplant recipient is a mammal. In some embodiments, the transplant recipient is a human. In some embodiments, the transplant recipient has received a transplant selected from a kidney transplant, liver transplant, pancreas transplant, islet cell transplant, intestinal transplant, heart transplant, lung transplant, bone marrow transplant, heart valve transplant, or a skin transplant. In some embodiments, the transplant recipient has received a kidney transplant. In some embodiments, the method may be performed on transplant recipients the day of or after transplant surgery, up to a year following transplant surgery.

In some embodiments, disclosed herein is a method of amplifying target loci of donor-derived cell-free DNA (dd-cfDNA) from a blood sample of a transplant recipient, the method comprising: a) extracting DNA from the blood sample of the transplant recipient, wherein the DNA comprises cell-free DNA derived from both the transplanted cells and from the transplant recipient, b) enriching the extracted DNA at target loci, wherein the target loci comprise 50 to 5000 target loci comprising polymorphic loci and non-polymorphic loci; and c) amplifying the target loci.

In some embodiments, disclosed herein is a method of detecting donor-derived cell-free DNA (dd-cfDNA) in a blood sample from a transplant recipient, the method comprising: a) extracting DNA from the blood sample of the transplant recipient, wherein the DNA comprises cell-free DNA derived from both the transplanted cells and from the transplant recipient, b) enriching the extracted DNA at target loci, wherein the target loci comprise 50 to 5000 target loci comprising polymorphic loci and non-polymorphic loci; c) amplifying the target loci; d) contacting the amplified target loci with probes that specifically hybridize to target loci; and e) detecting binding of the target loci with the probes, thereby detecting dd-cfDNA in the blood sample. In some embodiments, the probes are labelled with a detectable marker.

In some embodiments, disclosed herein is a method of determining the likelihood of transplant rejection within a transplant recipient, the method comprising: a) extracting DNA from the blood sample of the transplant recipient, wherein the DNA comprises cell-free DNA derived from both the transplanted cells and from the transplant recipient, b) enriching the extracted DNA at target loci, wherein the target loci comprise 50 to 5000 target loci comprising polymorphic loci and non-polymorphic loci; c) amplifying the target loci; and d) measuring an amount of transplant DNA and an amount of recipient DNA in the recipient blood sample; wherein a greater amount of dd-cfDNA indicates a greater likelihood of transplant rejection.

In some embodiments, disclosed herein is a method of diagnosing a transplant within a transplant recipient as undergoing acute rejection, the method comprising: a) extracting DNA from the blood sample of the transplant recipient, wherein the DNA comprises cell-free DNA derived from both the transplanted cells and from the transplant recipient, b) enriching the extracted DNA at target loci, wherein the target loci comprise 50 to 5000 target loci comprising polymorphic loci and non-polymorphic loci; c) amplifying the target loci; and d) measuring an amount of transplant DNA and an amount of recipient DNA in the recipient blood sample; wherein an amount of dd-cfDNA of greater than 1% indicates that the transplant is undergoing acute rejection.

In some embodiments, in the methods disclosed herein, the transplant rejection is antibody mediated transplant rejection. In some embodiments, the transplant rejection is T cell mediated transplant rejection. In some embodiments, an amount of dd-cfDNA of less than 1% indicates that the transplant is either undergoing borderline rejection, undergoing other injury, or stable.

In some embodiments, disclosed herein is a method of monitoring immunosuppressive therapy in a subject, the method comprising a) extracting DNA from the blood sample of the transplant recipient, wherein the DNA comprises cell-free DNA derived from both the transplanted cells and from the transplant recipient, b) enriching the extracted DNA at target loci, wherein the target loci comprise 50 to 5000 target loci comprising polymorphic loci and non-polymorphic loci; c) amplifying the target loci; and d) measuring an amount of transplant DNA and an amount of recipient DNA in the recipient blood sample; wherein a change in levels of dd-cfDNA over a time interval is indicative of transplant status. In some embodiments, the method further comprises adjusting immunosuppressive therapy based on the levels of dd-cfDNA over the time interval. In some embodiments, an increase in the levels of dd-cfDNA are indicative of transplant rejection and a need for adjusting immunosuppressive therapy. In some embodiments, a change or a decrease in the levels of dd-cfDNA indicates transplant tolerance or stability, and a need for adjusting immunosuppressive therapy.

In some embodiments, in the methods disclosed herein, the target loci that are amplified in amplicons of about 50-100 bp in length, or about 60-80 bp in length. In some embodiments, the amplicons are about 65 bp in length.

In some embodiments, the methods disclosed herein further comprise measuring an amount of transplant DNA and an amount of recipient DNA in the recipient blood sample.

In some embodiments, the methods disclosed herein do not comprise genotyping the transplant donor and the transplant recipient.

In some embodiments, the methods disclosed herein further comprise detecting the amplified target loci using a microarray.

6. In some embodiments, in the methods disclosed herein, the polymorphic loci and the non-polymorphic loci are amplified in a single reaction.

In some embodiments, in the methods disclosed herein, the DNA is preferentially enriched at the target loci.

In some embodiments, preferentially enriching the DNA in the sample at the plurality of polymorphic loci includes obtaining a plurality of pre-circularized probes where each probe targets one of the polymorphic loci, and where the 3' and 5' end of the probes are designed to hybridize to a region of DNA that is separated from the polymorphic site of the locus by a small number of bases, where the small number is 1, 2, 3, 4, 5, 6, 7, 8, 9, 10, 11, 12, 13, 14, 15, 16, 17, 18, 19, 20, 21 to 25, 26 to 30, 31 to 60, or a combination thereof, hybridizing the pre-circularized probes to DNA from the sample, filling the gap between the hybridized probe ends using DNA polymerase, circularizing the pre-circularized probe, and amplifying the circularized probe.

In some embodiments, preferentially enriching the DNA at the plurality of polymorphic loci includes obtaining a plurality of ligation-mediated PCR probes where each PCR probe targets one of the polymorphic loci, and where the upstream and downstream PCR probes are designed to hybridize to a region of DNA, on one strand of DNA, that is separated from the polymorphic site of the locus by a small number of bases, where the small number is 1, 2, 3, 4, 5, 6, 7, 8, 9, 10, 11, 12, 13, 14, 15, 16, 17, 18, 19, 20, 21 to 25, 26 to 30, 31 to 60, or a combination thereof, hybridizing the ligation-mediated PCR probes to the DNA from the first sample, filling the gap between the ligation-mediated PCR probe ends using DNA polymerase, ligating the ligation-mediated PCR probes, and amplifying the ligated ligation-mediated PCR probes.

In some embodiments, preferentially enriching the DNA at the plurality of polymorphic loci includes obtaining a plurality of hybrid capture probes that target the polymorphic loci, hybridizing the hybrid capture probes to the DNA in the sample and physically removing some or all of the unhybridized DNA from the first sample of DNA.

In some embodiments, the hybrid capture probes are designed to hybridize to a region that is flanking but not overlapping the polymorphic site. In some embodiments, the hybrid capture probes are designed to hybridize to a region that is flanking but not overlapping the polymorphic site, and where the length of the flanking capture probe may be selected from the group consisting of less than about 120 bases, less than about 110 bases, less than about 100 bases, less than about 90 bases, less than about 80 bases, less than about 70 bases, less than about 60 bases, less than about 50 bases, less than about 40 bases, less than about 30 bases, and less than about 25 bases. In some embodiments, the hybrid capture probes are designed to hybridize to a region that overlaps the polymorphic site, and where the plurality of hybrid capture probes comprise at least two hybrid capture probes for each polymorphic loci, and where each hybrid capture probe is designed to be complementary to a different allele at that polymorphic locus.

In some embodiments, preferentially enriching the DNA at a plurality of polymorphic loci includes obtaining a plurality of inner forward primers where each primer targets one of the polymorphic loci, and where the 3' end of the inner forward primers are designed to hybridize to a region of DNA upstream from the polymorphic site, and separated from the polymorphic site by a small number of bases, where the small number is selected from the group consisting of 1, 2, 3, 4, 5, 6 to 10, 11 to 15, 16 to 20, 21 to 25, 26 to 30, or 31 to 60 base pairs, optionally obtaining a plurality of inner reverse primers where each primer targets one of the polymorphic loci, and where the 3' end of the inner reverse primers are designed to hybridize to a region of DNA upstream from the polymorphic site, and separated from the polymorphic site by a small number of bases, where the small number is selected from the group consisting of 1, 2, 3, 4, 5, 6 to 10, 11 to 15, 16 to 20, 21 to 25, 26 to 30, or 31 to 60 base pairs, hybridizing the inner primers to the DNA, and amplifying the DNA using the polymerase chain reaction to form amplicons.

In some embodiments, the method also includes obtaining a plurality of outer forward primers where each primer targets one of the polymorphic loci, and where the outer forward primers are designed to hybridize to the region of DNA upstream from the inner forward primer, optionally obtaining a plurality of outer reverse primers where each primer targets one of the polymorphic loci, and where the outer reverse primers are designed to hybridize to the region of DNA immediately downstream from the inner reverse primer, hybridizing the first primers to the DNA, and amplifying the DNA using the polymerase chain reaction.

In some embodiments, the method also includes obtaining a plurality of outer reverse primers where each primer targets one of the polymorphic loci, and where the outer reverse primers are designed to hybridize to the region of DNA immediately downstream from the inner reverse primer, optionally obtaining a plurality of outer forward primers where each primer targets one of the polymorphic loci, and where the outer forward primers are designed to hybridize to the region of DNA upstream from the inner forward primer, hybridizing the first primers to the DNA, and amplifying the DNA using the polymerase chain reaction.

In some embodiments, preparing the first sample further includes appending universal adapters to the DNA in the first sample and amplifying the DNA in the first sample using the polymerase chain reaction. In some embodiments, at least a fraction of the amplicons that are amplified are less than 100 bp, less than 90 bp, less than 80 bp, less than 70 bp, less than 65 bp, less than 60 bp, less than 55 bp, less than 50 bp, or less than 45 bp, and where the fraction is 10%, 20%, 30%, 40%, 50%, 60%, 70%, 80%, 90%, or 99%.

In some embodiments, amplifying the DNA is done in one or a plurality of individual reaction volumes, and where each individual reaction volume contains more than 100 different forward and reverse primer pairs, more than 200 different forward and reverse primer pairs, more than 500 different forward and reverse primer pairs, more than 1,000 different forward and reverse primer pairs, more than 2,000 different forward and reverse primer pairs, more than 5,000 different forward and reverse primer pairs, more than 10,000 different forward and reverse primer pairs, more than 20,000 different forward and reverse primer pairs, more than 50,000 different forward and reverse primer pairs, or more than 100,000 different forward and reverse primer pairs.

In some embodiments, preparing the sample further comprises dividing the sample into a plurality of portions, and where the DNA in each portion is preferentially enriched at a subset of the plurality of polymorphic loci. In some embodiments, the inner primers are selected by identifying primer pairs likely to form undesired primer duplexes and removing from the plurality of primers at least one of the pair of primers identified as being likely to form undesired primer duplexes. In some embodiments, the inner primers contain a region that is designed to hybridize either upstream or downstream of the targeted polymorphic locus, and optionally contain a universal priming sequence designed to allow PCR amplification. In some embodiments, at least some of the primers additionally contain a random region that differs for each individual primer molecule. In some embodiments, at least some of the primers additionally contain a molecular barcode.

In some embodiments, the method comprises: (a) performing multiplex polymerase chain reaction (PCR) on a nucleic acid sample comprising target loci to simultaneously amplify at least 1,000 distinct target loci using either (i) at least 1,000 different primer pairs, or (ii) at least 1,000 target-specific primers and a universal or tag-specific primer, in a single reaction volume to produce amplified products comprising target amplicons; and (b) sequencing the amplified products. In some embodiments, the method does not comprise using a microarray.

In some embodiments, the method comprises (a) performing multiplex polymerase chain reaction (PCR) on the cell free DNA sample comprising target loci to simultaneously amplify at least 1,000 distinct target loci using either (i) at least 1,000 different primer pairs, or (ii) at least 1,000 target-specific primers and a universal or tag-specific primer, in a single reaction volume to produce amplified products comprising target amplicons; and b) sequencing the amplified products. In some embodiments, the method does not comprise using a microarray.

In some embodiments, the method also includes obtaining genotypic data from one or both of the transplant donor and the transplant recipient. In some embodiments, obtaining genotypic data from one or both of the transplant donor and the transplant recipient includes preparing the DNA from the donor and the recipient where the preparing comprises preferentially enriching the DNA at the plurality of polymorphic loci to give prepared DNA, optionally amplifying the prepared DNA, and measuring the DNA in the prepared sample at the plurality of polymorphic loci.

In some embodiments, building a joint distribution model for the expected allele count probabilities of the plurality of polymorphic loci on the chromosome is done using the obtained genetic data from the one or both of the transplant donor and the transplant recipient. In some embodiments, the first sample has been isolated from transplant recipient plasma and where the obtaining genotypic data from the transplant recipient is done by estimating the recipient genotypic data from the DNA measurements made on the prepared sample.

In some embodiments, preferential enrichment results in average degree of allelic bias between the prepared sample and the first sample of a factor selected from the group consisting of no more than a factor of 2, no more than a factor of 1.5, no more than a factor of 1.2, no more than a factor of 1.1, no more than a factor of 1.05, no more than a factor of 1.02, no more than a factor of 1.01, no more than a factor of 1.005, no more than a factor of 1.002, no more than a factor of 1.001 and no more than a factor of 1.0001. In some embodiments, the plurality of polymorphic loci are SNPs. In some embodiments, measuring the DNA in the prepared sample is done by sequencing.

In some embodiments, a diagnostic box is disclosed for helping to determine transplant status in a transplant recipient where the diagnostic box is capable of executing the preparing and measuring steps of the disclosed methods.

In some embodiments, the allele counts are probabilistic rather than binary. In some embodiments, measurements of the DNA in the prepared sample at the plurality of polymorphic loci are also used to determine whether or not the transplant has inherited one or a plurality of linked haplotypes.

In some embodiments, building a joint distribution model for allele count probabilities is done by using data about the probability of chromosomes crossing over at different locations in a chromosome to model dependence between polymorphic alleles on the chromosome. In some embodiments, building a joint distribution model for allele counts and the step of determining the relative probability of each hypothesis are done using a method that does not require the use of a reference chromosome.

In some embodiments, determining the relative probability of each hypothesis makes use of an estimated fraction of donor-derived cell-free DNA (dd-cfDNA) in the prepared sample. In some embodiments, the DNA measurements from the prepared sample used in calculating allele count probabilities and determining the relative probability of each hypothesis comprise primary genetic data. In some embodiments, selecting the transplant status corresponding to the hypothesis with the greatest probability is carried out using maximum likelihood estimates or maximum a posteriori estimates.

In some embodiments, calling the transplant status also includes combining the relative probabilities of each of the status hypotheses determined using the joint distribution model and the allele count probabilities with relative probabilities of each of the status hypotheses that are calculated using statistical techniques taken from a group consisting of a read count analysis, comparing heterozygosity rates, a statistic that is only available when parental genetic information is used, the probability of normalized genotype signals for certain donor/recipient contexts, a statistic that is calculated using an estimated transplant fraction of the first sample or the prepared sample, and combinations thereof.

In some embodiments, a confidence estimate is calculated for the called transplant status. In some embodiments, the method also includes taking a clinical action based on the called transplant status.

In some embodiments, a report displaying a determined transplant status is generated using the method. In some embodiments, a kit is disclosed for determining a transplant status designed to be used with the methods disclosed herein, the kit including a plurality of inner forward primers and optionally the plurality of inner reverse primers, where each of the primers is designed to hybridize to the region of DNA immediately upstream and/or downstream from one of the polymorphic sites on the target chromosome, and optionally additional chromosomes, where the region of hybridization is separated from the polymorphic site by a small number of bases, where the small number is selected from the group consisting of 1, 2, 3, 4, 5, 6 to 10, 11 to 15, 16 to 20, 21 to 25, 26 to 30, 31 to 60, and combinations thereof.

In some embodiments, the methods disclosed herein comprise a selection step to select for shorter cfDNA.

In some embodiments, the methods disclosed herein comprise a universal application step to enrich for cfDNA.

In some embodiments, the determination that the amount of dd-cfDNA above a cutoff threshold is indicative of acute rejection of the transplant. Machine learning may be used to resolve rejection vs non-rejection.

In some embodiments, the cutoff threshold value is expressed as percentage of dd-cfDNA (dd-cfDNA %) in the blood sample.

In some embodiments, the cutoff threshold value is expressed as copy number of dd-cfDNA per volume unit of the blood sample.

In some embodiments, the cutoff threshold value is expressed as copy number of dd-cfDNA per volume unit of the blood sample multiplied by body mass or blood volume of the transplant recipient.

In some embodiments, the cutoff threshold value takes into account the body mass or blood volume of the patient.

In some embodiments, the cutoff threshold value takes into account one or more of the followings: donor genome copies per volume of plasma, cell-free DNA yield per volume of plasma, donor height, donor weight, donor age, donor gender, donor ethnicity, donor organ mass, donor organ, live vs deceased donor, related vs unrelated donor, recipient height, recipient weight, recipient age, recipient gender, recipient ethnicity, creatinine, eGFR (estimated glomerular filtration rate), cfDNA methylation, DSA (donor-specific antibodies), KDPI (kidney donor profile index), medications (immunosuppression, steroids, blood thinners, etc.), infections (BKV, EBV, CMV, UTI), recipient and/or donor HLA alleles or epitope mismatches, Banff classification of renal allograft pathology, and for-cause vs surveillance or protocol biopsy.

In some embodiments, the cutoff threshold value is scaled according to the amount of total cfDNA in the blood sample.

In some embodiments, the method has a sensitivity of at least 80% in identifying acute rejection (AR) over non-AR when the dd-cfDNA amount is above the cutoff threshold value scaled according to the amount of total cfDNA in the blood sample and a confidence interval of 95%.

In some embodiments, the method has a specificity of at least 70% in identifying acute rejection (AR) over non-AR when the dd-cfDNA amount is above the cutoff threshold value scaled according to the amount of total cfDNA in the blood sample and a confidence interval of 95%.

In some embodiments, the method has a sensitivity of at least 80% in identifying acute rejection (AR) over non-AR when the dd-cfDNA amount is above the cutoff threshold value scaled according to the amount of total cfDNA in the blood sample and a confidence interval of 95%. In some embodiments, the method has a sensitivity of at least 85% in identifying acute rejection (AR) over non-AR when the dd-cfDNA amount is above the cutoff threshold value scaled according to the amount of total cfDNA in the blood sample and a confidence interval of 95%. In some embodiments, the method has a sensitivity of at least 90% in identifying acute rejection (AR) over non-AR when the dd-cfDNA amount is above the cutoff threshold value scaled according to the amount of total cfDNA in the blood sample and a confidence interval of 95%. In some embodiments, the method has a sensitivity of at least 95% in identifying acute rejection (AR) over non-AR when the dd-cfDNA amount is be above the cutoff threshold value scaled according to the amount of total cfDNA in the blood sample and a confidence interval of 95%.

In some embodiments, the method has a specificity of at least 70% in identifying acute rejection (AR) over non-AR when the dd-cfDNA amount is above the cutoff threshold value scaled according to the amount of total cfDNA in the blood sample and a confidence interval of 95%. In some embodiments, the method has a specificity of at least 75% in identifying acute rejection (AR) over non-AR when the dd-cfDNA amount is above the cutoff threshold value scaled according to the amount of total cfDNA in the blood sample and a confidence interval of 95%. In some embodiments, the method has a specificity of at least 85% in identifying acute rejection (AR) over non-AR when the dd-cfDNA amount is above the cutoff threshold value scaled according to the amount of total cfDNA in the blood sample and a confidence interval of 95%. In some embodiments, the method has a specificity of at least 90% in identifying acute rejection (AR) over non-AR when the dd-cfDNA amount is above the cutoff threshold value scaled according to the amount of total cfDNA in the blood sample and a confidence interval of 95%. In some embodiments, the method has a specificity of at least 95% in identifying acute rejection (AR) over non-AR when the dd-cfDNA amount is above the cutoff threshold value scaled according to the amount of total cfDNA in the blood sample and a confidence interval of 95%.

BRIEF DESCRIPTION OF THE DRAWINGS

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

FIG. 23A shows measured donor fractions for related samples from Lot 1. FIG. 23B shows measured donor fractions for unrelated samples from Lot 1. FIG. 23C shows measured donor fractions for related samples from Lot 2. FIG. 23D shows measured donor fractions for unrelated samples from Lot 2.

FIG. 38A-C: Graphs depicting measured donor fractions as a function of the corresponding attempted spike levels on log-log scale for cfDNA samples: from related cases only (A), from unrelated cases only (B), and related and unrelated cases tog ether (C).

FIG. 40A-B: Accuracy assessment of KidneyScan (A) and Grskovic et al assay (B).

Figure 1:
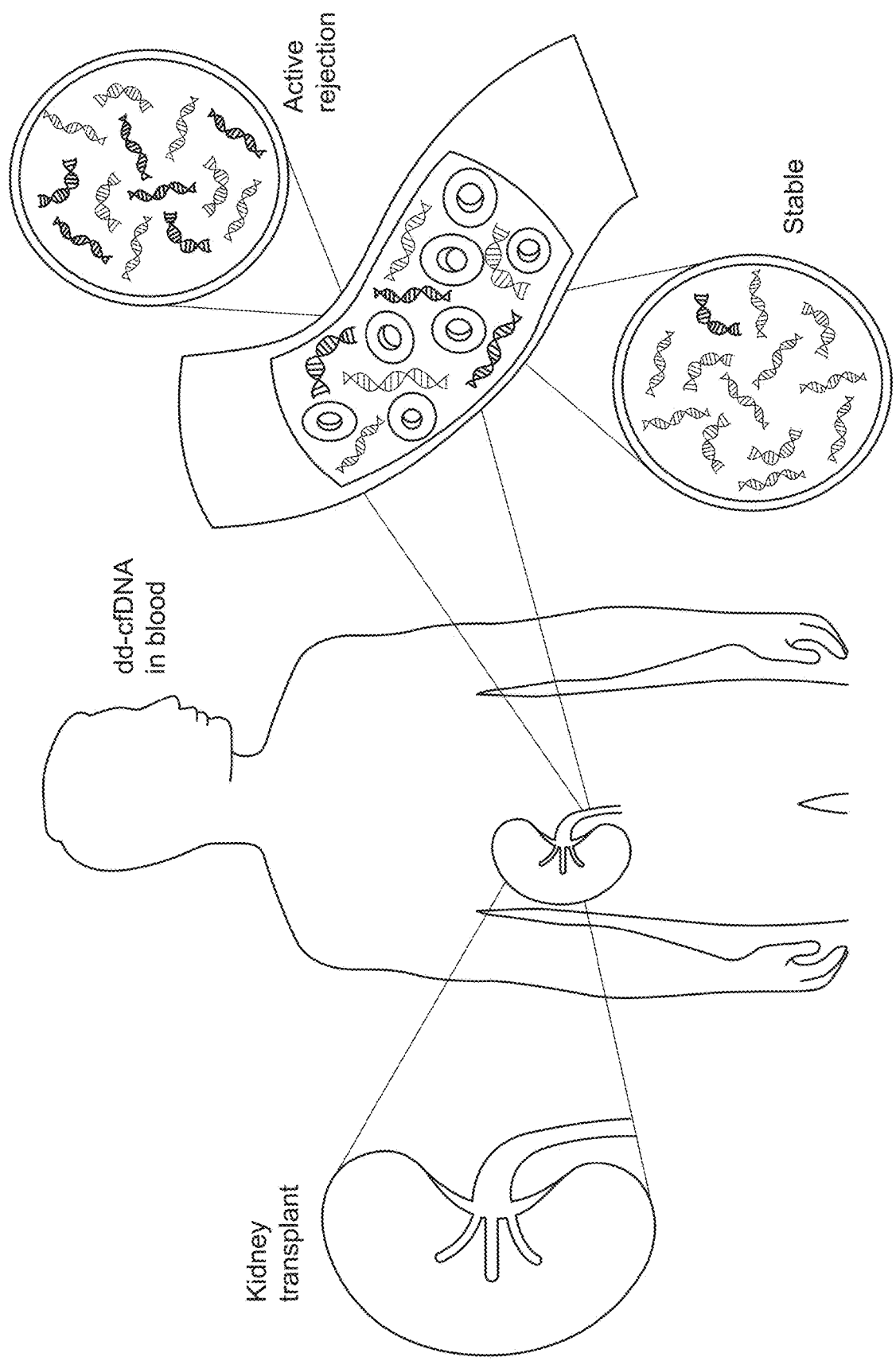
FIG. 1 exemplifies how DNA released from transplanted kidneys into the bloodstream is elevated in acute graft rejection.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

Disclosed herein are methods for detection of transplant donor-derived cell-free DNA (dd-cfDNA) in a sample from a transplant recipient.

In some embodiments, disclosed herein is a method of amplifying target loci of donor-derived cell-free DNA (dd-cfDNA) from a blood sample of a transplant recipient, the method comprising: a)
extracting DNA from the blood sample of the transplant recipient, wherein the DNA comprises cell-free DNA derived from both the transplanted cells and from the transplant recipient, b) enriching the extracted DNA at target loci, wherein the target loci comprise 50 to 5000 target loci comprising polymorphic loci and non-polymorphic loci; and c) amplifying the target loci.

In some embodiments, disclosed herein is a method of detecting donor-derived cell-free DNA (dd-cfDNA) in a blood sample from a transplant recipient, the method comprising: a) extracting DNA from the blood sample of the transplant recipient, wherein the DNA comprises cell-free DNA derived from both the transplanted cells and from the transplant recipient, b) enriching the extracted DNA at target loci, wherein the target loci comprise 50 to 5000 target loci comprising polymorphic loci and non-polymorphic loci; c) amplifying the target loci; d) contacting the amplified target loci with probes that specifically hybridize to target loci; and e) detecting binding of the target loci with the probes, thereby detecting dd-cfDNA in the blood sample. In some embodiments, the probes are labelled with a detectable marker.

In some embodiments, disclosed herein is a method of determining the likelihood of transplant rejection within a transplant recipient, the method comprising: a) extracting DNA from the blood sample of the transplant recipient, wherein the DNA comprises cell-free DNA derived from both the transplanted cells and from the transplant recipient, b) enriching the extracted DNA at target loci, wherein the target loci comprise 50 to 5000 target loci comprising polymorphic loci and non-polymorphic loci; c) amplifying the target loci; and d) measuring an amount of transplant DNA and an amount of recipient DNA in the recipient blood sample; wherein a greater amount of dd-cfDNA indicates a greater likelihood of transplant rejection.

In some embodiments, disclosed herein is a method of diagnosing a transplant within a transplant recipient as undergoing acute rejection, the method comprising: a)

extracting DNA from the blood sample of the transplant recipient, wherein the DNA comprises cell-free DNA derived from both the transplanted cells and from the transplant recipient, b) enriching the extracted DNA at target loci, wherein the target loci comprise 50 to 5000 target loci comprising polymorphic loci and non-polymorphic loci; c) amplifying the target loci; and d) measuring an amount of transplant DNA and an amount of recipient DNA in the recipient blood sample; wherein an amount of dd-cfDNA of greater than 1% indicates that the transplant is undergoing acute rejection.

In an embodiment, a method disclosed herein uses selective enrichment techniques that preserve the relative allele frequencies that are present in the original sample of DNA at each polymorphic locus from a set of polymorphic loci. In some embodiments the amplification and/or selective enrichment technique may involve PCR such as ligation mediated PCR, fragment capture by hybridization, MOLECULAR INVERSION PROBES, or other circularizing probes. In some embodiments, methods for amplification or selective enrichment may involve using probes where, upon correct hybridization to the target sequence, the 3-prime end or 5-prime end of a nucleotide probe is separated from the polymorphic site of the allele by a small number of nucleotides. This separation reduces preferential amplification of one allele, termed allele bias. This is an improvement over methods that involve using probes where the 3-prime end or 5-prime end of a correctly hybridized probe are directly adjacent to or very near to the polymorphic site of an allele. In an embodiment, probes in which the hybridizing region may or certainly contains a polymorphic site are excluded. Polymorphic sites at the site of hybridization can cause unequal hybridization or inhibit hybridization altogether in some alleles, resulting in preferential amplification of certain alleles. These embodiments are improvements over other methods that involve targeted amplification and/or selective enrichment in that they better preserve the original allele frequencies of the sample at each polymorphic locus, whether the sample is pure genomic sample from a single individual or mixture of individuals.

After blood draw and before DNA extraction, blood cells within a blood sample may burse and shed long fragments of DNA into the sample, which would increase the total amount of cell-free DNA (cfDNA) and background noise, distorting thd % of dd-cfDNA detected. In order to reduce such background noise, and based on the observation that dd-cfDNA is typically shorter than DNA shredded from a transplant recipient blood cell, two particular enrichments for dd-cfDNA are contemplated. In one embodiment, a size selection is applied to select for shorter cfDNA. In another embodiment, a universal amplification step is applied to reduce noise (e.g., before applying multiplex PCR), based on the hypothesis that shorter dd-cfDNA (often in mononucleosome form) is amplified more efficiently than longer transplant recipient-derived DNA In an embodiment, a method disclosed herein uses highly efficient highly multiplexed targeted PCR to amplify DNA followed by high throughput sequencing to determine the allele frequencies at each target locus. The ability to multiplex more than about 50 or 100 PCR primers in one reaction in a way that most of the resulting sequence reads map to targeted loci is novel and non-obvious. One technique that allows highly multiplexed targeted PCR to perform in a highly efficient manner involves designing primers that are unlikely to hybridize with one another. The PCR probes, typically referred to as primers, are selected by creating a thermodynamic model of potentially adverse interactions between at least 500, at least 1,000, at least 5,000, at least 10,000, at least 20,000, at least 50,000, or at least 100,000 potential primer pairs, or unintended interactions between primers and sample DNA, and then using the model to eliminate designs that are incompatible with other the designs in the pool. Another technique that allows highly multiplexed targeted PCR to perform in a highly efficient manner is using a partial or full nesting approach to the targeted PCR. Using one or a combination of these approaches allows multiplexing of at least 300, at least 800, at least 1,200, at least 4,000 or at least 10,000 primers in a single pool with the resulting amplified DNA comprising a majority of DNA molecules that, when sequenced, will map to targeted loci. Using one or a combination of these approaches allows multiplexing of a large number of primers in a single pool with the resulting amplified DNA comprising greater than 50%, greater than 80%, greater than 90%, greater than 95%, greater than 98%, or greater than 99% DNA molecules that map to targeted loci.

In an embodiment, a method disclosed herein yields a quantitative measure of the number of independent observations of each allele at a polymorphic locus. This is unlike most methods such as microarrays or qualitative PCR which provide information about the ratio of two alleles but do not quantify the number of independent observations of either allele. With methods that provide quantitative information regarding the number of independent observations, only the ratio is utilized in the relevant determinations, while the quantitative information by itself is not useful. To illustrate the importance of retaining information about the number of independent observations consider the sample locus with two alleles, A and B. In a first experiment twenty A alleles and twenty B alleles are observed, in a second experiment 200 A alleles and 200 B alleles are observed. In both experiments the ratio (A/(A+B)) is equal to 0.5, however the second experiment conveys more information than the first about the certainty of the frequency of the A or B allele. Some methods known in the prior art involve averaging or summing allele ratios (channel ratios) (i.e. $x_i/y_i$) from individual allele and analyzes this ratio, either comparing it to a reference chromosome or using a rule pertaining to how this ratio is expected to behave in particular situations. No allele weighting is implied in such methods known in the art, where it is assumed that one can ensure about the same amount of PCR product for each allele and that all the alleles should behave the same way. Such a method has a number of disadvantages, and more importantly, precludes the use a number of improvements that are described elsewhere in this disclosure.

The use of a joint distribution model is a different from and a significant improvement over methods that determine heterozygosity rates by treating polymorphic loci independently in that the resultant determinations are of significantly higher accuracy. Without being bound by any particular theory, it is believed that one reason they are of higher accuracy is that the joint distribution model takes into account the linkage between SNPs. The purpose of using the concept of linkage when creating the expected distribution of allele measurements for one or more hypotheses is that it allows the creation of expected allele measurements distributions that correspond to reality considerably better than when linkage is not used.

One reason that it is believed that ploidy determinations that use a method that comprises comparing the observed allele measurements to theoretical hypotheses corresponding to possible transplant states are of higher accuracy is that when sequencing is used to measure the alleles, this method can glean more information from data from alleles where the total number of reads is low than other methods; for example, a method that relies on calculating and aggregating allele ratios would produce disproportionately weighted stochastic noise. For example, imagine a case that involved measuring the alleles using sequencing, and where there was a set of loci where only five sequence reads were detected for each locus. In an embodiment, for each of the alleles, the data may be compared to the hypothesized allele distribution, and weighted according to the number of sequence reads; therefore the data from these measurements would be appropriately weighted and incorporated into the overall determination. This is in contrast to a method that involved quantitating a ratio of alleles at a heterozygous locus, as this method could only calculate ratios of 0%, 20%, 40%, 60%, 80% or 100% as the possible allele ratios; none of these may be close to expected allele ratios. In this latter case, the calculated allele rations would either have to be discarded due to insufficient reads or else would have disproportionate weighting and introduce stochastic noise into the determination, thereby decreasing the accuracy of the determination. In an embodiment, the individual allele measurements may be treated as independent measurements, where the relationship between measurements made on alleles at the same locus is no different from the relationship between measurements made on alleles at different loci.

In an embodiment, a method disclosed herein demonstrates how observing allele distributions at polymorphic loci can be used to determine the state of a transplant with greater accuracy than methods in the prior art. In an embodiment, the method observes the quantitative allele information obtained on the transplant donor/recipient mixture and evaluating which hypothesis fits the data best, where the transplant state corresponding to the hypothesis with the best fit to the data is called as the correct transplant state. In an embodiment, a method disclosed herein also uses the degree of fit to generate a confidence that the called genetic state is the correct transplant state. In an embodiment, a method disclosed herein involves using algorithms that analyze the distribution of alleles found for loci that have different contexts, and comparing the observed allele distributions to the expected allele distributions for different transplant states for the different genotypic contexts. This is different from and an improvement over methods that do not use methods that enable the estimation of the number of independent instances of each allele at each locus in a mixed sample.

In an embodiment, a method disclosed herein uses a joint distribution model that assumes that the allele frequencies at each locus are multinomial (and thus binomial when SNPs are biallelic) in nature. In some embodiments the joint distribution model uses beta-binomial distributions. When using a measuring technique, such as sequencing, provides a quantitative measure for each allele present at each locus, binomial model can be applied to each locus and the degree underlying allele frequencies and the confidence in that frequency can be ascertained. With methods known in the art that generate transplant status calls from allele ratios, or methods in which quantitative allele information is discarded, the certainty in the observed ratio cannot be ascertained. The instant method is different from and an improvement over methods that calculate allele ratios and aggregate those ratios to make a transplant status call, since any method that involves calculating an allele ratio at a particular locus, and then aggregating those ratios, necessarily assumes that the measured intensities or counts that are indicative of the amount of DNA from any given allele or locus will be distributed in a Gaussian fashion. The method disclosed herein does not involve calculating allele ratios. In some embodiments, a method disclosed herein may involve incorporating the number of observations of each allele at a plurality of loci into a model. In some embodiments, a method disclosed herein may involve calculating the expected distributions themselves, allowing the use of a joint binomial distribution model which may be more accurate than any model that assumes a Gaussian distribution of allele measurements. The likelihood that the binomial distribution model is significantly more accurate than the Gaussian distribution increases as the number of loci increases. For example, when fewer than 20 loci are interrogated, the likelihood that the binomial distribution model is significantly better is low. However, when more than 100, or especially more than 400, or especially more than 1,000, or especially more than 2,000 loci are used, the binomial distribution model will have a very high likelihood of being significantly more accurate than the Gaussian distribution model, thereby resulting in a more accurate transplant status determination. The likelihood that the binomial distribution model is significantly more accurate than the Gaussian distribution also increases as the number of observations at each locus increases. For example, when fewer than 10 distinct sequences are observed at each locus are observed, the likelihood that the binomial distribution model is significantly better is low. However, when more than 50 sequence reads, or especially more than 100 sequence reads, or especially more than 200 sequence reads, or especially more than 300 sequence reads are used for each locus, the binomial distribution model will have a very high likelihood of being significantly more accurate than the Gaussian distribution model, thereby resulting in a more accurate ploidy determination.

In an embodiment, a method disclosed herein uses sequencing to measure the number of instances of each allele at each locus in a DNA sample. Each sequencing read may be mapped to a specific locus and treated as a binary sequence read; alternately, the probability of the identity of the read and/or the mapping may be incorporated as part of the sequence read, resulting in a probabilistic sequence read, that is, the probable whole or fractional number of sequence reads that map to a given loci. Using the binary counts or probability of counts it is possible to use a binomial distribution for each set of measurements, allowing a confidence interval to be calculated around the number of counts. This ability to use the binomial distribution allows for more accurate ploidy estimations and more precise confidence intervals to be calculated. This is different from and an improvement over methods that use intensities to measure the amount of an allele present, for example methods that use microarrays, or methods that make measurements using fluorescence readers to measure the intensity of fluorescently tagged DNA in electrophoretic bands.

In an embodiment, a method disclosed herein uses aspects of the present set of data to determine parameters for the estimated allele frequency distribution for that set of data. This is an improvement over methods that utilize training set of data or prior sets of data to set parameters for the present expected allele frequency distributions, or possibly expected allele ratios. This is because there are different sets of conditions involved in the collection and measurement of every genetic sample, and thus a method that uses data from the instant set of data to determine the parameters for the joint distribution model that is to be used in the transplant status determination for that sample will tend to be more accurate.

In an embodiment, a method disclosed herein involves determining whether the distribution of observed allele measurements is indicative of transplant rejection status using a maximum likelihood technique. The use of a maximum likelihood technique is different from and a significant improvement over methods that use single hypothesis rejection technique in that the resultant determinations will be made with significantly higher accuracy. One reason is that single hypothesis rejection techniques set cut off thresholds based on only one measurement distribution rather than two, meaning that the thresholds are usually not optimal. Another reason is that the maximum likelihood technique allows the optimization of the cut off threshold for each individual sample instead of determining a cut off threshold to be used for all samples regardless of the particular characteristics of each individual sample. Another reason is that the use of a maximum likelihood technique allows the calculation of a confidence for each transplant status call. The ability to make a confidence calculation for each call allows a practitioner to know which calls are accurate, and which are more likely to be wrong. In some embodiments, a wide variety of methods may be combined with a maximum likelihood estimation technique to enhance the accuracy of the transplant status calls. In an embodiment, the maximum likelihood technique may be used in combination with the method described in U.S. Pat. No. 7,888,017. In an embodiment, the maximum likelihood technique may be used in combination with the method of using targeted PCR amplification to amplify the DNA in the mixed sample followed by sequencing and analysis using a read counting method such as used by TANDEM DIAGNOSTICS, as presented at the International Congress of Human Genetics 2011, in Montreal in October 2011. In an embodiment, a method disclosed herein involves estimating the donor fraction of DNA in the mixed sample and using that estimation to calculate both the transplant status call and the confidence of the transplant status call.

In an embodiment, a method disclosed herein takes into account the tendency for the data to be noisy and contain errors by attaching a probability to each measurement. The use of maximum likelihood techniques to choose the correct hypothesis from the set of hypotheses that were made using the measurement data with attached probabilistic estimates makes it more likely that the incorrect measurements will be discounted, and the correct measurements will be used in the calculations that lead to the transplant status call. To be more precise, this method systematically reduces the influence of data that is incorrectly measured on the transplant status call determination. This is an improvement over methods where all data is assumed to be equally correct or methods where outlying data is arbitrarily excluded from calculations leading to a transplant status call. Existing methods using channel ratio measurements claim to extend the method to multiple SNPs by averaging individual SNP channel ratios. Not weighting individual SNPs by expected measurement variance based on the SNP quality and observed depth of read reduces the accuracy of the resulting statistic, resulting in a reduction of the accuracy of the transplant status call significantly, especially in borderline cases.

In an embodiment, a method disclosed herein does not presuppose the knowledge of which SNPs or other polymorphic loci are heterozygous on the transplant. This method allows a ploidy call to be made in cases where paternal genotypic information is not available. This is an improvement over methods where the knowledge of which SNPs are heterozygous must be known ahead of time in order to appropriately select loci to target, or to interpret the genetic measurements made on the donor/recipient DNA sample.

The methods described herein are particularly advantageous when used on samples where a small amount of DNA is available, or where the percent of donor-derived DNA is low. This is due to the correspondingly higher allele dropout rate that occurs when only a small amount of DNA is available and/or the correspondingly higher donor allele dropout rate when the percent of donor DNA is low in a mixed sample of donor and transplant recipient DNA. A high allele dropout rate, meaning that a large percentage of the alleles were not measured for the target individual, results in poorly accurate donor fractions calculations, and poorly accurate transplant status determinations. Since methods disclosed herein may use a joint distribution model that takes into account the linkage in inheritance patterns between SNPs, significantly more accurate transplant status determinations may be made.

Further discussion of the points above may be found elsewhere in this document.

Non-Invasive Transplant Monitoring

The process of non-invasive transplant monitoring involves a number of steps. Some of the steps may include: (1) obtaining the genetic material from the transplant; (2) enriching the genetic material of the transplant that may be in a mixed sample, ex vivo; (3) amplifying the genetic material, ex vivo; (4) preferentially enriching specific loci in the genetic material, ex vivo; (5) measuring the genetic material, ex vivo; and (6) analyzing the genotypic data, on a computer, and ex vivo. Methods to reduce to practice these six and other relevant steps are described herein. At least some of the method steps are not directly applied on the body. In an embodiment, the present disclosure relates to methods of treatment and diagnosis applied to tissue and other biological materials isolated and separated from the body. At least some of the method steps are executed on a computer.

The high accuracy of the methods disclosed herein is a result of an informatics approach to analysis of the genotype data, as described herein. Modern technological advances have resulted in the ability to measure large amounts of genetic information from a genetic sample using such methods as high throughput sequencing and genotyping arrays. The methods disclosed herein allow a clinician to take greater advantage of the large amounts of data available, and make a more accurate diagnosis of the status of a transplant in a recipient. The details of a number of embodiments are given below. Different embodiments may involve different combinations of the aforementioned steps. Various combinations of the different embodiments of the different steps may be used interchangeably.

In an embodiment, a blood sample is taken from a transplant recipient, and the free floating DNA in the plasma of the transplant recipient's blood, which contains a mixture of both DNA of transplant donor origin, and DNA of transplant recipient origin, is isolated and used to determine the status of the transplant. In an embodiment, a method disclosed herein involves preferential enrichment of those DNA sequences in a mixture of DNA that correspond to polymorphic alleles in a way that the allele ratios and/or allele distributions remain mostly consistent upon enrichment. In an embodiment, a method disclosed herein involves the highly efficient targeted PCR based amplification such that a very high percentage of the resulting molecules correspond to targeted loci. In an embodiment, a method disclosed herein involves sequencing a mixture of DNA that contains both DNA of donor origin, and DNA of recipient origin. In an embodiment, a method disclosed herein involves using measured allele distributions to determine the state of a transplant in a transplant recipient. In an embodiment, a method disclosed herein involves reporting the determined transplant state to a clinician. In an embodiment, a method disclosed herein involves taking a clinical action, such as altering immunosuppressive therapy in the transplant recipient.

This application makes reference to U.S. Utility application Ser. No. 15/727,428, filed Oct. 6, 2017 (U.S. Publication No. 20180025109); U.S. Utility application Ser. No. 11/603,406, filed Nov. 28, 2006 (US Publication No.: 20070184467); U.S. Utility application Ser. No. 12/076,348, filed Mar. 17, 2008 (US Publication No.: 20080243398); PCT Utility Application Serial No. PCT/US09/52730, filed Aug. 4, 2009 (PCT Publication No.: WO/2010/017214); PCT Utility Application Serial No. PCT/US10/050824, filed Sep. 30, 2010 (PCT Publication No.: WO/2011/041485), and U.S. Utility application Ser. No. 13/110,685, filed May 18, 2011. Some of the vocabulary used in this filing may have its antecedents in these references. Some of the concepts described herein may be better understood in light of the concepts found in these references.

Screening Transplant Recipient Blood Comprising Free Floating Donor DNA

In an embodiment, blood may be drawn from a transplant recipient. Research has shown that transplant recipient blood may contain a small amount of free floating DNA from the derived from the transplant, in addition to free floating DNA of transplant recipient origin. There are many methods know in the art to isolate cell free DNA, or create fractions enriched in cell free DNA. For example, chromatography has been show to create certain fractions that are enriched in cell free DNA.

Once the sample of blood, plasma, or other fluid, drawn in a relatively non-invasive manner, and that contains an amount of donor-derived DNA, either cellular or free floating, either enriched in its proportion to the recipient-derived DNA, or in its original ratio, is in hand, one may genotype the DNA found in said sample. In some embodiments, the blood may be drawn using a needle to withdraw blood from a vein, for example, the basilica vein. The method described herein can be used to determine genotypic data of the transplant. For example, it can be used to determine the identity of one or a set of SNPs, including insertions, deletions, and translocations. It can be used to determine one or more haplotypes, including the parent of origin of one or more genotypic features.

Note that this method will work with any nucleic acids that can be used for any genotyping and/or sequencing methods, such as the ILLUMINA INFINIUM ARRAY platform, AFFYMETRIX GENECHIP, ILLUMINA GENOME ANALYZER, or LIFE TECHNOLGIES' SOLID SYSTEM. This includes extracted free-floating DNA from plasma or amplifications (e.g. whole genome amplification, PCR) of the same; genomic DNA from other cell types (e.g. human lymphocytes from whole blood) or amplifications of the same. For preparation of the DNA, any extraction or purification method that generates genomic DNA suitable for the one of these platforms will work as well. This method could work equally well with samples of RNA. In an embodiment, storage of the samples may be done in a way that will minimize degradation (e.g. below freezing, at about −20 C, or at a lower temperature).

Definitions

Single Nucleotide Polymorphism (SNP) Refers to a Single Nucleotide that May Differ Between the genomes of two members of the same species. The usage of the term should not imply any limit on the frequency with which each variant occurs.

Sequence refers to a DNA sequence or a genetic sequence. It may refer to the primary, physical structure of the DNA molecule or strand in an individual. It may refer to the sequence of nucleotides found in that DNA molecule, or the complementary strand to the DNA molecule. It may refer to the information contained in the DNA molecule as its representation in silico.

Locus refers to a particular region of interest on the DNA of an individual, which may refer to a SNP, the site of a possible insertion or deletion, or the site of some other relevant genetic variation. Disease-linked SNPs may also refer to disease-linked loci.

Polymorphic Allele, also "Polymorphic Locus," refers to an allele or locus where the genotype varies between individuals within a given species. Some examples of polymorphic alleles include single nucleotide polymorphisms, short tandem repeats, deletions, duplications, and inversions.

Polymorphic Site refers to the specific nucleotides found in a polymorphic region that vary between individuals.

Allele refers to the genes that occupy a particular locus.

Genetic Data also "Genotypic Data" refers to the data describing aspects of the genome of one or more individuals. It may refer to one or a set of loci, partial or entire sequences, partial or entire chromosomes, or the entire genome. It may refer to the identity of one or a plurality of nucleotides; it may refer to a set of sequential nucleotides, or nucleotides from different locations in the genome, or a combination thereof. Genotypic data is typically in silico, however, it is also possible to consider physical nucleotides in a sequence as chemically encoded genetic data. Genotypic Data may be said to be "on," "of," "at," "from" or "on" the individual(s). Genotypic Data may refer to output measurements from a genotyping platform where those measurements are made on genetic material.

Genetic Material also "Genetic Sample" refers to physical matter, such as tissue or blood, from one or more individuals comprising DNA or RNA Noisy Genetic Data refers to genetic data with any of the following: allele dropouts, uncertain base pair measurements, incorrect base pair measurements, missing base pair measurements, uncertain measurements of insertions or deletions, uncertain measurements of chromosome segment copy numbers, spurious signals, missing measurements, other errors, or combinations thereof.

Confidence refers to the statistical likelihood that the called SNP, allele, set of alleles, ploidy call, or determined number of chromosome segment copies correctly represents the real genetic state of the individual.

Chromosome may refer to a single chromosome copy, meaning a single molecule of DNA of which there are 46 in a normal somatic cell; an example is 'the maternally derived chromosome 18'. Chromosome may also refer to a chromosome type, of which there are 23 in a normal human somatic cell; an example is 'chromosome 18'.

Chromosomal Identity may refer to the referent chromosome number, i.e. the chromosome type. Normal humans have 22 types of numbered autosomal chromosome types, and two types of sex chromosomes. It may also refer to the parental origin of the chromosome. It may also refer to a specific chromosome inherited from the parent. It may also refer to other identifying features of a chromosome.

The State of the Genetic Material or simply "Genetic State" may refer to the identity of a set of SNPs on the DNA, to the phased haplotypes of the genetic material, and to the sequence of the DNA, including insertions, deletions, repeats and mutations. It may also refer to the ploidy state of one or more chromosomes, chromosomal segments, or set of chromosomal segments.

Allelic Data refers to a set of genotypic data concerning a set of one or more alleles. It may refer to the phased, haplotypic data. It may refer to SNP identities, and it may refer to the sequence data of the DNA, including insertions, deletions, repeats and mutations. It may include the parental origin of each allele.

Allelic State refers to the actual state of the genes in a set of one or more alleles. It may refer to the actual state of the genes described by the allelic data.

Allelic Ratio or allele ratio, refers to the ratio between the amount of each allele at a locus that is present in a sample or in an individual. When the sample was measured by sequencing, the allelic ratio may refer to the ratio of sequence reads that map to each allele at the locus. When the sample was measured by an intensity based measurement method, the allele ratio may refer to the ratio of the amounts of each allele present at that locus as estimated by the measurement method.

Allele Count refers to the number of sequences that map to a particular locus, and if that locus is polymorphic, it refers to the number of sequences that map to each of the alleles. If each allele is counted in a binary fashion, then the allele count will be whole number. If the alleles are counted probabilistically, then the allele count can be a fractional number.

Allele Count Probability refers to the number of sequences that are likely to map to a particular locus or a set of alleles at a polymorphic locus, combined with the probability of the mapping. Note that allele counts are equivalent to allele count probabilities where the probability of the mapping for each counted sequence is binary (zero or one). In some embodiments, the allele count probabilities may be binary. In some embodiments, the allele count probabilities may be set to be equal to the DNA measurements.

Allelic Distribution, or 'allele count distribution' refers to the relative amount of each allele that is present for each locus in a set of loci. An allelic distribution can refer to an individual, to a sample, or to a set of measurements made on a sample. In the context of sequencing, the allelic distribution refers to the number or probable number of reads that map to a particular allele for each allele in a set of polymorphic loci. The allele measurements may be treated probabilistically, that is, the likelihood that a given allele is present for a give sequence read is a fraction between 0 and 1, or they may be treated in a binary fashion, that is, any given read is considered to be exactly zero or one copies of a particular allele.

Allelic Distribution Pattern refers to a set of different allele distributions for different parental contexts. Certain allelic distribution patterns may be indicative of certain ploidy states.

Allelic Bias refers to the degree to which the measured ratio of alleles at a heterozygous locus is different to the ratio that was present in the original sample of DNA. The degree of allelic bias at a particular locus is equal to the observed allelic ratio at that locus, as measured, divided by the ratio of alleles in the original DNA sample at that locus. Allelic bias may be defined to be greater than one, such that if the calculation of the degree of allelic bias returns a value, x, that is less than 1, then the degree of allelic bias may be restated as 1/x. Allelic bias maybe due to amplification bias, purification bias, or some other phenomenon that affects different alleles differently.

Primer, also "PCR probe" refers to a single DNA molecule (a DNA oligomer) or a collection of DNA molecules (DNA oligomers) where the DNA molecules are identical, or nearly so, and where the primer contains a region that is designed to hybridize to a targeted polymorphic locus, and m contain a priming sequence designed to allow PCR amplification. A primer may also contain a molecular barcode. A primer may contain a random region that differs for each individual molecule.

Hybrid Capture Probe refers to any nucleic acid sequence, possibly modified, that is generated by various methods such as PCR or direct synthesis and intended to be complementary to one strand of a specific target DNA sequence in a sample. The exogenous hybrid capture probes may be added to a prepared sample and hybridized through a deanture-reannealing process to form duplexes of exogenous-endogenous fragments. These duplexes may then be physically separated from the sample by various means.

Sequence Read refers to data representing a sequence of nucleotide bases that were measured using a clonal sequencing method. Clonal sequencing may produce sequence data representing single, or clones, or clusters of one original DNA molecule. A sequence read may also have associated quality score at each base position of the sequence indicating the probability that nucleotide has been called correctly.

Mapping a sequence read is the process of determining a sequence read's location of origin in the genome sequence of a particular organism. The location of origin of sequence reads is based on similarity of nucleotide sequence of the read and the genome sequence.

Matched Copy Error, also "Matching Chromosome Aneuploidy" (MCA), refers to a state of aneuploidy where one cell contains two identical or nearly identical chromosomes. This type of aneuploidy may arise during the formation of the gametes in meiosis, and may be referred to as a meiotic non-disjunction error. This type of error may arise in mitosis. Matching trisomy may refer to the case where three copies of a given chromosome are present in an individual and two of the copies are identical.

Homologous Chromosomes refers to chromosome copies that contain the same set of genes that normally pair up during meiosis.

Identical Chromosomes refers to chromosome copies that contain the same set of genes, and for each gene they have the same set of alleles that are identical, or nearly identical.

Allele Drop Out (ADO) refers to the situation where at least one of the base pairs in a set of base pairs from homologous chromosomes at a given allele is not detected.

Locus Drop Out (LDO) refers to the situation where both base pairs in a set of base pairs from homologous chromosomes at a given allele are not detected.

Homozygous refers to having similar alleles as corresponding chromosomal loci.

Heterozygous refers to having dissimilar alleles as corresponding chromosomal loci.

Heterozygosity Rate refers to the rate of individuals in the population having heterozygous alleles at a given locus. The heterozygosity rate may also refer to the expected or measured ratio of alleles, at a given locus in an individual, or a sample of DNA.

Highly Informative Single Nucleotide Polymorphism (HISNP) refers to a SNP where the transplant has an allele that is not present in the transplant recipient's genotype.

Chromosomal Region refers to a segment of a chromosome, or a full chromosome.

Segment of a Chromosome refers to a section of a chromosome that can range in size from one base pair to the entire chromosome.

Chromosome refers to either a full chromosome, or a segment or section of a chromosome.

Copies refers to the number of copies of a chromosome segment. It may refer to identical copies, or to non-identical, homologous copies of a chromosome segment wherein the different copies of the chromosome segment contain a substantially similar set of loci, and where one or more of the alleles are different. Note that in some cases of aneuploidy, such as the M2 copy error, it is possible to have some copies of the given chromosome segment that are identical as well as some copies of the same chromosome segment that are not identical.

Haplotype refers to a combination of alleles at multiple loci that are typically inherited together on the same chromosome. Haplotype may refer to as few as two loci or to an entire chromosome depending on the number of recombination events that have occurred between a given set of loci. Haplotype can also refer to a set of single nucleotide polymorphisms (SNPs) on a single chromatid that are statistically associated.

Haplotypic Data, also "Phased Data" or "Ordered Genetic Data," refers to data from a single chromosome in a diploid or polyploid genome, i.e., either the segregated maternal or paternal copy of a chromosome in a diploid genome.

Phasing refers to the act of determining the haplotypic genetic data of an individual given unordered, diploid (or polyploidy) genetic data. It may refer to the act of determining which of two genes at an allele, for a set of alleles found on one chromosome, are associated with each of the two homologous chromosomes in an individual.

Phased Data refers to genetic data where one or more haplotypes have been determined.

Hypothesis refers to a possible ploidy state at a given set of chromosomes, or a set of possible allelic states at a given set of loci. The set of possibilities may comprise one or more elements.

Target Individual refers to the individual whose genetic state is being determined. In some embodiments, only a limited amount of DNA is available from the target individual. In some embodiments, the target individual is a transplant. In some embodiments, there may be more than one target individual. In some embodiments, each transplant that originated from a pair of parents may be considered to be target individuals. In some embodiments, the genetic data that is being determined is one or a set of allele calls. In some embodiments, the genetic data that is being determined is a ploidy call.

Related Individual refers to any individual who is genetically related to, and thus shares haplotype blocks with, the target individual. In one context, the related individual may be a genetic parent of the target individual, or any genetic material derived from a parent, such as a sperm, a polar body, an embryo, a transplant, or a child. It may also refer to a sibling, parent or a grandparent.

DNA of Donor Origin refers to DNA that was originally part of a cell whose genotype was essentially equivalent to that of the transplant donor.

DNA of Recipient Origin refers to DNA that was originally part of a cell whose genotype was essentially equivalent to that of the transplant recipient.

Transplant recipient plasma refers to the plasma portion of the blood from a female from a patient who has received an allograft, e.g., an organ transplant recipient.

Clinical Decision refers to any decision to take or not take an action that has an outcome that affects the health or survival of an individual.

Diagnostic Box refers to one or a combination of machines designed to perform one or a plurality of aspects of the methods disclosed herein. In an embodiment, the diagnostic box may be placed at a point of patient care. In an embodiment, the diagnostic box may perform targeted amplification followed by sequencing. In an embodiment the diagnostic box may function alone or with the help of a technician.

Informatics Based Method refers to a method that relies heavily on statistics to make sense of a large amount of data. In the context of prenatal diagnosis, it refers to a method designed to determine the ploidy state at one or more chromosomes or the allelic state at one or more alleles by statistically inferring the most likely state, rather than by directly physically measuring the state, given a large amount of genetic data, for example from a molecular array or sequencing.

Primary Genetic Data refers to the analog intensity signals that are output by a genotyping platform. In the context of SNP arrays, primary genetic data refers to the intensity signals before any genotype calling has been done. In the context of sequencing, primary genetic data refers to the analog measurements, analogous to the chromatogram, that comes off the sequencer before the identity of any base pairs have been determined, and before the sequence has been mapped to the genome.

Secondary Genetic Data refers to processed genetic data that are output by a genotyping platform. In the context of a SNP array, the secondary genetic data refers to the allele calls made by software associated with the SNP array reader, wherein the software has made a call whether a given allele is present or not present in the sample. In the context of sequencing, the secondary genetic data refers to the base pair identities of the sequences have been determined, and possibly also where the sequences have been mapped to the genome.

Preferential Enrichment of DNA that corresponds to a locus, or preferential enrichment of DNA at a locus, refers to any method that results in the percentage of molecules of DNA in a post-enrichment DNA mixture that correspond to the locus being higher than the percentage of molecules of DNA in the pre-enrichment DNA mixture that correspond to the locus. The method may involve selective amplification of DNA molecules that correspond to a locus. The method may involve removing DNA molecules that do not correspond to the locus. The method may involve a combination of methods. The degree of enrichment is defined as the percentage of molecules of DNA in the post-enrichment mixture that correspond to the locus divided by the percentage of molecules of DNA in the pre-enrichment mixture that correspond to the locus. Preferential enrichment may be carried out at a plurality of loci. In some embodiments of the present disclosure, the degree of enrichment is greater than 20. In some embodiments of the present disclosure, the degree of enrichment is greater than 200. In some embodiments of the present disclosure, the degree of enrichment is greater than 2,000. When preferential enrichment is carried out at a plurality of loci, the degree of enrichment may refer to the average degree of enrichment of all of the loci in the set of loci.

Amplification refers to a method that increases the number of copies of a molecule of DNA.

Selective Amplification may refer to a method that increases the number of copies of a particular molecule of DNA, or molecules of DNA that correspond to a particular region of DNA. It may also refer to a method that increases the number of copies of a particular targeted molecule of DNA, or targeted region of DNA more than it increases non-targeted molecules or regions of DNA. Selective amplification may be a method of preferential enrichment.

Universal Priming Sequence refers to a DNA sequence that may be appended to a population of target DNA molecules, for example by ligation, PCR, or ligation mediated PCR. Once added to the population of target molecules, primers specific to the universal priming sequences can be used to amplify the target population using a single pair of amplification primers. Universal priming sequences are typically not related to the target sequences.

Universal Adapters, or 'ligation adaptors' or 'library tags' are DNA molecules containing a universal priming sequence that can be covalently linked to the 5-prime and 3-prime end of a population of target double stranded DNA molecules. The addition of the adapters provides universal priming sequences to the 5-prime and 3-prime end of the target population from which PCR amplification can take place, amplifying all molecules from the target population, using a single pair of amplification primers.

Targeting refers to a method used to selectively amplify or otherwise preferentially enrich those molecules of DNA that correspond to a set of loci, in a mixture of DNA.

Joint Distribution Model refers to a model that defines the probability of events defined in terms of multiple random variables, given a plurality of random variables defined on the same probability space, where the probabilities of the variable are linked. In some embodiments, the degenerate case where the probabilities of the variables are not linked may be used.

Limit of Blank (LoB) is the highest apparent analyte concentration expected to be found when replicates of a blank sample containing no analyte are tested. For example, as used herein, LoB may be defined as the empirical 95th percentile value measured from a set of blank (no-analyte) samples. Accordingly, in an embodiment of the present disclosure, the sensitivity of the method of determining transplant status may be determined by a limit of blank (LoB). The desired LoB may be equal to or less than 5%; it may be equal to or less than 2%; it may be equal to or less than 1%; it may be equal to or less than 0.5%; it may be equal to or less than 0.25%; it may equal to or less than 0.23%; it may be equal to or less than 0.11%; it may be equal to or less than 0.08%; it may be equal to or less than 0.04%.

Limits of Detection (LoD) is the lowest analyte concentration likely to be reliably distinguished from the LoB and at which detection is feasible. LoD is determined by utilizing both the measured LoB and test replicates of a sample known to contain a low concentration of analyte. For example, LoD may be calculated following the parametric estimate method specified in EP-17A2, which computes LoD by adding a standard deviation term to the LoB. Accordingly, in an embodiment of the present disclosure, the sensitivity of the method of determining transplant status may be determined by a LoD less than 1%; it may be less than 0.5%; it may be less than 0.25%; it may equal to or less than 0.23%; it may be equal to or less than 0.11%; it may be equal to or less than 0.08%; it may be equal to or less than 0.04%.

Limits of Quantification (LoQ) is the lowest concentration at which the analyte can not only be reliably detected but at which some predefined goals of bias and imprecision are met. LoQ may be equivalent to LoD or it could be at a higher concentration.

Hypotheses

In the context of this disclosure, a hypothesis refers to a possible transplant status. In some embodiments, a set of hypotheses may be designed such that one hypothesis from the set will correspond to the actual transplant status of any given individual. In some embodiments, a set of hypotheses may be designed such that every possible transplant status may be described by at least one hypothesis from the set. In some embodiments of the present disclosure, one aspect of a method is to determine which hypothesis corresponds to the actual transplant status of the individual in question.

In another embodiment of the present disclosure, one step involves creating a hypothesis. Creating a hypothesis may refer to the act of setting the limits of the variables such that the entire set of possible transplant statuses that are under consideration are encompassed by those variables.

Genotypic Contexts

The genotypic context refers to the genetic state of a given allele, on each of the two relevant chromosomes for one or both of the two sources of the target. The genotypic context for a given SNP may consist of four base pairs; they may be the same or different from one another. It is typically written as "$m_1m_2|f_1f_2$," where $m_1$ and $m_2$ are the genetic state of the given SNP on the two donor chromosomes, and $f_1$ and $f_2$ are the genetic state of the given SNP on the two recipient chromosomes. In some embodiments, the genotypic context may be written as "$f_1f_2|m_1m_2$." Note that subscripts "1" and "2" refer to the genotype, at the given allele, of the first and second chromosome; also note that the choice of which chromosome is labeled "1" and which is labeled "2" is arbitrary.

Note that in this disclosure, A and B are often used to generically represent base pair identities; A or B could equally well represent C (cytosine), G (guanine), A (adenine) or T (thymine). For example, if, at a given SNP based allele, the transplant recipient's genotype was T at that SNP on one chromosome, and G at that SNP on the homologous chromosome, and the transplant donor's genotype at that allele is G at that SNP on both of the homologous chromosomes, one may say that the target individual's allele has the genotypic context of AB|BB; it could also be said that the allele has the genotypic context of AB|AA. Note that, in theory, any of the four possible nucleotides could occur at a given allele, and thus it is possible, for example, for the transplant recipient to have a genotype of AT, and the transplant donor to have a genotype of GC at a given allele. However, empirical data indicate that in most cases only two of the four possible base pairs are observed at a given allele. It is possible, for example when using single tandem repeats, to have more than two parental, more than four and even more than ten contexts. In this disclosure the discussion assumes that only two possible base pairs will be observed at a given allele, although the embodiments disclosed herein could be modified to take into account the cases where this assumption does not hold.

A "genotypic context" may refer to a set or subset of target SNPs that have the same genotypic context. For example, if one were to measure 1000 alleles on a given chromosome on a target individual, then the context AA|BB could refer to the set of all alleles in the group of 1,000 alleles where the genotype of the transplant recipient of the target was homozygous, and the genotype of the transplant donor of the target is homozygous, but where the recipient genotype and the donor genotype are dissimilar at that locus. If the data is not phased, and thus AB=BA, then there are nine possible genotypic contexts: AA|AA, AA|AB, AA|BB, AB|AA, AB|AB, AB|BB, BB|AA, BB|AB, and BB|BB. If the data is phased, and thus AB BA, then there are sixteen different possible genotypic contexts: AA|AA, AA|AB, AA|BA, AA|BB, AB|AA, AB|AB, AB|BA, AB|BB, BA|AA, BA|AB, BA|BA, BA|BB, BB|AA, BB|AB, BB|BA, and BB|BB. Every SNP allele on a chromosome, excluding some SNPs on the sex chromosomes, has one of these genotypic contexts. The set of SNPs wherein the genotypic context for one parent is heterozygous may be referred to as the heterozygous context.

Use of Genotypic Contexts in Non-Invasive Determination of Transplant State

Non-invasive determination of transplant state is an important technique that can be used to determine the genetic state of a transplant from genetic material that is obtained in a non-invasive manner, for example from a blood draw on the transplant recipient. The blood could be separated and the plasma isolated, followed by isolation of the plasma DNA. Size selection could be used to isolate the DNA of the appropriate length. The DNA may be preferentially enriched at a set of loci. This DNA can then be measured by a number of means, such as by hybridizing to a genotyping array and measuring the fluorescence, or by sequencing on a high throughput sequencer.

When considering which alleles to target, one may consider the likelihood that some parental contexts are likely to be more informative than others. For example, AA|BB and the symmetric context BB|AA are the most informative contexts, because the transplant is known to carry an allele that is different from the transplant recipient. For reasons of symmetry, both AA|BB and BB|AA contexts may be referred to as AA|BB. Another set of informative genotypic contexts are AA|AB and BB|AB, because in these cases the transplant has a 50% chance of carrying an allele that the transplant recipient does not have. For reasons of symmetry, both AA|AB and BB|AB contexts may be referred to as AA|AB. A third set of informative parental contexts are AB|AA and AB|BB, because in these cases the transplant is carrying a known donor allele, and that allele is also present in the recipient genome. For reasons of symmetry, both AB|AA and AB|BB contexts may be referred to as AB|AA. A fourth context is AB|AB where the transplant has an unknown allelic state, and whatever the allelic state, it is one in which the transplant recipient has the same alleles. The fifth context is AA|AA, where the transplant recipient and transplant donor are heterozygous.

Different Implementations of the Presently Disclosed Embodiments

In some embodiments the source of the genetic material to be used in determining the genetic state of the transplant may be transplanted donor-derived cells. The method may involve obtaining a blood sample from the transplant recipient.

In an embodiment of the present disclosure, the target individual is a transplant, and the different genotype measurements are made on a plurality of DNA samples from the transplant. In some embodiments of the present disclosure, the donor-derived DNA samples are from isolated transplanted cells where the donor-derived cells may be mixed with recipient cells. In some embodiments of the present disclosure, the donor-derived DNA samples are from free floating donor-derived DNA, where the donor DNA may be mixed with free floating recipient DNA.

In some embodiments, the genetic sample may be prepared and/or purified. There are a number of standard procedures known in the art to accomplish such an end. In some embodiments, the sample may be centrifuged to separate various layers. In some embodiments, the DNA may be isolated using filtration. In some embodiments, the preparation of the DNA may involve amplification, separation, purification by chromatography, liquid separation, isolation, preferential enrichment, preferential amplification, targeted amplification, or any of a number of other techniques either known in the art or described herein.

In some embodiments, a method of the present disclosure may involve amplifying DNA. Amplification of the DNA, a process which transforms a small amount of genetic material to a larger amount of genetic material that comprises a similar set of genetic data, can be done by a wide variety of methods, including, but not limited to polymerase chain reaction (PCR). One method of amplifying DNA is whole genome amplification (WGA). There are a number of methods available for WGA: ligation-mediated PCR (LM-PCR), degenerate oligonucleotide primer PCR (DOP-PCR), and multiple displacement amplification (MDA). In LM-PCR, short DNA sequences called adapters are ligated to blunt ends of DNA. These adapters contain universal amplification sequences, which are used to amplify the DNA by PCR. In DOP-PCR, random primers that also contain universal amplification sequences are used in a first round of annealing and PCR. Then, a second round of PCR is used to amplify the sequences further with the universal primer sequences. MDA uses the phi-29 polymerase, which is a highly processive and nonspecific enzyme that replicates DNA and has been used for single-cell analysis. The major limitations to amplification of material from a single cell are (1) necessity of using extremely dilute DNA concentrations or extremely small volume of reaction mixture, and (2) difficulty of reliably dissociating DNA from proteins across the whole genome. Regardless, single-cell whole genome amplification has been used successfully for a variety of applications for a number of years. There are other methods of amplifying DNA from a sample of DNA. The DNA amplification transforms the initial sample of DNA into a sample of DNA that is similar in the set of sequences, but of much greater quantity. In some cases, amplification may not be required.

In some embodiments, DNA may be amplified using a universal amplification, such as WGA or MDA. In some embodiments, DNA may be amplified by targeted amplification, for example using targeted PCR, or circularizing probes. In some embodiments, the DNA may be preferentially enriched using a targeted amplification method, or a method that results in the full or partial separation of desired from undesired DNA, such as capture by hybridization approaches. In some embodiments, DNA may be amplified by using a combination of a universal amplification method and a preferential enrichment method. A fuller description of some of these methods can be found elsewhere in this document.

The genetic data of the target individual and/or of the related individual can be transformed from a molecular state to an electronic state by measuring the appropriate genetic material using tools and or techniques taken from a group including, but not limited to: genotyping microarrays, and high throughput sequencing. Some high throughput sequencing methods include Sanger DNA sequencing, pyrosequencing, the ILLUMINA SOLEXA platform, ILLUMINA's GENOME ANALYZER, or APPLIED BIOSYSTEM's 454 sequencing platform, HELICOS's TRUE SINGLE MOLECULE SEQUENCING platform, HALCYON MOLECULAR's electron microscope sequencing method, or any other sequencing method. All of these methods physically transform the genetic data stored in a sample of DNA into a set of genetic data that is typically stored in a memory device en route to being processed.

A relevant individual's genetic data may be measured by analyzing substances taken from a group including, but not limited to: the individual's bulk diploid tissue, one or more diploid cells from the individual, one or more haploid cells from the individual, one or more blastomeres from the target individual, extra-cellular genetic material found on the individual, extra-cellular genetic material from the individual found in maternal blood, cells from the individual found in maternal blood, one or more embryos created from (a) gamete(s) from the related individual, one or more blastomeres taken from such an embryo, extra-cellular genetic material found on the related individual, genetic material known to have originated from the related individual, and combinations thereof.

In some embodiments, the knowledge of the determined transplant status may be used to make a clinical decision. This knowledge, typically stored as a physical arrangement of matter in a memory device, may then be transformed into a report. The report may then be acted upon. For example, the clinical decision may be to adjust immunosuppressive medication intake by a transplant recipient.

In an embodiment of the present disclosure, any of the methods described herein may be modified to allow for multiple targets to come from same target individual, for example, multiple blood draws from the same transplant recipient. This may improve the accuracy of the model, as multiple genetic measurements may provide more data with which the target genotype may be determined. In an embodiment, one set of target genetic data served as the primary data which was reported, and the other served as data to double-check the primary target genetic data. In an embodiment, a plurality of sets of genetic data, each measured from genetic material taken from the target individual, are considered in parallel.

In an embodiment, the raw genetic material of the transplant recipient and the transplant donor is transformed by way of amplification to an amount of DNA that is similar in sequence, but larger in quantity. Then, by way of a genotyping method, the genotypic data that is encoded by nucleic acids is transformed into genetic measurements that may be stored physically and/or electronically on a memory device, such as those described above. Then, through the execution of the computer program on the computer hardware, instead of being physically encoded bits and bytes, arranged in a pattern that represents raw measurement data, they become transformed into a pattern that represents a high confidence determination of the transplant status of the recipient. The details of this transformation will rely on the data itself and the computer language and hardware system used to execute the method described herein. Then, the data that is physically configured to represent a high quality transplant status determination of the recipient is transformed into a report which may be sent to a health care practitioner. This transformation may be carried out using a printer or a computer display. The report may be a printed copy, on paper or other suitable medium, or else it may be electronic. In the case of an electronic report, it may be transmitted, it may be physically stored on a memory device at a location on the computer accessible by the health care practitioner; it also may be displayed on a screen so that it may be read. In the case of a screen display, the data may be transformed to a readable format by causing the physical transformation of pixels on the display device. The transformation may be accomplished by way of physically firing electrons at a phosphorescent screen, by way of altering an electric charge that physically changes the transparency of a specific set of pixels on a screen that may lie in front of a substrate that emits or absorbs photons. This transformation may be accomplished by way of changing the nanoscale orientation of the molecules in a liquid crystal, for example, from nematic to cholesteric or smectic phase, at a specific set of pixels. This transformation may be accomplished by way of an electric current causing photons to be emitted from a specific set of pixels made from a plurality of light emitting diodes arranged in a meaningful pattern. This transformation may be accomplished by any other way used to display information, such as a computer screen, or some other output device or way of transmitting information. The health care practitioner may then act on the report, such that the data in the report is transformed into an action. The action may be to continue or discontinue immunosuppressive medication. In some embodiments, the action may be to increase or decrease immunosuppressive medication.

In some embodiments, the methods described herein can be used at a very early period of time following transplantation surgery, for example as early as the day of surgery, one day after surgery, two days after surgery, three days after surgery, four days after surgery, five days after surgery, six days after surgery, a week after surgery, two weeks after surgery, three weeks after surgery, four weeks after surgery, one month after surgery, two months after surgery, three months after surgery, four months after surgery, five months after surgery, six months after surgery, seven months after surgery, eight months after surgery, nine months after surgery, ten months after surgery, eleven months after surgery, or a year or more after surgery.

Any of the embodiments disclosed herein may be implemented in digital electronic circuitry, integrated circuitry, specially designed ASICs (application-specific integrated circuits), computer hardware, firmware, software, or in combinations thereof. Apparatus of the presently disclosed embodiments can be implemented in a computer program product tangibly embodied in a machine-readable storage device for execution by a programmable processor; and method steps of the presently disclosed embodiments can be performed by a programmable processor executing a program of instructions to perform functions of the presently disclosed embodiments by operating on input data and generating output. The presently disclosed embodiments can be implemented advantageously in one or more computer programs that are executable and/or interpretable on a programmable system including at least one programmable processor, which may be special or general purpose, coupled to receive data and instructions from, and to transmit data and instructions to, a storage system, at least one input device, and at least one output device. Each computer program can be implemented in a high-level procedural or object-oriented programming language or in assembly or machine language if desired; and in any case, the language can be a compiled or interpreted language. A computer program may be deployed in any form, including as a stand-alone program, or as a module, component, subroutine, or other unit suitable for use in a computing environment. A computer program may be deployed to be executed or interpreted on one computer or on multiple computers at one site, or distributed across multiple sites and interconnected by a communication network.

Computer readable storage media, as used herein, refers to physical or tangible storage (as opposed to signals) and includes without limitation volatile and non-volatile, removable and non-removable media implemented in any method or technology for the tangible storage of information such as computer-readable instructions, data structures, program modules or other data. Computer readable storage media includes, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other physical or material medium which can be used to tangibly store the desired information or data or instructions and which can be accessed by a computer or processor.

Any of the methods described herein may include the output of data in a physical format, such as on a computer screen, or on a paper printout. In explanations of any embodiments elsewhere in this document, it should be understood that the described methods may be combined with the output of the actionable data in a format that can be acted upon by a physician. In addition, the described methods may be combined with the actual execution of a clinical decision that results in a clinical treatment, or the execution of a clinical decision to make no action. Some of the embodiments described in the document for determining genetic data pertaining to a target individual may be combined with a clinical decision or action. Some of the embodiments described in the document for determining genetic data pertaining to a target individual may be combined with the notification of a potential transplant rejection, or lack thereof, with a medical professional. Some of the embodiments described herein may be combined with the output of the actionable data, and the execution of a clinical decision that results in a clinical treatment, or the execution of a clinical decision to make no action.

Targeted Enrichment and Sequencing

The use of a technique to enrich a sample of DNA at a set of target loci followed by sequencing as part of a method for non-invasive determination of transplant status in a transplant recipient may confer a number of unexpected advantages. In some embodiments of the present disclosure, the method involves measuring genetic data for use with an informatics based method. The ultimate outcome of some of the embodiments is the actionable data of the status of a transplant. There are many methods that may be used to measure the genetic data of the individual and/or the related individuals as part of embodied methods. In an embodiment, a method for enriching the concentration of a set of targeted alleles is disclosed herein, the method comprising one or more of the following steps: targeted amplification of genetic material, addition of loci specific oligonucleotide probes, ligation of specified DNA strands, isolation of sets of desired DNA, removal of unwanted components of a reaction, detection of certain sequences of DNA by hybridization, and detection of the sequence of one or a plurality of strands of DNA by DNA sequencing methods. In some cases the DNA strands may refer to target genetic material, in some cases they may refer to primers, in some cases they may refer to synthesized sequences, or combinations thereof. These steps may be carried out in a number of different orders. Given the highly variable nature of molecular biology, it is generally not obvious which methods, and which combinations of steps, will perform poorly, well, or best in various situations.

For example, a universal amplification step of the DNA prior to targeted amplification may confer several advantages, such as removing the risk of bottlenecking and reducing allelic bias. The DNA may be mixed an oligonucleotide probe that can hybridize with two neighboring regions of the target sequence, one on either side. After hybridization, the ends of the probe may be connected by adding a polymerase, a means for ligation, and any necessary reagents to allow the circularization of the probe. After circularization, an exonuclease may be added to digest to non-circularized genetic material, followed by detection of the circularized probe. The DNA may be mixed with PCR primers that can hybridize with two neighboring regions of the target sequence, one on either side. After hybridization, the ends of the probe may be connected by adding a polymerase, a means for ligation, and any necessary reagents to complete PCR amplification. Amplified or unamplified DNA may be targeted by hybrid capture probes that target a set of loci; after hybridization, the probe may be localized and separated from the mixture to provide a mixture of DNA that is enriched in target sequences.

In some embodiments the detection of the target genetic material may be done in a multiplexed fashion. The number of genetic target sequences that may be run in parallel can range from one to ten, ten to one hundred, one hundred to one thousand, one thousand to ten thousand, ten thousand to one hundred thousand, one hundred thousand to one million, or one million to ten million. Note that the prior art includes disclosures of successful multiplexed PCR reactions involving pools of up to about 50 or 100 primers, and not more. Prior attempts to multiplex more than 100 primers per pool have resulted in significant problems with unwanted side reactions such as primer-dimer formation.

In some embodiments, this method may be used to genotype a single cell, a small number of cells, two to five cells, six to ten cells, ten to twenty cells, twenty to fifty cell, fifty to one hundred cells, one hundred to one thousand cells, or a small amount of extracellular DNA, for example from one to ten picograms, from ten to one hundred pictograms, from one hundred pictograms to one nanogram, from one to ten nanograms, from ten to one hundred nanograms, or from one hundred nanograms to one microgram.

The use of a method to target certain loci followed by sequencing as part of a method for transplant state calling may confer a number of unexpected advantages. Some methods by which DNA may be targeted, or preferentially enriched, include using circularizing probes, linked inverted probes (LIPs, MIPs), capture by hybridization methods such as SURESELECT, and targeted PCR or ligation-mediated PCR amplification strategies.

There are many methods that may be used to measure the genetic data of the individual and/or the related individuals in the aforementioned contexts. The different methods comprise a number of steps, those steps often involving amplification of genetic material, addition of oligonucleotide probes, ligation of specified DNA strands, isolation of sets of desired DNA, removal of unwanted components of a reaction, detection of certain sequences of DNA by hybridization, detection of the sequence of one or a plurality of strands of DNA by DNA sequencing methods. In some cases the DNA strands may refer to target genetic material, in some cases they may refer to primers, in some cases they may refer to synthesized sequences, or combinations thereof. These steps may be carried out in a number of different orders. Given the highly variable nature of molecular biology, it is generally not obvious which methods, and which combinations of steps, will perform poorly, well, or best in various situations.

Note that in theory it is possible to target any number loci in the genome, anywhere from one loci to well over one million loci. If a sample of DNA is subjected to targeting, and then sequenced, the percentage of the alleles that are read by the sequencer will be enriched with respect to their natural abundance in the sample. The degree of enrichment can be anywhere from one percent (or even less) to ten-fold, a hundred-fold, a thousand-fold or even many million-fold. In the human genome there are roughly 3 billion base pairs, and nucleotides, comprising approximately 75 million polymorphic loci. The more loci that are targeted, the smaller the degree of enrichment is possible. The fewer the number of loci that are targeted, the greater degree of enrichment is possible, and the greater depth of read may be achieved at those loci for a given number of sequence reads.

In an embodiment of the present disclosure, the targeting or preferential may focus entirely on SNPs. In an embodiment, the targeting or preferential may focus on any polymorphic site. A number of commercial targeting products are available to enrich exons. Surprisingly, targeting exclusively SNPs, or exclusively polymorphic loci, is particularly advantageous. Those types of methodology that do not focus on polymorphic alleles would not benefit as much from targeting or preferential enrichment of a set of alleles.

In an embodiment of the present disclosure, it is possible to use a targeting method that focuses on SNPs to enrich a genetic sample in polymorphic regions of the genome. In an embodiment, it is possible to focus on a small number of SNPs, for example between 1 and 100 SNPs, or a larger number, for example, between 100 and 1,000, between 1,000 and 10,000, between 10,000 and 100,000 or more than 100,000 SNPs. In an embodiment, it is possible to focus on one or a small number of chromosomes that are correlated with live trisomic births, for example chromosomes 13, 18, 21, X and Y, or some combination thereof. In an embodiment, it is possible to enrich the targeted SNPs by a small factor, for example between 1.01 fold and 100 fold, or by a larger factor, for example between 100 fold and 1,000,000 fold, or even by more than 1,000,000 fold. In an embodiment of the present disclosure, it is possible to use a targeting method to create a sample of DNA that is preferentially enriched in polymorphic regions of the genome. In an embodiment, it is possible to use this method to create a mixture of DNA with any of these characteristics where the mixture of DNA contains transplant recipient DNA and also free floating donor-derive DNA. In an embodiment, it is possible to use this method to create a mixture of DNA that has any combination of these factors. Any of the targeting methods described herein can be used to create mixtures of DNA that are preferentially enriched in certain loci.

In some embodiments, a method of the present disclosure further includes measuring the DNA in the mixed fraction using a high throughput DNA sequencer, where the DNA in the mixed fraction contains a disproportionate number of sequences from one or more chromosomes.

Described herein are three methods: multiplex PCR, targeted capture by hybridization, and linked inverted probes (LIPs), which may be used to obtain and analyze measurements from a sufficient number of polymorphic loci from a transplant recipient plasma sample in order to detect transplant rejection; this is not meant to exclude other methods of selective enrichment of targeted loci. Other methods may equally well be used without changing the essence of the method. In each case the polymorphism assayed may include single nucleotide polymorphisms (SNPs), small indels, or STRs. A preferred method involves the use of SNPs. Each approach produces allele frequency data; allele frequency data for each targeted locus and/or the joint allele frequency distributions from these loci may be analyzed to determine the rejection and/or injury status of the transplant. Each approach has its own considerations due to the limited source material and the fact that transplant recipient plasma consists of mixture of recipient and donor-derived DNA. This method may be combined with other approaches to provide a more accurate determination. In an embodiment, this method may be combined with a sequence counting approach such as that described in U.S. Pat. No. 7,888,017.

Accurately Measuring the Allelic Distributions in a Sample

Current sequencing approaches can be used to estimate the distribution of alleles in a sample. One such method involves randomly sampling sequences from a pool DNA, termed shotgun sequencing. The proportion of a particular allele in the sequencing data is typically very low and can be determined by simple statistics. The human genome contains approximately 3 billion base pairs. So, if the sequencing method used make 100 bp reads, a particular allele will be measured about once in every 30 million sequence reads.

In an embodiment, a method of the present disclosure is used to determine the presence or absence of two or more different haplotypes that contain the same set of loci in a sample of DNA from the measured allele distributions of loci from that chromosome. Alleles that are polymorphic between the haplotypes tend to be more informative, however any alleles where the transplant recipient and transplant donor are not both homozygous for the same allele will yield useful information through measured allele distributions beyond the information that is available from simple read count analysis.

Shotgun sequencing of such a sample, however, is extremely inefficient as it results in many sequences for regions that are not polymorphic between the different haplotypes in the sample, or are for chromosomes that are not of interest, and therefore reveal no information about the proportion of the target haplotypes. Described herein are methods that specifically target and/or preferentially enrich segments of DNA in the sample that are more likely to be polymorphic in the genome to increase the yield of allelic information obtained by sequencing. Note that for the measured allele distributions in an enriched sample to be truly representative of the actual amounts present in the target individual, it is critical that there is little or no preferential enrichment of one allele as compared to the other allele at a given loci in the targeted segments. Current methods known in the art to target polymorphic alleles are designed to ensure that at least some of any alleles present are detected. However, these methods were not designed for the purpose of measuring the unbiased allelic distributions of polymorphic alleles present in the original mixture. It is non-obvious that any particular method of target enrichment would be able to produce an enriched sample wherein the measured allele distributions would accurately represent the allele distributions present in the original unamplified sample better than any other method. While many enrichment methods may be expected, in theory, to accomplish such an aim, an ordinary person skilled in the art is well aware that there is a great deal of stochastic or deterministic bias in current amplification, targeting and other preferential enrichment methods. One embodiment of a method described herein allows a plurality of alleles found in a mixture of DNA that correspond to a given locus in the genome to be amplified, or preferentially enriched in a way that the degree of enrichment of each of the alleles is nearly the same. Another way to say this is that the method allows the relative quantity of the alleles present in the mixture as a whole to be increased, while the ratio between the alleles that correspond to each locus remains essentially the same as they were in the original mixture of DNA. Methods in the prior art preferential enrichment of loci can result in allelic biases of more than 1%, more than 2%, more than 5% and even more than 10%. This preferential enrichment may be due to capture bias when using a capture by hybridization approach, or amplification bias which may be small for each cycle, but can become large when compounded over 20, 30 or 40 cycles. For the purposes of this disclosure, for the ratio to remain essentially the same means that the ratio of the alleles in the original mixture divided by the ratio of the alleles in the resulting mixture is between 0.95 and 1.05, between 0.98 and 1.02, between 0.99 and 1.01, between 0.995 and 1.005, between 0.998 and 1.002, between 0.999 and 1.001, or between 0.9999 and 1.0001. Note that the calculation of the allele ratios presented here may not be used in the determination of the transplant status of the transplant recipient, and may only be a metric to be used to measure allelic bias.

In an embodiment, once a mixture has been preferentially enriched at the set of target loci, it may be sequenced using any one of the previous, current, or next generation of sequencing instruments that sequences a clonal sample (a sample generated from a single molecule; examples include ILLUMINA GAIIx, ILLUMINA HiSeq, LIFE TECHNOLOGIES SOLiD, 5500XL). The ratios can be evaluated by sequencing through the specific alleles within the targeted region. These sequencing reads can be analyzed and counted according the allele type and the rations of different alleles determined accordingly. For variations that are one to a few bases in length, detection of the alleles will be performed by sequencing and it is essential that the sequencing read span the allele in question in order to evaluate the allelic composition of that captured molecule. The total number of captured molecules assayed for the genotype can be increased by increasing the length of the sequencing read. Full sequencing of all molecules would guarantee collection of the maximum amount of data available in the enriched pool. However, sequencing is currently expensive, and a method that can measure allele distributions using a lower number of sequence reads will have great value. In addition, there are technical limitations to the maximum possible length of read as well as accuracy limitations as read lengths increase. The alleles of greatest utility will be of one to a few bases in length, but theoretically any allele shorter than the length of the sequencing read can be used. While allele variations come in all types, the examples provided herein focus on SNPs or variants contained of just a few neighboring base pairs. Larger variants such as segmental copy number variants can be detected by aggregations of these smaller variations in many cases as whole collections of SNP internal to the segment are duplicated. Variants larger than a few bases, such as STRs require special consideration and some targeting approaches work while others will not.

There are multiple targeting approaches that can be used to specifically isolate and enrich a one or a plurality of variant positions in the genome. Typically, these rely on taking advantage of the invariant sequence flanking the variant sequence. There is prior art related to targeting in the context of sequencing where the substrate is maternal plasma (see, e.g., Liao et al., Clin. Chem. 2011; 57(1): pp. 92-101). However, the approaches in the prior art all use targeting probes that target exons, and do not focus on targeting polymorphic regions of the genome. In an embodiment, a method of the present disclosure involves using targeting probes that focus exclusively or almost exclusively on polymorphic regions. In an embodiment, a method of the present disclosure involves using targeting probes that focus exclusively or almost exclusively on SNPs. In some embodiments of the present disclosure, the targeted polymorphic sites consist of at least 10% SNPs, at least 20% SNPs, at least 30% SNPs, at least 40% SNPs, at least 50% SNPs, at least 60% SNPs, at least 70% SNPs, at least 80% SNPs, at least 90% SNPs, at least 95% SNPs, at least 98% SNPs, at least 99% SNPs, at least 99.9% SNPs, or exclusively SNPs.

In an embodiment, a method of the present disclosure can be used to determine genotypes (base composition of the DNA at specific loci) and relative proportions of those genotypes from a mixture of DNA molecules, where those DNA molecules may have originated from one or a number of genetically distinct individuals. In an embodiment, a method of the present disclosure can be used to determine the genotypes at a set of polymorphic loci, and the relative ratios of the amount of different alleles present at those loci. In an embodiment the polymorphic loci may consist entirely of SNPs. In an embodiment, the polymorphic loci can comprise SNPs, single tandem repeats, and other polymorphisms. In an embodiment, a method of the present disclosure can be used to determine the relative distributions of alleles at a set of polymorphic loci in a mixture of DNA, where the mixture of DNA comprises DNA that originates from a transplant recipient, and DNA that originates from a transplant. In an embodiment, the joint allele distributions can be determined on a mixture of DNA isolated from blood from a transplant recipient. In an embodiment, the allele distributions at a set of loci can be used to determine the transplant rejection and/or injury status of a transplant.

In an embodiment, the mixture of DNA molecules could be derived from DNA extracted from multiple cells of one individual. In an embodiment, the original collection of cells from which the DNA is derived may comprise a mixture of diploid or haploid cells of the same or of different genotypes, if that individual is mosaic (germline or somatic). In an embodiment, the mixture of DNA molecules could also be derived from DNA extracted from single cells. In an embodiment, the mixture of DNA molecules could also be derived from DNA extracted from mixture of two or more cells of the same individual, or of different individuals. In an embodiment, the mixture of DNA molecules could be derived from DNA isolated from biological material that has already liberated from cells such as blood plasma, which is known to contain cell free DNA. In an embodiment, the this biological material may be a mixture of DNA from one or more individuals, as is the case during pregnancy where it has been shown that fetal DNA is present in the mixture. In an embodiment, the biological material could be from a mixture of cells that were found in transplant recipient blood, where some of the cells originate from the transplant.

Circularizing Probes

Some embodiments of the present disclosure involve the use of "Linked Inverted Probes" (LIPs), which have been previously described in the literature. LIPs is a generic term meant to encompass technologies that involve the creation of a circular molecule of DNA, where the probes are designed to hybridize to targeted region of DNA on either side of a targeted allele, such that addition of appropriate polymerases and/or ligases, and the appropriate conditions, buffers and other reagents, will complete the complementary, inverted region of DNA across the targeted allele to create a circular loop of DNA that captures the information found in the targeted allele. LIPs may also be called pre-circularized probes, pre-circularizing probes, or circularizing probes. The LIPs probe may be a linear DNA molecule between 50 and 500 nucleotides in length, and in an embodiment between 70 and 100 nucleotides in length; in some embodiments, it may be longer or shorter than described herein. Others embodiments of the present disclosure involve different incarnations, of the LIPs technology, such as Padlock Probes and MOLECULAR INVERSION PROBES (MIPs).

One method to target specific locations for sequencing is to synthesize probes in which the 3' and 5' ends of the probes anneal to target DNA at locations adjacent to and on either side of the targeted region, in an inverted manner, such that the addition of DNA polymerase and DNA ligase results in extension from the 3' end, adding bases to single stranded probe that are complementary to the target molecule (gap-fill), followed by ligation of the new 3' end to the 5' end of the original probe resulting in a circular DNA molecule that can be subsequently isolated from background DNA. The probe ends are designed to flank the targeted region of interest. One aspect of this approach is commonly called MIPS and has been used in conjunction with array technologies to determine the nature of the sequence filled in. One drawback to the use of MIPs in the context of measuring allele ratios is that the hybridization, circularization and amplification steps do not happed at equal rates for different alleles at the same loci. This results in measured allele ratios that are not representative of the actual allele ratios present in the original mixture.

In an embodiment, the circularizing probes are constructed such that the region of the probe that is designed to hybridize upstream of the targeted polymorphic locus and the region of the probe that is designed to hybridize downstream of the targeted polymorphic locus are covalently connected through a non-nucleic acid backbone. This backbone can be any biocompatible molecule or combination of biocompatible molecules. Some examples of possible biocompatible molecules are poly(ethylene glycol), polycarbonates, polyurethanes, polyethylenes, polypropylenes, sulfone polymers, silicone, cellulose, fluoropolymers, acrylic compounds, styrene block copolymers, and other block copolymers.

In an embodiment of the present disclosure, this approach has been modified to be easily amenable to sequencing as a means of interrogating the filled in sequence. In order to retain the original allelic proportions of the original sample at least one key consideration must be taken into account. The variable positions among different alleles in the gap-fill region must not be too close to the probe binding sites as there can be initiation bias by the DNA polymerase resulting in differential of the variants. Another consideration is that additional variations may be present in the probe binding sites that are correlated to the variants in the gap-fill region which can result unequal amplification from different alleles. In an embodiment of the present disclosure, the 3' ends and 5' ends of the pre-circularized probe are designed to hybridize to bases that are one or a few positions away from the variant positions (polymorphic sites) of the targeted allele. The number of bases between the polymorphic site (SNP or otherwise) and the base to which the 3' end and/or 5' of the pre-circularized probe is designed to hybridize may be one base, it may be two bases, it may be three bases, it may be four bases, it may be five bases, it may be six bases, it may be seven to ten bases, it may be eleven to fifteen bases, or it may be sixteen to twenty bases, twenty to thirty bases, or thirty to sixty bases. The forward and reverse primers may be designed to hybridize a different number of bases away from the polymorphic site. Circularizing probes can be generated in large numbers with current DNA synthesis technology allowing very large numbers of probes to be generated and potentially pooled, enabling interrogation of many loci simultaneously. It has been reported to work with more than 300,000 probes. Two papers that discuss a method involving circularizing probes that can be used to measure the genomic data of the target individual include: Porreca et al., Nature Methods, 2007 4(11), pp. 931-936; and also Turner et al., Nature Methods, 2009, 6(5), pp. 315-316. The methods described in these papers may be used in combination with other methods described herein. Certain steps of the method from these two papers may be used in combination with other steps from other methods described herein.

In some embodiments of the methods disclosed herein, the genetic material of the target individual is optionally amplified, followed by hybridization of the pre-circularized probes, performing a gap fill to fill in the bases between the two ends of the hybridized probes, ligating the two ends to form a circularized probe, and amplifying the circularized probe, using, for example, rolling circle amplification. Once the desired target allelic genetic information is captured by circularizing appropriately designed oligonucleic probes, such as in the LIPs system, the genetic sequence of the circularized probes may be being measured to give the desired sequence data. In an embodiment, the appropriately designed oligonucleotides probes may be circularized directly on unamplified genetic material of the target individual, and amplified afterwards. Note that a number of amplification procedures may be used to amplify the original genetic material, or the circularized LIPs, including rolling circle amplification, MDA, or other amplification protocols. Different methods may be used to measure the genetic information on the target genome, for example using high throughput sequencing, Sanger sequencing, other sequencing methods, capture-by-hybridization, capture-by-circularization, multiplex PCR, other hybridization methods, and combinations thereof.

Once the genetic material of the individual has been measured using one or a combination of the above methods, an informatics based method, along with the appropriate genetic measurements, can then be used to determination the transplant status of a transplant recipient.

Applying an informatics based method to determine the transplant status of a transplant recipient from genetic data as measured by hybridization arrays, such as the ILLUMINA INFINIUM array, or the AFFYMETRIX gene chip has been described in documents references elsewhere in this document. However, the method described herein shows improvements over methods described previously in the literature. For example, the LIPs based approach followed by high throughput sequencing unexpectedly provides better genotypic data due to the approach having better capacity for multiplexing, better capture specificity, better uniformity, and low allelic bias. Greater multiplexing allows more alleles to be targeted, giving more accurate results. Better uniformity results in more of the targeted alleles being measured, giving more accurate results. Lower rates of allelic bias result in lower rates of miscalls, giving more accurate results. More accurate results result in an improvement in clinical outcomes, and better medical care.

It is important to note that LIPs may be used as a method for targeting specific loci in a sample of DNA for genotyping by methods other than sequencing. For example, LIPs may be used to target DNA for genotyping using SNP arrays or other DNA or RNA based microarrays.

Ligation-Mediated PCR

Ligation-mediated PCR is method of PCR used to preferentially enrich a sample of DNA by amplifying one or a plurality of loci in a mixture of DNA, the method comprising: obtaining a set of primer pairs, where each primer in the pair contains a target specific sequence and a non-target sequence, where the target specific sequence is designed to anneal to a target region, one upstream and one downstream from the polymorphic site, and which can be separated from the polymorphic site by 0, 1, 2, 3, 4, 5, 6, 7, 8, 9, 10, 11-20, 21-30, 31-40, 41-50, 51-100, or more than 100; polymerization of the DNA from the 3-prime end of upstream primer to the fill the single strand region between it and the 5-prime end of the downstream primer with nucleotides complementary to the target molecule; ligation of the last polymerized base of the upstream primer to the adjacent 5-prime base of the downstream primer; and amplification of only polymerized and ligated molecules using the non-target sequences contained at the 5-prime end of the upstream primer and the 3-prime end of the downstream primer. Pairs of primers to distinct targets may be mixed in the same reaction. The non-target sequences serve as universal sequences such that of all pairs of primers that have been successfully polymerized and ligated may be amplified with a single pair of amplification primers.

Capture by Hybridization

Preferential enrichment of a specific set of sequences in a target genome can be accomplished in a number of ways. Elsewhere in this document is a description of how LIPs can be used to target a specific set of sequences, but in all of those applications, other targeting and/or preferential enrichment methods can be used equally well for the same ends. One example of another targeting method is the capture by hybridization approach. Some examples of commercial capture by hybridization technologies include AGILENT's SURE SELECT and ILLUMINA's TRUSEQ. In capture by hybridization, a set of oligonucleotides that is complimentary or mostly complimentary to the desired targeted sequences is allowed to hybridize to a mixture of DNA, and then physically separated from the mixture. Once the desired sequences have hybridized to the targeting oligonucleotides, the effect of physically removing the targeting oligonucleotides is to also remove the targeted sequences. Once the hybridized oligos are removed, they can be heated to above their melting temperature and they can be amplified. Some ways to physically remove the targeting oligonucleotides is by covalently bonding the targeting oligos to a solid support, for example a magnetic bead, or a chip. Another way to physically remove the targeting oligonucleotides is by covalently bonding them to a molecular moiety with a strong affinity for another molecular moiety. An example of such a molecular pair is biotin and streptavidin, such as is used in SURE SELECT. Thus that targeted sequences could be covalently attached to a biotin molecule, and after hybridization, a solid support with streptavidin affixed can be used to pull down the biotinylated oligonucleotides, to which are hybridized to the targeted sequences.

Hybrid capture involves hybridizing probes that are complementary to the targets of interest to the target molecules. Hybrid capture probes were originally developed to target and enrich large fractions of the genome with relative uniformity between targets. In that application, it was important that all targets be amplified with enough uniformity that all regions could be detected by sequencing, however, no regard was paid to retaining the proportion of alleles in original sample. Following capture, the alleles present in the sample can be determined by direct sequencing of the captured molecules. These sequencing reads can be analyzed and counted according the allele type. However, using the current technology, the measured allele distributions the captured sequences are typically not representative of the original allele distributions.

In an embodiment, detection of the alleles is performed by sequencing. In order to capture the allele identity at the polymorphic site, it is essential that the sequencing read span the allele in question in order to evaluate the allelic composition of that captured molecule. Since the capture molecules are often of variable lengths upon sequencing cannot be guaranteed to overlap the variant positions unless the entire molecule is sequenced. However, cost considerations as well as technical limitations as to the maximum possible length and accuracy of sequencing reads make sequencing the entire molecule unfeasible. In an embodiment, the read length can be increased from about 30 to about 50 or about 70 bases can greatly increase the number of reads that overlap the variant positions within the targeted sequences.

Another way to increase the number of reads that interrogate the position of interest is to decrease the length of the probe, as long as it does not result in bias in the underlying enriched alleles. The length of the synthesized probe should be long enough such that two probes designed to hybridize to two different alleles found at one locus will hybridize with near equal affinity to the various alleles in the original sample. Currently, methods known in the art describe probes that are typically longer than 120 bases. In a current embodiment, if the allele is one or a few bases then the capture probes may be less than about 110 bases, less than about 100 bases, less than about 90 bases, less than about 80 bases, less than about 70 bases, less than about 60 bases, less than about 50 bases, less than about 40 bases, less than about 30 bases, and less than about 25 bases, and this is sufficient to ensure equal enrichment from all alleles. When the mixture of DNA that is to be enriched using the hybrid capture technology is a mixture comprising free floating DNA isolated from blood, for example maternal blood, the average length of DNA is quite short, typically less than 200 bases. The use of shorter probes results in a greater chance that the hybrid capture probes will capture desired DNA fragments. Larger variations may require longer probes. In an embodiment, the variations of interest are one (a SNP) to a few bases in length. In an embodiment, targeted regions in the genome can be preferentially enriched using hybrid capture probes wherein the hybrid capture probes are of a length below 90 bases, and can be less than 80 bases, less than 70 bases, less than 60 bases, less than 50 bases, less than 40 bases, less than 30 bases, or less than 25 bases. In an embodiment, to increase the chance that the desired allele is sequenced, the length of the probe that is designed to hybridize to the regions flanking the polymorphic allele location can be decreased from above 90 bases, to about 80 bases, or to about 70 bases, or to about 60 bases, or to about 50 bases, or to about 40 bases, or to about 30 bases, or to about 25 bases.

There is a minimum overlap between the synthesized probe and the target molecule in order to enable capture. This synthesized probe can be made as short as possible while still being larger than this minimum required overlap.

The effect of using a shorter probe length to target a polymorphic region is that there will be more molecules that overlap the target allele region. The state of fragmentation of the original DNA molecules also affects the number of reads that will overlap the targeted alleles. Some DNA samples such as plasma samples are already fragmented due to biological processes that take place in vivo. However, samples with longer fragments by benefit from fragmentation prior to sequencing library preparation and enrichment. When both probes and fragments are short (~60-80 bp) maximum specificity may be achieved relatively few sequence reads failing to overlap the critical region of interest.

In an embodiment, the hybridization conditions can be adjusted to maximize uniformity in the capture of different alleles present in the original sample. In an embodiment, hybridization temperatures are decreased to minimize differences in hybridization bias between alleles. Methods known in the art avoid using lower temperatures for hybridization because lowering the temperature has the effect of increasing hybridization of probes to unintended targets. However, when the goal is to preserve allele ratios with maximum fidelity, the approach of using lower hybridization temperatures provides optimally accurate allele ratios, despite the fact that the current art teaches away from this approach. Hybridization temperature can also be increased to require greater overlap between the target and the synthesized probe so that only targets with substantial overlap of the targeted region are captured. In some embodiments of the present disclosure, the hybridization temperature is lowered from the normal hybridization temperature to about 40° C., to about 45° C., to about 50° C., to about 55° C., to about 60° C., to about 65, or to about 70° C.

In an embodiment, the hybrid capture probes can be designed such that the region of the capture probe with DNA that is complementary to the DNA found in regions flanking the polymorphic allele is not immediately adjacent to the polymorphic site. Instead, the capture probe can be designed such that the region of the capture probe that is designed to hybridize to the DNA flanking the polymorphic site of the target is separated from the portion of the capture probe that will be in van der Waals contact with the polymorphic site by a small distance that is equivalent in length to one or a small number of bases. In an embodiment, the hybrid capture probe is designed to hybridize to a region that is flanking the polymorphic allele but does not cross it; this may be termed a flanking capture probe. The length of the flanking capture probe may be less than about 120 bases, less than about 110 bases, less than about 100 bases, less than about 90 bases, and can be less than about 80 bases, less than about 70 bases, less than about 60 bases, less than about 50 bases, less than about 40 bases, less than about 30 bases, or less than about 25 bases. The region of the genome that is targeted by the flanking capture probe may be separated by the polymorphic locus by 1, 2, 3, 4, 5, 6, 7, 8, 9, 10, 11-20, or more than 20 base pairs.

Description of a targeted capture based disease screening test using targeted sequence capture. Custom targeted sequence capture, like those currently offered by AGILENT (SURE SELECT), ROCHE-NIMBLEGEN, or ILLUMINA. Capture probes could be custom designed to ensure capture of various types of mutations. For point mutations, one or more probes that overlap the point mutation should be sufficient to capture and sequence the mutation.

For small insertions or deletions, one or more probes that overlap the mutation may be sufficient to capture and sequence fragments comprising the mutation. Hybridization may be less efficient between the probe-limiting capture efficiency, typically designed to the reference genome sequence. To ensure capture of fragments comprising the mutation one could design two probes, one matching the normal allele and one matching the mutant allele. A longer probe may enhance hybridization. Multiple overlapping probes may enhance capture. Finally, placing a probe immediately adjacent to, but not overlapping, the mutation may permit relatively similar capture efficiency of the normal and mutant alleles.

For Simple Tandem Repeats (STRs), a probe overlapping these highly variable sites is unlikely to capture the fragment well. To enhance capture a probe could be placed adjacent to, but not overlapping the variable site. The fragment could then be sequenced as normal to reveal the length and composition of the STR.

For large deletions, a series of overlapping probes, a common approach currently used in exome capture systems may work. However, with this approach it may be difficult to determine whether or not an individual is heterozygous. Targeting and evaluating SNPs within the captured region could potentially reveal loss of heterozygosity across the region indicating that an individual is a carrier. In an embodiment, it is possible to place non-overlapping or singleton probes across the potentially deleted region and use the number of fragments captured as a measure of heterozygosity. In the case where an individual caries a large deletion, one-half the number of fragments are expected to be available for capture relative to a non-deleted (diploid) reference locus. Consequently, the number of reads obtained from the deleted regions should be roughly half that obtained from a normal diploid locus. Aggregating and averaging the sequencing read depth from multiple singleton probes across the potentially deleted region may enhance the signal and improve confidence of the diagnosis. The two approaches, targeting SNPs to identify loss of heterozygosity and using multiple singleton probes to obtain a quantitative measure of the quantity of underlying fragments from that locus can also be combined. Either or both of these strategies may be combined with other strategies to better obtain the same end.

There are a number of ways to decrease depth of read (DOR) variability: for example, one could increase primer concentrations, one could use longer targeted amplification probes, or one could run more STA cycles (such as more than 25, more than 30, more than 35, or even more than 40)

Targeted PCR

In some embodiments, PCR can be used to target specific locations of the genome. In plasma samples, the original DNA is highly fragmented (typically less than 500 bp, with an average length less than 200 bp). In PCR, both forward and reverse primers must anneal to the same fragment to enable amplification. Therefore, if the fragments are short, the PCR assays must amplify relatively short regions as well. Like MIPS, if the polymorphic positions are too close the polymerase binding site, it could result in biases in the amplification from different alleles. Currently, PCR primers that target polymorphic regions, such as those containing SNPs, are typically designed such that the 3' end of the primer will hybridize to the base immediately adjacent to the polymorphic base or bases. In an embodiment of the present disclosure, the 3' ends of both the forward and reverse PCR primers are designed to hybridize to bases that are one or a few positions away from the variant positions (polymorphic sites) of the targeted allele. The number of bases between the polymorphic site (SNP or otherwise) and the base to which the 3' end of the primer is designed to hybridize may be one base, it may be two bases, it may be three bases, it may be four bases, it may be five bases, it may be six bases, it may be seven to ten bases, it may be eleven to fifteen bases, or it may be sixteen to twenty bases. The forward and reverse primers may be designed to hybridize a different number of bases away from the polymorphic site.

PCR assay can be generated in large numbers, however, the interactions between different PCR assays makes it difficult to multiplex them beyond about one hundred assays. Various complex molecular approaches can be used to increase the level of multiplexing, but it may still be limited to fewer than 100, perhaps 200, or possibly 500 assays per reaction. Samples with large quantities of DNA can be split among multiple sub-reactions and then recombined before sequencing. For samples where either the overall sample or some subpopulation of DNA molecules is limited, splitting the sample would introduce statistical noise. In an embodiment, a small or limited quantity of DNA may refer to an amount below 10 pg, between 10 and 100 pg, between 100 pg and 1 ng, between 1 and 10 ng, or between 10 and 100 ng. Note that while this method is particularly useful on small amounts of DNA where other methods that involve splitting into multiple pools can cause significant problems related to introduced stochastic noise, this method still provides the benefit of minimizing bias when it is run on samples of any quantity of DNA. In these situations a universal pre-amplification step may be used to increase the overall sample quantity. Ideally, this pre-amplification step should not appreciably alter the allelic distributions.

In an embodiment, a method of the present disclosure can generate PCR products that are specific to a large number of targeted loci, specifically 1,000 to 5,000 loci, 5,000 to 10,000 loci or more than 10,000 loci, for genotyping by sequencing or some other genotyping method, from limited samples such as single cells or DNA from body fluids. Currently, performing multiplex PCR reactions of more than 5 to 10 targets presents a major challenge and is often hindered by primer side products, such as primer dimers, and other artifacts. When detecting target sequences using microarrays with hybridization probes, primer dimers and other artifacts may be ignored, as these are not detected. However, when using sequencing as a method of detection, the vast majority of the sequencing reads would sequence such artifacts and not the desired target sequences in a sample. Methods described in the prior art used to multiplex more than 50 or 100 reactions in one reaction followed by sequencing will typically result in more than 20%, and often more than 50%, in many cases more than 80% and in some cases more than 90% off-target sequence reads.

In general, to perform targeted sequencing of multiple (n) targets of a sample (greater than 50, greater than 100, greater than 500, or greater than 1,000), one can split the sample into a number of parallel reactions that amplify one individual target. This has been performed in PCR multiwell plates or can be done in commercial platforms such as the FLUIDIGM ACCESS ARRAY (48 reactions per sample in microfluidic chips) or DROPLET PCR by RAIN DANCE TECHNOLOGY (100s to a few thousands of targets). Unfortunately, these split-and-pool methods are problematic for samples with a limited amount of DNA, as there is often not enough copies of the genome to ensure that there is one copy of each region of the genome in each well. This is an especially severe problem when polymorphic loci are targeted, and the relative proportions of the alleles at the polymorphic loci are needed, as the stochastic noise introduced by the splitting and pooling will cause very poorly accurate measurements of the proportions of the alleles that were present in the original sample of DNA. Described here is a method to effectively and efficiently amplify many PCR reactions that is applicable to cases where only a limited amount of DNA is available. In an embodiment, the method may be applied for analysis of single cells, body fluids, mixtures of DNA such as the free floating DNA found in transplant recipient plasma, biopsies, environmental and/or forensic samples.

In an embodiment, the targeted sequencing may involve one, a plurality, or all of the following steps. a) Generate and amplify a library with adaptor sequences on both ends of DNA fragments. b) Divide into multiple reactions after library amplification. c) Generate and optionally amplify a library with adaptor sequences on both ends of DNA fragments. d) Perform 1000- to 10,000-plex amplification of selected targets using one target specific "Forward" primer per target and one tag specific primer. e) Perform a second amplification from this product using "Reverse" target specific primers and one (or more) primer specific to a universal tag that was introduced as part of the target specific forward primers in the first round. f) Perform a 1000-plex preamplification of selected target for a limited number of cycles. g) Divide the product into multiple aliquots and amplify subpools of targets in individual reactions (for example, 50 to 500-plex, though this can be used all the way down to singleplex. h) Pool products of parallel subpools reactions. i) During these amplifications primers may carry sequencing compatible tags (partial or full length) such that the products can be sequenced.

Highly Multiplexed PCR

Disclosed herein are methods that permit the targeted amplification of over a hundred to tens of thousands of target sequences (e.g. SNP loci) from genomic DNA obtained from plasma. The amplified sample may be relatively free of primer dimer products and have low allelic bias at target loci. If during or after amplification the products are appended with sequencing compatible adaptors, analysis of these products can be performed by sequencing.

Performing a highly multiplexed PCR amplification using methods known in the art results in the generation of primer dimer products that are in excess of the desired amplification products and not suitable for sequencing. These can be reduced empirically by eliminating primers that form these products, or by performing in silico selection of primers. However, the larger the number of assays, the more difficult this problem becomes.

One solution is to split the 5000-plex reaction into several lower-plexed amplifications, e.g. one hundred 50-plex or fifty 100-plex reactions, or to use microfluidics or even to split the sample into individual PCR reactions. However, if the sample DNA is limited, such as in non-invasive prenatal diagnostics from pregnancy plasma, dividing the sample between multiple reactions should be avoided as this will result in bottlenecking.

Described herein are methods to first globally amplify the plasma DNA of a sample and then divide the sample up into multiple multiplexed target enrichment reactions with more moderate numbers of target sequences per reaction. In an embodiment, a method of the present disclosure can be used for preferentially enriching a DNA mixture at a plurality of loci, the method comprising one or more of the following steps: generating and amplifying a library from a mixture of DNA where the molecules in the library have adaptor sequences ligated on both ends of the DNA fragments, dividing the amplified library into multiple reactions, performing a first round of multiplex amplification of selected targets using one target specific "forward" primer per target and one or a plurality of adaptor specific universal "reverse" primers. In an embodiment, a method of the present disclosure further includes performing a second amplification using "reverse" target specific primers and one or a plurality of primers specific to a universal tag that was introduced as part of the target specific forward primers in the first round. In an embodiment, the method may involve a fully nested, hemi-nested, semi-nested, one sided fully nested, one sided hemi-nested, or one sided semi-nested PCR approach. In an embodiment, a method of the present disclosure is used for preferentially enriching a DNA mixture at a plurality of loci, the method comprising performing a multiplex preamplification of selected targets for a limited number of cycles, dividing the product into multiple aliquots and amplifying subpools of targets in individual reactions, and pooling products of parallel subpools reactions. Note that this approach could be used to perform targeted amplification in a manner that would result in low levels of allelic bias for 50-500 loci, for 500 to 5,000 loci, for 5,000 to 50,000 loci, or even for 50,000 to 500,000 loci. In an embodiment, the primers carry partial or full length sequencing compatible tags.

The workflow may entail (1) extracting plasma DNA, (2) preparing fragment library with universal adaptors on both ends of fragments, (3) amplifying the library using universal primers specific to the adaptors, (4) dividing the amplified sample "library" into multiple aliquots, (5) performing multiplex (e.g. about 100-plex, 1,000, or 10,000-plex with one target specific primer per target and a tag-specific primer) amplifications on aliquots, (6) pooling aliquots of one sample, (7) barcoding the sample, (8) mixing the samples and adjusting the concentration, (9) sequencing the sample. The workflow may comprise multiple sub-steps that contain one of the listed steps (e.g. step (2) of preparing the library step could entail three enzymatic steps (blunt ending, dA tailing and adaptor ligation) and three purification steps). Steps of the workflow may be combined, divided up or performed in different order (e.g. bar coding and pooling of samples).

It is important to note that the amplification of a library can be performed in such a way that it is biased to amplify short fragments more efficiently. In this manner it is possible to preferentially amplify shorter sequences, e.g. mononucleosomal DNA fragments as the cell free fetal DNA (of placental origin) found in the circulation of pregnant women. Note that PCR assays can have the tags, for example sequencing tags, (usually a truncated form of 15-25 bases). After multiplexing, PCR multiplexes of a sample are pooled and then the tags are completed (including bar coding) by a tag-specific PCR (could also be done by ligation). Also, the full sequencing tags can be added in the same reaction as the multiplexing. In the first cycles targets may be amplified with the target specific primers, subsequently the tag-specific primers take over to complete the SQ-adaptor sequence. The PCR primers may carry no tags. The sequencing tags may be appended to the amplification products by ligation.

In an embodiment, highly multiplex PCR followed by evaluation of amplified material by clonal sequencing may be used to detect transplant rejection status. Whereas traditional multiplex PCRs evaluate up to fifty loci simultaneously, the approach described herein may be used to enable simultaneous evaluation of more than 50 loci simultaneously, more than 100 loci simultaneously, more than 500 loci simultaneously, more than 1,000 loci simultaneously, more than 5,000 loci simultaneously, more than 10,000 loci simultaneously, more than 50,000 loci simultaneously, and more than 100,000 loci simultaneously. Experiments have shown that up to, including and more than 10,000 distinct loci can be evaluated simultaneously, in a single reaction, with sufficiently good efficiency and specificity to make non-invasive transplant staut calls with high accuracy. Assays may be combined in a single reaction with the entirety of a cfDNA sample isolated from transplant recipient plasma, a fraction thereof, or a further processed derivative of the cfDNA sample. The cfDNA or derivative may also be split into multiple parallel multiplex reactions. The optimum sample splitting and multiplex is determined by trading off various performance specifications. Due to the limited amount of material, splitting the sample into multiple fractions can introduce sampling noise, handling time, and increase the possibility of error. Conversely, higher multiplexing can result in greater amounts of spurious amplification and greater inequalities in amplification both of which can reduce test performance.

Two crucial related considerations in the application of the methods described herein are the limited amount of original plasma and the number of original molecules in that material from which allele frequency or other measurements are obtained. If the number of original molecules falls below a certain level, random sampling noise becomes significant, and can affect the accuracy of the test. Typically, data of sufficient quality for making non-invasive prenatal aneuploidy diagnoses can be obtained if measurements are made on a sample comprising the equivalent of 500-1000 original molecules per target locus. There are a number of ways of increasing the number of distinct measurements, for example increasing the sample volume. Each manipulation applied to the sample also potentially results in losses of material. It is essential to characterize losses incurred by various manipulations and avoid, or as necessary improve yield of certain manipulations to avoid losses that could degrade performance of the test.

In an embodiment, it is possible to mitigate potential losses in subsequent steps by amplifying all or a fraction of the original cfDNA sample. Various methods are available to amplify all of the genetic material in a sample, increasing the amount available for downstream procedures. In an embodiment, ligation mediated PCR (LM-PCR) DNA fragments are amplified by PCR after ligation of either one distinct adaptors, two distinct adapters, or many distinct adaptors. In an embodiment, multiple displacement amplification (MDA) phi-29 polymerase is used to amplify all DNA isothermally. In DOP-PCR and variations, random priming is used to amplify the original material DNA. Each method has certain characteristics such as uniformity of amplification across all represented regions of the genome, efficiency of capture and amplification of original DNA, and amplification performance as a function of the length of the fragment.

In an embodiment LM-PCR may be used with a single heteroduplexed adaptor having a 3-prime tyrosine. The heteroduplexed adaptor enables the use of a single adaptor molecule that may be converted to two distinct sequences on 5-prime and 3-prime ends of the original DNA fragment during the first round of PCR. In an embodiment, it is possible to fractionate the amplified library by size separations, or products such as AMPURE, TASS or other similar methods. Prior to ligation, sample DNA may be blunt ended, and then a single adenosine base is added to the 3-prime end. Prior to ligation the DNA may be cleaved using a restriction enzyme or some other cleavage method. During ligation the 3-prime adenosine of the sample fragments and the complementary 3-prime tyrosine overhang of adaptor can enhance ligation efficiency. The extension step of the PCR amplification may be limited from a time standpoint to reduce amplification from fragments longer than about 200 bp, about 300 bp, about 400 bp, about 500 bp or about 1,000 bp. Since longer DNA found in the transplant recipient plasma is nearly exclusively maternal, this may result in the enrichment of fetal DNA by 10-50% and improvement of test performance. A number of reactions were run using conditions as specified by commercially available kits; the resulted in successful ligation of fewer than 10% of sample DNA molecules. A series of optimizations of the reaction conditions for this improved ligation to approximately 70%.

Mini-PCR

Traditional PCR assay design results in significant losses of distinct donor-derive nucleic acid molecules, but losses can be greatly reduced by designing very short PCR assays, termed mini-PCR assays. cfDNA in recipient serum is highly fragmented and the fragment sizes are distributed in approximately a Gaussian fashion with a mean of 160 bp, a standard deviation of 15 bp, a minimum size of about 100 bp, and a maximum size of about 220 bp. The distribution of fragment start and end positions with respect to the targeted polymorphisms, while not necessarily random, vary widely among individual targets and among all targets collectively and the polymorphic site of one particular target locus may occupy any position from the start to the end among the various fragments originating from that locus. Note that the term mini-PCR may equally well refer to normal PCR with no additional restrictions or limitations.

During PCR, amplification will only occur from template DNA fragments comprising both forward and reverse primer sites. Because donor derived cfDNA fragments are short, the likelihood of both primer sites being present the likelihood of a fetal fragment of length L comprising both the forward and reverse primers sites is ratio of the length of the amplicon to the length of the fragment. Under ideal conditions, assays in which the amplicon is 45, 50, 55, 60, 65, or 70 bp will successfully amplify from 72%, 69%, 66%, 63%, 59%, or 56%, respectively, of available template fragment molecules. The amplicon length is the distance between the 5-prime ends of the forward and reverse priming sites. Amplicon length that is shorter than typically used by those known in the art may result in more efficient measurements of the desired polymorphic loci by only requiring short sequence reads. In an embodiment, a substantial fraction of the amplicons should be less than 100 bp, less than 90 bp, less than 80 bp, less than 70 bp, less than 65 bp, less than 60 bp, less than 55 bp, less than 50 bp, or less than 45 bp. In some embodiments, the amplicons are between 50 to 100 bp in length, or between 60 and 80 bp in length. In some embodiments, the amplicons are about 65 bp in length.

Note that in methods known in the prior art, short assays such as those described herein are usually avoided because they are not required and they impose considerable constraint on primer design by limiting primer length, annealing characteristics, and the distance between the forward and reverse primer.

Also note that there is the potential for biased amplification if the 3-prime end of the either primer is within roughly 1-6 bases of the polymorphic site. This single base difference at the site of initial polymerase binding can result in preferential amplification of one allele, which can alter observed allele frequencies and degrade performance. All of these constraints make it very challenging to identify primers that will amplify a particular locus successfully and furthermore, to design large sets of primers that are compatible in the same multiplex reaction. In an embodiment, the 3' end of the inner forward and reverse primers are designed to hybridize to a region of DNA upstream from the polymorphic site, and separated from the polymorphic site by a small number of bases. Ideally, the number of bases may be between 6 and 10 bases, but may equally well be between 4 and 15 bases, between three and 20 bases, between two and 30 bases, or between 1 and 60 bases, and achieve substantially the same end.

Multiplex PCR may involve a single round of PCR in which all targets are amplified or it may involve one round of PCR followed by one or more rounds of nested PCR or some variant of nested PCR. Nested PCR consists of a subsequent round or rounds of PCR amplification using one or more new primers that bind internally, by at least one base pair, to the primers used in a previous round. Nested PCR reduces the number of spurious amplification targets by amplifying, in subsequent reactions, only those amplification products from the previous one that have the correct internal sequence. Reducing spurious amplification targets improves the number of useful measurements that can be obtained, especially in sequencing. Nested PCR typically entails designing primers completely internal to the previous primer binding sites, necessarily increasing the minimum DNA segment size required for amplification. For samples such as transplant recipient plasma cfDNA, in which the DNA is highly fragmented, the larger assay size reduces the number of distinct cfDNA molecules from which a measurement can be obtained. In an embodiment, to offset this effect, one may use a partial nesting approach where one or both of the second round primers overlap the first binding sites extending internally some number of bases to achieve additional specificity while minimally increasing in the total assay size.

In an embodiment, a multiplex pool of PCR assays are designed to amplify potentially heterozygous SNP or other polymorphic or non-polymorphic loci on one or more chromosomes and these assays are used in a single reaction to amplify DNA. The number of PCR assays may be between 50 and 200 PCR assays, between 200 and 1,000 PCR assays, between 1,000 and 5,000 PCR assays, or between 5,000 and 20,000 PCR assays (50 to 200-plex, 200 to 1,000-plex, 1,000 to 5,000-plex, 5,000 to 20,000-plex, more than 20,000-plex respectively). In an embodiment, a multiplex pool of about 10,000 PCR assays (10,000-plex) are designed to amplify potentially heterozygous SNP loci on chromosomes X, Y, 13, 18, and 21 and 1 or 2 and these assays are used in a single reaction to amplify cfDNA obtained from a material plasma sample, chorion villus samples, amniocentesis samples, single or a small number of cells, other bodily fluids or tissues, cancers, or other genetic matter. The SNP frequencies of each locus may be determined by clonal or some other method of sequencing of the amplicons. Statistical analysis of the allele frequency distributions or ratios of all assays may be used to determine if the sample contains a trisomy of one or more of the chromosomes included in the test. In another embodiment the original cfDNA samples is split into two samples and parallel 5,000-plex assays are performed. In another embodiment the original cfDNA samples is split into n samples and parallel (~10,000/n)-plex assays are performed where n is between 2 and 12, or between 12 and 24, or between 24 and 48, or between 48 and 96. Data is collected and analyzed in a similar manner to that already described. Note that this method is equally well applicable to detecting translocations, deletions, duplications, and other chromosomal abnormalities.

In an embodiment, tails with no homology to the target genome may also be added to the 3-prime or 5-prime end of any of the primers. These tails facilitate subsequent manipulations, procedures, or measurements. In an embodiment, the tail sequence can be the same for the forward and reverse target specific primers. In an embodiment, different tails may used for the forward and reverse target specific primers. In an embodiment, a plurality of different tails may be used for different loci or sets of loci. Certain tails may be shared among all loci or among subsets of loci. For example, using forward and reverse tails corresponding to forward and reverse sequences required by any of the current sequencing platforms can enable direct sequencing following amplification. In an embodiment, the tails can be used as common priming sites among all amplified targets that can be used to add other useful sequences. In some embodiments, the inner primers may contain a region that is designed to hybridize either upstream or downstream of the targeted polymorphic locus. In some embodiments, the primers may contain a molecular barcode. In some embodiments, the primer may contain a universal priming sequence designed to allow PCR amplification.

In an embodiment, a 10,000-plex PCR assay pool is created such that forward and reverse primers have tails corresponding to the required forward and reverse sequences required by a high throughput sequencing instrument such as the HISEQ, GAIIX, or MYSEQ available from ILLUMINA. In addition, included 5-prime to the sequencing tails is an additional sequence that can be used as a priming site in a subsequent PCR to add nucleotide barcode sequences to the amplicons, enabling multiplex sequencing of multiple samples in a single lane of the high throughput sequencing instrument.

In an embodiment, a 10,000-plex PCR assay pool is created such that reverse primers have tails corresponding to the required reverse sequences required by a high throughput sequencing instrument. After amplification with the first 10,000-plex assay, a subsequent PCR amplification may be performed using a another 10,000-plex pool having partly nested forward primers (e.g. 6-bases nested) for all targets and a reverse primer corresponding to the reverse sequencing tail included in the first round. This subsequent round of partly nested amplification with just one target specific primer and a universal primer limits the required size of the assay, reducing sampling noise, but greatly reduces the number of spurious amplicons. The sequencing tags can be added to appended ligation adaptors and/or as part of PCR probes, such that the tag is part of the final amplicon.

The mini-PCR method described in this disclosure enables highly multiplexed amplification and analysis of hundreds to thousands or even millions of loci in a single reaction, from a single sample. At the same, the detection of the amplified DNA can be multiplexed; tens to hundreds of samples can be multiplexed in one sequencing lane by using barcoding PCR. This multiplexed detection has been successfully tested up to 49-plex, and a much higher degree of multiplexing is possible. In effect, this allows hundreds of samples to be genotyped at thousands of SNPs in a single sequencing run. For these samples, the method allows determination of genotype and heterozygosity rate. This method may be used for any amount of DNA or RNA, and the targeted regions may be SNPs, other polymorphic regions, non-polymorphic regions, and combinations thereof.

In some embodiments, ligation mediated universal-PCR amplification of fragmented DNA may be used. The ligation mediated universal-PCR amplification can be used to amplify plasma DNA, which can then be divided into multiple parallel reactions. It may also be used to preferentially amplify short fragments, thereby enriching fetal fraction. In some embodiments the addition of tags to the fragments by ligation can enable detection of shorter fragments, use of shorter target sequence specific portions of the primers and/or annealing at higher temperatures which reduces unspecific reactions.

The methods described herein may be used for a number of purposes where there is a target set of DNA that is mixed with an amount of contaminating DNA. In some embodiments, the target and contaminating DNA may be from the same individual, but where the target and contaminating DNA are different by one or more mutations, for example in the case of cancer. (see e.g. H. Mamon et al. *Preferential Amplification of Apoptotic DNA from Plasma: Potential for Enhancing Detection of Minor DNA Alterations in Circulating DNA*. Clinical Chemistry 54:9 (2008). In some embodiments, the DNA may be found in cell culture (apoptotic) supernatant. In some embodiments, it is possible to induce apoptosis in biological samples (e.g. blood) for subsequent library preparation, amplification and/or sequencing. A number of enabling workflows and protocols to achieve this end are presented elsewhere in this disclosure.

In some embodiments, the target DNA may originate from single cells, from samples of DNA consisting of less than one copy of the target genome, from low amounts of DNA, from DNA from mixed origin, from other body fluids, from cell cultures, from culture supernatants, from forensic samples of DNA, from ancient samples of DNA (e.g. insects trapped in amber), from other samples of DNA, and combinations thereof.

In some embodiments, a short amplicon size may be used. Short amplicon sizes are especially suited for fragmented DNA (see e.g. A. Sikora, et sl. Detection of increased amounts of cell-free fetal DNA with short PCR amplicons. Clin Chem. 2010 January; 56(1):136-8.)

The use of short amplicon sizes may result in some significant benefits. Short amplicon sizes may result in optimized amplification efficiency. Short amplicon sizes typically produce shorter products, therefore there is less chance for nonspecific priming. Shorter products can be clustered more densely on sequencing flow cell, as the clusters will be smaller. In an embodiment, a substantial fraction of the amplicons should be less than 100 bp, less than 90 bp, less than 80 bp, less than 70 bp, less than 65 bp, less than 60 bp, less than 55 bp, less than 50 bp, or less than 45 bp. In some embodiments, the amplicons are between 50 to 100 bp in length, or between 60 and 80 bp in length. In some embodiments, the amplicons are about 65 bp in length.

Note that the methods described herein may work equally well for longer PCR amplicons. Amplicon length may be increased if necessary, for example, when sequencing larger sequence stretches. Experiments with 146-plex targeted amplification with assays of 100 bp to 200 bp length as first step in a nested-PCR protocol were run on single cells and on genomic DNA with positive results.

In some embodiments, the methods described herein may be used to amplify and/or detect SNPs, copy number, nucleotide methylation, mRNA levels, other types of RNA expression levels, other genetic and/or epigenetic features. The mini-PCR methods described herein may be used along with next-generation sequencing; it may be used with other downstream methods such as microarrays, counting by digital PCR, real-time PCR, Mass-spectrometry analysis etc.

In some embodiment, the mini-PCR amplification methods described herein may be used as part of a method for accurate quantification of minority populations. It may be used for absolute quantification using spike calibrators. It may be used for mutation/minor allele quantification through very deep sequencing, and may be run in a highly multiplexed fashion. It may be used for standard paternity and identity testing of relatives or ancestors, in human, animals, plants or other creatures. It may be used for forensic testing. It may be used for rapid genotyping and copy number analysis (CN), on any kind of material, e.g. amniotic fluid and CVS, sperm, product of conception (POC). It may be used for single cell analysis, such as genotyping on samples biopsied from embryos. It may be used for rapid embryo analysis (within less than one, one, or two days of biopsy) by targeted sequencing using min-PCR.

In some embodiments, it may be used for tumor analysis: tumor biopsies are often a mixture of health and tumor cells. Targeted PCR allows deep sequencing of SNPs and loci with close to no background sequences. It may be used for copy number and loss of heterozygosity analysis on tumor DNA. Said tumor DNA may be present in many different body fluids or tissues of tumor patients. It may be used for detection of tumor recurrence, and/or tumor screening. It may be used for quality control testing of seeds. It may be used for breeding, or fishing purposes. Note that any of these methods could equally well be used targeting non-polymorphic loci for the purpose of ploidy calling.

Some literature describing some of the fundamental methods that underlie the methods disclosed herein include: (1) Wang H Y, Luo M, Tereshchenko I V, Frikker D M, Cui X, Li J Y, Hu G, Chu Y, Azaro M A, Lin Y, Shen L, Yang Q, Kambouris M E, Gao R, Shih W, Li H. Genome Res. 2005 February; 15(2):276-83. Department of Molecular Genetics, Microbiology and Immunology/The Cancer Institute of New Jersey, Robert Wood Johnson Medical School, New Brunswick, N.J. 08903, USA. (2) High-throughput genotyping of single nucleotide polymorphisms with high sensitivity. Li H, Wang H Y, Cui X, Luo M, Hu G, Greenawalt D M, Tereshchenko I V, Li J Y, Chu Y, Gao R. Methods Mol Biol. 2007; 396-PubMed PMID: 18025699. (3) A method comprising multiplexing of an average of 9 assays for sequencing is described in: Nested Patch PCR enables highly multiplexed mutation discovery in candidate genes. Varley K E, Mitra R D. Genome Res. 2008 November; 18(11): 1844-50. Epub 2008 Oct. 10. Note that the methods disclosed herein allow multiplexing of orders of magnitude more than in the above references.

Primer Design

Highly multiplexed PCR can often result in the production of a very high proportion of product DNA that results from unproductive side reactions such as primer dimer formation. In an embodiment, the particular primers that are most likely to cause unproductive side reactions may be removed from the primer library to give a primer library that will result in a greater proportion of amplified DNA that maps to the genome. The step of removing problematic primers, that is, those primers that are particularly likely to firm dimers has unexpectedly enabled extremely high PCR multiplexing levels for subsequent analysis by sequencing. In systems such as sequencing, where performance significantly degrades by primer dimers and/or other mischief products, greater than 10, greater than 50, and greater than 100 times higher multiplexing than other described multiplexing has been achieved. Note this is opposed to probe based detection methods, e.g. microarrays, TAQMAN, PCR etc. where an excess of primer dimers will not affect the outcome appreciably. Also note that the general belief in the art is that multiplexing PCR for sequencing is limited to about 100 assays in the same well. E.g. Fluidigm and Rain Dance offer platforms to perform 48 or 1000s of PCR assays in parallel reactions for one sample.

There are a number of ways to choose primers for a library where the amount of non-mapping primer-dimer or other primer mischief products are minimized. Empirical data indicate that a small number of 'bad' primers are responsible for a large amount of non-mapping primer dimer side reactions. Removing these 'bad' primers can increase the percent of sequence reads that map to targeted loci. One way to identify the 'bad' primers is to look at the sequencing data of DNA that was amplified by targeted amplification; those primer dimers that are seen with greatest frequency can be removed to give a primer library that is significantly less likely to result in side product DNA that does not map to the genome. There are also publicly available programs that can calculate the binding energy of various primer combinations, and removing those with the highest binding energy will also give a primer library that is significantly less likely to result in side product DNA that does not map to the genome.

Multiplexing large numbers of primers imposes considerable constraint on the assays that can be included. Assays that unintentionally interact result in spurious amplification products. The size constraints of miniPCR may result in further constraints. In an embodiment, it is possible to begin with a very large number of potential SNP targets (between about 500 to greater than 1 million) and attempt to design primers to amplify each SNP. Where primers can be designed it is possible to attempt to identify primer pairs likely to form spurious products by evaluating the likelihood of spurious primer duplex formation between all possible pairs of primers using published thermodynamic parameters for DNA duplex formation. Primer interactions may be ranked by a scoring function related to the interaction and primers with the worst interaction scores are eliminated until the number of primers desired is met. In cases where SNPs likely to be heterozygous are most useful, it is possible to also rank the list of assays and select the most heterozygous compatible assays. Experiments have validated that primers with high interaction scores are most likely to form primer dimers. At high multiplexing it is not possible to eliminate all spurious interactions, but it is essential to remove the primers or pairs of primers with the highest interaction scores in silico as they can dominate an entire reaction, greatly limiting amplification from intended targets. We have performed this procedure to create multiplex primer sets of up 10,000 primers. The improvement due to this procedure is substantial, enabling amplification of more than 80%, more than 90%, more than 95%, more than 98%, and even more than 99% on target products as determined by sequencing of all PCR products, as compared to 10% from a reaction in which the worst primers were not removed. When combined with a partial semi-nested approach as previously described, more than 90%, and even more than 95% of amplicons may map to the targeted sequences.

Note that there are other methods for determining which PCR probes are likely to form dimers. In an embodiment, analysis of a pool of DNA that has been amplified using a non-optimized set of primers may be sufficient to determine problematic primers. For example, analysis may be done using sequencing, and those dimers which are present in the greatest number are determined to be those most likely to form dimers, and may be removed.

This method has a number of potential application, for example to SNP genotyping, heterozygosity rate determination, copy number measurement, and other targeted sequencing applications. In an embodiment, the method of primer design may be used in combination with the miniPCR method described elsewhere in this document. In some embodiments, the primer design method may be used as part of a massive multiplexed PCR method.

The use of tags on the primers may reduce amplification and sequencing of primer dimer products. Tag-primers can be used to shorten necessary target-specific sequence to below 20, below 15, below 12, and even below 10 base pairs. This can be serendipitous with standard primer design when the target sequence is fragmented within the primer binding site or, or it can be designed into the primer design. Advantages of this method include: it increases the number of assays that can be designed for a certain maximal amplicon length, and it shortens the "non-informative" sequencing of primer sequence. It may also be used in combination with internal tagging (see elsewhere in this document).

In an embodiment, the relative amount of nonproductive products in the multiplexed targeted PCR amplification can be reduced by raising the annealing temperature. In cases where one is amplifying libraries with the same tag as the target specific primers, the annealing temperature can be increased in comparison to the genomic DNA as the tags will contribute to the primer binding. In some embodiments we are using considerably lower primer concentrations than previously reported along with using longer annealing times than reported elsewhere. In some embodiments the annealing times may be longer than 10 minutes, longer than 20 minutes, longer than 30 minutes, longer than 60 minutes, longer than 120 minutes, longer than 240 minutes, longer than 480 minutes, and even longer than 960 minutes. In an embodiment, longer annealing times are used than in previous reports, allowing lower primer concentrations. In some embodiments, the primer concentrations are as low as 50 nM, 20 nM, 10 nM, 5 nM, 1 nM, and lower than 1 uM. This surprisingly results in robust performance for highly multiplexed reactions, for example 1,000-plex reactions, 2,000-plex reactions, 5,000-plex reactions, 10,000-plex reactions, 20,000-plex reactions, 50,000-plex reactions, and even 100,000-plex reactions. In an embodiment, the amplification uses one, two, three, four or five cycles run with long annealing times, followed by PCR cycles with more usual annealing times with tagged primers.

To select target locations, one may start with a pool of candidate primer pair designs and create a thermodynamic model of potentially adverse interactions between primer pairs, and then use the model to eliminate designs that are incompatible with other the designs in the pool.

Targeted PCR Variants—Nesting

There are many workflows that are possible when conducting PCR; some workflows typical to the methods disclosed herein are described. The steps outlined herein are not meant to exclude other possible steps nor does it imply that any of the steps described herein are required for the method to work properly. A large number of parameter variations or other modifications are known in the literature, and may be made without affecting the essence of the invention. One particular generalized workflow is given below followed by a number of possible variants. The variants typically refer to possible secondary PCR reactions, for example different types of nesting that may be done (step 3). It is important to note that variants may be done at different times, or in different orders than explicitly described herein.

1. The DNA in the sample may have ligation adapters, often referred to as library tags or ligation adaptor tags (LTs), appended, where the ligation adapters contain a universal priming sequence, followed by a universal amplification. In an embodiment, this may be done using a standard protocol designed to create sequencing libraries after fragmentation. In an embodiment, the DNA sample can be blunt ended, and then an A can be added at the 3' end. A Y-adaptor with a T-overhang can be added and ligated. In some embodiments, other sticky ends can be used other than an A or T overhang. In some embodiments, other adaptors can be added, for example looped ligation adaptors. In some embodiments, the adaptors may have tag designed for PCR amplification.

2. Specific Target Amplification (STA): Pre-amplification of hundreds to thousands to tens of thousands and even hundreds of thousands of targets may be multiplexed in one reaction. STA is typically run from 10 to 30 cycles, though it may be run from 5 to 40 cycles, from 2 to 50 cycles, and even from 1 to 100 cycles. Primers may be tailed, for example for a simpler workflow or to avoid sequencing of a large proportion of dimers. Note that typically, dimers of both primers carrying the same tag will not be amplified or sequenced efficiently. In some embodiments, between 1 and 10 cycles of PCR may be carried out; in some embodiments between 10 and 20 cycles of PCR may be carried out; in some embodiments between 20 and 30 cycles of PCR may be carried out; in some embodiments between 30 and 40 cycles of PCR may be carried out; in some embodiments more than 40 cycles of PCR may be carried out. The amplification may be a linear amplification. The number of PCR cycles may be optimized to result in an optimal depth of read (DOR) profile. Different DOR profiles may be desirable for different purposes. In some embodiments, a more even distribution of reads between all assays is desirable; if the DOR is too small for some assays, the stochastic noise can be too high for the data to be too useful, while if the depth of read is too high, the marginal usefulness of each additional read is relatively small.

Primer tails may improve the detection of fragmented DNA from universally tagged libraries. If the library tag and the primer-tails contain a homologous sequence, hybridization can be improved (for example, melting temperature ($T_M$) is lowered) and primers can be extended if only a portion of the primer target sequence is in the sample DNA fragment. In some embodiments, 13 or more target specific base pairs may be used. In some embodiments, 10 to 12 target specific base pairs may be used. In some embodiments, 8 to 9 target specific base pairs may be used. In some embodiments, 6 to 7 target specific base pairs may be used. In some embodiments, STA may be performed on pre-amplified DNA, e.g. MDA, RCA, other whole genome amplifications, or adaptor-mediated universal PCR. In some embodiments, STA may be performed on samples that are enriched or depleted of certain sequences and populations, e.g. by size selection, target capture, directed degradation.

3. In some embodiments, it is possible to perform secondary multiplex PCRs or primer extension reactions to increase specificity and reduce undesirable products. For example, full nesting, semi-nesting, hemi-nesting, and/or subdividing into parallel reactions of smaller assay pools are all techniques that may be used to increase specificity. Experiments have shown that splitting a sample into three 400-plex reactions resulted in product DNA with greater specificity than one 1,200-plex reaction with exactly the same primers. Similarly, experiments have shown that splitting a sample into four 2,400-plex reactions resulted in product DNA with greater specificity than one 9,600-plex reaction with exactly the same primers. In an embodiment, it is possible to use target-specific and tag specific primers of the same and opposing directionality.

4. In some embodiments, it is possible to amplify a DNA sample (dilution, purified or otherwise) produced by an STA reaction using tag-specific primers and "universal amplification", i.e. to amplify many or all pre-amplified and tagged targets. Primers may contain additional functional sequences, e.g. barcodes, or a full adaptor sequence necessary for sequencing on a high throughput sequencing platform.

These methods may be used for analysis of any sample of DNA, and are especially useful when the sample of DNA is particularly small, or when it is a sample of DNA where the DNA originates from more than one individual, such as in the case of transplant recipient plasma. These methods may be used on DNA samples such as a single or small number of cells, genomic DNA, plasma DNA, amplified plasma libraries, amplified apoptotic supernatant libraries, or other samples of mixed DNA. In an embodiment, these methods may be used in the case where cells of different genetic constitution may be present in a single individual, such as with cancer or transplants.

Protocol Variants (Variants and/or Additions to the Workflow Above)

Direct multiplexed mini-PCR: In some embodiments, specific target amplification (STA) of a plurality of target sequences with tagged primers is performed. In some embodiments, STA may be done on more than 100, more than 200, more than 500, more than 1,000, more than 2,000, more than 5,000, more than 10,000, more than 20,000, more than 50,000, more than 100,000 or more than 200,000 targets. In a subsequent reaction, tag-specific primers amplify all target sequences and lengthen the tags to include all necessary sequences for sequencing, including sample indexes. In an embodiment, primers may not be tagged or only certain primers may be tagged. Sequencing adaptors may be added by conventional adaptor ligation. In an embodiment, the initial primers may carry the tags.

In an embodiment, primers are designed so that the length of DNA amplified is unexpectedly short. Prior art demonstrates that ordinary people skilled in the art typically design 100+ bp amplicons. In an embodiment, the amplicons may be designed to be less than 80 bp. In an embodiment, the amplicons may be designed to be less than 70 bp. In an embodiment, the amplicons may be designed to be less than 60 bp. In an embodiment, the amplicons may be designed to be less than 50 bp. In an embodiment, the amplicons may be designed to be less than 45 bp. In an embodiment, the amplicons may be designed to be less than 40 bp. In an embodiment, the amplicons may be designed to be less than 35 bp. In an embodiment, the amplicons may be designed to be between 40 and 65 bp.

Sequential PCR: After STA1 multiple aliquots of the product may be amplified in parallel with pools of reduced complexity with the same primers. The first amplification can give enough material to split. This method is especially good for small samples, for example those that are about 6-100 pg, about 100 pg to 1 ng, about 1 ng to 10 ng, or about 10 ng to 100 ng. The protocol was performed with 1200-plex into three 400-plexes. Mapping of sequencing reads increased from around 60 to 70% in the 1200-plex alone to over 95%.

Semi-nested mini-PCR: In some embodiments, after STA 1 a second STA is performed comprising a multiplex set of internal nested Forward primers and one (or few) tag-specific Reverse primers. With this workflow usually greater than 95% of sequences map to the intended targets. The nested primer may overlap with the outer Forward primer sequence but introduces additional 3'-end bases. In some embodiments it is possible to use between one and 20 extra 3' bases. Experiments have shown that using 9 or more extra 3' bases in a 1200-plex designs works well.

Fully nested mini-PCR: After STA step 1, it is possible to perform a second multiplex PCR (or parallel m.p. PCRs of reduced complexity) with two nested primers carrying tags (A, a, B, b). In some embodiments, it is possible to use two full sets of primers. Experiments using a fully nested mini-PCR protocol were used to perform 146-plex amplification on single and three cells without the step of appending universal ligation adaptors and amplifying.

Hemi-nested mini-PCR: It is possible to use target DNA that has and adaptors at the fragment ends. STA is performed comprising a multiplex set of Forward primers (B) and one (or few) tag-specific Reverse primers (A). A second STA can be performed using a universal tag-specific Forward primer and target specific Reverse primer. In this workflow, target specific Forward and Reverse primers are used in separate reactions, thereby reducing the complexity of the reaction and preventing dimer formation of forward and reverse primers. Note that in this example, primers A and B may be considered to be first primers, and primers 'a' and 'b' may be considered to be inner primers. This method is a big improvement on direct PCR as it is as good as direct PCR, but it avoids primer dimers. After first round of hemi nested protocol one typically sees ~99% non-targeted DNA, however, after second round there is typically a big improvement.

Triply hemi-nested mini-PCR: It is possible to use target DNA that has and adaptor at the fragment ends. STA is performed comprising a multiplex set of Forward primers (B) and one (or few) tag-specific Reverse primers (A) and (a). A second STA can be performed using a universal tag-specific Forward primer and target specific Reverse primer. Note that in this example, primers 'a' and B may be considered to be inner primers, and A may be considered to be a first primer. Optionally, both A and B may be considered to be first primers, and 'a' may be considered to be an inner primer. The designation of reverse and forward primers may be switched. In this workflow, target specific Forward and Reverse primers are used in separate reactions, thereby reducing the complexity of the reaction and preventing dimer formation of forward and reverse primers. This method is a big improvement on direct PCR as it is as good as direct PCR, but it avoids primer dimers. After first round of hemi nested protocol one typically sees ~99% non-targeted DNA, however, after second round there is typically a big improvement.

One-sided nested mini-PCR: It is possible to use target DNA that has an adaptor at the fragment ends. STA may also be performed with a multiplex set of nested Forward primers and using the ligation adapter tag as the Reverse primer. A second STA may then be performed using a set of nested Forward primers and a universal Reverse primer. This method can detect shorter target sequences than standard PCR by using overlapping primers in the first and second STAs. The method is typically performed off a sample of DNA that has already undergone STA step 1 above—appending of universal tags and amplification; the two nested primers are only on one side, other side uses the library tag. The method was performed on libraries of apoptotic supernatants and pregnancy plasma. With this workflow around 60% of sequences mapped to the intended targets. Note that reads that contained the reverse adaptor sequence were not mapped, so this number is expected to be higher if those reads that contain the reverse adaptor sequence are mapped One-sided mini-PCR: It is possible to use target DNA that has an adaptor at the fragment ends. STA may be performed with a multiplex set of Forward primers and one (or few)

tag-specific Reverse primer. This method can detect shorter target sequences than standard PCR. However it may be relatively unspecific, as only one target specific primer is used. This protocol is effectively half of the one sided nested mini PCR Reverse semi-nested mini-PCR: It is possible to use target DNA that has an adaptor at the fragment ends. STA may be performed with a multiplex set of Forward primers and one (or few) tag-specific Reverse primer. This method can detect shorter target sequences than standard PCR.

There also may be more variants that are simply iterations or combinations of the above methods such as doubly nested PCR, where three sets of primers are used. Another variant is one-and-a-half sided nested mini-PCR, where STA may also be performed with a multiplex set of nested Forward primers and one (or few) tag-specific Reverse primer.

Note that in all of these variants, the identity of the Forward primer and the Reverse primer may be interchanged. Note that in some embodiments, the nested variant can equally well be run without the initial library preparation that comprises appending the adapter tags, and a universal amplification step. Note that in some embodiments, additional rounds of PCR may be included, with additional Forward and/or Reverse primers and amplification steps; these additional steps may be particularly useful if it is desirable to further increase the percent of DNA molecules that correspond to the targeted loci.

Looped Ligation Adaptors

When adding universal tagged adaptors for example for the purpose of making a library for sequencing, there are a number of ways to ligate adaptors. One way is to blunt end the sample DNA, perform A-tailing, and ligate with adaptors that have a T-overhang. There are a number of other ways to ligate adaptors. There are also a number of adaptors that can be ligated. For example, a Y-adaptor can be used where the adaptor consists of two strands of DNA where one strand has a double strand region, and a region specified by a forward primer region, and where the other strand specified by a double strand region that is complementary to the double strand region on the first strand, and a region with a reverse primer. The double stranded region, when annealed, may contain a T-overhang for the purpose of ligating to double stranded DNA with an A overhang.

In an embodiment, the adaptor can be a loop of DNA where the terminal regions are complementary, and where the loop region contains a forward primer tagged region (LFT), a reverse primer tagged region (LRT), and a cleavage site between the two. LFT refers to the ligation adaptor Forward tag, and the LRT refers to the ligation adaptor Reverse tag. The complementary region may end on a T overhang, or other feature that may be used for ligation to the target DNA. The cleavage site may be a series of uracils for cleavage by UNG, or a sequence that may be recognized and cleaved by a restriction enzyme or other method of cleavage or just a basic amplification. These adaptors can be uses for any library preparation, for example, for sequencing. These adaptors can be used in combination with any of the other methods described herein, for example the mini-PCR amplification methods.

Internally Tagged Primers

When using sequencing to determine the allele present at a given polymorphic locus, the sequence read typically begins upstream of the primer binding site (a), and then to the polymorphic site (X). In order to avoid nonspecific hybridization, the primer binding site (region of target DNA complementary to 'a') is typically 18 to 30 bp in length. Sequence tag 'b' is typically about 20 bp; in theory these can be any length longer than about 15 bp, though many people use the primer sequences that are sold by the sequencing platform company. The distance '4:1' between 'a' and 'X' may be at least 2 bp so as to avoid allele bias. When performing multiplexed PCR amplification using the methods disclosed herein or other methods, where careful primer design is necessary to avoid excessive primer interaction, the window of allowable distance 'd' between 'a' and 'X' may vary quite a bit: from 2 bp to 10 bp, from 2 bp to 20 bp, from 2 bp to 30 bp, or even from 2 bp to more than 30 bp. Therefore, when using certain primer configurations, sequence reads must be a minimum length to obtain reads long enough to measure the polymorphic locus, and depending on the lengths of 'a' and 'd' the sequence reads may need to be up to 60 or 75 bp. Usually, the longer the sequence reads, the higher the cost and time of sequencing a given number of reads, therefore, minimizing the necessary read length can save both time and money. In addition, since, on average, bases read earlier on the read are read more accurately than those read later on the read, decreasing the necessary sequence read length can also increase the accuracy of the measurements of the polymorphic region.

In an embodiment, termed internally tagged primers, the primer binding site (a) is split in to a plurality of segments (a', a", a''' . . . ), and the sequence tag (b) is on a segment of DNA that is in the middle of two of the primer binding sites. This configuration allows the sequencer to make shorter sequence reads. In an embodiment, a'+a" should be at least about 18 bp, and can be as long as 30, 40, 50, 60, 80, 100 or more than 100 bp. In an embodiment, a" should be at least about 6 bp, and in an embodiment is between about 8 and 16 bp. All other factors being equal, using the internally tagged primers can cut the length of the sequence reads needed by at least 6 bp, as much as 8 bp, 10 bp, 12 bp, 15 bp, and even by as many as 20 or 30 bp. This can result in a significant money, time and accuracy advantage.

Primers with Ligation Adaptor Binding Region

One issue with fragmented DNA is that since it is short in length, the chance that a polymorphism is close to the end of a DNA strand is higher than for a long strand. Since PCR capture of a polymorphism requires a primer binding site of suitable length on both sides of the polymorphism, a significant number of strands of DNA with the targeted polymorphism will be missed due to insufficient overlap between the primer and the targeted binding site. In cases where the binding region is shorter than the 18 bp typically required for hybridization, the region (cr) on the primer than is complementary to the library tag is able to increase the binding energy to a point where the PCR can proceed. Note that any specificity that is lost due to a shorter binding region can be made up for by other PCR primers with suitably long target binding regions. Note that this embodiment can be used in combination with direct PCR, or any of the other methods described herein, such as nested PCR, semi nested PCR, hemi nested PCR, one sided nested or semi or hemi nested PCR, or other PCR protocols.

When using the sequencing data to determine ploidy in combination with an analytical method that involves comparing the observed allele data to the expected allele distributions for various hypotheses, each additional read from alleles with a low depth of read will yield more information than a read from an allele with a high depth of read. Therefore, ideally, one would wish to see uniform depth of read (DOR) where each locus will have a similar number of representative sequence reads. Therefore, it is desirable to minimize the DOR variance. In an embodiment, it is possible to decrease the coefficient of variance of the DOR (this may be defined as the standard deviation of the DOR/the average DOR) by increasing the annealing times. In some embodiments the annealing temperatures may be longer than 2 minutes, longer than 4 minutes, longer than ten minutes, longer than 30 minutes, and longer than one hour, or even longer. Since annealing is an equilibrium process, there is no limit to the improvement of DOR variance with increasing annealing times. In an embodiment, increasing the primer concentration may decrease the DOR variance.

Diagnostic Box

In an embodiment, the present disclosure comprises a diagnostic box that is capable of partly or completely carrying out any of the methods described in this disclosure. In an embodiment, the diagnostic box may be located at a physician's office, a hospital laboratory, or any suitable location reasonably proximal to the point of patient care. The box may be able to run the entire method in a wholly automated fashion, or the box may require one or a number of steps to be completed manually by a technician. In an embodiment, the box may be able to analyze at least the genotypic data measured on the transplant recipient plasma. In an embodiment, the box may be linked to means to transmit the genotypic data measured on the diagnostic box to an external computation facility which may then analyze the genotypic data, and possibly also generate a report. The diagnostic box may include a robotic unit that is capable of transferring aqueous or liquid samples from one container to another. It may comprise a number of reagents, both solid and liquid. It may comprise a high throughput sequencer. It may comprise a computer.

Primer Kit

In some embodiments, a kit may be formulated that comprises a plurality of primers designed to achieve the methods described in this disclosure. The primers may be outer forward and reverse primers, inner forward and reverse primers as disclosed herein, they could be primers that have been designed to have low binding affinity to other primers in the kit as disclosed in the section on primer design, they could be hybrid capture probes or pre-circularized probes as described in the relevant sections, or some combination thereof. In an embodiment, a kit may be formulated for determining the transplant status of a transplant recipient and designed to be used with the methods disclosed herein, the kit comprising a plurality of inner forward primers and optionally the plurality of inner reverse primers, and optionally outer forward primers and outer reverse primers, where each of the primers is designed to hybridize to the region of DNA immediately upstream and/or downstream from one of the polymorphic sites on the target chromosome, and optionally additional chromosomes. In an embodiment, the primer kit may be used in combination with the diagnostic box described elsewhere in this document.

Compositions of DNA

When performing an informatics analysis on sequencing data measured on a mixture of donor and transplant recipient DNA to determine information pertaining to the transplant, for example the ploidy state of the transplant, it may be advantageous to measure the allele distributions at a set of alleles. Unfortunately, in many cases, such as when attempting to determine the state of a transplant from the DNA mixture found in the plasma of a transplant recipient blood sample, the amount of DNA available is not sufficient to directly measure the allele distributions with good fidelity in the mixture. In these cases, amplification of the DNA mixture will provide sufficient numbers of DNA molecules that the desired allele distributions may be measured with good fidelity. However, current methods of amplification typically used in the amplification of DNA for sequencing are often very biased, meaning that they do not amplify both alleles at a polymorphic locus by the same amount. A biased amplification can result in allele distributions that are quite different from the allele distributions in the original mixture. For most purposes, highly accurate measurements of the relative amounts of alleles present at polymorphic loci are not needed. In contrast, in an embodiment of the present disclosure, amplification or enrichment methods that specifically enrich polymorphic alleles and preserve allelic ratios is advantageous.

A number of methods are described herein that may be used to preferentially enrich a sample of DNA at a plurality of loci in a way that minimizes allelic bias. Some examples are using circularizing probes to target a plurality of loci where the 3' ends and 5' ends of the pre-circularized probe are designed to hybridize to bases that are one or a few positions away from the polymorphic sites of the targeted allele. Another is to use PCR probes where the 3' end PCR probe is designed to hybridize to bases that are one or a few positions away from the polymorphic sites of the targeted allele. Another is to use a split and pool approach to create mixtures of DNA where the preferentially enriched loci are enriched with low allelic bias without the drawbacks of direct multiplexing. Another is to use a hybrid capture approach where the capture probes are designed such that the region of the capture probe that is designed to hybridize to the DNA flanking the polymorphic site of the target is separated from the polymorphic site by one or a small number of bases.

In the case where measured allele distributions at a set of polymorphic loci are used to determine the transplant state of a transplant recipient, it is desirable to preserve the relative amounts of alleles in a sample of DNA as it is prepared for genetic measurements. This preparation may involve WGA amplification, targeted amplification, selective enrichment techniques, hybrid capture techniques, circularizing probes or other methods meant to amplify the amount of DNA and/or selectively enhance the presence of molecules of DNA that correspond to certain alleles.

In some embodiments of the present disclosure, there is a set of DNA probes designed to target loci where the loci have maximal minor allele frequencies. In some embodiments of the present disclosure, there is a set of probes that are designed to target where the loci have the maximum likelihood of the transplant having a highly informative SNP at those loci. In some embodiments of the present disclosure, there is a set of probes that are designed to target loci where the probes are optimized for a given population subgroup. In some embodiments of the present disclosure, there is a set of probes that are designed to target loci where the probes are optimized for a given mix of population subgroups. In some embodiments of the present disclosure, there is a set of probes that are designed to target loci where the probes are optimized for a given pair of parents which are from different population subgroups that have different minor allele frequency profiles. In some embodiments of the present disclosure, there is a circularized strand of DNA that comprises at least one base pair that annealed to a piece of DNA that is of transplant origin. In some embodiments of the present disclosure, there is a circularized strand of DNA that circularized while at least some of the nucleotides were annealed to DNA that was of transplant origin. In some embodiments of the present disclosure, there is a set of probes wherein some of the probes target single tandem repeats, and some of the probes target single nucleotide polymorphisms. In some embodiments, the loci are selected for the purpose of non-invasive diagnosis of transplant status. In some embodiments, the loci are targeted using a method that could include circularizing probes, MIPs, capture by hybridization probes, probes on a SNP array, or combinations thereof. In some embodiments, the probes are used as circularizing probes, MIPs, capture by hybridization probes, probes on a SNP array, or combinations thereof. In some embodiments, the loci are sequenced for the purpose of determination of transplant status.

In the case where the relative informativeness of a sequence is greater when combined with relevant genotypic contexts, it follows that maximizing the number of sequence reads that contain a SNP for which the genotypic context is known may maximize the informativeness of the set of sequencing reads on the mixed sample. In an embodiment, the number of sequence reads that contain a SNP for which the genotypic contexts are known may be enhanced by using qPCR to preferentially amplify specific sequences. In an embodiment, the number of sequence reads that contain a SNP for which the genotypic contexts are known may be enhanced by using circularizing probes (for example, MIPs) to preferentially amplify specific sequences. In an embodiment, the number of sequence reads that contain a SNP for which the genotypic contexts are known may be enhanced by using a capture by hybridization method (for example SURESELECT) to preferentially amplify specific sequences. Different methods may be used to enhance the number of sequence reads that contain a SNP for which the genotypic contexts are known. In an embodiment, the targeting may be accomplished by extension ligation, ligation without extension, capture by hybridization, or PCR.

In a sample of fragmented genomic DNA, a fraction of the DNA sequences map uniquely to individual chromosomes; other DNA sequences may be found on different chromosomes. Note that DNA found in plasma, is typically fragmented, often at lengths under 500 bp. In a typical genomic sample, roughly 3.3% of the mappable sequences will map to chromosome 13; 2.2% of the mappable sequences will map to chromosome 18; 1.35% of the mappable sequences will map to chromosome 21; 4.5% of the mappable sequences will map to chromosome X in a female; 2.25% of the mappable sequences will map to chromosome X (in a male); and 0.73% of the mappable sequences will map to chromosome Y (in a male). Also, among short sequences, approximately 1 in 20 sequences will contain a SNP, using the SNPs contained on dbSNP. The proportion may well be higher given that there may be many SNPs that have not been discovered.

In an embodiment of the present disclosure, targeting methods may be used to enhance the fraction of DNA in a sample of DNA that map to a given chromosome such that the fraction significantly exceeds the percentages listed above that are typical for genomic samples. In an embodiment of the present disclosure, targeting methods may be used to enhance the fraction of DNA in a sample of DNA such that the percentage of sequences that contain a SNP are significantly greater than what may be found in typical for genomic samples. In an embodiment of the present disclosure, targeting methods may be used to target DNA from a chromosome or from a set of SNPs in a mixture of donor-derived and transplant recipient-derive DNA for the purposes of determination of transplant status.

By making use of targeting approaches in sequencing the mixed sample, it may be possible to achieve a certain level of accuracy with fewer sequence reads. The accuracy may refer to sensitivity, it may refer to specificity, or it may refer to some combination thereof. The desired level of accuracy may be between 90% and 95%; it may be between 95% and 98%; it may be between 98% and 99%; it may be between 99% and 99.5%; it may be between 99.5% and 99.9%; it may be between 99.9% and 99.99%; it may be between 99.99% and 99.999%, it may be between 99.999% and 100%. Levels of accuracy above 95% may be referred to as high accuracy.

In an embodiment, accuracy may be measured by using linear regression on measured donor fractions as a function of the corresponding attempted spike levels to calculate a linearity, a slope value, and an intercept value. The linearity may be represented by the $R^2$ valued determined from the linear regression analysis. In some embodiments, the linearity is from about 0.9 to 1.0; it may be from about 0.95 to 1.0; it may be from about 0.98 to 1.0; it may be from about 0.99 to 1.0; it may be from about 0.999 to 1.0; it may be 0.999. The slope value may be from 0.5 to 5.0, it may be from 0.5 to 2.5; it may be from 0.5 to 2.0; it may 0.5 to 1.5; it may from 0.75 to 1.25; it may be from 0.9 to 1.2. The intercept value may be from about −0.01 to about 0.1; it may be from about −0.001 to about 0.1; it may be from about −0.0001 to about 0.1; it may be from about −0.0001 to about 0.01; it may be from about −0.0001 to about 0.001; it may be from about −0.0001 to about 0.0001; it may be 0.

In an embodiment, accuracy may refer to precision as determined by calculating a coefficient of variation (CV) and a confidence interval of 95% for the determination of the targeted donor fraction. Estimation of precision by calculating a CV may also be referred to as a measurement of reproducibility. The CV value may be represented with a confidence interval. The confidence interval for the CV may be 99%; it may be 95%; it may be 90%. The CV may be less than 10%; it may be less than 9%; it may be less than 8%; it may be less than 7%; it may be less than 6%; it may be less than 5%; it may be less than 4%; it may be less than 3%; it may be less than 2%; it may be less than 1%. The CV may be different depending on the targeted donor fraction. For a 0.6% targeted donor fraction, the CV may be 1.85% with a confidence interval of 95%. For a 2.4% targeted donor fraction, the CV may be 1.22% with a confidence interval of 95%. The CV may be different depending on amount of DNA in the sample. For example, for 15 ng DNA, the CV may be 3.1% with a 95% confidence interval; for 30 ng DNA, the CV may be 3.07% with a 95% confidence interval; for 45 ng DNA, the CV may be 1.99% with a 95% confidence interval.

In an embodiment of the present disclosure, an accurate transplant status determination may be made by using targeted sequencing, using any method of targeting, for example qPCR, ligand mediated PCR, other PCR methods, capture by hybridization, or circularizing probes, wherein the number of loci along a chromosome that need to be targeted may be between 5,000 and 2,000 loci; it may be between 2,000 and 1,000 loci; it may be between 1,000 and 500 loci; it may be between 500 and 300 loci; it may be between 300 and 200 loci; it may be between 200 and 150 loci; it may be between 150 and 100 loci; it may be between 100 and 50 loci; it may be between 50 and 20 loci; it may be between 20 and 10 loci. Optimally, it may be between 100 and 500 loci. The high level of accuracy may be achieved by targeting a small number of loci and executing an unexpectedly small number of sequence reads. The number of reads may be between 100 million and 50 million reads; the number of reads may be between 50 million and 20 million reads; the number of reads may be between 20 million and 10 million reads; the number of reads may be between 10 million and 5 million reads; the number of reads may be between 5 million and 2 million reads; the number of reads may be between 2 million and 1 million; the number of reads may be between 1 million and 500,000; the number of reads may be between 500,000 and 200,000; the number of reads may be between 200,000 and 100,000; the number of reads may be between 100,000 and 50,000; the number of reads may be between 50,000 and 20,000; the number of reads may be between 20,000 and 10,000; the number of reads may be below 10,000. Fewer number of read are necessary for larger amounts of input DNA.

In some embodiments, a composition is described comprising a mixture of DNA of donor origin, and DNA of recipient origin, wherein the percent of sequences that uniquely map to a chromosome, and that contains at least one single nucleotide polymorphism is greater than 0.2%, greater than 0.3%, greater than 0.4%, greater than 0.5%, greater than 0.6%, greater than 0.7%, greater than 0.8%, greater than 0.9%, greater than 1%, greater than 1.2%, greater than 1.4%, greater than 1.6%, greater than 1.8%, greater than 2%, greater than 2.5%, greater than 3%, greater than 4%, greater than 5%, greater than 6%, greater than 7%, greater than 8%, greater than 9%, greater than 10%, greater than 12%, greater than 15%, or greater than 20%, and where the chromosome is taken from the group 13, 18, 21, X, or Y. In some embodiments of the present disclosure, there is a composition comprising a mixture of DNA of donor origin, and DNA of recipient origin, wherein the percent of sequences that uniquely map to a chromosome and that contain at least one single nucleotide polymorphism from a set of single nucleotide polymorphisms is greater than 0.15%, greater than 0.2%, greater than 0.3%, greater than 0.4%, greater than 0.5%, greater than 0.6%, greater than 0.7%, greater than 0.8%, greater than 0.9%, greater than 1%, greater than 1.2%, greater than 1.4%, greater than 1.6%, greater than 1.8%, greater than 2%, greater than 2.5%, greater than 3%, greater than 4%, greater than 5%, greater than 6%, greater than 7%, greater than 8%, greater than 9%, greater than 10%, greater than 12%, greater than 15%, or greater than 20%, where the chromosome is taken from the set of chromosome 13, 18, 21, X and Y, and where the number of single nucleotide polymorphisms in the set of single nucleotide polymorphisms is between 1 and 10, between 10 and 20, between 20 and 50, between 50 and 100, between 100 and 200, between 200 and 500, between 500 and 1,000, between 1,000 and 2,000, between 2,000 and 5,000, between 5,000 and 10,000, between 10,000 and 20,000, between 20,000 and 50,000, and between 50,000 and 100,000.

In theory, each cycle in the amplification doubles the amount of DNA present; however, in reality, the degree of amplification is slightly lower than two. In theory, amplification, including targeted amplification, will result in bias free amplification of a DNA mixture; in reality, however, different alleles tend to be amplified to a different extent than other alleles. When DNA is amplified, the degree of allelic bias typically increases with the number of amplification steps. In some embodiments, the methods described herein involve amplifying DNA with a low level of allelic bias. Since the allelic bias compounds with each additional cycle, one can determine the per cycle allelic bias by calculating the nth root of the overall bias where n is the base 2 logarithm of degree of enrichment. In some embodiments, there is a composition comprising a second mixture of DNA, where the second mixture of DNA has been preferentially enriched at a plurality of polymorphic loci from a first mixture of DNA where the degree of enrichment is at least 10, at least 100, at least 1,000, at least 10,000, at least 100,000 or at least 1,000,000, and where the ratio of the alleles in the second mixture of DNA at each locus differs from the ratio of the alleles at that locus in the first mixture of DNA by a factor that is, on average, less than 1,000%, 500%, 200%, 100%, 50%, 20%, 10%, 5%, 2%, 1%, 0.5%, 0.2%, 0.1%, 0.05%, 0.02%, or 0.01%. In some embodiments, there is a composition comprising a second mixture of DNA, where the second mixture of DNA has been preferentially enriched at a plurality of polymorphic loci from a first mixture of DNA where the per cycle allelic bias for the plurality of polymorphic loci is, on average, less than 10%, 5%, 2%, 1%, 0.5%, 0.2%, 0.1%, 0.05%, or 0.02%. In some embodiments, the plurality of polymorphic loci comprises at least 10 loci, at least 20 loci, at least 50 loci, at least 100 loci, at least 200 loci, at least 500 loci, at least 1,000 loci, at least 2,000 loci, at least 5,000 loci, at least 10,000 loci, at least 20,000 loci, or at least 50,000 loci.

Maximum Likelihood Estimates

Most methods known in the art for detecting the presence or absence of biological phenomenon or medical condition involve the use of a single hypothesis rejection test, where a metric that is correlated with the condition is measured, and if the metric is on one side of a given threshold, the condition is present, while of the metric falls on the other side of the threshold, the condition is absent. A single-hypothesis rejection test only looks at the null distribution when deciding between the null and alternate hypotheses. Without taking into account the alternate distribution, one cannot estimate the likelihood of each hypothesis given the observed data and therefore cannot calculate a confidence on the call. Hence with a single-hypothesis rejection test, one gets a yes or no answer without a feeling for the confidence associated with the specific case.

In some embodiments, the method disclosed herein is able to detect the presence or absence of biological phenomenon or medical condition using a maximum likelihood method. This is a substantial improvement over a method using a single hypothesis rejection technique as the threshold for calling absence or presence of the condition can be adjusted as appropriate for each case.

The maximum likelihood estimation method uses the distributions associated with each hypothesis to estimate the likelihood of the data conditioned on each hypothesis. These conditional probabilities can then be converted to a hypothesis call and confidence. Similarly, maximum a posteriori estimation method uses the same conditional probabilities as the maximum likelihood estimate, but also incorporates population priors when choosing the best hypothesis and determining confidence.

Therefore, the use of a maximum likelihood estimate (MLE) technique, or the closely related maximum a posteriori (MAP) technique give two advantages, first it increases the chance of a correct call, and it also allows a confidence to be calculated for each call. In an embodiment, selecting the ploidy state corresponding to the hypothesis with the greatest probability is carried out using maximum likelihood estimates or maximum a posteriori estimates. In an embodiment, a method is disclosed for determining the transplant status in a transplant recipient that involves taking any method currently known in the art that uses a single hypothesis rejection technique and reformulating it such that it uses a MLE or MAP technique. Some examples of methods that can be significantly improved by applying these techniques can be found in U.S. Pat. Nos. 8,008,018, 7,888,017, or U.S. Pat. No. 7,332,277.

In an embodiment, a method is described for determining presence or absence of fetal aneuploidy in a transplant recipient plasma sample comprising fetal and maternal genomic DNA, the method comprising: obtaining a transplant recipient plasma sample; measuring the DNA fragments found in the plasma sample with a high throughput sequencer; calculating the fraction of donor-derived DNA in the plasma sample; and using a MLE or MAP determine which of the distributions is most likely to be correct, thereby indicating the presence or absence of a transplant undergoing acute rejection, borderline rejection, other injury or stability. In an embodiment, the measuring the DNA from the plasma may involve conducting massively parallel shotgun sequencing. In an embodiment, the measuring the DNA from the plasma sample may involve sequencing DNA that has been preferentially enriched, for example through targeted amplification, at a plurality of polymorphic or non-polymorphic loci. The purpose of the preferential enrichment is to increase the number of sequence reads that are informative for the transplant status determination.

Transplant Status Calling Informatics Methods

Described herein is a method for determining the state of a transplant given sequence data. In some embodiments, this sequence data may be measured on a high throughput sequencer. In some embodiments, the sequence data may be measured on DNA that originated from free floating DNA isolated from recipient blood, wherein the free floating DNA comprises some DNA of transplant recipient origin, and some DNA of transplant donor origin. This section will describe one embodiment of the present disclosure in which the state of the transplant is determined assuming that fraction of donor-derived DNA in the mixture that has been analyzed is not known and will be estimated from the data. It will also describe an embodiment in which the fraction of donor-derived DNA ("donor fraction") or the percentage of donor-derived DNA in the mixture can be measured by another method. In some embodiments the donor fraction can be calculated using only the genotyping measurements made on the blood sample itself, which is a mixture of donor and transplant recipient DNA. In some embodiments the fraction may be calculated also using the measured or otherwise known genotype of the transplant recipient and/or the measured or otherwise known genotype of the transplant donor. In another embodiment, the state of the transplant can be determined solely based on the calculated fraction of donor-derived DNA.

Informatics methods useful and relevant to the methods disclosed herein can be found in U.S. Patent Publication No. 20180025109, incorporated by reference herein, wherein the informatics methods are disclosed in the context of determination of genetic state of a fetus via non-invasive prenatal testing.

For example, in an embodiment, the informatics method may incorporate random bias. As is often the case, suppose that there is a bias in the measurements, so that the probability of getting an A on this SNP is equal to q, which is a bit different than p as defined above. How much different p is from q depends on the accuracy of the measurement process and number of other factors and can be quantified by standard deviations of q away from p. In an embodiment, it is possible to model q as having a beta distribution, with parameters $\alpha$, $\beta$ depending on the mean of that distribution being centered at p, and some specified standard deviation s. In particular, this gives $X|q \sim \text{Bin}(q, D_i)$, where $q \sim \text{Beta}(\alpha, \beta)$. If we let $E(q)=p$, $V(q)=s^2$, and parameters $\alpha$, $\beta$ can be derived as $\alpha=pN$, $\beta=(1-p)N$, where $N=p(1-p)/s^2-1$.

In some embodiments, the method may be written to specifically take into account additional noise, differential sample quality, differential SNP quality, and random sampling bias. In some embodiments, the method involves several steps that each introduce different kind of noise and/or bias to the final model:

(1) Suppose the first sample that comprises a mixture of maternal and fetal DNA contains an original amount of DNA of size=No molecules, usually in the range 1,000-40,000, where p=true % refs (2) In the amplification using the universal ligation adaptors, assume that $N_1$ molecules are sampled; usually $N_1 \sim N_0/2$ molecules and random sampling bias is introduced due to sampling. The amplified sample may contain a number of molecules $N_2$ where $N_2 \gg N_1$. Let $X_1$ represent the amount of reference loci (on per SNP basis) out of $N_1$ sampled molecules, with a variation in $p_1=X_1/N_1$ that introduces random sampling bias throughout the rest of protocol. This sampling bias is included in the model by using a Beta-Binomial (BB) distribution instead of using a simple Binomial distribution model. Parameter N of the Beta-Binomial distribution may be estimated later on per sample basis from training data after adjusting for leakage and amplification bias, on SNPs with $0<p<1$. Leakage is the tendency for a SNP to be read incorrectly.

(3) The amplification step will amplify any allelic bias, thus amplification bias introduced due to possible uneven amplification. Suppose that one allele at a locus is amplified f times another allele at that locus is amplified g times, where $f=ge^b$, where b=0 indicates no bias. The bias parameter, b, is centered at 0, and indicates how much more or less the A allele get amplified as opposed to the B allele on a particular SNP. The parameter b may differ from SNP to SNP. Bias parameter b may be estimated on per SNP basis, for example from training data.

(4) The sequencing step involves sequencing a sample of amplified molecules. In this step there may be leakage, where leakage is the situation where a SNP is read incorrectly. Leakage may result from any number of problems, and may result in a SNP being read not as the correct allele A, but as another allele B found at that locus or as an allele C or D not typically found at that locus. Suppose the sequencing measures the sequence data of a number of DNA molecules from an amplified sample of size $N_3$, where $N_3<N_2$. In some embodiments, $N_3$ may be in the range of 20,000 to 100,000; 100,000 to 500,000; 500,000 to 4,000,000; 4,000,000 to 20,000,000; or 20,000,000 to 100,000,000. Each molecule sampled has a probability $p_g$ of being read correctly, in which case it will show up correctly as allele A. The sample will be incorrectly read as an allele unrelated to the original molecule with probability $1-p_g$, and will look like allele A with probability $p_r$, allele B with probability $p_m$ or allele C or allele D with probability $p_o$, where $p_r+p_m+p_o=1$. Parameters $p_g$, $p_r$, $p_m$, $p_o$ are estimated on per SNP basis from the training data.

Different protocols may involve similar steps with variations in the molecular biology steps resulting in different amounts of random sampling, different levels of amplification and different leakage bias. The following model may be equally well applied to each of these cases. The model for the amount of DNA sampled, on per SNP basis, is given by:

$$X_3 \sim \text{BetaBinomial}(L(F(p,b),p_r,p_g), N^*H(p,b))$$

where p=the true amount of reference DNA, b=per SNP bias, and as described above, $p_g$ is the probability of a correct read, $P_r$ is the probability of read being read incorrectly but serendipitously looking like the correct allele, in case of a bad read, as described above, and:

$$F(p,b)=pe^b/(pe^b+(1-p)), H(p,b)=(e^b p+(1-p))^2/e^b, L(p, p_r,p_g)=p^*p_g+p_r^*(1-p_g).$$

In some embodiments, the method uses a Beta-Binomial distribution instead of a simple binomial distribution; this takes care of the random sampling bias. Parameter N of the Beta-Binomial distribution is estimated on per sample basis on an as needed basis. Using bias correction F(p,b), H(p,b), instead of just p, takes care of the amplification bias. Parameter b of the bias is estimated on per SNP basis from training data ahead of time.

In some embodiments the method uses leakage correction $L(p,p_r,p_g)$, instead of just p; this takes care of the leakage bias, i.e. varying SNP and sample quality. In some embodiments, parameters $p_g$, $p_r$, $p_o$ are estimated on per SNP basis from the training data ahead of time. In some embodiments, the parameters $p_g$, $p_r$, $p_o$ may be updated with the current sample on the go, to account for varying sample quality.

The model described herein is quite general and can account for both differential sample quality and differential SNP quality. Different samples and SNPs are treated differently, as exemplified by the fact that some embodiments use Beta-Binomial distributions whose mean and variance are a function of the original amount of DNA, as well as sample and SNP quality.

Platform Modeling

An observation at a SNP consists of the number of mapped reads with each allele present, $n_a$ and $n_b$, which sum to the depth of read d. Assume that thresholds have already been applied to the mapping probabilities and phred scores such that the mappings and allele observations can be considered correct. A phred score is a numerical measure that relates to the probability that a particular measurement at a particular base is wrong. In an embodiment, where the base has been measured by sequencing, the phred score may be calculated from the ratio of the dye intensity corresponding to the called base to the dye intensity of the other bases. The simplest model for the observation likelihood is a binomial distribution which assumes that each of the d reads is drawn independently from a large pool that has allele ratio r. Equation 2 describes this model.

$$P(n_a, n_b | r) = p_{bino}(n_a; n_a + n_b, r) = \binom{n_a + n_b}{n_a} r^{n_a} (1 - r)^{n_b} \quad (2)$$

The binomial model can be extended in a number of ways. When the donor and recipient genotypes are either all A or all B, the expected allele ratio in plasma will be 0 or 1, and the binomial probability will not be well-defined. In practice, unexpected alleles are sometimes observed in practice. In an embodiment, it is possible to use a corrected allele ratio $\hat{r}=1/(n_a+n_b)$ to allow a small number of the unexpected allele. In an embodiment, it is possible to use training data to model the rate of the unexpected allele appearing on each SNP, and use this model to correct the expected allele ratio. When the expected allele ratio is not 0 or 1, the observed allele ratio may not converge with a sufficiently high depth of read to the expected allele ratio due to amplification bias or other phenomena. The allele ratio can then be modeled as a beta distribution centered at the expected allele ratio, leading to a beta-binomial distribution for $P(n_a, n_b | r)$ which has higher variance than the binomial.

The platform model for the response at a single SNP will be defined as F(a, b, $g_c$, $g_m$, f) (3), or the probability of observing $n_a$=a and $n_b$=b given the maternal and fetal genotypes, which also depends on the fetal fraction through equation 1. The functional form of F may be a binomial distribution, beta-binomial distribution, or similar functions as discussed above.

$$F(a,b,g_c,g_m,f)=P(n_a=a,n_b=b|g_c,g_m,f)=P(n_a=a,n_b=b|r(g_c,g_m,f)) \quad (3)$$

In an embodiment, a method of the present disclosure is used to determine the transplant status of the plant recipient involves taking into account the fraction of donor DNA in the sample. In another embodiment of the present disclosure, the method involves the use of maximum likelihood estimations. In an embodiment, a method of the present disclosure involves calculating the percent of DNA in a sample that is donor-derived. In an embodiment, the threshold for calling acute rejection of a transplant is adaptively adjusted based on the calculated percent donor-derived DNA.

In an embodiment of the present disclosure, the fraction of donor-derived DNA, or the percentage of donor DNA in the mixture can be measured. In some embodiments the fraction can be calculated using only the genotyping measurements made on the transplant recipient plasma sample itself, which is a mixture of donor-derived and transplant recipient DNA. In some embodiments the fraction may be calculated also using the measured or otherwise known genotype of the transplant recipient and/or the measured or otherwise known genotype of the transplant donor. In some embodiments the percent donor DNA may be calculated using the measurements made on the mixture of donor-derived and transplant recipient DNA along with the knowledge of the genotypic contexts. In an embodiment, the fraction of donor DNA may be calculated using population frequencies to adjust the model on the probability on particular allele measurements.

In an embodiment of the present disclosure, a confidence may be calculated on the accuracy of the determination of transplant status. In an embodiment, the confidence of the hypothesis of greatest likelihood ($H_{major}$) may be calculated as $(1-H_{major})/\Sigma(\text{all H})$. It is possible to determine the confidence of a hypothesis if the distributions of all of the hypotheses are known. It is possible to determine the distribution of all of the hypotheses if the donor and recipient genotype information is known. In an embodiment one may use the knowledge of the distribution of a test statistic around a normal hypothesis and around an abnormal hypothesis to determine both the reliability of the call as well as refine the threshold to make a more reliable call. This is particularly useful when the amount and/or percent of donor DNA in the mixture is low.

Further Discussion of the Method

In an embodiment, a method disclosed herein utilizes a quantitative measure of the number of independent observations of each allele at a polymorphic locus, where this does not involve calculating the ratio of the alleles. This is different from methods, such as some microarray based methods, which provide information about the ratio of two alleles at a locus but do not quantify the number of independent observations of either allele. Some methods known in the art can provide quantitative information regarding the number of independent observations, but the calculations leading to the ploidy determination utilize only the allele ratios, and do not utilize the quantitative information. To illustrate the importance of retaining information about the number of independent observations consider the sample locus with two alleles, A and B. In a first experiment twenty A alleles and twenty B alleles are observed, in a second experiment 200 A alleles and 200 B alleles are observed. In both experiments the ratio (A/(A+B)) is equal to 0.5, however the second experiment conveys more information than the first about the certainty of the frequency of the A or B allele. The instant method, rather than utilizing the allele ratios, uses the quantitative data to more accurately model the most likely allele frequencies at each polymorphic locus.

In an embodiment, a reference chromosome is used to determine the donor fraction and noise level amount or probability distribution. The instant method works without the reference chromosome, as well as without fixing the particular donor fraction or noise level.

Measurements of DNA are noisy and/or error prone, especially measurements where the amount of DNA is small, or where the DNA is mixed with contaminating DNA. This noise results in less accurate genotypic data, and less accurate transplant status determination. In some embodiments, platform modeling or some other method of noise modeling may be used to counter the deleterious effects of noise on the transplant status determination. The instant method uses a joint model of both channels, which accounts for the random noise due to the amount of input DNA, DNA quality, and/or protocol quality.

In particular, errors in the measurements typically do not specifically depend on the measured channel intensity ratio, which reduces the model to using one-dimensional information. Accurate modeling of noise, channel quality and channel interaction requires a two-dimensional joint model, which can not be modeled using allele ratios.

In particular, projecting two channel information to the ratio r where $f(x,y)$ is $r=x/y$, does not lend itself to accurate channel noise and bias modeling. Noise on a particular SNP is not a function of the ratio, i.e. $noise(x,y) \neq f(x,y)$ but is in fact a joint function of both channels. For example, in the binomial model, noise of the measured ratio has a variance of $r(1-r)/(x+y)$ which is not a function purely of r. In such a model, where any channel bias or noise is included, suppose that on SNP i, the observed channel X value is $x=a_iX+b_i$, where X is the true channel value, $b_i$ is the extra channel bias and random noise. Similarly, suppose that $y=c_iY+d_i$. The observed ratio $r=x/y$ cannot accurately predict the true ratio X/Y or model the leftover noise, since $(a_iX+b_i)/(c_iY+d_i)$ is not a function of X/Y.

The method disclosed herein describes an effective way to model noise and bias using joint binomial distributions of all of the measurement channels individually. Relevant equations may be found elsewhere in the document in sections which speaks of per SNP consistent bias, P(good) and P(ref|bad), P(mut|bad) which effectively adjust SNP behavior. In an embodiment, a method of the present disclosure uses a BetaBinomial distribution, which avoids the limiting practice of relying on the allele ratios only, but instead models the behavior based on both channel counts.

In an embodiment, a method disclosed herein can call the transplant status of a transplant recipient from genetic data found in transplant recipient plasma by using all available measurements. Some methods known in the art only use measured genetic data where the genotypic context is from the AA|BB context, that is, where the donor and recipient are both homozygous at a given locus, but for a different allele. One problem with this method is that a small proportion of polymorphic loci are from the AA|BB context, typically less than 10%. In an embodiment of a method disclosed herein, the method does not use genetic measurements of the transplant recipient plasma made at loci where the genotypic context is AA|BB. In an embodiment, the instant method uses plasma measurements for only those polymorphic loci with the AA|AB, AB|AA, and AB|AB genotypic context.

Variable Read Depth to Minimize Sequencing Cost

In many clinical trials concerning a diagnostic, for example, in Chiu et al. BMJ 2011; 342:c7401, a protocol with a number of parameters is set, and then the same protocol is executed with the same parameters for each of the patients in the trial. In the case of determining the transplant status in a transplant recipient using sequencing as a method to measure genetic material one pertinent parameter is the number of reads. The number of reads may refer to the number of actual reads, the number of intended reads, fractional lanes, full lanes, or full flow cells on a sequencer. In these studies, the number of reads is typically set at a level that will ensure that all or nearly all of the samples achieve the desired level of accuracy. Sequencing is currently an expensive technology, a cost of roughly $200 per 5 mappable million reads, and while the price is dropping, any method which allows a sequencing based diagnostic to operate at a similar level of accuracy but with fewer reads will necessarily save a considerable amount of money.

The accuracy of a transplant status determination is typically dependent on a number of factors, including the number of reads and the fraction of donor-derived DNA in the mixture. The accuracy is typically higher when the fraction of donor-derived DNA in the mixture is higher. At the same time, the accuracy is typically higher if the number of reads is greater. It is possible to have a situation with two cases where the transplant state is determined with comparable accuracies wherein the first case has a lower fraction of donor-derived DNA in the mixture than the second, and more reads were sequenced in the first case than the second. It is possible to use the estimated fraction of donor DNA in the mixture as a guide in determining the number of reads necessary to achieve a given level of accuracy.

In an embodiment of the present disclosure, a set of samples can be run where different samples in the set are sequenced to different reads depths, wherein the number of reads run on each of the samples is chosen to achieve a given level of accuracy given the calculated fraction of donor DNA in each mixture. In an embodiment of the present disclosure, this may entail making a measurement of the mixed sample to determine the fraction of donor DNA in the mixture; this estimation of the donor fraction may be done with sequencing, it may be done with TAQMAN, it may be done with qPCR, it may be done with SNP arrays, it may be done with any method that can distinguish different alleles at a given loci. The need for a donor fraction estimate may be eliminated by including hypotheses that cover all or a selected set of donor fractions in the set of hypotheses that are considered when comparing to the actual measured data. After the fraction of donor DNA in the mixture has been determined, the number of sequences to be read for each sample may be determined.

Using Raw Genotyping Data

There are a number of methods that can accomplish the methods disclosed herein using donor genetic information measured on donor-derived DNA found in transplant recipient blood. Some of these methods involve making measurements of the fetal DNA using SNP arrays, some methods involve untargeted sequencing, and some methods involve targeted sequencing. The targeted sequencing may target SNPs, it may target STRs, it may target other polymorphic loci, it may target non-polymorphic loci, or some combination thereof. Some of these methods may involve using a commercial or proprietary allele caller that calls the identity of the alleles from the intensity data that comes from the sensors in the machine doing the measuring. For example, the ILLUMINA INFINIUM system or the AFFYMETRIX GENECHIP microarray system involves beads or micro-chips with attached DNA sequences that can hybridize to complementary segments of DNA; upon hybridization, there is a change in the fluorescent properties of the sensor molecule that can be detected. There are also sequencing methods, for example the ILLUMINA SOLEXA GENOME SEQUENCER or the ABI SOLID GENOME SEQUENCER, wherein the genetic sequence of fragments of DNA are sequenced; upon extension of the strand of DNA complementary to the strand being sequenced, the identity of the extended nucleotide is typically detected via a fluorescent or radio tag appended to the complementary nucleotide. In all of these methods the genotypic or sequencing data is typically determined on the basis of fluorescent or other signals, or the lack thereof. These systems are typically combined with low level software packages that make specific allele calls (secondary genetic data) from the analog output of the fluorescent or other detection device (primary genetic data). For example, in the case of a given allele on a SNP array, the software will make a call, for example, that a certain SNP is present or not present if the fluorescent intensity is measure above or below a certain threshold. Similarly, the output of a sequencer is a chromatogram that indicates the level of fluorescence detected for each of the dyes, and the software will make a call that a certain base pair is A or T or C or G. High throughput sequencers typically make a series of such measurements, called a read, that represents the most likely structure of the DNA sequence that was sequenced. The direct analog output of the chromatogram is defined here to be the primary genetic data, and the base pair/SNP calls made by the software are considered here to be the secondary genetic data. In an embodiment, primary data refers to the raw intensity data that is the unprocessed output of a genotyping platform, where the genotyping platform may refer to a SNP array, or to a sequencing platform. The secondary genetic data refers to the processed genetic data, where an allele call has been made, or the sequence data has been assigned base pairs, and/or the sequence reads have been mapped to the genome.

Many higher level applications take advantage of these allele calls, SNP calls and sequence reads, that is, the secondary genetic data, that the genotyping software produces. For example, DNA NEXUS, ELAND or MAQ will take the sequencing reads and map them to the genome. In the context of non-invasive determination of transplant status it may be possible to take a set of sequence reads that have been measured on DNA present in transplant recipient plasma, and map them to the genome. One may then take a normalized count of the reads that are mapped to each chromosome, or section of a chromosome, and use that data to determine the transplant state of a transplant recipient.

However, in reality, the initial output of the measuring instruments is an analog signal. When a certain base pair is called by the software that is associated with the sequencing software, for example the software may call the base pair a T, in reality the call is the call that the software believes to be most likely. In some cases, however, the call may be of low confidence, for example, the analog signal may indicate that the particular base pair is only 90% likely to be a T, and 10% likely to be an A. In another example, the genotype calling software that is associated with a SNP array reader may call a certain allele to be G. However, in reality, the underlying analog signal may indicate that it is only 70% likely that the allele is G, and 30% likely that the allele is T. In these cases, when the higher level applications use the genotype calls and sequence calls made by the lower level software, they are losing some information. That is, the primary genetic data, as measured directly by the genotyping platform, may be messier than the secondary genetic data that is determined by the attached software packages, but it contains more information. In mapping the secondary genetic data sequences to the genome, many reads are thrown out because some bases are not read with enough clarity and or mapping is not clear. When the primary genetic data sequence reads are used, all or many of those reads that may have been thrown out when first converted to secondary genetic data sequence read can be used by treating the reads in a probabilistic manner.

In an embodiment of the present disclosure, the higher level software does not rely on the allele calls, SNP calls, or sequence reads that are determined by the lower level software. Instead, the higher level software bases its calculations on the analog signals directly measured from the genotyping platform. In an embodiment of the present disclosure, all genetic calls, SNPs calls, sequence reads, sequence mapping is treated in a probabilistic manner by using the raw intensity data as measured directly by the genotyping platform, rather than converting the primary genetic data to secondary genetic calls. In an embodiment, the DNA measurements from the prepared sample used in calculating allele count probabilities and determining the relative probability of each hypothesis comprise primary genetic data.

In some embodiments, the method can increase the accuracy of genetic data of a target individual which incorporates genetic data of at least one related individual, the method comprising obtaining primary genetic data specific to a target individual's genome and genetic data specific to the genome(s) of the related individual(s), creating a set of one or more hypotheses concerning possibly which segments of which chromosomes from the related individual(s) correspond to those segments in the target individual's genome, determining the probability of each of the hypotheses given the target individual's primary genetic data and the related individual(s)'s genetic data, and using the probabilities associated with each hypothesis to determine the most likely state of the actual genetic material of the target individual. In an embodiment, a method of the present disclosure can determine an allelic state in a set of alleles, in a target individual, and from one or both parents of the target individual, and optionally from one or more related individuals, the method comprising obtaining primary genetic data from the target individual, and from the one or both parents, and from any related individuals, creating a set of at least one allelic hypothesis for the target individual, and for the one or both parents, and optionally for the one or more related individuals, where the hypotheses describe possible allelic states in the set of alleles, determining a statistical probability for each allelic hypothesis in the set of hypotheses given the obtained genetic data, and determining the allelic state for each of the alleles in the set of alleles for the target individual, and for the one or both parents, and optionally for the one or more related individuals, based on the statistical probabilities of each of the allelic hypotheses.

In some embodiments, the genetic data of the mixed sample may comprise sequence data wherein the sequence data may not uniquely map to the human genome. In some embodiments, the genetic data of the mixed sample may comprise sequence data wherein the sequence data maps to a plurality of locations in the genome, wherein each possible mapping is associated with a probability that the given mapping is correct. In some embodiments, the sequence reads are not assumed to be associated with a particular position in the genome. In some embodiments, the sequence reads are associated with a plurality of positions in the genome, and an associated probability belonging to that position.

Combining Methods of Transplant Status Determination

Figure 7:
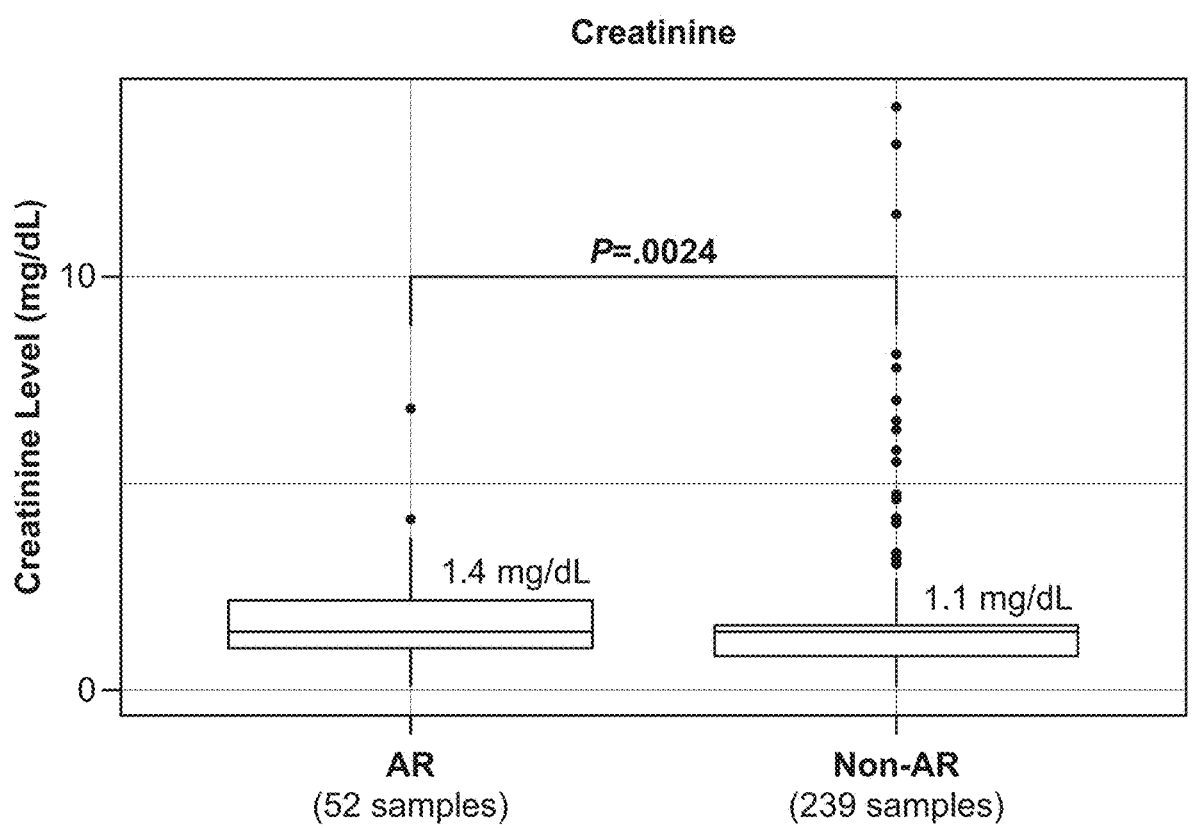
FIG. 7 exemplifies the discriminatory ability of serum creatinine levels to discriminate between transplants undergoing acute rejection (AR) and those not undergoing acute rejection (Non-AR).

Disclosed herein is a method for making more accurate predictions about the genetic state of a transplant, that comprises combining predictions of transplant state with other known methods to make such a determination. For example, serum creatinine levels have previously been used to try to determine the status of a kidney transplant. See FIG. 7.

There are many ways to combine the predictions, for example, one could convert the hormone measurements into a multiple of the median (MoM) and then into likelihood ratios (LR). Similarly, other measurements could be transformed into LRs using the mixture model of NT distributions. Detection rates (DRs) and false-positive rates (FPRs) could be calculated by taking the proportions with risks above a given risk threshold.

In an embodiment, it is possible to evoke central limit theorem to assume distribution on g(y|a or e) is Gaussian, and measure mean and standard deviation by looking at multiple samples.

In another embodiment, one could assume they are not independent given the outcome and collect enough samples to estimate the joint distribution $p(x_1, x_2, x_3, x_4|a$ or $e)$.

In an embodiment, the transplant status is determined to be the transplant status that is associated with the hypothesis whose probability is the greatest. In some cases, one hypothesis will have a normalized, combined probability greater than 90%. Each hypothesis is associated with one, or a set of, transplant statuses, and the transplant associated with the hypothesis whose normalized, combined probability is greater than 90%, or some other threshold value, such as 50%, 80%, 95%, 98%, 99%, or 99.9%, may be chosen as the threshold required for a hypothesis to be called as the determined transplant status.

Determining the Number of DNA Molecules in a Sample.

A method is described herein to determine the number of DNA molecules in a sample by generating a uniquely identified molecule for each original DNA molecules in the sample during the first round of DNA amplification. Described here is a procedure to accomplish the above end followed by a single molecule or clonal sequencing method.

The approach entails targeting one or more specific loci and generating a tagged copy of the original molecules such manner that most or all of the tagged molecules from each targeted locus will have a unique tag and can be distinguished from one another upon sequencing of this barcode using clonal or single molecule sequencing. Each unique sequenced barcode represents a unique molecule in the original sample. Simultaneously, sequencing data is used to ascertain the locus from which the molecule originates. Using this information one can determine the number of unique molecules in the original sample for each locus.

This method can be used for any application in which quantitative evaluation of the number of molecules in an original sample is required. Furthermore, the number of unique molecules of one or more targets can be related to the number of unique molecules to one or more other targets to determine the relative copy number, allele distribution, or allele ratio. Alternatively, the number of copies detected from various targets can be modeled by a distribution in order to identify the mostly likely number of copies of the original targets. Applications include but are not limited to detection of insertions and deletions such as those found in carriers of Duchenne Muscular Dystrophy; quantitation of deletions or duplications segments of chromosomes such as those observed in copy number variants; chromosome copy number of samples from born individuals; chromosome copy number of samples from unborn individuals such as embryos or fetuses.

The method can be combined with simultaneous evaluation of variations contained in the targeted by sequence. This can be used to determine the number of molecules representing each allele in the original sample.

In an embodiment, the method as it pertains to a single target locus may comprise one or more of the following steps: (1) Designing a standard pair of oligomers for PCR amplification of a specific locus. (2) Adding, during synthesis, a sequence of specified bases with no or minimal complementarity to the target locus or genome to the 5' end of the one of the target specific oligomer. This sequence, termed the tail, is a known sequence, to be used for subsequent amplification, followed by a sequence of random nucleotides. These random nucleotides comprise the random region. The random region comprises a randomly generated sequence of nucleic acids that probabilistically differ between each probe molecule. Consequently, following synthesis, the tailed oligomer pool will consists of a collection of oligomers beginning with a known sequence followed by unknown sequence that differs between molecules, followed by the target specific sequence. (3) Performing one round of amplification (denaturation, annealing, extension) using only the tailed oligomer. (4) adding exonuclease to the reaction, effectively stopping the PCR reaction, and incubating the reaction at the appropriate temperature to remove forward single stranded oligos that did not anneal to temple and extend to form a double stranded product. (5) Incubating the reaction at a high temperature to denature the exonuclease and eliminate its activity. (6) Adding to the reaction a new oligonucleotide that is complementary to tail of the oligomer used in the first reaction along with the other target specific oligomer to enable PCR amplification of the product generated in the first round of PCR. (7) Continuing amplification to generate enough product for downstream clonal sequencing. (8) Measuring the amplified PCR product by a multitude of methods, for example, clonal sequencing, to a sufficient number of bases to span the sequence.

In an embodiment, a method of the present disclosure involves targeting multiple loci in parallel or otherwise. Primers to different target loci can be generated independently and mixed to create multiplex PCR pools. In an embodiment, original samples can be divided into sub-pools and different loci can be targeted in each sub-pool before being recombined and sequenced. In an embodiment, the tagging step and a number of amplification cycles may be performed before the pool is subdivided to ensure efficient targeting of all targets before splitting, and improving subsequent amplification by continuing amplification using smaller sets of primers in subdivided pools.

In some circumstances, especially in cases where there is a very small amount of DNA, for example, fewer than 5,000 copies of the genome, fewer than 1,000 copies of the genome, fewer than 500 copies of the genome, and fewer than 100 copies of the genome, one can encounter a phenomenon called bottlenecking. This is where there are a small number of copies of any given allele in the initial sample, and amplification biases can result in the amplified pool of DNA having significantly different ratios of those alleles than are in the initial mixture of DNA. By applying a unique or nearly unique set of barcodes to each strand of DNA before standard PCR amplification, it is possible to exclude n−1 copies of DNA from a set of n identical molecules of sequenced DNA that originated from the same original molecule.

For example, imagine a heterozygous SNP in the genome of an individual, and a mixture of DNA from the individual where ten molecules of each allele are present in the original sample of DNA. After amplification there may be 100,000 molecules of DNA corresponding to that locus. Due to stochastic processes, the ratio of DNA could be anywhere from 1:2 to 2:1, however, since each of the original molecules was tagged with a unique tag, it would be possible to determine that the DNA in the amplified pool originated from exactly 10 molecules of DNA from each allele. This method would therefore give a more accurate measure of the relative amounts of each allele than a method not using this approach. For methods where it is desirable for the relative amount of allele bias to be minimized, this method will provide more accurate data.

Association of the sequenced fragment to the target locus can be achieved in a number of ways. In an embodiment, a sequence of sufficient length is obtained from the targeted fragment to span the molecule barcode as well a sufficient number of unique bases corresponding to the target sequence to allow unambiguous identification of the target locus. In another embodiment, the molecular bar-coding primer that contains the randomly generated molecular barcode can also contain a locus specific barcode (locus barcode) that identifies the target to which it is to be associated. This locus barcode would be identical among all molecular bar-coding primers for each individual target and hence all resulting amplicons, but different from all other targets. In an embodiment, the tagging method described herein may be combined with a one-sided nesting protocol.

In an embodiment, the design and generation of molecular barcoding primers may be reduced to practice as follows: the molecular barcoding primers may consist of a sequence that is not complementary to the target sequence followed by random molecular barcode region followed by a target specific sequence. The sequence 5' of molecular barcode may be used for subsequence PCR amplification and may comprise sequences useful in the conversion of the amplicon to a library for sequencing. The random molecular barcode sequence could be generated in a multitude of ways. The preferred method synthesize the molecule tagging primer in such a way as to include all four bases to the reaction during synthesis of the barcode region. All or various combinations of bases may be specified using the IUPAC DNA ambiguity codes. In this manner the synthesized collection of molecules will contain a random mixture of sequences in the molecular barcode region. The length of the barcode region will determine how many primers will contain unique barcodes. The number of unique sequences is related to the length of the barcode region as $N^L$ where N is the number of bases, typically 4, and L is the length of the barcode. A barcode of five bases can yield up to 1024 unique sequences; a barcode of eight bases can yield 65536 unique barcodes. In an embodiment, the DNA can be measured by a sequencing method, where the sequence data represents the sequence of a single molecule. This can include methods in which single molecules are sequenced directly or methods in which single molecules are amplified to form clones detectable by the sequence instrument, but that still represent single molecules, herein called clonal sequencing.

In some embodiments, the molecular barcodes described herein are Molecular Index Tags ("MITs"), which are attached to a population of nucleic acid molecules from a sample to identify individual sample nucleic acid molecules from the population of nucleic acid molecules (i.e. members of the population) after sample processing for a sequencing reaction. MITs are described in detail in U.S. Pat. No. 10,011,870 to Zimmermann et al., which is incorporated herein by reference in its entirety. Unlike prior art methods that relate to unique identifiers and teach having a diversity of unique identifiers that is greater than the number of sample nucleic acid molecules in a sample in order to tag each sample nucleic acid molecule with a unique identifier, the present disclosure typically involves many more sample nucleic acid molecules than the diversity of MITs in a set of MITs. In fact, methods and compositions herein can include more than 1,000, $1\times10^6$, $1\times10^9$, or even more starting molecules for each different MIT in a set of MITs. Yet the methods can still identify individual sample nucleic acid molecules that give rise to a tagged nucleic acid molecule after amplification.

In the methods and compositions herein, the diversity of the set of MITs is advantageously less than the total number of sample nucleic acid molecules that span a target locus but the diversity of the possible combinations of attached MITs using the set of MITs is greater than the total number of sample nucleic acid molecules that span a target locus. Typically, to improve the identifying capability of the set of MITs, at least two MITs are attached to a sample nucleic acid molecule to form a tagged nucleic acid molecule. The sequences of attached MITs determined from sequencing reads can be used to identify clonally amplified identical copies of the same sample nucleic acid molecule that are attached to different solid supports or different regions of a solid support during sample preparation for the sequencing reaction. The sequences of tagged nucleic acid molecules can be compiled, compared, and used to differentiate nucleotide mutations incurred during amplification from nucleotide differences present in the initial sample nucleic acid molecules.

Sets of MITs in the present disclosure typically have a lower diversity than the total number of sample nucleic acid molecules, whereas many prior methods utilized sets of "unique identifiers" where the diversity of the unique identifiers was greater than the total number of sample nucleic acid molecules. Yet MITs of the present disclosure retain sufficient tracking power by including a diversity of possible combinations of attached MITs using the set of MITs that is greater than the total number of sample nucleic acid molecules that span a target locus. This lower diversity for a set of MITs of the present disclosure significantly reduces the cost and manufacturing complexity associated with generating and/or obtaining sets of tracking tags. Although the total number of MIT molecules in a reaction mixture is typically greater than the total number of sample nucleic acid molecules, the diversity of the set of MITs is far less than the total number of sample nucleic acid molecules, which substantially lowers the cost and simplifies the manufacturability over prior art methods. Thus, a set of MIT's can include a diversity of as few as 3, 4, 5, 10, 25, 50, or 100 different MITs on the low end of the range and 10, 25, 50, 100, 200, 250, 500, or 1000 MITs on the high end of the range, for example. Accordingly, in the present disclosure this relatively low diversity of MITs results in a far lower diversity of MITs than the total number of sample nucleic acid molecules, which in combination with a greater total number of MITs in the reaction mixture than total sample nucleic acid molecules and a higher diversity in the possible combinations of any 2 MITs of the set of MITs than the number of sample nucleic acid molecules that span a target locus, provides a particularly advantageous embodiment that is cost-effective and very effective with complex samples isolated from nature.

In some embodiments, the population of nucleic acid molecules has not been amplified in vitro before attaching the MITs and can include between $1\times10^8$ and $1\times10^{13}$, or in some embodiments, between $1\times10^9$ and $1\times10^{12}$ or between $1\times10^{10}$ and $1\times10^{12}$, sample nucleic acid molecules. In some embodiments, a reaction mixture is formed including the population of nucleic acid molecules and a set of MITs, wherein the total number of nucleic acid molecules in the population of nucleic acid molecules is greater than the diversity of MITs in the set of MITs and wherein there are at least three MITs in the set. In some embodiments, the diversity of the possible combinations of attached MITs using the set of MITs is more than the total number of sample nucleic acid molecules that span a target locus and less than the total number of sample nucleic acid molecules in the population. In some embodiments, the diversity of set of MITs can include between 10 and 500 MITs with different sequences. The ratio of the total number of nucleic acid molecules in the population of nucleic acid molecules in the sample to the diversity of MITs in the set, in certain methods and compositions herein, can be between 1,000:1 and 1,000,000,000:1. The ratio of the diversity of the possible combinations of attached MITs using the set of MITs to the total number of sample nucleic acid molecules that span a target locus can be between 1.01:1 and 10:1. The MITs typically are composed at least in part of an oligonucleotide between 4 and 20 nucleotides in length as discussed in more detail herein. The set of MITs can be designed such that the sequences of all the MITs in the set differ from each other by at least 2, 3, 4, or 5 nucleotides.

In some embodiments, provided herein, at least one (e.g. 2, 3, 5, 10, 20, 30, 50, 100) MIT from the set of MITs are attached to each nucleic acid molecule or to a segment of each nucleic acid molecule of the population of nucleic acid molecules to form a population of tagged nucleic acid molecules. MITs can be attached to a sample nucleic acid molecule in various configurations, as discussed further herein. For example, after attachment one MIT can be located on the 5' terminus of the tagged nucleic acid molecules or 5' to the sample nucleic acid segment of some, most, or typically each of the tagged nucleic acid molecules, and/or another MIT can be located 3' to the sample nucleic acid segment of some, most, or typically each of the tagged nucleic acid molecules. In other embodiments, at least two MITs are located 5' and/or 3' to the sample nucleic acid segments of the tagged nucleic acid molecules, or 5' and/or 3' to the sample nucleic acid segment of some, most, or typically each of the tagged nucleic acid molecules. Two MITs can be added to either the 5' or 3' by including both on the same polynucleotide segment before attaching or by performing separate reactions. For example, PCR can be performed with primers that bind to specific sequences within the sample nucleic acid molecules and include a region 5' to the sequence-specific region that encodes two MITs. In some embodiments, at least one copy of each MIT of the set of MITs is attached to a sample nucleic acid molecule, two copies of at least one MIT are each attached to a different sample nucleic acid molecule, and/or at least two sample nucleic acid molecules with the same or substantially the same sequence have at least one different MIT attached. A skilled artisan will identify methods for attaching MITs to nucleic acid molecules of a population of nucleic acid molecules. For example, MITs can be attached through ligation or appended 5' to an internal sequence binding site of a PCR primer and attached during a PCR reaction as discussed in more detail herein.

After or while MITs are attached to sample nucleic acids to form tagged nucleic acid molecules, the population of tagged nucleic acid molecules are typically amplified to create a library of tagged nucleic acid molecules. Methods for amplification to generate a library, including those particularly relevant to a high-throughput sequencing workflow, are known in the art. For example, such amplification can be a PCR-based library preparation. These methods can further include clonally amplifying the library of tagged nucleic acid molecules onto one or more solid supports using PCR or another amplification method such as an isothermal method. Methods for generating clonally amplified libraries onto solid supports in high-throughput sequencing sample preparation workflows are known in the art. Additional amplification steps, such as a multiplex amplification reaction in which a subset of the population of sample nucleic acid molecules are amplified, can be included in methods for identifying sample nucleic acids provided herein as well.

In some embodiments, a nucleotide sequence of the MITs and at least a portion of the sample nucleic acid molecule segments of some, most, or all (e.g. at least 2, 3, 4, 5, 6, 7, 8, 9, 10, 20, 25, 50, 75, 100, 150, 200, 250, 500, 1,000, 2,500, 5,000, 10,000, 15,000, 20,000, 25,000, 50,000, 100,000, 1,000,000, 5,000,000, 10,000,000, 25,000,000, 50,000,000, 100,000,000, 250,000,000, 500,000,000, $1\times10^9$, $1\times10^{10}$, $1\times10^{11}$, $1\times10^{12}$, or $1\times10^{13}$ tagged nucleic acid molecules or between 10, 20, 25, 30, 40, 50, 60, 70, 80, or 90% of the tagged nucleic acid molecules on the low end of the range and 20, 25, 30, 40, 50, 60, 70, 80, or 90, 95, 96, 97, 98, 99, and 100% on the high end of the range) of the tagged nucleic acid molecules in the library of tagged nucleic acid molecules is then determined. The sequence of a first MIT and optionally a second MIT or more MITs on clonally amplified copies of a tagged nucleic acid molecule can be used to identify the individual sample nucleic acid molecule that gave rise to the clonally amplified tagged nucleic acid molecule in the library.

In some embodiments, sequences determined from tagged nucleic acid molecules sharing the same first and optionally the same second MIT can be used to identify amplification errors by differentiating amplification errors from true sequence differences at target loci in the sample nucleic acid molecules. For example, in some embodiments, the set of MITs are double stranded MITs that, for example, can be a portion of a partially or fully double-stranded adapter, such as a Y-adapter. In these embodiments, for every starting molecule, a Y-adapter preparation generates 2 daughter molecule types, one in a + and one in a − orientation. A true mutation in a sample molecule should have both daughter molecules paired with the same 2 MITs in these embodiments where the MITs are a double stranded adapter, or a portion thereof. Additionally, when the sequences for the tagged nucleic acid molecules are determined and bucketed by the MITs on the sequences into MIT nucleic acid segment families, considering the MIT sequence and optionally its complement for double-stranded MITs, and optionally considering at least a portion of the nucleic acid segment, most, and typically at least 75% in double-stranded MIT embodiments, of the nucleic acid segments in an MIT nucleic acid segment family will include the mutation if the starting molecule that gave rise to the tagged nucleic acid molecules had the mutation. In the event of an amplification (e.g. PCR) error, the worst-case scenario is that the error occurs in cycle 1 of the $1^{st}$ PCR. In these embodiments, an amplification error will cause 25% of the final product to contain the error (plus any additional accumulated error, but this should be <<1%). Therefore, in some embodiments, if an MIT nucleic acid segment family contains at least 75% reads for a particular mutation or polymorphic allele, for example, it can be concluded that the mutation or polymorphic allele is truly present in the sample nucleic acid molecule that gave rise to the tagged nucleic acid molecule. The later an error occurs in a sample preparation process, the lower the proportion of sequence reads that include the error in a set of sequencing reads grouped (i.e. bucketed) by MITs into a paired MIT nucleic acid segment family. For example, an error in a library preparation amplification will result in a higher percentage of sequences with the error in a paired MIT nucleic acid segment family, than an error in a subsequent amplification step in the workflow, such as a targeted multiplex amplification. An error in the final clonal amplification in a sequencing workflow creates the lowest percentage of nucleic acid molecules in a paired MIT nucleic acid segment family that includes the error.

In some embodiments disclosed herein, the ratio of the total number of the sample nucleic acid molecules to the diversity of the MITs in the set of MITs or the diversity of the possible combinations of attached MITs using the set of MITs can be between 10:1, 20:1, 30:1, 40:1, 50:1, 60:1, 70:1, 80:1, 90:1, 100:1 200:1, 300:1, 400:1, 500:1, 600:1, 700:1, 800:1, 900:1, 1,000:1, 2,000:1, 3,000:1, 4,000:1, 5,000:1, 6,000:1, 7,000:1, 8,000:1, 9,000:1, 10,000:1, 15,000:1, 20,000:1, 25,000:1, 30,000:1, 40,000:1, 50,000:1, 60,000:1, 70,000:1, 80,000:1, 90,000:1, 100,000:1, 200,000:1, 300,000:1, 400,000:1, 500,000:1, 600,000:1, 700,000:1, 800,000:1, 900,000:1, and 1,000,000:1 on the low end of the range and 100:1 200:1, 300:1, 400:1, 500:1, 600:1, 700:1, 800:1, 900:1, 1,000:1, 2,000:1, 3,000:1, 4,000:1, 5,000:1, 6,000:1, 7,000:1, 8,000:1, 9,000:1, 10,000:1, 15,000:1, 20,000:1, 25,000:1, 30,000:1, 40,000:1, 50,000:1, 60,000:1, 70,000:1, 80,000:1, 90,000:1, 100,000:1, 200,000:1, 300,000:1, 400,000:1, 500,000:1, 600,000:1, 700,000:1, 800,000:1, 900,000:1, 1,000,000:1, 2,000,000:1, 3,000,000:1, 4,000,000:1, 5,000,000:1, 6,000,000:1, 7,000,000:1, 8,000,000:1, 9,000,000:1, 10,000,000:1, 50,000,000:1, 100,000,000:1, and 1,000,000,000:1 on the high end of the range.

In some embodiments, the sample is a human cfDNA sample. In such a method, as disclosed herein, the diversity is between about 20 million and about 3 billion. In these embodiments, the ratio of the total number of sample nucleic acid molecules to the diversity of the set of MITs can be between 100,000:1, $1\times10^6$:1, $1\times10^7$:1, $2\times10^7$:1, and $2.5\times10^7$:1 on the low end of the range and $2\times10^7$:1, $2.5\times10^7$:1, $5\times10^7$:1, $1\times10^8$:1, $2.5\times10^8$:1, $5\times10^8$:1, and $1\times10^9$:1 on the high end of the range.

In some embodiments, the diversity of possible combinations of attached MITs using the set of MITs is preferably greater than the total number of sample nucleic acid molecules that span a target locus. For example, if there are 100 copies of the human genome that have all been fragmented into 200 bp fragments such that there are approximately 15,000,000 fragments for each genome, then it is preferable that the diversity of possible combinations of MITs be greater than 100 (number of copies of each target locus) but less than 1,500,000,000 (total number of nucleic acid molecules). For example, the diversity of possible combinations of MITs can be greater than 100 but much less than 1,500,000,000, such as 200, 300, 400, 500, 600, 700, 800, 900, or 1,000 possible combinations of attached MITs. While the diversity of MITs in the set of MITs is less than the total number of nucleic acid molecules, the total number of MITs in the reaction mixture is in excess of the total number of nucleic acid molecules or nucleic acid molecule segments in the reaction mixture. For example, if there are 1,500,000,000 total nucleic acid molecules or nucleic acid molecule segments, then there will be more than 1,500,000,000 total MIT molecules in the reaction mixture. In some embodiments, the ratio of the diversity of MITs in the set of MITs can be lower than the number of nucleic acid molecules in a sample that span a target locus while the diversity of the possible combinations of attached MITs using the set of MITs can be greater than the number of nucleic acid molecules in the sample that span a target locus. For example, the ratio of the number of nucleic acid molecules in a sample that span a target locus to the diversity of MITs in the set of MITs can be at least 10:1, 25:1, 50:1, 100:1, 125:1, 150:1, or 200:1 and the ratio of the diversity of the possible combinations of attached MITs using the set of MITs to the number of nucleic acid molecules in the sample that span a target locus can be at least 1.01:1, 1.1:1, 2:1, 3:1, 4:1, 5:1, 6:1, 7:1, 8:1, 9:1, 10:1, 20:1, 25:1, 50:1, 100:1, 250:1, 500:1, or 1,000:1.

Typically, the diversity of MITs in the set of MITs is less than the total number of sample nucleic acid molecules that span a target locus whereas the diversity of the possible combinations of attached MITs is greater than the total number of sample nucleic acid molecules that span a target locus. In embodiments where 2 MITs are attached to sample nucleic acid molecules, the diversity of MITs in the set of MITs is less than the total number of sample nucleic acid molecules that span a target locus but greater than the square root of the total number of sample nucleic acid molecules that span a target locus. In some embodiments, the diversity of MITs is less than the total number of sample nucleic acid molecules that span a target locus but 1, 2, 3, 4, or 5 more than the square root of the total number of sample nucleic acid molecules that span a target locus. Thus, although the diversity of MITs is less than the total number of sample nucleic acid molecules that span a target locus, the total number of combinations of any 2 MITs is greater than the total number of sample nucleic acid molecules that span a target locus. The diversity of MITs in the set is typically less than one half the number of sample nucleic acid molecules than span a target locus in samples with at least 100 copies of each target locus. In some embodiments, the diversity of MITs in the set can be at least 1, 2, 3, 4, or 5 more than the square root of the total number of sample nucleic acid molecules that span a target locus but less than $\frac{1}{5}$, $\frac{1}{10}$, $\frac{1}{20}$, $\frac{1}{50}$, or $\frac{1}{100}$ the total number of sample nucleic acid molecules that span a target locus. For samples with between 2,000 and 1,000,000 sample nucleic acid molecules that span a target locus, the number of MITs in the set does not exceed 1,000. For example, in a sample with 10,000 copies of the genome in a genomic DNA sample such as a circulating cell-free DNA sample such that the sample has 10,000 sample nucleic acid molecules that span a target locus, the diversity of MITs can be between 101 and 1,000, or between 101 and 500, or between 101 and 250. In some embodiments, the diversity of MITs in the set of MITs can be between the square root of the total number of sample nucleic acid molecules that span a target locus and 1, 10, 25, 50, 100, 125, 150, 200, 250, 300, 400, 500, 600, 700, 800, 900, or 1,000 less than the total number of sample nucleic acid molecules that span a target locus. In some embodiments, the diversity of MITs in the set of MITs can be between 0.01%, 0.05%, 0.1%, 0.5%, 1%, 2%, 3%, 4%, 5%, 10%, 15%, 20%, 25%, 30%, 35%, 40%, 45%, 50%, 55%, 60%, 65%, 70%, 75%, and 80% of the number of sample nucleic acid molecules that span a target locus on the low end of the range and 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 96%, 97%, 98%, and 99% of the number of sample nucleic acid molecules that span a target locus on the high end of the range.

In some embodiments, the ratio of the total number of MITs in the reaction mixture to the total number of sample nucleic acid molecules in the reaction mixture can be between 1.01, 1.1:1, 2:1, 3:1, 4:1, 5:1, 6:1, 7:1, 8:1, 9:1, 10:1, 25:1 50:1, 100:1, 200:1, 300:1, 400:1, 500:1, 600:1, 700:1, 800:1, 900:1, 1,000:1, 2,000:1, 3,000:1, 4,000:1, 5,000:1, 6,000:1, 7,000:1, 8,000:1, 9,000:1, and 10,000:1 on the low end of the range and 25:150:1, 100:1, 200:1, 300:1, 400:1, 500:1, 600:1, 700:1, 800:1, 900:1, 1,000:1, 2,000:1, 3,000:1, 4,000:1, 5,000:1, 6,000:1, 7,000:1, 8,000:1, 9,000:1, 10,000:1, 15,000:1, 20,000:1, 25,000:1, 30,000:1, 40,000:1, and 50,000:1 on the high end of the range. In some embodiments, the total number of MITs in the reaction mixture is at least 50%, 60%, 70%, 80%, 90%, 95%, 96%, 97%, 98% 99%, or 99.9% of the total number of sample nucleic acid molecules in the reaction mixture. In other embodiments, the ratio of the total number of MITs in the reaction mixture to the total number of sample nucleic acid molecules in the reaction mixture can be at least enough MITs for each sample nucleic acid molecule to have the appropriate number of MITs attached, i.e. 2:1 for 2 MITs being attached, 3:1 for 3 MITs, 4:1 for 4 MITs, 5:1 for 5 MITs, 6:1 for 6 MITs, 7:1 for 7 MITs, 8:1 for 8 MITs, 9:1 for 0 MITs, and 10:1 for 10 MITs.

In some embodiments, the ratio of the total number of MITs with identical sequences in the reaction mixture to the total number of nucleic acid segments in the reaction mixture can be between 0.1:1, 0.2:1, 0.3:1, 0.4:1, 0.5:1, 0.6:1, 0.7:1, 0.8:1, 0.9:1, 1:1, 1.1:1, 1.2:1, 1.3:1, 1.4:1, 1.5:1, 1.6:1, 1.7:1, 1.8:1, 1.9:1, 2:1, 2.25:1, 2.5:1, 2.75:1, 3:1, 3.5:1, 4:1, 4.5:1, and 5:1 on the low end of the range and 0.5:1, 0.6:1, 0.7:1, 0.8:1, 0.9:1, 1:1, 1.1:1, 1.2:1, 1.3:1, 1.4:1, 1.5:1, 1.6:1, 1.7:1, 1.8:1, 1.9:1, 2:1, 2.25:1, 2.5:1, 2.75:1,3:1, 3.5:1, 4:1, 4.5:1, 5:1, 6:1, 7:1, 8:1, 9:1, 10:1, 20:1, 30:1, 40:1, 50:1, 60:1, 70:1, 80:1, 90:1, and 100:1 on the high end of the range.

The set of MITs can include, for example, at least three MITs or between 10 and 500 MITs. As discussed herein in some embodiments, nucleic acid molecules from the sample are added directly to the attachment reaction mixture without amplification. These sample nucleic acid molecules can be purified from a source, such as a living cell or organism, as disclosed herein, and then MITs can be attached without amplifying the nucleic acid molecules. In some embodiments, the sample nucleic acid molecules or nucleic acid segments can be amplified before attaching MITs. As discussed herein, in some embodiments, the nucleic acid molecules from the sample can be fragmented to generate sample nucleic acid segments. In some embodiments, other oligonucleotide sequences can be attached (e.g. ligated) to the ends of the sample nucleic acid molecules before the MITs are attached.

In some embodiments disclosed herein the ratio of sample nucleic acid molecules, nucleic acid segments, or fragments that include a target locus to MITs in the reaction mixture can be between 1.01:1, 1.05, 1.1:1, 1.2:1 1.3:1, 1.4:1, 1.5:1, 1.6:1, 1.7:1, 1.8:1, 1.9:1, 2:1, 2.5:1, 3:1, 4:1, 5:1, 6:1, 7:1, 8:1, 9:1, 10:1, 15:1, 20:1, 25:1, 30:1, 35:1, 40:1, 45:1, and 50:1 on the low end and 5:1, 6:1, 7:1, 8:1, 9:1, 10:1, 15:1, 20:1, 25:1, 30:1, 35:1, 40:1, 45:1, 50:1 60:1, 70:1, 80:1, 90:1, 100:1, 125:1, 150:1, 175:1, 200:1, 300:1, 400:1 and 500:1 on the high end. For example, in some embodiments, the ratio of sample nucleic acid molecules, nucleic acid segments, or fragments with a specific target locus to MITs in the reaction mixture is between 5:1, 6:1, 7:1, 8:1, 9:1, 10:1, 15:1, 20:1, 25:1, 30:1, 35:1, 40:1, 45:1, and 50:1 on the low end and 20:1, 25:1, 30:1, 35:1, 40:1, 45:1, 50:1, 60:1, 70:1, 80:1, 90:1, 100:1, and 200:1 on the high end. In some embodiments, the ratio of sample nucleic acid molecules or nucleic acid segments to MITs in the reaction mixture can be between 25:1, 30:1, 35:1, 40:1, 45:1, 50:1 on the low end and 50:1 60:1, 70:1, 80:1, 90:1, 100:1 on the high end. In some embodiments, the diversity of the possible combinations of attached MITs can be greater than the number of sample nucleic acid molecules, nucleic acid segments, or fragments that span a target locus. For example, in some embodiments, the ratio of the diversity of the possible combinations of attached MITs to the number of sample nucleic acid molecules, nucleic acid segments, or fragments that span a target locus can be at least 1.01, 1.1:1, 2:1, 3:1, 4:1, 5:1, 6:1, 7:1, 8:1, 9:1, 10:1, 20:1, 25:1, 50:1, 100:1, 250:1, 500:1, or 1,000:1.

Reaction mixtures for tagging nucleic acid molecules with MITs (i.e. attaching nucleic acid molecules to MITs), as provided herein, can include additional reagents in addition to a population of sample nucleic acid molecules and a set of MITs. For example, the reaction mixtures for tagging can include a ligase or polymerase with suitable buffers at an appropriate pH, adenosine triphosphate (ATP) for ATP-dependent ligases or nicotinamide adenine dinucleotide for NAD-dependent ligases, deoxynucleoside triphosphates (dNTPs) for polymerases, and optionally molecular crowding reagents such as polyethylene glycol. In certain embodiments the reaction mixture can include a population of sample nucleic acid molecules, a set of MITs, and a polymerase or ligase, wherein the ratio of the number of sample nucleic acid molecules, nucleic acid segments, or fragments with a specific target locus to the number of MITs in the reaction mixture can be any of the ratios disclosed herein, for example between 2:1 and 100:1, or between 10:1 and 100:1 or between 25:1 and 75:1, or is between 40:1 and 60:1, or between 45:1 and 55:1, or between 49:1 and 51:1.

In some embodiments disclosed herein the number of different MITs (i.e. diversity) in the set of MITs can be between 3, 4, 5, 6, 7, 8, 9, 10, 11, 12, 13, 14, 15, 16, 17, 18, 19, 20, 25, 30, 35, 40, 45, 50, 60, 70, 80, 90, 100, 125, 150, 175, 200, 250, 300, 350, 400, 450, 500, 600, 700, 800, 900, 1,000, 1,500, 2,000, 2,500, and 3,000 MITs with different sequences on the low end and 4, 5, 6, 7, 8, 9, 10, 11, 12, 13, 14, 15, 16, 17, 18, 19, 20, 25, 30, 35, 40, 45, 50, 60, 70, 80, 90, 100, 125, 150, 175, 200, 250, 300, 350, 400, 450, 500, 600, 700, 800, 900, 1,000, 2,000, 3,000, 4,000, and 5,000 MITs with different sequences on the high end. For example, the diversity of different MITs in the set of MITs can be between 20, 25, 30, 35, 40, 45, 50, 60, 70, 80, 90, and 100 different MIT sequences on the low end and 50, 60, 70, 80, 90, 100, 125, 150, 175, 200, 250, and 300 different MIT sequences on the high end. In some embodiments, the diversity of different MITs in the set of MITs can be between 50, 60, 70, 80, 90, 100, 125, and 150 different MIT sequences on the low end and 100, 125, 150, 175, 200, and 250 different MIT sequences on the high end. In some embodiments, the diversity of different MITs in the set of MITs can be between 3 and 1,000, or 10 and 500, or 50 and 250 different MIT sequences. In some embodiments, the diversity of possible combinations of attached MITs using the set of MITs can be between 4, 5, 6, 7, 8, 9, 10, 15, 20, 25, 30, 40, 50, 75, 100, 150, 200, 250, 300, 400, 500, and 1,000, 2,000, 3,000, 4,000, 5,000, 6,000, 7,000, 8,000, 9,000, 10,000, 20,000, 30,000, 40,000, 50,000, 60,000, 70,000, 80,000, 90,000, 100,000, 250,000, 500,000, 1,000,000, possible combinations of attached MITs on the low end of the range and 10, 15, 20, 25, 30, 40, 50, 75, 100, 150, 200, 250, 300, 400, 500, 1,000, 2,000, 3,000, 4,000, 5,000, 6,000, 7,000, 8,000, 9,000, 10,000, 20,000, 30,000, 40,000, 50,000, 60,000, 70,000, 80,000, 90,000, 100,000, 250,000, 500,000, 1,000,000, 2,000,000, 3,000,000, 4,000,000, 5,000,000, 6,000,000, 7,000,000, 8,000,000, 9,000,000, and 10,000,000 possible combinations of attached MITs on the high end of the range.

The MITs in the set of MITs are typically all the same length. For example, in some embodiments, the MITs can be any length between 2, 3, 4, 5, 6, 7, 8, 9, 10, 11, 12, 13, 14, 15, 16, 17, 18, 19, and 20 nucleotides on the low end and 4, 5, 6, 7, 8, 9, 10, 11, 12, 13, 14, 15, 16, 17, 18, 19, 20, 21, 22, 23, 24, 25, 26, 27, 28, 29, and 30 nucleotides on the high end. In certain embodiments, the MITs are any length between 3, 4, 5, 6, 7, or 8 nucleotides on the low end and 5, 6, 7, 8, 9, 10, or 11 nucleotides on the high end. In some embodiments, the lengths of the MITs can be any length between 4, 5, or 6, nucleotides on the low end and 5, 6, or 7 nucleotides on the high end. In some embodiments, the length of the MITs is 5, 6, or 7 nucleotides.

As will be understood, a set of MITs typically includes many identical copies of each MIT member of the set. In some embodiments, a set of MITs includes between 10, 20, 25, 30, 40, 50, 100, 500, 1,000, 10,000, 50,000, and 100,000 times more copies on the low end of the range, and 100, 500, 1,000, 10,000, 50,000, 100,000, 250,000, 500,000 and 1,000,000 more copies on the high end of the range, than the total number of sample nucleic acid molecules that span a target locus. For example, in a human circulating cell-free DNA sample isolated from plasma, there can be a quantity of DNA fragments that includes, for example, 1,000-100,000 circulating fragments that span any target locus of the genome. In certain embodiments, there are no more than ⅒, ¼, ½, or ¾ as many copies of any given MIT as total unique MITs in a set of MITs. Between members of the set, there can be 1, 2, 3, 4, 5, 6, 7, 8, 9, or 10 differences between any sequence and the rest of the sequences. In some embodiments, the sequence of each MIT in the set differs from all the other MITs by at least 1, 2, 3, 4, 5, 6, 7, 8, 9, or 10 nucleotides. To reduce the chance of misidentifying an MIT, the set of MITs can be designed using methods a skilled artisan will recognize, such as taking into consideration the Hamming distances between all the MITs in the set of MITs. The Hamming distance measures the minimum number of substitutions required to change one string, or nucleotide sequence, into another. Here, the Hamming distance measures the minimum number of amplification errors required to transform one MIT sequence in a set into another MIT sequence from the same set. In certain embodiments, different MITs of the set of MITs have a Hamming distance of less than 1, 2, 3, 4, 5, 6, 7, 8, 9, or 10 between each other.

In certain embodiments, a set of isolated MITs as provided herein is one embodiment of the present disclosure. The set of isolated MITs can be a set of single stranded, or partially, or fully double stranded nucleic acid molecules, wherein each MIT is a portion of, or the entire, nucleic acid molecule of the set. In certain examples, provided herein is a set of Y-adapter (i.e. partially double-stranded) nucleic acids that each include a different MIT. The set of Y-adapter nucleic acids can each be identical except for the MIT portion. Multiple copies of the same Y-adapter MIT can be included in the set. The set can have a number and diversity of nucleic acid molecules as disclosed herein for a set of MITs. As a non-limiting example, the set can include 2, 5, 10, or 100 copies of between 50 and 500 MIT-containing Y-adapters, with each MIT segment between 4 and 8 nucleic acids in length and each MIT segment differing from the other MIT segments by at least 2 nucleotides, but contain identical sequences other than the MIT sequence. Further details regarding Y-adapter portion of the set of Y-adapters is provided herein.

In other embodiments, a reaction mixture that includes a set of MITs and a population of sample nucleic acid molecules is one embodiment of the present disclosure. Furthermore, such a composition can be part of numerous methods and other compositions provided herein. For example, in further embodiments, a reaction mixture can include a polymerase or ligase, appropriate buffers, and supplemental components as discussed in more detail herein. For any of these embodiments, the set of MITs can include between 25, 50, 100, 200, 250, 300, 400, 500, or 1,000 MITs on the low end of the range, and 100, 200, 250, 300, 400, 500, 1,000, 1,500, 2,000, 2,500, 5,000, 10,000, or 25,000 MITs on the high end of the range. For example, in some embodiments, a reaction mixture includes a set of between 10 and 500 MITs.

Molecular Index Tags (MITs) as discussed in more detail herein can be attached to sample nucleic acid molecules in the reaction mixture using methods that a skilled artisan will recognize. In some embodiments, the MITs can be attached alone, or without any additional oligonucleotide sequences. In some embodiments, the MITs can be part of a larger oligonucleotide that can further include other nucleotide sequences as discussed in more detail herein. For example, the oligonucleotide can also include primers specific for nucleic acid segments or universal primer binding sites, adapters such as sequencing adapters such as Y-adapters, library tags, ligation adapter tags, and combinations thereof. A skilled artisan will recognize how to incorporate various tags into oligonucleotides to generate tagged nucleic acid molecules useful for sequencing, especially high-throughput sequencing. The MITs of the present disclosure are advantageous in that they are more readily used with additional sequences, such as Y-adapter and/or universal sequences because the diversity of nucleic acid molecules is less, and therefore they can be more easily combined with additional sequences on an adapter to yield a smaller, and therefore more cost effective set of MIT-containing adapters.

In some embodiments, the MITs are attached such that one MIT is 5' to the sample nucleic acid segment and one MIT is 3' to the sample nucleic acid segment in the tagged nucleic acid molecule. For example, in some embodiments, the MITs can be attached directly to the 5' and 3' ends of the sample nucleic acid molecules using ligation. In some embodiments disclosed herein, ligation typically involves forming a reaction mixture with appropriate buffers, ions, and a suitable pH in which the population of sample nucleic acid molecules, the set of MITs, adenosine triphosphate, and a ligase are combined. A skilled artisan will understand how to form the reaction mixture and the various ligases available for use. In some embodiments, the nucleic acid molecules can have 3' adenosine overhangs and the MITs can be located on double-stranded oligonucleotides having 5' thymidine overhangs, such as directly adjacent to a 5' thymidine.

In further embodiments, MITs provided herein can be included as part of Y-adapters before they are ligated to sample nucleic acid molecules. Y-adapters are well-known in the art and are used, for example, to more effectively provide primer binding sequences to the two ends of the nucleic acid molecules before high-throughput sequencing. Y-adapters are formed by annealing a first oligonucleotide and a second oligonucleotide where a 5' segment of the first oligonucleotide and a 3' segment of the second oligonucleotide are complementary and wherein a 3' segment of the first oligonucleotide and a 5' segment of the second oligonucleotide are not complementary. In some embodiments, Y-adapters include a base-paired, double-stranded polynucleotide segment and an unpaired, single-stranded polynucleotide segment distal to the site of ligation. The double-stranded polynucleotide segment can be between 3, 4, 5, 6, 7, 8, 9, 10, 11, 12, 13, 14, 15, 16, 17, 18, 19, or 20 nucleotides in length on the low end of the range and 4, 5, 6, 7, 8, 9, 10, 11, 12, 13, 14, 15, 16, 17, 18, 19, 20, 21, 22, 23, 24, 25, 26, 27, 28, 29, and 30 nucleotides in length on the high end of the range. The single-stranded polynucleotide segments on the first and second oligonucleotides can be between 3, 4, 5, 6, 7, 8, 9, 10, 11, 12, 13, 14, 15, 16, 17, 18, 19, or 20 nucleotides in length on the low end of the range and 4, 5, 6, 7, 8, 9, 10, 11, 12, 13, 14, 15, 16, 17, 18, 19, 20, 21, 22, 23, 24, 25, 26, 27, 28, 29, and 30 nucleotides in length on the high end of the range. In these embodiments, MITs are typically double stranded sequences added to the ends of Y-adapters, which are ligated to sample nucleic acid segments to be sequenced. In some embodiments, the non-complementary segments of the first and second oligonucleotides can be different lengths.

In some embodiments, double-stranded MITs attached by ligation will have the same MIT on both strands of the sample nucleic acid molecule. In certain aspects the tagged nucleic acid molecules derived from these two strands will be identified and used to generate paired MIT families. In downstream sequencing reactions, where single stranded nucleic acids are typically sequenced, an MIT family can be identified by identifying tagged nucleic acid molecules with identical or complementary MIT sequences. In these embodiments, the paired MIT families can be used to verify the presence of sequence differences in the initial sample nucleic acid molecule as discussed herein.

In some embodiments, MITs can be attached to the sample nucleic acid segment by being incorporated 5' to forward and/or reverse PCR primers that bind sequences in the sample nucleic acid segment. In some embodiments, the MITs can be incorporated into universal forward and/or reverse PCR primers that bind universal primer binding sequences previously attached to the sample nucleic acid molecules. In some embodiments, the MITs can be attached using a combination of a universal forward or reverse primer with a 5' MIT sequence and a forward or reverse PCR primer that bind internal binding sequences in the sample nucleic acid segment with a 5' MIT sequence. After 2 cycles of PCR, sample nucleic acid molecules that have been amplified using both the forward and reverse primers with incorporated MIT sequences will have MITs attached 5' to the sample nucleic acid segments and 3' to the sample nucleic acid segments in each of the tagged nucleic acid molecules. In some embodiments, the PCR is done for 2, 3, 4, 5, 6, 7, 8, 9, or 10 cycles in the attachment step.

In some embodiments disclosed herein the two MITs on each tagged nucleic acid molecule can be attached using similar techniques such that both MITs are 5' to the sample nucleic acid segments or both MITs are 3' to the sample nucleic acid segments. For example, two MITs can be incorporated into the same oligonucleotide and ligated on one end of the sample nucleic acid molecule or two MITs can be present on the forward or reverse primer and the paired reverse or forward primer can have zero MITs. In other embodiments, more than two MITs can be attached with any combination of MITs attached to the 5' and/or 3' locations relative to the nucleic acid segments.

As discussed herein, other sequences can be attached to the sample nucleic acid molecules before, after, during, or with the MITs. For example, ligation adapters, often referred to as library tags or ligation adaptor tags (LTs), appended, with or without a universal primer binding sequence to be used in a subsequent universal amplification step. In some embodiments, the length of the oligonucleotide containing the MITs and other sequences can be between 5, 6, 7, 8, 9, 10, 11, 12, 13, 14, 15, 16, 17, 18, 29, 20, 21, 22, 23, 24, 25, 26, 27, 28, 29, 30, 35, 40, 45, 50, 55, 60, 65, 70, 75, 80, 85, 90, 95, and 100 nucleotides on the low end of the range and 10, 11, 12, 13, 14, 15, 16, 17, 18, 29, 20, 21, 22, 23, 24, 25, 26, 27, 28, 29, 30, 35, 40, 45, 50, 55, 60, 65, 70, 75, 80, 85, 90, 95, 100, 110, 120, 130, 140, 150, 160, 170, 180, 190, and 200 nucleotides on the high end of the range. In certain aspects the number of nucleotides in the MIT sequences can be a percentage of the number of nucleotides in the total sequence of the oligonucleotides that include MITs. For example, in some embodiments, the MIT can be at most 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% of the total nucleotides of an oligonucleotide that is ligated to a sample nucleic acid molecule.

After attaching MITs to the sample nucleic acid molecules through a ligation or PCR reaction, it may be necessary to clean up the reaction mixture to remove undesirable components that could affect subsequent method steps. In some embodiments, the sample nucleic acid molecules can be purified away from the primers or ligases. In other embodiments, the proteins and primers can be digested with proteases and exonucleases using methods known in the art.

After attaching MITs to the sample nucleic acid molecules, a population of tagged nucleic acid molecules is generated, itself forming embodiments of the present disclosure. In some embodiments, the size ranges of the tagged nucleic acid molecules can be between 10, 20, 30, 40, 50, 60, 70, 80, 90, 100, 125, 150, 175, 200, 250, 300, 400, and 500 nucleotides on the low end of the range and 100, 125, 150, 175, 200, 250, 300, 400, 500, 600, 700, 800, 900, 1,000, 2,000, 3,000, 4,000, and 5,000 nucleotides on the high end of the range.

Such a population of tagged nucleic acid molecules can include between 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 225, 250, 300, 350, 400, 450, 500, 600, 700, 800, 900, 1,000, 2,000, 3,000, 4,000, 5,000, 6,000, 7,000, 8,000, 9,000, 10,000, 15,000, 20,000, 30,000, 40,000, 50,000, 100,000, 200,000, 300,000, 400,000, 500,000, 600,000, 700, 000, 800,000, 900,000, 1,000,000, 1,250,000, 1,500,000, 2,000,000, 2,500,000, 3,000,000, 4,000,000, 5,000,000, 10,000,000, 20,000,000, 30,000,000, 40,00,000, 50,000, 000, 50,000,000, 100,000,000, 200,000,000, 300,000,000, 400,000,000, 500,000,000, 600,000,000, 700,000,000, 800, 000,000, 900,000,000, and 1,000,000,000 tagged nucleic acid molecules on the low end of the range and 10, 15, 20, 25, 30, 40, 50, 60, 70, 80, 90, 100, 150, 200, 250, 300, 400, 500, 600, 700, 800, 900, 1,000, 2,000, 3,000, 4,000, 5,000, 6,000, 7,000, 8,000, 9,000, 10,000, 15,000, 20,000, 30,000, 40,000, 50,000, 100,000, 200,000, 300,000, 400,000, 500, 000, 600,000, 700,000, 800,000, 900,000, 1,000,000, 1,250, 000, 1,500,000, 2,000,000, 2,500,000, 3,000,000, 4,000,000, 5,000,000, 6,000,000, 7,000,000, 8,000,000, 9,000,000, 10,000,000, 20,000,000, 30,000,000, 40,00,000, 50,000,000, 100,000,000, 200,000,000, 300,000,000, 400,000,000, 500,000,000, 600,000,000, 700,000,000, 800,000,000, 900,000,000, 1,000,000,000, 2,000,000,000, 3,000,000,000, 4,000,000,000, 5,000,000,000, 6,000,000,000, 7,000,000,000, 8,000,000,000, 9,000,000,000, and 10,000,000,000, tagged nucleic acid molecules on the high end of the range. In some embodiments, the population of tagged nucleic acid molecules can include between 100,000,000, 200,000,000, 300,000,000, 400,000,000, 500,000,000, 600,000,000, 700,000,000, 800,000,000, 900,000,000, and 1,000,000,000 tagged nucleic acid molecules on the low end of the range and 500,000,000, 600,000,000, 700,000,000, 800,000,000, 900,000,000, 1,000,000,000, 2,000,000,000, 3,000,000,000, 4,000,000,000, 5,000,000,000 tagged nucleic acid molecules on the high end of the range.

In certain aspects a percentage of the total sample nucleic acid molecules in the population of sample nucleic acid molecules can be targeted to have MITs attached. In some embodiments, at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or 99.9% of the sample nucleic acid molecules can be targeted to have MITs attached. In other aspects a percentage of the sample nucleic acid molecules in the population can have MITs successfully attached. In any of the embodiments disclosed herein at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or 99.9% of the sample nucleic acid molecules can have MITs successfully attached to form the population of tagged nucleic acid molecules. In any of the embodiments disclosed herein at least 1, 2, 3, 4, 5, 6, 7, 8, 9, 10, 15, 20, 25, 30, 40, 50, 75, 100, 200, 300, 500, 600, 700, 800, 900, 1,000, 2,000, 3,000, 4,000, 5,000, 6,000, 7,000, 8,000, 9,000, 10,000, 15,000, 20,000, 30,000, 40,000, or 50,000 of the sample nucleic acid molecules can have MITs successfully attached to form the population of tagged nucleic acid molecules.

In some embodiments disclosed herein, MITs can be oligonucleotide sequences of ribonucleotides or deoxyribonucleotides linked through phosphodiester linkages. Nucleotides as disclosed herein can refer to both ribonucleotides and deoxyribonucleotides and a skilled artisan will recognize when either form is relevant for a particular application. In certain embodiments, the nucleotides can be selected from the group of naturally-occurring nucleotides consisting of adenosine, cytidine, guanosine, uridine, 5-methyluridine, deoxyadenosine, deoxycytidine, deoxyguanosine, deoxythymidine, and deoxyuridine. In some embodiments, the MITs can be non-natural nucleotides. Non-natural nucleotides can include: sets of nucleotides that bind to each other, such as, for example, d5SICS and dNaM; metal-coordinated bases such as, for example, 2,6-bis(ethylthiomethyl)pyridine (SPy) with a silver ion and mondentate pyridine (Py) with a copper ion; universal bases that can pair with more than one or any other base such as, for example, 2'-deoxyinosine derivatives, nitroazole analogues, and hydrophobic aromatic non-hydrogen-bonding bases; and xDNA nucleobases with expanded bases. In certain embodiments, the oligonucleotide sequences can be predetermined while in other embodiments, the oligonucleotide sequences can be degenerate.

In some embodiments, MITs include phosphodiester linkages between the natural sugars ribose and/or deoxyribose that are attached to the nucleobase. In some embodiments, non-natural linkages can be used. These linkages include, for example, phosphorothioate, boranophosphate, phosphonate, and triazole linkages. In some embodiments, combinations of the non-natural linkages and/or the phosphodiester linkages can be used. In some embodiments, peptide nucleic acids can be used wherein the sugar backbone is instead made of repeating N-(2-aminoethyl)-glycine units linked by peptide bonds. In any of the embodiments disclosed herein non-natural sugars can be used in place of the ribose or deoxyribose sugar. For example, threose can be used to generate α-(L)-threofuranosyl-(3'-2') nucleic acids (TNA). Other linkage types and sugars will be apparent to a skilled artisan and can be used in any of the embodiments disclosed herein.

In some embodiments, nucleotides with extra bonds between atoms of the sugar can be used. For example, bridged or locked nucleic acids can be used in the MITs. These nucleic acids include a bond between the 2'-position and 4'-position of a ribose sugar.

In certain embodiments, the nucleotides incorporated into the sequence of the MIT can be appended with reactive linkers. At a later time, the reactive linkers can be mixed with an appropriately-tagged molecule in suitable conditions for the reaction to occur. For example, aminoallyl nucleotides can be appended that can react with molecules linked to a reactive leaving group such as succinimidyl ester and thiol-containing nucleotides can be appended that can react with molecules linked to a reactive leaving group such as maleimide. In other embodiments, biotin-linked nucleotides can be used in the sequence of the MIT that can bind streptavidin-tagged molecules.

Various combinations of the natural nucleotides, non-natural nucleotides, phosphodiester linkages, non-natural linkages, natural sugars, non-natural sugars, peptide nucleic acids, bridged nucleic acids, locked nucleic acids, and nucleotides with appended reactive linkers will be recognized by a skilled artisan and can be used to form MITs in any of the embodiments disclosed herein.

Error Modeling

Figure 8:
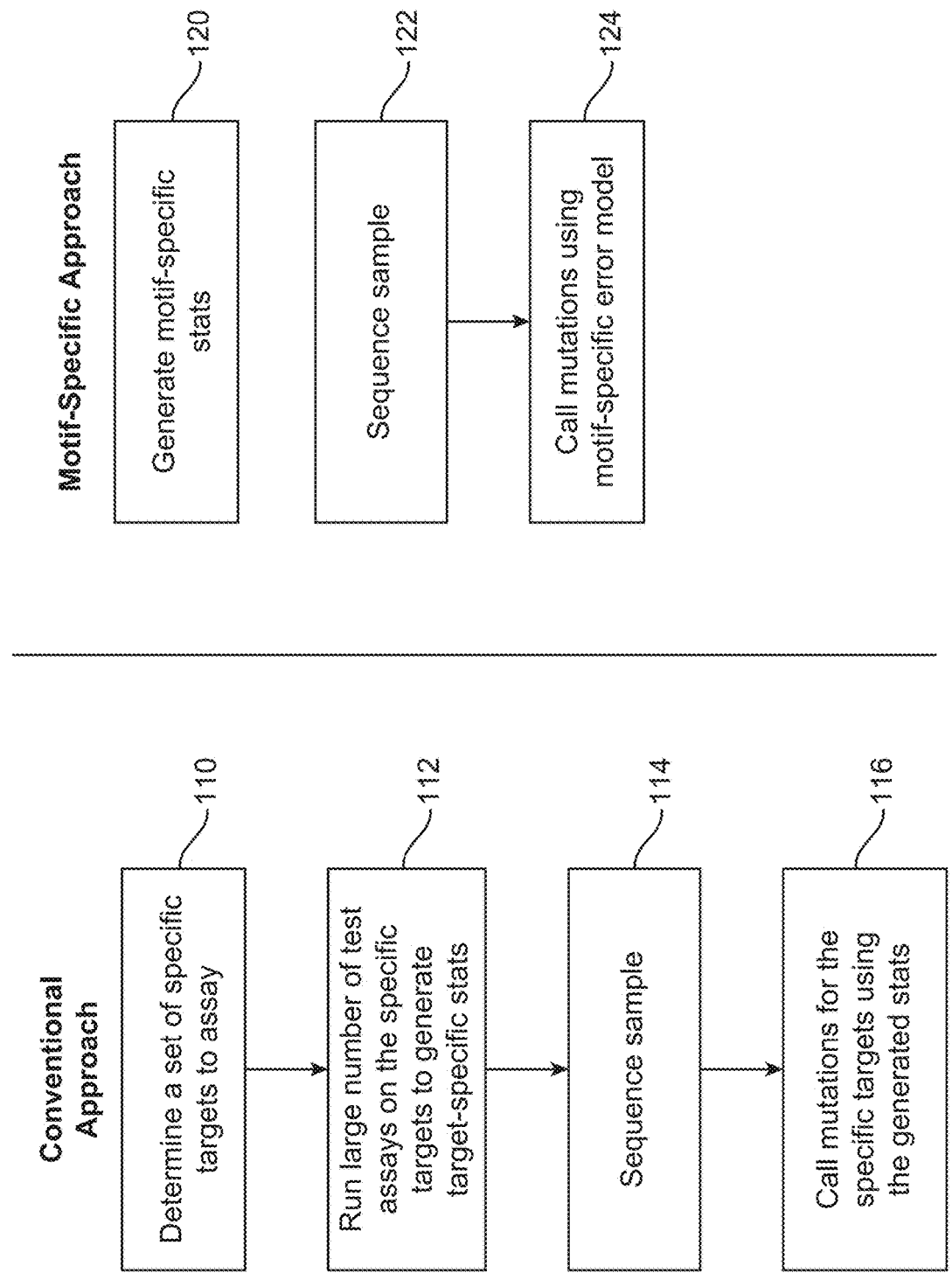
FIG. 8 is a flow-chart illustrating a conventional approach to mutation calling and a motif-specific approach to mutation calling.

Referring now to FIG. 8, an illustration of a base-specific analysis and a motif-specific analysis of a sample are shown. The conventional approach includes at least four steps: determining a set of specific targets to assay (BLOCK 110), running a large number of test assays on the specific targets to generate target-specific statistics (BLOCK 112), sequencing a sample (BLOCK 114), and calling mutations for the specific targets using the generated statistics (BLOCK 116).

At BLOCK 110, a set of specific targets to be assayed is determine. Calling mutation using the conventional approach shown in FIG. 8 is limited to calling mutations for the specific targets determined at BLOCK 110. At BLOCK 112, dozens or hundreds of test assays may be performed for each target of interest (each target determined in BLOCK 110) to generate test data. For example, the test assays may include performing a PCR process on genetic segments extracted from a test sample. The amplified result of the PCR process may be exhaustively sequenced to generate background error statistics. For example, errors or mutations detected in the amplified result may be ascribed to errors induced by the PCR process, and a PCR propagation error rate may be estimated for the genetic sequences being assayed. A large number of test assays may be performed for each specific target to improve the estimate of the PCR propagation error rate.

At BLOCK 114, a genetic sample can be sequenced, and at BLOCK 116 mutations can be called using the determined PCR propagation error rate to account for at least some background error, and/or using other statistics generated at BLOCK 112. Mutations can only be called for the specific targets for which statistics were generated at BLOCK 112. Thus, to call mutations for a large number of targets of the sequenced sample, a very large number of test assays are performed, which can be expensive and time consuming.

The motif-specific approach improves on the conventional approach by providing for omission of the large number of target-specific test assays. Instead of generating target-specific statistics, an error model that provides for motif-specific statistics is used, which can be applied in a more general manner than can the target-specific approach (e.g. can be applied to any target having a same or similar motif as a motif used to generate test statistics). At BLOCK 120, using the methods and systems described herein, motif-specific statistics can be generated, which can constitute, or be used as part of, a motif-specific error model. Once a motif-specific error model has been established, the motif-specific approach can be implemented by sequencing a sample at BLOCK 122 and by calling mutations to targets having a specific motif using the motif-specific error model at BLOCK 124. The motif-specific error model has wide applicability. For example, a new sample can differ in at least some regards from a training sample used to generate the motif-specific error model, and it may be desirable to sequence targets for which no target-specific statistics exist (or for which existent statistics have an unacceptably or undesirably high degree of uncertainty). By using the motif-specific approach that leverages the tendency of background error to be motif-specific, the motif-specific error model can provide for accurate estimates of error associated with target bases in a sample that have a same motif as was analyzed and incorporated into the motif-specific error model, even though the target bases may be at different positions than the bases included in the training data used to generate the motif-specific error model. Thus, a large number of motif-specific test assays need not be performed for each sequencing and calling process for a sample to be sequenced. The motif-specific approach provides for accurate estimates of expected background error, which in turn can provide for highly accurate calling of mutations.

The present disclosure describes systems and methods that can be used to implement the motif-specific approach described above. The present disclosure describes statistical models, algorithms, and their implementation (e.g. for recurrence monitoring (RM)). RM can detect tumor specific mutations (targets) in a subject's plasma that are contributed by circulating tumor DNA (ctDNA). For that purpose targeted sequencing of a subject's plasma sample can be employed. Denoting the number of reads for a mutation at a certain position by E and the total number of reads at this position by X, and assuming that E comes from a Beta-Binomial distribution with parameters X and $p(\alpha, \beta)$ $$E \sim BB(X, p(\alpha, \beta)) \quad (1)$$

where p comes from Beta distribution with parameters $\alpha$ and $\beta$ that are functions of replication efficiency and background error specific to sample preparation, these parameters can be estimated from a set of training samples with no mutations. In addition, these parameters are considered to be dependent on the fraction of ctDNA having the mutation, also called the real error as opposed to the background error of the PCR process generated in sample preparation. Since the fraction of ctDNA present in the plasma sample may be unknown, $\alpha$ and $\beta$ can be evaluated on a grid of values, and a mutation fraction that produces the highest probability for the data can be selected.

Training or Sample Data Preparation

Figure 9:
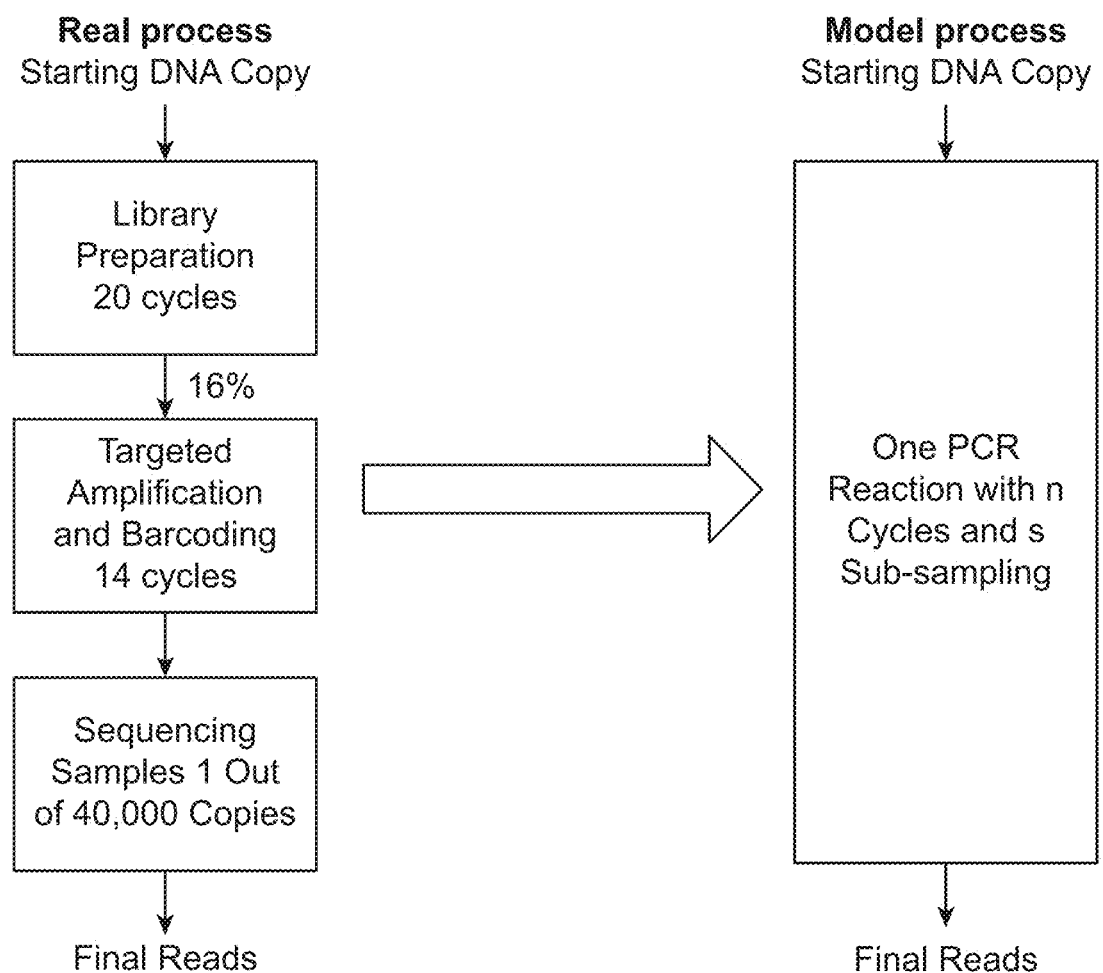
FIG. 9 illustrates one or more implementations of modelling a sample preparation process.

In some RM applications, samples are prepared in the lab in the course of two separate PCR reactions. After each reaction, only a portion of the product is passed to the next stage. This may be referred to as subsampling. To simplify computations, the present disclosure model the process by one PCR reaction with combined subsampling as illustrated in FIG. 9.

Some example implementations consider a total subsampling rate of $6 \times 10^{-5}$ to model the process. The model assumes that a) the replication rate, or efficiency, p is constant from cycle to cycle; b) error rate $p_e$ is small compared to replication rate; c) an error occurs only once in the replication process, meaning that if a nucleotide base is substituted by another it will keep replicating unchanged for the rest of the process.

Number of PCR Cycles

An RM variant calling algorithm estimates random SNV or indel error rate during the PCR reaction. The resulting frequency of PCR induced mutations depends on the number of PCR cycles that sample goes through. The number of cycles increases dynamically for samples with low initial DNA amounts as the saturation is reached later. Only the library preparation PCR reaction is affected by variable number of cycles. The starcoding reaction (targeted amplification and barcoding) is assumed to have the same number of cycles. Therefore, the total number of cycles is given by $n_{total} = n_{libprep} + n_{starcoding}$. Based on the DNA input amount to library preparation step the algorithm estimates the total number of cycles to compute the expected PCR error more accurately. The number of cycles during library preparation is computed assuming the following starting_copies* $(1+p)^{nlibprep}$*libprep_loss=libprep_output_copies, where p is replication efficiency taken to be 0.9, libprep_loss is 0.75, libprep_output_copies=$3*10^6$, and $$\text{starting\_copies} = \frac{x_{input}}{3.3 * 10^{-3}},$$

where $x_{input}$ is the DNA input amount in nanograms (ng). The $n_{starcoding}$ is calibrated from the data to generated $10^4$ starting copies for samples with 33 ng input amount.

Estimating a Mutation Fraction Distribution and Parameters

Estimating the above mentioned parameters $\alpha$ and $\beta$ from the expectation and variance of the error rate can be implemented as follows. If $\mu$ is the expectation of the error rate after the PCR process and var is its variance as in $$\mu = \mathbb{E}\left(\frac{E}{X}\right) \quad (2)$$

$$\text{var} = \mathbb{V}\left(\frac{E}{X}\right) \quad (3)$$

then $\alpha$ and $\beta$ of the corresponding Beta distribution are computed as $$\alpha = \mu^2 \frac{1-\mu}{\text{var}} - \mu \quad (4)$$

$$\beta = \alpha \frac{1}{\mu} - 1 \quad (5)$$

The following expansion can be used to estimate µ and var $$\mu = \mathbb{E}\left(\frac{E}{X}\right) \approx \frac{\mathbb{E}(E)}{\mathbb{E}(X)} - \frac{\text{Cov}(E, X)}{(\mathbb{E}(X))^2} + \frac{\mathbb{E}(E)\mathbb{V}(X)}{(\mathbb{E}(X))^3} \quad (6)$$

$$\text{var} = \mathbb{V}\left(\frac{E}{X}\right) \approx \frac{\mathbb{V}(E)}{(\mathbb{E}(X))^2} - \frac{2\mathbb{E}(E)\text{Cov}(E, X)}{(\mathbb{E}(X))^3} + \frac{(\mathbb{E}(E))^2 \mathbb{V}(X)}{(\mathbb{E}(X))^4} \quad (7)$$

Here, as defined above, X is the total number of reads and E is the number of reads for an error base, meaning the base that is different from the reference base. Since there are three possible changes from the reference (e.g. A can change to T, C, or G), there will be three expected error rates, one per each mutant base, or channel. The total error counts come from at least two sources—mutation in tumor DNA that is present before replication process and an erroneous substitution during the PCR process used in sample preparation. The former is referred to as the real error, and the latter as the background error.

$$E = E^r + E^b \quad (8)$$

To determine a mutation fraction, or a probability distribution thereof, the replication efficiency and the probability of the background error per cycle is estimated from a set of training samples that are not expected to have any real mutations. Then, the starting count (or starting copy) is estimated based on the PCR efficiency. Using this estimate, the expectation and variance of total and error counts after the PCR process are computed, and can be plugged into Equations 6 and 7. Then, using Equations 4 and 5, the mutation fraction distribution parameters α and β can be determined.

Modeling of the PCR Process and Useful Formulas

Assuming that at each PCR cycle n a) new DNA molecules are generated from the molecules present at the end of the previous cycle n−1 as governed by a binomial random process; b) molecules with a background error come from replication of errors from the previous cycle and new errors that occur at the current cycle randomly according the binomial random process with probability of error $p_e$, having zero background errors present at the beginning of the PCR process; c) replication error occurs once per molecule and is not reversible; d) real errors are replicated with the same efficiency as normal molecules and their initial quantity is a fraction of the total molecules (e.g. if the starting copy is denoted by $X_0$ then there are f $X_0$ mutant molecules among them), then $$X_n - X_{n-1} \sim B(X_{n-1}, p)$$

$$E_n^b - E_{n-1}^b \sim B((X_{n-1} - E_{n-1}^b), p_e) + B(E_{n-1}^b, p)$$

$$E_0^r = f X_0 \quad (9)$$

Several values of f can be considered to find one that fits the data best.

1. Expectation and Variance of Total Reads

From Equations 9, the expectation of the number of total reads conditioned on replication efficiency is given by $$\mathbb{E}_{(X_n|p)} = \mathbb{E}_{(X_{n-1}|p)} + p \, \mathbb{E}_{(X_{n-1}|p)} = (1+p)^n \, \mathbb{E}_{(X_0)} \quad (10)$$

The variance of this variable is given by $$\mathbb{V}(X_n|p) = p(1-p)\mathbb{E}(X_{n-1}|p) + \mathbb{V}(X_{n-1}|p) = \quad (11)$$
$$(1-p)(1+p)^{n-1}((1+p)^n - 1)\mathbb{E}(X_0) + (1+p)^{2n}\mathbb{V}(X_0)$$

Here the last equality in each equation is produced by solving the recursive relation from the first part of the equation.

2. Expectation and Variance for the Real Error Reads

Similarly to the total number of reads, for the real error the following equations apply:

$$\mathbb{E}_{(E_n^r|p)} = f(1+p)^n \, \mathbb{E}_{(X_0)}$$

$$\mathbb{V}_{(E_n^r|p)} = f(1-p)(1+p)^{n-1}((1+p)^n - 1) \, \mathbb{E}_{(X_0)} + f^2 (1+p)^{2n} \, \mathbb{V}_{(X_0)} \quad (12)$$

3. Expectation and Variance for Background Error

For the sake of shortening the notations, in this section explicit reference to conditioning on p is omitted, but the statistics are conditional on p.

Expectation of Background Error Reads

From Equations 9:

$$\mathbb{E}_{(E_n^b|E_{n-1}^b X_{n-1})} = (1+p)E_{n-1}^b + p_e(X_{n-1} - n - E_{n-1}^b)$$

which gives $$\mathbb{E}(E_n^b) = (1 + p - p_e)\mathbb{E}(E_{n-1}^b) + p_e \mathbb{E}(X_{n-1}) =$$
$$(1 + p - p_e)\mathbb{E}(E_{n-1}^b) + p_e(1+p)^{n-1}\mathbb{E}(X_0)$$

where Equation 10 was used. Solving the recursive relation provides $$\mathbb{E}(E_n^b) = ((1+p)^n - (1+p-p_e)^n)\mathbb{E}(X_0) = (1+p)^n\left(1 - \left(1 - \frac{p_e}{1+p}\right)^n\right)\mathbb{E}(X_0)$$

For subsequent derivations, the approximation of this expression that comes from the equation above under the assumption that $p_e \ll p$ is used $$\mathbb{E}_{(E_n^b)} \approx n p_e (1+p)^{n-1} \, \mathbb{E}_{(X_0)} \quad (13)$$

Variance of Background Error Reads

Some intermediate expressions that will be used in the following derivation are as follows:

$$\mathbb{E}_{(E_n^b|E_{n-1}^b X_{n-1})} = (1+p-p_e)E_{n-1}^b + p_e X_{n-1} \quad (14)$$

$$\mathbb{V}_{(E_n^b|E_{n-1}^b X_{n-1})} = p(1-p) - p_e(1-p_e(1-p_e))E_{n-1}^b + p_e(1-p_e)X_{n-1} \quad (15)$$

These follow directly from Equation 9. In deriving the last equation, the fact that $\text{Cov}(B(E_n^b, p), B(X_n - E_n^b, p_e)) = 0$ was used.

With these, the variance term for the background error can be written as $$\mathbb{V}(E_n^b) = \mathbb{E}(\mathbb{V}(E_n^b|E_{n-1}^b X_{n-1})) + \mathbb{V}(\mathbb{E}(E_n^b|E_{n-1}^b X_{n-1})) == \quad (16)$$
$$\mathbb{E}((p(1-p) - p_e(1-p_e))E_{n-1}^b +$$
$$\mathbb{E}(p_e(1-p_e)X_{n-1}) + + \mathbb{V}((1+p-p_e)E_{n-1}^b + p_e X_{n-1} ==$$
$$(p(1-p) - p_e(1-p_e))\mathbb{E}(E_{n-1}^b) +$$
$$p_e(1-p_e)\mathbb{E}(X_{n-1}) + + p_e^2 \mathbb{V}(X_{n-1}) +$$
$$2p_e(1+p-p_e)\text{Cov}(E_{n-1}^b, X_{n-1}) + (1+p-p_e)^2 \mathbb{V}(E_{n-1}^b)$$

In the last equation, all terms except the last two have been computed. The very last term is used in a recursive relation that can provide the solution for variance. Thus the only term left to compute is the covariance.

The covariance term is computed separately since it is going to be useful by itself for the covariance of the total error with the total reads that enters Equations 6.

$$\mathrm{Cov}(E_n^b, X_n) =$$
$$\mathbb{E}(\mathrm{Cov}(E_n^b, X_n | E_{n-1}^b X_{n-1}) + \mathrm{Cov}(\mathbb{E}(E_b^n | E_{n-1}^b X_{n-1}), \mathbb{E}(X_n | E_{n-1}^b X_{n-1})) ==$$
$$\mathbb{E}(\mathrm{Cov}(E_{n-1}^b + B(E_{n-1}^b, p) +$$
$$B(X_{n-1} - E_{n-1}^b, p_e), X_{n-1} + B(X_{n-1}, p) | E_{n-1}^b X_{n-1})) +$$
$$\mathrm{Cov}(\mathbb{E}(E_n^b | E_{n-1}^b X_{n-1}), \mathbb{E}(X_n | E_{n-1}^b X_{n-1})) = T_1 + T_2$$

Here $B(\ldots)$ stands for a random variable distributed according to binomial distribution with corresponding parameters, as defined in Equation 9. Two terms in the above equation are denoted by $T_1$ and $T_2$ and are computed separately below. For the next step in derivation, the expression $$B(X_{n-1}, p) = B(E_{n-1}^b, p) + B(X_{n-1} - E_{n-1}^b, p)$$

is used, which holds if $X_{n-1}$ and $E_{n-1}^b$ are constants as opposed to random variables. This is satisfied because these expressions enter conditional statistics. Using this, for the first term:

$$T_1 = \mathbb{E}(\mathrm{Cov}(B(E_{n-1}^b, p), B(X_{n-1}, p) | E_{n-1}^b X_{n-1}) ++$$
$$\mathrm{Cov}(B(X_{n-1} - E_{n-1}^b, p_e), B(x_{n-1}, P) | E_{n-1}^b X_{n-1} ==$$
$$\mathbb{E}(\mathrm{Cov}(B(E_{n-1}^b, p), B(E_{n-1}^b, p) + B(X_{n-1} - E_{n-1}^b, p) | E_{n-1}^b X_{n-1}) ++$$
$$\mathrm{Cov}(B(X_{n-1} - E_{n-1}^b, p_e),$$
$$B(E_{n-1}^b, p) + B(X_{n-1} - E_{n-1}^b, p) | E_{n-1}^b X_{n-1})) ==$$
$$\mathbb{E}(\mathrm{Cov}(B(E_{n-1}^b, p), B(E_{n-1}^b, p) | E_{n-1}^b X_{n-1}) ++$$
$$\mathrm{Cov}(B(E_{n-1}^b, p), B(X_{n-1} - E_{n-1}^b, p) | E_{n-1}^b X_{n-1}) ++$$
$$\mathrm{Cov}(B(X_{n-1} - E_{n-1}^b, p_e), B(E_{n-1}^b, p) | E_{n-1}^b X_{n-1}) ++$$
$$\mathrm{Cov}(B(X_{n-1} - E_{n-1}^b, p_e), B(X_{n-1} - E_{n-1}^b, p) | E_{n-1}^b X_{n-1}))$$

where the two crossed out terms amount to zero due to considerations for the physical process being modelled. The first crossed out term describes replication of error and normal molecules that, while conditioned on $X_{n-1}$ and $E_{n-1}^b$, is uncorrelated. The second crossed out term describes replication of error molecules and creation of new error molecules which are independent. Proceeding with evaluation of $T_1$:

$$T_1 = \mathbb{E}(\mathbb{V}(B(E_{n-1}^b, p) | E_{n-1}^b X_{n-1}) ++$$
$$\mathrm{Cov}(B(X_{n-1} - E_{n-1}^b, p_e), B(X_{n-1} - E_{n-1}^b, p) | E_{n-1}^b X_{n-1})) =$$
$$p(1-p)\mathbb{E}(E_{n-1}^b) + p_e(1-p)\mathbb{E}(X_{n-1} - E_{n-1}^b)$$

Here, the first term follows from the definition of variance for binomial distribution. The second term uses the following property: for two random binomial variables, Y and Z distributed as Y~B(n, p) and Z~B(Y, q) then $$\mathrm{Cov}(Y, Z) =$$
$$\mathbb{E}(YZ) - \mathbb{E}(Y)\mathbb{E}(Z) = \mathbb{E}(\mathbb{E}(YZ|Y)) - np\mathbb{E}(\mathbb{E}(Z|Y)) == \mathbb{E}(Y\mathbb{E}(Z|Y)) - n^2 p^2 q =$$
$$\mathbb{E}(qY^2) - n^2 p^2 q == q(np(1-p) + n^2 p^2) - n^2 p^2 q = qpn(1-p)$$

In the present case, Y represents the number of normal molecules replicating at cycle n−1 and Z—number of error molecules generated out of those molecules, and $p_e$ represents the probability of error given the probability of replication, so it is effectively $p_q$ in the example above.

The second term, $T_2$ for the covariance expression is pretty straight forward.

$$T_2 = \mathrm{Cov}((1 + p - p_e)E_{n-1}^b + p_e X_{n-1}, (1 + p)X_{n-1}) ==$$
$$(1 + p)(1 + p - p_e)\mathrm{Cov}(E_{n-1}^b, X_{n-1}) + p_e(1 + p)\mathbb{V}(X_{n-1})$$

Putting together all the terms for covariance expression, a recursive relation is obtained:

$$\mathrm{Cov}(E_n^b, X_n) = (1+p)(1+p-p_e)\mathrm{Cov}(E_{n-1}^b, X_{n-1}) + p_e(1-p)(1+p)^{2n}\mathbb{E}(X_0)$$

Thus, a solution to the recursive relation in the following form would be useful:

$$a_n = c_1 a_{n-1} + c_2 d^{2(n-1)} + c_3(n-1)d^{n-2}$$

with $$a_n = \mathrm{Cov}(E_n^b, X_n)$$

$$c_1 = (1+p)(1+p-p_e)$$

$$c_2 = p_e(1-p)\mathbb{E}(X_0) + p_e(1+p)\mathbb{V}(X_0)$$

$$c_3 + (p-p_e)(1-p)p_e \mathbb{E}(X_0)$$

$$d = (1+p)$$

After applying the recursive formula n times, the following pattern emerges:

$$a_n = c_1^n a_0 ++ c_2(c_1^{n-1} + c_1^{n-2} d^2 + c_1^{n-3}(d^2)^2 + \ldots + c_1(d^2)^{n-2} + (d^2)^{n-1}) ++$$
$$c_3 \frac{\partial}{\partial d}(c_1^{n-1} + c_1^{n-2} d + \ldots + c_1 d^{n-2} + d^{n-1}) ==$$
$$c_2 \frac{c_1^n - (d^2)^n}{c_1 - d^2} + c_3 \frac{\partial}{\partial d} \frac{c_1^n - d^n}{c_1 - d}$$

where the formula for the sum of geometric progression $S_n = \Sigma_{k=0}^n s^{n-k} t^k = s^n \Sigma_{k=0}^n (t/s)^k = (s^{n+1} - t^{n+1})/(s-t)$ was used. Substituting all the coefficients and simplifying the expression provides the answer for covariance between the background error counts and the total number of reads as $$\mathrm{Cov}(E_n^b, X_n) = \quad (17)$$
$$n(1+p)^{2n-2} p_e(1-p)\mathbb{E}(X_0) ++ n(1+p)^{2n-2}(1+p)p_e\mathbb{V}(X_0) ++$$
$$(1+p)^{2n-2}\frac{1-p}{p-p_e}\mathbb{E}(X_0) -- (1+p)^{n-1} p_e \frac{1-p}{p-p_e}\mathbb{E}(X_0)$$

Substituting Equation 17 back into Equation 16 and grouping similar terms, the recursive relation for the variance is $$\mathbb{V}(E_n^b) = c_1 \mathbb{V}(e_{n-1}^b) + c_2(1+p)n^{-1} + c_3(n-1)(1+p)^{n-2} ++$$
$$c_4(1+p)^{2(n-1)} + c_5(n-1)(1+p)^{2n-4}$$

with coefficients in this expression defined as $$c_1 = (1+p)^2 - 2(1+p)p_e + p_e^2 \quad (18)$$

$$c_2 = \left(p_e - p_e^2 - \frac{p_e^2(1-p(p+2))}{p(1+p)}\right)\mathbb{E}(X_0)$$

$$c_3 = (p_e p(1-p) - p_e^2)\mathbb{E}(X_0)$$

$$C_4 = p_e^2 \mathbb{V}(X_0) + p_e^2 \frac{(1-p)(p+2)}{p(1+p)} \mathbb{E}(X_0)$$

$$c_5 = 2p_e^2((1-p^2)\mathbb{E}(X_0) + (1+p)^2\mathbb{V}(X_0))$$

where only terms up to $p_e^2$ are kept. Going through a similar process as for Cov to solve this recursive relation, the solution for the variance of background error $$\mathbb{V}(E_n^b|pp_e) = c_2 \frac{c_1^n - x^n}{c_1 - x} + c_3 \frac{c_1^n - x^n - nx^{n-1}(c_1 - x)}{(c_1 - x)^2} \quad (19)$$

is obtained, where the coefficients defined above and notations $$x = 1+p$$

$$y = (1+p)^2$$

are used.

Overview of Some Implementations

The derivations in the previous sections produce quantities conditioned on replication efficiency per cycle p and error rate per cycle $p_e$. In order to evaluate absolute quantity Q, the following equations can be used $$\mathbb{E}(Q) = \mathbb{E}(\mathbb{E}(Q|p)) = \int_0^1 E((Q|p)f(p)dp$$

$$\mathbb{V}(Q) = \mathbb{E}(\mathbb{V}(Q|p)) + \mathbb{V}(\mathbb{E}(Q|p))$$

where f(p) stands for distribution of p that is to be estimated from the data. To remove conditioning on $p_e$ the mean and variance of error rate is estimated and used to evaluate expressions as $p_e$=mean(pe) and $p_e^2$=var($p_e$)+mean($p_e$)$^2$. It is also useful to compute $\mathbb{E}(X_0)$ and $\mathbb{V}(X_0)$ from data. Sequencing data including reads at targeted positions in a genome can be used. The present description distinguishes between a reference read $R_r$, counts for the base specified in the reference genome, and error reads $R_e$, counts for the bases different from reference. The total reads, then, are defined as $R = R^r + \Sigma_{nonref} R^e$ With these definitions, the following can be implemented.

4. Estimation of Efficiency and Error from the Training Data

Using a set of normal samples that are not expected to have any cancer related mutation, the efficiency can be estimated from relation $R=(1+p)^n X_0$ at each position. Assuming that starting copy or count $X_0$ is the same for each position, and assigning some arbitrary (relatively high) efficiency p* to positions with number of reads R* in high percentile (e.g. 99$^{th}$ percentile), $$\frac{1+p}{1+p^*} = \frac{(R/X_0)^{1/n}}{(R^*/X_0)^{1/n}} \Rightarrow p = \left(\frac{R}{R^*}\right)^{\frac{1}{n}}(1+p^*) - 1 \quad (20)$$

Using this estimate for efficiency, the error rate per cycle at each position can be estimated from Equation 13 as $$p_e = \frac{R^e}{n(1+p)^{n-1} X_0} = \frac{R^e(1+p)}{nR} \quad (21)$$

The mean and standard deviation of these quantities are found for each position by computing the statistics over multiple normal samples supplied in the data set. These values are later combined over bases sharing the same motifs, as described in more detail herein, and can be saved to be used for calling mutations in different samples.

5. Estimation of Starting Copy for a Test Sample

Using the mean and standard deviation of efficiency for each position found previously from normal samples, the starting copy at each position for a test sample can be estimated as $$X_0 = \int_0^1 \frac{R}{(1+p)^n} f(p)dp \quad (22)$$

where $f(p) = B(\alpha, \beta)$ is the beta distribution with parameters $\alpha$ and $\beta$ found from mean and standard deviation of efficiency. The mean and standard deviation of $X_0$ over positions belonging to the same sequenced genetic fragment can be computed and assigned to each position in the fragment.

6. Adjusting Efficiency for a Test Sample

In some implementations, an update or correction of the efficiency values can be performed based on the found staring copy according to $$p = \int \left(\left(\frac{R}{X_0}\right)^{1/n} - 1\right) g(x_0) dx_0 \quad (23)$$

where $g(x0) = N(\mu, \sigma)$ is normal distribution with mean and standard deviation found for starting copy at particular position.

Training Algorithms

In order to determine the mutation fraction distribution, appropriate training can be used to estimate the distribution parameters.

7. Base Specific Training

For base specific training, the model parameters for each base can be estimated separately in the target panel. A basic assumption of this training process is that each base in the panel has a certain amplification rate and error rate. For this training method to work, control samples from normal subjects can be used. For example, 20-30 normal samples to estimate model parameters using base specific training can be used. The below algorithm outlines a basic flowchart of a base specific error model.

Algorithm 1 Base specific training algorithm

Training: $D_{i,k} = (R_{i,k}, \text{RefAllele}_i, A_{i,k}, C_{i,k}, G_{i,k}, T_{j,k})$ where $i \in \{1, 2, \ldots, B\}$ denotes a base and $k \in \{1, 2, \ldots, n\}$ denotes a sample, $\text{RefAllele}_i$ is the reference/wildtype allele for base i, $R_{i,k}$ is the total depth of reads, $A_{i,k}, C_{i,k}, G_{i,k}, T_{i,k}$ are the number of reads from alleles A, C, G, T respectively.

Test: $D_{i,k}^{Test} = (R_i^{Test}, \text{RefAllele}_i, A_i^{Test}, C_i^{Test}, G_i^{Test}, T_i^{Test})$ for $i = 1, 2, \ldots, B$. Mutation call confidence scores for non-reference alleles in the test set for all bases $1, 2, \ldots, B$.

for $i = 1, 2, \ldots, B$ do

1. Estimate efficiency and error from training data as explained above for base i, using the data $D_{i,k}$.
2. Estimate starting copy for base i for test data at base i, using methods described above;
3. Adjust efficiency parameter at base i using methods described above.
4. For a grid of values of $\theta \in [0, \tau_{max}]$ (where $\tau_{max}$ is ideally 1 but for practical purpose, it suffices to set $\tau_{max} \approx 0.15$) of candidate mutation fractions, plug in the estimated efficiency and error parameters in equation (6) and (7) to compute the likelihood $L(\theta)$ of test data using the beta-binomial model in (1).
5. Find Maximum Likelihood Estimate of $\theta$, $\hat{\theta}_{MLE} := \text{argmax}_\theta L(\theta)$
6. Compute confidence score as $$C = \frac{L(\hat{\theta}_{MLE})}{L(\hat{\theta}_{MLE}) + L(0)}$$

8. Motif-Specific Training

Motif-specific training are useful in part because the sequence context around the base of interest contributes to the PCR error rate. Thus an error model can be generated from training data for each 3-base motif such that a base of interest is always the middle base. Other motifs can be used alternatively or additionally. For example, a motif may include one or more adjacent bases on only one side of the target base, or may include a symmetric (equal) or an asymmetric (not equal) number of bases on the two sides of the target base. Any number of adjacent bases may be defined as a motif. The motif specific error model estimates the middle base error parameters for each motif keeping the flanking bases same (e.g. estimates the error parameters for A<u>T</u>A→A<u>C</u>A, G<u>T</u>C→G<u>A</u>C, etc.). For example, in some implementations the algorithm estimates the error for

| | | |
|---|---|---|
| AAAA<u>T</u>C | → | AAAA<u>C</u>C |
| GA<u>T</u>CA | → | GA<u>C</u>CA |
| GTG<u>G</u>C | → | GC<u>G</u>GC |
| . . . | | |

Dynamic flanking bases may also be implemented, and motifs may be variable based on the sequence context. In some embodiments, the motif comprises 1, 2, 3, 4, or 5 adjacent bases before the target base. In some embodiments, the motif comprises 1, 2, 3, 4, or 5 adjacent bases after the target base.

Estimating Parameters for Motifs

Some implementations include performing the following steps:
1. From the training set, remove (bases, channel) data pairs for error rates more than or equal to $\alpha$, where $\alpha = \min\{a$ predetermined number (e.g. 0.2), a predetermined percentile of the error rates in the training sample (e.g. the $99^{th}$ percentile)$\}$.
2. Compute per cycle error rate per base per channel.
3. Compute mean and variance per motif using a grouped or pooled mean and variance formula. For example if $\mu_1, \mu_2, \ldots, \mu_n$ are the means and $\sigma_1^2, \sigma_2^2, \ldots, \sigma_n^2$ are the variances error rates of bases that share the same motif, then the pooled mean and variance may be calculated as $$\mu_{pooled} = \frac{1}{n}\sum_{i=1}^{n} \mu_i$$

$$\sigma_{pooled}^2 = \frac{1}{n}\sum_{i=1}^{n} \sigma_i^2$$

4. If there are multiple training runs, then the pooling can be done stepwise, first pooling samples in individual runs and then pooling all runs. While pooling runs, the error rates can be weighted by number of occurrences of the motif in the run. In other implementations, the error rates are averaged without weighting.
5. Since the efficiency is not necessarily a function of motif, the efficiency parameter for each motif need not be averaged separately. Instead the mean and variances of the efficiency parameter is averaged over all samples to come up with one prior estimate for efficiency parameters. This prior estimate is no-longer position dependent. In other implementations, the efficiency parameter may be determined on a motif-specific basis, similarly to the determination of the motif-specific error rates.

Some implementations include fitting a regression model of the estimated efficiency values using the amplicon GC content, temperature, and so forth, as covariates and using this model to estimate the prior parameters instead of using a constant prior.

Algorithm 2 Motif Specific Training Algorithm

Training Data: $D_{i,k} = (R_{i,k}, \text{RefAllele}_i, A_{i,k}, C_{i,k}, G_{i,k}, T_{i,k})$ where $i \in \{1, 2, \ldots, B_{Training}\}$ denotes a base and $k \in \{1, 2, \ldots, n\}$ denotes a sample, $\text{RefAllele}_i$ is the reference/wildtype allele for base I, $R_{i,k}$ is the total depth of reads, $A_{i,k}, C_{i,k}, G_{i,k}, T_{i,k}$ are the number of reads from alleles A, C, G, T respectively. $M_{i,k}$ denotes the motif for the i-th base in sample k where $M_{i,k} \in \mathbb{M} := \{X_1 X_2 X_3\}$ such that $X_j \in \{A, C, G, T\} \forall j$ Test Data: $D_{i,k}^{Test} = (R_i^{Test}, \text{RefAllele}_i, A_i^{Test}, C_i^{Test}, G_i^{Test}, T_i^{Test}, M_i^{Test})$ for $i = 1, 2, \ldots, B_{TestData}$.

Result: Mutation call confidence scores for non-reference alleles in the test set for all bases $1, 2, \ldots, B$.

for Training do >Training Block
1: 1. Let $\alpha = \min\{$a predetermined threshold, a predetermined percentile of observed hetrates in the training data.
2. $\forall i = 1, 2, \ldots, B_{Training}; \forall k = 1, 2, \ldots, n$, compute per cycle efficiency $p_{i,k}$ and error rate pe,i,k using the data $D_{i,k}$. If hetrate is $\geq \alpha$ for some (base,channel) combination, then skip error estimation for that combination.
3. Group the bases by motifs such that bases sharing the same motif are assigned to same group, forming M groups.
4. $\forall m \in \mathbb{M}$, compute mean and variance of error rates for m using the grouped data.
5. Pool all bases together to compute the mean and variance of the efficiency parameter.

for $i = 1, 2, \ldots, B_{Test}$ do >Test Block
2: 1. If the motif for base i is $m_i$, use universal efficiency parameters from last step and error parameters for motif $m_i$ for subsequent steps.
2. Estimate starting copy for base i for test data at base i.
3. Adjust efficiency parameter at base i.
4. For a grid of values of $\theta \in [0, \tau_{max}]$ (where $\tau_{max}$ is ideally 1 but for practical purpose, it suffices to set $\tau_{max} \approx 0.15$) for candidate mutation fractions, plug in the estimated efficiency and error parameters in equation (6) and (7) to compute the likelihood $L(\theta)$ of test data using the beta-binomial model in (1).

5. Find Maximum Likelihood Estimate of $\theta$, $\hat{\theta}$, $\hat{\theta}_{MLE}$:= argmax$_\theta$L($\theta$).

6. Compute confidence score as $$C = \frac{L(\hat{\theta}_{MLE})}{L(\hat{\theta}_{MLE}) + L(0)}$$

Figure 10:
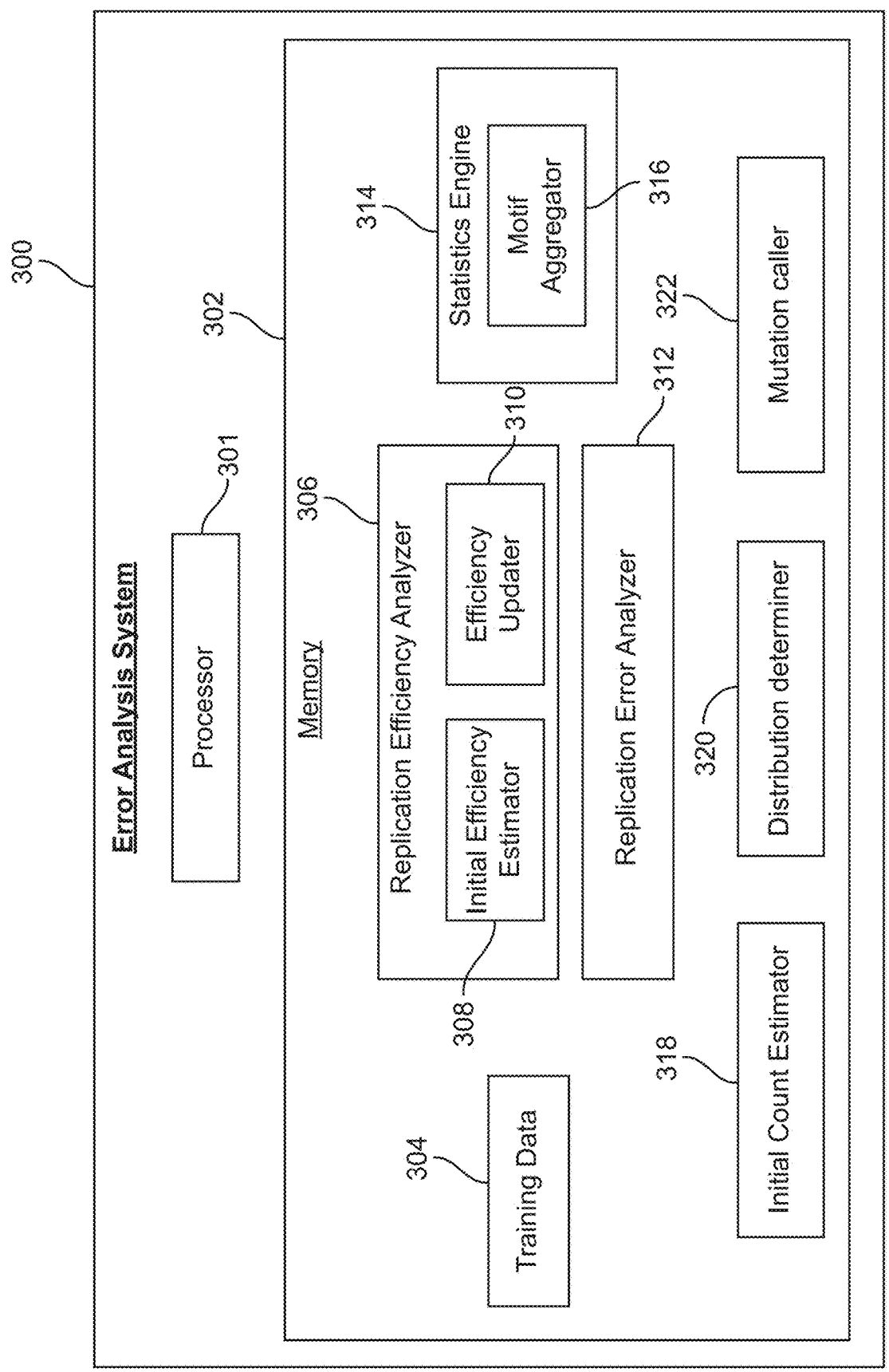
FIG. 10 illustrates a block diagram of one or more implementations of an error analysis system.

Referring now to FIG. 10, FIG. 10 is a block diagram showing an embodiment of an error analysis system 300. The error analysis system 300 can include one or more processors 301, and a memory 302. The one or more processors 301 may include one or more microprocessors, application-specific integrated circuits (ASIC), a field-programmable gate arrays (FPGA), etc., or combinations thereof. The memory 302 may include, but is not limited to, electronic, magnetic, or any other storage or transmission device capable of providing processor with program instructions. The memory may include magnetic disk, memory chip, read-only memory (ROM), random-access memory (RAM), Electrically Erasable Programmable Read-Only Memory (EEPROM), erasable programmable read only memory (EPROM), flash memory, or any other suitable memory from which processor can read instructions. The memory 302 may include components, subsystems, modules, scripts, applications, or one or more sets of processor-executable instructions for implementing error analysis processes, including any processes described herein. For example, the memory 302 may include training data 304, a replication efficiency analyzer 306, a replication error analyzer 312, a statistics engine 314, an initial count estimator 318, a distribution determiner 320, and a mutation caller 322.

The training data 304 can include, for example, data of the following type: $(R_{i,k}, \text{RefAllele}_i, A_{i,k}, C_{i,k}, G_{i,k}, T_{i,k})$ where $i \in \{1,2,\ldots,B_{Training}\}$ denotes a base and $k \in \{1,2,\ldots,n\}$ denotes a sample, RefAllele$_i$ is the reference/wildtype allele for base I, $R_{i,k}$ is the total depth of reads, $A_{i,k}, C_{i,ki}, G_{i,k}, T_{i,k}$ are the number of reads from alleles A, C, G, T respectively. $M_{i,k}$ denotes the motif for the i-th base in sample k where $M_{i,k} \in \mathbb{M} := \{X_1 X_2 X_3\}$ such that $X_j \in \{A, C, G, T\} \forall j$. The training data may be derived from one or more one or more samples taken from one or more subjects. The training data may include only genetic material that does not include mutations of interest (e.g. mutations for which a mutation fraction is being determined).

The replication efficiency analyzer 306 may include components, subsystems, modules, scripts, applications, or one or more sets of processor-executable instructions for determining a replication efficiency of a PCR process, using the training data. The replication efficiency analyzer 306 may include an initial efficiency estimator 308 that determines an initial estimate of the replication efficiency. For example, the replication efficiency analyzer 306 may estimate the replication efficiency from the relation $R=(1+p)^n X_0$ at each position. The replication efficiency analyzer 306 may determine the initial replication efficiency estimate using Equation 20. The replication efficiency analyzer 306 may include an efficiency updater 310. The efficiency updater 310 may update or correct an initial efficiency estimate using an initial count determined by the initial count estimator 318 (described in more detail below). The efficiency updater 310 may update or correct the initial efficiency estimate using Equation 23.

The replication error analyzer 312 may include components, subsystems, modules, scripts, applications, or one or more sets of processor-executable instructions for determining a replication error rate. For example, the replication error analyzer 312 can determine an error rate per cycle at each position using equation 21. The determined error rate may correspond to background error, including error induced by the PCR process. The replication error analyzer 312 can determine the error rate per cycle at each position using the training data (e.g. based on the number of erroneous reads and the total number of reads made).

The statistics engine 314 may include components, subsystems, modules, scripts, applications, or one or more sets of processor-executable instructions for determining statistical values for the replication efficiencies determined by the replication efficiency analyzer 306, and for the replication error rates determined by the replication error analyzer 312. For example, the statistics engine 314 may determine a mean or estimated replication efficiency based on the replication efficiencies determined by the replication efficiency analyzer 306, and may determine a variance thereof. For example, the statistics engine 314 may determine the mean over all samples analyzed samples in a position-independent manner.

The statistics engine 314 may determine a mean or estimated replication error rate, and variance thereof, based on the replication error rates determined by the replication error analyzer 312. The mean or estimated replication error rate may be motif-specific. For example, the statistics engine 314 may include a motif aggregator 316 that groups the target bases to be analyzed by motif (that is, into groups in which all target bases of the group have a same motif). In some implementations, the motif aggregator 316 references a data structure that specifies motif parameters (e.g. a first number of adjacent bases sequentially prior to the target base, and a second number of adjacent bases sequentially following the target base) that define the motifs. For example, if a plurality of mean replication error rates $\mu_1, \mu_2, \ldots, \mu_n$ and a plurality of variances thereof $\sigma_1^2, \sigma_2^2, \ldots, \sigma_n^2$ are determined by the statistics engine 314 based on data determined by the replication error analyzer 312, the motif-specific grouped mean and variance may be calculated as $$\mu_{pooled} = \frac{1}{n}\sum_{i=1}^{n} \mu_i$$

$$\sigma_{pooled}^2 = \frac{1}{n}\sum_{i=1}^{n} \sigma_i^2$$

The grouping can be done stepwise, first grouping samples in individual runs and then grouping all runs. While grouping runs, the error rates can be weighted by number of occurrences of the motif in the run. In other implementations, the error rates are averaged without weighting.

The statistics engine 314 may implement a filtering policy to sanitize the data. For example, the statistics engine 314 may remove from the training set (bases, channel) data pairs for error rates more than or equal to $\alpha$, where $\alpha=\min\{a$ predetermined number (e.g. 0.2), a predetermined percentile of the error rates in the training sample (e.g. the $99^{th}$ percentile)$\}$.

The initial count estimator 318 may include components, subsystems, modules, scripts, applications, or one or more sets of processor-executable instructions for determining an initial count of a target base for one or more samples. For example, the initial count estimator 318 may use Equation 22 to determine a plurality of initial count estimates for each base being analyzed. The initial count estimator 318 (or, in some implementations, the statistics engine 314) may determine a plurality of estimates or mean values for the initial count, and variances thereof, over positions belonging to a same sequenced genetic fragment, and may assign those values to each position in the genetic fragment. Those values may be used by the initial efficiency updater 310 to update an initial efficiency estimate, as described herein.

The distribution determiner 320 may include components, subsystems, modules, scripts, applications, or one or more sets of processor-executable instructions for determining parameters for a distribution representing a mutation fraction of one or more analyzed samples. For example, the distribution determiner 320 may determine parameters for a Beta Binomial distribution of the mutation fraction. The distribution determiner 320 may, for a grid of values of $\theta \in [0, \tau_{max}]$ (where $\tau_{max}$ is ideally 1 but for practical purpose, it suffices to set $\tau_{max} \approx 0.15$) for candidate mutation fractions, plug in the estimated efficiency and error parameters in to equation (6) and (7) to compute the likelihood $L(\theta)$ of test data using the beta-binomial model in (1). The distribution determiner 320 may select a highest likelihood mutation fraction as the determined mutation fraction for the one or more analyzed samples.

The mutation caller 322 may include components, subsystems, modules, scripts, applications, or one or more sets of processor-executable instructions for determining parameters for calling mutations. The mutation caller 322 may call mutations based on one or more parameter values being equal to, or above, a predetermined threshold. For example, the parameter values can include a mutation fraction, an absolute number of detected errors or mutations, or a number of standard deviations by which those parameter values deviate from a reference or mean value. The mutation caller 322 may also determine a confidence corresponding to the called mutation (e.g. based at least in part on a difference between the parameter value and the threshold).

Figure 11:
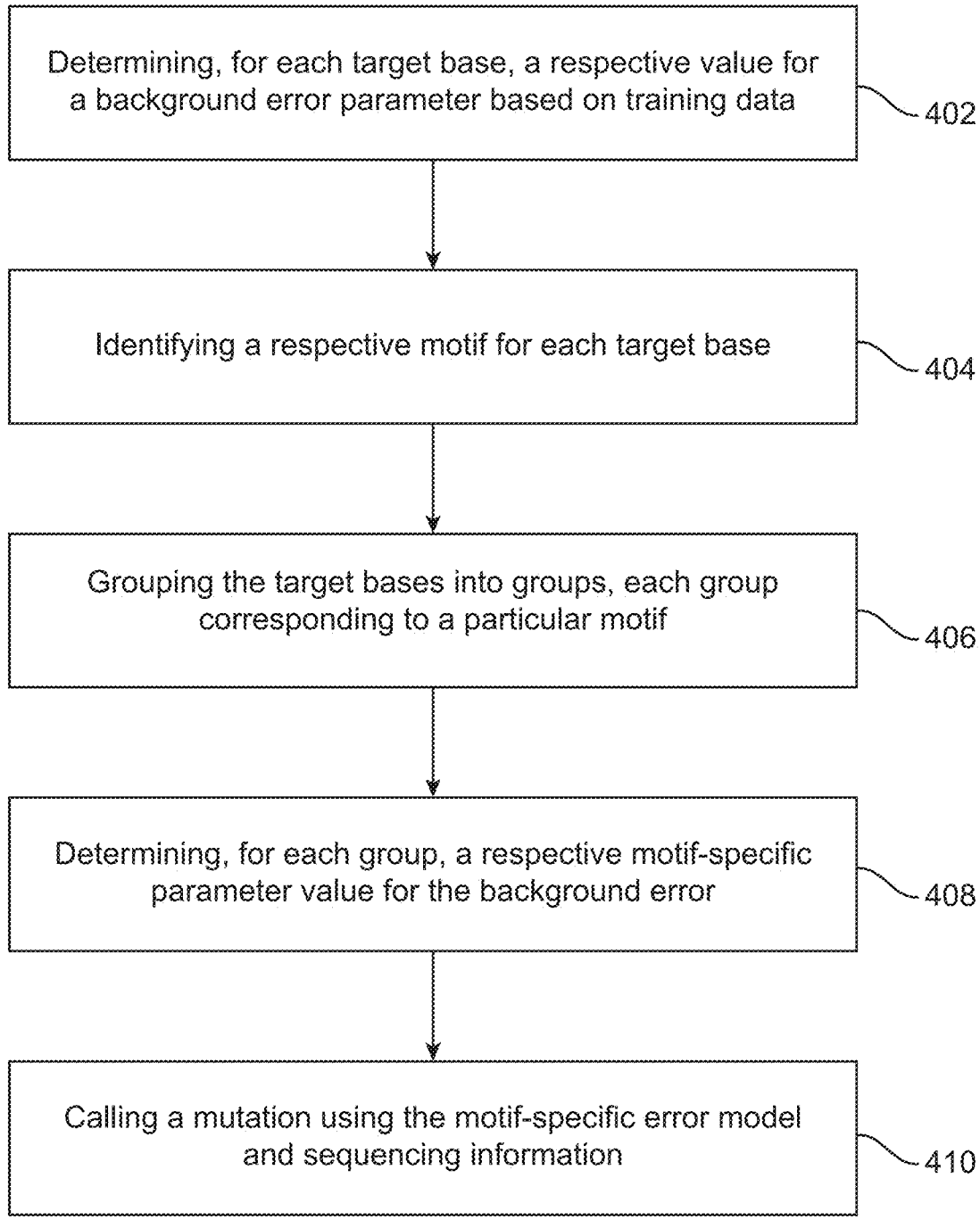
FIG. 11 illustrates one or more implementations of a method for calling a mutation using a motif-specific error model.

Referring now to FIG. 11, a method for calling a mutation using a motif-specific error model is shown. The method includes BLOCK 402 through BLOCK 410. In a brief overview, at BLOCK 402, the error analysis system 300 determines, for each target base of a plurality of target bases, a respective value for a background error parameter based on training data. At BLOCK 404, the error analysis system 300 identifies a respective motif for each target base. At BLOCK 406, the error analysis system 300 groups the target bases into groups, each group corresponding to a particular motif. At BLOCK 408, the error analysis system 300 determines, for each group, a respective motif-specific parameter value for the background error. At BLOCK 410, the error analysis system 300 calls a mutation using the motif-specific error model and sequencing information.

In more detail, at BLOCK 402, the error analysis system 300 determines, for each target base of a plurality of target bases, a respective value for a background error parameter based on training data. For example, the replication error analyzer 312 can determine an error rate per cycle for each target base of a plurality of target bases using equation 21. The determined error rate may correspond to background error, including error induced by the PCR process. The replication error analyzer 312 can determine the error rate per cycle at each position using the training data (e.g. based on the number of erroneous reads and the total number of reads made).

At BLOCK 404, the error analysis system 300 identifies a respective motif for each target base, and at BLOCK 406, the error analysis system 300 groups the target bases into groups, each group corresponding to a particular motif. For example, the motif aggregator 316 references a data structure that specifies motif parameters (e.g. a first number of adjacent bases sequentially prior to the target base, and a second number of adjacent bases sequentially following the target base) that define the motifs. For example, if a plurality of mean replication error rates $\mu_1, \mu_2, \ldots, \mu_n$ and a plurality of variances thereof $\sigma_1^2, \sigma_2^2, \ldots, \sigma_n^2$ are determined by the statistics engine 314 based on data determined by the replication error analyzer 312, the motif-specific grouped mean and variance may be calculated as $$\mu_{pooled} = \frac{1}{n}\sum_{i=1}^{n} \mu_i$$

$$\sigma_{pooled}^2 = \frac{1}{n}\sum_{i=1}^{n} \sigma_i^2$$

The grouping can be done stepwise, first grouping samples in individual runs and then grouping all runs. While grouping runs, the error rates can be weighted by number of occurrences of the motif in the run. In other implementations, the error rates are averaged without weighting.

At BLOCK 408, the error analysis system 300 determines, for each group, a respective motif-specific parameter value for the background error. For example, the statistics engine 314 may determine a mean or estimated replication error rate, and variance thereof, for each group determined by the motif aggregator 316. Thus, the determined mean or estimated replication error rate may be motif-specific.

At BLOCK 410, the error analysis system 300 calls a mutation using the motif-specific error model and sequencing information. For example, the distribution determiner 320 may determine parameters for a Beta Binomial distribution of the mutation fraction. The distribution determiner 320 may, for a grid of values of $\theta \in [0, \tau_{max}]$ (where $\tau_{max}$ is ideally 1 but for practical purpose, it suffices to set $\tau_{max} \approx 0.15$) for candidate mutation fractions, plug in the estimated efficiency and error parameters in to equation (6) and (7) to compute the likelihood $L(\theta)$ of test data using the beta-binomial model in (1). The distribution determiner 320 may select a highest likelihood mutation fraction as the determined mutation fraction for the one or more analyzed samples. The mutation caller 322 may call mutations based on one or more parameter values being equal to, or above, a predetermined threshold. For example, the parameter values can include the mutation fraction determined by the distribution determiner 320. The mutation caller 322 may also determine a confidence corresponding to the called mutation (e.g. based at least in part on a difference between the parameter value and the threshold). Thus, a mutation can be accurately called using a motif-specific approach.

Figure 12:
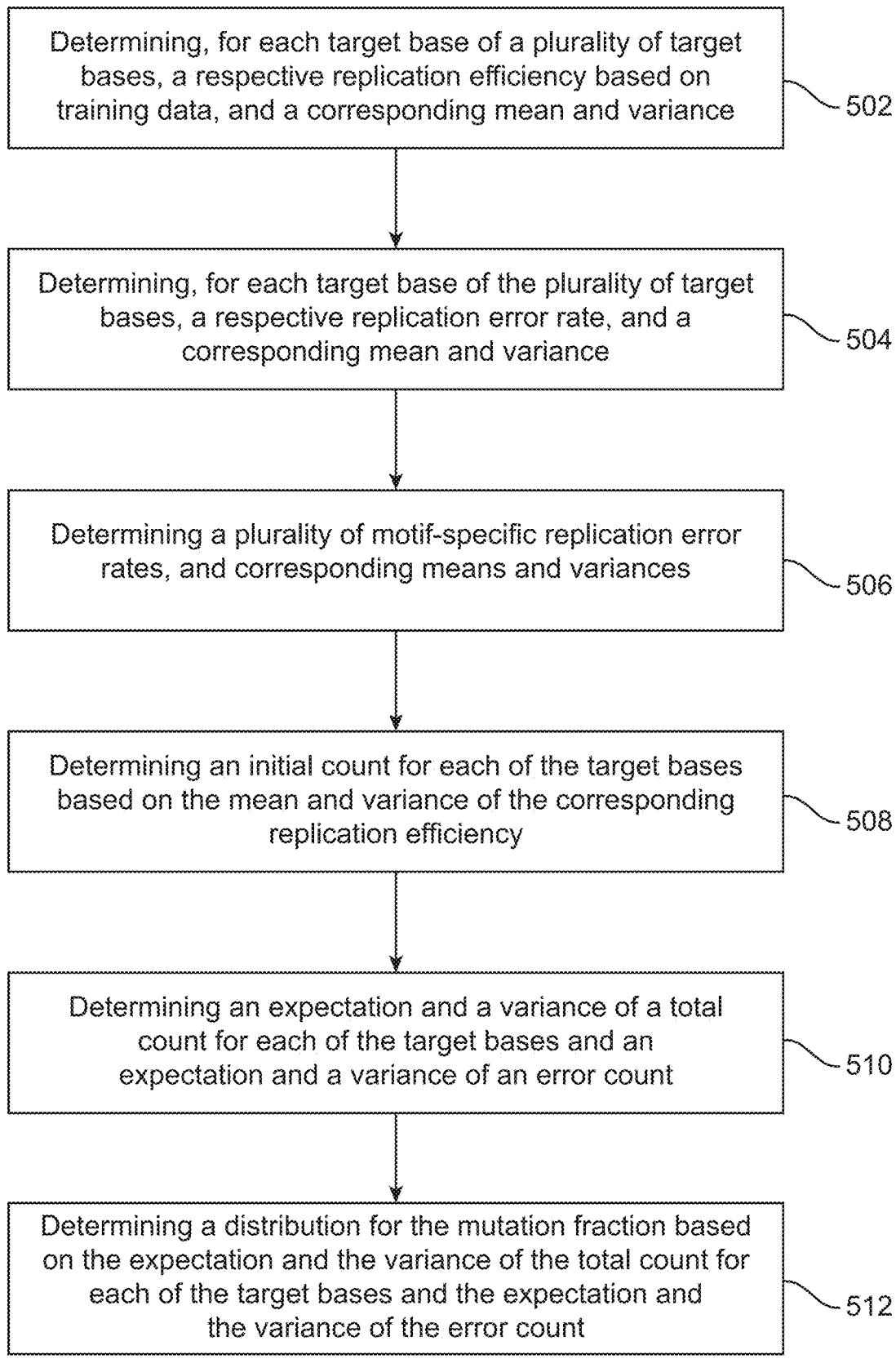
FIG. 12 illustrates one or more implementations of a method for determining a mutation fraction.

Referring now to FIG. 12, a method for determining a distribution for a mutation fraction is shown. The method includes BLOCK 502 through BLOCK 512. In a brief overview, at BLOCK 502, the error analysis system 300 determines, for each target base of a plurality of target bases, a respective replication efficiency based on training data, and a corresponding mean and variance. At BLOCK 504, the error analysis system 300 determines for each target base of the plurality of target bases, a respective replication error rate, and a corresponding mean and variance. At BLOCK 506, the error analysis system 300 determines a plurality of motif-specific replication error rates, and corresponding means and variances. At BLOCK 508, the error analysis system 300 determines an initial count for each of the target bases based on the mean and variance of the corresponding replication efficiency. At BLOCK 510, the error analysis system 300 determines an expectation and a variance of a total count for each of the target bases and an expectation and a variance of an error count. At BLOCK 512, the error analysis system 300 determines a distribution for the mutation fraction based on the expectation and the variance of the total count for each of the target bases and the expectation and the variance of the error count.

In more detail, at BLOCK 502, the replication efficiency analyzer 306 may determine an initial estimate of the replication efficiency. For example, the replication efficiency analyzer 306 may estimate the replication efficiency from the relation $R=(1+p)^n X_0$ at each position. The replication efficiency analyzer 306 may determine the initial replication efficiency estimate using Equation 20. The statistics engine 314 can determine corresponding mean values and variances.

At BLOCK 504, the replication error analyzer 312 may determine an error rate per cycle at each position using equation 21. The determined error rate may correspond to background error, including error induced by the PCR process. The replication error analyzer 312 can determine the error rate per cycle at each position using the training data (e.g. based on the number of erroneous reads and the total number of reads made). The statistics engine 314 can determine corresponding mean values and variances.

At BLOCK 506, the motif aggregator 316 may group the target bases to be analyzed by motif (that is, into groups in which all target bases of the group have a same motif). In some implementations, the motif aggregator 316 references a data structure that specifies motif parameters (e.g. a first number of adjacent bases sequentially prior to the target base, and a second number of adjacent bases sequentially following the target base) that define the motifs. The grouping can be done stepwise, first grouping samples in individual runs and then grouping all runs. While grouping runs, the error rates can be weighted by number of occurrences of the motif in the run. In other implementations, the error rates are averaged without weighting. The statistics engine 314 may determine motif-specific mean or estimated replication error rates, and variances thereof, based on the determined groups.

At BLOCK 508, the initial count estimator 318 may use Equation 22 to determine a plurality of initial count estimates for each base being analyzed. The initial count estimator 318 (or, in some implementations, the statistics engine 314) may determine a plurality of estimates or mean values for the initial count, and variances thereof, over positions belonging to a same sequenced genetic fragment, and may assign those values to each position in the genetic fragment. Those values may be used by the initial efficiency updater 310 to update an initial efficiency estimate, as described herein.

At BLOCK 510, the error analysis system 300 determines an expectation and a variance of a total count for each of the target bases and an expectation and a variance of an error count, and at BLOCK 512, the error analysis system 300 determines a distribution for the mutation fraction based on the expectation and the variance of the total count for each of the target bases and the expectation and the variance of the error count. This can include, for a grid of values of $\theta \in [0, \tau_{max}]$ (where $\tau_{max}$ is ideally 1 but for practical purpose, it suffices to set $\tau_{max} \approx 0.15$) for candidate mutation fractions, plugging in the estimated efficiency and error parameters in equation (6) and (7) to compute the likelihood $L(\theta)$ of test data using the beta-binomial model in (1). The process can further include finding a Maximum Likelihood Estimate of $\theta$, $\theta$, $\hat{\theta}_{MLE} := \text{argmax}_\theta L(\theta)$, and computing confidence score as $$C = \frac{L(\hat{\theta}_{MLE})}{L(\hat{\theta}_{MLE}) + L(0)}.$$

The distribution determiner 320 may select a highest likelihood mutation fraction, and may select the corresponding mutation fraction distribution as a mutation fraction distribution corresponding to an analyzed sample. Thus, a mutation fraction and a distribution thereof may be determined using a motif-specific approach The above-described embodiments can be implemented in any of numerous ways. For example, the embodiments may be implemented using hardware, software, or a combination thereof. When implemented in software, the software code can be executed on any suitable processor or collection of processors, whether provided in a single computer or distributed among multiple computers. For example, the error analysis system 300 can be executed on a computer or specialty logic system that includes one or more processors.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards and pointing devices, such as mice, touch pads, and digitizing tablets. As another example, a computer may receive input information through speech recognition or in other audible format.

Such computers may be interconnected by one or more networks in any suitable form, including a local area network or a wide area network, such as an enterprise network, an intelligent network (IN), or the Internet. Such networks may be based on any suitable technology and may operate according to any suitable protocol and may include wireless networks, wired networks, or fiber optic networks.

A computer employed to implement at least a portion of the functionality described herein may comprise a memory, one or more processing units (also referred to herein simply as "processors"), one or more communication interfaces, one or more display units, and one or more user input devices. The memory may comprise any computer-readable media, and may store computer instructions (also referred to herein as "processor-executable instructions") for implementing the various functionalities described herein. The processing unit(s) may be used to execute the instructions. The communication interface(s) may be coupled to a wired or wireless network, bus, or other communication means and may therefore allow the computer to transmit communications to and/or receive communications from other devices. The display unit(s) may be provided, for example, to allow a user to view various information in connection with execution of the instructions. The user input device(s) may be provided, for example, to allow the user to make manual adjustments, make selections, enter data or various other information, and/or interact in any of a variety of manners with the processor during execution of the instructions.

The various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, various inventive concepts may be embodied as a computer-readable storage medium (or multiple computer-readable storage media) (e.g., a computer memory, one or more floppy discs, compact discs, optical discs, magnetic tapes, flash memories, circuit configurations in Field Programmable Gate Arrays or other semiconductor devices, or other non-transitory medium or tangible computer storage medium) encoded with one or more programs that, when executed on one or more computers or other processors, perform methods that implement the various embodiments of the present disclosure discussed above. The computer-readable medium or media can be transportable, such that the program or programs stored thereon can be loaded onto one or more different computers or other processors to implement various aspects of the present disclosure as discussed above.

The terms "application" or "script" are used herein in a generic sense to refer to any type of computer code or set of processor-executable instructions that can be employed to program a computer or other processor to implement various aspects of embodiments as discussed above. Additionally, it should be appreciated that according to one aspect, one or more computer programs that when executed perform methods of the present disclosure need not reside on a single computer or processor, but may be distributed in a modular fashion amongst a number of different computers or processors to implement various aspects of the present disclosure.

Processor-executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that conveys relationship between the fields. However, any suitable mechanism may be used to establish a relationship between information in fields of a data structure, including through the use of pointers, tags, or other mechanisms that establish relationship between data elements.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

While operations are depicted in the drawings in a particular order, such operations are not required to be performed in the particular order shown or in sequential order, and all illustrated operations are not required to be performed. Actions described herein can be performed in a different order.

The separation of various system components does not require separation in all implementations, and the described program components can be included in a single hardware or software product.

Method for Detection Cancer-Associated Mutations

In further aspect, the present disclosure provides a method for detecting a mutation associated with cancer, comprising: isolating cell-free DNA from a biological sample of a subject; amplifying from the isolated cell-free DNA a plurality of single-nucleotide variant (SNV) loci that comprise a plurality of target bases, wherein the SNV loci are known to be associated with cancer; sequencing the amplification products to obtain sequence reads of a plurality of motifs, wherein each motif comprises one of the plurality of target bases; and determining a mutation fraction distribution for each of the plurality of target bases and identifying a mutation associated with cancer based on the mutation fraction distribution. In some embodiments, the biological sample is selected from blood, serum, plasma, and urine. In some embodiments, at least 10, or at least 20, or at least 50, or at least 100, or at least 200, or at least 500, or at least 1,000 SNV loci known to be associated with cancer are amplified from the isolated cell-free DNA. In some embodiments, the amplification products are sequenced with a depth of read of at least 200, or at least 500, or at least 1,000, or at least 2,000, or at least 5,000, or at least 10,000, or at least 20,000, or at least 50,000, or at least 100,000. In some embodiments, the plurality of single nucleotide variance loci are selected from SNV loci identified in the TCGA and COSMIC data sets for cancer.

In an additional aspect, the present disclosure provides a method for detecting a mutation associated with early relapse or metastasis of cancer, comprising: isolating cell-free DNA from a biological sample of a subject who has received treatment for a cancer; performing a multiplex amplification reaction to amplify from the isolated cell-free DNA a plurality of single-nucleotide variant (SNV) loci that comprise a plurality of target bases, wherein the SNV loci are patient-specific SNV loci associated with the cancer for which the subject has received treatment; sequencing the amplification products to obtain sequence reads of a plurality of motifs, wherein each motif comprises one of the plurality of target bases; and determining a mutation fraction distribution for each of the plurality of target bases and identifying a mutation associated with early relapse or metastasis of cancer based on the mutation fraction distribution. In some embodiments, the biological sample is selected from blood, serum, plasma, and urine. In some embodiments, the multiplex amplification reaction amplifies at least 4, or at least 8, or at least 16, or at least 32, or at least 64, or at least 128 patient-specific SNV loci associated with the cancer for which the subject has received treatment. In some embodiments, the amplification products are sequenced with a depth of read of at least 200, or at least 500, or at least 1,000, or at least 2,000, or at least 5,000, or at least 10,000, or at least 20,000, or at least 50,000, or at least 100,000. In some embodiments, the method comprising collecting and analyzing a plurality of biological samples from the patient longitudinally.

The terms "cancer" and "cancerous" refer to or describe the physiological condition in animals that is typically characterized by unregulated cell growth. A "tumor" comprises one or more cancerous cells. There are several main types of cancer. Carcinoma is a cancer that begins in the skin or in tissues that line or cover internal organs. Sarcoma is a cancer that begins in bone, cartilage, fat, muscle, blood vessels, or other connective or supportive tissue. Leukemia is a cancer that starts in blood-forming tissue, such as the bone marrow, and causes large numbers of abnormal blood cells to be produced and enter the blood. Lymphoma and multiple myeloma are cancers that begin in the cells of the immune system. Central nervous system cancers are cancers that begin in the tissues of the brain and spinal cord.

In some embodiments, the cancer comprises an acute lymphoblastic leukemia; acute myeloid leukemia; adrenocortical carcinoma; AIDS-related cancers; AIDS-related lymphoma; anal cancer; appendix cancer; astrocytomas; atypical teratoid/rhabdoid tumor; basal cell carcinoma; bladder cancer; brain stem glioma; brain tumor (including brain stem glioma, central nervous system atypical teratoid/rhabdoid tumor, central nervous system embryonal tumors, astrocytomas, craniopharyngioma, ependymoblastoma, ependymoma, medulloblastoma, medulloepithelioma, pineal parenchymal tumors of intermediate differentiation, supratentorial primitive neuroectodermal tumors and pineoblastoma); breast cancer; bronchial tumors; Burkitt lymphoma; cancer of unknown primary site; carcinoid tumor; carcinoma of unknown primary site; central nervous system atypical teratoid/rhabdoid tumor; central nervous system embryonal tumors; cervical cancer; childhood cancers; chordoma; chronic lymphocytic leukemia; chronic myelogenous leukemia; chronic myeloproliferative disorders; colon cancer; colorectal cancer; craniopharyngioma; cutaneous T-cell lymphoma; endocrine pancreas islet cell tumors; endometrial cancer; ependymoblastoma; ependymoma; esophageal cancer; esthesioneuroblastoma; Ewing sarcoma; extracranial germ cell tumor; extragonadal germ cell tumor; extrahepatic bile duct cancer; gallbladder cancer; gastric (stomach) cancer; gastrointestinal carcinoid tumor; gastrointestinal stromal cell tumor; gastrointestinal stromal tumor (GIST); gestational trophoblastic tumor; glioma; hairy cell leukemia; head and neck cancer; heart cancer; Hodgkin lymphoma; hypopharyngeal cancer; intraocular melanoma; islet cell tumors; Kaposi sarcoma; kidney cancer; Langerhans cell histiocytosis; laryngeal cancer; lip cancer; liver cancer; malignant fibrous histiocytoma bone cancer; medulloblastoma; medulloepithelioma; melanoma; Merkel cell carcinoma; Merkel cell skin carcinoma; mesothelioma; metastatic squamous neck cancer with occult primary; mouth cancer; multiple endocrine neoplasia syndromes; multiple myeloma; multiple myeloma/plasma cell neoplasm; mycosis fungoides; myelodysplastic syndromes; myeloproliferative neoplasms; nasal cavity cancer; nasopharyngeal cancer; neuroblastoma; Non-Hodgkin lymphoma; nonmelanoma skin cancer; non-small cell lung cancer; oral cancer; oral cavity cancer; oropharyngeal cancer; osteosarcoma; other brain and spinal cord tumors; ovarian cancer; ovarian epithelial cancer; ovarian germ cell tumor; ovarian low malignant potential tumor; pancreatic cancer; papillomatosis; paranasal sinus cancer; parathyroid cancer; pelvic cancer; penile cancer; pharyngeal cancer; pineal parenchymal tumors of intermediate differentiation; pineoblastoma; pituitary tumor; plasma cell neoplasm/multiple myeloma; pleuropulmonary blastoma; primary central nervous system (CNS) lymphoma; primary hepatocellular liver cancer; prostate cancer; rectal cancer; renal cancer; renal cell (kidney) cancer; renal cell cancer; respiratory tract cancer; retinoblastoma; rhabdomyosarcoma; salivary gland cancer; Sezary syndrome; small cell lung cancer; small intestine cancer; soft tissue sarcoma; squamous cell carcinoma; squamous neck cancer; stomach (gastric) cancer; supratentorial primitive neuroectodermal tumors; T-cell lymphoma; testicular cancer; throat cancer; thymic carcinoma; thymoma; thyroid cancer; transitional cell cancer; transitional cell cancer of the renal pelvis and ureter; trophoblastic tumor; ureter cancer; urethral cancer; uterine cancer; uterine sarcoma; vaginal cancer; vulvar cancer; Waldenstrom macroglobulinemia; or Wilm's tumor.

In certain examples, the methods includes identifying a confidence value for each allele determination at each of the set of single nucleotide variance loci, which can be based at least in part on a depth of read for the loci. The confidence limit can be set at least 75%, 80%, 85%, 90%, 95%, 96%, 96%, 98%, or 99%. The confidence limit can be set at different levels for different types of mutations In any of the methods for detecting SNVs herein that include a ctDNA SNV amplification/sequencing workflow, improved amplification parameters for multiplex PCR can be employed. For example, wherein the amplification reaction is a PCR reaction and the annealing temperature is between 1, 2, 3, 4, 5, 6, 7, 8, 9, or 10° C. greater than the melting temperature on the low end of the range, and 2, 3, 4, 5, 6, 7, 8, 9, 10, 11, 12, 13, 14 or 15° on the high end the range for at least 10, 20, 25, 30, 40, 50, 06, 70, 75, 80, 90, 95 or 100% the primers of the set of primers.

In certain embodiments, wherein the amplification reaction is a PCR reaction the length of the annealing step in the PCR reaction is between 10, 15, 20, 30, 45, and 60 minutes on the low end of the range, and 15, 20, 30, 45, 60, 120, 180, or 240 minutes on the high end of the range. In certain embodiments, the primer concentration in the amplification, such as the PCR reaction is between 1 and 10 nM. Furthermore, in exemplary embodiments, the primers in the set of primers, are designed to minimize primer dimer formation.

Accordingly, in an example of any of the methods herein that include an amplification step, the amplification reaction is a PCR reaction, the annealing temperature is between 1 and 10° C. greater than the melting temperature of at least 90% of the primers of the set of primers, the length of the annealing step in the PCR reaction is between 15 and 60 minutes, the primer concentration in the amplification reaction is between 1 and 10 nM, and the primers in the set of primers, are designed to minimize primer dimer formation. In a further aspect of this example, the multiplex amplification reaction is performed under limiting primer conditions.

A sample analyzed in methods of the present invention, in certain illustrative embodiments, is a blood sample, or a fraction thereof. Methods provided herein, in certain embodiments, are specially adapted for amplifying DNA fragments, especially tumor DNA fragments that are found in circulating tumor DNA (ctDNA). Such fragments are typically about 160 nucleotides in length.

It is known in the art that cell-free nucleic acid (e.g. cfDNA), can be released into the circulation via various forms of cell death such as apoptosis, necrosis, autophagy and necroptosis. The cfDNA, is fragmented and the size distribution of the fragments varies from 150-350 bp to >10000 bp. (see Kalnina et al. *World J Gastroenterol.* 2015 Nov. 7; 21(41): 11636-11653). For example the size distributions of plasma DNA fragments in hepatocellular carcinoma (HCC) patients spanned a range of 100-220 bp in length with a peak in count frequency at about 166 bp and the highest tumor DNA concentration in fragments of 150-180 bp in length (see: Jiang et al. *Proc Natl Acad Sci USA* 112:E1317-E1325).

In an illustrative embodiment the circulating tumor DNA (ctDNA) is isolated from blood using EDTA-2Na tube after removal of cellular debris and platelets by centrifugation. The plasma samples can be stored at −80° C. until the DNA is extracted using, for example, QIAamp DNA Mini Kit (Qiagen, Hilden, Germany), (e.g. Hamakawa et al., *Br J Cancer.* 2015; 112:352-356). Hamakava et al. reported median concentration of extracted cell free DNA of all samples 43.1 ng per ml plasma (range 9.5-1338 ng ml/) and a mutant fraction range of 0.001-77.8%, with a median of 0.90%.

Methods of the present invention in certain embodiments, typically include a step of generating and amplifying a nucleic acid library from the sample (i.e. library preparation). The nucleic acids from the sample during the library preparation step can have ligation adapters, often referred to as library tags or ligation adaptor tags (LTs), appended, where the ligation adapters contain a universal priming sequence, followed by a universal amplification. In an embodiment, this may be done using a standard protocol designed to create sequencing libraries after fragmentation. In an embodiment, the DNA sample can be blunt ended, and then an A can be added at the 3' end. A Y-adaptor with a T-overhang can be added and ligated. In some embodiments, other sticky ends can be used other than an A or T overhang. In some embodiments, other adaptors can be added, for example looped ligation adaptors. In some embodiments, the adaptors may have tag designed for PCR amplification.

A number of the embodiments provided herein, include detecting the SNVs in a ctDNA sample. Such methods in illustrative embodiments, include an amplification step and a sequencing step (Sometimes referred to herein as a "ctDNA SNV amplification/sequencing workflow). In an illustrative example, a ctDNA amplification/sequencing workflow can include generating a set of amplicons by performing a multiplex amplification reaction on nucleic acids isolated from a sample of blood or a fraction thereof from an individual, such as an individual suspected of having cancer wherein each amplicon of the set of amplicons spans at least one single nucleotide variant loci of a set of single nucleotide variant loci, such as an SNV loci known to be associated with cancer; and determining the sequence of at least a segment of at each amplicon of the set of amplicons, wherein the segment comprises a single nucleotide variant loci. In this way, this exemplary method determines the single nucleotide variants present in the sample.

Exemplary ctDNA SNV amplification/sequencing workflows in more detail can include forming an amplification reaction mixture by combining a polymerase, nucleotide triphosphates, nucleic acid fragments from a nucleic acid library generated from the sample, and a set of primers that each binds an effective distance from a single nucleotide variant loci, or a set of primer pairs that each span an effective region that includes a single nucleotide variant loci. The single nucleotide variant loci, in exemplary embodiments, is one known to be associated with cancer. Then, subjecting the amplification reaction mixture to amplification conditions to generate a set of amplicons comprising at least one single nucleotide variant loci of a set of single nucleotide variant loci, preferably known to be associated with cancer; and determining the sequence of at least a segment of each amplicon of the set of amplicons, wherein the segment comprises a single nucleotide variant loci.

The effective distance of binding of the primers can be within 1, 2, 3, 4, 5, 6, 7, 8, 9, 10, 11, 12, 13, 14, 15, 20, 25, 30, 35, 40, 45, 50, 75, 100, 125, or 150 base pairs of a SNV loci. The effective range that a pair of primers spans typically includes an SNV and is typically 160 base pairs or less, and can be 150, 140, 130, 125, 100, 75, 50 or 25 base pairs or less. In other embodiments, the effective range that a pair of primers spans is 20, 25, 30, 40, 50, 60, 70, 75, 100, 110, 120, 125, 130, 140, or 150 nucleotides from an SNV loci on the low end of the range, and 25, 30, 40, 50, 60, 70, 75, 100, 110, 120, 125, 130, 140, or 150, 160, 170, 175, or 200 on the high end of the range.

Primer tails can improve the detection of fragmented DNA from universally tagged libraries. If the library tag and the primer-tails contain a homologous sequence, hybridization can be improved (for example, melting temperature (Tm) is lowered) and primers can be extended if only a portion of the primer target sequence is in the sample DNA fragment. In some embodiments, 13 or more target specific base pairs may be used. In some embodiments, 10 to 12 target specific base pairs may be used. In some embodiments, 8 to 9 target specific base pairs may be used. In some embodiments, 6 to 7 target specific base pairs may be used.

In one embodiment, Libraries are generated from the samples above by ligating adaptors to the ends of DNA fragments in the samples, or to the ends of DNA fragments generated from DNA isolated from the samples. The fragments can then be amplified using PCR, for example, according to the following exemplary protocol: 95° C., 2 min; 15×[95° C., 20 sec, 55° C., 20 sec, 68° C., 20 sec], 68° C. 2 min, 4° C. hold.

Many kits and methods are known in the art for generation of libraries of nucleic acids that include universal primer binding sites for subsequent amplification, for example clonal amplification, and for subsequence sequencing. To help facilitate ligation of adapters library preparation and amplification can include end repair and adenylation (i.e. A-tailing). Kits especially adapted for preparing libraries from small nucleic acid fragments, especially circulating free DNA, can be useful for practicing methods provided herein. For example, the NEXTflex Cell Free kits available from Bioo Scientific or the Natera Library Prep Kit (available from Natera, Inc. San Carlos, Calif.). However, such kits would typically be modified to include adaptors that are customized for the amplification and sequencing steps of the methods provided herein. Adaptor ligation can be performed using commercially available kits such as the ligation kit found in the AGILENT SURESELECT kit (Agilent, Calif.).

Target regions of the nucleic acid library generated from DNA isolated from the sample, especially a circulating free DNA sample for the methods of the present invention, are then amplified. For this amplification, a series of primers or primer pairs, which can include between 5, 10, 15, 20, 25, 50, 100, 125, 150, 250, 500, 1000, 2500, 5000, 10,000, 20,000, 25,000, or 50,000 on the low end of the range and 15, 20, 25, 50, 100, 125, 150, 250, 500, 1000, 2500, 5000, 10,000, 20,000, 25,000, 50,000, 60,000, 75,000, or 100,000 primers on the upper end of the range, that each bind to one of a series of primer binding sites.

Primer designs can be generated with Primer3 (Untergrasser A, Cutcutache I, Koressaar T, Ye J, Faircloth B C, Remm M, Rozen S G (2012) "Primer3—new capabilities and interfaces." Nucleic Acids Research 40(15):e115 and Koressaar T, Remm M (2007) "Enhancements and modifications of primer design program Primer3." Bioinformatics 23(10):1289-91) source code available at primer3.sourceforge.net). Primer specificity can be evaluated by BLAST and added to existing primer design pipeline criteria:

Primer specificities can be determined using the BLASTn program from the ncbi-blast-2.2.29+ package. The task option "blastn-short" can be used to map the primers against hg19 human genome. Primer designs can be determined as "specific" if the primer has less than 100 hits to the genome and the top hit is the target complementary primer binding region of the genome and is at least two scores higher than other hits (score is defined by BLASTn program). This can be done in order to have a unique hit to the genome and to not have many other hits throughout the genome.

The final selected primers can be visualized in IGV (James T. Robinson, Helga Thorvaldsdóttir, Wendy Winckler, Mitchell Guttman, Eric S. Lander, Gad Getz, Jill P. Mesirov. Integrative Genomics Viewer. Nature Biotechnology 29, 24-26 (2011)) and UCSC browser (Kent W J, Sugnet C W, Furey T S, Roskin K M, Pringle T H, Zahler A M, Haussler D. The human genome browser at UCSC. Genome Res. 2002 June; 12(6):996-1006) using bed files and coverage maps for validation.

Methods described herein, in certain embodiments, include forming an amplification reaction mixture. The reaction mixture typically is formed by combining a polymerase, nucleotide triphosphates, nucleic acid fragments from a nucleic acid library generated from the sample, a set of forward and reverse primers specific for target regions that contain SNVs. The reaction mixtures provided herein, themselves forming in illustrative embodiments, a separate aspect of the invention.

An amplification reaction mixture useful for the present invention includes components known in the art for nucleic acid amplification, especially for PCR amplification. For example, the reaction mixture typically includes nucleotide triphosphates, a polymerase, and magnesium. Polymerases that are useful for the present invention can include any polymerase that can be used in an amplification reaction especially those that are useful in PCR reactions. In certain embodiments, hot start Taq polymerases are especially useful. Amplification reaction mixtures useful for practicing the methods provided herein, such as AmpliTaq Gold master mix (Life Technologies, Carlsbad, Calif.), are available commercially.

Amplification (e.g. temperature cycling) conditions for PCR are well known in the art. The methods provided herein can include any PCR cycling conditions that result in amplification of target nucleic acids such as target nucleic acids from a library. Non-limiting exemplary cycling conditions are provided in the Examples section herein.

There are many workflows that are possible when conducting PCR; some workflows typical to the methods disclosed herein are provided herein. The steps outlined herein are not meant to exclude other possible steps nor does it imply that any of the steps described herein are required for the method to work properly. A large number of parameter variations or other modifications are known in the literature, and may be made without affecting the essence of the invention.

In certain embodiments of the method provided herein, at least a portion and in illustrative examples the entire sequence of an amplicon, such as an outer primer target amplicon, is determined. Methods for determining the sequence of an amplicon are known in the art. Any of the sequencing methods known in the art, e.g. Sanger sequencing, can be used for such sequence determination. In illustrative embodiments high throughput next-generation sequencing techniques (also referred to herein as massively parallel sequencing techniques) such as, but not limited to, those employed in MYSEQ (ILLUMINA), HISEQ (ILLUMINA), ION TORRENT (LIFE TECHNOLOGIES), GENOME ANALYZER ILX (ILLUMINA), GS FLEX+ (ROCHE 454), can be used for sequencing the amplicons produced by the methods provided herein.

High throughput genetic sequencers are amenable to the use of barcoding (i.e., sample tagging with distinctive nucleic acid sequences) so as to identify specific samples from individuals thereby permitting the simultaneous analysis of multiple samples in a single run of the DNA sequencer. The number of times a given region of the genome in a library preparation (or other nucleic preparation of interest) is sequenced (number of reads) will be proportional to the number of copies of that sequence in the genome of interest (or expression level in the case of cDNA containing preparations). Biases in amplification efficiency can be taken into account in such quantitative determination.

Target Genes. Target genes of the present invention in exemplary embodiments, are cancer-related genes, and in many illustrative embodiments, cancer-related genes. A cancer-related gene refers to a gene associated with an altered risk for a cancer or an altered prognosis for a cancer. Exemplary cancer-related genes that promote cancer include oncogenes; genes that enhance cell proliferation, invasion, or metastasis; genes that inhibit apoptosis; and pro-angiogenesis genes. Cancer-related genes that inhibit cancer include, but are not limited to, tumor suppressor genes; genes that inhibit cell proliferation, invasion, or metastasis; genes that promote apoptosis; and anti-angiogenesis genes.

An embodiment of the mutation detection method begins with the selection of the region of the gene that becomes the target. The region with known mutations is used to develop primers for mPCR-NGS to amplify and detect the mutation.

Methods provided herein can be used to detect virtually any type of mutation, especially mutations known to be associated with cancer and most particularly the methods provided herein are directed to mutations, especially SNVs, associated with cancer. Exemplary SNVs can be in one or more of the following genes: EGFR, FGFR1, FGFR2, ALK, MET, ROS1, NTRK1, RET, HER2, DDR2, PDGFRA, KRAS, NF1, BRAF, PIK3CA, MEK1, NOTCH1, MLL2, EZH2, TET2, DNMT3A, SOX2, MYC, KEAP1, CDKN2A, NRG1, TP53, LKB1, and PTEN, which have been identified in various lung cancer samples as being mutated, having increased copy numbers, or being fused to other genes and combinations thereof (Non-small-cell lung cancers: a heterogeneous set of diseases. Chen et al. Nat. Rev. Cancer. 2014 Aug. 14(8):535-551). In another example, the list of genes are those listed above, where SNVs have been reported, such as in the cited Chen et al. reference.

Other exemplary polymorphisms or mutations are in one or more of the following genes: TP53, PTEN, PIK3CA, APC, EGFR, NRAS, NF2, FBXW7, ERBBs, ATAD5, KRAS, BRAF, VEGF, EGFR, HER2, ALK, p53, BRCA, BRCA1, BRCA2, SETD2, LRP1B, PBRM, SPTA1, DNMT3A, ARID1A, GRIN2A, TRRAP, STAG2, EPHA3/5/7, POLE, SYNE1, C20orf80, CSMD1, CTNNB1, ERBB2. FBXW7, KIT, MUC4, ATM, CDH1, DDX11, DDX12, DSPP, EPPK1, FAM186A, GNAS, HRNR, KRTAP4-11, MAP2K4, MLL3, NRAS, RB1, SMAD4, TTN, ABCC9, ACVR1B, ADAM29, ADAMTS19, AGAP10, AKT1, AMBN, AMPD2, ANKRD30A, ANKRD40, APOBR, AR, BIRC6, BMP2, BRAT1, BTNL8, C12orf4, C1QTNF7, C20orf186, CAPRIN2, CBWD1, CCDC30, CCDC93, CD5L, CDC27, CDC42BPA, CDH9, CDKN2A, CHD8, CHEK2, CHRNA9, CIZ1, CLSPN, CNTN6, COL14A1, CREBBP, CROCC, CTSF, CYP1A2, DCLK1, DHDDS, DHX32, DKK2, DLEC1, DNAH14, DNAH5, DNAH9, DNASE1L3, DUSP16, DYNC2H1, ECT2, EFHB, RRN3P2, TRIM49B, TUBB8P5, EPHA7, ERBB3, ERCC6, FAM21A, FAM21C, FCGBP, FGFR2, FLG2, FLT1, FOLR2, FRYL, FSCB, GAB1, GABRA4, GABRP, GH2, GOLGA6L1, GPHB5, GPR32, GPX5, GTF3C3, HECW1, HIST1H3B, HLA-A, HRAS, HS3ST1, HS6ST1, HSPD1, IDH1, JAK2, KDM5B, KIAA0528, KRT15, KRT38, KRTAP21-1, KRTAP4-5, KRTAP4-7, KRTAP5-4, KRTAP5-5, LAMA4, LATS1, LMF1, LPAR4, LPPR4, LRRFIP1, LUM, LYST, MAP2K1, MARCH1, MARCO, MB21D2, MEGF10, MMP16, MORC1, MRE11A, MTMR3, MUC12, MUC17, MUC2, MUC20, NBPF10, NBPF20, NEK1, NFE2L2, NLRP4, NOTCH2, NRK, NUP93, OBSCN, OR11H1, OR2B11, OR2M4, OR4Q3, OR5D13, OR812, OXSM, PIK3R1, PPP2R5C, PRAME, PRF1, PRG4, PRPF19, PTH2, PTPRC, PTPRJ, RAC1, RAD50, RBM12, RGPD3, RGS22, ROR1, RP11-671M22.1, RP13-996F3.4, RP1L1, RSBN1L, RYR3, SAMD3, SCN3A, SEC31A, SF1, SF3B1, SLC25A2, SLC44A1, SLC4A11, SMAD2, SPTA1, ST6GAL2, STK11, SZT2, TAF1L, TAX1BP1, TBP, TGFBI, TIF1, TMEM14B, TMEM74, TPTE, TRAPPC8, TRPS1, TXNDC6, USP32, UTP20, VASN, VPS72, WASH3P, WWTR1, XPO1, ZFHX4, ZMIZ1, ZNF167, ZNF436, ZNF492, ZNF598, ZRSR2, ABL1, AKT2, AKT3, ARAF, ARFRP1, ARID2, ASXL1, ATR, ATRX, AURKA, AURKB, AXL, BAP1, BARD1, BCL2, BCL2L2, BCL6, BCOR, BCORL1, BLM, BRIP1, BTK, CARD11, CBFB, CBL, CCND1, CCND2, CCND3, CCNE1, CD79A, CD79B, CDC73, CDK12, CDK4, CDK6, CDK8, CDKN1B, CDKN2B, CDKN2C, CEBPA, CHEK1, CIC, CRKL, CRLF2, CSF1R, CTCF, CTNNA1, DAXX, DDR2, DOT1L, EMSY (C11orf30), EP300, EPHA3, EPHA5, EPHB1, ERBB4, ERG, ESR1, EZH2, FAM123B (WTX), FAM46C, FANCA, FANCC, FANCD2, FANCE, FANCF, FANCG, FANCL, FGF10, FGF14, FGF19, FGF23, FGF3, FGF4, FGF6, FGFR1, FGFR2, FGFR3, FGFR4, FLT3, FLT4, FOXL2, GATA1, GATA2, GATA3, GID4 (C17orf39), GNA11, GNA13, GNAQ, GNAS, GPR124, GSK3B, HGF, IDH1, IDH2, IGF1R, IKBKE, IKZF1, IL7R, INHBA, IRF4, IRS2, JAK1, JAK3, JUN, KAT6A (MYST3), KDM5A, KDM5C, KDM6A, KDR, KEAP1, KLHL6, MAP2K2, MAP2K4, MAP3K1, MCL1, MDM2, MDM4, MED12, MEF2B, MEN1, MET, MITF, MLH1, MLL, MLL2, MPL, MSH2, MSH6, MTOR, MUTYH, MYC, MYCL1, MYCN, MYD88, NF1, NFKBIA, NKX2-1, NOTCH1, NPM1, NRAS, NTRK1, NTRK2, NTRK3, PAK3, PALB2, PAX5, PBRM1, PDGFRA, PDGFRB, PDK1, PIK3CG, PIK3R2, PPP2R1A, PRDM1, PRKAR1A, PRKDC, PTCH1, PTPN11, RAD51, RAF1, RARA, RET, RICTOR, RNF43, RPTOR, RUNX1, SMARCA4, SMARCB1, SMO, SOCS1, SOX10, SOX2, SPEN, SPOP, SRC, STAT4, SUFU, TET2, TGFBR2, TNFAIP3, TNFRSF14, TOP1, TP53, TSC1, TSC2, TSHR, VHL, WISPS, WT1, ZNF217, ZNF703, and combinations thereof (Su et al., J Mol Diagn 2011, 13:74-84; DOI:10.1016/j.jmoldx.2010.11.010; and Abaan et al., "The Exomes of the NCI-60 Panel: A Genomic Resource for Cancer Biology and Systems Pharmacology", Cancer Research, Jul. 15, 2013, which are each hereby incorporated by reference in its entirety). Exemplary polymorphisms or mutations can be in one or more of the following microRNAs: miR-15a, miR-16-1, miR-23a, miR-23b, miR-24-1, miR-24-2, miR-27a, miR-27b, miR-29b-2, miR-29c, miR-146, miR-155, miR-221, miR-222, and miR-223 (Calin et al. "A microRNA signature associated with prognosis and progression in chronic lymphocytic leukemia." N Engl J Med 353:1793-801, 2005, which is hereby incorporated by reference in its entirety).

Amplification (e.g. PCR) Reaction Mixtures

Methods of the present invention, in certain embodiments, include forming an amplification reaction mixture. The reaction mixture typically is formed by combining a polymerase, nucleotide triphosphates, nucleic acid fragments from a nucleic acid library generated from the sample, a series of forward target-specific outer primers and a first strand reverse outer universal primer. Another illustrative embodiment is a reaction mixture that includes forward target-specific inner primers instead of the forward target-specific outer primers and amplicons from a first PCR reaction using the outer primers, instead of nucleic acid fragments from the nucleic acid library. The reaction mixtures provided herein, themselves forming in illustrative embodiments, a separate aspect of the invention. In illustrative embodiments, the reaction mixtures are PCR reaction mixtures. PCR reaction mixtures typically include magnesium.

In some embodiments, the reaction mixture includes ethylenediaminetetraacetic acid (EDTA), magnesium, tetramethyl ammonium chloride (TMAC), or any combination thereof. In some embodiments, the concentration of TMAC is between 20 and 70 mM, inclusive. While not meant to be bound to any particular theory, it is believed that TMAC binds to DNA, stabilizes duplexes, increases primer specificity, and/or equalizes the melting temperatures of different primers. In some embodiments, TMAC increases the uniformity in the amount of amplified products for the different targets. In some embodiments, the concentration of magnesium (such as magnesium from magnesium chloride) is between 1 and 8 mM.

The large number of primers used for multiplex PCR of a large number of targets may chelate a lot of the magnesium (2 phosphates in the primers chelate 1 magnesium). For example, if enough primers are used such that the concentration of phosphate from the primers is ~9 mM, then the primers may reduce the effective magnesium concentration by ~4.5 mM. In some embodiments, EDTA is used to decrease the amount of magnesium available as a cofactor for the polymerase since high concentrations of magnesium can result in PCR errors, such as amplification of non-target loci. In some embodiments, the concentration of EDTA reduces the amount of available magnesium to between 1 and 5 mM (such as between 3 and 5 mM).

In some embodiments, the pH is between 7.5 and 8.5, such as between 7.5 and 8, 8 and 8.3, or 8.3 and 8.5, inclusive. In some embodiments, Tris is used at, for example, a concentration of between 10 and 100 mM, such as between 10 and 25 mM, 25 and 50 mM, 50 and 75 mM, or 25 and 75 mM, inclusive. In some embodiments, any of these concentrations of Tris are used at a pH between 7.5 and 8.5. In some embodiments, a combination of KCl and $(NH_4)_2SO_4$ is used, such as between 50 and 150 mM KCl and between 10 and 90 mM $(NH_4)_2SO_4$, inclusive. In some embodiments, the concentration of KCl is between 0 and 30 mM, between 50 and 100 mM, or between 100 and 150 mM, inclusive. In some embodiments, the concentration of $(NH_4)_2SO_4$ is between 10 and 50 mM, 50 and 90 mM, 10 and 20 mM, 20 and 40 mM, 40 and 60 mM, or 60 and 80 mM $(NH_4)_2SO_4$, inclusive. In some embodiments, the ammonium $[NH_4^+]$ concentration is between 0 and 160 mM, such as between 0 to 50, 50 to 100, or 100 to 160 mM, inclusive. In some embodiments, the sum of the potassium and ammonium concentration ($[K^+]+[NH_4^+]$) is between 0 and 160 mM, such as between 0 to 25, 25 to 50, 50 to 150, 50 to 75, 75 to 100, 100 to 125, or 125 to 160 mM, inclusive. An exemplary buffer with $[K^+]+[NH_4^+]=120$ mM is 20 mM KCl and 50 mM $(NH_4)_2SO_4$. In some embodiments, the buffer includes 25 to 75 mM Tris, pH 7.2 to 8, 0 to 50 mM KCl, 10 to 80 mM ammonium sulfate, and 3 to 6 mM magnesium, inclusive. In some embodiments, the buffer includes 25 to 75 mM Tris pH 7 to 8.5, 3 to 6 mM $MgCl_2$, 10 to 50 mM KCl, and 20 to 80 mM $(NH_4)_2SO_4$, inclusive. In some embodiments, 100 to 200 Units/mL of polymerase are used. In some embodiments, 100 mM KCl, 50 mM $(NH_4)_2SO_4$, 3 mM $MgCl_2$, 7.5 nM of each primer in the library, 50 mM TMAC, and 7 ul DNA template in a 20 ul final volume at pH 8.1 is used.

In some embodiments, a crowding agent is used, such as polyethylene glycol (PEG, such as PEG 8,000) or glycerol. In some embodiments, the amount of PEG (such as PEG 8,000) is between 0.1 to 20%, such as between 0.5 to 15%, 1 to 10%, 2 to 8%, or 4 to 8%, inclusive. In some embodiments, the amount of glycerol is between 0.1 to 20%, such as between 0.5 to 15%, 1 to 10%, 2 to 8%, or 4 to 8%, inclusive. In some embodiments, a crowding agent allows either a low polymerase concentration and/or a shorter annealing time to be used. In some embodiments, a crowding agent improves the uniformity of the DOR and/or reduces dropouts (undetected alleles).

In some embodiments, a polymerase with proof-reading activity, a polymerase without (or with negligible) proof-reading activity, or a mixture of a polymerase with proof-reading activity and a polymerase without (or with negligible) proof-reading activity is used. In some embodiments, a hot start polymerase, a non-hot start polymerase, or a mixture of a hot start polymerase and a non-hot start polymerase is used. In some embodiments, a HotStarTaq DNA polymerase is used (see, for example, QIAGEN catalog No. 203203). In some embodiments, AmpliTaq Gold® DNA Polymerase is used. In some embodiments a PrimeSTAR GXL DNA polymerase, a high fidelity polymerase that provides efficient PCR amplification when there is excess template in the reaction mixture, and when amplifying long products, is used (Takara Clontech, Mountain View, Calif.). In some embodiments, KAPA Taq DNA Polymerase or KAPA Taq HotStart DNA Polymerase is used; they are based on the single-subunit, wild-type Taq DNA polymerase of the thermophilic bacterium *Thermus aquaticus*. KAPA Taq and KAPA Taq HotStart DNA Polymerase have 5'-3' polymerase and 5'-3' exonuclease activities, but no 3' to 5' exonuclease (proofreading) activity (see, for example, KAPA BIOSYSTEMS catalog No. BK1000). In some embodiments, Pfu DNA polymerase is used; it is a highly thermostable DNA polymerase from the hyperthermophilic archaeum *Pyrococcus furiosus*. The enzyme catalyzes the template-dependent polymerization of nucleotides into duplex DNA in the 5'→3' direction. Pfu DNA Polymerase also exhibits 3'→5' exonuclease (proofreading) activity that enables the polymerase to correct nucleotide incorporation errors. It has no 5'→3' exonuclease activity (see, for example, Thermo Scientific catalog No. EP0501). In some embodiments Klentaq1 is used; it is a Klenow-fragment analog of Taq DNA polymerase, it has no exonuclease or endonuclease activity (see, for example, DNA POLYMERASE TECHNOLOGY, Inc, St. Louis, Mo., catalog No. 100). In some embodiments, the polymerase is a PHUSION DNA polymerase, such as PHUSION High Fidelity DNA polymerase (M0530S, New England BioLabs, Inc.) or PHUSION Hot Start Flex DNA polymerase (M0535S, New England BioLabs, Inc.). In some embodiments, the polymerase is a Q5® DNA Polymerase, such as Q5® High-Fidelity DNA Polymerase (M0491S, New England BioLabs, Inc.) or Q5® Hot Start High-Fidelity DNA Polymerase (M0493S, New England BioLabs, Inc.). In some embodiments, the polymerase is a T4 DNA polymerase (M0203S, New England BioLabs, Inc.).

In some embodiment, between 5 and 600 Units/mL (Units per 1 mL of reaction volume) of polymerase is used, such as between 5 to 100, 100 to 200, 200 to 300, 300 to 400, 400 to 500, or 500 to 600 Units/mL, inclusive.

PCR Methods. In some embodiments, hot-start PCR is used to reduce or prevent polymerization prior to PCR thermocycling. Exemplary hot-start PCR methods include initial inhibition of the DNA polymerase, or physical separation of reaction components reaction until the reaction mixture reaches the higher temperatures. In some embodiments, slow release of magnesium is used. DNA polymerase requires magnesium ions for activity, so the magnesium is chemically separated from the reaction by binding to a chemical compound, and is released into the solution only at high temperature. In some embodiments, non-covalent binding of an inhibitor is used. In this method a peptide, antibody, or aptamer are non-covalently bound to the enzyme at low temperature and inhibit its activity. After incubation at elevated temperature, the inhibitor is released and the reaction starts. In some embodiments, a cold-sensitive Taq polymerase is used, such as a modified DNA polymerase with almost no activity at low temperature. In some embodiments, chemical modification is used. In this method, a molecule is covalently bound to the side chain of an amino acid in the active site of the DNA polymerase. The molecule is released from the enzyme by incubation of the reaction mixture at elevated temperature. Once the molecule is released, the enzyme is activated.

In some embodiments, the amount to template nucleic acids (such as an RNA or DNA sample) is between 20 and 5,000 ng, such as between 20 to 200, 200 to 400, 400 to 600, 600 to 1,000; 1,000 to 1,500; or 2,000 to 3,000 ng, inclusive.

In some embodiments a QIAGEN Multiplex PCR Kit is used (QIAGEN catalog No. 206143). For 100×50 µl multiplex PCR reactions, the kit includes 2× QIAGEN Multiplex PCR Master Mix (providing a final concentration of 3 mM $MgCl_2$, 3×0.85 ml), 5× Q-Solution (1×2.0 ml), and RNase-Free Water (2×1.7 ml). The QIAGEN Multiplex PCR Master Mix (MM) contains a combination of KCl and $(NH_4)_2SO_4$ as well as the PCR additive, Factor MP, which increases the local concentration of primers at the template. Factor MP stabilizes specifically bound primers, allowing efficient primer extension by HotStarTaq DNA Polymerase. HotStarTaq DNA Polymerase is a modified form of Taq DNA polymerase and has no polymerase activity at ambient temperatures. In some embodiments, HotStarTaq DNA Polymerase is activated by a 15-minute incubation at 95° C. which can be incorporated into any existing thermal-cycler program.

In some embodiments, 1x QIAGEN MM final concentration (the recommended concentration), 7.5 nM of each primer in the library, 50 mM TMAC, and 7 ul DNA template in a 20 ul final volume is used. In some embodiments, the PCR thermocycling conditions include 95° C. for 10 minutes (hot start); 20 cycles of 96° C. for 30 seconds; 65° C. for 15 minutes; and 72° C. for 30 seconds; followed by 72° C. for 2 minutes (final extension); and then a 4° C. hold.

In some embodiments, 2× QIAGEN MM final concentration (twice the recommended concentration), 2 nM of each primer in the library, 70 mM TMAC, and 7 ul DNA template in a 20 ul total volume is used. In some embodiments, up to 4 mM EDTA is also included. In some embodiments, the PCR thermocycling conditions include 95° C. for 10 minutes (hot start); 25 cycles of 96° C. for 30 seconds; 65° C. for 20, 25, 30, 45, 60, 120, or 180 minutes; and optionally 72° C. for 30 seconds); followed by 72° C. for 2 minutes (final extension); and then a 4° C. hold.

Another exemplary set of conditions includes a semi-nested PCR approach. The first PCR reaction uses 20 ul a reaction volume with 2× QIAGEN MM final concentration, 1.875 nM of each primer in the library (outer forward and reverse primers), and DNA template. Thermocycling parameters include 95° C. for 10 minutes; 25 cycles of 96° C. for 30 seconds, 65° C. for 1 minute, 58° C. for 6 minutes, 60° C. for 8 minutes, 65° C. for 4 minutes, and 72° C. for 30 seconds; and then 72° C. for 2 minutes, and then a 4° C. hold. Next, 2 ul of the resulting product, diluted 1:200, is used as input in a second PCR reaction. This reaction uses a 10 ul reaction volume with 1× QIAGEN MM final concentration, 20 nM of each inner forward primer, and 1 uM of reverse primer tag. Thermocycling parameters include 95° C. for 10 minutes; 15 cycles of 95° C. for 30 seconds, 65° C. for 1 minute, 60° C. for 5 minutes, 65° C. for 5 minutes, and 72° C. for 30 seconds; and then 72° C. for 2 minutes, and then a 4° C. hold. The annealing temperature can optionally be higher than the melting temperatures of some or all of the primers, as discussed herein (see U.S. patent application Ser. No. 14/918,544, filed Oct. 20, 2015, which is herein incorporated by reference in its entirety).

The melting temperature ($T_m$) is the temperature at which one-half (50%) of a DNA duplex of an oligonucleotide (such as a primer) and its perfect complement dissociates and becomes single strand DNA. The annealing temperature ($T_A$) is the temperature one runs the PCR protocol at. For prior methods, it is usually 5° C. below the lowest $T_m$ of the primers used, thus close to all possible duplexes are formed (such that essentially all the primer molecules bind the template nucleic acid). While this is highly efficient, at lower temperatures there are more unspecific reactions bound to occur. One consequence of having too low a $T_A$ is that primers may anneal to sequences other than the true target, as internal single-base mismatches or partial annealing may be tolerated. In some embodiments of the present inventions, the $T_A$ is higher than $T_m$, where at a given moment only a small fraction of the targets have a primer annealed (such as only ~1-5%). If these get extended, they are removed from the equilibrium of annealing and dissociating primers and target (as extension increases $T_m$ quickly to above 70° C.), and a new ~1-5% of targets has primers. Thus, by giving the reaction a long time for annealing, one can get ~100% of the targets copied per cycle.

In various embodiments, the annealing temperature is between 1, 2, 3, 4, 5, 6, 7, 8, 9, 10, 11, 12, 13° C. and 2, 3, 4, 5, 6, 7, 8, 9, 10, 11, 12, 13, or 15° C. on the high end of the range, greater than the melting temperature (such as the empirically measured or calculated $T_m$) of at least 25, 50, 60, 70, 75, 80, 90, 95, or 100% of the non-identical primers. In various embodiments, the annealing temperature is between 1 and 15° C. (such as between 1 to 10, 1 to 5, 1 to 3, 3 to 5, 5 to 10, 5 to 8, 8 to 10, 10 to 12, or 12 to 15° C., inclusive) greater than the melting temperature (such as the empirically measured or calculated $T_m$) of at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; 100,000; or all of the non-identical primers. In various embodiments, the annealing temperature is between 1 and 15° C. (such as between 1 to 10, 1 to 5, 1 to 3, 3 to 5, 3 to 8, 5 to 10, 5 to 8, 8 to 10, 10 to 12, or 12 to 15° C., inclusive) greater than the melting temperature (such as the empirically measured or calculated $T_m$) of at least 25%, 50%, 60%, 70%, 75%, 80%, 90%, 95%, or all of the non-identical primers, and the length of the annealing step (per PCR cycle) is between 5 and 180 minutes, such as 15 and 120 minutes, 15 and 60 minutes, 15 and 45 minutes, or 20 and 60 minutes, inclusive.

Exemplary Multiplex PCR. In various embodiments, long annealing times (as discussed herein and exemplified in Example 12) and/or low primer concentrations are used. In fact, in certain embodiments, limiting primer concentrations and/or conditions are used. In various embodiments, the length of the annealing step is between 15, 20, 25, 30, 35, 40, 45, or 60 minutes on the low end of the range and 20, 25, 30, 35, 40, 45, 60, 120, or 180 minutes on the high end of the range. In various embodiments, the length of the annealing step (per PCR cycle) is between 30 and 180 minutes. For example, the annealing step can be between 30 and 60 minutes and the concentration of each primer can be less than 20, 15, 10, or 5 nM. In other embodiments the primer concentration is 1, 2, 3, 4, 5, 6, 7, 8, 9, 10, 15, 20, or 25 nM on the low end of the range, and 2, 3, 4, 5, 6, 7, 8, 9, 10, 15, 20, 25, and 50 on the high end of the range.

At high level of multiplexing, the solution may become viscous due to the large amount of primers in solution. If the solution is too viscous, one can reduce the primer concentration to an amount that is still sufficient for the primers to bind the template DNA. In various embodiments, between 1,000 and 100,000 different primers are used and the concentration of each primer is less than 20 nM, such as less than 10 nM or between 1 and 10 nM, inclusive.

EXPERIMENTAL SECTION

The presently disclosed embodiments are described in the following Examples, which are set forth to aid in the understanding of the disclosure, and should not be construed to limit in any way the scope of the disclosure as defined in the claims which follow thereafter. The following examples are put forth so as to provide those of ordinary skill in the art with a complete disclosure and description of how to use the described embodiments, and are not intended to limit the scope of the disclosure nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by volume, and temperature is in degrees Centigrade. It should be understood that variations in the methods as described may be made without changing the fundamental aspects that the experiments are meant to illustrate.

Example 1

Retrospective analysis of blood samples from kidney transplant recipients (292 plasma samples from 187 unique patients, with 8 samples excluded) was performed after patients were assessed for graft condition by biopsy. Biopsies were graded by Banff classification for T cell- and antibody-mediated acute rejection (AR) or non-AR (borderline, stable, or other injury). The biopsy-analyzed samples were found to include 52 samples in acute rejection (AR) and 240 samples in non-acute rejection (Non-AR), including being in borderline rejection, having other injury, or being stable.

Circulating free DNA from 2 mL of plasma from each sample was extracted by the Qiagen cfDNA kit. The amount of cfDNA was then quantified, using LapChip. Library preparation was accomplished using the Natera Panorama Library Prep Kit using the standard protocol, except that library was amplified by 18 PCR cycles (as opposed to the standard 9 cycles). The amplified library was then purified using Ampure beads (Agencourt). The amplified library product was then quantified again using LabChip and a quality control step was performed. This was followed by Panorama V2 OneSTAR, dilution, and BC-PCR.

The samples were then pooled for sequencing, purification (Qiagen Kit), quantification (Qubit), and quality control (Bioanalyzer).

The percentage of donor derived cell free DNA in the transplant recipient plasma was determined using massively multiplexed PCR, which targeted 13,392 single-nucleotide polymorphisms (SNPs), followed by NGS sequencing on a HiSeq2500 machine (Illumina) for 50 cycles (28-29 samples/run=10-11M reads/sample).

Figure 2:
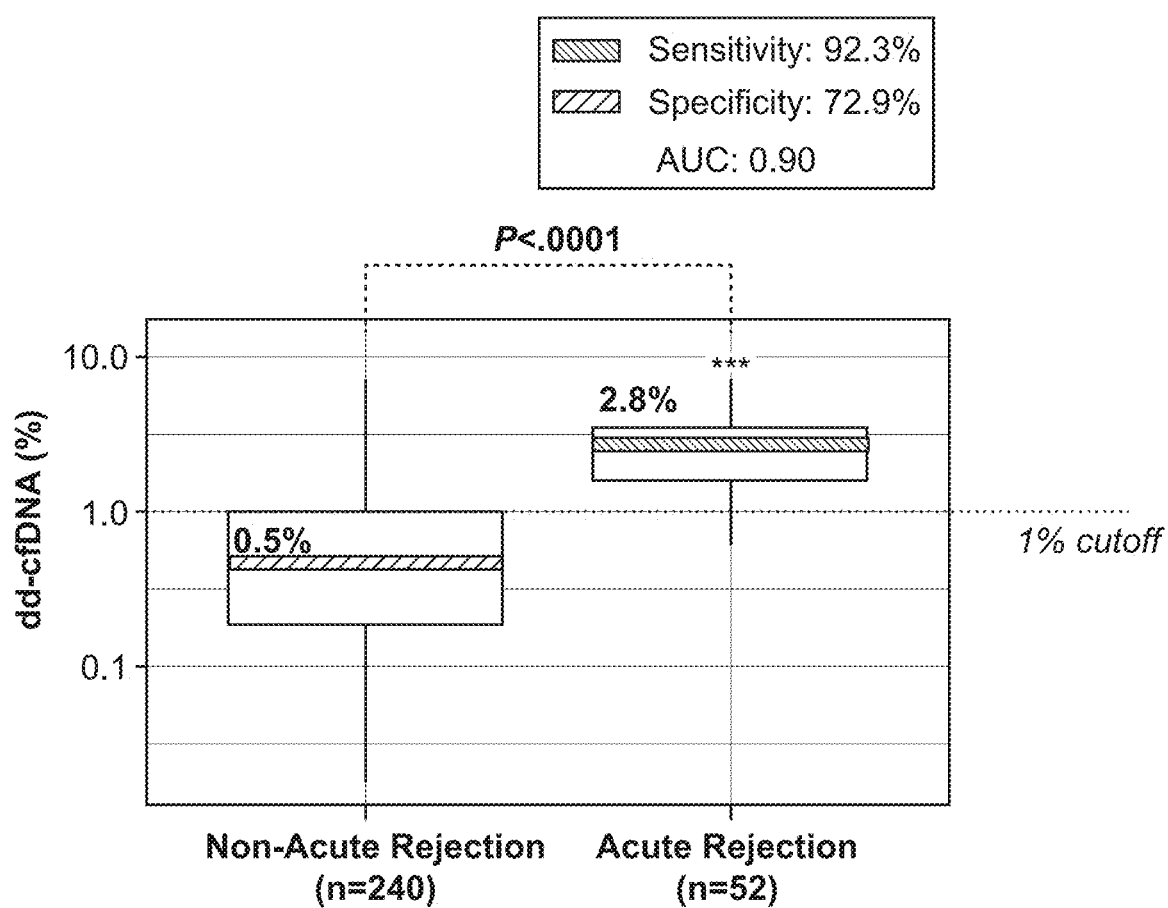
FIG. 2 exemplifies the high capacity that dd-cfDNA demonstrates for detection of kidney transplant rejection. Using a threshold of 1% dd-cfDNA, a sensitivity of 92.3%, a specificity of 72.9% and an AUC of 0.9 is achieved.
Figure 3:
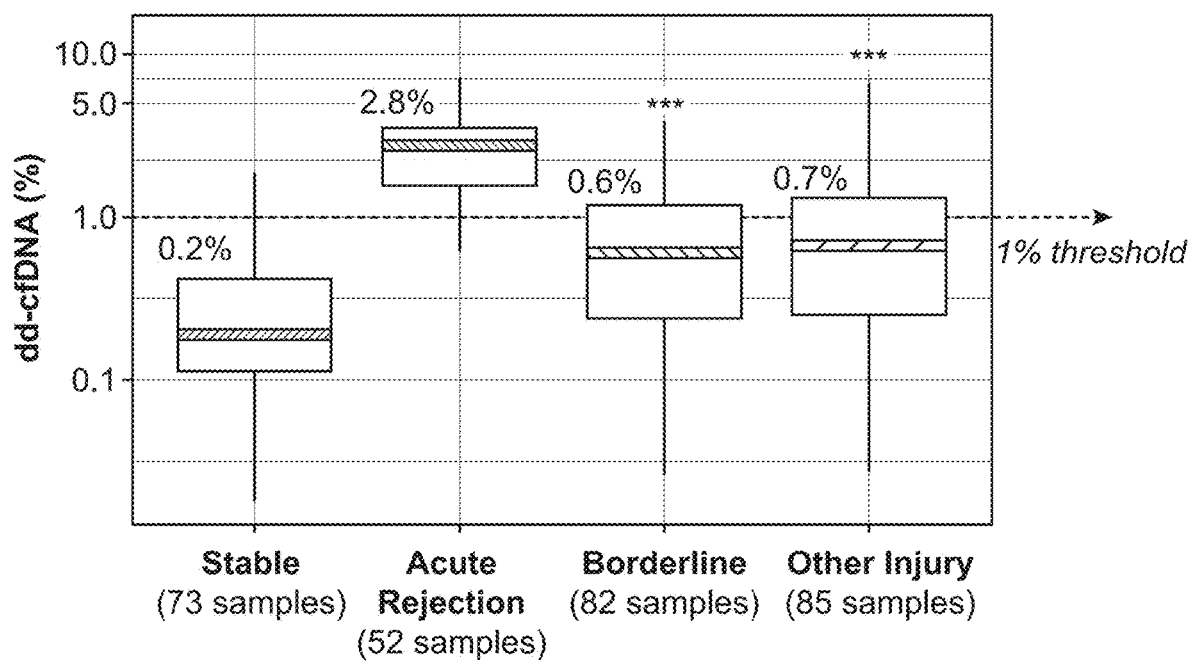
FIG. 3 exemplifies the % dd-cfDNA between kidney transplant recipients that were either stable, undergoing acute rejection, undergoing borderline rejection, or experiencing other transplant injury.

Levels of dd-cfDNA were then correlated with rejection and transplant injury status and were found to demonstrate high capacity for detection of kidney transplant rejection. Specifically, it was found that dd-cfDNA at a level of above 1% (out of total free circulating DNA) serves as a suitable threshold for classifying a kidney transplant as undergoing acute rejection (AR). See FIG. 2. For transplants not undergoing acute rejection, each of the categories of the transplants being stable, borderline rejected or undergoing other injury were alone each under the 1% dd-cfDNA threshold level. See FIG. 3.

Further, when classifying samples where dd-cfDNA was greater than 1%, it was found that less than 1 in 20 were stable.

| Group | Stable | Borderline Rejection | Other Injury | Acute Rejection |
|---|---|---|---|---|
| >1% dd-cfDNA, n (%) | 5 (4.4) | 26 (23.0) | 34 (30.1) | 48 (42.5) |

Figure 4:
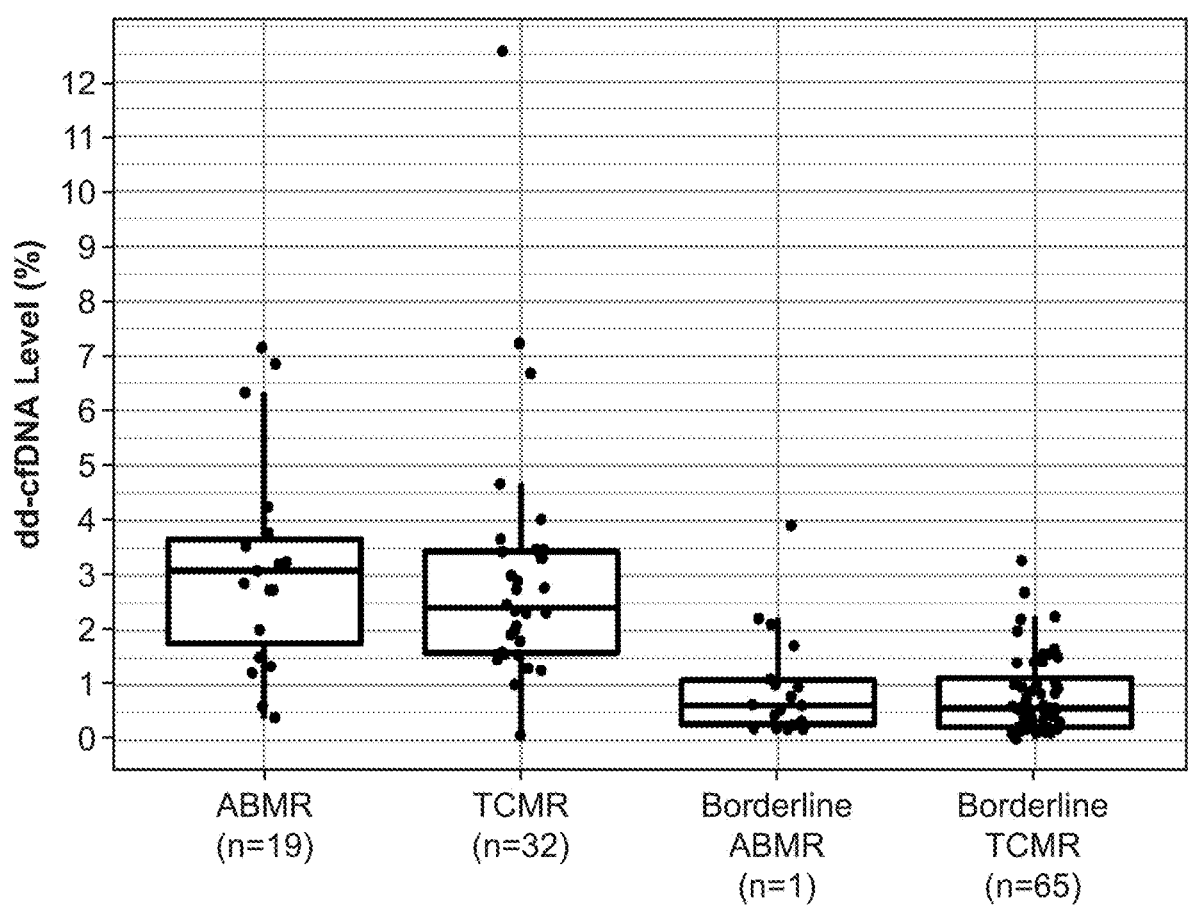
FIG. 4 exemplifies the ability of the disclosed methods to detect either borderline or acute transplant rejections where the transplants are undergoing either antibody-mediated rejection (ABMR) or T-cell mediated rejection (TCMR).

In the 52 samples undergoing acute rejection, 19 were classified by biopsy as undergoing antibody mediated rejection (ABMR), 32 were classified as undergoing T-cell mediated rejection (TCMR) and 1 sample was classified as undergoing both types of rejection. It was found that the fraction of dd-cfDNA did not differ significantly between ABMR and TCMR cohorts or between borderline ABMR and TCMR cohorts. See FIG. 4.

Figure 5:
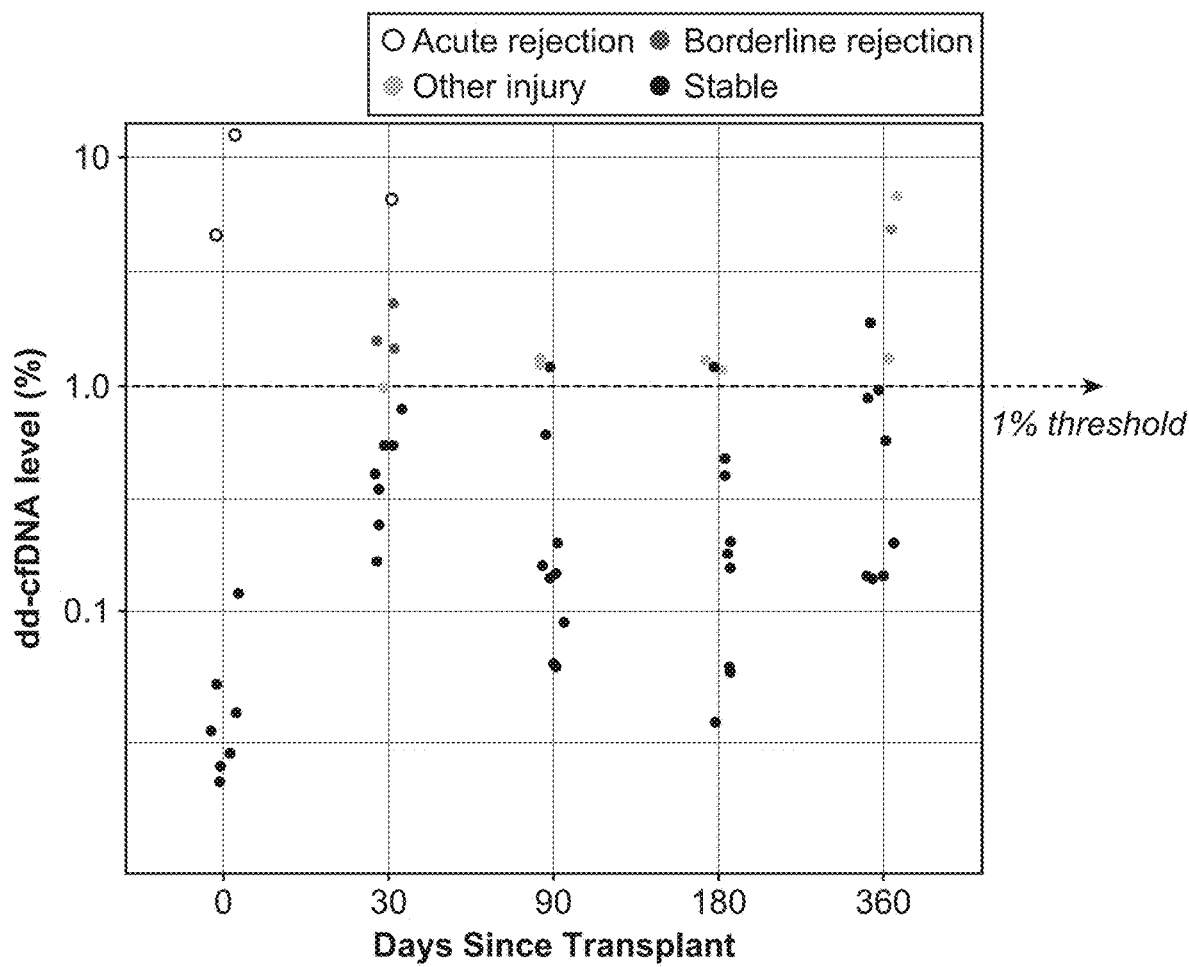
FIG. 5 exemplifies the clinical relevance of detecting dd-cfDNA, as disclosed herein, for detection of transplant rejection immediately following surgery.

Further, when the days since transplant was compared to the percentage level of dd-cfDNA and rejection status of kidney transplants, it was found that the 1% dd-cfDNA threshold level served as a clinically relevant biomarker immediately following surgery. See FIG. 5.

Figure 6:
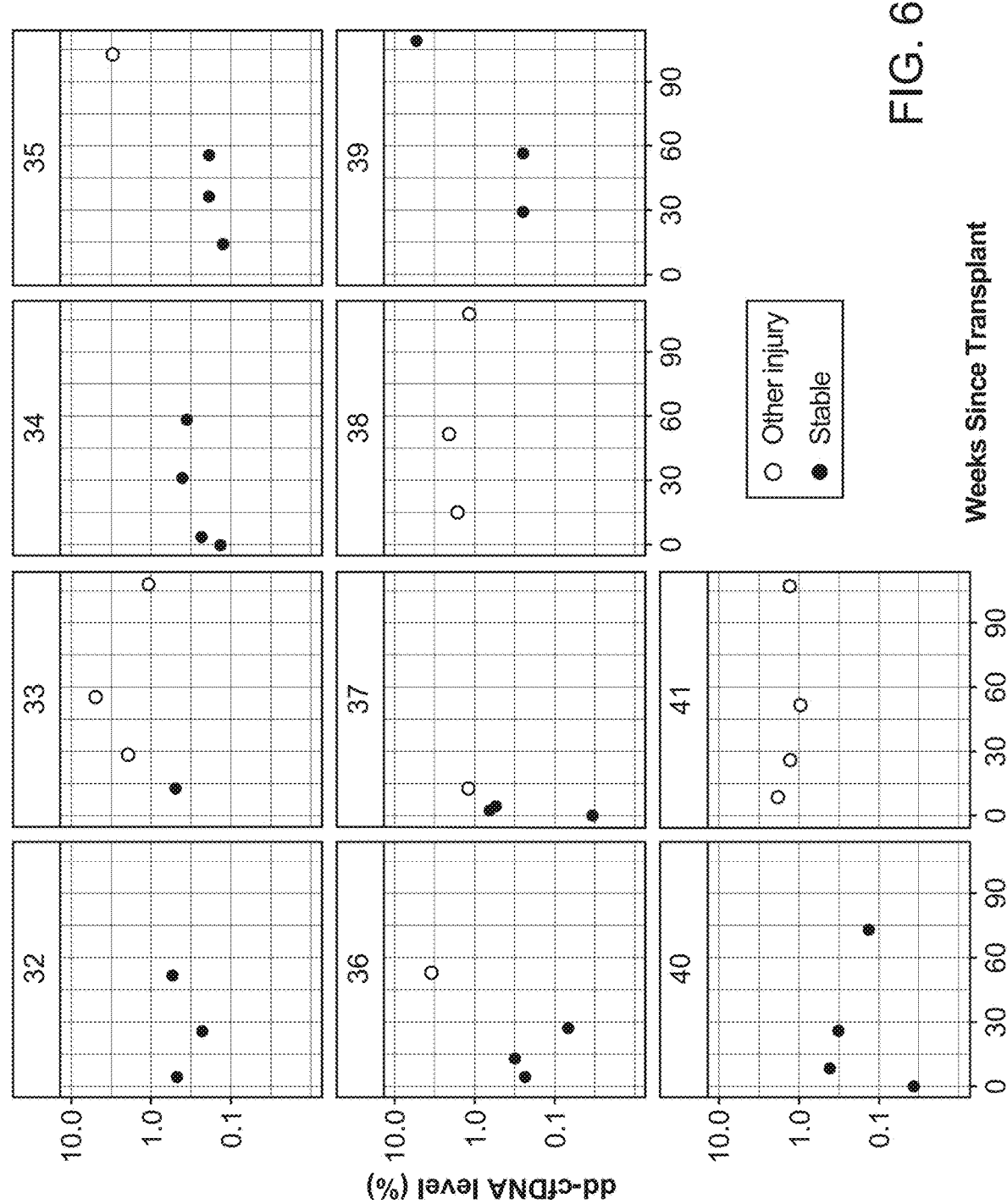
FIG. 6 exemplifies the value of repeated measurements within individual transplant recipient patients following transplantation surgery.

Value was also found in repeated measurements within individual patients, as the change from a stable transplant to an injured transplant could be monitored over time. See FIG. 6.

When the performance metrics of the current study was compared to a previous study from Bloom, R D et al., Cell-Free DNA and Active Rejection in Kidney Allografts, J. Am. Soc. Nephrol., 2017; 287(7):2221-2232, it was found that the present methods resulted in significantly greater sensitivity and specificity.

| | Current Study (292 samples) | Bloom et al. (107 samples) |
|---|---|---|
| | Performance Metrics | |
| Sensitivity | 92% (n = 52) | 59% (n = 27) |
| Specificity | 73% (n = 240) | 85% (n = 80) |

| | Current Study (292 samples) | Bloom et al. (107 samples) |
|---|---|---|
| AUC | 0.90 | 0.74 |
| | Assuming 25% Prevalence | |
| NPV | 97% | 84% |
| PPV | 53% | 61% |

As such, the presently disclosed assay offers certain technical advantages. For example, the assay disclosed herein comprised advanced cfDNA isolation and preparation, with size selection to eliminate background noise and is able to filer PCR and NGS errors through advanced error modeling. Further, the present assay used more SNPS (13, 392 v. 266 disclosed in Bloom et al.) with advanced SNP selections.

Example 2. Optimizing Detection of Kidney Transplant Injury by Assessment of Donor-Derived Cell-Free DNA by Massively Multiplex PCR Introduction Precision medicine and personalized tailoring of immunosuppressive drug regimens can improve the current state of organ transplant management. Transplantation injuries are often detected late given that invasive biopsies are best avoided, where possible, for the sake of the patient experience. Though advancements in immunosuppressive drugs, organ procurement methods, and human leukocyte antigen-typing has lowered the number of clinical- and biopsy-confirmed acute rejection episodes, sub-clinical acute rejection of kidney grafts remains a significant risk. Kidney transplant management is particularly challenging owing to redundancy of the serum creatinine assay, which, in addition to the late detection of transplant injuries, makes immunosuppression dosage and adjustment far from personalized. Therefore, rapid and non-invasive detection and prediction of allograft injury/rejection holds promise for significant improvement of management in kidney transplantation patients.

Diagnosis of acute renal transplant rejection is generally dependent on an increase in serum creatinine levels or its algorithmic derivative, eGFR, which indicates altered renal filtration functioning. Since there are many causes of the baseline drift in altered renal filtering in these patients, biopsy is required for definitive diagnosis. Methods of estimating kidney rejection in allograft recipients based on CR or eGFR lack sufficient accuracy. However, biopsies are invasive and can be costly procedures, which limit their use in clinical practice. Furthermore, biopsy results are often plagued by expert reader variance and can lead to delayed diagnosis of acute rejection, after which irreversible organ damage has already taken place. Therefore, there is a current unmet need for a rapid, accurate, and noninvasive approach to detecting allograft rejection and/or injury—one which may require integration of the current "gold" standard morphological assessments with modern molecular diagnostic tools.

Donor-derived cell-free DNA (dd-cfDNA) detected in the blood of transplant recipients has been reported as a noninvasive marker to diagnose allograft injury/rejection, and holds promise for producing faster and more quantitative results compared with current treatment options. Recently, it was demonstrated that plasma levels of dd-cfDNA can discriminate active rejection status from stable organ function in kidney transplant recipients, using a 1% cutoff. Previously we validated the clinical application of a targeted, single-nucleotide polymorphism (SNP)-based cell-free assay targeting greater than 10,000 loci as a successful screening tool for the detection of fetal chromosomal abnormalities and show here that a similar approach targeting 13,392 SNPs can be used to evaluate differences in donor cfDNA burden in different transplant rejection injuries over time. This study uses a novel SNP-based mmPCR-NGS methodology to measure dd-cfDNA in renal transplant recipients for the detection of allograft rejection/injury without prior knowledge of donor genotypes.

Materials and Methods

Study Design

This study was a retrospective analysis of blood samples from kidney transplant recipients who had transplant surgeries at the University of California-San Francisco (USCF) Medical Center. The study was approved by the institutional review board at the UCSF Medical Center. All patients provided written informed consent to participate in the research, in full adherence to the Declaration of Helsinki. The clinical and research activities being reported are consistent with the Principles of the Declaration of Istanbul as outlined in the Declaration of Istanbul on Organ Trafficking and Transplant Tourism.

Study Population and Samples

Blood samples were collected from male or female adult or young adult recipients of kidney transplants at various time points following transplantation surgery. The selection of study samples was based on (a) if there is adequate plasma sample available, (b) if the blood sample is associated biopsy information that could be used in data analysis. Patients had received a kidney from related or unrelated living donors, or unrelated deceased donors. Plasma samples were obtained from an existing biorepository, of which 53% were matched with a biopsy collected at the time of blood collection. Patients without a matching biopsy were categorized as STA; all non-STA patients were biopsy-matched.

Biopsy Samples

All kidney biopsies were analyzed in a blinded manner by a UCSF pathologist and were graded by the Banff classification for acute rejection (AR); intragraft C4d stains were performed to assess for acute humoral rejection. Transplant "injury" was defined as a >20% increase in serum creatinine from its previous steady-state baseline value and an associated biopsy that was classified as either AR, BL, or OI (e.g., drug toxicity, viral infection). AR was defined, at minimum, by the following criteria: 1) TCMR consisting of either a tubulitis (t) score >2 accompanied by an interstitial inflammation (i) score >2 or vascular changes (v) score >0; 2) C4d positive ABMR consisting of positive donor specific antibodies (DSA) with a glomerulitis (g) score >0/or peritubular capillaritis score (ptc) >0 or v>0 with unexplained acute tubular necrosis/thrombotic micro angiopathy (ATN/TMA) with C4d=2; or 3) C4d negative ABMR consisting of positive DSA with unexplained ATN/TMA with g+ptc≥2 and C4d is either 0 or 1. Borderline change (BL) was defined by t1+i0, or t1+i1, or t2+i0 without explained cause (e.g., polyomavirus-associated nephropathy [PVAN]/infectious cause/ATN). Other criteria used for BL changes were g>0 and/or ptc>0, or v>0 without DSA, or C4d or positive DSA, or positive C4d without nonzero g or ptc scores. Normal (STA) allografts were defined by an absence of significant injury pathology as defined by Banff schema. Samples were stratified into an AR or non-AR groups (BL, STA, or OI) for analyses.

dd-cfDNA Measurement in Blood Samples

Cell-free DNA was extracted from the plasma samples using the QIAamp Circulating Nucleic Acid Kit (Qiagen) and quantified on the LabChip NGS 5k kit (Perkin Elmer) following the manufacturer's instructions. Extracted cfDNA was used as input into library preparation using the Natera Library Prep kit, with a modification of 18 cycles of library amplification to plateau the libraries. The purified libraries were quantified using LabChip NGS 5k. Target enrichment was accomplished using massively multiplexed-PCR (mmPCR). This was performed using a modified version of a previously described method, with 13,392 single nucleotide polymorphisms (SNPs) targeted. The amplicons were then sequenced on an Illumina HiSeq 2500 Rapid Run, 50 cycles single end, with 10-11 million reads per sample.

Statistical Analyses of dd-cfDNA, Creatinine, and eGFR

In each sample, dd-cfDNA levels were measured and correlated with rejection status; the results of dd-cfDNA analyses were compared with creatinine and eGFR levels. Where applicable, all tests are two sided. Significance was always set at $P<0.05$. Because the distribution of dd-cfDNA level found in patients was severely skewed among the groups of interest, these data were analyzed using a Kruskal-Wallis rank sum test followed by Dunn multiple comparison tests with Holm correction. The eGFR (creatinine in mg/dL) was calculated as described previously. Briefly, $eGFR=186 * Serum\ Creatinine^{-1.154} * Age^{-0.203} * [1.210\ if\ Black] * [0.742\ if\ Female]$.

To evaluate the performance of dd-cfDNA level, creatinine, and eGFR score (mL/min/1.73 m$^2$) as rejection markers, samples were separated into an AR group and a non-AR group (BL+STA+OI). Using this categorization, sensitivity, specificity, PPV, and NPV of each marker was determined using the following AR classification cut-offs: >1% for dd-cfDNA, >1.8 mg/dL for creatinine, and <40.0 for eGFR. AUC of the receiver operating characteristic (ROC) curve—an additional measure of discriminating between AR and non-AR—was also calculated for each marker. Confidence intervals for sensitivity and specificity were calculated using exact Binomial tests (Clopper-Pearson). Confidence intervals for PPV and NPV were calculated with a normal approximation. Confidence interval for AUC was calculated using the DeLong method.

Subanalyses evaluated dd-cfDNA levels by Banff score for individual histological features (glomerulitis, allograft glomerulopathy, mesangial matrix increase, interstitial fibrosis, tubular atrophy, interstitial inflammation, total interstitial inflammation, tubulitis, atrophic tubulitis, peritubular capillaritis, arteriolar hyalinosis, alternative arteriolar hyalinosis, vascular intimal thickening, intimal arteritis, c4d staining). Elevated scores of glomerulitis, interstitial inflammation, total interstitial inflammation, tubulitis, peritubular capillaritis, and c4d staining correlate with elevated levels of dd-cfDNA by using a Kruskal-Wallis rank sum test followed by Dunn multiple comparison tests. Differences in dd-cfDNA levels by donor type (living related, living non-related, and deceased non-related) were also evaluated. Significance was determined using the Kruskal-Wallis rank sum test as described above. Inter- and intra-variability in dd-cfDNA over time was evaluated using a mixed effects model with a logarithmic transformation on dd-cfDNA. The 95% confidence intervals for the intra- and inter-patient standard deviations were calculated using a likelihood profile method.

All analyses were done using R 3.3.2 using the FSA (for Dunn tests), lme4 (for mixed effect modeling) and pROC (for AUC calculations) packages.

Results

Patients and Blood Samples

Figure 13:
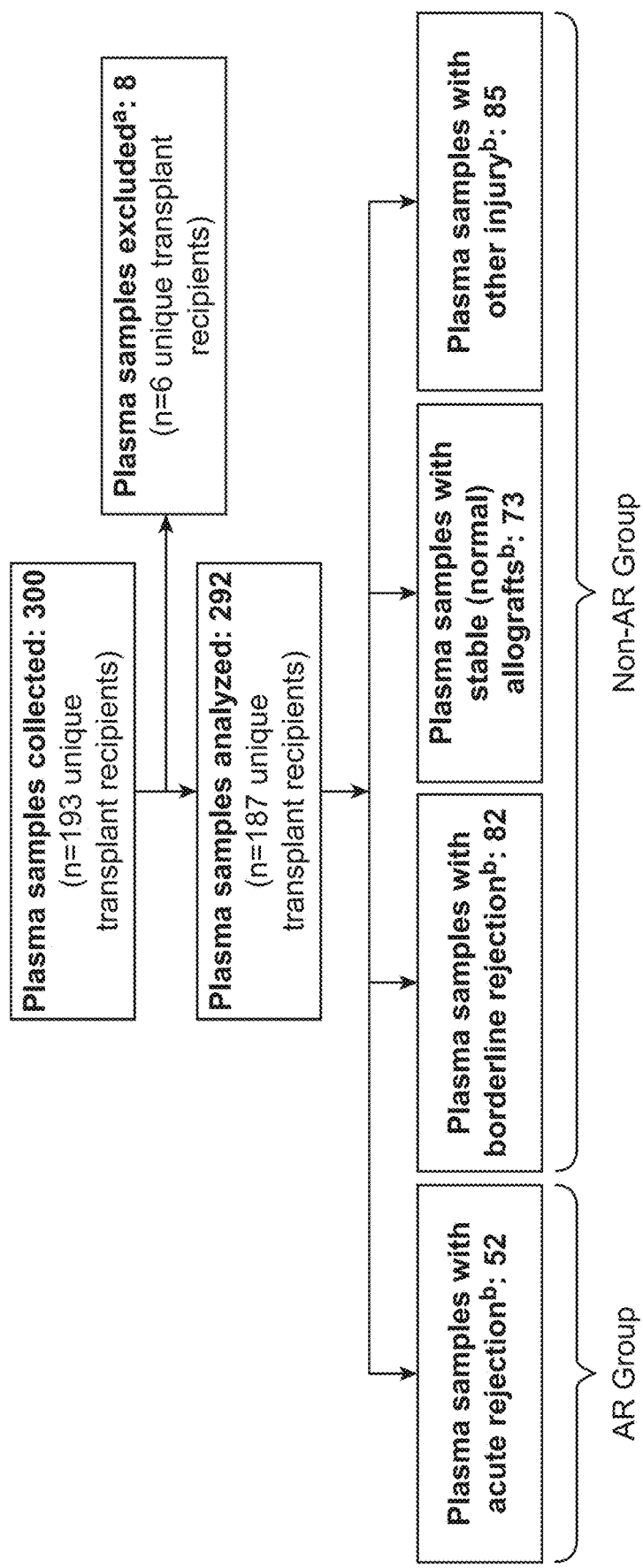
FIG. 13: Plasma Sample Breakdown.

A total of 300 plasma samples were collected from 193 unique renal transplant recipients; of these, 8 samples from 6 patients were unable to be sequenced and were excluded from analyses. Among the 292 analyzed samples, 52 were collected from patients with biopsy-proven acute rejection (AR), 82 were from patients with biopsy-proven borderline rejection (BL), 73 were from patients with normal, stable allografts (STA), and 85 were from patients with biopsy indicating other injury (OI) (FIG. 13). Because it is desirable to detect the existence of AR versus any other condition, we defined non-AR as the group including all specimens that were classified as STA, BL, or OI. A summary of demographic information and sample characteristics are provided in Table A. All pathology samples were read at UCSF, verified at the same institution and were rated by all observers using the Banff criteria.

dd-cfDNA in Plasma of Kidney Transplant Recipients

Figure 14A:
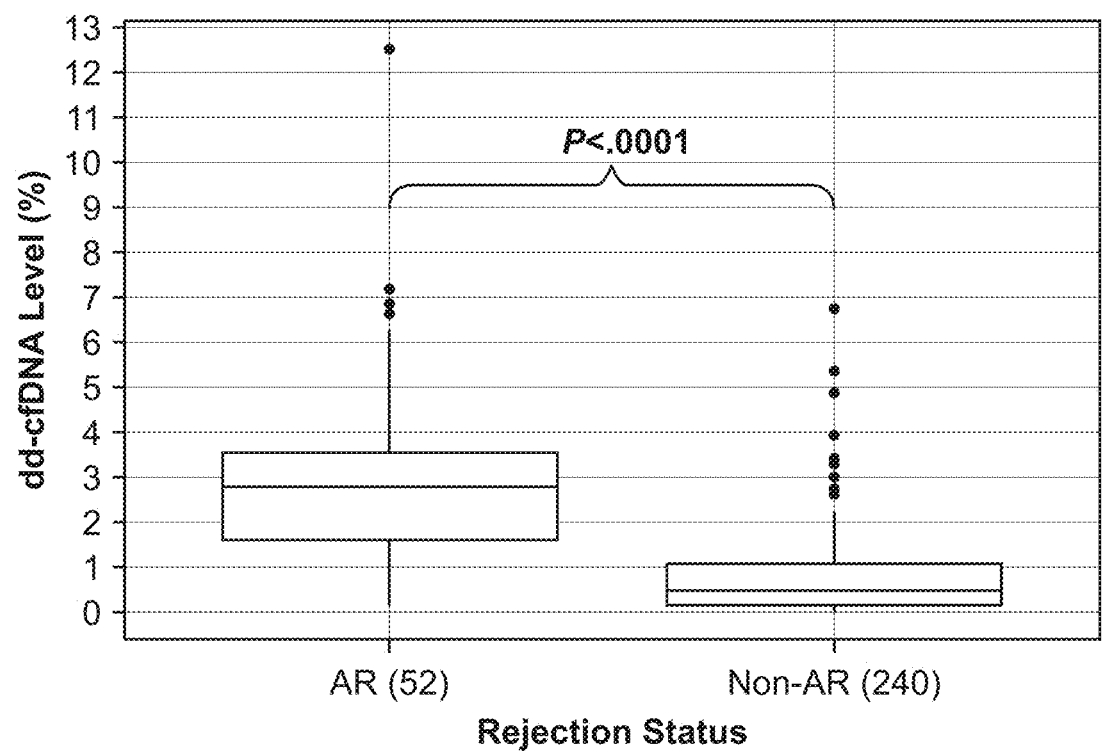
FIG. 14A-C: Discrimination of active rejection by dd-cfDNA (A) versus creatinine (B) and eGFR (C). Boxes indicate interquartile range ($25^{th}$ to $75^{th}$ percentile); horizontal lines in boxes represent medians; dots indicate outliers >1.5 times the upper quartile value. For Panel C, eGFR values were only calculated for 200 samples due to the availably of data; the non-AR group for eGFR analysis included 79 borderline, 65 other injury, and 7 stable samples. P-values for dd-cfDNA adjusted using Kruskal-Wallis rank sum test followed by Dunn multiple comparison tests with Holm correction; P-values for creatinine and eGFR adjusted via Tukey's test.

The amount of dd-cfDNA was significantly higher in the circulating plasma of the AR group (median=2.76%) compared with the non-AR group (median=0.47%; P<0.0001) (FIG. 14A). Additionally, the median level of dd-cfDNA was significantly higher in the AR group compared with all 3 individual non-rejection subgroups: BL group (0.59%), STA group (0.19%), and OI (0.70%; all comparisons, P<0.0001) (Table B). Donor-derived cfDNA levels were significantly lower in the STA group than in the BL or OI groups (P<0.0001). There was no significant difference in the level of dd-cfDNA between the BL and OI groups (P=0.496) (Table B).

Creatinine and eGFR Levels

Figure 14B:
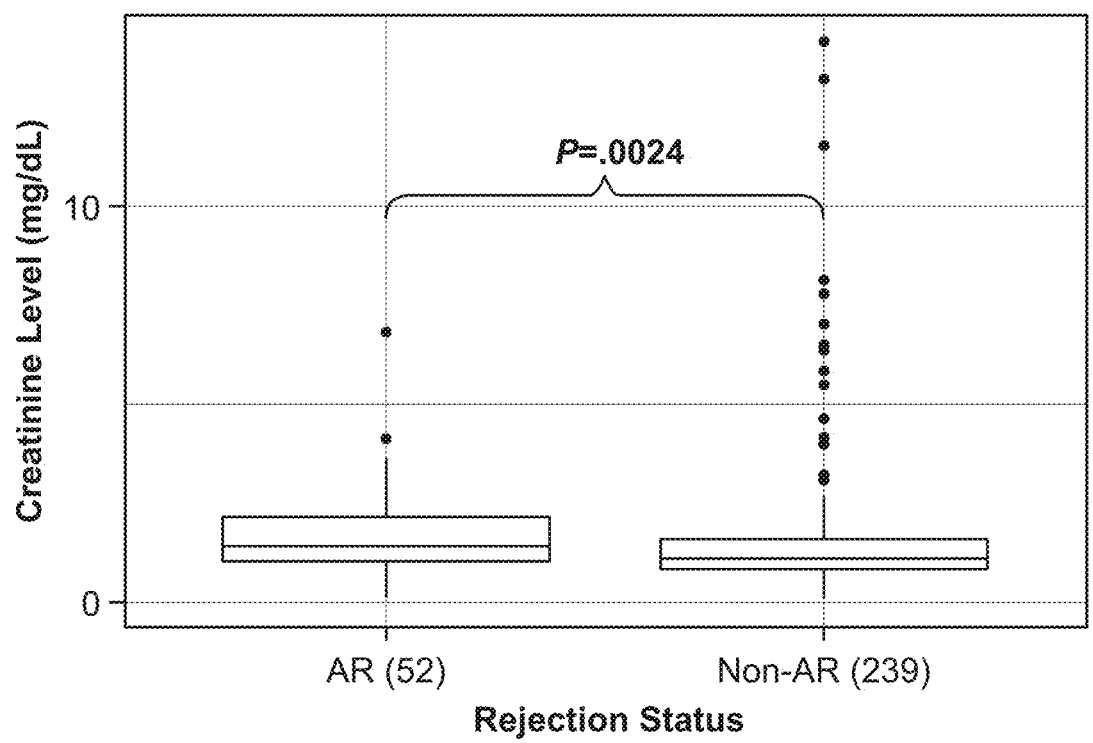

In contrast to dd-cfDNA, evaluation of creatinine levels did not appear to have as much discriminatory ability for differentiating AR and non-AR groups (FIG. 14B). The median creatinine level in the AR group (1.4 mg/dL) was significantly higher than that observed in the non-AR group (1.1 mg/dL; P=0.0024). However, unlike the dd-cfDNA results, there was no difference in median creatinine levels between the AR and BL groups (both 1.4 mg/dL; P=0.8653) (Table B). Median creatinine levels were significantly lower in the OI group (1.1 mg/dL) versus AR group (1.4; P=0.0078) and significantly lower in the STA group (0.9 mg/dL) versus BL group (1.4 mg/dL; P<0.0001); creatinine level was numerically lower in the STA group compared with the OI group (1.1 mg/dL), though the difference was not statistically significant (P=0.1887).

Figure 14C:
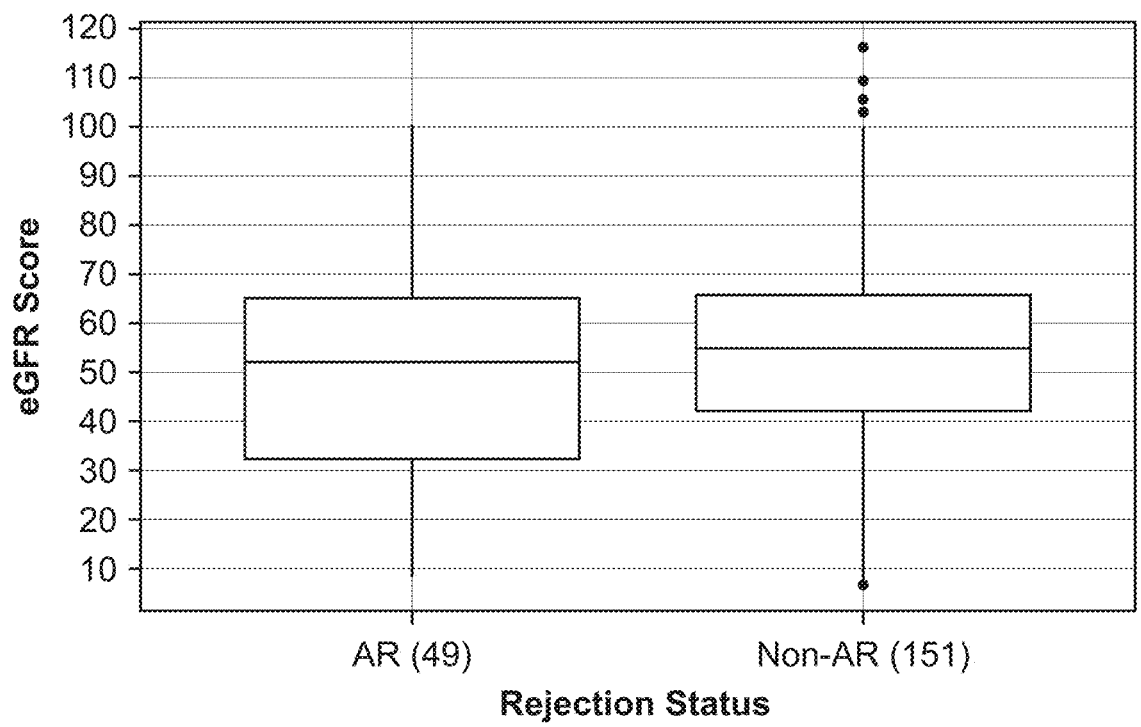

For samples with available eGFR scores (AR, n=52; non-AR, n=151 [BL, n=79; OI, n=65; STA, n=7]) median eGFR were similar between the AR group (52.5) and the non-AR group (54.7; P=0.2379) (FIG. 14C). There was a significant difference between eGFR levels in the AR group versus the STA group (69.3; P=0.0125), but no difference in eGFR score between AR and BL groups (52.0 vs 51.8; P=0.902) (Table B). Additionally, compared with the STA group, eGFR levels were significantly higher in the BL (51.8; P=0.0254) and OI (55.1; P=0.0413) groups.

Performance Estimates for Discriminatory Ability of Tests

Figure 15A:
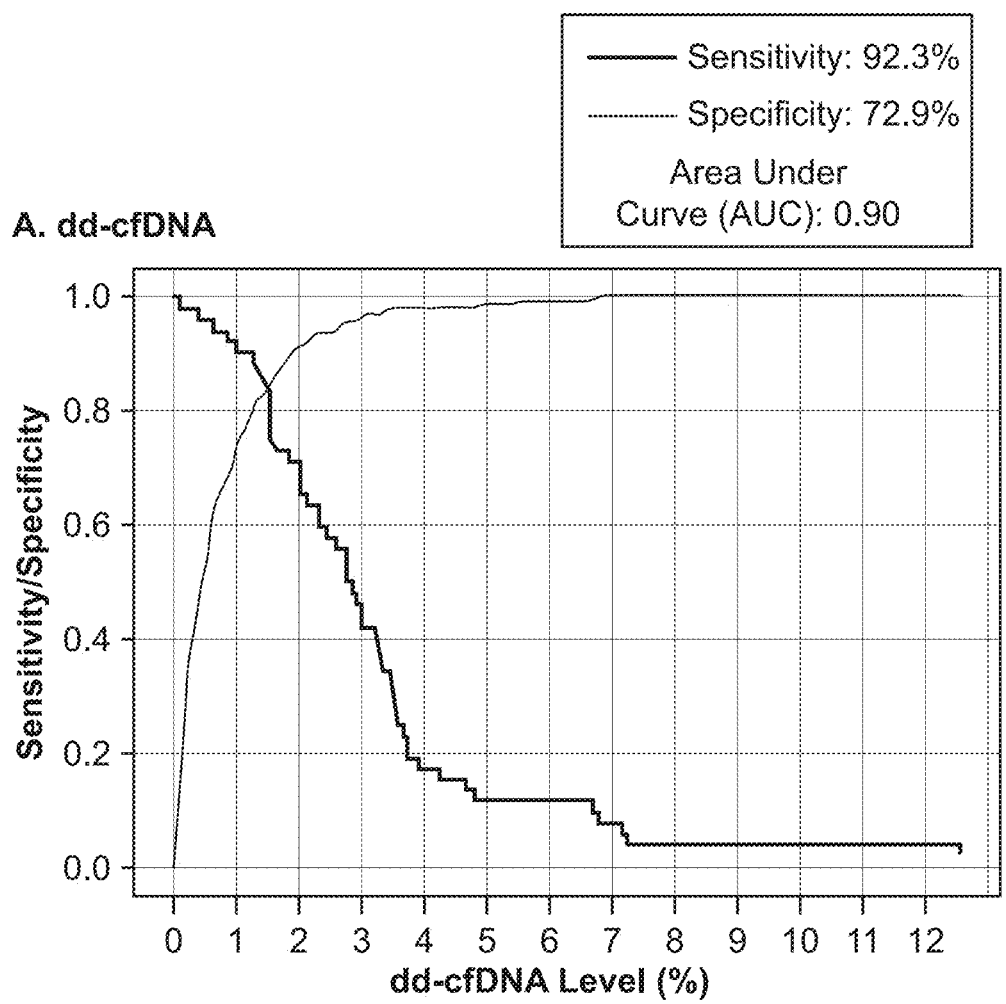
FIG. 15A-C: Predictive statistics for acute rejection versus non-acute rejection.

With a cutoff of >1%, the mmPCR-NGS method had a 92.3% sensitivity (95% confidence interval [CI], 81.5%-97.9%) and 72.9% specificity (95% CI, 66.8%-78.4%) for detection of AR. Sensitivity and specificity values are shown over the range of dd-cfDNA cutoffs in FIG. 15A. The area under the curve (AUC) was 0.90 (95% CI, 0.85-0.95). Based on a 25% prevalence of rejection in an at-risk population, the positive predictive value (PPV) was projected to be 53.2% (95% CI, 47.7%-58.7%) and the negative predictive value (NPV) was projected to be 96.6% (95% CI, 69.8%-100%).

Figure 15B:
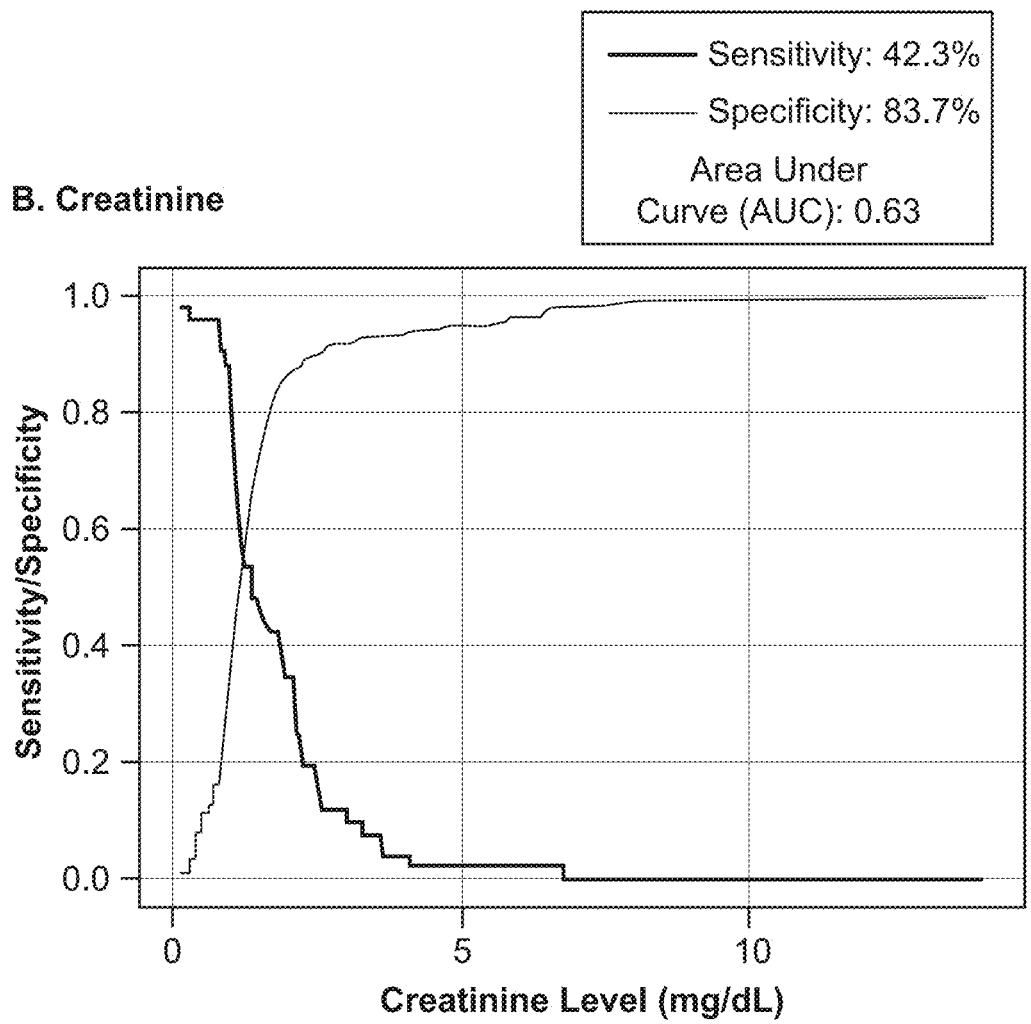
Figure 15C:
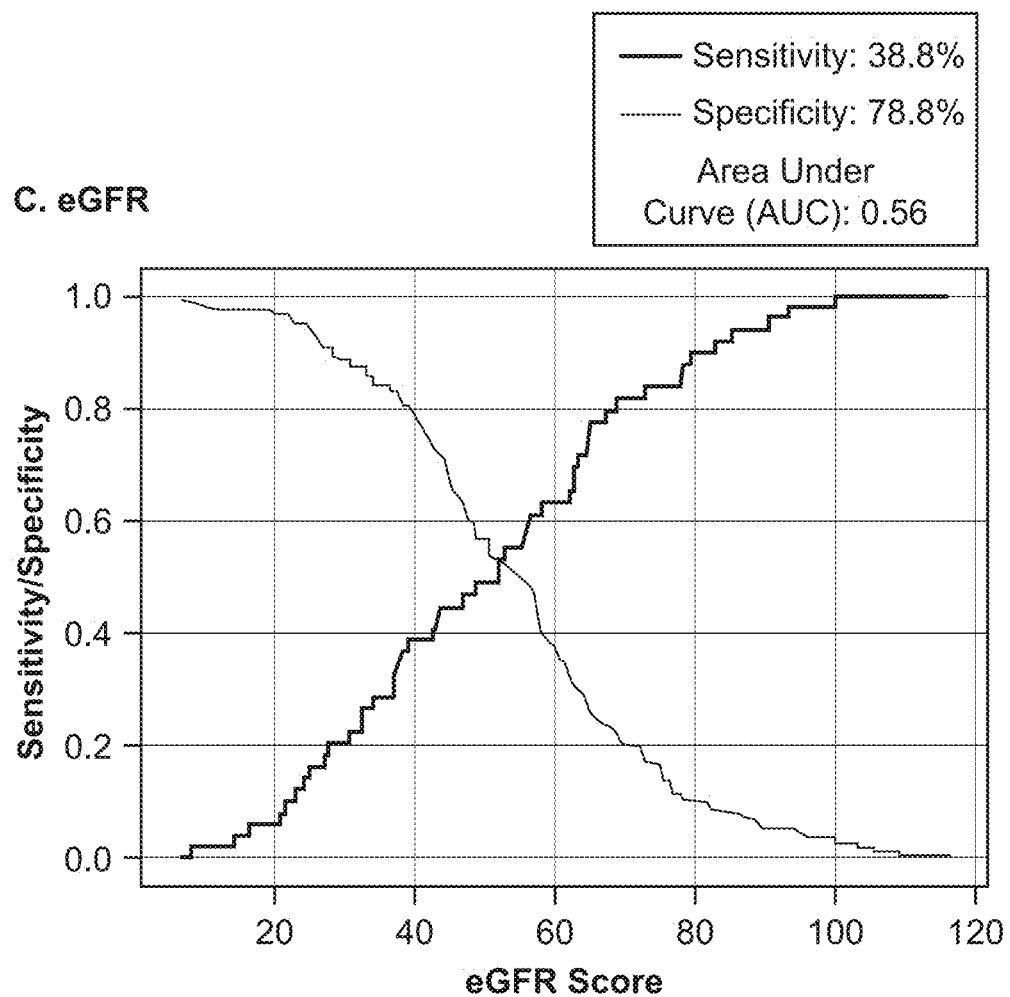

Sensitivity and specificity was lower using creatinine and eGFR as discriminatory tests (FIG. 15B-C). Using a creatinine level cutoff of 1.8 mg/dL for AR, sensitivity and specificity values were 42.3% (95% CI, 28.7%-56.8%) and 83.7% (78.3%-88.1%), respectively, with an AUC of 0.63 (0.54-0.71). The projected PPV and NPV values of creatinine were 46.4% (35.7%-57.0%) and 81.3% (50.5%-100%), respectively. The sensitivity for eGFR analysis using a cutoff score of <40 was 38.8% (25.2%-53.8%) and the specificity was 78.8% (71.4% to 85.0%) with an AUC of 0.56 (0.46-0.66).

Figure 16:
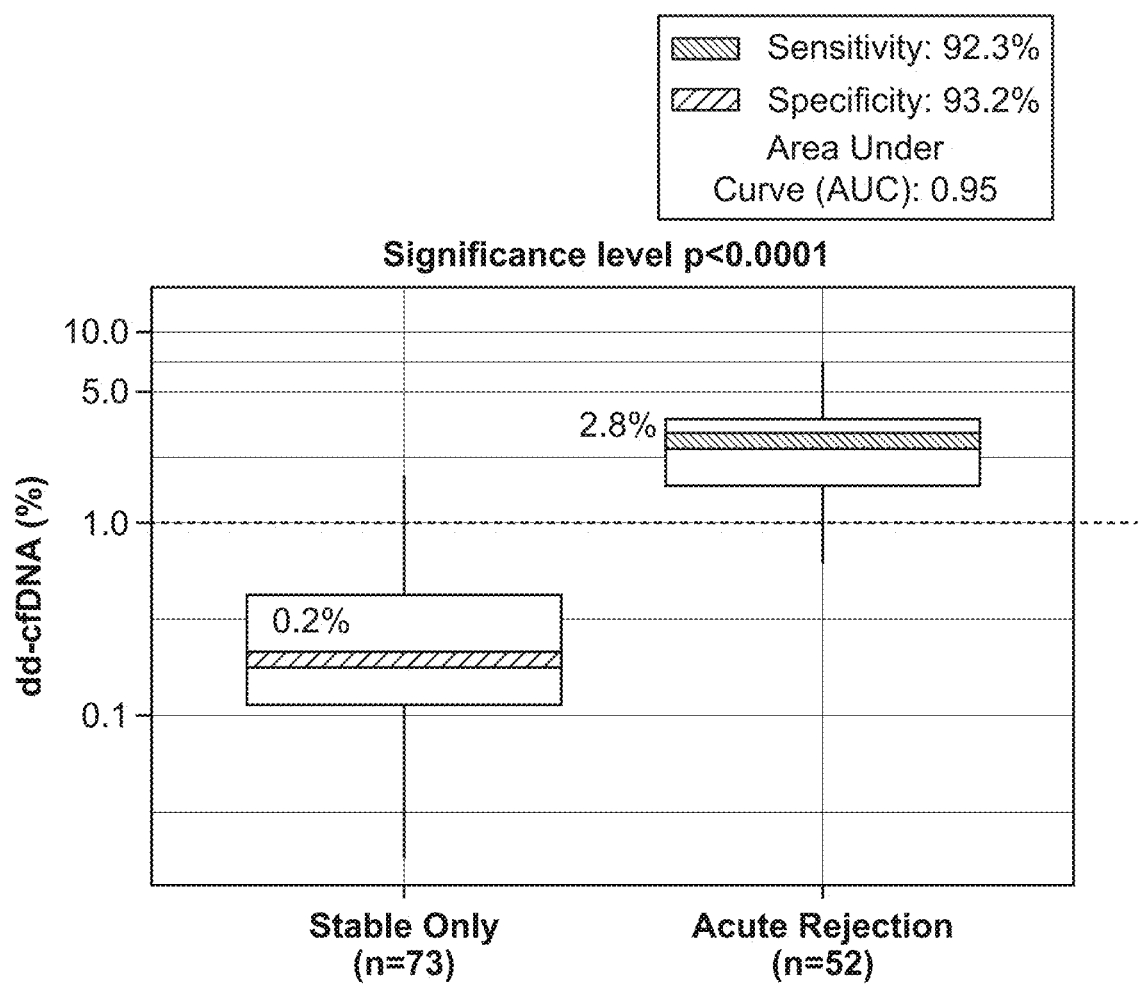
FIG. 16: Predictive statistics for acute rejection versus stable. Boxes indicate inter-quartile range, horizontal lines represent medians.

When comparing AR to STA only, the dd-cfDNA assay had a 92.3% sensitivity (95% confidence interval [CI], 81.5%-97.9%) and 93.2% specificity (95% CI, 84.7%-97.7%). Sensitivity and specificity values are shown over the range of dd-cfDNA cutoffs in FIG. 16. The area under the curve (AUC) was 0.951 (95% CI, 0.91-1.0).

dd-cfDNA>1% by Rejection Status

Of the 292 patient samples, 113 (38.7%) had dd-cfDNA levels >1%. Of those, less than 1 in 20 were STA (5 samples [4.4%]); the remainder were AR (48 samples [42.5%]), OI (34 samples [30.1%]), or BL (26 samples [23.0%]).

Relationship Between dd-cfDNA and Acute Rejection Type

Figure 17:
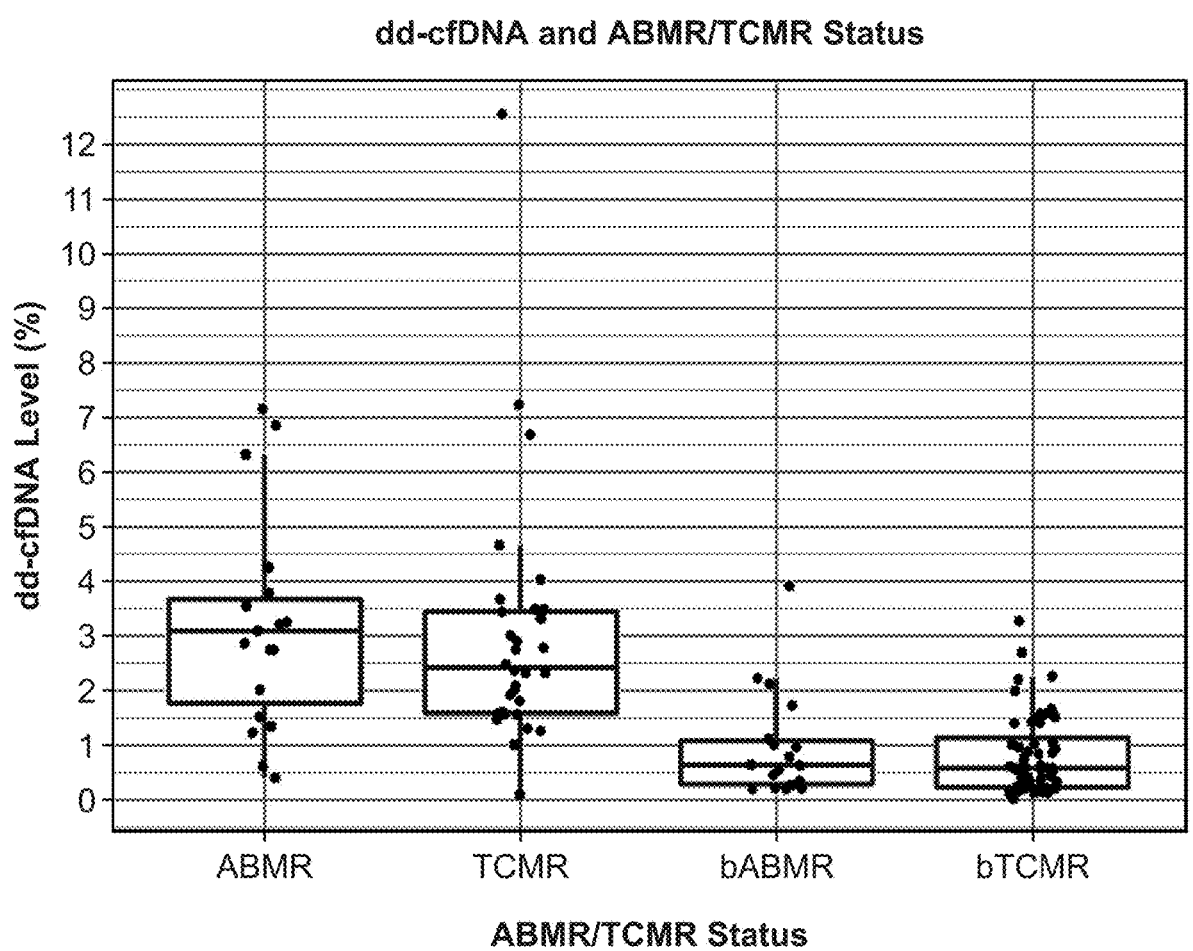
FIG. 17: dd-cfDNA as a function of antibody-mediated-versus T-cell-mediated rejection. Boxes indicate inter-quartile range ($25^{th}$ to $75^{th}$ percentile); horizontal lines in boxes represent medians; dots indicate all individual data points. P-values for dd-cfDNA adjusted using Kruskal-Wallis rank sum test followed by Dunn multiple comparison tests with Holm correction. ABMR, antibody-mediated rejection; b, borderline; TCMR, T-cell-mediated rejection.
Figure 18A:
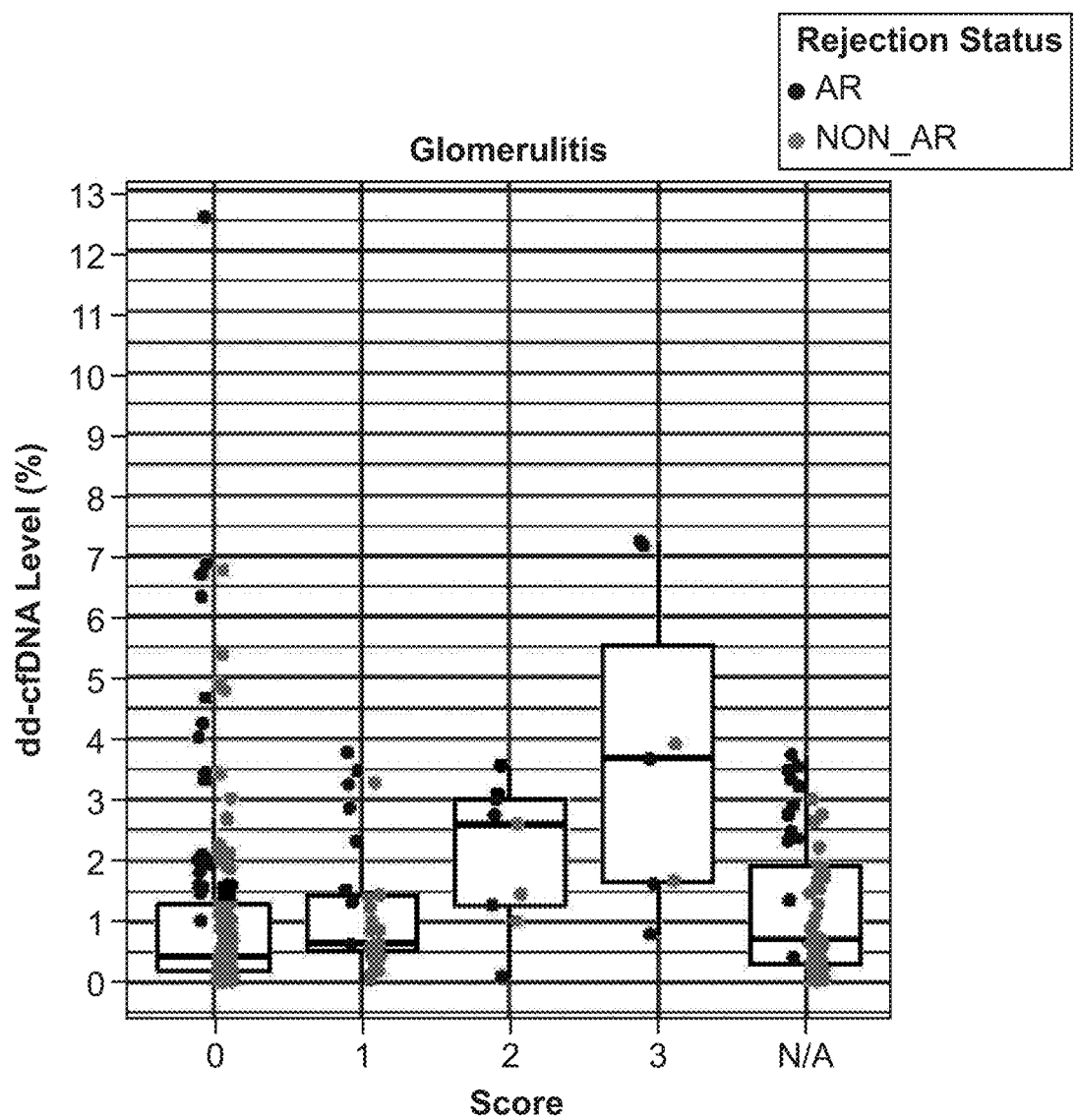
FIG. 18A-F: Modeling dd-cfDNA as a function of Banff scores. Six (of 15) histological features with significant differences in dd-cfDNA level by Banff scores are shown here (P<0.01 for all). Boxes indicate interquartile range ($25^{th}$ to $75^{th}$ percentile); horizontal lines in boxes represent medians; dots indicate all individual data points by rejection status. P-values for dd-cfDNA adjusted using Kruskal-Wallis rank sum test followed by Dunn multiple comparison tests with Holm correction.
Figure 18B:
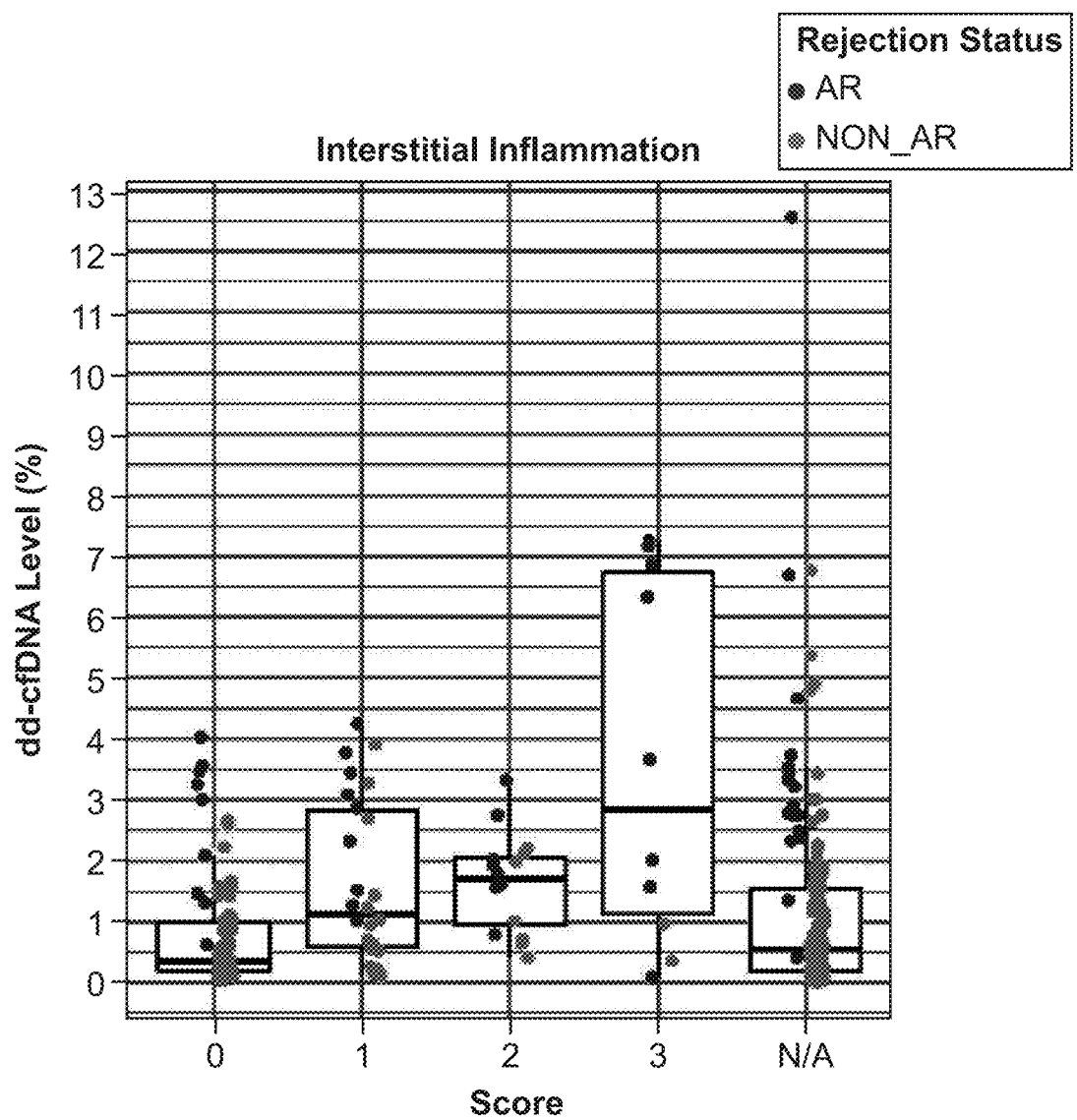
Figure 18C:
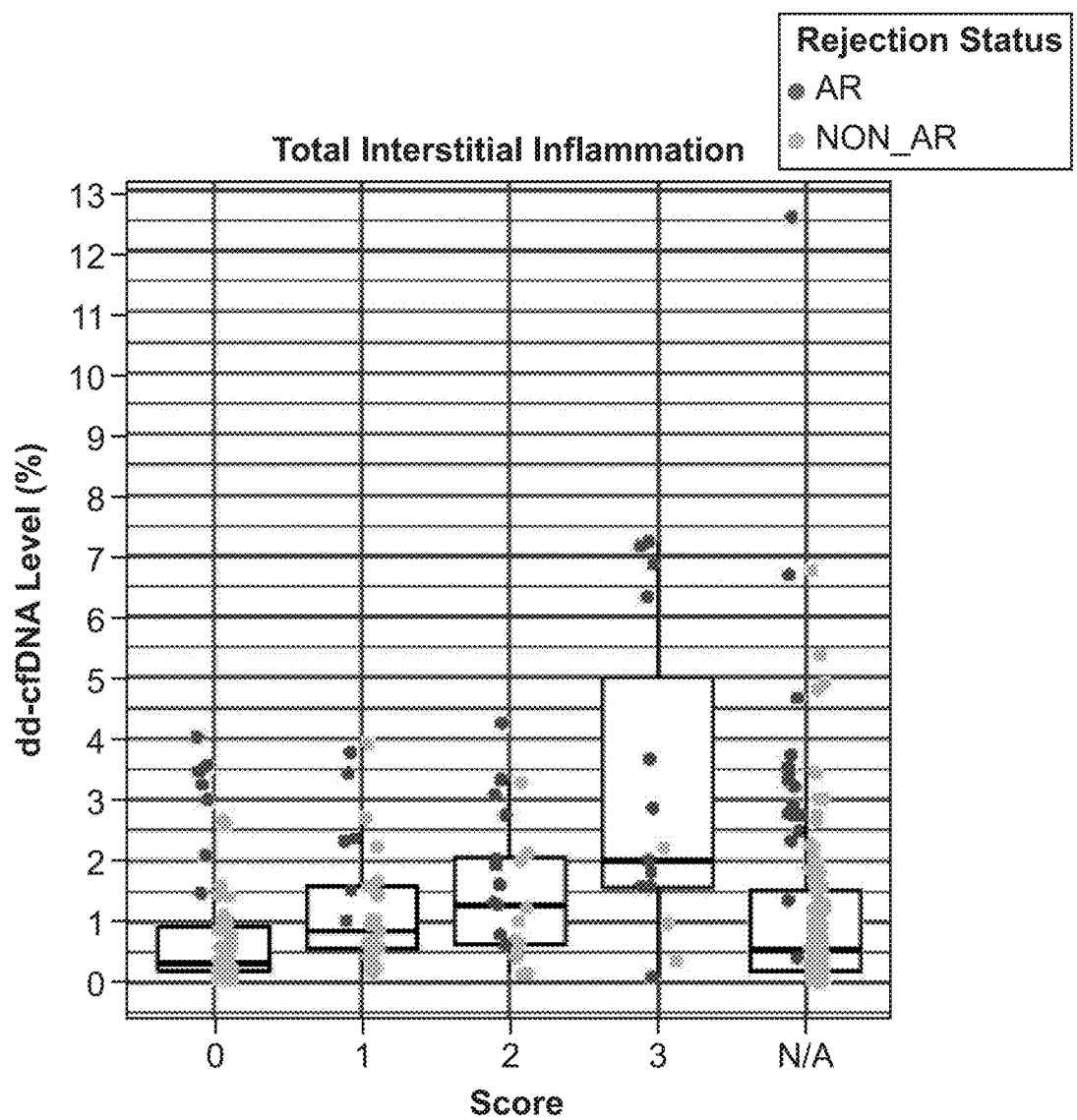
Figure 18D:
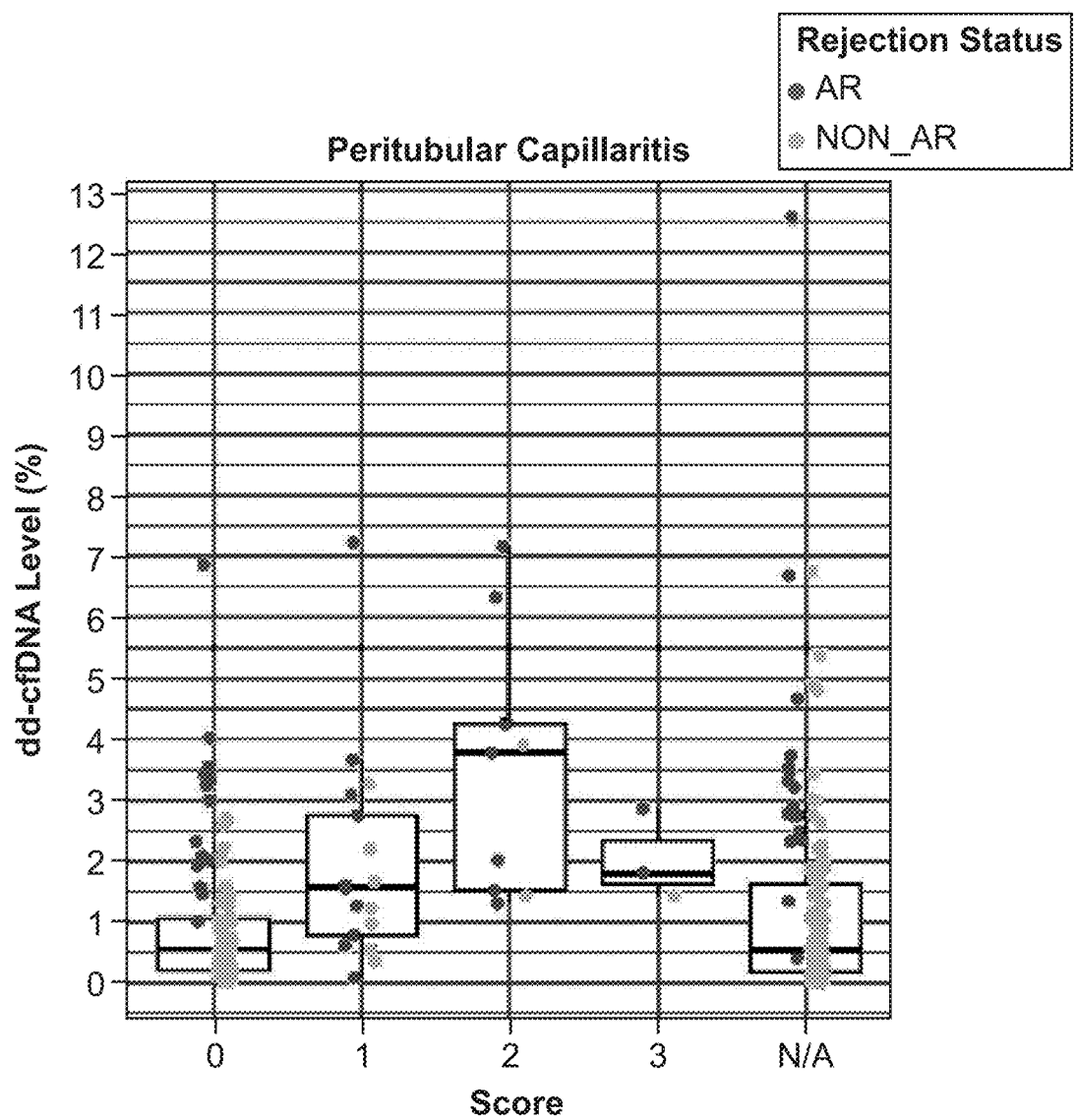
Figure 18E:
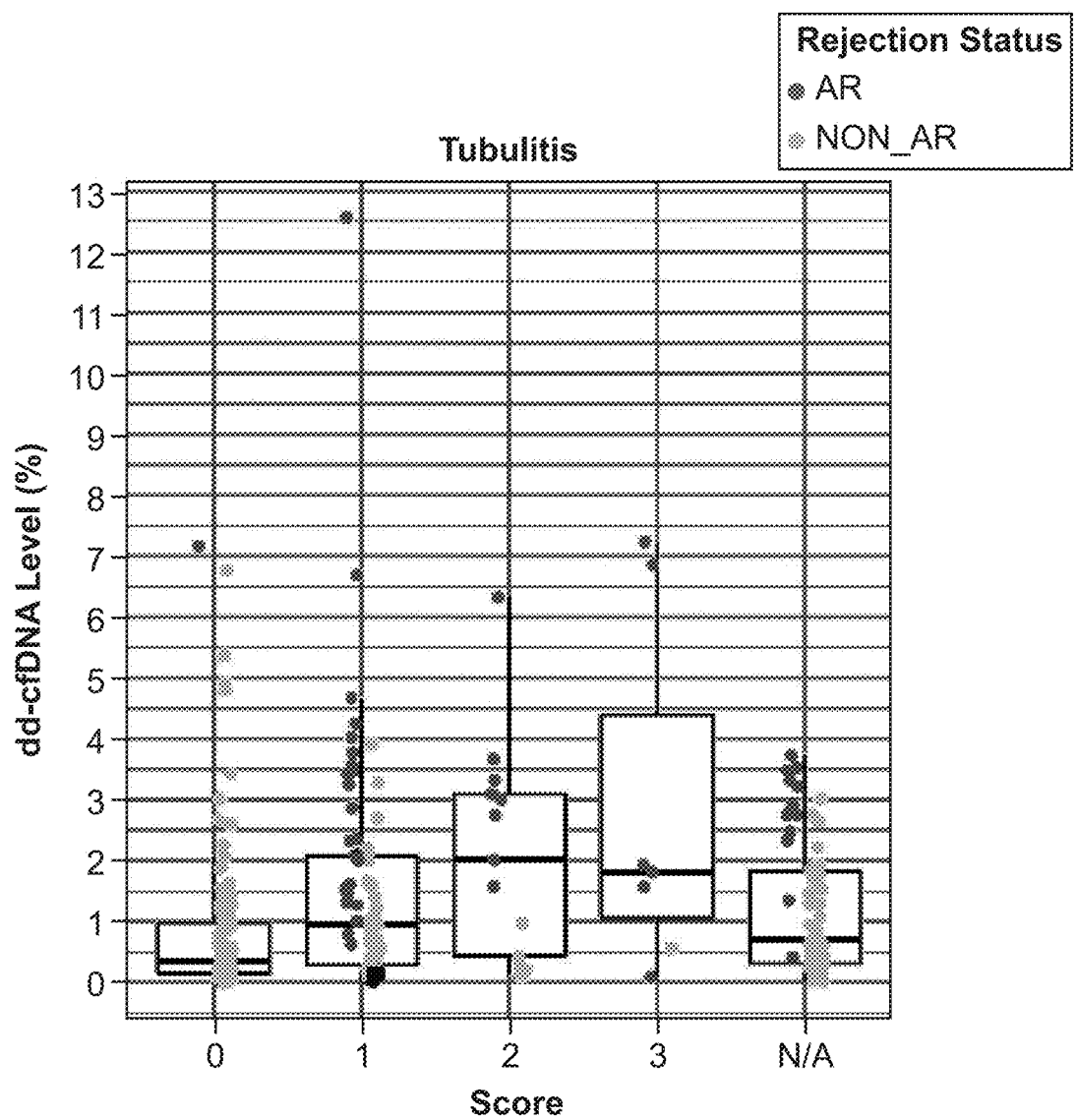
Figure 18F:
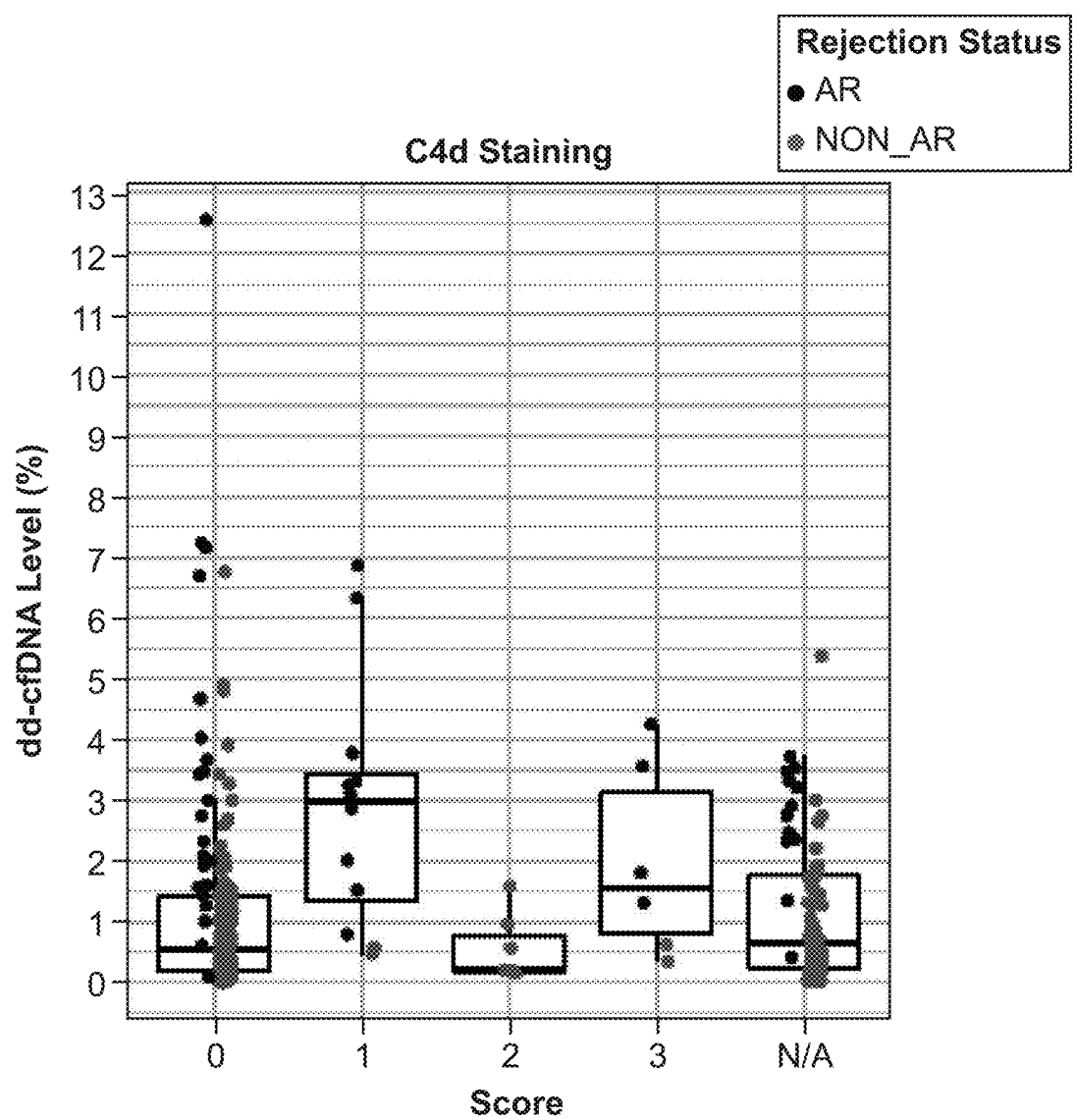

Of the 52 patients with biopsy-proven AR, 19 were classified as antibody-mediated rejection (ABMR) and 32 were classified as T-cell-mediated rejection (TCMR); 1 patient had a combination of both ABMR and TCMR. In addition, 18 patients had borderline ABMR (bAMBR) and 64 patients had borderline TCMR (bTCMR). FIG. 17 shows the relationship between dd-cfDNA level and type of rejection. Median dd-cfDNA did not differ significantly between AMBR (3.1%) or TCMR groups (2.4%; P=0.520) or between bAMBR (0.64%) and bTCMR groups (0.58; P=0.420). Significant differences were observed between ABMR and bABMR (P<0.001) and TCMR and bTCMR (P<0.001), in alignment with AR versus BL differences observed with dd-cfDNA.

Modelling of dd-cfDNA as a Function of Banff Score

The distribution of dd-cfDNA level across different Banff scores was evaluated for samples with a confirmed biopsy. Of 15 histological features evaluated, six had significant results in dd-cfDNA level by score: glomerulitis (P=0.0031), total interstitial inflammation (P=0.0001), interstitial inflammation (P<0.0001), peritubular capillaritis (P=0.0001), tubulitis (P=0.0082), and c4d staining (P=0.0049) (FIG. 18). For each of the six histological features, dd-cfDNA levels by score and summary statistics for score comparisons are shown in Tables C and D, respectively. Interstitial inflammation scores were highly significant, where dd-cfDNA level in group 0 was significantly lower than those in groups 1, 2, and 3. (FIG. 18). In in groups with a score of 0, glomerulitis and peritubular capillaritis dd-cfDNA levels were significantly lower than those found in groups with a score of 3 and 2, respectively (FIG. 18; Table D).

dd-cfDNA Levels by Donor Type

Figure 19:
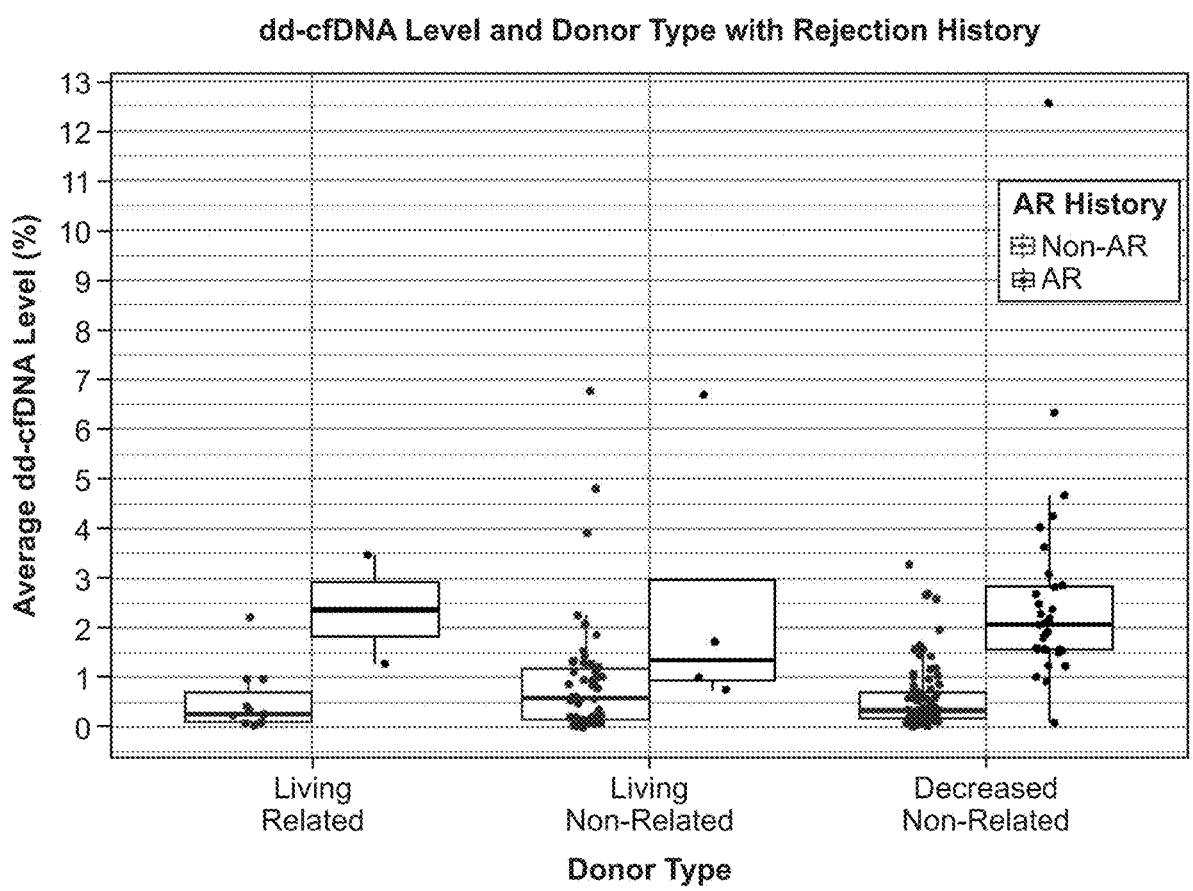
FIG. 19: Relationship between dd-cfDNA and donor type. No significant difference by donor type was observed (P>0.46). P-values for dd-cfDNA adjusted using Kruskal-Wallis rank sum test followed by Dunn multiple comparison tests with Holm correction.

A Kruskal-Wallis rank sum test was used to assess the relationship between dd-cfDNA level and donor type (living related, living non-related, and deceased non-related). Patients were grouped by their donor relationship and rejection status (AR/non-AR). For patients with multiple samples the mean dd-cfDNA was taken. Looking at each rejection status group, there was no significant difference among the medians of dd-cfDNA level by donor type in either the AR (P=0.677) or non-AR group (P=0.463; FIG. 19).

dd-cfDNA Variability Over Time

Figure 20A:
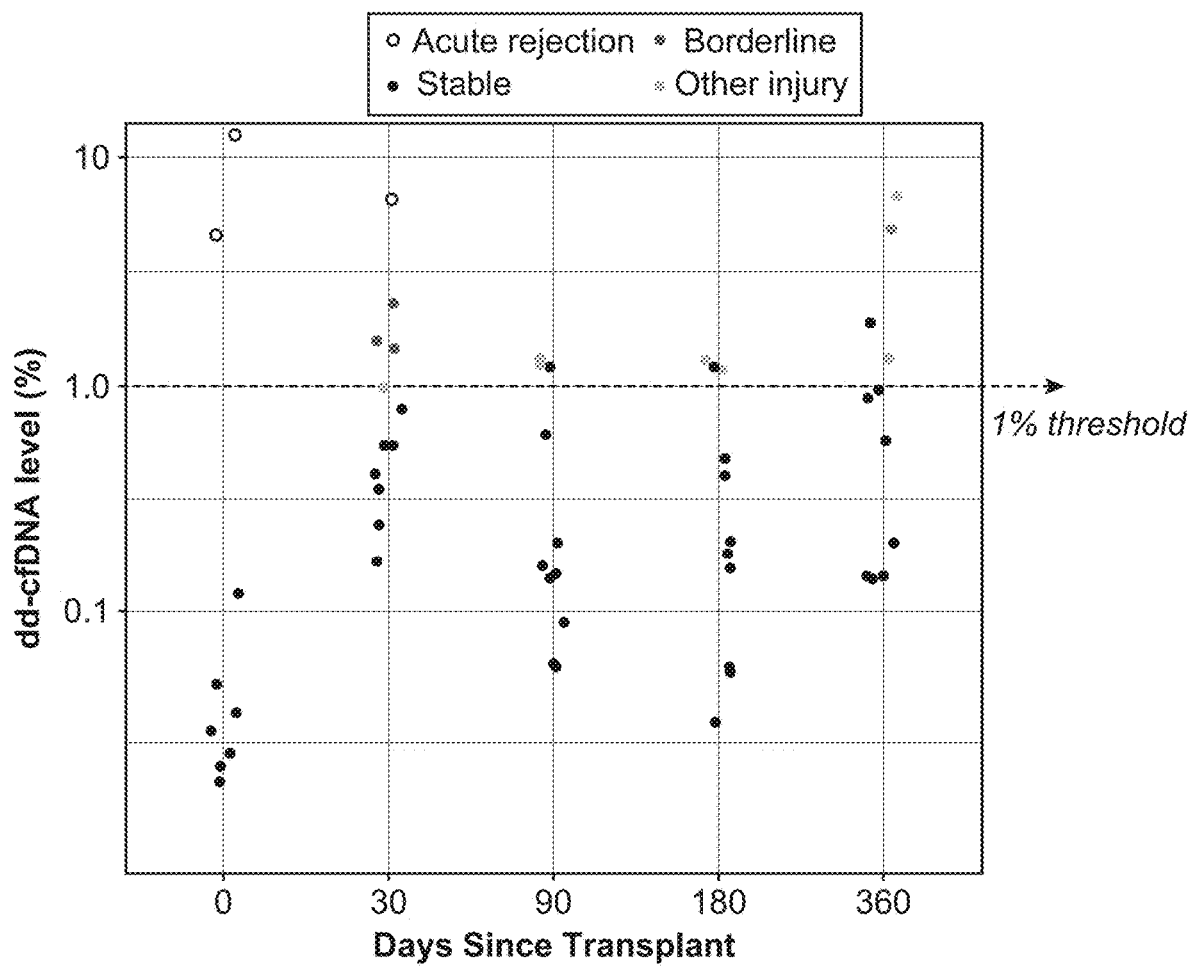
FIG. 20A-B: Variability in dd-cfDNA over time. (A) Inter-patient variability (60 samples from 60 patients over time). (B) Intra-patient variability (samples from the same 10 patients over time)
Figure 20B:
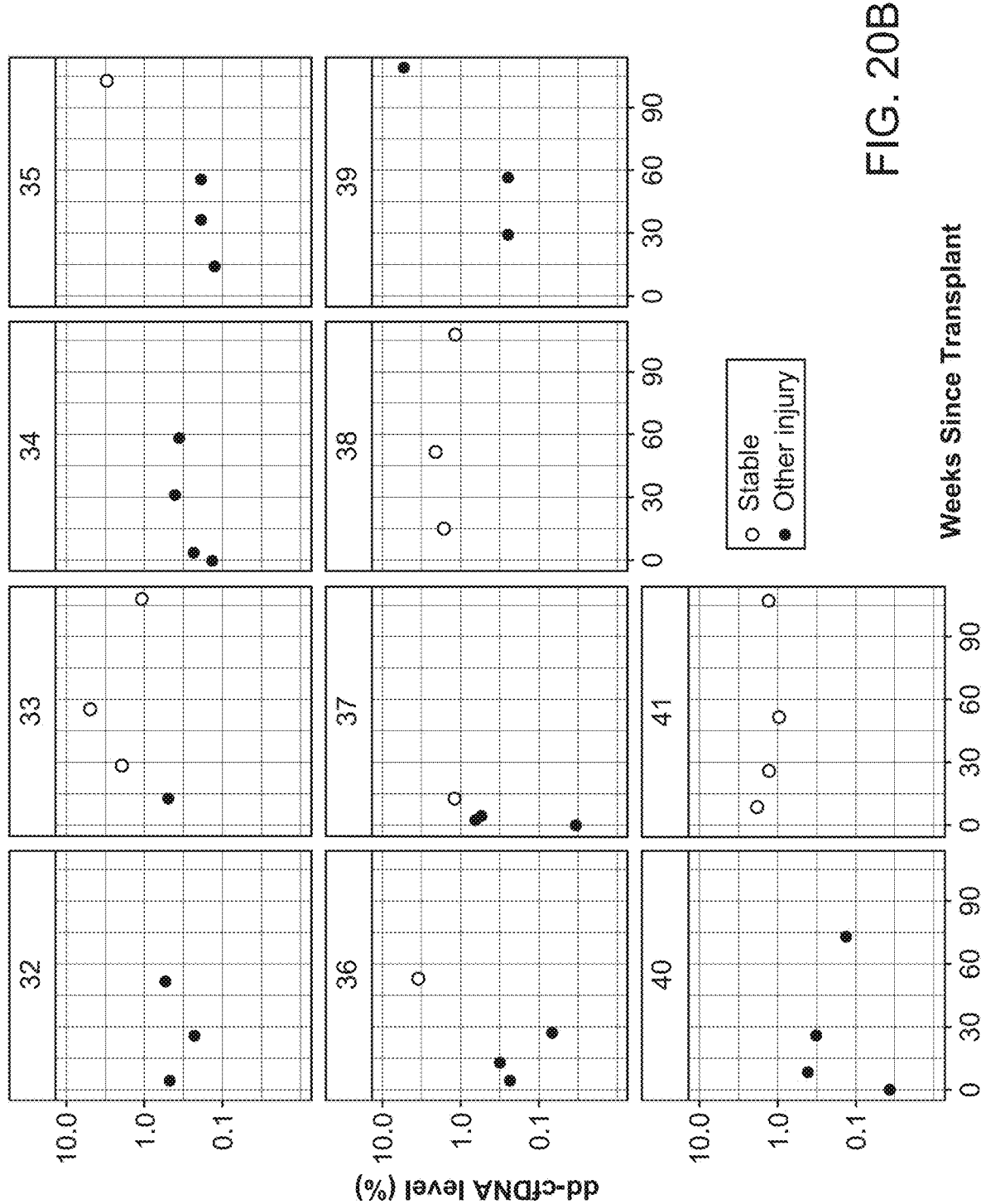
Figure 21A:
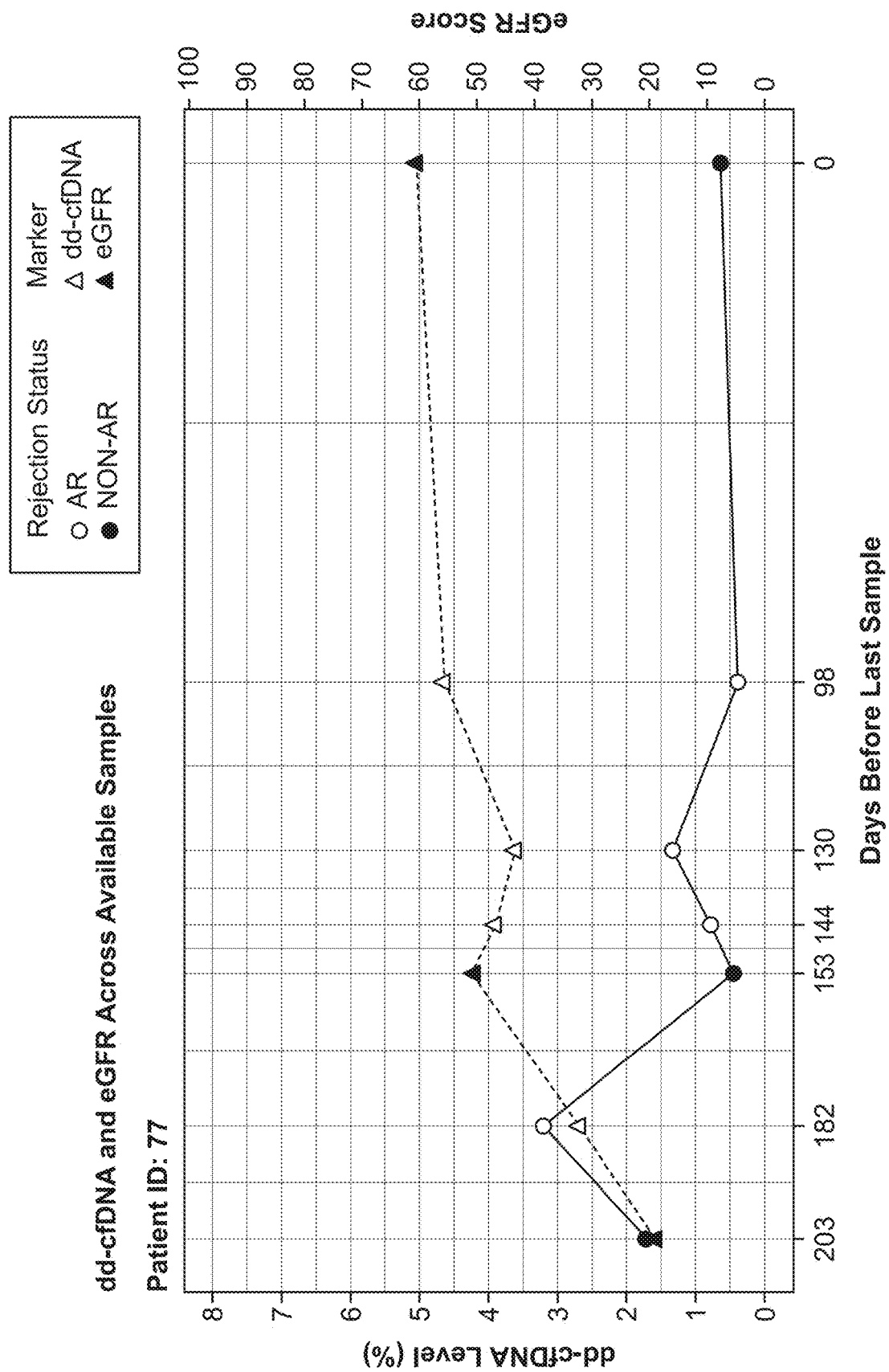
FIG. 21A-D: dd-cfDNA Levels over Time in Patients with Acute Rejection.
Figure 21B:
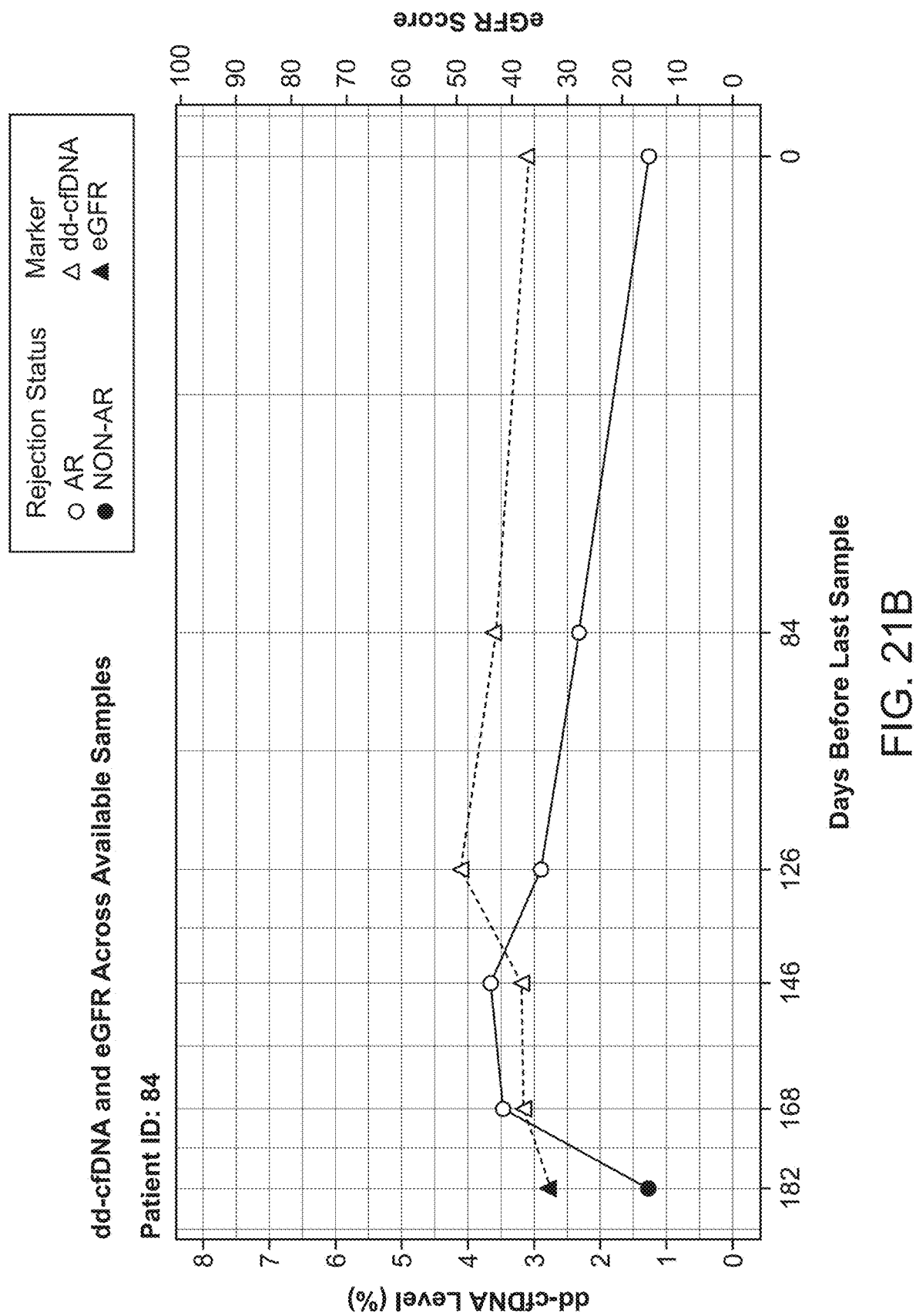
Figure 21C:
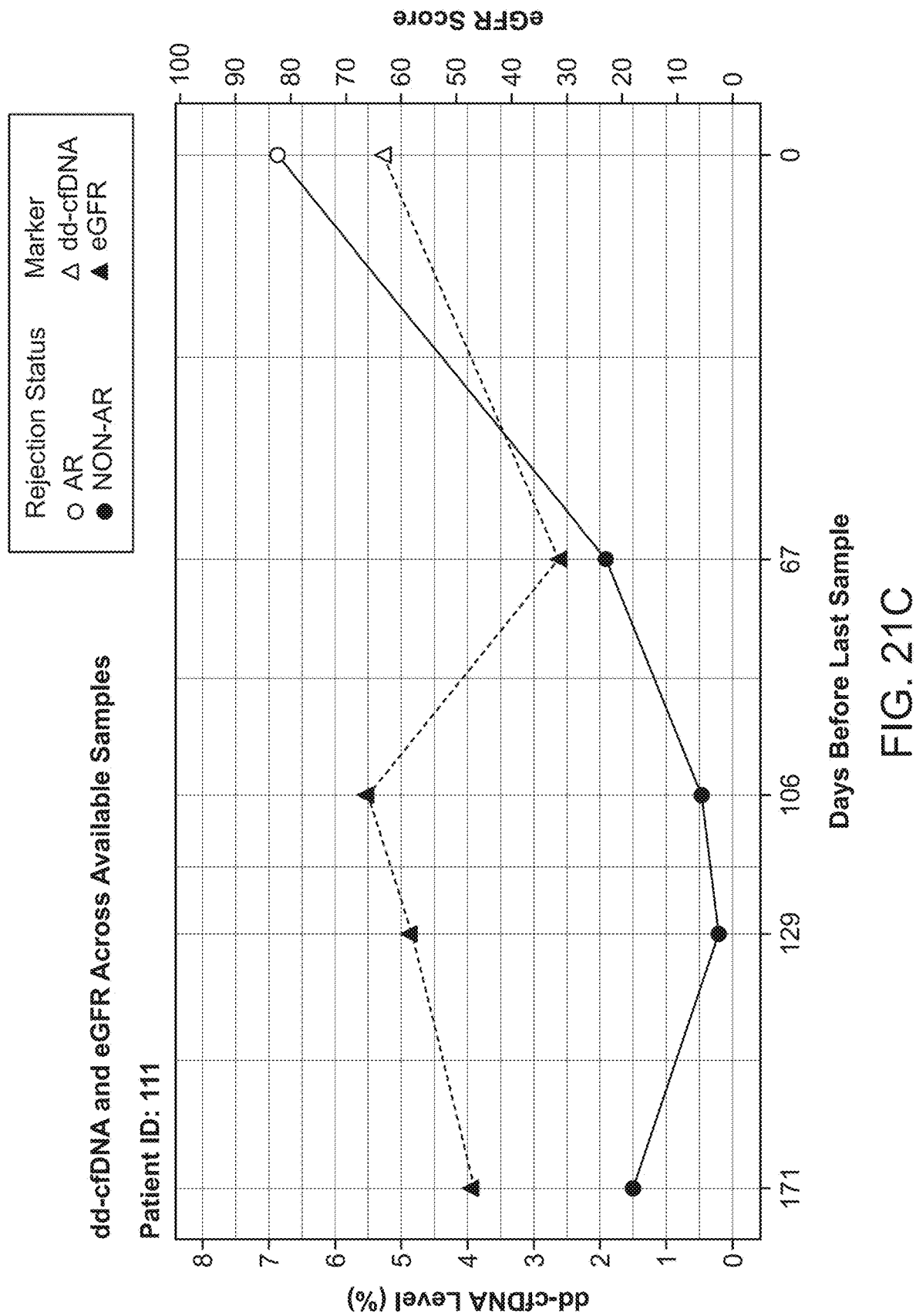
Figure 21D:
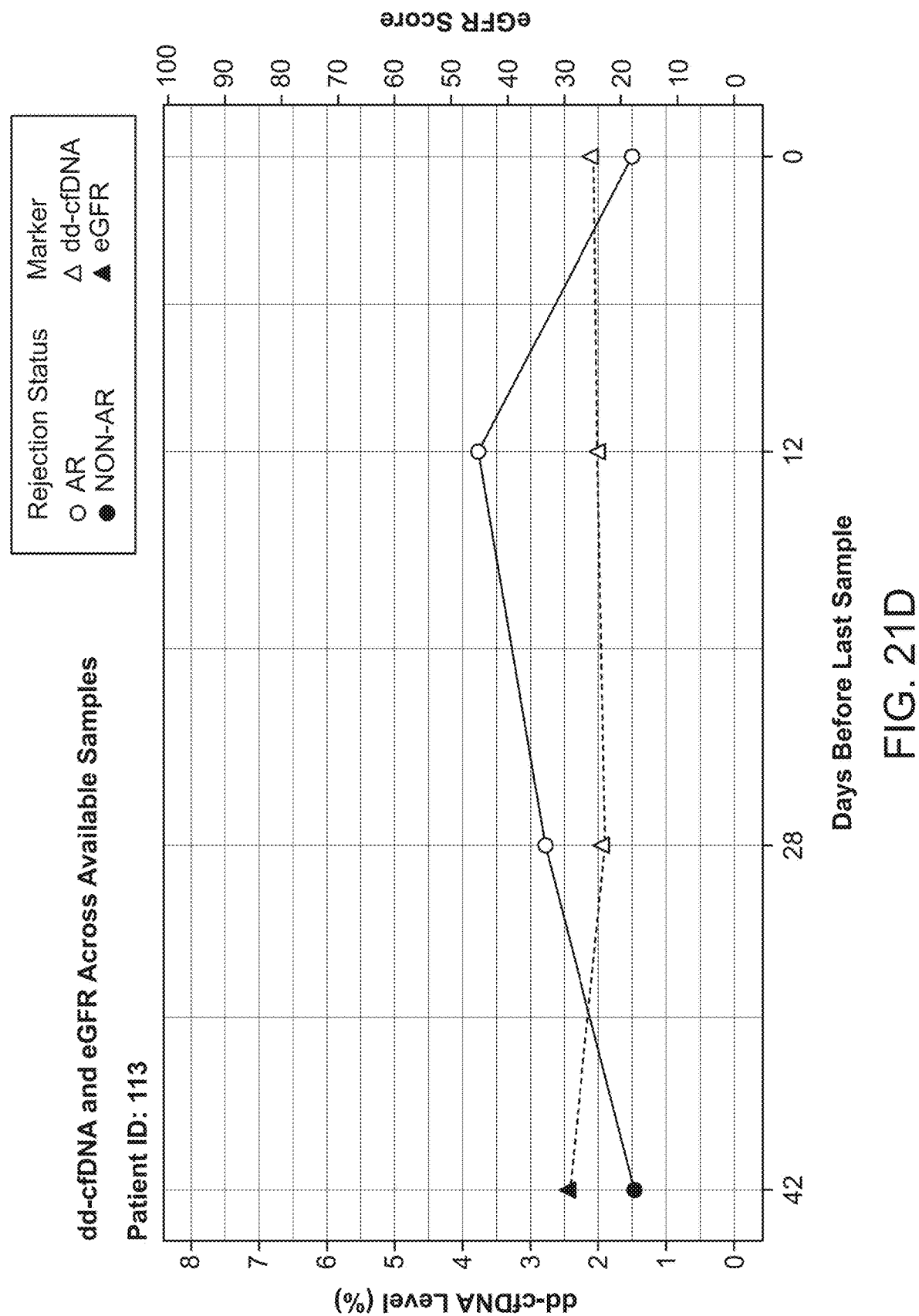

Two subanalyses designed to evaluate the natural variability in dd-cfDNA over time were conducted. The first was a cross-sectional analysis of 60 plasma samples from 60 different patients, collected immediately following surgery (within 3 days ["0 months"]) or at 1, 3, 6, or 12 months postsurgery. Among these STA patients, dd-cfDNA levels were lower at month 0 than subsequent timepoints; however, for most of these STA samples dd-cfDNA levels were <1% across all timepoints (FIG. 20A). For patients with AR, BL, or OI, nearly all were above the 1% dd-cfDNA threshold across all timepoints evaluated. To evaluate the normal intra-patient variation in donor fraction, the second subanalysis longitudinally assessed 10 individual patients across 4 time points (variable for each patient). Overall, organ injury occurred at dd-cfDNA levels above 1% and cfDNA levels in STA and OI patients did not fluctuate over time (FIG. 20B).

To compare inter- and intra-variability a linear-mixed model was constructed to stabilize the variance after logarithmic transforming dd-cfDNA levels. Using this approach and adjusting for time and AR/non-AR groups, an intra-class standard deviation of 0.25496 (95% CI, 0.1093-0.3481) and an inter-patient standard deviation of 0.4296 (95% CI, 0.3751-0.4915) was obtained. This resulted in an intraclass correlation coefficient of 0.2523 indicating high dissimilarity within patients.

Discussion

In this study, median dd-cfDNA was significantly higher in the AR group (2.76%) versus the non-AR group (0.47%; P<0.0001). Analysis of performance estimates demonstrated that the mmPCR-NGS method was able to discriminate active from non-active rejection status with an AUC of 0.90 and high sensitivity (92.3%) and specificity (72.9%) at the AR cutoff of >1% dd-cfDNA. Based on a 25% prevalence of rejection, projected PPV and NPV were 96.6% and 53.2%, respectively. In contrast, serum creatinine levels and eGFR were generally less discriminatory, with a 42.3% sensitivity and 83.7% specificity, and projected PPV and NPV of 46.4% and 81.3%, respectively. Therefore, if static serum creatinine measurements were used as the sole clinical decision point, about 1 in 5 patients would not be referred for an indication biopsy—this is in comparison to the projected NPV of dd-cfDNA, which suggests that only 3-4 in 100 patients would miss an indication biopsy where it might be clinically necessary. Taken together, the superior performance of this SNP-based dd-cfDNA assay over that of the current standard of care for the evaluation of allograft rejection status holds promise for enabling patients a greater opportunity for timely therapy in the case of an allograft injury.

Levels of dd-cfDNA also provided discrimination of AR from all three non-AR subgroups (STA, BL, and OI); median dd-cfDNA levels were significantly higher for samples with biopsy-proven AR (2.8%) versus BL (0.6%), OI (0.7%), and STA (0.2%).

In a recent study that amplified hundreds of target SNPs in dd-cfDNA to detect active rejection in kidney allografts, that method was able to discriminate AR from non-AR with an AUC of 0.74 and 59% sensitivity, 85% specificity. In comparison with that study, the novel dd-cfDNA test described in the current study showed a higher AUC value (0.90) as well as greater sensitivity (92%). On the other hand, specificity (73%) was slightly lower in the current study, indicating that there may have been more false positives in this study. This is supported given that the specificity rose to 93.2% when AR and STA groups were compared, which suggests that the false positives in the non-AR group were likely driven by the BL and/or OI groups.

Another important finding of this study was that the fraction of dd-cfDNA did not differ between ABMR and TCMR groups, with dd-cfDNA levels of 3.1% and 2.4%, respectively. These results are of interest considering that previous study found significantly higher dd-cfDNA levels for ABMR-based rejections (2.9%) than for TCMR-based rejections (≤1.2%). Though the assay used in that study also measured dd-cfDNA, the methodologies between the two assays are of different design. It is unclear whether that test could not differentiate AR from non-AR in cases of TCMR or if the result was due to the smaller sample size of that group in that study (n=11), given that different TCMR groups may behave differently. Regardless, in the larger TCMR group evaluated in this study (n=32), it appears that dd-cfDNA levels can accurately discriminate AR from non-AR in both the ABMR and TCMR groups. In addition, dd-cfDNA levels were 0.6% in both borderline ABMR and TCMR, suggesting that the test may be sensitive enough to discriminate borderline cases from more severe cases in both groups.

One barrier to widespread clinical use of dd-cfDNA as a diagnostic tool for monitoring organ transplant has been the limitations in measuring dd-cfDNA in certain cases, such as when the donor genotype is unknown or when the donor is a close relative. Given the design of the assay used here, it is possible to quantify dd-cfDNA without prior recipient or donor genotyping. Further, there is no need for a computational adjustment based on whether the donor is related to the recipient. In this study, evaluation of dd-cfDNA levels by donor type revealed that regardless of donor type (living related, living non-related, deceased non-related), dd-cfDNA levels were similar across all donor types within the AR and non-AR categories.

This study is a retrospective analysis of archived samples from a single-center. However, the central geographical area enabled all biopsies to be performed by a single pathologist, which may have helped minimize variability in biopsy classification. Overall, samples were selected based on the availability of biopsy information, which led to missing information from some patient samples and may have impacted analyses. For example, due to limited demographic information for some patients, it was not possible to calculate eGFR for all samples; this led to a reduced number of STA samples in the non-AR group for this marker, which may have contributed to the lack of significant difference observed between the AR and non-AR groups. Importantly, all experimenters were kept blinded during the process of data generation. Finally, the retrospective study design may have led to differences in patient characteristics across the rejection groups; though the STA group was enriched with younger patients compared with the other groups, this is not surprising as younger patients are better suited immunologically to tolerate transplanted organs compared to older-aged patients; further, the age differences likely did not affect the viability of the study objectives.

Strengths of this study include the variety of patient samples included in the non-AR group, which comprised not only STA, but also BL and OI samples. This allowed for additional analyses in this study, which found that dd-cfDNA was significantly different in the AR group versus BL and OI groups. Additional subanalyses by type of AR (ABMR and TCMR) as well as by donor type demonstrated that dd-cfDNA levels were able to discriminate AR versus non-AR in a variety of patient types. Further, the SNP-based mmPCR methodology used has been validated with over a million samples in fetal cfDNA determinations; evidence indicates that it is highly sensitive and specific for detecting rare or minor nucleic acid fractions in an in vivo plasma mixture. Finally, the inclusion of longitudinal data enabled a unique evaluation of the natural variability of dd-cfDNA in transplant patients over time. Inter-patient variability data demonstrated that between 0 and 12 months post-surgery, most patients with STA biopsies had dd-cfDNA levels below 1%. This suggests that the dd-cfDNA test may be used immediately after surgery to differentiate whether a patient is stable or showing signs of AR, BL, or OI. Intra-patient variability data demonstrated that the results of the assay are generally consistent over time. Taken together, these data suggest that this test can not only offer routine monitoring of the same patients but also offer a variety of patients a reliable test to determine rejection status at any time point post-surgery.

In conclusion, this study validates the use of dd-cfDNA in the blood as an accurate marker of kidney injury/rejection. This rapid, accurate, and noninvasive technology may offer detection of significant renal injury in select patients better than the current standard of care and therefore offer the potential for better management and survival of kidney allografts and recipient renal function.

TABLE A

Demographics and Characteristics[a]

| | | | Non-Acute Rejection | |
|---|---|---|---|---|
| Phenotype Characteristic | Acute Rejection (52 samples) | Stable (81 samples)[b] | Borderline AR (82 samples) | Other Injury (85 samples)[c] |
| Recipient age, yr | | | | |
| Mean ± SD | 42.94 ± 15.39 | 18.41 ± 11.42 | 46.51 ± 14.20 | 45.81 ± 20.85 |
| Range | 4-69 | 2-70 | 5-74 | 3-80 |
| Male/female/NA | | | | |
| Male | 24 (46.2) | 46 (56.8) | 40 (48.8) | 33 (38.8) |
| Female | 28 (53.8) | 34 (42.0) | 42 (51.2) | 52 (61.2) |
| Unknown | 0 (0) | 1 (1.2) | 0 (0) | 0 (0) |
| Ethnicity | | | | |
| Hispanic or Latino | 18 (34.5) | 3 (3.7) | 29 (35.4) | 23 (27.1) |
| Not Hispanic or Latino | 31 (59.6) | 4 (4.9) | 50 (61) | 42 (49.4) |
| Unknown | 3 (3.7) | 74 (91.4) | 3 (3.7) | 20 (23.5) |
| Race groups, no. (%) | | | | |
| White or Caucasian | 15 (28.8) | 1 (1.2) | 14 (17.1) | 22 (25.9) |
| Black or African American | 6 (11.5) | 1 (1.2) | 15 (18.3) | 7 (8.2) |
| Asian or Pacific Islander | 8 (15.4) | 1 (1.2) | 18 (22) | 4 (4.7) |
| Other/Not reported | 23 (44.2) | 78 (96.3) | 35 (42.7) | 52 (61.2) |
| Recipient weight, kg | | | | |
| Mean ± SD | 82.0 ± 19.9 | 64.8 ± 11.2 | 78.6 ± 18.3 | 81.2 ± 18.9 |
| Range | 45-119 | 50-76 | 46-134 | 47-125 |
| Unknown | 10 | 75 | 9 | 23 |
| DSA positive, no. (%) | | | | |
| Yes | 18 (34.6) | 0 (0) | 19 (23.2) | 4 (4.7) |
| No | 18 (34.6) | 1 (1.2) | 53 (64.6) | 20 (23.5) |
| Not recorded | 16 (30.8) | 80 (98.8) | 10 (12.2) | 61 (71.8) |
| Indication for renal transplantation, no. (%) | | | | |
| Glomerulonephritis | 1 (1.9) | 4 (4.9) | 2 (2.4) | 3 (3.5) |
| Focal segmental glomerulosclerosis | 6 (11.5) | 4 (4.9) | 10 12.2) | 2 (12.2) |
| Diabetes mellitus | 1 (1.9) | 1 1.2) | 16 (19.5) | 22 (25.9) |
| Thin basement membrane nephropathy | 4 (7.7) | 0 (0) | 2 (2.4) | 3 (3.5) |
| Polycystic kidney disease | 5 (9.6) | 3 (3.7) | 7 (8.5) | 7 (8.2) |
| Solitary kidney | 0 (0) | 0 (0) | 3 3.7) | 0 (0) |
| Hypertension | 5 (9.6) | 1 (1.2) | 13 15.9) | 5 (5.9) |
| IgA nephropathy | 7 (13.5) | 0 (0) | 8 (9.8) | 0 (0) |
| Lupus nephritis | 2 (3.8) | 0 (0) | 1 (1.2) | 3 3.5) |
| ANCA-vasculitis | 1 (1.9) | 0 (0) | 2 (2.4) | 0 (0) |
| Other/Unknown | 19 (38.5) | 68 (84.0) | 18 (22.0) | 40 (47.1) |
| Donor source, no. (%) | | | | |
| Living related | 2 (3.8) | 2 (2.5) | 9 (11) | 6 (7.1) |
| Living unrelated | 4 (7.7) | 44 (54.3) | 19 (23.2) | 31 (36.5) |
| Deceased unrelated | 46 (88.5) | 35 (43.2) | 54 (65.9) | 48 (56.5) |

[a]Characteristics and demographic information is based on all samples; data reflects multiple samples for some patients.
[b]Of the 81 samples linked to stable biopsy, 8 were unable to be sequenced and were excluded from analyses.
[c]Other injury patients had other causes of graft dysfunction: chronic allograft nephropathy (57 samples), drug toxicity (18 samples), BK nephritis (4 samples), acute tubular necrosis (3 samples), and transplant glomerulopathy (3 samples).
DSA, donor specific antibodies; SD, standard deviation.

TABLE B

Summary Statistics for dd-cfDNA, Creatinine, and eGFR Tests

| Parameter | Acute Rejection | Non-Acute Rejection | | |
|---|---|---|---|---|
| | | Stable | Borderline | Other Injury |
| dd-cfDNA | | | | |
| Number of samples | 52 | 73 | 82 | 85 |
| Mean (SD), % | 3.08 (2.14) | 0.43 (0.85) | 0.83 (0.77) | 1.05 (1.11) |
| Median, (Range), % | 2.76 (0.1-12.6) | 0.19 (0.0-5.4) | 0.59 (0.03-3.9) | 0.70 (0.03-6.8) |
| Creatinine | | | | |
| Number of samples | 52 | 72 | 82 | 85 |
| Mean (SD), mg/dL | 1.76 (1.11) | 1.81 (2.66) | 1.62 (0.98) | 1.33 (1.06) |
| Median, (Range), mg/dL | 1.41 (0.1-6.8) | 0.91 (0.1-14.1) | 1.40 (0.3-7.0) | 1.10 (0.1-7.8) |
| eGFR | | | | |
| Number of samples | 49 | 7 | 79 | 65 |
| Mean (SD), score | 50.5 (22.6) | 76.52 (23.3) | 53.1 (20.7) | 54.4 (19.5) |
| Median, (Range), score | 51.99 (8-100) | 69.25 (47-109) | 51.82 (6-109) | 55.07 (7-106) | dd-cfDNA, donor-derived cell-free DNA; eGFR, estimate glomerular filtration rate.

TABLE C

Donor-derived cfDNA Levels in Six Histological Features with Significant Differences in dd-cfDNA by Banff score

| Variable | Score | Count | Mean dd-cfDNA (%) | StdDev dd-cfDNA (%) | Median dd-cfDNA (%) |
|---|---|---|---|---|---|
| Glomerulitis | 0 | 177 | 1.048542373 | 1.602791733 | 0.415 |
| Glomerulitis | 1 | 32 | 1.153 | 1.067370359 | 0.6345 |
| Glomerulitis | 2 | 9 | 2.089888889 | 1.169621674 | 2.592 |
| Glomerulitis | 3 | 7 | 3.719714286 | 2.630592057 | 3.666 |
| Glomerulitis | N/A | 67 | 1.217925373 | 1.097801678 | 0.703 |
| Interstitial Inflammation | 0 | 86 | 0.758093023 | 0.895235265 | 0.3495 |
| Interstitial Inflammation | 1 | 26 | 1.631115385 | 1.329326997 | 1.13 |
| Interstitial Inflammation | 2 | 16 | 1.6524375 | 0.794761681 | 1.7085 |
| Interstitial Inflammation | 3 | 10 | 3.6249 | 2.989179205 | 2.8375 |
| Interstitial Inflammation | N/A | 154 | 1.160019481 | 1.594593679 | 0.5465 |
| Total Interstitial Inflammation | 0 | 67 | 0.752522388 | 0.965722172 | 0.32 |
| Total Interstitial Inflammation | 1 | 33 | 1.225666667 | 1.048161684 | 0.843 |
| Total Interstitial Inflammation | 2 | 24 | 1.480333333 | 1.171649809 | 1.2485 |
| Total Interstitial Inflammation | 3 | 15 | 3.084 | 2.541016866 | 2.009 |
| Total Interstitial Inflammation | N/A | 153 | 1.152169935 | 1.596842599 | 0.544 |
| Tubulitis | 0 | 118 | 0.899567797 | 1.066300911 | 0.5555 |
| Tubulitis | 1 | 17 | 1.936117647 | 1.73272967 | 1.562 |
| Tubulitis | 2 | 9 | 3.523111111 | 2.162920505 | 3.775 |
| Tubulitis | 3 | 3 | 2.033666667 | 0.742930234 | 1.809 |
| Tubulitis | N/A | 145 | 1.186648276 | 1.635198975 | 0.544 |
| Peritubular Capillaritis | 0 | 124 | 0.811048387 | 1.235469167 | 0.346 |
| Peritubular Capillaritis | 1 | 78 | 1.499705128 | 1.841726957 | 0.954 |
| Peritubular Capillaritis | 2 | 13 | 2.134153846 | 1.80764155 | 2.016 |
| Peritubular Capillaritis | 3 | 7 | 2.865 | 2.936962093 | 1.809 |
| Peritubular Capillaritis | N/A | 70 | 1.194142857 | 1.068454149 | 0.703 |
| C4d Staining | 0 | 184 | 1.104027174 | 1.592462534 | 0.551 |
| C4d Staining | 1 | 12 | 2.905666667 | 2.066374442 | 2.9775 |
| C4d Staining | 2 | 7 | 0.554142857 | 0.540281849 | 0.204 |
| C4d Staining | 3 | 6 | 1.9865 | 1.587761538 | 1.56 |
| C4d Staining | N/A | 83 | 1.14613253 | 1.138562549 | 0.637 |

TABLE D

Histological Features with Significant Differences in dd-cfDNA, by Banff score

| Variable | Comparison | Z Statistic | Unadj. P-Value | Adj. P-Value |
|---|---|---|---|---|
| Glomerulitis | 0 vs 1 | -1.52 | 0.1279 | 1.0000 |
| Glomerulitis | 0 vs 2 | -2.69 | 0.0072 | 0.1740 |
| Glomerulitis | 0 vs 3 | -3.59 | 0.0003 | 0.0107 |
| Glomerulitis | 1 vs 2 | -1.64 | 0.1006 | 1.0000 |
| Glomerulitis | 1 vs 3 | -2.61 | 0.0092 | 0.2062 |
| Glomerulitis | 2 vs 3 | -0.93 | 0.3524 | 1.0000 |
| Peritubular Capillaritis | 0 vs 1 | -3.02 | 0.0025 | 0.0686 |
| Peritubular Capillaritis | 0 vs 2 | -4.15 | 0.0000 | 0.0011 |
| Peritubular Capillaritis | 0 vs 3 | -1.52 | 0.1290 | 1.0000 |
| Peritubular Capillaritis | 1 vs 2 | -1.99 | 0.0468 | 0.8894 |
| Peritubular Capillaritis | 1 vs 3 | -0.56 | 0.5722 | 1.0000 |
| Peritubular Capillaritis | 2 vs 3 | 0.42 | 0.6776 | 1.0000 |
| Interstitial Inflammation | 0 vs 1 | -3.41 | 0.0007 | 0.0198 |
| Interstitial Inflammation | 0 vs 2 | -3.91 | 0.0001 | 0.0031 |
| Interstitial Inflammation | 0 vs 3 | -3.54 | 0.0004 | 0.0123 |
| Interstitial Inflammation | 1 vs 2 | -0.91 | 0.3625 | 1.0000 |
| Interstitial Inflammation | 1 vs 3 | -1.09 | 0.2736 | 1.0000 |
| Interstitial Inflammation | 2 vs 3 | -0.29 | 0.7696 | 1.0000 |
| Total Interstitial Inflammation | 0 vs 1 | -2.87 | 0.0041 | 0.1019 |
| Total Interstitial Inflammation | 0 vs 2 | -3.14 | 0.0017 | 0.0476 |
| Total Interstitial Inflammation | 0 vs 3 | -4.52 | 0.0000 | 0.0002 |
| Total Interstitial Inflammation | 1 vs 2 | -0.52 | 0.6053 | 1.0000 |
| Total Interstitial Inflammation | 1 vs 3 | -2.15 | 0.0312 | 0.6243 |
| Total Interstitial Inflammation | 2 vs 3 | -1.61 | 0.1084 | 1.0000 |
| Tubulitis | 0 vs 1 | -3.00 | 0.0027 | 0.0698 |
| Tubulitis | 0 vs 2 | -3.19 | 0.0014 | 0.0410 |
| Tubulitis | 0 vs 3 | -1.44 | 0.1488 | 1.0000 |
| Tubulitis | 1 vs 2 | -2.61 | 0.0090 | 0.2062 |
| Tubulitis | 1 vs 3 | -1.24 | 0.2150 | 1.0000 |
| Tubulitis | 2 vs 3 | -0.12 | 0.9050 | 1.0000 |
| c4d Staining | 0 vs 1 | -3.85 | 0.0001 | 0.0038 |
| c4d Staining | 0 vs 2 | 0.21 | 0.8299 | 1.0000 |

TABLE D-continued

Histological Features with Significant Differences in dd-cfDNA, by Banff score

| | Comparison | Z Statistic | Unadj. P-Value | Adj. P-Value |
|---|---|---|---|---|
| c4d Staining | 0 vs 3 | −1.95 | 0.0517 | 0.9309 |
| c4d Staining | 1 vs 2 | 2.27 | 0.0233 | 0.4883 |
| c4d Staining | 1 vs 3 | 0.79 | 0.4292 | 1.0000 |
| c4d Staining | 2 vs 3 | −1.43 | 0.1524 | 1.0000 |

All patents, patent applications, and published references cited herein are hereby incorporated by reference in their entirety. While the methods of the present disclosure have been described in connection with the specific embodiments thereof, it will be understood that it is capable of further modification. Furthermore, this application is intended to cover any variations, uses, or adaptations of the methods of the present disclosure, including such departures from the present disclosure as come within known or customary practice in the art to which the methods of the present disclosure pertain, and as fall within the scope of the appended claims.

Example 3. Validation of Detection of Kidney Transplant Injury by Assessment of Donor-Derived Cell-Free DNA by Massively Multiplex PCR and Next-Generation Sequencing Introduction Kidney transplantation is the best option for patients with end-stage renal disease. According to United Network for Organ Sharing, more than 19,000 kidneys were transplanted in the United States in 2016 (cen.acs.org), and approximately, 200,000 patients are living with a functional kidney transplant (NIH Medline plus). Despite life-long immunosuppressive maintenance regimens designed to optimize the therapeutic outcome, approximately, 20-30% of patients experienced overall renal graft failure within the first 5 years, and only 55% of transplanted kidneys survive to 10 years (cen.acs.org). Thus, a compelling need exists for early intervention strategies to avoid or minimize acute/subclinical rejection episodes, nephrotoxicity, and be able to manage and monitor co-morbidities for better therapeutic outcomes.

Current standard-of-care clinical options to monitor kidney health in transplant recipients include protocol-biopsies and assessing dynamic changes in serum creatinine and other parameters, such as proteinuria and levels of immunosuppressive drugs. Although, protocol-biopsies are considered the "gold standard", their clinical utility is significantly limited due to invasiveness, cost, inadequate sampling, and poor reproducibility. Serum creatinine, the current standard-of-care marker to screen renal allograft dysfunction and indicate when biopsy and histological evaluation of renal tissue is warranted is a poor marker, due to its low sensitivity and specificity. (Sigdel et al., Optimizing detection of kidney transplant injury by assessment of donor-derived cell-free DNA by massively multiplex PCR, *PLoS One*, Manuscript in preparation 2018). Moreover, creatinine is a lagging indicator of renal injury; by the time serum creatinine levels increase, the allograft has already undergone severe and irreversible damage. Thus, an unmet medical need exists to non-invasively detect early onset of transplant rejection and assist physicians make proactive decisions with regards to managing immunosuppressive therapy and prevent graft injury and loss.

Donor-derived cell-free DNA (dd-cfDNA) can be detected noninvasively in the plasma of transplant patients, and is a proven non-invasive biomarker for kidney transplant rejection. The present disclosure provides an assay that can estimate dd-cfDNA fraction in renal transplant recipients by measuring allele frequency at 13,962 SNPs. A recent clinical validation study demonstrated the ability of this method to discriminate active rejection from non-rejection with a sensitivity of 88.7%, specificity of 73.2%, and AUC of 0.87 using a dd-cfDNA threshold of 1% (Sigdel et al. 2018). Sigdel et al. 2018 showed a significant difference in the dd-cfDNA levels in both antibody-mediated rejection (ABMR) and T-cell mediated rejection (TCMR) case than non-rejection cases, including those with stable allografts, borderline rejection, and other injuries. The present disclosure analytically validated our clinical-grade NGS test by determining the limit of blank (LoB), lower limit of detection (LoD) and lower limit of quantification (LoQ), linearity, precision (reproducibility and repeatability) and accuracy in measuring the fraction of dd-cfDNA in recipients of kidney transplant.

Materials and Methods

Figure 22:
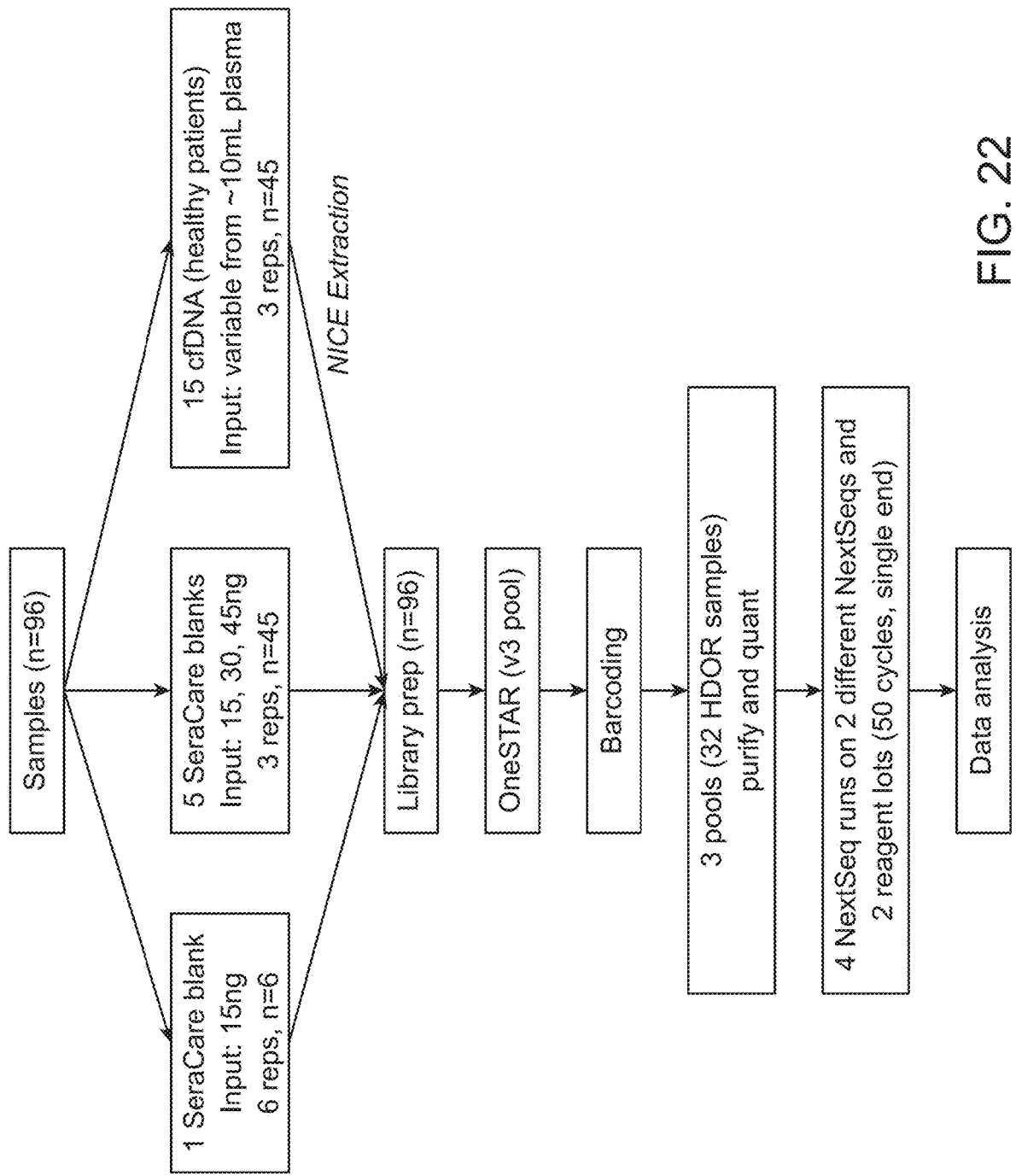
FIG. 22: Flow diagram of the experimental design
Figure 23A:
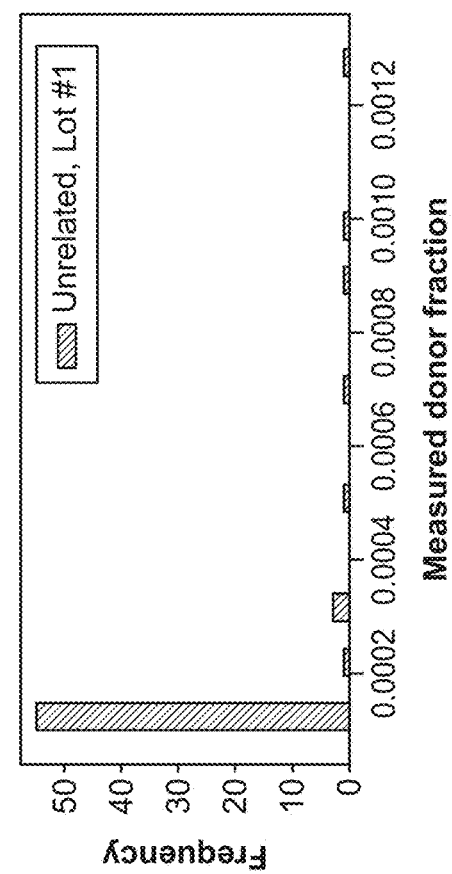
FIG. 23A-D: Histograms of measured donor fractions.
Figure 23B:
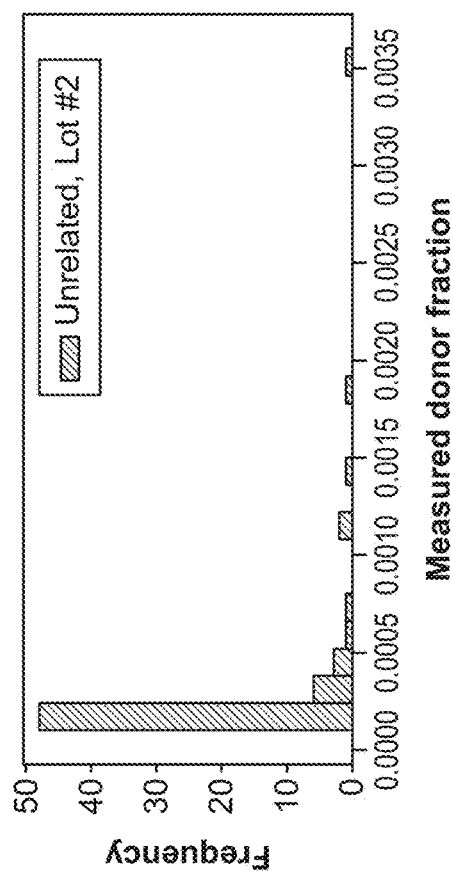
Figure 23C:
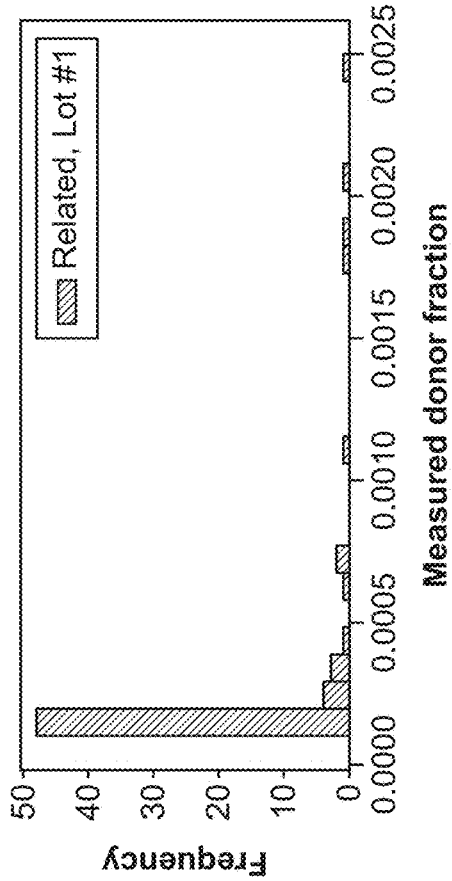
Figure 23D:
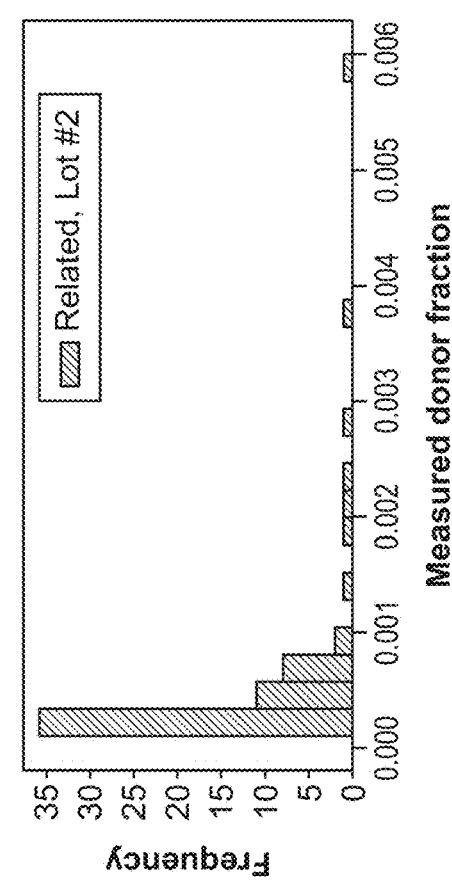

The general workflow of this study is shown in FIG. 22.

Plasma Samples

Whole blood samples (20 mL) were collected from healthy volunteers (n=15) and transplant patients (n=6) in Cell-Free DNA BCT tubes (Streck, Omaha, Nebr.). Plasma (5-10 mL) was isolated from blood after centrifugation at 3220×g for 30 minutes at 22° C. and stored at −80° C. Cell-free DNA was extracted either using Applicant's in-house chemistry for extraction (NICE) (San Carlos, Calif.) or QIAamp® Circulating Nucleic Acid Kit (Qiagen, Germatown, Md.).

Reference Samples (Cell-Line Derived)

Reference samples were procured from SeraCare Lifesciences (Milford, Mass.) and were developed by mixing genomic DNA (gDNA) from 5 different cell lines to develop 3 binary female (recipient)/male (donor) mixtures; 1 related and 2 unrelated, at specific percentages (0, 0.1, 0.3, 0.6, 1.2, 2.4, 5, 10, and 15%) of donor fraction. The percentage of donor fraction in each mixture was verified by digital droplet PCR (ddPCR) by SeraCare. The gDNA mixtures were sheared by sonication and size selected to mimic expected cfDNA fragments of 160 base pairs. Concentration of the reference samples was quantified using Quant-iT® or Qubit® (ThermoFisher, Carlsbad, Calif.) High-Sensitivity kits.

cfDNA Mixture Samples (Plasma-Derived)

cfDNA extracted from plasma of healthy volunteers (n=16) was used to develop 3 unrelated and 6 related binary cfDNA mixtures. The 3 unrelated mixtures were prepared at 7 different target dd-cfDNA levels (0.1, 0.3, 0.6, 1.2, 2.4, 5, 10%). Out of the 6 related cfDNA mixtures, 4 were developed at donor fractions: 0.1, 0.3, 0.6, 1.2%, and the remaining 2 mixture samples were developed at donor fractions 0.3 and 0.6%. Concentration of cfDNA mixture samples was quantified using Quant-iT® or Qubit® (ThermoFisher, City and State) High-Sensitivity kits.

Targeted Amplification, SNP Selection, Sequencing Data Analysis and Quality Control Reference samples and extracted cfDNA mixture samples were used as input for library preparation followed by PCR amplification. Subsequently, targeted amplification was achieved by performing mmPCR as previously described in Ryan et al., Validation of an Enhanced Version of a Single-Nucleotide Polymorphism-Based Noninvasive Prenatal Test for Detection of Fetal Aneuploidies, *Fetal diagnosis and*

*therapy*, 40(3):219-223 (2016), but with a different primer pool targeting 13,926 SNP positions. The SNPs were designed for high variant allele frequency across different ethnicities. Bi-allelic SNPs were selected on chromosomes 2, 13, 18, 21, 22 and X, but only chromosomes 2, 13, 18 and 21 were included in the donor fraction analysis. To ensure accurate donor fraction estimate regardless of patient ethnicity, SNPs were required to have high minor allele frequency across the major ethnic groups defined in the 1000 Genomes project (1000 genome). Specifically, at least 75% of SNPs were required to have minor allele frequency greater than 25% in European, African, Asian and American ethnic groups.

The PCR amplicons achieved after targeted amplification were barcoded and combined to generate 32-plex pools, which were sequenced using NGS technology (Illumina NextSeq 500 instrument, 50 cycles, single end reads). Sequenced reads were demultiplexed and mapped to the hg19 reference genome using Novoalign version 2.3.4 (Website novocraft). Bases with Phred quality score <30 and reads with mapping quality score <30 were filtered. Multiple quality checks (QCs) (cluster density, mapping rate, etc.) were applied to the sequencing run and each sample was confirmed to have the desired number of reads (8 million) after filtering. Any pool failing sequencing run QCs was re-sequenced. Any sample that failed to produce the necessary number of reads was removed from the analysis.

Percent dd-cfDNA Calculation

For each sample, fraction of donor-derived cfDNA (donor fraction) was estimated based on the minor allele frequencies measured for all SNPs where the recipient was homozygous. The donor fraction calculation was based on a maximum likelihood estimate over a search range from 0.0001 to 0.25 at increments of 0.0001. Our approach did not include a separate donor sample, and donor genotypes were represented by a probability model that incorporated both population-based prior probabilities (1000 genome) and the observed allele ratios. No heuristic adjustment was needed for related donors due to lack of in-built assumptions regarding fraction of genotype concordance between the recipient and the donor. Instead, the corresponding genotype inheritance constraints were incorporated into the donor genotype probability model. This estimate mode was referred to as "related estimate" and the unconstrained estimate was referred as "standard estimate".

Experimental Plan and Statistical Analysis

To evaluate the analytical performance of the test, LoB, LoD, LoQ, linearity, precision, and accuracy were measured based on CLSI guidelines (EP-17A2, EP05-A3) as further described below. Tables 1A-1B below shows the experimental design.

TABLE 1A

Experimental design for determining LoB, LoD, LoQ and linearity

| | Parameters | | | | | | | | |
|---|---|---|---|---|---|---|---|---|---|
| | LoB | | | LoD | | | | LoQ, Linearity | |
| | Ref. samples | Healthy blood donors | Ref. Samples | Healthy blood donors (n = 16) | | | Ref. Samples | Healthy blood donors (n = 14) | |
| Sample | (n = 5 blanks) | (n = 15) | | | | | | | |
| Input mass (ng) | 15, 30, 45 | Variable | 15, 30, 45 | 15 | 15 | Variable | 15, 30, 45 | 15 | Variable |
| Sample mixtures | N/A | N/A | 3: 2 Unrelated, 1 related | 3: Unrelated cfDNA mixes | 3: Related cfDNA mixes | 3: Related library mixes | 3: 2 Unrelated, 1 related | 3: Unrelated cfDNA mixes | 3: Related library mixes |
| Donor fractions (%) | N/A | N/A | 0.1, 0.3, 0.6 | 0.1, 0.3, 0.6 | 0.1, 0.3, 0.6 | 0.3, 0.6 | 0.1, 0.3, 0.6, 1.2, 2.4, 5, 10, 15 | 0.1, 0.3, 0.6, 1.2, 2.4, 5, 10 | 0.1, 0.3, 0.6, 1.2 | 0.3, 0.6 |
| Number of Measurements | 68 | 60 | 274 | 60 | 27 | 28 | 638 | 96 | 36 | 28 |
| Total Measurements | 128 | | 389 | | | | 798 | | |

TABLE 1B

Experimental design for determining accuracy, reproducibility, and repeatability.

| | Accuracy | Reproducibility | Repeatability | |
|---|---|---|---|---|
| Sample | Ref. Samples | Ref. Samples | Transplant Samples (n = 6) | Ref. Samples |
| Input mass (ng) | 15, 30, 45 | 15, 30, 45 | Variable | 30 |
| Sample mixtures | 3:2 Unrelated, 1 related | 3:2 Unrelated, 1 related | N/A | 1:Related |
| Donor fractions (%) | 0.1, 0.3, 0.6, 1.2, 2.4, 5, 10, 15 | 0.1, 0.3, 0.6, 1.2, 2.4, 5, 10 | Variable | 0.6, 2.4 |
| Number of Measurements | 638 | 504 | 12 | 128 |
| Total Measurements | 638 | 516 | | 128 |

Limit of Blank

Limit of Blank (LoB) was established using 1) reference samples (blanks or single genome), developed from sheared gDNA of 5 different pure cell lines, obtained from SeraCare, and 2) plasma-derived cfDNA samples (n=15) collected from healthy blood donors who never had a transplant or recent blood transfusion. For reference samples, each of the pure cell lines were tested at 3 different library input amounts (15, 30, and 45 ng) to mimic the expected cfDNA yield achieved from 20 mL blood collections. However, for the plasma-derived cfDNA samples, the input amounts were kept variable for library prep to simulate input variation in real samples. In compliance with CLSI guidelines, samples were tested in triplicates on 3 different days with 2 different sequencing reagent lots that consisted of at least 60 measurements per lot for a total of 128 blank measurements.

LoB is defined as the empirical 95th percentile value measured from a set of blank (no-analyte) samples. The calculation was performed twice for the cell-line derived reference samples (once for each reagent lot), and again for the plasma-derived cfDNA. The plasma-derived cfDNA samples included fewer replicates than recommended by the CLSI guidelines and were used for consistency check only. The final LoB is the maximum of the lot 1 LoB and the lot 2 LoB. All calculations were performed once using the standard donor fraction estimate and once using the related donor fraction estimate in order to measure the corresponding LoB s for the two estimate methods.

Limit of Detection and Limit of Quantification

Limit of Detection (LoD) and Limit of Quantification (LoQ) were measured using both cell-line derived reference samples from SeraCare and plasma-derived cfDNA mixtures from healthy volunteers. The reference samples were tested at 3 different cfDNA input amounts (15, 30 and 45 ng). LoD was measured at the three lowest donor fraction levels (0.1, 0.3, 0.6%), in 6 replicates by 2 operators on different days using different reagents lots, and sequencing instruments. Plasma-derived cfDNA mixtures were tested at 15 ng input, for both unrelated and related mixtures. The three unrelated cfDNA mixtures were tested at 3 lowest donor fraction levels (0.1, 0.3, 0.6%) in 6 replicates. Among 6 related cfDNA mixtures, three were tested at the 3 lowest donor fraction levels (0.1, 0.3, 0.6%) in triplicate and the remaining three (mother-son) were tested at 2 donor fraction levels (0.3, 0.6%), processed in duplicates. LoQ analysis included all the samples used for LoD as well as a corresponding set of replicates at higher donor fractions (1.2, 2.4, 5, 10, 15% for cell lines and 1.2, 2.4, 5, 10% for plasma-derived cfDNA).

LoD is calculated following the parametric estimate method specified in EP-17A2, which computes LoD by adding a standard deviation term to the LoB. The standard deviation term consists of the pooled standard deviation (estimated from the set of replicates described in the LoD), multiplied by a correction factor specified based on the number of samples. LoD is calculated for each input mass and donor fraction estimate method, by combining the corresponding LoB with the corresponding standard deviation measurement.

An appropriate LoQ assessment was selected based on the quantification requirements of the test process. LoQ is defined as the lowest value of donor fraction at which sufficient relative measurement precision is achieved, lower bounded by the LoD. Sufficient relative measurement precision was defined as 20% coefficient of variation (CV), and CV was defined as the measurement standard deviation divided by the mean. CV of donor fraction was observed to depend on the donor fraction (d) with the relationship $CV = a + b \cdot \exp(-c \cdot d)$, where the model parameters a, b and c are estimated from the data using a non-linear least squares procedure. The CV model (described by parameters a, b, c) was estimated for each input mass and donor fraction estimate method, and the corresponding LoQ was the lowest value for which the model satisfies the CV requirement with LoD as the lowest possible LoQ. This model-based approach requires inclusion of higher donor fraction measurements for the LoQ assessment in order to ensure convergence to an appropriate constant value at high donor fraction.

Linearity and Accuracy

Linearity was measured using cell-line derived reference samples at cfDNA input amounts (15, 30, 45 ng) at all manufactured donor fractions levels (0.1, 0.3, 0.6, 1.2, 2.4, 5, 10, 15%) by 2 operators on different days using different reagent lots, and sequencing instruments. All seven donor fractions (0.1, 0.3, 0.6, 1.2, 2.4, 5, 10%) of unrelated plasma-derived cfDNA mixture samples at 15 ng input were used to compare linearity with the cell line derived data. For the plasma-derived cfDNA mixtures, 6 replicates of the 3 lowest donor fractions (0.1, 0.3, 0.6%) and triplicates of 4 high donor fractions (1.2, 2.4, 5, 10%) were assayed. In order to evaluate the accuracy, or trueness, of the transplant test, SeraCare reference mixtures at 8 donor fractions up to were 15% were used at 15, 30 and 45 ng input.

Linearity was evaluated based on the $R^2$ value produced by a standard linear regression analysis of the relationship between measured donor fraction and targeted mixture fractions. Accuracy was evaluated based on the linear regression analysis of the relationship between measured donor fraction and the orthogonal ddPCR measurement.

Precision

Precision was measured by testing reproducibility (inter-run) and repeatability (intra-run) across 632 reference samples. To assess inter-run reproducibility, 3 SeraCare donor-recipient mixtures (0.1, 0.3, 0.6, 1.2, 2.4, 5, 10%) were tested with replicates at 15, 30, 45 ng input. Repeatability was determined by measuring variability between technical replicates of samples measured under similar conditions. One related (mother-son) SeraCare reference mixture at 0.6 and 2.4% donor fractions was assayed by a single operator, reagent lot, and instrument for a total of 128 measurements. In addition to cfDNA mixtures, matched blood draws (4 tubes/patient) from transplant recipients were run in duplicates and evaluated for reproducibility in clinical samples. Samples were processed by 2 different operators on 8 different days (24 runs across 23 days) with 3 reagent lots and 17 sequencing instruments.

Repeatability was defined as the coefficient of variation (CV) measured across the set of replicates at a single targeted donor fraction, under matched conditions. Thus, CV was calculated once at 0.6% donor fraction and once at 2.4%. Reproducibility was also measured using CV, calculated separately for each combination of DNA input amount and mixture fraction.

Results

LoB was calculated using 64 measurements for each of two reagent lots. The LoB was 0.11% using the unrelated donor estimate and 0.23% using the related donor method. Evaluation of plasma-derived cfDNA measurements only (combined across both lots) resulted in LoB 0.04% (unrelated) and 0.08% (related), suggesting that the LoB in patient samples may be equivalent or superior to that measured using reference samples, although the sample size is limited (60 measurements). There was no significant difference between DNA input amounts. FIG. 23 shows histograms of the relevant donor fraction measurements broken down by method and lot.

LoD was calculated from 168 unrelated and 220 related measurements, resulting in LoD of 0.15% (unrelated) and 0.29% (unrelated). These numbers exclude one sample that failed QC due to insufficient number of reads. Note that the difference in LoD for related versus unrelated donors was approximately equal to the difference in corresponding LoB, meaning that the measurement variance near the LoD was approximately the same in the two methods. There was no significant impact due to DNA input amount. Following an approach similar to the one taken for LoB analysis, restriction to plasma-derived cfDNA measurements resulted in lower estimated LoD: 0.05% (unrelated) and 0.11% (related), although the number of measurements was less than ideal (54 related, 60 unrelated).

Figure 24B:
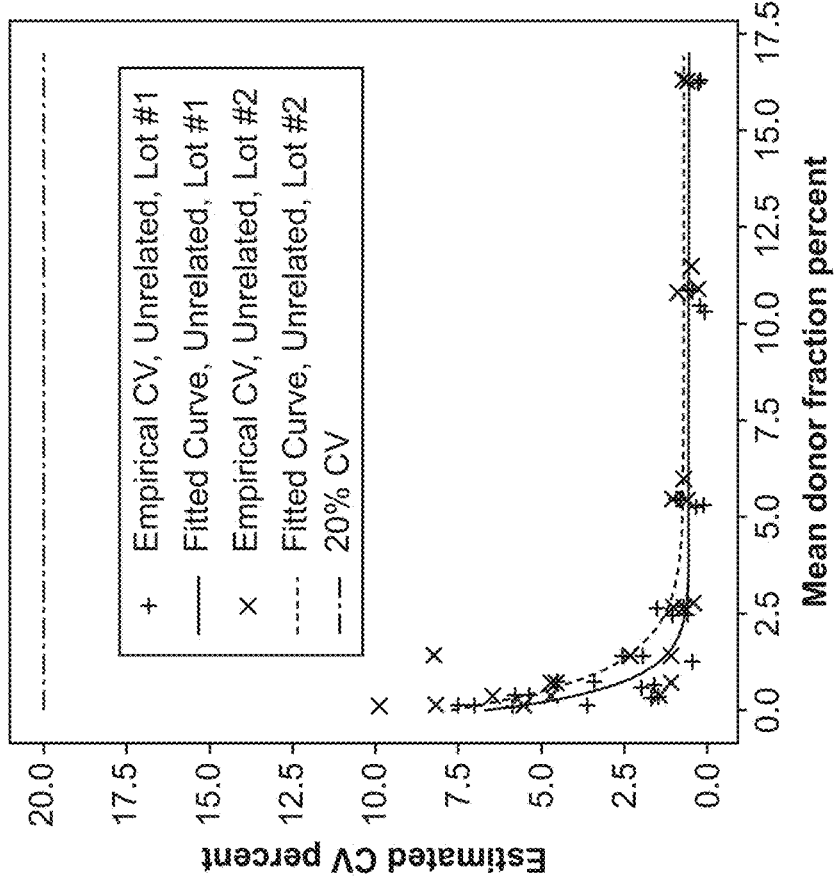
FIG. 24A-B: Graphs showing measured percent CV values as a function of the corresponding percent empirical means for related samples (A) and unrelated samples (B).
Figure 24A:
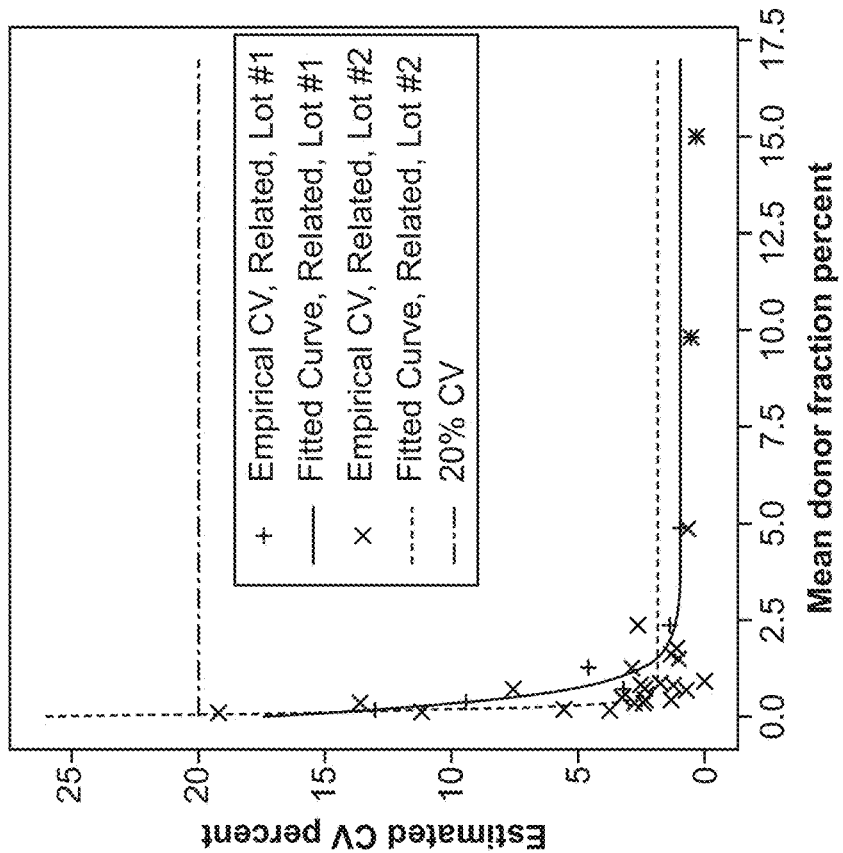

LoQ was calculated from 381 unrelated and 412 related measurements, after exclusion of 5 samples due to insufficient number of reads. Empirical CVs were calculated in the set of sample replicates at each targeted donor fraction and they were all less than 20%, including cell line-derived and plasma-derived cfDNA. Parametric models were fit for each reagent lot, once for related mixtures and once for unrelated. Empirical CVs and the resulting parametric models are shown in FIG. 24. The modeled CVs were also less than 20% for all donor fractions greater than or equal to the LoD. Thus, the LoQ was equal to the LoD for all scenarios.

LoB Analysis: Tables 2-4 below summarize the mean, median, and standard deviation values of the measured donor fractions for each lot and mode of the test.

TABLE 2

Mean values of measured donor fractions for related and unrelated cases for Lots 1 and 2.

| Mean Donor Fraction | Lot 1 | Lot 2 |
|---|---|---|
| Related | 0.03% | 0.06% |
| Unrelated | 0.02% | 0.03% |

TABLE 3

Median values of measure donor fractions for related and unrelated cases for Lots 1 and 2.

| Median Donor Fraction | Lot 1 | Lot 2 |
|---|---|---|
| Related | 0.01% | 0.03% |
| Unrelated | 0.01% | 0.01% |

TABLE 4

Standard deviation values of measured donor fractions for related and unrelated cases for Lots 1 and 2.

| Std. Dev. Donor Fraction | Lot 1 | Lot 2 |
|---|---|---|
| Related | 0.05% | 0.1% |
| Unrelated | 0.02% | 0.05% |

To demonstrate the performance of the test for gDNA and cfDNA samples separately, we computed LoB for each case by using 60 (resp. 68) measurements coming from cfDNA (resp. gDNA) samples. To increase the sample size, we did not distinguish between the lots. Histograms showing (resp. LoB values) for each DNA type and mode of the test are depicted in FIG. 29 (resp. Table 5).

TABLE 5

LoB values for related and unrelated modes of the test gDNA and cfDNA samples.

| LoB | gDNA | cfDNA |
|---|---|---|
| Related | 0.23% | 0.08% |
| Unrelated | 0.11% | 0.04% |

Figures 31A, 31B:
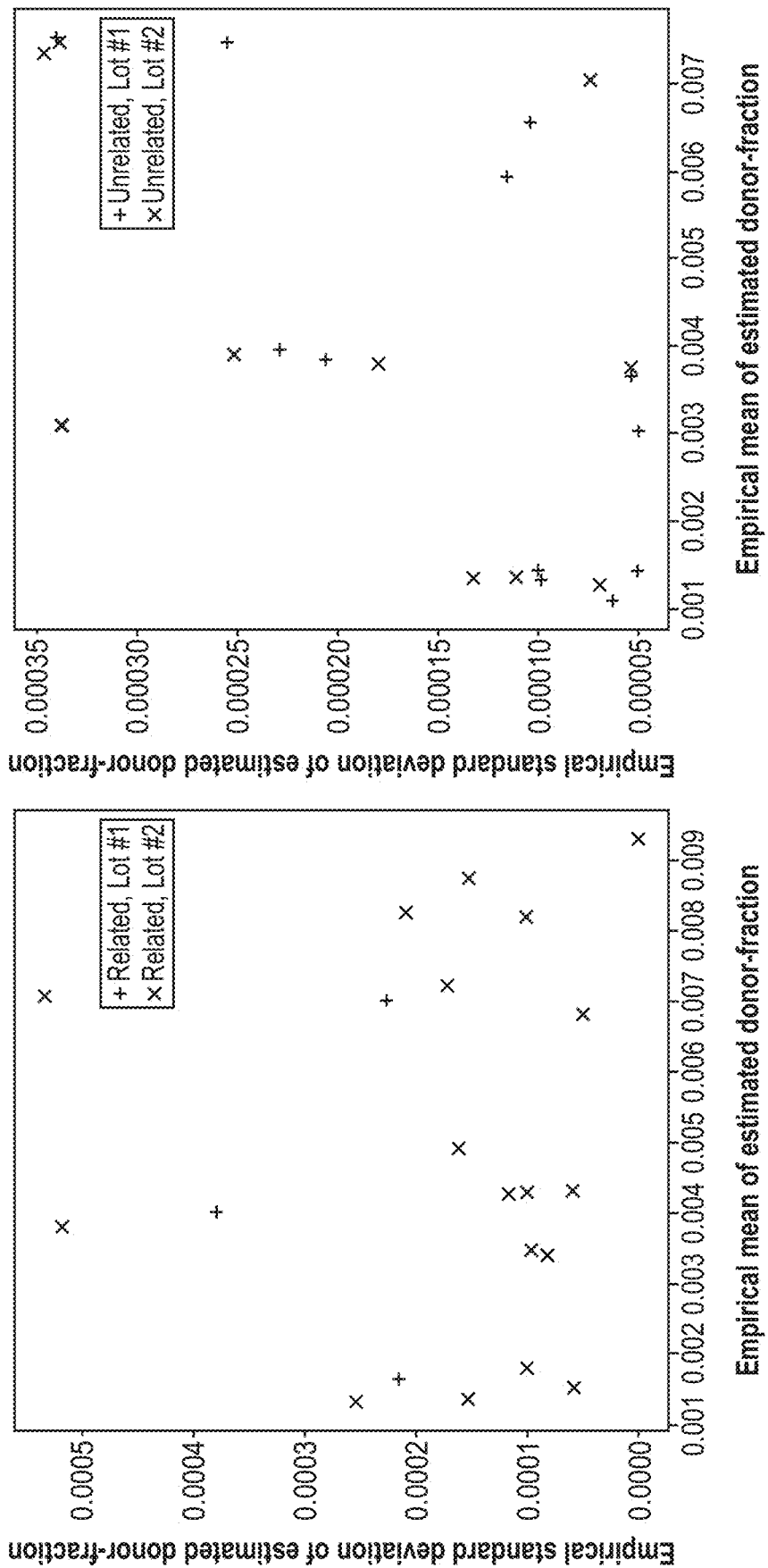
FIG. 31A-B: Graphs depicting empirical standard deviations as a function of the corresponding empirical means for: related samples from Lot 1 and Lot 2 (A), unrelated samples from Lot 1 and Lot 2 (B).

LoD Analysis: The parametric LoD computation method necessitated that: (i) the measurements from low-level samples (approximately) followed a Gaussian distribution, and (ii) the empirical standard deviations of the said samples (approximately) remained constant as a function of empirical mean. Histograms of centered, measured donor fractions for each lot and each test mode are shown in FIG. 30. The empirical standard deviation as a function of empirical mean for both lots and test modes is shown in FIG. 31. The data disclosed in FIGS. 30 and 31 demonstrated that these two conditions are satisfied for both related and unrelated low-level samples.

To demonstrate LoD for gDNA and cfDNA samples separately, as well as to see the effect of input amount for gDNA samples, the above outlined LoD analysis was performed for these sets of samples separately, by using the corresponding LoB values for each case. Specifically, 54 related and 60 unrelated measurements were used for cfDNA case. Further, for gDNA case, 18 related, 36 unrelated measurements were used for 15 ng and 45 ng inputs; and 130 related, 36 unrelated measurements were used for 30 ng input. The computed LoD values with respect to test mode and input amount for gDNA samples are shown in Table 6 below, whereas the LoD values for two different test modes for cfDNA samples are shown in Table 7 below.

TABLE 6

LoD values for related and unrelated modes of the test for 15, 30, 45 ng inputs for gDNA samples.

| gDNA-LoD | 15 ng | 30 ng | 45 ng |
|---|---|---|---|
| Related | 0.28% | 0.26% | 0.25% |
| Unrelated | 0.13% | 0.13% | 0.12% |

TABLE 7

LoD values for related and unrelated modes of the test for cfDNA samples.

| cfDNA | LoD |
|---|---|
| Related | 0.11% |
| Unrelated | 0.05% |

Figures 32A, 32B:
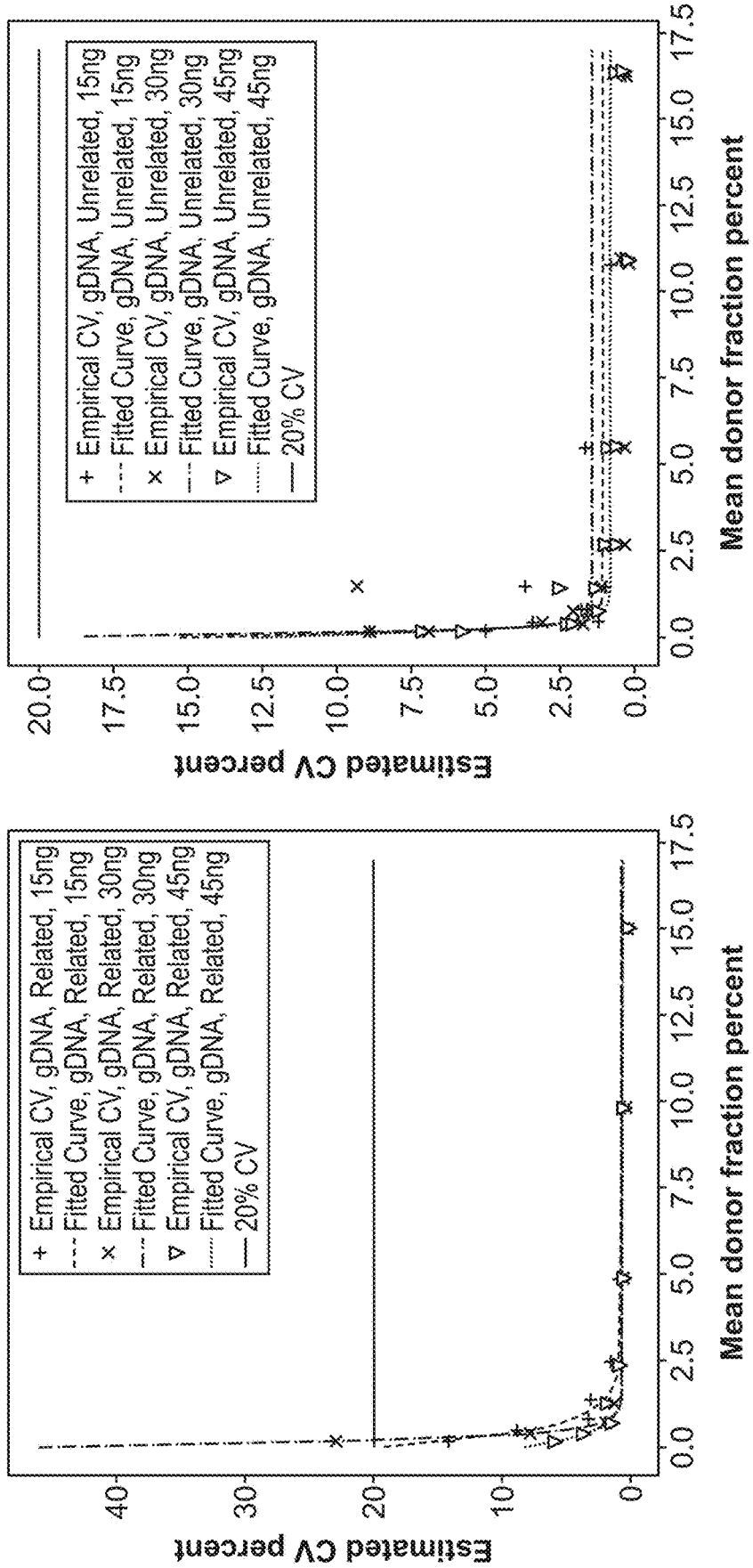
FIG. 32A-B: Graphs depicting measured percent CV values as a function of the corresponding percent empirical means, particularized with respect to input amount, for gDNA samples: from related samples (A) and from unrelated Samples (B).
Figure 33A:
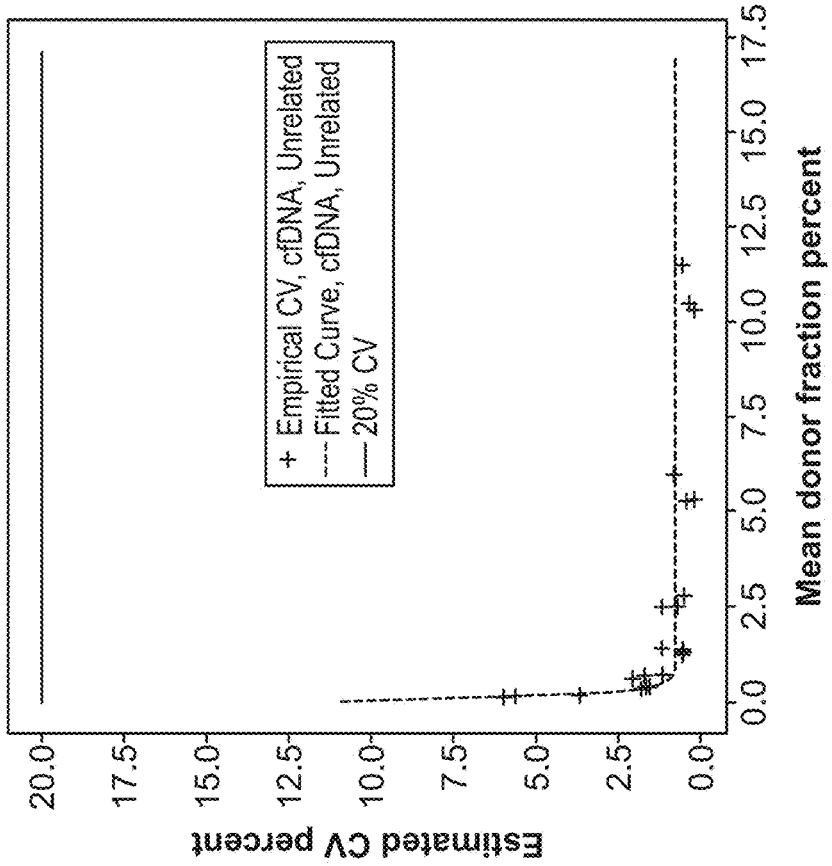
FIG. 33A-B: Graphs depicting measured percent. CV values as a function of the corresponding percent empirical means for cfDNA samples: from related samples (A) and from unrelated samples (B).
Figure 33B:
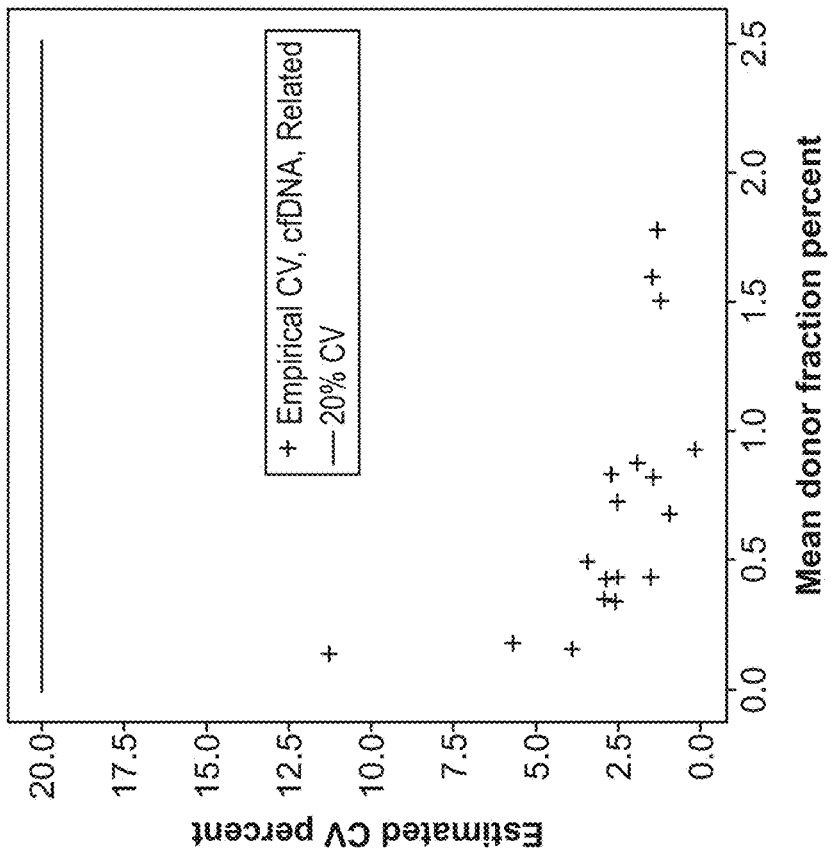

LoQ Analysis: Similar to LoD analysis, we evaluated LoQ numbers for gDNA samples, which were further partitioned with respect to their input amounts. As depicted in FIG. 32, all the measured CV values for all the spike levels tested were below 20% cutoff for related samples at all input levels, as well as related samples at 15 and 45 ng input levels. Thus, for all these cases, lower LoQ was equal to LoD, by definition. For related samples with 30 ng input level, fitted curve intersected with 20% CV level at approx. 0.174%, which was lower than the corresponding LoD, i.e., 0.26%, for this case. Thus, the lower LoQ was again equal to LoD, by definition. Further, we also computed LoQ values for cfDNA samples, as depicted in FIG. 33. Clearly, for both cases, we had lower LoQ equal to the corresponding LoD. The estimated parameters of the non-linear fit for CV for every scenario we report LoQ values is shown in Table 8 below.

TABLE 8

Estimated parameters of the exponential decaying model of the CV for every scenario we report LoQ values

| Data Set | a | b | c |
| --- | --- | --- | --- |
| cfDNA + gDNA, Related, Lot 1 | 0.950216 | 16.4685 | 1.88562 |
| cfDNA + gDNA, Related, Lot 2 | 1.82651 | 24.2948 | 6.82745 |
| cfDNA + gDNA, Unrelated, Lot 1 | 0.557873 | 6.16417 | 1.53284 |
| cfDNA + gDNA, Unrelated, Lot 2 | 0.715364 | 7.00144 | 1.00344 |
| gDNA, Related, 15 ng | 0.907757 | 18.3994 | 1.97114 |
| gDNA, Related, 30 ng | 0.798892 | 45.2805 | 4.943 |
| gDNA, Related, 45 ng | 0.746606 | 7.69009 | 2.62489 |
| gDNA, Unrelated, 15 ng | 1.06598 | 14.2357 | 6.04647 |
| gDNA, Unrelated, 30 ng | 1.4362 | 17.0526 | 7.3715 |
| gDNA, Unrelated, 45 ng | 0.801393 | 12.0185 | 5.69333 |
| cfDNA, Related | 1.88546 | 13275.4 | 53.5112 |
| cfDNA, Unrelated | 0.654995 | 10.1971 | 6.67823 |

Linearity, Accuracy and Precision

Figures 25A, 25B, 25C:
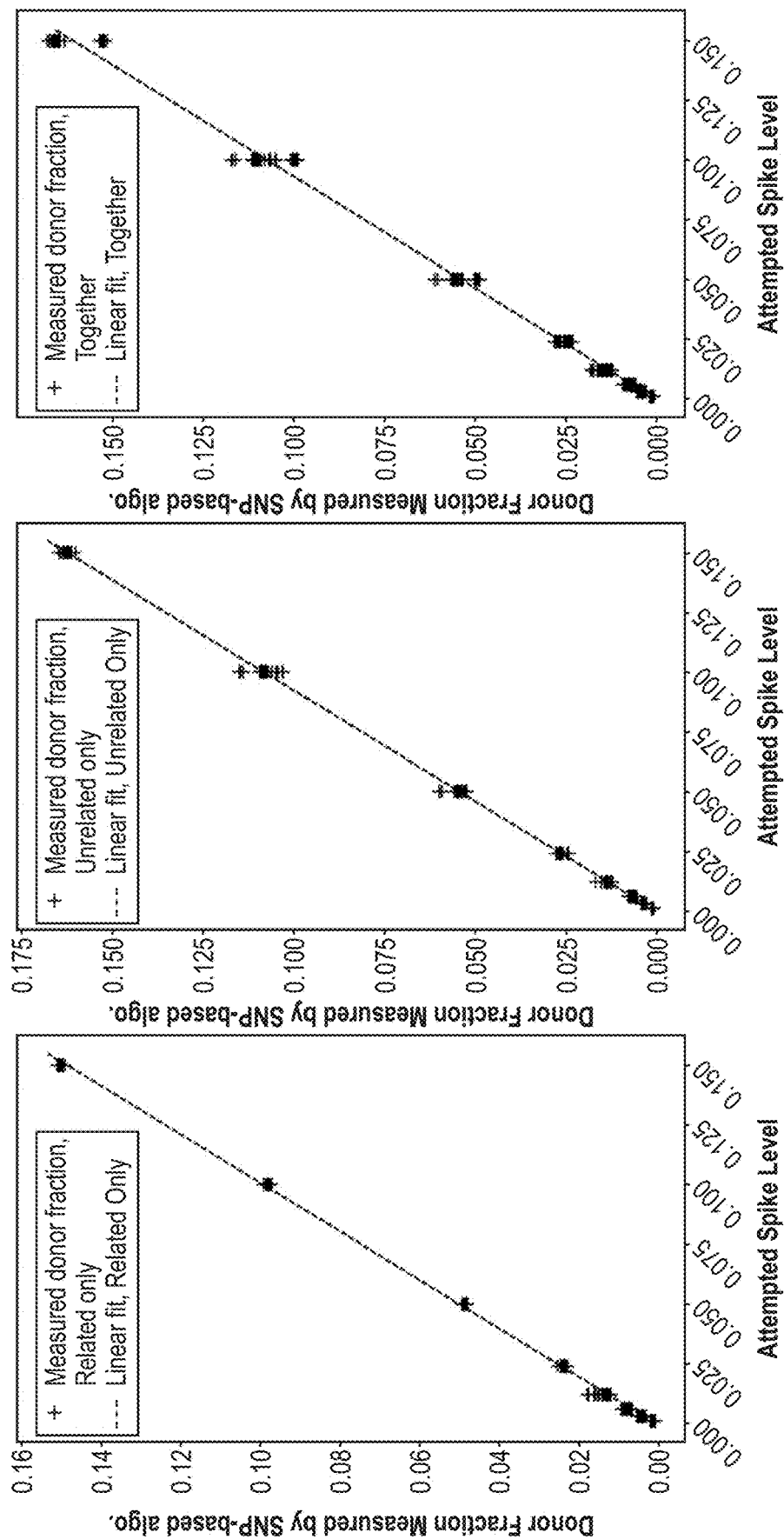
FIG. 25A-C: Graphs showing measured donor fractions as a function of the corresponding attempted spike levels, along with the calculated linear fit for related cases only (A), for unrelated cases only (B), for related and unrelated cases together (C).
Figure 26C:
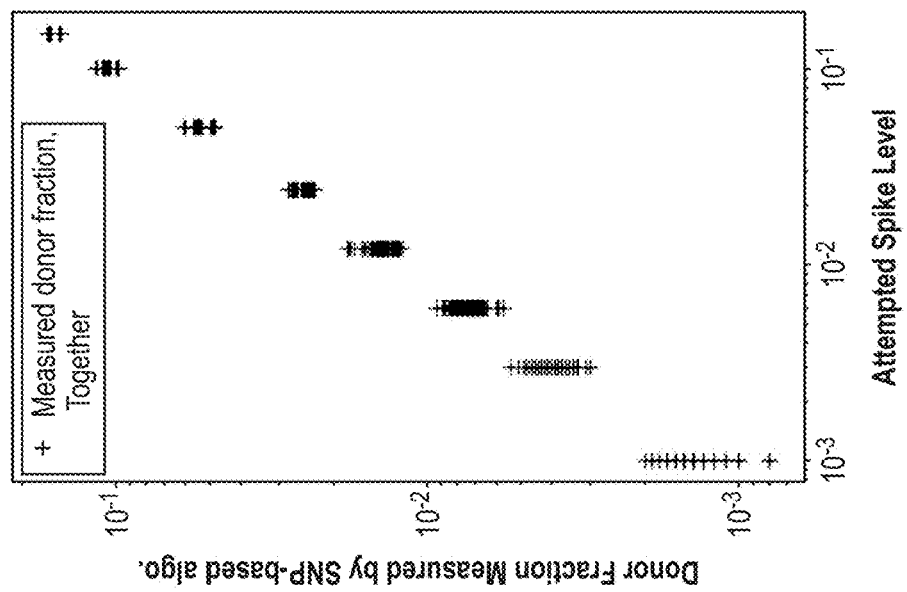
FIG. 26A-C: Graphs showing measured donor fractions as a function of the corresponding attempted spike levels on log-log scale for related cases only (A), for unrelated cases only (B), for related and unrelated cases together (C).
Figure 26B:
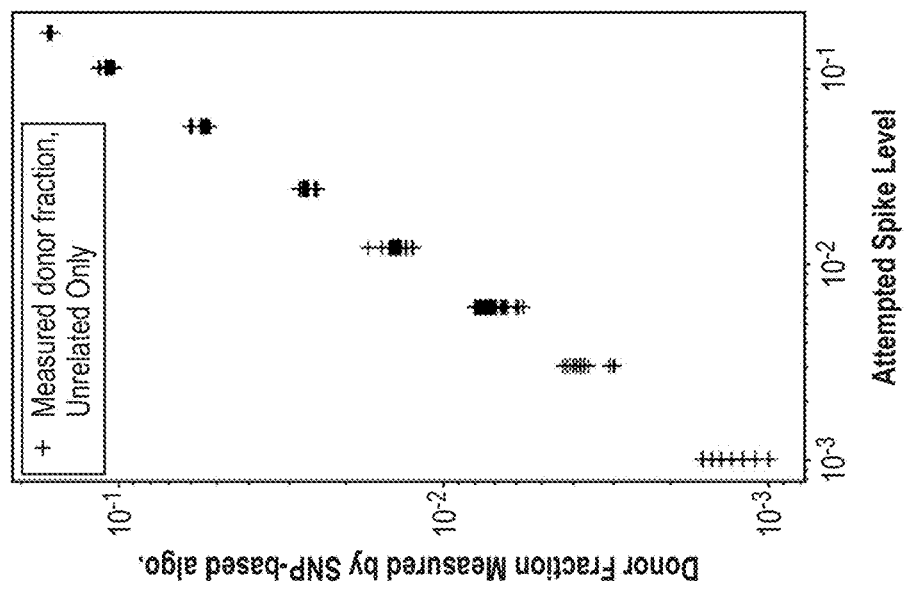
Figure 26A:
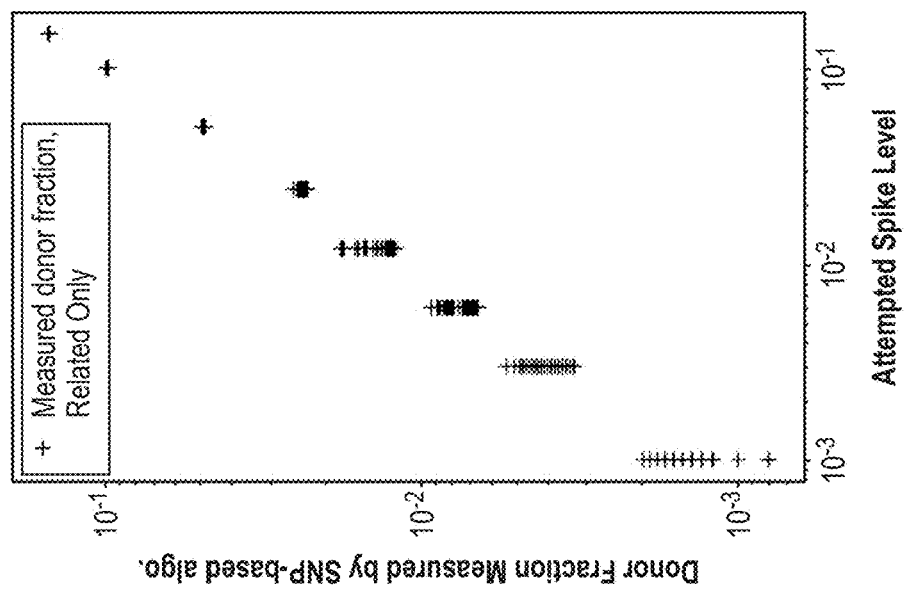

Linearity was measured from 381 unrelated and 412 related samples, after removal of 5 samples that failed QC due to insufficient number of reads. Accuracy was measured from the subset of these (the cell line-derived reference samples) for which ddPCR donor fraction was available as a reference: 285 unrelated and 349 related, after exclusion of 4 samples due to insufficient number of reads. The individual measurements and linear regression lines are shown in FIG. 25 (linearity) and FIG. 26 (accuracy). Linearity was measured by linear regression against the targeted donor fraction, and accuracy was measured by linear regression against the ddPCR-measured donor fraction. The linear regression results are shown in Tables 9 and 10 below. The donor fraction measurement was shown to be highly linear ($R^2$ greater than 0.99 in all models) and accurate (slope approximately 1, intercept approximately zero). There was no significant difference between related and unrelated donors as determined by combined regression.

TABLE 9

Linear regression results for linearity and accuracy, including 95% confidence interval.

| | slope | intercept | $R^2$ |
| --- | --- | --- | --- |
| accuracy, combined | 1.0591 (0.9763, 1.1418) | 0.0001 (−0.0045, 0.0047) | 0.9988 (0.9987, 0.9990) |
| accuracy, related | 1.0333 (0.9241, 1.1425) | −0.0001 (−0.0047, 0.0046) | 0.9989 (0.9986, 0.9990) |
| accuracy, unrelated | 1.0664 (0.9416, 1,1912) | 0.0008 (−0.0076, 0.0092) | 0.9997 (0.9997, 0.9998) |
| linearity, combined | 1.0516 (0.9781, 1.1251) | 0.0004 (−0.0033, 0.0042) | 0.9968 (0.9964, 0.9972) |
| linearity, related | 0.9852 (0.8895, 1.0809) | 0.0008 (−0.0031, 0.0047) | 0.9991 (0.9989, 0.9992) |
| linearity, unrelated | 1.0813 (0.9721, 1.1906) | 0.0006 (−0.0060, 0.0071) | 0.9995 (0.9994, 0.9996) |

TABLE 10

Linear regression results for linearity, including 95% confidence intervals, for clinical samples

| slope | intercept | $R^2$ |
| --- | --- | --- |
| 1.0125 (−0.3932, 2.4183) | −0.0002 (−0.0121, 0.0117) | 0.9998 (0.9984, 1.0000) |

The precision of the herein disclosed methods were evaluated by measuring repeatability within a single experiment run and set of conditions and reproducibility across a varied set of conditions. Repeatability was measured using CV at two targeted donor fractions (0.6% and 2.4%), each using 64 cell line-derived sample measurements with no samples removed due to QC failure. The CV was 1.85% (95% CI: 1.34%-2.73%) at 0.6% targeted donor fraction, and CV was 1.22% (95% CI: 0.88%-1.80%) at 2.4% targeted donor fraction. Per input reproducibility was calculated by using 498 measurements, after removal of 6 samples that failed QC due to insufficient number of reads. For 15 ng input, the CV was 3.10% (95% CI: 1.58%-4.37%); for 30 ng input, the CV was 3.07% (95% CI: 1.42%-4.50%); for 45 ng the CV was 1.99% (95% CI: 1.10%-2.75%). Per lot reproducibility was calculated from a subset of the aforementioned samples, whose cardinality is 374, which excludes 4 samples that failed QC due to insufficient number of samples. The CV for Lot 1 was 3.99% (95% CI: 2.42%-5.41%) and the CV for Lot 2 was 4.44% (95% CI: 2.69%-6.02%).

Figures 27A, 27B, 27C:
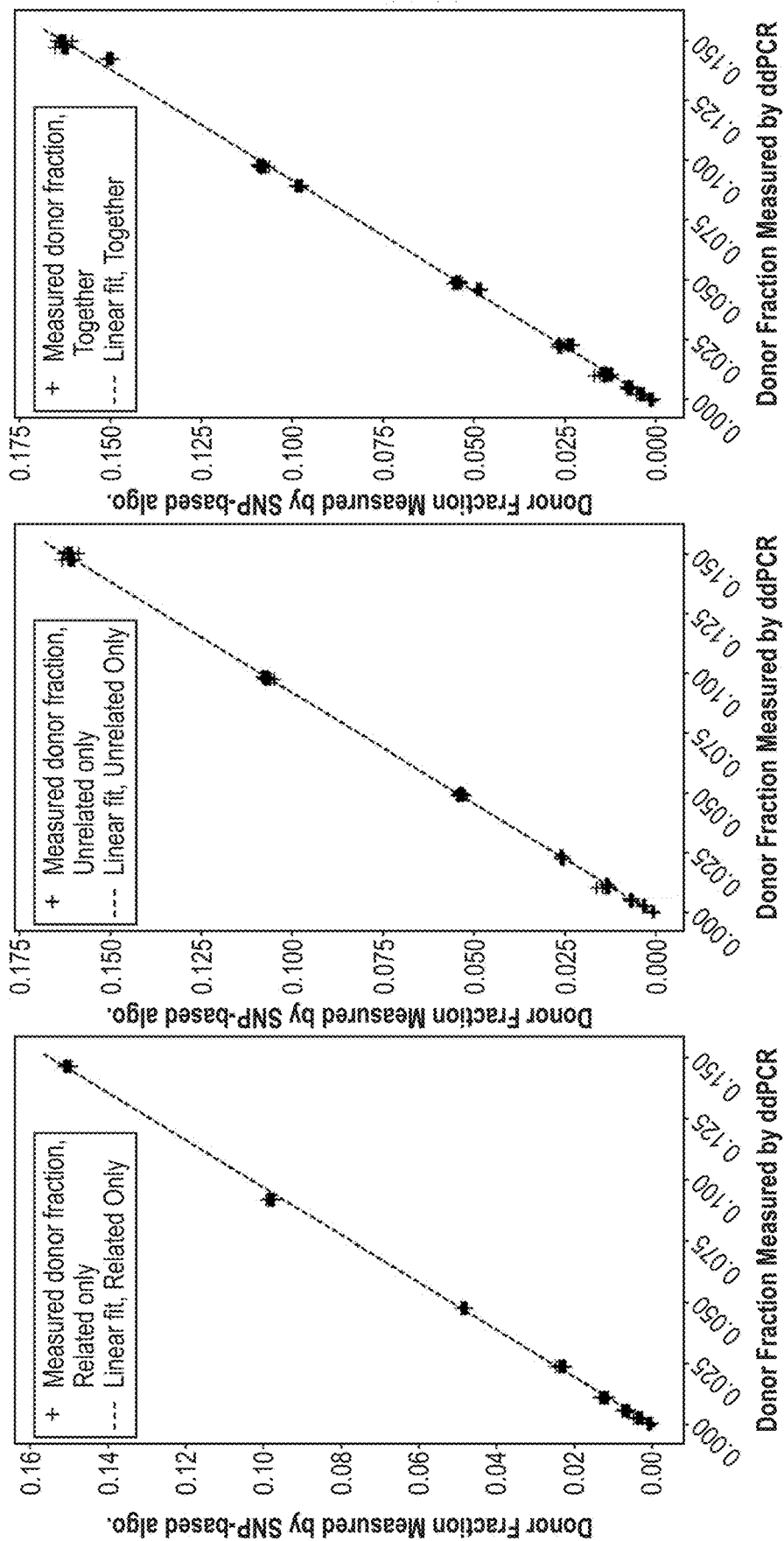
FIG. 27A-C: Graphs showing measured donor fractions as a function of the corresponding ddPCR values, along with the calculated linear fit for related cases only (A), unrelated cases only (B), related and unrelated cases together (C).
Figure 28B:
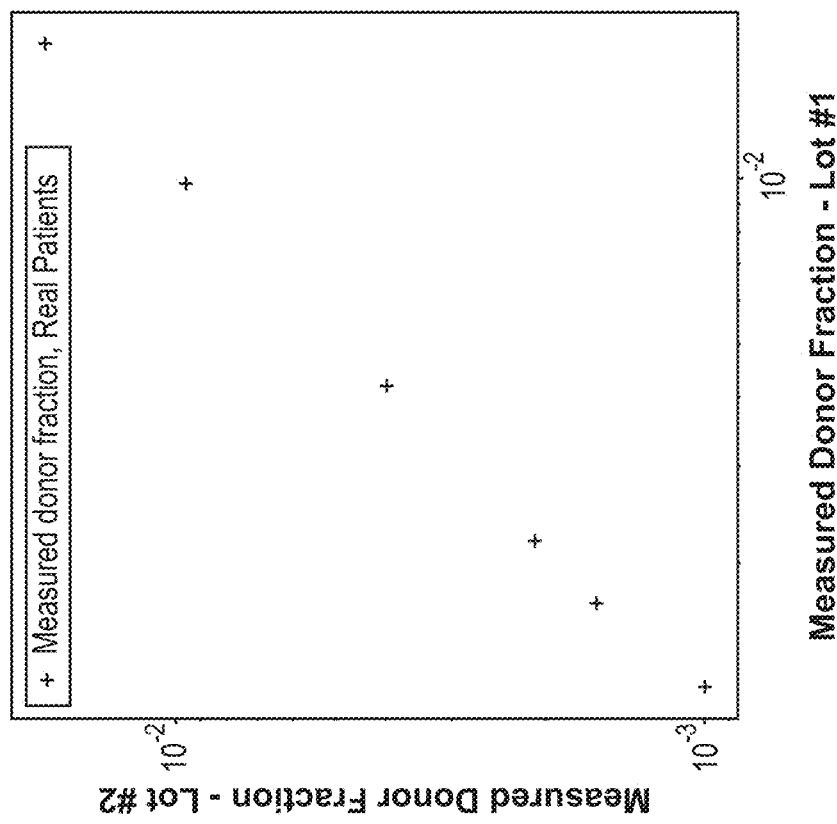
FIG. 28A-B: Graphs showing measured donor fractions from Lot 2 as a function of the values from Lot 1 on linear scale, along with the calculated linear fit (A) and on log-log scale (B).
Figure 28A:
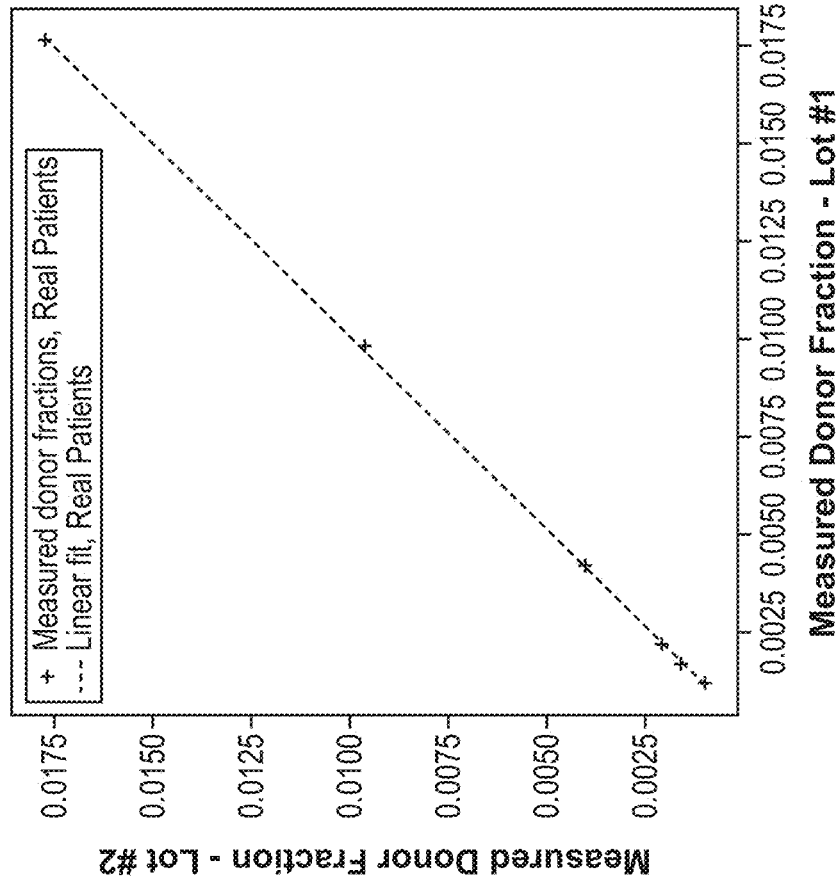
Figure 29A:
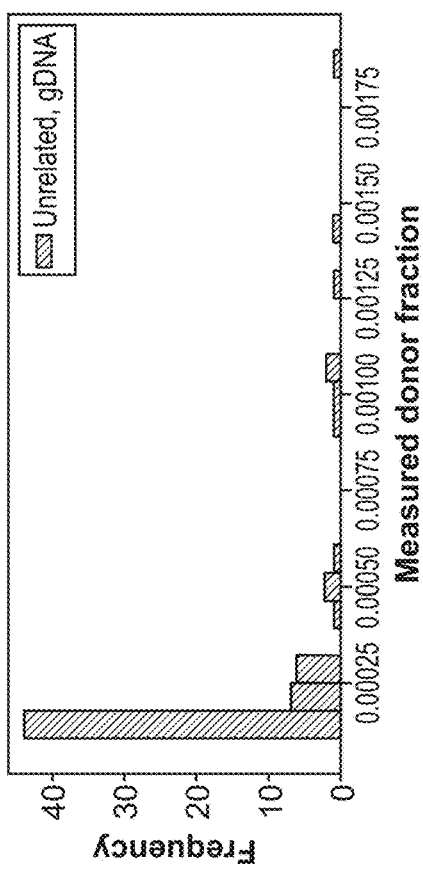
FIG. 29A-D: Graphs showing histograms of measured donor fractions for: related gDNA (A), unrelated gDNA (B), related cfDNA (C), and unrelated cfDNA samples (D).
Figure 29B:
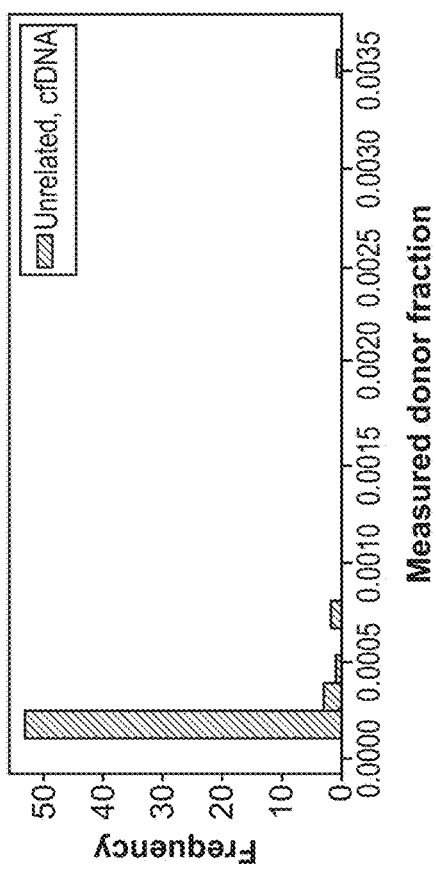
Figure 29C:
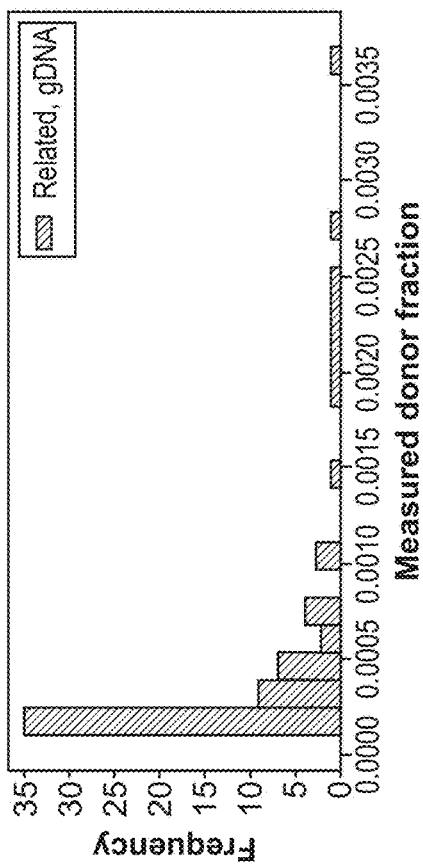
Figure 29D:
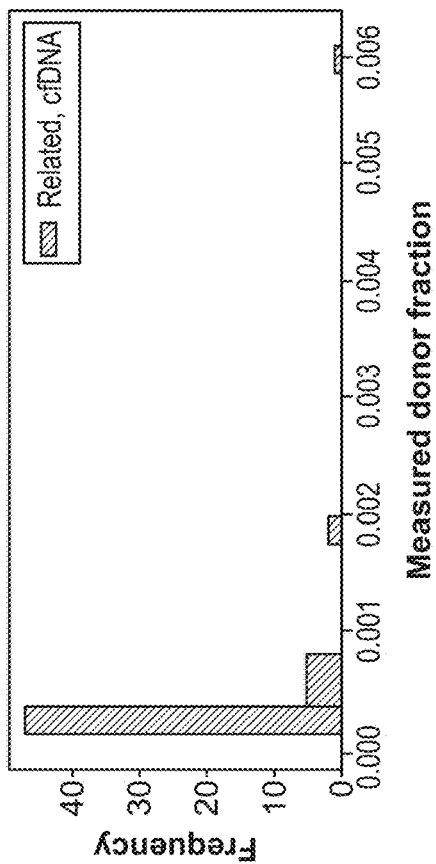
Figure 30A:
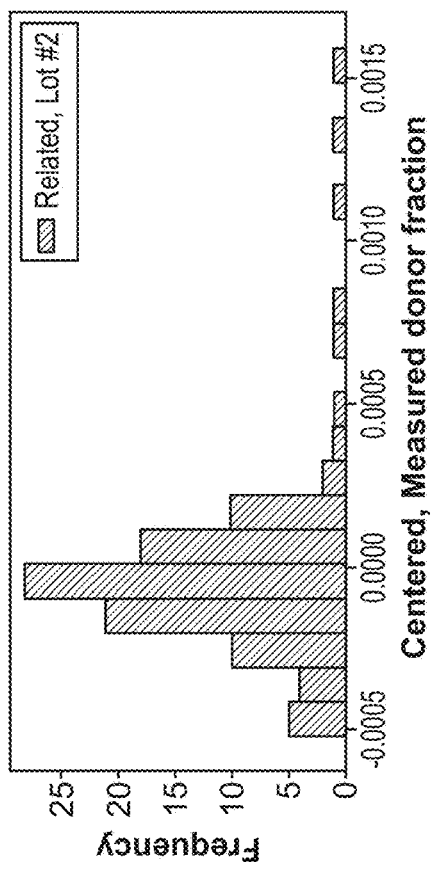
FIG. 30A-D: Graphs showing histograms of centered, measured donor fractions for: related samples from Lot 1 (A), related samples from Lot 2 (B), unrelated samples from Lot 1 (C), and unrelated samples from Lot 2 (D).
Figure 30B:
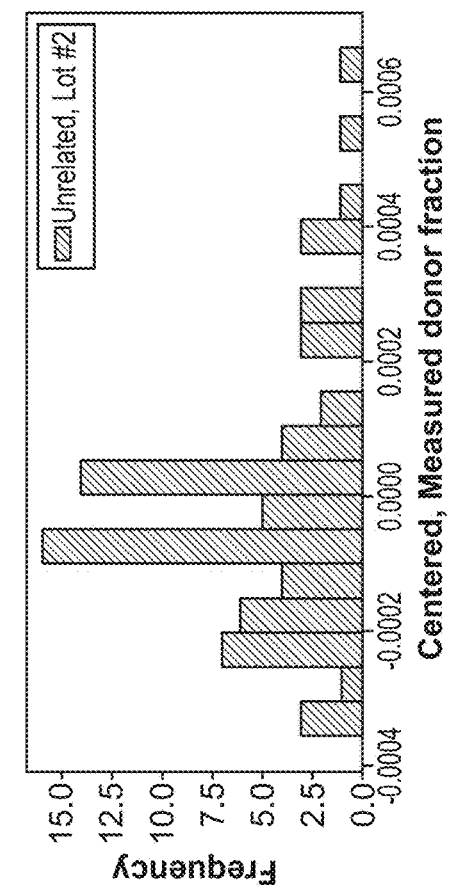
Figure 30C:
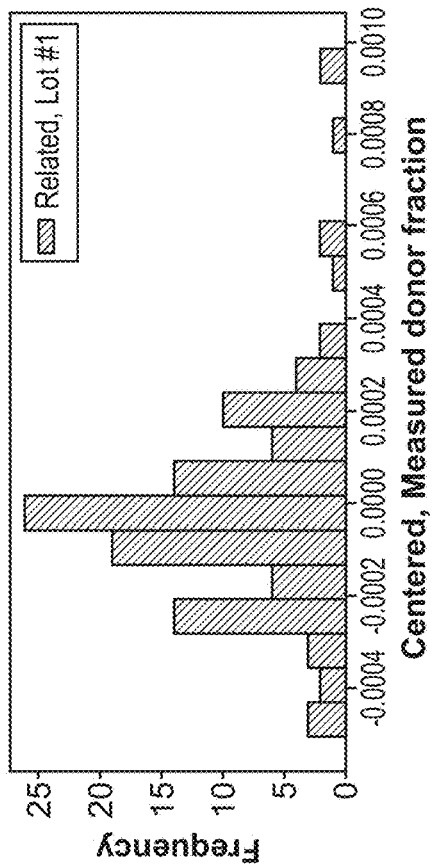
Figure 30D:
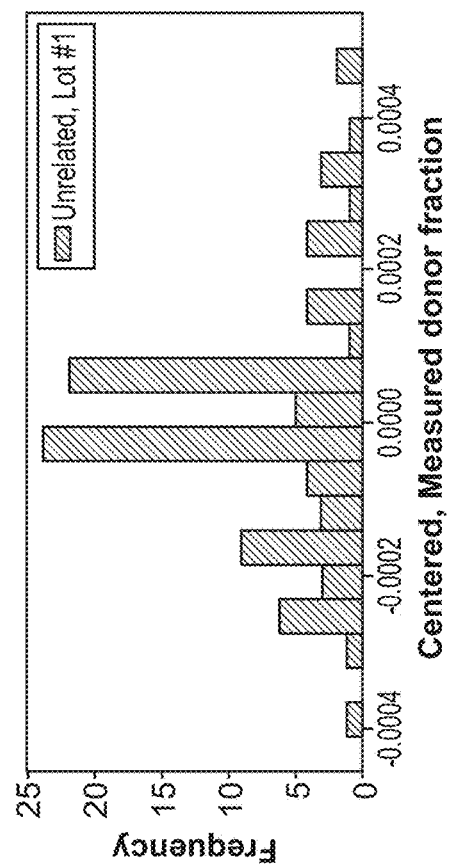

We also evaluated linearity and precision of the test for clinical transplant samples, in line with the aforementioned analysis. To this end, 12 measurements, none of which failed due to QC, were used. Linearity was measured by performing linear regression of the measured donor fraction from Lot 2 against Lot 1. The measurements and linear regression lines are shown in FIG. 27, and the corresponding linear regression results are provided. The estimated precision of the tested was determined to have a CV of 4.29% (95% CI: 0.65%-6.86%). Finally, we observed 100% concordance (95% CI: 54.07%-100%) between replicates.

Figures 34A, 34B, 34C:
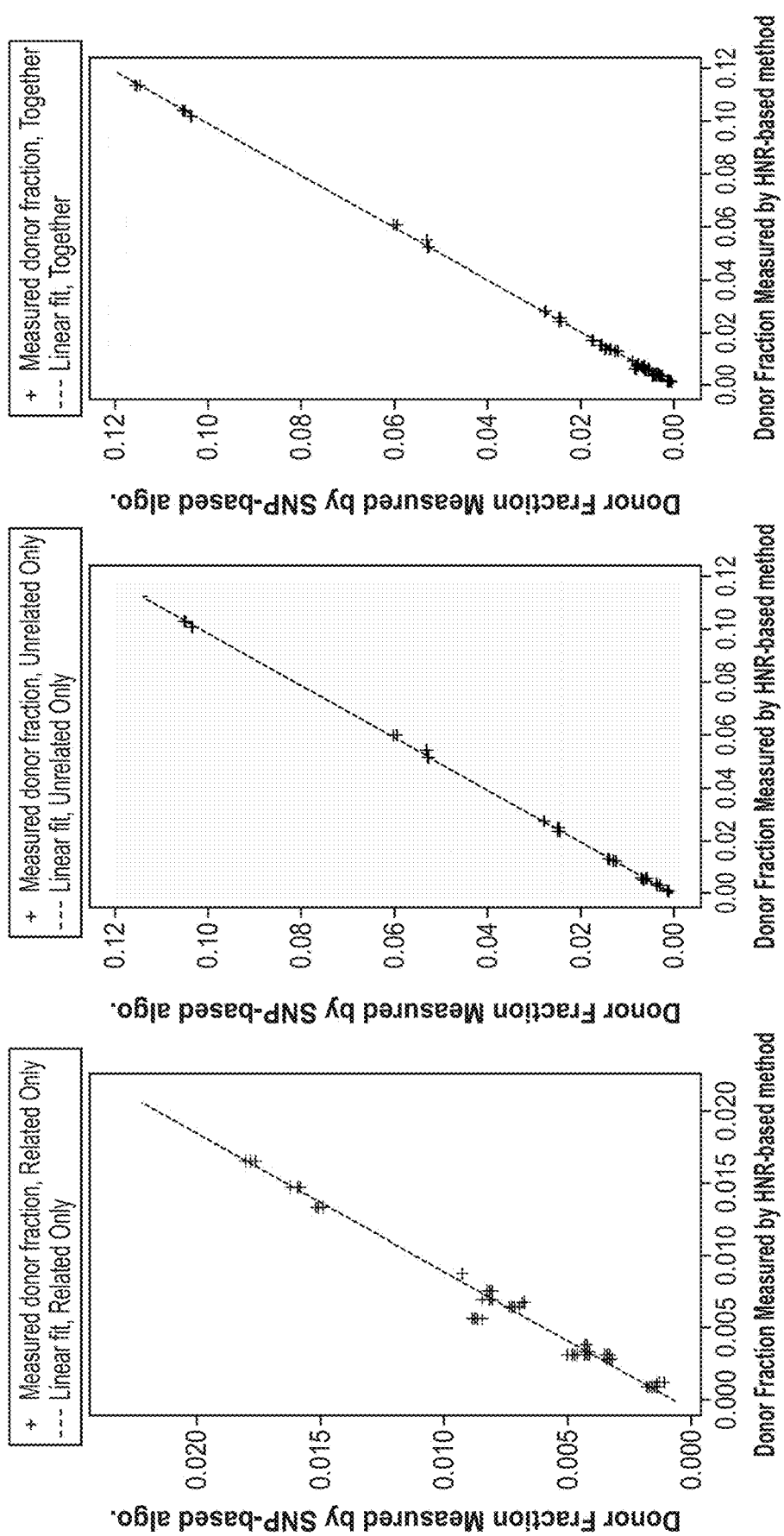
FIG. 34A-C: Graphs depicting measured donor fractions as a function of the corresponding donor fraction values measure by using HNR, along with the calculated linear fit for related cases only (A), for unrelated cases only (B), and both related and unrelated cases (C).

Accuracy Analysis: To demonstrate the accuracy for cfDNA samples, we used donor fraction estimated by using SNP's from HNR in lieu of ddPCR for gDNA. The rationale of using this method as a more precise alternative to the conventional donor fraction estimate using non-HNR SNP's was due to the following: since HNR were non-recombining, and the cfDNA samples were designed to have a female background with male spike-in, the Y chromosome allele measurements were directly attributable to the donor signal. The accuracy analysis was carried out by using 63 related and 96 unrelated cfDNA measurements, which excluded one sample that failed QC due to insufficient number of reads. The individual measurements and linear regression lines are shown in FIG. 34, and the corresponding linear regression results are shown in Table 11 below. It should be noted that relatively wider confidence intervals for cfDNA estimates compared with their gDNA counterparts is probably a result of the relatively smaller sample size of the former compared with the latter.

TABLE 11

Linear regression results for accuracy of cfDNA samples, including 95% confidence intervals.

| cfDNA-accuracy | slope | intercept | $R^2$ |
|---|---|---|---|
| Unrelated | 1.0108 (0.8038, 1.2179) | 0.0002 (−0.0076, 0.0080) | 0.9996 (0.9994, 0.9997) |
| Related | 1.0440 (0.7727, 1.3153) | 0.0007 (−0.0012, 0.0027) | 0.9706 (0.9517, 0.9993) |
| Combined | 1.0073 (0.8484, 1.1662) | 0.0005 (−0.0042, 0.0053) | 0.9991 (0.9987, 0.9993) |

Figures 35A, 35B, 35C:
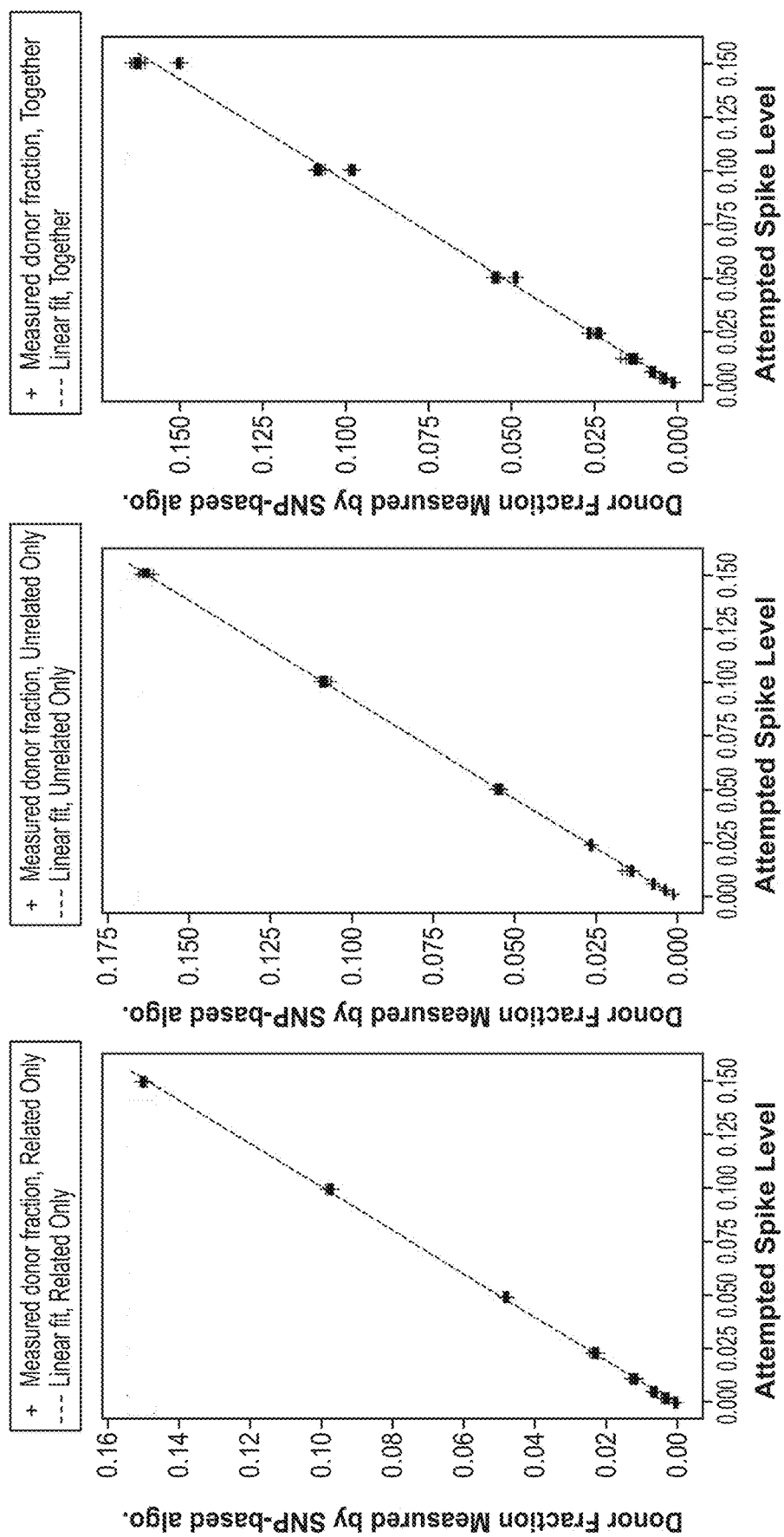
FIG. 35A-C: Graphs depicting measured donor fractions as a function of the corresponding attempted spike levels, along with the calculated linear fit, for gDNA samples from related cases only (A), from unrelated cases only (B), and both related and unrelated cases together (C).
Figures 36A, 36B, 36C:
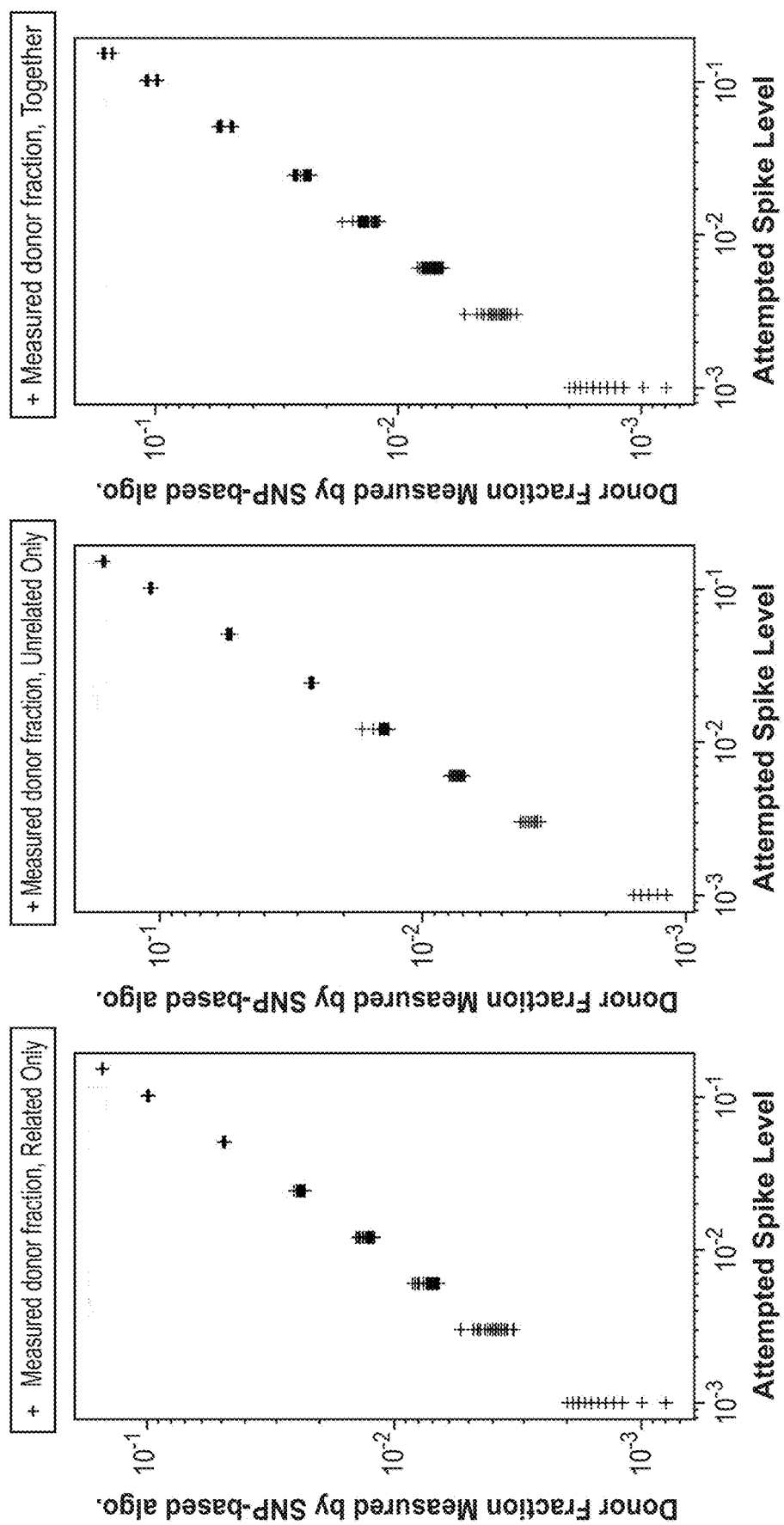
FIG. 36A-C: Graphs depicting measured donor fractions as a function of the corresponding attempted spike levels on log-log scale for gDNA samples: from related cases only (A), from unrelated cases only (B), and related and unrelated cases together (C).
Figures 37A, 37B, 37C:
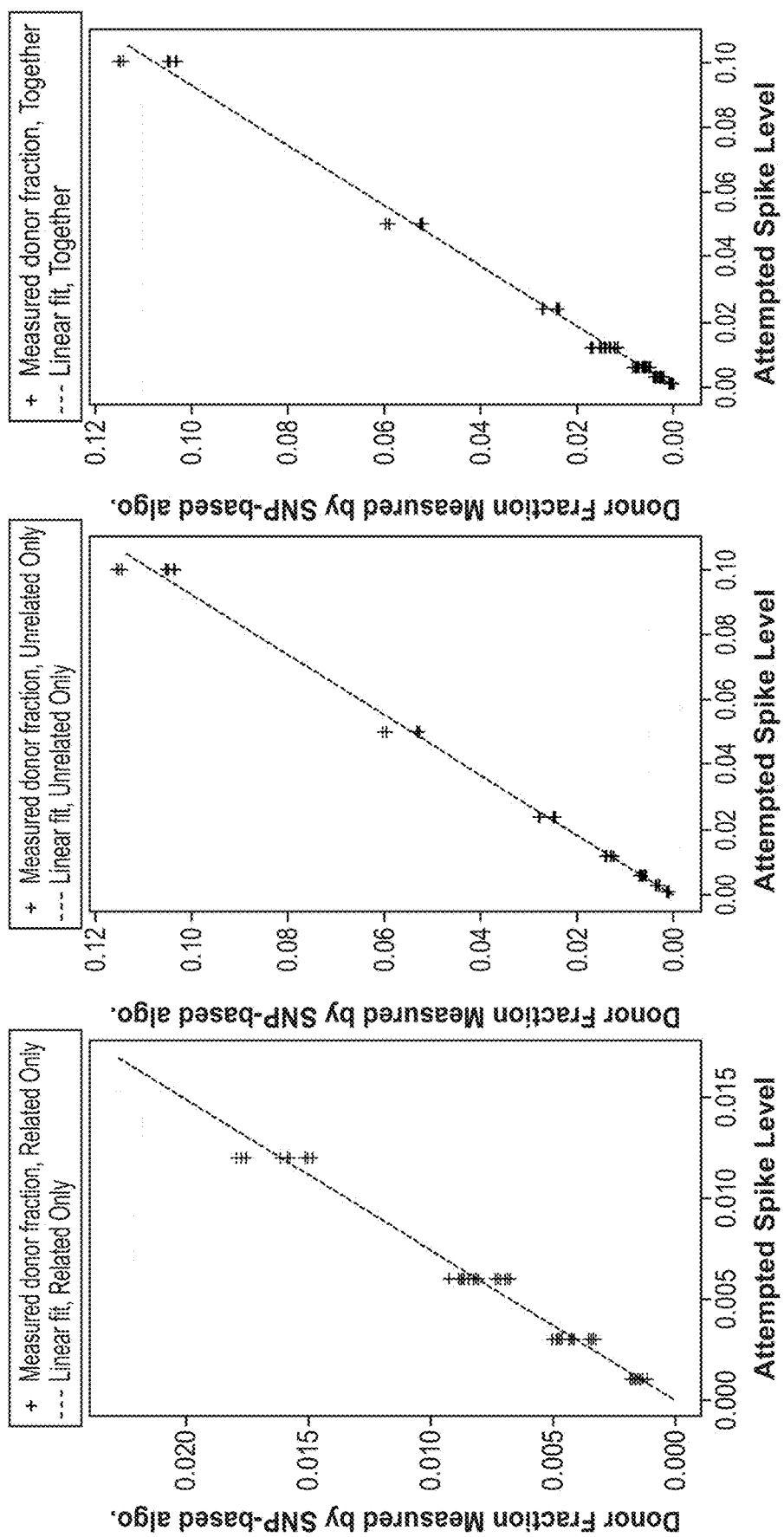
FIG. 37A-C: Graphs depicting measured donor fractions as a function of the corresponding attempted spike levels, along with the calculated linear fit, for cfDNA samples from related cases only (A), from unrelated cases only (B), and from related and unrelated cases together (C).

Linearity Analysis: Similar to previous performance metrics, we broke down the linearity analysis for gDNA and cfDNA samples separately. Specifically, for gDNA analysis, 349 related and 285 unrelated measurements were used, and for cfDNA analysis, 63 related and 96 unrelated measurements were used. The individual measurements and linear regression lines (resp. individual measurements on a log-log scale) for gDNA samples are shown in FIG. 35 (resp. FIG. 36). Similarly, the individual measurements and linear regression lines (resp. individual measurements on a log-log scale) for cfDNA samples are shown in FIG. 37 (resp. FIG. 38) depicts Tables 12 and 13 contain corresponding linear regression results for gDNA and cfDNA, respectively.

TABLE 12

Linear regression results for accuracy of gDNA samples, including 95% confidence intervals.

| gDNA-linearity | slope | intercept | $R^2$ |
|---|---|---|---|
| Unrelated | 1.0804 (0.9540, 1.2069) | 0.0007 (−0.0077, 0.0091) | 0.99989 (0.99986, 0.99992) |
| Related | 0.9876 (0.8833, 1.0920) | 0.0005 (−0.0041, 0.0052) | 0.9994 (0.9974, 0.9995) |
| Combined | 1.0515 (0.9693, 1.1338) | 0.0003 (−0.0043, 0.0049) | 0.9969 (0.9964, 0.9974) |

TABLE 13

Linear reg

| cfDNA-linearity | slope | intercept | $R^2$ |
|---|---|---|---|
| Unrelated | 1.0787 (0.8574, 1.300) | 0.0002 (−0.0076, 0.0080) | 0.9962 (0.9943, 0.9975) |
| Related | 1.3368 (0.9895, 1.6841) | 0.0001 (−0.0020, 0.0022) | 0.9713 (0.9528, 0.9965) |
| Combined | 1.0734 (0.9038, 1.2430) | 0.0008 (−0.0039, 0.0055) | 0.9953 (0.9935, 0.9965) |

Figure 39B:
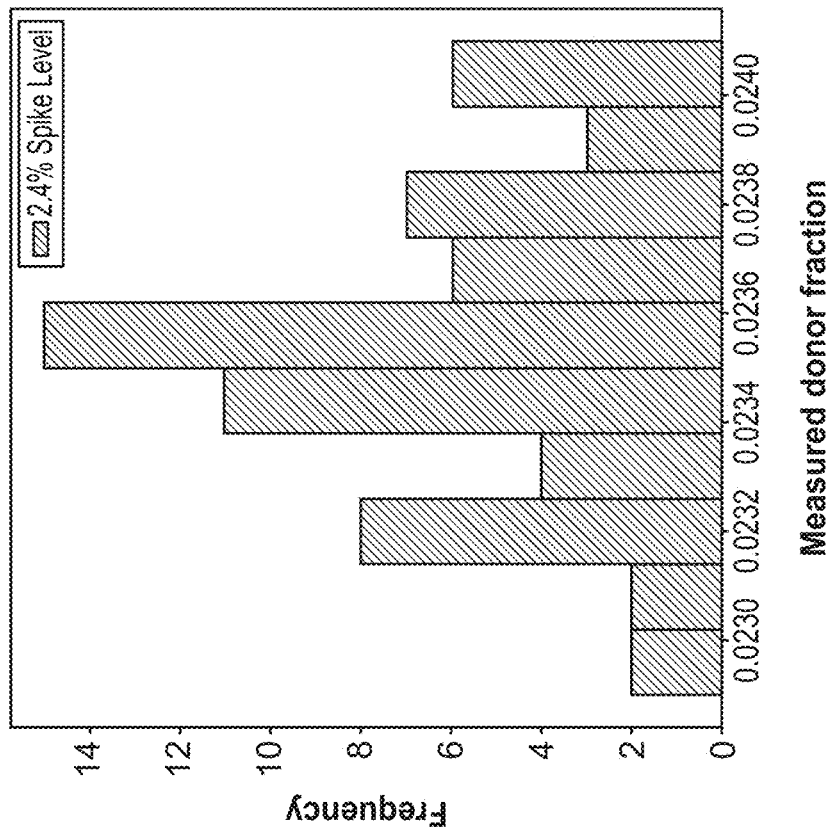
FIG. 39A-B: Graphs showing histograms of measured donor fractions for (A) 0.6% spike level and (B) 2.4% spike level.
Figure 39A:
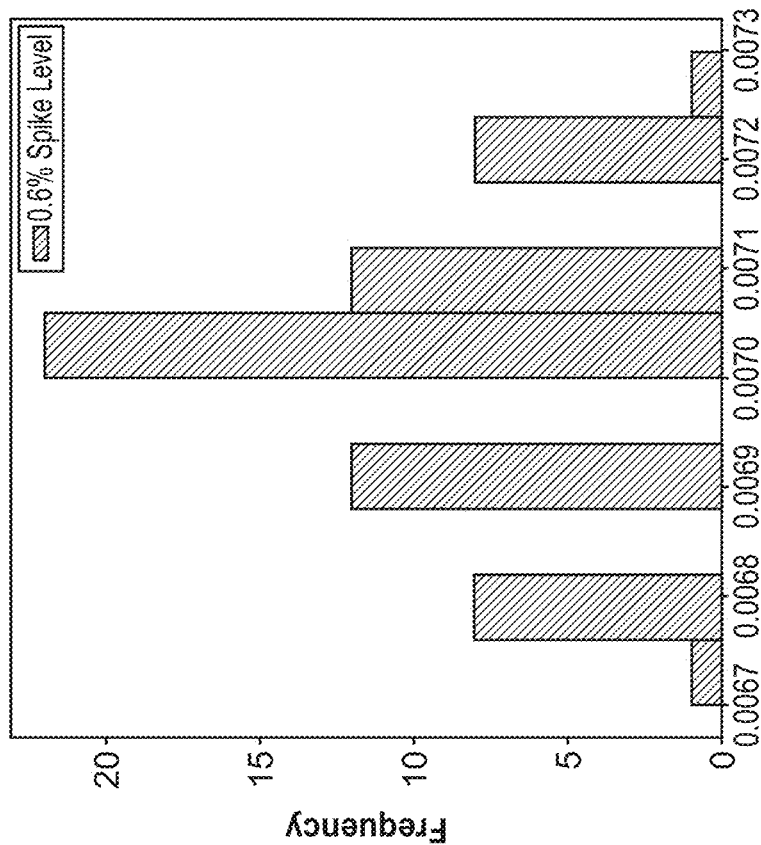

Repeatability and Reproducibility Analysis: To compute the confidence intervals on the estimated CV's for repeatability analysis, we used the classical bounds as described in McKay, "Distribution of the coefficient of variation and the extended t distribution," *Journal of the Royal Statistics Society,* 95(4): 695-698 (1932), based on a chi-squared approximation. The derivation of these bounds assumes that the underlying measurements from which CV is estimated are realizations from Gaussian distributions, Histograms in FIG. 39 verified that said assumption is justified in our case.

It should be noted that chi-squared approximation-based bounds used in the repeatability analysis is not suitable to compute the confidence intervals of the estimated CV's for reproducibility analysis because the underlying measurements from which CV value is estimated do not follow a Gaussian distribution, due to the broad range of underlying donor fractions. Thus, we computed confidence intervals by a standard bootstrapping technique. Because of the inherent stochasticity of the approach, the particular values may slightly vary for each trial of the method. Confidence intervals of the estimated concordance between clinical samples was computed via. Clopper-Pearson method for binomial proportions. Specifically, we used the closed-form expression of the said method for 100% observed success rate.

Discussion

Kidney transplantation, pioneered in 1954 at Brigham hospital, has resulted in a dramatic improvement in the quality of life for patients with kidney failure. Introduction of several generations of immunosuppressive treatments has brought down the rejection rate, however, it remains unacceptably high at about 5% per year, with more than half of allografts failing by year ten. Early detection of rejection in kidney transplant recipients holds the promise to improve this further but remains an unmet need due to non-availability of sensitive and non-invasive diagnostic kits. To diagnose acute renal transplant rejection, measurement of renal filtration function is most commonly recommended through a serum creatinine test. Although the serum creatinine test is an inexpensive test for transplant rejection, detecting transplant rejection by measuring serum creatinine has physiologic limitations and is highly imprecise. The most definitive diagnosis of renal allograft dysfunction thus relies on the histopathological evaluation of a percutaneous ultrasound-guided biopsy, which is invasive and can lead to major/minor complications such as bleeding. In addition, the interobserver variability impedes the reliability of biopsies. Given the existing limitations with current methods, there remain a medical need for improved methods for detecting transplant rejection that are non-invasive, inexpensive, sensitive, specific, and have a rapid turnaround. The present disclosure provided a strong case for dd-cfDNA, as a biomarker to monitor health of renal transplant that fulfilled this need.

The present disclosure addressed the analytical validity of the donor fraction quantification method used in Sigdel et al. 2018. The clinical interpretation described in Sigdel et al. 2018 classified a patient as having increased risk of organ rejection when the donor fraction is greater than 1%. Thus, the analytical performance described herein should be interpreted in the context of accurately classifying a sample with respect to that threshold. From that perspective, we observe that the LoD and LoQ are 0.15% for unrelated donors and 0.29% for related donors based on an LoQ definition of 20% CV, implying ability to accurately quantify donor fraction at a level significantly lower than the classification threshold. These measurements were based on cell line-derived reference samples and performance was estimated to be equivalent or superior using a smaller number of plasma-derived cfDNA samples. Similarly, the method was confirmed to have high accuracy based on linear regression with respect to an orthogonal measurement, with linear regression parameter confidence intervals including slope equal to one and intercept equal to zero, based on 349 related and 285 unrelated measurements. Performance was evaluated with respect to a range of DNA input mass, which did not drive any consistently detectable performance difference over the tested range from 15 ng to 45 ng. Precision studies showed that the donor fraction measurement was stable across in-run and cross-run replicates, across multiple lots of critical reagents, and between repeat (concurrent) blood draws from the same patient. Accordingly, this study indicated that the test was appropriate for clinical implementation.

The present study was designed to assess performance independently in related versus independent donors due to concern that the higher rate of genotype concordance (implying lower rate of informative genotypes) in a related donor scenario might limit the accuracy of the donor fraction estimate. This was tested using a large number of replicates of a mother-child cell line-derived donor pair along with smaller number of replicates from plasma-derived DNA from other subject pairs with relationships including siblings and lesser degree of relatedness. We observed that LoB was higher in related donor pairs, which led to correspondingly higher LoD. However, all of the other metrics including linearity and the various precision metrics were equivalent between related and unrelated donor pairs, showing that the quantitative performance of the test was not meaningfully impacted by the reduced number of informative genotypes, based on confirmation from a variety of contrived samples. This statistical approach was also superior to a probability-based approach for modeling donor genotypes, because the statistical approach does not have to make any assumptions about the fraction of SNPs in which the donor has one allele versus two alleles different from the recipient.

Multiple ongoing registry studies are expected to demonstrate clinical utility for the dd-cfDNA assay, for example, it is expected to lead to more effective use of biopsy. As dd-cfDNA is a marker indicating ongoing allograft injury, as opposed to creatinine which is a lagging indicator showing decreased functioning, it is expected to lead to earlier detection of kidney rejection. Earlier detection allows more rapid intervention in the case of rejection, possibly leading to lower de novo DSA levels, less allograft damage, and improved graft survival rates. Additionally, it may give nephrologists a tool that would allow them to better optimize immunosuppressive regimens, with the goal of minimizing immunosuppressant-related toxicity without an increase in the rate of rejection.

Example 4. KidneyScan

Introduction

With 20-30% of transplanted kidneys failing within five years and only 55% survive to ten years, the limitations of current standard-of-care for monitoring renal allograft rejection are severe and costly. The cost associated with a failed renal transplant patient may be 500% more than a patient with a functioning transplant. As such, there is a clear need for timely, sensitive, specific, non-invasive diagnostic tools to improve kidney transplant management. Applicant has created an assay, KidneyScan, that aids physicians in detecting rejection events earlier, avoiding unnecessary biopsies and more safely optimizing immunosuppression levels to increase kidney graft survival rates.

KidneyScan is a non-invasive blood test validated for first-time kidney allograft recipients >18 years of age at a minimum of two weeks post-transplant across ethnicities. The assay is to be used upon physician-assessed pretest to further assess the probability of active renal allograft rejection. A step before new biopsy, KidneyScan may help appropriately rule in rejection when patient otherwise appears stable and suspicion is unclear; or appropriately rule out rejection when patient presents with a clinical risk of rejection.

The single-nucleotide polymorphism (SNP)-based massively multiplexed PCR (mmPCR) assay targets 13,926 SNPs to accurately detect allograft rejection/injury without the need for donor genotypes. Leveraging a proven biomarker and an established methodology, the SNP-based dd-cfDNA assay identifies active rejection by measuring the fraction of donor derived cell-free DNA (dd-cfDNA) in the patient's blood, a mixture of donor and recipient cell-free DNA. Because cells release dd-cfDNA upon graft injury or death, a higher dd-cfDNA fraction indicates a higher likelihood of active rejection.

In a recent blinded, large scale prospective study of 217 biopsy-matched renal allograft samples, a retrospective analysis of the SNP-based dd-cfDNA assay demonstrated superior accuracy in detecting active rejection over current standard of care (eGFR and serum creatinine) with high sensitivity (88.7% vs. 67.7% vs. 51.6%), specificity (72.6% vs. 65.3% vs. 67.5%) and AUC (0.87 vs. 0.74 vs. 0.68). Additionally, the SNP-based dd-cfDNA assay distinguished acute rejection from each non-rejection (borderline injury, other injury and stable) significantly better than eGFR ($P<0.0001$ for each). These findings established dd-cfDNA as an earlier, more accurate biomarker for active rejection than the standard-of-care that can be used prior to the deterioration of renal function. Acknowledged by the KDIGO guidelines, "detecting kidney allograft dysfunction as soon as possible will allow timely diagnosis and treatment".

Furthermore, the SNP-based dd-cfDNA assay accurately identified a broad distribution of rejection types (antibody-mediated rejection, T-cell mediated rejection and combination) from non-rejection at the predefined cut-off of >1%. This distribution encompasses the leading causes of allograft failure occurring in 20-25% of patients in the first 12-24 months and are missed through current standard of care tools. Incorporating the SNP-based dd-cfDNA assay into transplant assessment protocols may lead to timely detection of rejection and earlier tailored immunosuppression treatments. KidneyScan offers physicians the clinical advantage of identifying active rejection (including subclinical) earlier, comprehensively and non-invasively to ultimately improve the care of kidney transplant patients.

Background

Chronic kidney disease (CKD), a worldwide health burden, affects 10% of global population and results in adverse outcomes such as kidney failure, cardiovascular disease and premature death. Approximately, 15% (30 million) of adults in the United States are estimated to have CKD with close to 1 million persons having end stage renal disease (ESRD). Lifestyle diseases such as diabetes, atherosclerosis and hypertension related to the aging society have led to an increased prevalence of ESRD.

Kidney Transplantation

Kidney transplantation is a preferred treatment for ESRD and is associated with lower morbidity, mortality, improved quality of life and is cost effective when compared to renal replacement therapy. However, according to the 2018 annual report published by United States of Renal System, in 2016, 70.1% of patients with ESRD were being treated with dialysis, and only 29.6% had a functioning kidney transplant. The annual US Medicare spending for combined for CKD and ESRD exceeded $114 billion with a yearly per-patient cost of approximately $90,971 for hemodialysis and $34,780 for kidney transplant in 2016. At present, more than 19,000 kidney transplants are performed in the US annually, resulting in approximately 200,000 patients living with a functioning kidney.

Challenges and Unmet Need

Although kidney transplantation is a treatment of choice over dialysis, it poses a unique set of challenges, wherein the patient is maintained on life-long immunosuppressive regimens. Approximately 20-30% of patients, posttransplant, experience overall renal graft failure within first 5 years and only 55% of transplanted kidneys survive to 10 years. Kidney allograft rejection diagnosed pathologically is categorized into T-cell and antibody mediated rejection (TCMR/ABMR), based on Banff 2013 schema. Therapeutic strategies focusing on improving graft survival outcomes primarily relate to the reduction in the incidence and consequence of TCMR but not ABMR. Despite advances in immunosuppression therapies and desensitization techniques, the long-term graft survival depends on ABO or Human leukocyte antigens (HLA) compatibility, with the latter being identified as a significant risk factor for developing ABMR, ultimately leading to allograft loss. ABMR is a continuous process that can occur at different time points, leading to acute and chronic damage. With the advances in therapeutic strategies, acute renal dysfunction can be reversed but cannot eliminate donor specific anti-HLA antibodies being secreted from plasma cells, originating from spleen and bone marrow that lead to a slowly progressive form of ABMR, referred as subclinical ABMR that can only be diagnosed through protocol biopsies. Another major factor that impacts the long-term allograft health of transplant recipients are a variety of viral infections such as, cytomegalovirus, Epstein Barr virus, or BK virus, which are caused by chronic immunosuppression. With the above-mentioned clinical challenges, it is evident that a need exists for an efficient posttransplant, standard-of-care that can bring precision medicine with personalized tailoring of immunosuppressive drug regimens in order to improve the management of kidney transplant.

Current Standard-of-Care and Limitations

Current standard-of-care options to monitor kidney health in transplant recipients include protocol (or surveillance) biopsies as well as assessing dynamic changes in serum creatinine and other parameters, such as proteinuria and levels of immunosuppressive drugs. Although protocol biopsies are considered the "gold standard", their clinical utility is significantly limited due to invasiveness, cost, inadequate sampling, and poor reproducibility. In addition, protocol biopsies may be contraindicated in patients with uncontrolled hypertension, renal vascular anomalies, anticoagulant use and acute pyelonephritis. In order to diagnose acute renal transplant rejection, measurement of renal filtration function is most commonly recommended through a serum creatinine test or its algorithmic derivative: estimated glomerular filtration rate (eGFR). Although inexpensive, serum creatinine is highly imprecise due to its low sensitivity and specificity and has physiologic limitations (it is influenced by diet, muscle mass, medications such as trimethoprim and cimetidine, and new/recurrence of a disease). Moreover, creatinine is a lagging indicator of renal injury; by the time serum creatinine levels increase, the allograft has already undergone severe and irreversible damage.

The limitations of current standard-of-care expose an unmet need for a rapid, accurate, and noninvasive approach to detect allograft rejection and/or injury, which may require integration of the current "gold" standard morphological assessments with modern molecular diagnostic tools.

Donor-Derived Cell-Free DNA (dd-cfDNA)—Noninvasive Biomarker

Donor-derived cell-free DNA (dd-cfDNA), detectable noninvasively in the plasma of transplant patients, is a proven non-invasive biomarker for kidney transplant rejection, and holds promise for producing faster and more quantitative results compared with current treatment options. With a short half-life of cfDNA (<1 hr) in blood, it provides an opportunity for rapid, dynamic assessment and potentially early diagnosis of allograft health. Specifically, it has the potential to improve the use of protocol biopsies, i.e. reduce unnecessary biopsy. In addition, propose a possible need for a biopsy in patients with subclinical rejection who appear to be clinically stable thereby, facilitating personalization of treatment regimens for an optimal outcome.

Applicant has an established, long-standing expertise in dd-cfDNA domain ranging from reproductive health to oncology, and are looking forward to applying this technology to help nephrologists better care for their renal transplant patients. The following sections present a detailed overview of KidneyScan, Applicant's SNP-based dd-cfDNA technology, followed by a description of our analytical and clinical validation of the assay.

Sample Processing and Sequencing

Applicant's transplant test measures the fraction of donor derived cell-free DNA (ddcfDNA) in total cell-free DNA (cfDNA) derived from blood plasma of transplant patients. The method is described in and has since included minor updates for compatibility with Applicant's CLIA lab, such as changing from HiSeq to NextSeq sequencer. The plasma workflow includes cfDNA extraction using Applicant's in-house proprietary chemistry, library amplification, and amplification of a set of single nucleotide polymorphism (SNP) loci using targeted massively multiplex PCR. Donor fraction is estimated using thousands of SNPs located on chromosomes 2, 13, 18 and 21. The SNPs were selected for high minor allele frequency across multiple ethnicities based on a large reference dataset. High throughput sequencing is performed on Illumina NextSeq, followed by demultiplexing and mapping to the human reference genome. The donor fraction estimate is based on the allele ratios observed at the targeted SNP locations.

Donor Fraction Calculation

Donor fraction is calculated from the set of SNPs where the recipient is homozygous, with genotype either RR (homozygous reference allele) or MM (homozygous mutant allele). The general principle is that when the recipient has genotype RR and the donor has genotype RM, the observed fraction of M allele corresponds to half the donor fraction. When the recipient has genotype RR and the donor has genotype MM, the observed fraction of M allele corresponds to the full donor fraction. When the recipient and host both have genotype RR the SNP does not inform the estimate. The set of genotype combinations where the recipient is MM is interpreted in the same way.

The mathematical approach is a maximum likelihood estimate over a fixed search range, combining data from recipient-homozygous SNPs. The data likelihood is calculated for each candidate donor fraction and the donor fraction estimate is the candidate value that produces the maximum data likelihood. This can be interpreted as choosing the candidate value which best explains the observed sequencing data according to a mathematical model. Donor genotype estimates are incorporated into the data likelihood calculation based on their prior (population-based) probabilities and the observed data. This method does not require any heuristic adjustment factors for varying degrees of recipient-donor relationship. However, when there is a relationship (indicated on the test requisition form) we constrain the genotype prior probabilities to reflect the required genotype concordance.

Summary of Analytical Performance

Analytical performance was assessed according to CLSI guidelines. All of the analytical performance results including accuracy, limit of quantitation and precision were satisfactory in the context of the proposed clinical use. We highlight two important findings from our analytical performance studies: (1) Performance of the assay in related and unrelated donor/recipient pairs given that 10-15% of renal allografts involve highly related individuals; (2) Comparison of performance to another commercially available dd-cfDNA assay which has received a positive limited coverage decision (LCD) from MolDx Analytical Performance in Related VS Unrelated Samples SNP-based donor fraction estimates depend on differences between the recipient and host genotypes. Variations from the expected rates of different host-vs-donor genotype pairs may impact the accuracy of the estimate and methods using insufficient number of SNP measurements are especially susceptible to these risks. KidneyScan's use of probabilistic genotype modeling combined with thousands of SNP measurements enables equivalent performance in related versus unrelated donor scenarios, confirmed by testing on mixture samples created from related individuals. KidneyScan achieves equivalent accuracy and precision for related versus unrelated donors; the only difference in performance is in the LoB, leading to corresponding (minimal) difference in LoD and LoQ, which all remain far from the classification threshold.

Comparison of KidneyScan Analytical Performance to Other dd-cfDNA Assays

KidneyScan analytical performance was compared to a commercially available dd-cfDNA assay with analytical performance described in Grskovic et al, 2016. FIG. 40 shows similarly high quality accuracy assessment data for the two assays, both comparing to digital droplet PCR as the orthogonal reference measurement. KidneyScan is accurate with respect to the reference measurement, indicated by a linear fit with slope approximately 1, intercept approximately zero, and R-squared approximately one.

KidneyScan has analytical limits (LoB, LoD, LoQ) similar to the previously published assay. Additionally, none of the relevant limits are close to the classification threshold at 1%, which implies that they will not limit clinical accuracy. Additionally, KidneyScan has better repeatability (5 fold) and inter-run precision (2.3 fold) as measured by CV near the classification threshold. Table 14 shows performance for unrelated donors because the Grskovic study did not directly assess performance in the case of related donors, but rather addressed this scenario using in silico adjustment from measurements of unrelated donors.

TABLE 14

Comparison of KidneyScan and Grskovic dd-cfDNA assay key performance metrics

| | KidneyScan | Bloom et al [Grskovic et al, 2016] |
|---|---|---|
| Limit of Blank (%) | 0.11 | 0.10 |
| Limit of Detection (%) | 0.15 | 0.15 |
| Limit of Quantitation (%) | 0.15 | 0.20 |
| Repeatability (within run) at 0.6% donor fraction (CV) | 1.85 | 9.2 |
| Inter-run precision (CV) | 1.99 | 4.5 |

Clinical Validity

Our assay has been shown to identify all types of active rejection (AR) with greater sensitivity and specificity than serum creatinine or estimated glomerular filtration rate (eGFR), the current standard of care. This performance validation underscores the assay's potential use as (1) a better tool for the early, non-invasive identification of AR; (2) avoidance of biopsy when it is unnecessary (no actionable finding) or contraindicated; and (3) personalization of immunosuppression therapy. In brief, this section includes a short description of the clinical validation that has been conducted as well as discussion of five performance aspects by which this test was clinically evaluated:

89% sensitivity and 73% specificity for detection of AR
High accuracy in detecting subclinical rejection with 92% sensitivity
More reliable than SCr and eGFR for detection of AR
Test performance independent of rejection type, including ABMR and TCMR
Test performance independent of donor type, including living/deceased and related/unrelated
Test performance was validated in a population with broad diversity of age and ethnicity. This is a clinically significant advantage of our study vs. Bloom et al, 2017, whose patient population was less diverse. Graft survival and patient management are known to vary by ethnicity, for example, the eGFR metric is calculated based on serum creatinine (SCr), with adjustment for age, sex and ethnicity.

89% Sensitivity and 73% Specificity for Detection of AR

A comparison of Applicant's dd-cfDNA test, the dd-cfDNA test described in Bloom et al, 2017, and eGFR shows the superiority of dd-cfDNA compared with the current standard (Table 15). It also shows higher sensitivity, AUC, and NPV of Applicant's dd-cfDNA assay compared with Bloom, indicating performance of Applicant's methods that is as good or better than the one outlined in Bloom.

TABLE 15

Comparison of dd-cfDNA Tests Performance to eGFR

| | Applicant's dd-cfDNA Test | Bloom et al, 2017 | eGFR |
|---|---|---|---|
| Cutoff level for identifying AR | >1% | >1% | <60 |
| | Overall Performance | | |
| Sensitivity | 88.7% (95% confidence interval [CI], 77.7%-99.8%) | 59% (95% CI, 44%-74%) | 67.8% (95% CI, 51.3%-84.2%) |
| Specificity | 72.6% (95% CI, 65.4%-79.8%) | 85% (95% CI, 79%-91%) | 65.3% (95% CI, 57.6%-73.0%) |
| AUC | 0.87 (95% CI, 0.80-0.95) | 0.74 (95% CI, 0.61-0.86) | 0.74 (95% CI, 0.66-0.83) |
| PPV* | 52.0% (95% CI, 44.7%-59.2%) | 57% | 39.4% (95% CI, 31.6%-47.3%) |
| NPV* | 95.1% (95% CI, 90.5%-99.7%) | 86% | 85.9% (95% CI, 75.9%-92.2%) |

TABLE 15-continued

Comparison of dd-cfDNA Tests Performance to eGFR

|  | Applicant's dd-cfDNA Test | Bloom et al, 2017 | eGFR |
| --- | --- | --- | --- |
| PPV† | 36.4% (95% CI, 29.6%-43.1%) | 41% | 25.6% (95% CI, 19.4%-31.9%) |
| NPV† | 97.3% (95% CI, 94.8%-99.9%) | 92% | 92.0% (95% CI, 88.1%-95.8%) |

*Assumes a 25% prevalence of rejection (at-risk population)
†Assumes a 15% prevalence of rejection (lower risk population)

High Accuracy in Detecting Subclinical Rejection with 92% Sensitivity

Figure 41:
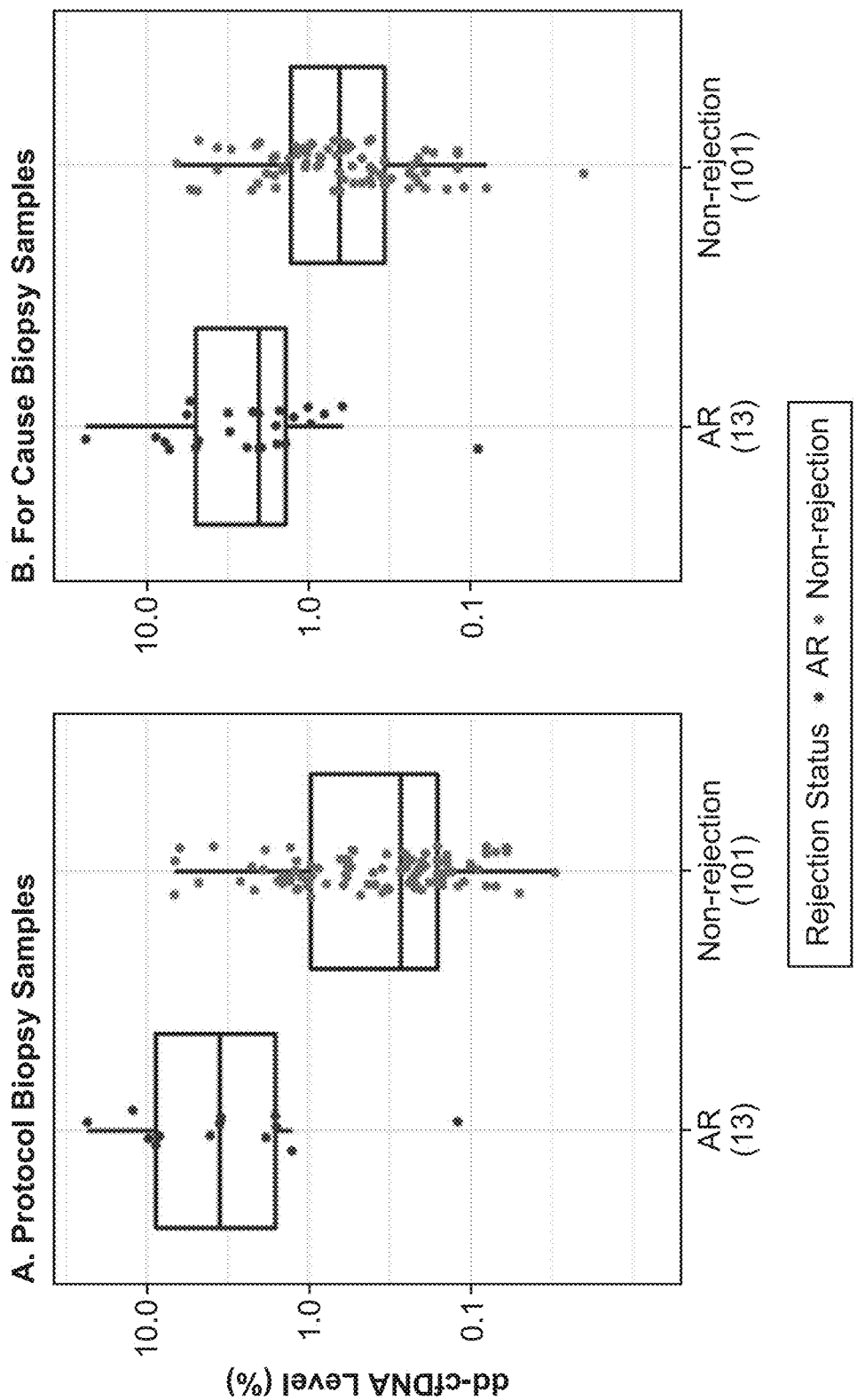
FIG. 41: Discrimination of active rejection by dd-cfDNA in biopsy-matched samples (data stratified by biopsy type). Boxes indicate inter-quartile range, horizontal lines represent medians.

FIG. 41 shows assay performance for the subset of samples drawn at the time of a for-cause biopsy and protocol biopsy; performance shown in protocol biopsies is expected to reflect performance when the assay is used in routine surveillance, that is, when there are no signs of renal injury. This cohort of 114 samples showed detection of AR with:
  92.3% sensitivity (95% CI, 64.0%-99.8%)
  75.2% specificity (95% CI, 65.7%-83.3%)
  0.89 area under the curve (AUC) (95% CI, 0.76-0.99)

Based on a 25% prevalence of rejection in an at-risk population, the following value projections could be made:
  Positive predictive value (PPV) of 55.4% (95% CI, 46.2%-64.7%)
  Negative predictive value (NPV) of 96.7% (95% CI, 90.6%-99.9%)

More Reliable than SCr and eGFR for Detection of AR

Figure 42:
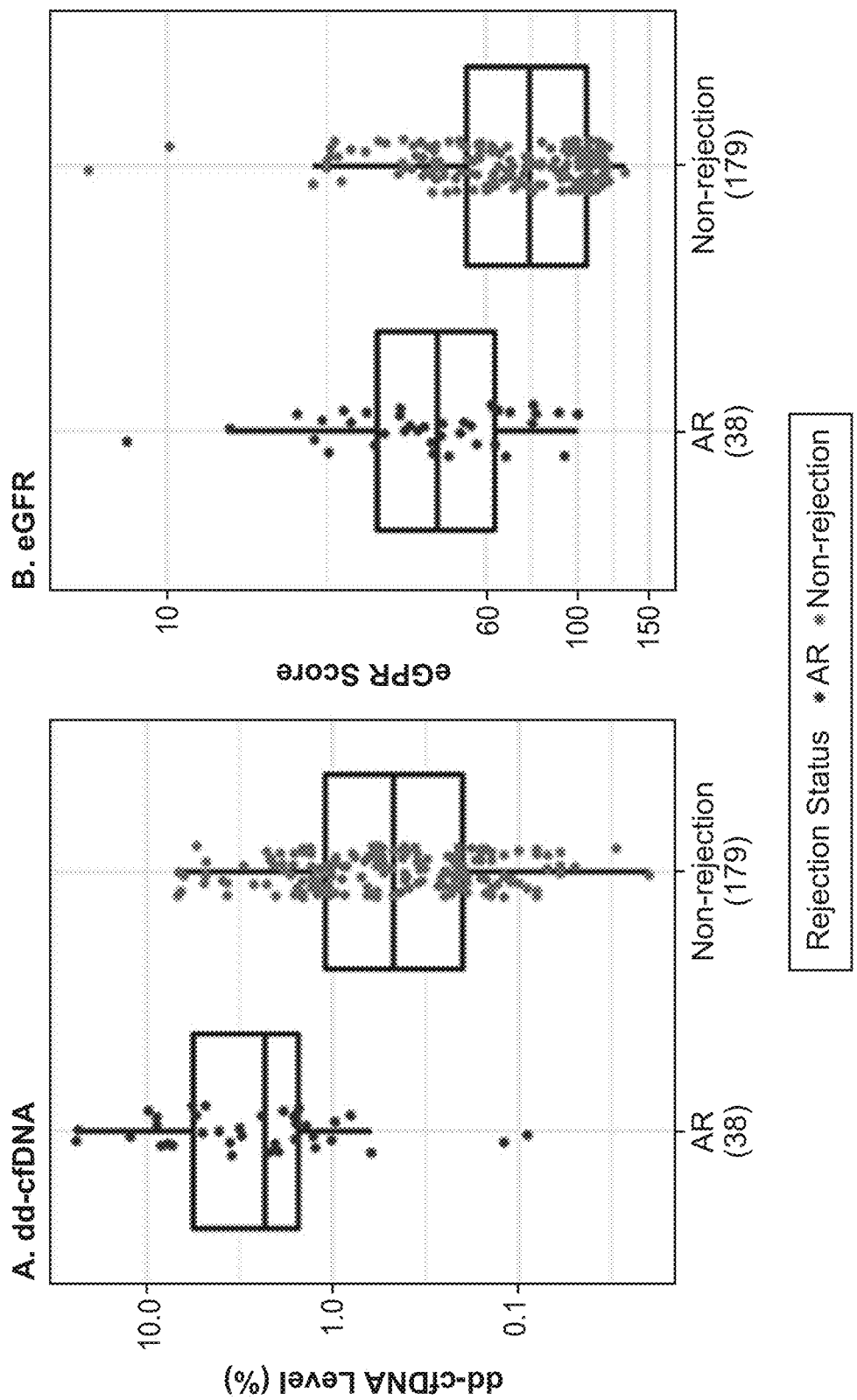
FIG. 42: Discrimination of active rejection by dd-cfDNA (A) versus eGFR (B). Boxes indicate interquartile range ($25^{th}$ to $75^{th}$ percentile); horizontal lines in boxes represent medians; dots indicate outliers >1.5 dines the upper quartile value. P-values for dd-CfDNA and eGFR, using Kruskal-Wallis rank sum test indicate a significant difference between the medians of the AR and non-rejection groups for both markers

The data showed that Applicants assay distinguishes accurately between AR vs. non-AR grafts, with the fraction of dd-cfDNA significantly higher in the circulating plasma of the AR group (median=2.32%) than the non-rejection group (median=0.47%; P<0.0001) (FIG. 42). In contrast to dd-cfDNA, eGFR scores did not have as much discriminatory ability for differentiating AR and individual non-rejection groups.

TABLE 16

Summary Statistics for dd-cfDNA and eGFR Tests

| Parameter | Active Rejection | Non-Rejection |
| --- | --- | --- |
| dd-cfDNA | | |
| Number of samples | 38 | 179 (82.5) |
| Mean (SD), % | 4.64 (5.45) | 0.92 (1.28) |
| Median, (Range), % | 2.32 (0.1-23.9) | 0.47 (0.04-6.78) |
| eGFR | | |
| Number of samples | 38 | 179 (82.5) |
| Mean (SD), score | 49.0 (22.3) | 77.0 (8.45) |
| Median, (Range), score | 45.67 (8.0-100.4) | 76.06 (6.4-131.1) |

*One sample had missing weight information needed to calculate eGFR.

Test Performance Independent of Rejection Type, Including ABMR and TCMR

Figure 43:
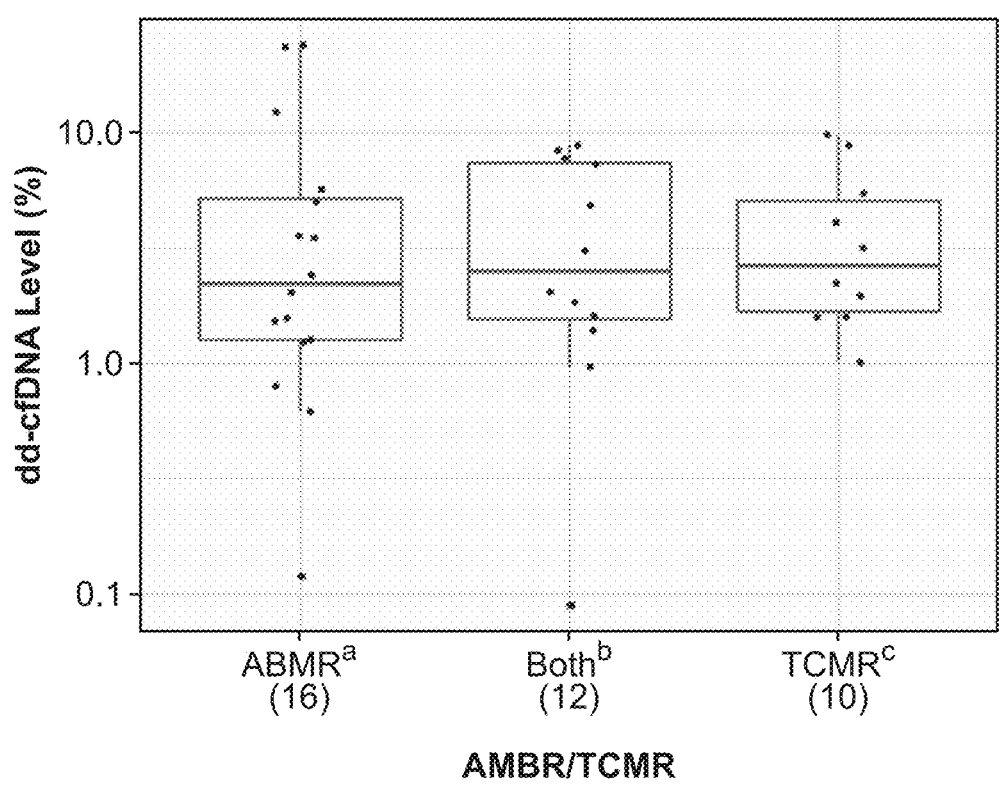
FIG. 43: dd-cfDNA as a function of antibody-mediated versus T-cell-mediated rejection. Boxes indicate inter-quartile range ($25^{th}$ to $75^{th}$ percentile); horizontal lines in boxes represent medians; dots indicate all individual data points, P-values for del-cfDNA adjusted using Kruskal-Wallis rank sum test followed by Dunn multiple comparison tests with Holm correction. $^a$Samples assigned ABMR and bTCMR, $^b$Samples assign ABMR and TCMR. $^c$Samples assigned TCMR and bABMR. ABMR, antibody-mediated rejection; b, borderline; TCMR, T-cell-mediated rejection.

FIG. 43 shows the relationship between dd-cfDNA level and type of rejection. Median dd-cfDNA did not differ significantly between AMBR (2.2%), ABMR/TCMR (2.6%), or TCMR (2.7%) groups (P=0.855). The study contained a range of pathologies, and the data indicate that this assay is robust to all different types of active rejection.

Figure 44:
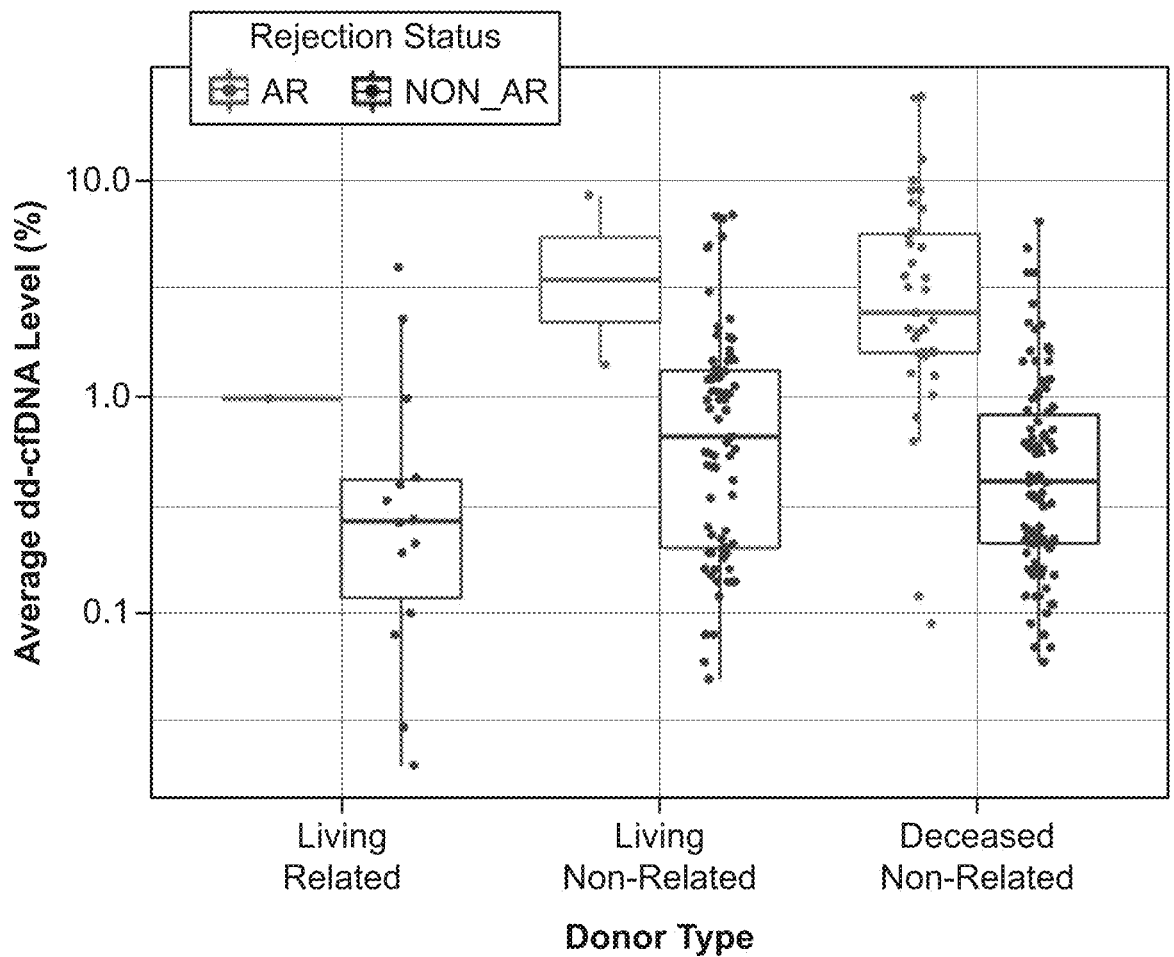
FIG. 44: Relationship between dd-cfDNA and donor type. No significant difference by donor type was observed (P>0.46). P-values for dd-cfDNA adjusted using Kruskal-Wallis rank sum test followed by Dunn multiple comparison tests with Holm correction.

These results are novel considering that a previously conducted study by Bloom, et al., 2017, which used a different assay, demonstrated an inability to differentiate TCMR from STA. That study found significantly lower dd-cfDNA levels for TCMR (≤1.2%) than for ABMR (2.9%). This is a clinically significant finding that differentiates Applicant's assay and supports expanded clinical utility relative to currently available tests on the market Test Performance Independent of Donor Type, Including Living/Deceased and Related/Unrelated Given the design of the assay used here, it is possible to quantify dd-cfDNA without prior recipient or donor genotyping. There was no significant difference among the dd-cfDNA level medians between any of the non-rejection donor groups; though the AR groups appeared similar between the donor groups, there were not enough samples to make a statistical comparison (FIG. 44). Evaluation of dd-cfDNA levels by donor type revealed that regardless of donor type (living related, living non-related, deceased non-related), dd-cfDNA levels were similar across all donor types within in the AR and non-rejection categories.

In conclusion, this rapid, accurate, and noninvasive technology allows for detection of clinically impactful renal injury in patients better than the current standard of care, with the potential for better patient management, more targeted biopsies, and improved renal allograft function and survival.

Example 5. Clinical Utility

The clinical utility of early detection and treatment of active allograft rejection is well-established. We have previously outlined the limitations of existing diagnostic tools for detecting active rejection, and the need for a test that is both sensitive and non-invasive. Our dd-cfDNA assay meets this need, with utility to be measured in terms of:
  Fewer unnecessary biopsies (where there is no AR diagnosis)
  More frequent detection of subclinical AR
  More targeted and personalized use of immunosuppression therapy. This change will likely take more time to observe than the change in biopsy use, since physicians may be slower to adjust their immunosuppression treatment patterns than their biopsy decisions.

How the Test Will be Used in Practice

We recommend clinical use of the test by physicians whenever there is a suspicion of rejection, to help rule-in and rule-out active rejection, to inform the need for a diagnostic biopsy, and to inform treatment decisions when a biopsy is contraindicated. Incidence of AR is highest in the first 12 months post-transplant, so we anticipate more frequent use in that period, and then less frequent use after 12 months post-transplant.

Turnaround time of test results will be as fast as 3 calendar days from specimen receipt in the laboratory. We are highly confident in our laboratory's ability to process these specimens with speed and quality, as we already process >1000 cfDNA tests on a daily basis for OBGYN physicians to support care for their pregnant patients.

Test results will include the observed dd-cfDNA level (a.k.a. "Donor fraction"), a clear communication of whether this falls above or below the predetermined cutoff of 1%, a summary statement indicating high or low risk of rejection, and the post-test risk of rejection estimated using a background AR prevalence of 25%.

How the Test Will Change Physician Decision-Making

There are many cases when physicians suspect active rejection but are uncertain, leading to missed diagnoses as well as unnecessary biopsies.

In cases of stable SCr and donor fraction >1%, we believe physicians will switch their decision from observation to biopsy, to catch subclinical rejection and begin treatment.

In cases of moderately elevated SCr and donor fraction <<1%, we believe physicians will often switch their decision from biopsy to observation, and will seek other explanations for decreased kidney function besides active rejection. It is well-established that SCr will often return to normal levels without any additional treatment.

In cases of severely elevated SCr (such as SCr>2.5), we believe physicians will pursue diagnostic biopsy without waiting for the dd-cfDNA result.

In the Sigdel et al. 2017 study, 76% of clinically indicated biopsies (for-cause) and 89% of surveillance/protocol biopsies did not result in a diagnosis of active rejection, implying that the biopsies were unnecessary. With overall test specificity of 73%, if physicians made clinical decisions based solely on the dd-cfDNA test result, then 73% of the unnecessary biopsies could have been avoided. However, we anticipate that physicians will incorporate dd-cfDNA result as one among several factors in the biopsy decision, not the sole factor. Therefore, we hypothesize that a significant portion of these unnecessary biopsies will be avoided, perhaps 40-50%. This hypothesis will be evaluated in prospective outcomes studies, as described below.

Renal transplant recipients are fundamentally a high-risk population with ESRD, the unmet need is high, and the test performance is strong. The outcomes study is designed to answer the question of how much clinical practice will change, not whether it will change.

Clinical Advantage: Identifying Active Rejection and Subclinical Rejection

The immunological processes that lead to renal allograft rejection are heterogeneous, caused by humoral and cellular immune responses. In addition to ABMR and TCMR, which are the leading cause of allograft failure, subclinical rejection is also associated with chronic allograft nephropathy. Subclinical rejection, defined as histologically-proven acute rejection is considered the most common cause of late renal allograft failure, occurring in 20-25% of patients in the first 12-24 months. The likelihood of subclinical rejection depends on the time after transplantation, prior acute rejection, HLA mismatch and immunosuppression. A study showed patients with subclinical rejection had lower graft survival rates than patients with normal or borderline changes at 1, 5, and 10 years.

Timely treatment of subclinical rejection has potential to change the long-term therapeutic outcome of renal transplant health as evidenced by a study that showed treatment of subclinical rejection led to reduction in early (months 2 and 3) and late (>6 months) clinical rejections, a lower chronic tubulointerstitial score at 6 months, and better graft function at 2 yr. The major limitation with the treatment of subclinical rejection is that the high proportion of the cases remain unrecognized due to limited sensitivity of current standard-of-care, which in turn require surveillance biopsy for a definite diagnosis. Thus, early detection techniques, such as dd-cfDNA testing has potential to non-invasively detect the possibility of subclinical rejection, thereby facilitating better treatment outcomes and increase graft survival rates.

Patient Risk Stratification and Utility of dd-cfDNA

Recipients of kidney transplant represent a heterogeneous population with varying risk of rejection and infection based on patient subgroups. Below are some of the factors that collectively influence a clinician's classification of patient risk for rejection De novo donor-specific antibody (dnDSA) formation
Interstitial fibrosis and tubular atrophy (IF/TA)
Delayed allograft function
Panel reactive antibody (PRA)>30%
Inadequate immunosuppressive therapy
Calcineurin inhibitor nephrotoxicity
Underlying disease
Deceased donor
Younger recipient age
Older donor age
African American ethnicity
Cold ischemia time >24 hours
HLA mismatch
ABO incompatibility The treatment regimen for each patient is highly variable and depends on the risk-category. At present no clear guidelines exist that can stratify patients into different risk-groups. In general, patients with a higher risk for rejection are monitored more closely and their management is handled solely at the physician's discretion. This leads to high variability with non-optimal outcomes in many situations. Applicant's methods can be highly effective at addressing this unmet need, wherein dd-cfDNA can optimize and enable physicians to take a well-informed decision by stratifying patients into risk groups, improve treatment variability, and avoid unnecessary biopsies.

In addition to increasing the likelihood of long-term graft survival, early detection of active injury by dd-cfDNA has other potential benefits. An accurate dd-cfDNA assay can help physicians manage renal allograft health by maintaining a minimally effective dose of immunosuppressives to prevent rejection, while avoiding their associated complications, such as:

BK viremia
Increased susceptibility to other infections
Calcineurin inhibitor nephrotoxicity
Increased incidence of cancer Studies examining morbidity and mortality in long-term allograft recipients demonstrate that cardiovascular disease and cancer are the two most common causes of death. Risk stratification models have been proposed to implement individual risk profiles to tailor immunosuppressive and antibacterial treatments. We believe that the test will support accelerated tapering of immunosuppression, for patients who have dd-cfDNA levels consistently <1%.

Supporting Studies Currently Underway

In order to provide additional evidence of the clinical utility of Applicant's dd-cfDNA test, two studies are currently in progress, the results of which will be submitted for peer-reviewed publication.

1. dd-cfDNA Clinical Utility Randomized Controlled Trial
   a. Timeline: Preliminary results expected early 2019
   b. Design: Pre-post, two round controlled trial of care practices in a nationally representative sample of practicing nephrologists. Nephrologists manage virtual patient cases before and after receiving education about dd-cfDNA assay and test results.
   c. Objective(s):
      i. Determine current management protocols and variations in post-transplant management among practicing nephrologists
      ii. Assess impact of novel dd-cfDNA biomarker in patient management
   d. Expected outcome(s):
      i. Nephrologists are highly variable in their ability and approach to assess kidney health and transplant rejection status
      ii. Applicant's transplant rejection test will improve patient management in key use cases, enabling nephrologists to better monitor post-kidney transplant patients' health, and optimize biopsy use and immunosuppressant regimens.
2. dd-cfDNA Registry Study
   a. Timeline: Five years to study read completion, with annual read out.
   b. Design: 1,500 patients tested at 1, 2, 3, 4, 6, 9 and 12 months post-transplant, and quarterly thereafter. Blood also drawn at the time of and one month after for-cause biopsies. Patients followed for three years.
   c. Objective: to show change in clinical practice and improved outcomes
   d. Primary study endpoints:
      i. Precision biopsy usage (% of biopsies resulting in active rejection diagnosis)
      ii. Physician decision-making (with and without cfDNA result)

Summary

The limitations of current standard-of-care for monitoring active/early injury in patients post-kidney transplant impacts long-term graft survival outcome. Medical advances that have improved short-term kidney graft survival rate have not impacted long-term graft survival rates. Furthermore, current literature supports the evidence that subclinical rejection is an underlying cause for adverse clinical outcomes leading to long-term graft failure.

dd-cfDNA is an ideal biomarker to add to post-transplant management of active rejection as it can non-invasively detect early active rejection and subclinical rejection with superior sensitivity and specificity compared to serum creatinine and eGFR. This allows for timely tailoring of immunosuppressive regimen based on the inflammatory status of the graft, providing a more personalized approach to minimizing the incidence of rejection, and the unwanted side effects. Frequent analysis, combined with early detection can improve long-term allograft function and decrease the number of unnecessary biopsies in stable patients.

Example 6. KidneyScan® Donor-Derived Cell-Free DNA Test

Summary of Evidence

In 2016, over 20,000 kidney transplants were performed in the United States. In addition, over 80,000 surgical candidates were on dialysis while they waited for an available kidney. After transplantation, patients are put on immunosuppressant drug therapy and routinely monitored to prolong the survival of the donor kidney. Despite established protocols, allograft survival rates ten years post-transplant are estimated to be as low as 48% for deceased donors and 65% for living donors.

Advances in kidney transplantation and post-transplantation care have continued to improve organ functioning and survival rates over time. While this has been most evident in the successful treatment of acute kidney rejection in the first year post-transplant, success after this time period has remained relatively unchanged for decades (failure rates of 3-5% per year for deceased donor and 2-3% per year for living donor kidneys). Kidney injury, leading to irreversible damage and eventual graft loss, is often asymptomatic for weeks or months, and can be challenging to detect given current standard of care of measuring levels of serum creatinine (SCr) or its algorithmic derivative, estimated glomerular filtration rate (eGFR). Both have significant limitations for early injury detection.

The KidneyScan test detects donor-derived cell-free DNA (dd-cfDNA) in a recipient's blood, which is elevated during active rejection due to increased cell death in the organ. KidneyScan is an effective, non-invasive method of assessing kidney allograft status with better performance than the current standard of care.

KidneyScan Donor-Derived Cell-Free DNA Test Description and Performance

The KidneyScan assay is a cell-free DNA-based, next-generation sequencing assay that analyzes over 13,000 single-nucleotide polymorphisms (SNPs) to accurately quantify the fraction of dd-cfDNA in the transplant recipient's blood, even in related recipient/donor pairs, without separate genotyping of either donor or recipient. The dd-cfDNA fraction in cfDNA can be measured with a turn-around time of 5 days or less; this turnaround time is necessary for the appropriate management of transplant recipients.

The clinical performance of KidneyScan was evaluated in a retrospective analysis of 217 samples from 178 unique transplant recipients whose kidney transplant was performed at the University of California at San Francisco (UCSF) Medical Center. The data showed that the dd-cfDNA levels in patients with active rejection (AR) was significantly higher than patients with stable allograft (STA), borderline (BL), or other injury (04 Importantly, the trend was clear regardless of the type of rejection—antibody mediated rejection (ABMR) or T-cell mediated rejection (TCMR). We believe the elevated dd-cfDNA levels are indicative of ongoing injury to the transplanted organ. We therefore analyzed the ability of the assay to detect AR versus non-rejection, where non-rejection is defined as all specimens that were classified as STA, BL, or M.

The amount of dd-cfDNA was significantly higher in the circulating plasma of the AR group (median=2.32%) compared with the non-rejection group (median=0.47%; $P<0.0001$).

Using a predetermined dd-cfDNA cutoff of 1%, the data showed the KidneyScan assay to have an 88.7% sensitivity (95% confidence interval [CI], 77.7%-99.8%) and 72.6% specificity (95% CI, 65.4%-79.8%) for detection of AR. The area under the curve (AUC) was 0.87 (95% CI, 0.80-0.95). Based on a 25% prevalence of rejection in an at-risk population, the positive predictive value (PPV) was projected to be 52.0% (95% CI, 44.7%-59.2%) and the negative predictive value (NPV) was projected to be 95.1% (95% CI, 90.5%-99.7%).

Furthermore, the KidneyScan assay performance for the subset of 114 samples drawn at the time of a protocol biopsy, which is expected to reflect performance when the assay is used in routine surveillance showed detection of AR with 92.3% sensitivity (95% CI, 64.0%-99.8%), 75.2% specificity (95% CI, 65.7%-83.3%), and a 0.89 area under the curve (AUC) (95% CI, 0.76-0.99). Based on a 25% prevalence of rejection in an at-risk population, the PPV was projected to be 55.4% (95% CI, 46.2%-64.7%) and the NPV was projected to be 96.7% (95% CI, 90.6%-99.9%). These data suggest that application of the KidneyScan assay in a clinical setting could potentially reduce the need for protocol biopsies. It also may be appropriate for use post-rejection to determine whether immunosuppressant dosing has led to clearance of the rejection episode, in place of biopsy.

Median dd-cfDNA did not differ significantly between different types of rejection: AMBR (2.2%), ABMR/TCMR (2.6%), or TCMR (2.7%) groups (P=0.855). These results are novel considering that a previously study, using a different assay, found significantly higher dd-cfDNA levels for ABMR (2.9%) than for TCMR (≤1.2%), indicating an inability to detect T-cell mediated rejections. Though the assay used in that study also measured dd-cfDNA, the methods used by the two assays differ significantly. It is unclear whether that test could not differentiate AR from non-rejection in cases of TCMR or if the result was due to the smaller sample size of that group in that study (n=11). Regardless, the KidneyScan assay can accurately discriminate AR from non-rejection across a range of pathologies, including both acute and chronic findings, in both the ABMR and TCMR groups.

The analytical and clinical performance of the Kidney-Scan assay is summarized below.

General

Intended Use. The KidneyScan test is intended to supplement the evaluation and management of kidney injury and active rejection in patients who have undergone renal transplantation. It can inform decision making along with standard clinical assessments Specimen Type. Plasma collected in Streck Cell-Free DNA BCT® tubes Description Results Accuracy.

Unrelated donor:

Slope=1.0664 (95% CI 0.9416, 1.1912)

Intercept=0.0008 (95% CI −0.0076, 0.0092)

R-squared=0.9997 (95% CI 0.9997, 0.9998)

Related donor:

Slope=1.0333 (95% CI 0.9241, 1.1425)

Intercept=−0.0001 (95% CI −0.0047, 0.0046)

R-squared=0.9989 (95% CI 0.9986, 0.9990)

Accuracy was assessed using linear regression with respect to digital droplet PCR (ddPCR) (for CNV2 using probes specific for chromosome 1 as reference and chromosome Y as unknown) as a reference method. Three cell-line reference mixtures (1 related donor, 2 unrelated donors) at mixture fractions from 0.1% to 15% were run in minimum triplicates at 15, 30, 45 ng input DNA mass. The total number of measurements were 285 unrelated and 349 related.

Intermediate Precision (Inter-Assay Total Variability)

Quantitative:

Mean CV with 15 ng input=3.10% (95% CI 1.58%, 4.37%)

Mean CV with 30 ng input=3.07% (95% CI 1.42%, 4.50%)

Mean CV with 45 ng input=1.99% (95% CI 1.10%, 2.75%)

Qualitative: 100% concordance (95% CI 54.07%, 100%) between replicates of 6 transplant patient samples.

To quantitatively assess inter-run precision, 3 reference panels (2 unrelated, 1 related) with 15, 30, 45 ng input DNA mass at 0.1, 0.3, 0.6, 1.2, 2.4, 5, 10% donor fractions were used. A total of 24 runs (across 23 days) on 17 instruments by different operators using different reagent lots were performed. 15 ng input samples were run with 12 replicates, whereas 30 and 45 ng input samples were run with 6 replicates, resulting in 248, 124, 126 measurements for 15 ng, 30 ng, 45 ng input DNA mass, respectively. To qualitatively assess inter-run precision, 6 transplant patient samples were assayed at variable input (20 mL blood each) in duplicates, resulting in 12 measurements.

Sensitivity-Minimum Input 15 ng minimum input tested in samples where input cfDNA concentration was measured.

Limit of Detection 0.15% unrelated donor 0.29% related donor

Limit of Detection was assessed from 3 cell-line (2 unrelated, 1 related) reference panels at 15, 30, 45 ng input DNA mass, and 16 plasma-derived cfDNA mixtures at variable input mass, at mixture fractions 0.1, 0.3, 0.6%. Samples were run in minimum triplicates by two operators using two reagent lots, for a total of 168 (94 from Lot 1, 74 from Lot 2) and 220 (115 from Lot 1, 105 from Lot 2) measurements for unrelated and related donors, respectively. Samples from each reagent lot were evaluated using each of the two dfe methods, unrelated and related donor. LoD values for each lot and each dfe method are calculated by using the LoB values of the corresponding method. For each method, the final LoD is the maximum of lot 1 and lot 2 LoD values calculated with the corresponding method. Calculations followed the parametric method described in EP17A2.

Lower Limit of Quantitation

Lower limits:

0.15% unrelated donor 0.29% related donor

Lower limit is assessed on the same sample set used for LoD, with a broader range of mixture fractions. Specifically, reference samples were tested at mixture fractions 0.1, 0.3, 0.6, 1.2, 2.4, 5, 10, 15%, and plasma-derived cfDNA mixtures were tested at mixture fractions 0.1, 0.3, 0.6, 1.2, 2.4, 5, 10%. Samples were run in minimum triplicates by two operators using two reagent lots, for a total of 381 (207 from Lot 1, 174 from Lot 2) and 412 (239 from Lot 1, 173 from Lot 2) measurements for unrelated and related donors, respectively. Lower limit is defined as the lowest value of donor fraction at which measurement CV (defined as the measurement standard deviation divided by the mean) is less than 20%. The requirement is satisfied over the entire tested range, for each reagent lot and dfe method, so the lower LoQ is equal to the LoD by constraint that it cannot be less.

Upper Limit of Quantitation

Upper limit of quantitation=15% for unrelated and related donors based on highest value tested.

Reference Range

Reference range defined as 0 to 1% based on previously published and approved technology using same analyte with corresponding patient population [Bromberg et al, 2017].

Interfering Substances

Interference of excess ethanol carry-over and excess EDTA on the multiplex PCR reaction was evaluated using Applicant's cfDNA protocol. Inhibitory effect on mmPCR reaction was observed at ethanol concentration of 5% and higher and EDTA concentration of 10 mM and higher. Visually hemolyzed samples are excluded from processing.

Critical Reagent Shelf-Life and (as Applicable) Open Stability

Real time stability studies were used to establish shelf life of mmPCR primer pool. Manufacturer recommended shelf life is used for reagents acquired from third party vendor (PCR mastermix, library preparation enzymes and buffers, standard primers and NGS reagents for sequencing). Reagent stability is additionally monitored by in-line quality control metrics in every run. Incoming reagent qualification procedures were established for all critical reagents (primer pool, PCR enzymes, library preparation enzymes, standard primers and NGS reagents for sequencing) in the workflow and only pre-qualified reagents, within established expiration dates are used in sample processing.

Specimen Stability: Primary Sample

Primary sample stability was established using retrospective analysis of data derived from Applicant's cfDNA protocol using 227450 samples processed between 1 and 8 days after collection. Data was categorized based on age after sample collection and performance was compared across different time points after collection. The maximum acceptable sample age for blood collected using Streck BCT tubes was established to be 8 days based on the above analysis.

Specimen Stability: Intermediate

Intermediate sample stability for plasma stored at −80° C. and cfDNA libraries stored at −20° C. were established using retrospective data analysis and concordant results of Applicant's cfDNA protocol with original time point. Stability of plasma at −80° C. is 25-27 months; stability of cfDNA library at −20° C. is 26-30 months Clinical Performance: Validity

| Description | Results (with 95% Confidence Intervals if applicable)* | |
| --- | --- | --- |
| Active vs No Rejection | In Protocol Biopsy Cohort | |
| Sensitivity | 88.7% (77.7%-99.8%) | 92.3% (64.0%-99.8%) |
| Specificity | 72.6% (65.4%-79.8%) | 75.2% (65.7%-83.3%) |
| NPV | 95.1% (90.5%-99.7%) | 96.7% (90.6%-99.9%) |
| PPV | 52.0% (44.7%-59.2%) | 55.4% (46.2%-64.7%) |

The amount of dd-cfDNA was significantly higher in the circulating plasma of the AR group (median=2.32%) compared with the non-rejection group (median=0.47%; P<0.0001). Median dd-cfDNA did not differ significantly between different types of rejection: AMBR (2.2%), ABMR/TCMR (2.6%), or TCMR (2.7%) groups (P=0.855). The data demonstrate that the KidneyScan assay can accurately discriminate AR from non-rejection across a range of pathologies, including both acute and chronic findings, in both the ABMR and TCMR groups.

At least 2 weeks post-transplant to allow any renal injury occurring immediately at surgery or as a result of cadaveric origin to resolve itself prior to testing. KidneyScan data is currently equivocal in this timeframe. For this reason, and to be consistent with other commercially-available dd-cfDNA tests, we have adopted this criterion for patient safety and data integrity purposes.

Example 7. Further Technology Description

Sample Processing and Sequencing

Whole blood is collected in Streck Cell-Free DNA BCT (blood collection tubes) and shipped to Applicant's CAP/CLIA laboratory, where they are processed using the following steps.

Patient blood samples are centrifuged to separate plasma from blood cells

Applicant's in-house proprietary extraction chemistry is used for cfDNA extraction from plasma Extracted cfDNA is subsequently made into a library by ligation of adapters followed by PCR amplification to increase the total available cfDNA The selected set of thousands of SNP loci are amplified by targeted massively multiplex PCR (mmPCR)

Amplified samples are barcoded, multiplexed and sequenced using NGS technology (Illumina NextSeq, 50 cycle SE reads)

Figure 45:
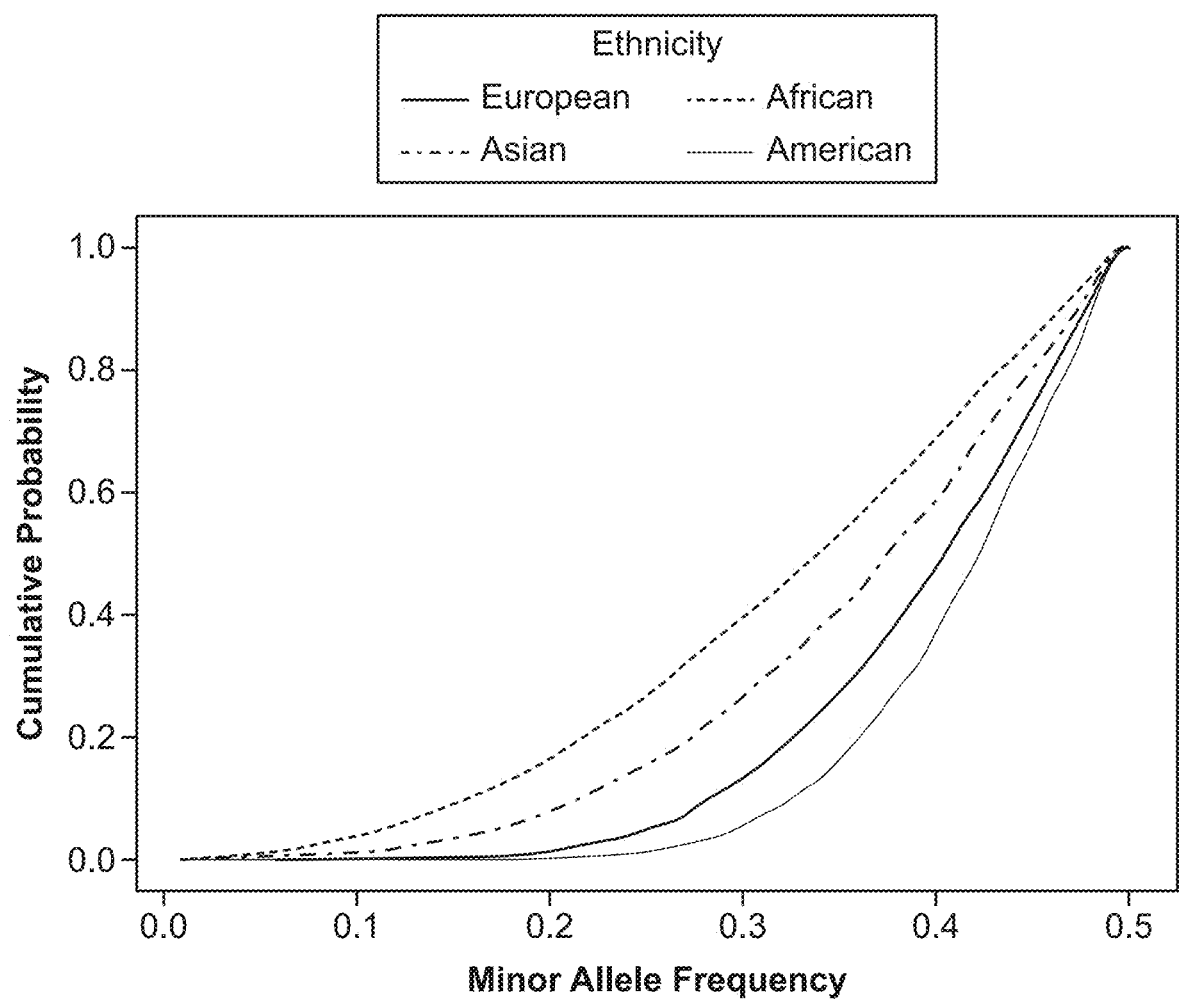
FIG. 45: Cumulative distributions of SNP minor allele frequency according to ethnicity.

The mmPCR protocol uses Applicant's proprietary chemistry and amplification conditions to achieve uniform amplification across the target set and at the same time maintaining an extremely low PCR introduced error rate. The application of a similar mmPCR approach to non-invasive prenatal testing has been published in multiple studies and resulted in over one million patient test results. The SNPs were selected for high variant allele frequency across different ethnicities (FIG. 45). The PCR amplicons are barcoded to enable sample level multiplexing and barcoded samples are pooled and then sequenced using Illumina NextSeq instrument, 50 cycles, single end reads. FIG. 45 shows cumulative distributions of SNP minor allele frequency according to ethnicity Sequencing Analysis Sequenced reads are demultiplexed and mapped to the standardized human reference genome (hg19) using Novoalign version 2.3.4. Bases are filtered based on Phred quality score and reads are filtered based on mapping quality score. Multiple quality checks on metrics such as cluster density and mapping rate are applied to the sequencing run and each sample is confirmed to have obtained the minimum required number of reads after filtering.

From each sequence read we extract only the allele observed at the targeted SNP position. The allele is labeled as reference or mutant following the definitions in the hg19 reference genome and all following calculations are based on the set of reference and mutant allele counts. At each SNP, the fraction of reference counts compared to the total is defined as the SNP's allele ratio.

Donor Fraction Calculation

Figure 46:
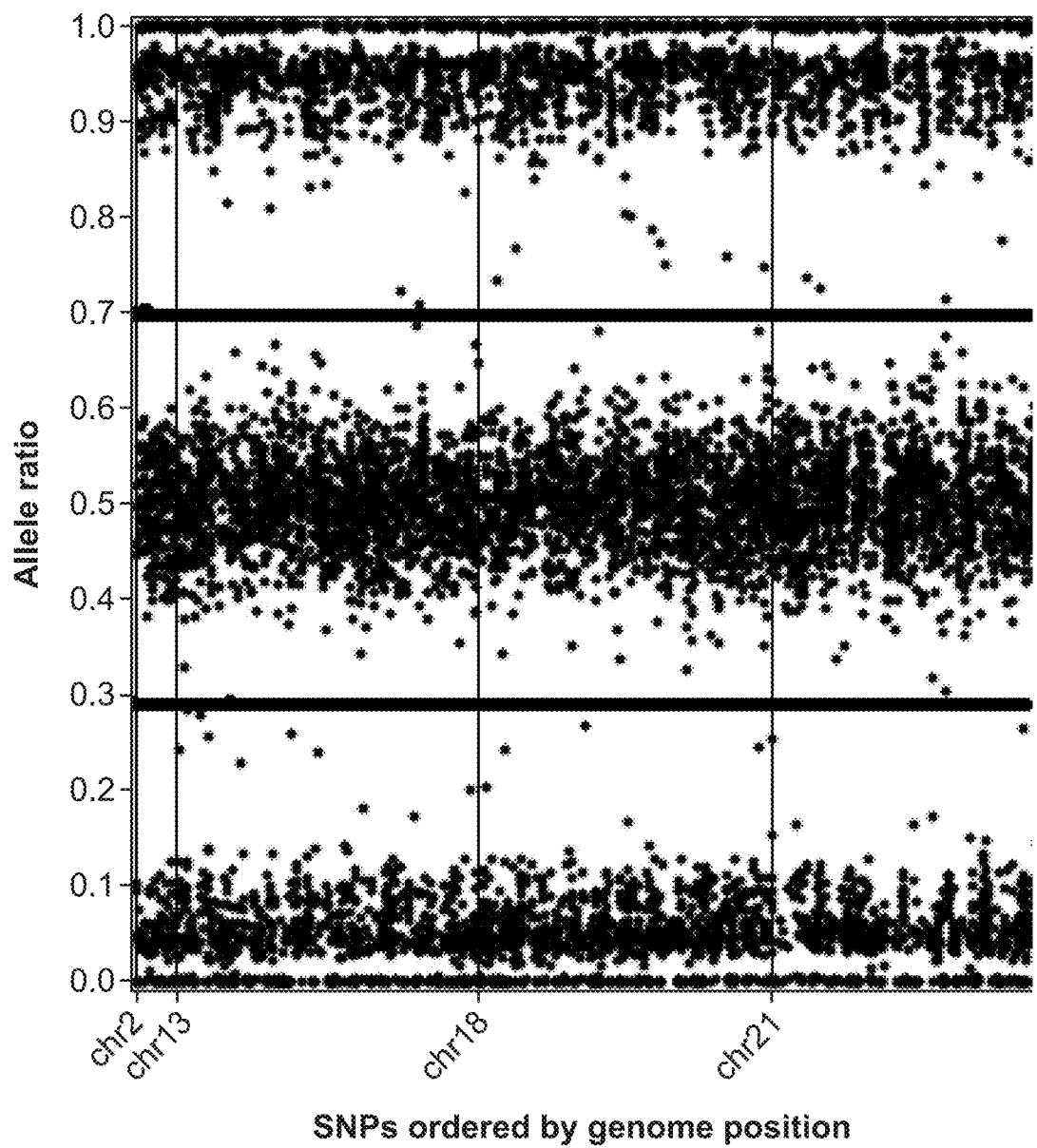
FIG. 46: Allele ratios for SNPs on chromosomes 13, 18, 21 for sample with 9% donor fraction. The SNPs between the black horizontal lines are removed from the calculation.

The donor fraction calculation begins by estimating recipient genotypes and eliminating SNPs where the recipient is heterozygous (allele ratio between 30% and 70% (FIG. 46)). We define the homozygous reference genotype as RR, homozygous mutant genotype as MM, and heterozygous genotype as RM. The donor fraction is calculated from the set of SNPs where the recipient is homozygous, by a method based on considering all of the possible donor genotypes.

Figure 47:
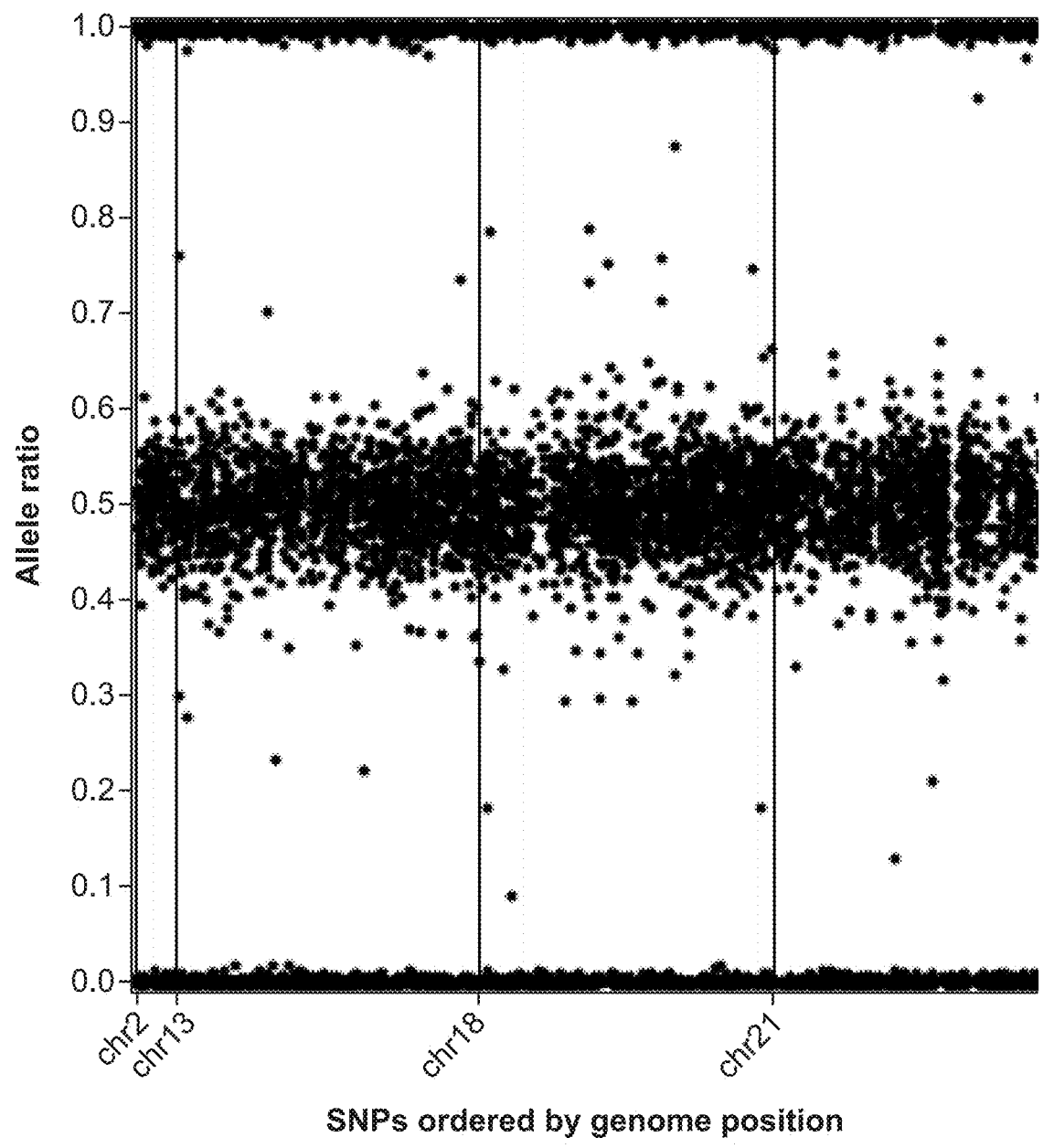
FIG. 47: Allele ratios for SNPs on chromosomes 13, 18, 21 for sample with 0.4% donor fraction.

When the donor fraction is approximately zero, the observed allele ratios simply reflect the recipient genotypes and so all SNPs where the recipient is homozygous have allele ratio approximately zero or 1 (FIG. 47).

The likelihood of a candidate donor fraction is defined as the probability of producing the observed sequencing data according to a mathematical model for how the data depends on the donor fraction. We assume that the data at each SNP is independent conditioned on the donor fraction, which implies that the combined likelihood is the product of the likelihoods calculated at each SNP.

The likelihood calculation at a single SNP incorporates two sources of uncertainty: the donor genotypes and the sequencing data. The donor genotypes are modeled probabilistically by summing over the set of possible genotypes and weighting them according to the prior probability, defined by the population minor allele frequencies. The sequencing data is modeled using a binomial distribution as a function of the expected allele ratio and measured number of reads, given an assumed donor genotype and estimated error rates due to sequencing plus PCR.

Materials and Equipment

Major equipment and reagents used in the execution of this assay are detailed in Table 17.

TABLE 17

Critical Equipment and Reagents

| Item | Manufacturer | Use |
|---|---|---|
| NextSeq Instrument | Illumina | Next Generation Sequencing |
| GeneAmp PCR System 9700 Thermocycler | Thermo Fisher | Library preparation and PCR Amplification |
| NextSeq High Output Reagent Cartridge v2, 75 cycles | Illumina | Next Generation Sequencing |
| NextSeq 500/550 Buffer Cartridge v2 | Illumina | Next Generation Sequencing |
| NextSeq Row Cell v2 | Illumina | Next Generation Sequencing |
| Natera library prep kit | Natera | Preparation of library from cfDNA |
| Natera cfDNA extraction kit | Natera | cfDNA extraction from plasma |
| mmPCR primer pool | Natera | Targeted amplification of SNP loci |

Example 8. Improved Determination of Transplant Rejection by Using a Threshold Metric that Takes into Account the Body Mass of the Patient The data acquired in Example 6 was evaluated by using a threshold based on donor copies/ml and a further threshold that additionally takes into account the body mass of the patient. The data from Example 6 was derived from 217 biopsy matched samples (193 patients), out of which 38 samples showed active or acute rejection (AR) and 179 showed non rejection (NON-AR). The cfDNA was quantified for 215 of the samples and patient mass was measured for 123 of the samples (excluding pediatric). The data from these 123 samples are shown in Table 18 below.

TABLE 18

Re-analysis of data from 123 patient from which body mass was measured.

| | Original Set | | New Set | |
|---|---|---|---|---|
| | Samples | % of Set | Samples | % of Set |
| AR | 38 | 18% | 31 | 25% |
| NON-AR | 179 | 82% | 92 | 75% |
| BL | 72 | 33% | 64 | 52% |
| OI | 25 | 12% | 18 | 15% |
| STA | 82 | 38% | 10 | 8% |
| Total | 217 | | 123 | |
| Sensitivity | 86.8%* | | 83.9% | |
| Specificity | 70.9%* | | 75.0% | |
| Protocol AR | 12 of 13 | | 9 of 10 | |

*Recalculed from raw data without accounting for multiple samples from the same patient.

The data were first analyzed using donor-derived copies/mL, which was calculated as follows: (ng cfDNA)/(3.3 pg/haploid genome)*(dd-cfDNA %)/(mL plasma).

To take into account the body mass of the patient, the data were analyzed using donor-derived copies/mL*Patient Mass (abbreviated "donor copies/mL*kg"), which was calculated as follows: (ng cfDNA)/(3.3 pg/haploid genome)*(dd-cfDNA %)/(mL plasma)*(patient kg). This analysis accounts for host blood volume (approximated using patient mass) diluting a signal from a fixed transplant mass.

As shown in Table 19 below, a threshold of 976 donor copies/mL*kg and a threshold of 13.4 donor copies/mL corresponds to a threshold of 1.00% dd-cfDNA.

TABLE 19

| | Median | Min | Max | Threshold |
|---|---|---|---|---|
| ng cfDNA/mL | 4.0 | 0.2 | 353 | N/A |
| dd-cfDNA % | 0.62% | 0.02% | 23.90% | 1.00% |
| Donor copies/mL | 9.9 | 0.6 | 857 | 13.4 |
| Donor copies/mL * kg | 727 | 40 | 68,544 | 976 |

Figure 48:
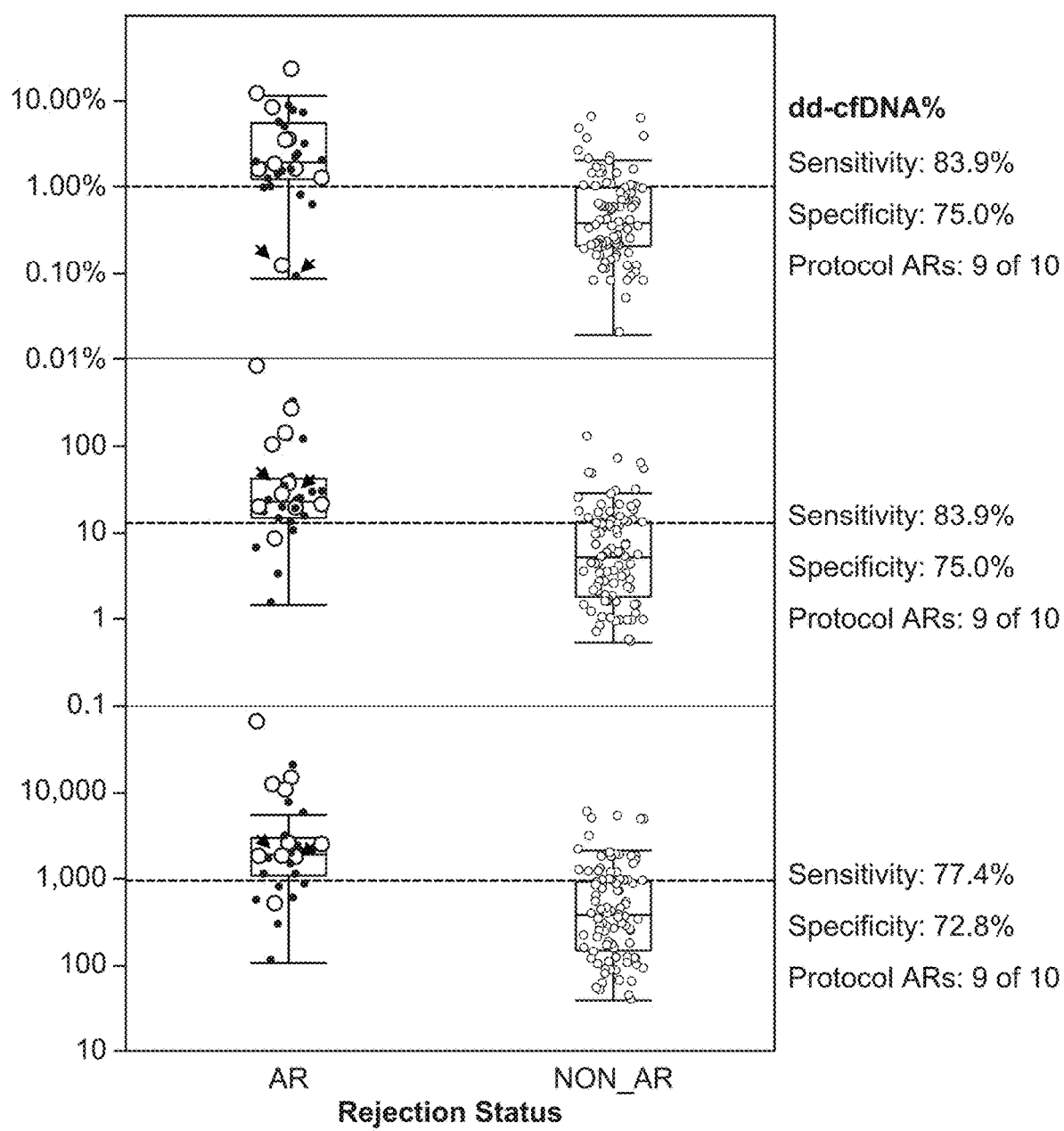
FIG. 48: Performance of using donor copies/mL and donor copies/mL*kg as the metric with fixed threshold. Black arrows shows protocol active rejection and T-cell mediated rejections missed by using dd-cfDNA % as the threshold metric.

Analyzing the data from Example 6 by using the donor copies/mL metric and the donor copies/mL*kg metric as the fixed threshold instead of dd-cfDNA % resulted in the sensitivity and specificity as shown in FIG. 48. Using dd-cfDNA % as the threshold metric resulted in a sensitivity of 83.9% and a specificity of 75.0%, and protocol active rejections were correctly called 9 of 10. Using donor copies/mL as the threshold metric resulted in a sensitivity of 83.9% and a specificity of 75.0%, and protocol active rejections were correctly called 9 of 10. Using donor copies/mL*kg as the threshold metric resulted in a sensitivity of 77.4% and a specificity of 72.8%, and protocol active rejections were correctly called 9 of 10. Analyzing the data by using donor copies/mL or donor copies/mL*kg as the threshold metric correctly called a protocol active rejection and a T-cell mediated rejection missed by dd-cfDNA % (shown with black arrows in FIG. 48).

Example 9. Developing a Scaled Threshold to Improve Performance in Monitoring Transplant by Quantifying Donor Derived cfDNA The purpose of this Example is to develop a scaled or dynamic threshold depending on cfDNA ng/mL in the blood samples obtained from the patients. It was observed that low input dd-cfDNA % influenced the estimated dd-cfDNA %. In particular, analyzing the relationship between estimated dd-cfDNA % and input dd-cfDNA % revealed that below 9 ng cfDNA input, the pipeline estimated dd-cfDNA % increased.

Figure 49:
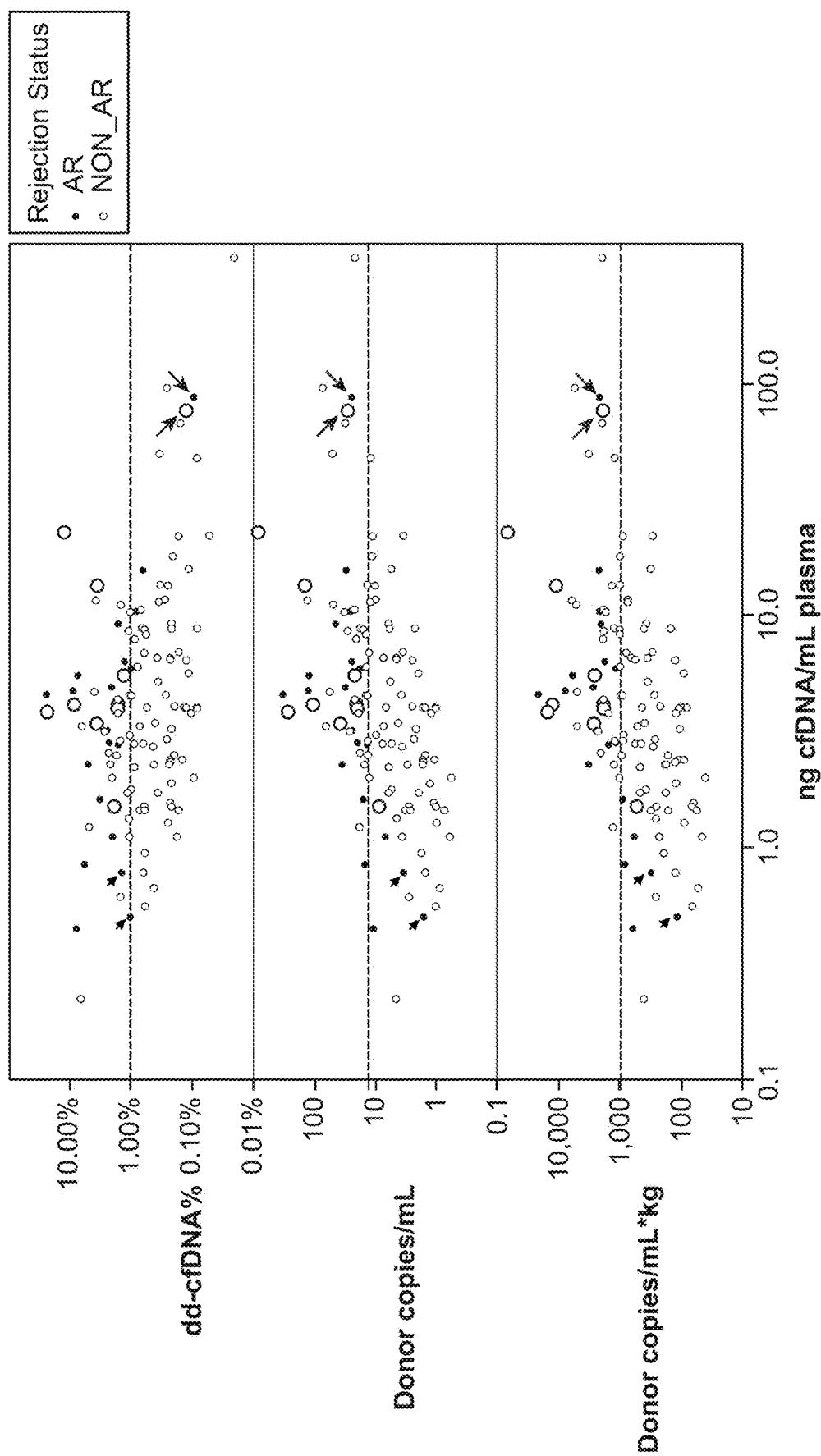
FIG. 49: Graph depicting dd-cfDNA % (upper panel), donor copies/mL (middle panel), and donor copies/mL*kg (lower panel) from patient data as a function of ng cfDNA/mL plasma.
Figure 50:
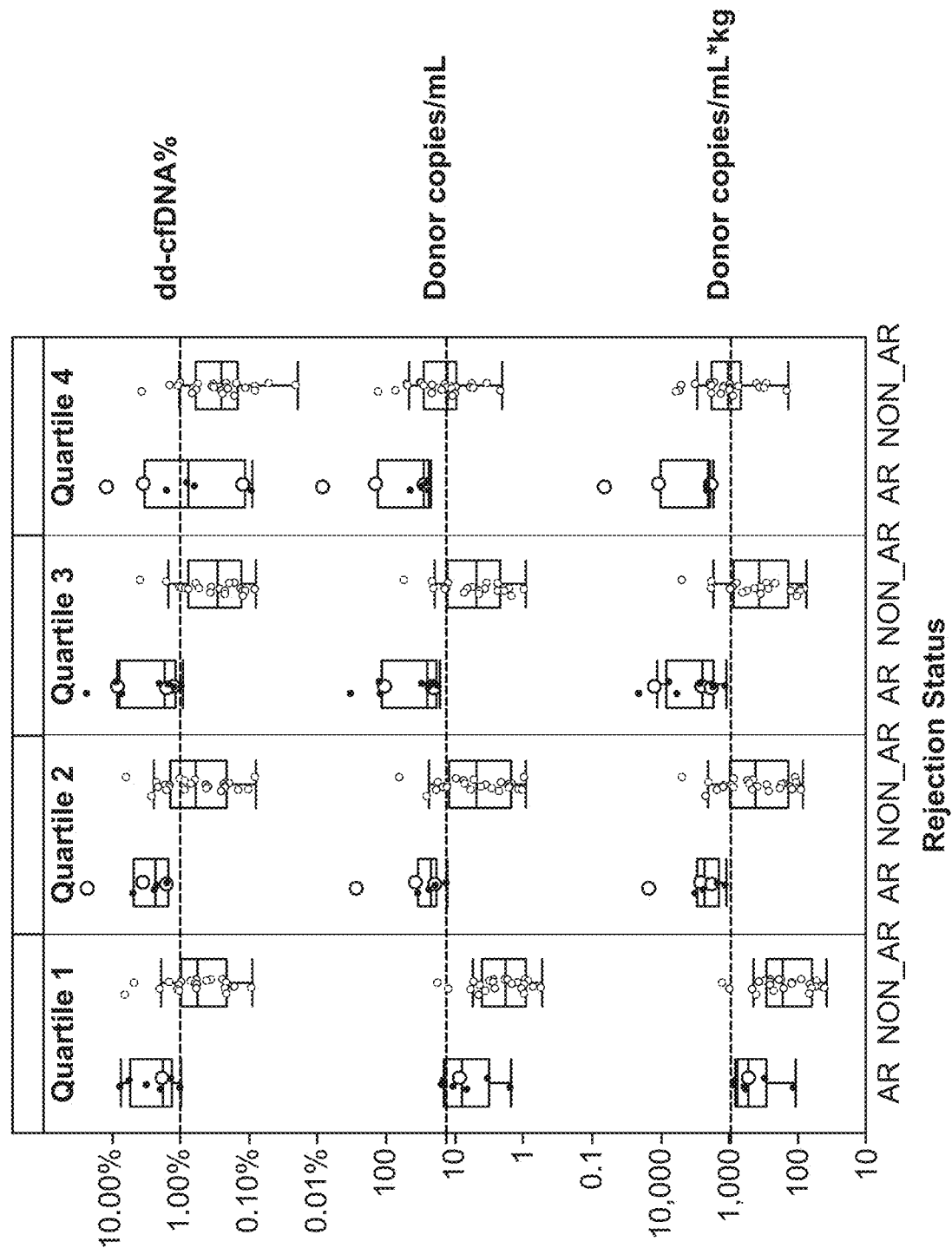
FIG. 50: Stratification of samples by cfDNA ng/mL amounts. As cfDNA ng/mL increases, both sensitivity and specificity increase for donor copies/mL and donor copies/mL*kg as the metric.
Figure 51:
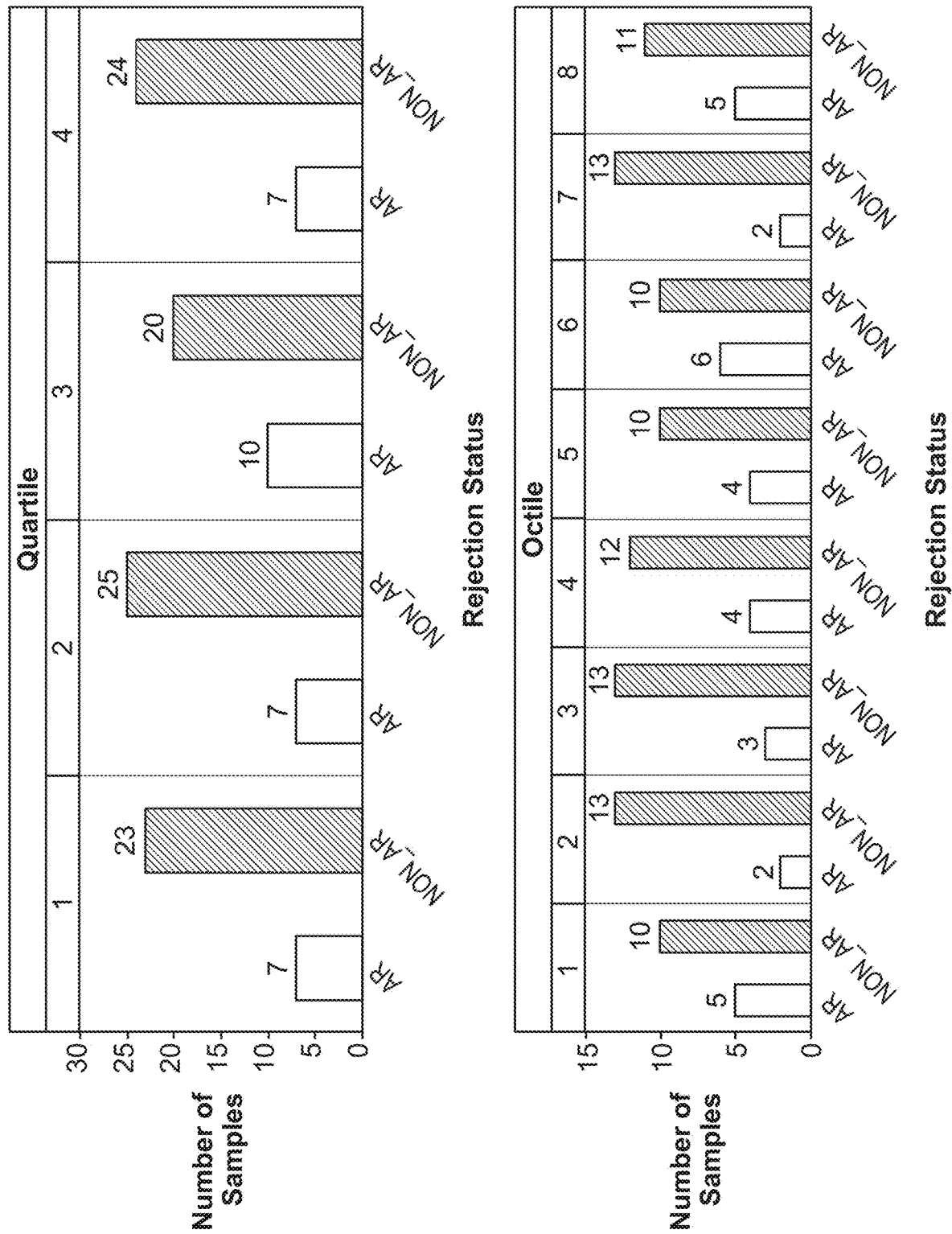
FIG. 51: Distribution of active rejection (AR) and non rejection (NON_AR) samples across quartile (upper panel) and octile (lower panel) stratification of samples by cfDNA ng/mL amounts.
Figure 52:
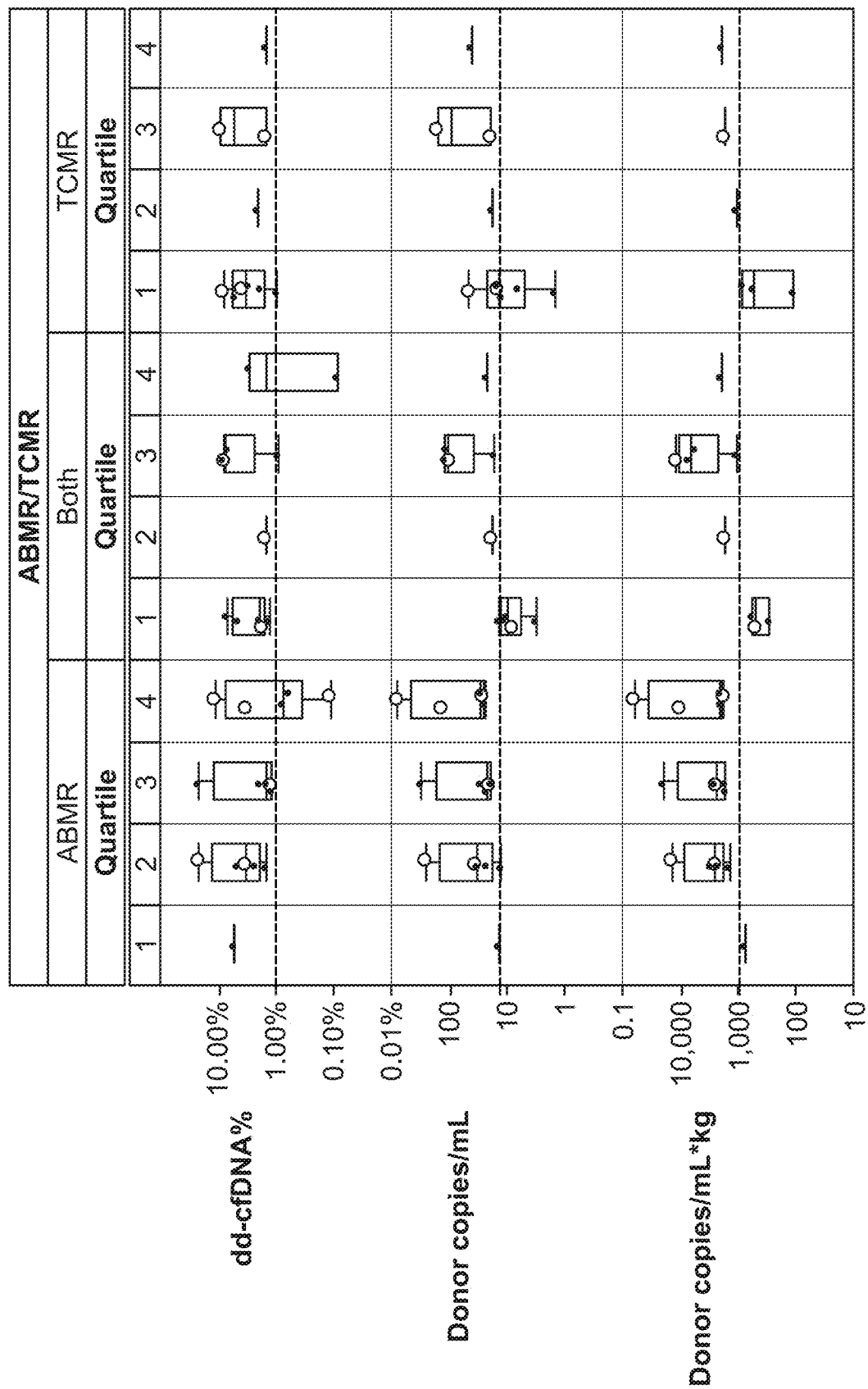
FIG. 52: Stratification of samples by cfDNA ng/mL amounts and further categorized based on determination of antibody mediated rejection (ABMR) or T-cell mediated rejection (TCMR). The panels shows determination of ABMR or TCMR based on dd-cfDNA %, donor copies/mL, or donor copies/mL*kg threshold metrics as indicated in the figure panel.

Moreover, there appeared to be a linear relationship between the dd-cfDNA %, donor copies/mL, or donor copies/mL*kg, and the amount of cfDNA (ng cfDNA/mL) in the blood samples as shown in FIG. 49. To further test if the threshold value varies depending on ng cfDNA/mL plasma, the sample data was stratified according to quartiles of ng cfDNA/mL plasma as shown in FIG. 50. Stratification of the data based on ng cfDNA/mL plasma clearly showed that performance could be improved by scaling the threshold value for the different quartiles of cfDNA amount. FIG. 52, showed that the effect of stratification of the data is similar for both antibody mediated rejection (ABMR) and T-cell mediated rejection (TCMR). As shown in FIG. 51, both active or acute rejection (AR) and non-rejection (NON-AR) samples were distributed across the quartiles or octiles of cfDNA amount.

When the dd-cfDNA % threshold metric is used, the results presented in FIG. 50 showed that as cfDNA ng/mL increased, the specificity increased and the sensitivity decreased. The analysis using dd-cfDNA % threshold metric missed a protocol active rejection in Q4. Table 20 below shows more detailed results from the comparison of using fixed versus dynamic threshold for the dd-cfDNA % threshold.

TABLE 20

Comparison of fixed threshold and scaled threshold for the dd-cfDNA % threshold metric.

| | Fixed Threshold | | | | Scaled Threshold | | | | | Overall | |
|---|---|---|---|---|---|---|---|---|---|---|---|
| | Q1 | Q2 | Q3 | Q4 | Q1 | Q2 | Q3 | Q4 | | Fixed | Scaled |
| Threshold | | 1.00% | | | 1.33% | 1.00% | | 0.60% | Sensitivity | 83.9% | 87.1% |
| Sensitivity | 100% | 100% | 90% | 43% | 86% | 100% | 90% | 71% | Specificity | 75.0% | 76.1% |
| Specificity | 70% | 64% | 85% | 83% | 83% | 64% | 85% | 75% | Protocol ARs | 9/10 | 9/10 |

For the donor copies/mL threshold metric, the analysis presented in FIG. 50 showed that both sensitivity and specificity increased with increasing cfDNA ng/mL plasma. The analysis using donor copies/mL threshold metric missed a protocol active rejection in Q1. Table 21 below, shows more detailed results from the comparison of using fixed versus dynamic threshold for the donor copies/mL threshold metric.

TABLE 21

Comparison of fixed threshold and scaled threshold for the donor copies/mL threshold metric.

| | Fixed Threshold | | | | Scaled Threshold | | | | | Overall | |
|---|---|---|---|---|---|---|---|---|---|---|---|
| | Q1 | Q2 | Q3 | Q4 | Q1 | Q2 | Q3 | Q4 | | Fixed | Scaled |
| Threshold | | 13.4 | | | 5.0 | 13.4 | | 25.0 | Sensitivity | 83.9% | 90.3% |
| Sensitivity | 29% | 100% | 100% | 100% | 71% | 100% | 100% | 86% | Specificity | 75.0% | 77.2% |
| Specificity | 96% | 80% | 75% | 50% | 83% | 80% | 75% | 71% | Protocol ARs | 9/10 | 10/10 |

For the donor copies/mL*kg threshold metric, the analysis presented in FIG. 50 showed that both sensitivity and specificity increased with increasing cfDNA ng/mL plasma. The analysis using donor copies/mL*kg threshold metric missed a protocol active rejection in Q1. Table 22 below, shows more detailed results from the comparison of using fixed versus dynamic threshold for the donor copies/mL*kg threshold metric.

TABLE 22

Comparison of fixed threshold and scaled threshold for the donor copies/mL*kg threshold metric.

| | Fixed Threshold | | | | Scaled Threshold | | | | | Overall | |
|---|---|---|---|---|---|---|---|---|---|---|---|
| | Q1 | Q2 | Q3 | Q4 | Q1 | Q2 | Q3 | Q4 | | Fixed | Scaled |
| Threshold | | 976 | | | 324 | 976 | | 1952 | Sensitivity | 77.4% | 90.3% |
| Sensitivity | 0% | 100% | 100% | 100% | 71% | 100% | 100% | 86% | Specificity | 72.8% | 80.4% |
| Specificity | 91% | 76% | 85% | 42% | 78% | 76% | 85% | 83% | Protocol ARs | 9/10 | 10/10 |

It was also found that the performance of the analysis can be further improved by splitting the data into smaller ng/mL grouping as shown in Table 23 below.

TABLE 23

Comparison of fixed threshold and scaled threshold for the donor copies/mL*kg threshold metric when the data is stratified into octiles based on ng cfDNA/mL plasma.

| | | | | | | | | | | Fixed |
|---|---|---|---|---|---|---|---|---|---|---|
| Initial performance at 1% fixed: | | | | | | Sensitivity | | | | 83.9% |
| | | | | | | Specificity | | | | 75.0% |

| | | Octile 1 | Octile 2 | Octile 3 | Octile 4 | Octile 5 | Octile 6 | Octile 7 | Octile 8 | | Overall |
|---|---|---|---|---|---|---|---|---|---|---|---|
| Donor copies/mL | Threshold | 5.0 | 8.0 | 13.4 | 17.0 | | | 22.0 | | Scaled | |
| | Sensitivity | 60% | 100% | 100% | 100% | 100% | 100% | 100% | 100% | Sensitivity | 93.5% |
| | Specificity | 90% | 92% | 85% | 75% | 80% | 90% | 69% | 73% | Specificity | 81.5% |
| Donor copies/mL*kg | Threshold | 500 | | 976 | 1,600 | | 1,800 | | | Scaled | |
| | Sensitivity | 60% | 100% | 100% | 100% | 100% | 83% | 100% | 100% | Sensitivity | 90.3% |
| | Specificity | 90% | 92% | 85% | 83% | 80% | 90% | 69% | 64% | Specificity | 81.5% |
| Donor copies/mL*kg | Threshold | 100 | 500 | | 1,000 | | | 1,825 | | Scaled | |
| | Sensitivity | 100% | 100% | 100% | 100% | 100% | 100% | 100% | 100% | Sensitivity | 100.0% |
| | Specificity | 40% | 92% | 85% | 67% | 80% | 90% | 77% | 64% | Specificity | 75.0% |

In summary, this example showed that the performance of the transplantation monitoring method disclosed herein may be improved by using a scaled or dynamic threshold metric that takes into account the ng cfDNA/mL plasma obtained from the samples, including improved sensitivity and specificity. 100% of protocol biopsy active rejection cases were called correctly when using the scaled thresholds with the new metrics.

Additional Embodiments

Embodiment 1. A method of quantifying the amount of donor-derived cell-free DNA (dd-cfDNA) in a blood sample of a transplant recipient, comprising:
a) extracting DNA from the blood sample of the transplant recipient, wherein the DNA comprises donor-derived cell-free DNA and recipient-derived cell-free DNA;
b) performing targeted amplification at 500-50,000 target loci in a single reaction volume using 500-50,000 primer pairs, wherein the target loci comprise polymorphic loci and non-polymorphic loci, and wherein each primer pair is designed to amplify a target sequence of no more than 100 bp; and
c) quantifying the amount of donor-derived cell-free DNA in the amplification products.

Embodiment 2. A method of quantifying the amount of donor-derived cell-free DNA (dd-cfDNA) in a blood sample of a transplant recipient, comprising:
a) extracting DNA from the blood sample of the transplant recipient, wherein the DNA comprises donor-derived cell-free DNA and recipient-derived cell-free DNA, and wherein the extracting step comprises size selection to enrich for donor-derived cell-free DNA and reduce the amount of recipient-derived cell-free DNA disposed from bursting white-blood cells;
b) performing targeted amplification at 500-50,000 target loci in a single reaction volume using 500-50,000 primer pairs, wherein the target loci comprise polymorphic loci and non-polymorphic loci; and
c) quantifying the amount of donor-derived cell-free DNA in the amplification products.

Embodiment 3. A method of detecting donor-derived cell-free DNA (dd-cfDNA) in a blood sample of a transplant recipient, comprising:
a) extracting DNA from the blood sample of the transplant recipient, wherein the DNA comprises donor-derived cell-free DNA and recipient-derived cell-free DNA;
b) performing targeted amplification at 500-50,000 target loci in a single reaction volume using 500-50,000 primer pairs, wherein the target loci comprise polymorphic loci and non-polymorphic loci;
c) sequencing the amplification products by high-throughput sequencing; and
d) quantifying the amount of donor-derived cell-free DNA.

Embodiment 4. The method of any of the preceding Embodiments, further comprising performing universal amplification of the extracted DNA.

Embodiment 5. The method of any of the preceding Embodiments, wherein the transplant recipient is a mammal.

Embodiment 6. The method of any of the preceding Embodiments, wherein the transplant recipient is a human.

Embodiment 7. The method of any of the preceding Embodiments, wherein the transplant recipient has received a transplant selected from organ transplant, tissue transplant, cell transplant, and fluid transplant.

Embodiment 8. The method of any of the preceding Embodiments, wherein the transplant recipient has received a transplant selected from kidney transplant, liver transplant, pancreas transplant, intestinal transplant, heart transplant, lung transplant, heart/lung transplant, stomach transplant, testis transplant, penis transplant, ovary transplant, uterus transplant, thymus transplant, face transplant, hand transplant, leg transplant, bone transplant, bone marrow transplant, cornea transplant, skin transplant, pancreas islet cell transplant, heart valve transplant, blood vessel transplant, and blood transfusion.

Embodiment 9. The method of any of the preceding Embodiments, wherein the transplant recipient has received a kidney transplant.

Embodiment 10. The method of any of the preceding Embodiments, wherein the quantifying step comprises determining the percentage of donor-derived cell-free DNA out of the total of donor-derived cell-free DNA and recipient-derived cell-free DNA in the blood sample.

Embodiment 11. The method of any of the preceding Embodiments, wherein the quantifying step comprises determining the number of copies of donor-derived cell-free DNA per volume unit of the blood sample.

Embodiment 12. The method of any of the preceding Embodiments, wherein the method further comprises detecting the occurrence or likely occurrence of active rejection of transplantation using the quantified amount of donor-derived cell-free DNA.

Embodiment 13. The method of any of the preceding Embodiments, wherein the method is performed without prior knowledge of donor genotypes.

Embodiment 14. The method of any of the preceding Embodiments, wherein each primer pair is designed to amplify a target sequence of about 50-100 bp.

Embodiment 15. The method of any of the preceding Embodiments, wherein each primer pair is designed to amplify a target sequence of about 60-75 bp.

Embodiment 16. The method of any of the preceding Embodiments, wherein each primer pair is designed to amplify a target sequence of about 65 bp.

Embodiment 17. The method of any of the preceding Embodiments, wherein the targeted amplification comprises amplifying at least 1,000 polymorphic loci in a single reaction volume.

Embodiment 18. The method of any of the preceding Embodiments, wherein the targeted amplification comprises amplifying at least 2,000 polymorphic loci in a single reaction volume.

Embodiment 19. The method of any of the preceding Embodiments, wherein the targeted amplification comprises amplifying at least 5,000 polymorphic loci in a single reaction volume.

Embodiment 20. The method of any of the preceding Embodiments, wherein the method further comprises measuring an amount of one or more alleles at the target loci that are polymorphic loci.

Embodiment 21. The method of any of the preceding Embodiments, wherein the quantifying step comprises detecting the amplified target loci using a microarray.

Embodiment 22. The method of any of the preceding Embodiments, wherein the quantifying step does not comprise using a microarray.

Embodiment 23. The method of any of the preceding Embodiments, wherein the polymorphic loci and the non-polymorphic loci are amplified in a single reaction.

Embodiment 24. The method of any of the preceding Embodiments, wherein the targeted amplification comprises simultaneously amplifying 500-50,000 target loci in a single reaction volume using (i) at least 500-50,000 different primer pairs, or (ii) at least 500-50,000 target-specific primers and a universal or tag-specific primer 500-50,000 primer pairs.

Embodiment 25. A method of determining the likelihood of transplant rejection within a transplant recipient, the method comprising:
a) extracting DNA from the blood sample of the transplant recipient, wherein the DNA comprises donor-derived cell-free DNA and recipient-derived cell-free DNA;
b) performing universal amplification of the extracted DNA;
c) performing targeted amplification at 500-50,000 target loci in a single reaction volume using 500-50,000 primer pairs, wherein the target loci comprise polymorphic loci and non-polymorphic loci;
d) sequencing the amplification products by high-throughput sequencing; and
e) quantifying the amount of donor-derived cell-free DNA in the blood sample, wherein a greater amount of dd-cfDNA indicates a greater likelihood of transplant rejection.

Embodiment 26. A method of diagnosing a transplant within a transplant recipient as undergoing acute rejection, the method comprising:
a) extracting DNA from the blood sample of the transplant recipient, wherein the DNA comprises donor-derived cell-free DNA and recipient-derived cell-free DNA;
b) performing universal amplification of the extracted DNA;
c) performing targeted amplification at 500-50,000 target loci in a single reaction volume using 500-50,000 primer pairs, wherein the target loci comprise polymorphic loci and non-polymorphic loci;
d) sequencing the amplification products by high-throughput sequencing; and
e) quantifying the amount of donor-derived cell-free DNA in the blood sample, wherein an amount of dd-cfDNA of greater than 1% indicates that the transplant is undergoing acute rejection.

Embodiment 27. The method of Embodiments 25 or 26, wherein the transplant rejection is antibody mediated transplant rejection.

Embodiment 28. The method of Embodiments 25 or 26, wherein the transplant rejection is T cell mediated transplant rejection.

Embodiment 29. The method of any of Embodiments 25-28, wherein an amount of dd-cfDNA of less than 1% indicates that the transplant is either undergoing borderline rejection, undergoing other injury, or stable.

Embodiment 30. A method of monitoring immunosuppressive therapy in a subject, the method comprising
a) extracting DNA from the blood sample of the transplant recipient, wherein the DNA comprises donor-derived cell-free DNA and recipient-derived cell-free DNA;
b) performing universal amplification of the extracted DNA;
c) performing targeted amplification at 500-50,000 target loci in a single reaction volume using 500-50,000 primer pairs, wherein the target loci comprise polymorphic loci and non-polymorphic loci;
d) sequencing the amplification products by high-throughput sequencing; and
e) quantifying the amount of donor-derived cell-free DNA in the blood sample, wherein a change in levels of dd-cfDNA over a time interval is indicative of transplant status.

Embodiment 31. The method of Embodiment 30, further comprising adjusting immunosuppressive therapy based on the levels of dd-cfDNA over the time interval.

Embodiment 32. The method of Embodiment 31, wherein an increase in the levels of dd-cfDNA are indicative of transplant rejection and a need for adjusting immunosuppressive therapy Embodiment 33. The method of Embodiment 31, wherein no change or a decrease in the levels of dd-cfDNA indicates transplant tolerance or stability, and a need for adjusting immunosuppressive therapy.

Embodiment 34. The method of any of Embodiments 30-33, wherein an amount of dd-cfDNA of greater than 1% indicates that the transplant is undergoing acute rejection.

Embodiment 35. The method of Embodiment 34, wherein the transplant rejection is antibody mediated transplant rejection.

Embodiment 36. The method of Embodiment 34, wherein the transplant rejection is T cell mediated transplant rejection.

Embodiment 37. The method of any of Embodiments 30-33, wherein an amount of dd-cfDNA of less than 1% indicates that the transplant is either undergoing borderline rejection, undergoing other injury, or stable.

Embodiment 38. The method of any of Embodiments 25-37, wherein the method does not comprise genotyping the transplant donor and/or the transplant recipient.

Embodiment 39. The method of any of Embodiments 25-38, wherein the method further comprises measuring an amount of one or more alleles at the target loci that are polymorphic loci.

Embodiment 40. The method of any of Embodiments 25-39, wherein the target loci comprise at least 1,000 polymorphic loci, or at least 2,000 polymorphic loci, or at least 5,000 polymorphic loci, or at least 10,000 polymorphic loci.

Embodiment 41. The method of any of Embodiments 25-40, wherein the target loci that are amplified in amplicons of about 50-100 bp in length, or about 50-90 bp in length, or about 60-80 bp in length, or about 60-75 bp in length.

Embodiment 42. The method of Embodiment 41, wherein the amplicons are about 65 bp in length.

Embodiment 43. The method of any of Embodiments 25-42, wherein the transplant recipient is a human.

Embodiment 44. The method of any of Embodiments 25-43, wherein the transplant recipient has received a transplant selected from kidney transplant, liver transplant, pancreas transplant, intestinal transplant, heart transplant, lung transplant, heart/lung transplant, stomach transplant, testis transplant, penis transplant, ovary transplant, uterus transplant, thymus transplant, face transplant, hand transplant, leg transplant, bone transplant, bone marrow transplant, cornea transplant, skin transplant, pancreas islet cell transplant, heart valve transplant, blood vessel transplant, and blood transfusion.

Embodiment 45. The method of Embodiment 44, wherein the transplant recipient has received a kidney transplant.

Embodiment 46. The method of any of Embodiments 25-45, wherein the extracting step comprises size selection to enrich for donor-derived cell-free DNA and reduce the amount of recipient-derived cell-free DNA disposed from bursting white-blood cells.

Embodiment 47. The method of any of Embodiments 25-45, wherein the universal amplification step preferentially amplifies donor-derived cell-free DNA over recipient-derived cell-free DNA that are disposed from bursting white-blood cells.

Embodiment 48. The method of any one of Embodiments 25-47, further comprising longitudinally collecting a plurality of blood samples from the transplant recipient after transplantation, and repeating steps (a) to (e) for each blood sample collected.

Embodiment 49. The method of any one of Embodiments 1-48, wherein the method has a sensitivity of at least 80% in identifying acute rejection (AR) over non-AR with a cutoff threshold of 1% dd-cfDNA and a confidence interval of 95%.

Embodiment 50. The method of any one of Embodiments 1-48, wherein the method has a specificity of at least 70% in identifying AR over non-AR with a cutoff threshold of 1% dd-cfDNA and a confidence interval of 95%.

Embodiment 51. The method of any one of Embodiments 1-48, wherein the method has an area under the curve (AUC) of at least 0.85 in identifying AR over non-AR with a cutoff threshold of 1% dd-cfDNA and a confidence interval of 95%.

Embodiment 52. The method of any one of Embodiments 1-48, wherein the method has a sensitivity of at least 80% in identifying AR over normal, stable allografts (STA) with a cutoff threshold of 1% dd-cfDNA and a confidence interval of 95%.

Embodiment 53. The method of any one of Embodiments 1-48, wherein the method has a specificity of at least 80% in identifying AR over STA with a cutoff threshold of 1% dd-cfDNA and a confidence interval of 95%.

Embodiment 54. The method of any one of Embodiments 1-48, wherein the method has an AUC of at least 0.9 in identifying AR over STA with a cutoff threshold of 1% dd-cfDNA and a confidence interval of 95%.

Embodiment 55. The method of any one of Embodiments 49-54, wherein the AR is antibody-mediated rejection (ABMR).

Embodiment 56. The method of any one of Embodiments 49-54, wherein the AR is T-cell-mediated rejection (TCMR).

Embodiment 57. The method of any one of the preceding Embodiments, wherein the method has a sensitivity as determined by a limit of blank (LoB) of about 0.5% or less, and a limit of detection (LoD) of about 0.5% or less.

Embodiment 58. The method of Embodiment 57, wherein the LoB is about 0.23% or less, and the LoD is about 0.29% or less.

Embodiment 59. The method of Embodiment 57, wherein the sensitivity is further determined by a limit of quantitation (LoQ), wherein the LoQ is about equal to or greater than the LoD.

Embodiment 60. The method of Embodiment 59, wherein the LoB is about 0.04% or less, and the LoD is about 0.05% or less, and the LoQ is about equal to the LoD.

Embodiment 61. The method of any of the preceding Embodiments, wherein the method has an accuracy as determined by evaluating a linearity value obtained from linear regression analysis of measured donor fractions as a function of the corresponding attempted spike levels, wherein the linearity value is a R2 value, wherein the R2 value is from about 0.98 to about 1.0.

Embodiment 62. The method of Embodiment 61, wherein the R2 value is about 0.999

Embodiment 63. The method of any one of the preceding Embodiments, wherein the method has an accuracy as determined by using linear regression on measured donor fractions as a function of the corresponding attempted spike levels to calculate a slope value and an intercept value, wherein the slope value is from about 0.9 to about 1.2 and the intercept value is from about −0.0001 to about 0.01.

Embodiment 64. The method of Embodiment 63, wherein the slope value is about 1, and the intercept value is about 0.

Embodiment 65. The method of any one of the preceding Embodiments, wherein the method has a precision as determined by calculating a coefficient of variation (CV), wherein the CV is less than about 10.0%.

What is claimed is:

1. A method of preparing a preparation of amplified DNA from a blood sample of a transplant recipient useful for determining likelihood of transplant rejection, comprising:
   (a) extracting DNA from the blood sample of the transplant recipient, wherein the DNA comprises donor-derived cell-free DNA and recipient-derived cell-free DNA;
   (b) preparing a preparation of amplified DNA by performing targeted amplification at 200-50,000 target loci in a single reaction volume using 200-50,000 target-specific primer pairs to obtain amplification products, wherein the target loci comprise polymorphic loci and non-polymorphic loci, wherein the targeted amplification comprises an annealing step having a length of at least 10 minutes, and wherein each target-specific primer has a concentration of less than 20 nM;
   (c) performing high-throughput sequencing on the amplification products to obtain a sequencing readout and quantifying an amount of donor-derived cell-free DNA and in the blood sample based on the sequencing readout;

wherein a cutoff threshold value of donor-derived cell-free DNA for the blood sample of the transplant recipient is scaled according to the amount of total cell-free DNA and on data of at least one of donor height or donor weight; and wherein the likelihood of transplant rejection is determined based on comparing the amount of donor-derived cell-free DNA or a function thereof to the scaled cutoff threshold value.

2. The method of claim 1, further comprising: comparing the quantified amount of donor-derived cell-free DNA and the cutoff threshold value to determine a relative level of donor-derived cell-free DNA.

3. The method of claim 2, wherein the transplant recipient has received a transplant selected from an organ transplant, a tissue transplant, a cell transplant, and a fluid transplant.

4. The method of claim 2, wherein the cutoff threshold value is expressed as a percentage of donor-derived cell-free DNA in the blood sample.

5. The method of claim 2, wherein the cutoff threshold value is expressed as a copy number of donor-derived cell-free DNA in the blood sample.

6. The method of claim 2, wherein the amount of donor-derived cell-free DNA is quantified based on the sequencing readout and the received data.

7. The method of claim 2, further comprising:
adjusting the cutoff threshold value based on the quantified amount of donor-derived cell-free DNA.

8. The method of claim 2, wherein quantifying the amount of donor-derived cell-free DNA comprises identifying donor-derived cell-free DNA and recipient-derived cell-free DNA based on genetic features at the 200-50,000 target loci in the sequencing readout.

9. The method of claim 1, wherein the targeted amplification comprises PCR, and the 200-50,000 target-specific primer pairs comprise forward and reverse PCR primers.

10. The method of claim 1, wherein b) comprises performing targeted amplification at 1,000-10,000 target loci in a single reaction volume using 1,000-10,000 target-specific primer pairs to obtain amplification products.

11. The method of claim 1, wherein the target loci are single nucleotide polymorphisms (SNPs).

12. The method of claim 1, further comprising: prior to performing high-throughput sequencing, attaching tags to the amplification products.

13. The method of claim 12, wherein the tags comprise sequencing-compatible adaptors.

14. The method of claim 13, wherein each amplification product is a DNA fragment having a first end and a second end, and wherein attaching tags to the amplification products comprises ligating an individual sequencing-compatible adaptor to each of the first end and the second end of each amplification product.

15. The method of claim 13, wherein the tags are attached to the amplification products prior to performing targeted amplification, and wherein the primer pairs are adaptor-specific universal primers.

16. The method of claim 12, wherein the tags are unique to the blood sample, and wherein the method further comprises:
pooling the amplification products with additional samples prior to high-throughput sequencing;
wherein the amplification products and additional samples are sequenced together in a single run during the high-throughput sequencing.

17. The method of claim 1, wherein the high-throughput sequencing comprises clonal sequencing.

18. The method of claim 1, wherein the 200-50,000 target loci comprise at least 1,000 distinct target loci.

19. The method of claim 2, further comprising determining whether the percentage of donor-derived cell-free DNA is above a cutoff threshold and whether the copy number of donor-derived cell-free DNA or a function thereof is above a cutoff threshold.

* * * * *